US012565614B2

(12) United States Patent
Kim et al.

(10) Patent No.: US 12,565,614 B2

(45) Date of Patent: Mar. 3, 2026

(54) HETEROCYCLIC COMPOUND, ORGANIC LIGHT-EMITTING DEVICE COMPRISING SAME, COMPOSITION FOR ORGANIC MATERIAL LAYER OF ORGANIC LIGHT-EMITTING DEVICE, AND METHOD FOR MANUFACTURING ORGANIC LIGHT-EMITTING DEVICE

(71) Applicant: LT MATERIALS CO., LTD., Yongin-si (KR)

(72) Inventors: Ji-Young Kim, Yongin-si (KR); Jong-Su Lee, Yongin-si (KR); Jun-Tae Mo, Yongin-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 969 days.

(21) Appl. No.: 17/775,330

(22) PCT Filed: Dec. 4, 2020

(86) PCT No.: PCT/KR2020/017602

§ 371 (c)(1),
(2) Date: May 9, 2022

(87) PCT Pub. No.: WO2021/132930

PCT Pub. Date: Jul. 1, 2021

(65) Prior Publication Data

US 2023/0016632 A1 Jan. 19, 2023

(30) Foreign Application Priority Data

Dec. 24, 2019 (KR) ........................ 10-2019-0174330

(51) Int. Cl.

| | |
|---|---|
| ***H01L 51/54*** | (2006.01) |
| ***C07D 307/91*** | (2006.01) |
| ***C07D 307/93*** | (2006.01) |
| ***C07D 333/78*** | (2006.01) |
| ***C09K 11/06*** | (2006.01) |
| ***H10K 85/60*** | (2023.01) |
| *H10K 50/11* | (2023.01) |
| *H10K 101/00* | (2023.01) |

(52) U.S. Cl.

CPC ............ *C09K 11/06* (2013.01); *C07D 307/91* (2013.01); *C07D 307/93* (2013.01); *C07D 333/78* (2013.01); *H10K 85/631* (2023.02); *H10K 85/636* (2023.02); *H10K 85/654* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 2101/90* (2023.02)

(58) Field of Classification Search

None

See application file for complete search history.

(56) References Cited

U.S. PATENT DOCUMENTS

| | | | |
|---|---|---|---|
| 2017/0012205 A1 | 1/2017 | Jung et al. | |
| 2018/0053902 A1 | 2/2018 | Kim et al. | |

FOREIGN PATENT DOCUMENTS

| | | | | |
|---|---|---|---|---|
| CN | 109385266 A | 2/2019 | | |
| KR | 10-2015-0064682 A | 6/2015 | | |
| KR | 20150145131 A | * 12/2015 | ........... H10K 85/657 | |
| KR | 20160122974 A | * 10/2016 | ........... C07D 307/93 | |
| KR | 10-2017-0006345 A | 1/2017 | | |
| KR | 10-2018-0021340 A | 3/2018 | | |
| KR | 10-2019-0079339 A | 7/2019 | | |
| WO | WO-2019132399 A1 | * 7/2019 | ............. C09K 11/06 | |

OTHER PUBLICATIONS

Machine translation of KR2015-145131. (Year: 2015).*
Machine translation of KR2016-122974. (Year: 2016).*
Machine translation of WO 2019/132399. (Year: 2019).*
International Search Report, issued in PCT/KR2020/017602, dated Mar. 17, 2021.

* cited by examiner

*Primary Examiner* — Andrew K Bohaty

(74) *Attorney, Agent, or Firm* — Birch, Stewart, Kolasch & Birch, LLP

(57) ABSTRACT

The present specification provides a heterocyclic compound represented by Chemical Formula 1, an organic light emitting device comprising the same, a composition for an organic material layer of an organic light emitting device, and a method for manufacturing an organic light emitting device.

13 Claims, 2 Drawing Sheets

【FIG. 1】
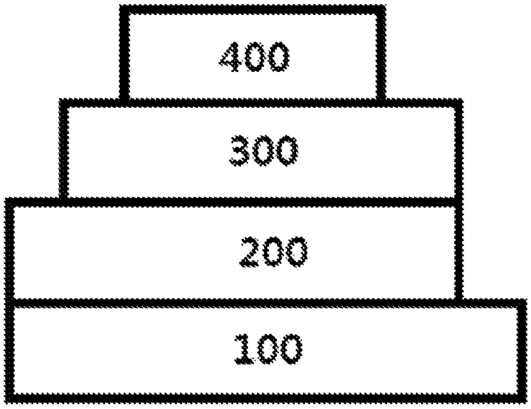
【FIG. 2】
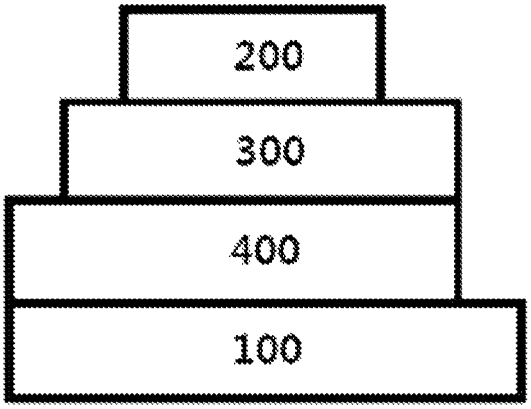

【FIG. 3】
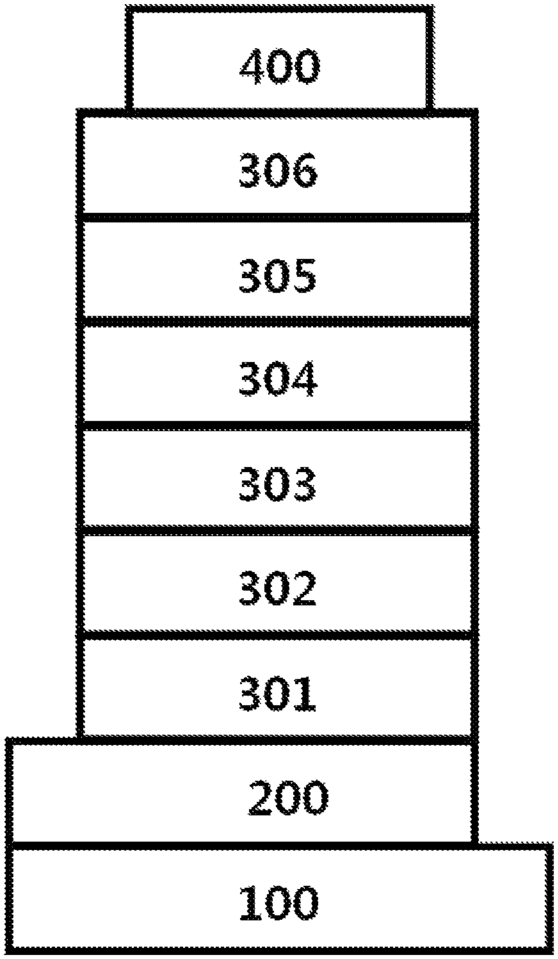

HETEROCYCLIC COMPOUND, ORGANIC LIGHT-EMITTING DEVICE COMPRISING SAME, COMPOSITION FOR ORGANIC MATERIAL LAYER OF ORGANIC LIGHT-EMITTING DEVICE, AND METHOD FOR MANUFACTURING ORGANIC LIGHT-EMITTING DEVICE

TECHNICAL FIELD

This application claims priority to and the benefits of Korean Patent Application No. 10-2019-0174330, filed with the Korean Intellectual Property Office on Dec. 24, 2019, the entire contents of which are incorporated herein by reference.

The present specification relates to a heterocyclic compound, an organic light emitting device comprising the same, a composition for an organic material layer of an organic light emitting device, and a method for manufacturing an organic light emitting device.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

Studies on an organic light emitting device comprising a compound capable of satisfying conditions required for materials usable in an organic light emitting device, for example, satisfying proper energy level, electrochemical stability, thermal stability and the like, and having a chemical structure capable of performing various roles required in an organic light emitting device depending on substituents have been required.

PRIOR ART DOCUMENTS

Patent Documents

U.S. Pat. No. 4,356,429

DISCLOSURE

Technical Problem

The present application relates to a heterocyclic compound, an organic light emitting device comprising the same, a composition for an organic material layer of an organic light emitting device, and a method for manufacturing an organic light emitting device.

Technical Solution

One embodiment of the present application provides a heterocyclic compound represented by the following Chemical Formula 1.

[Chemical Formula 1]

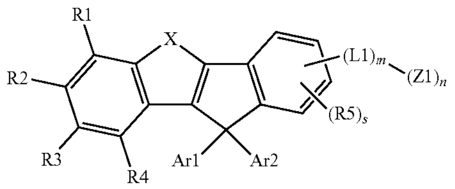

In Chemical Formula 1,

X is O; or S,

R1 to R5 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, Ar1 and Ar2 are the same as or different from each other, and each independently a substituted or unsubstituted C1 to C60 alkyl group; a substituted or unsubstituted C6 to C60 aryl group; or a substituted or unsubstituted C2 to C60 heteroaryl group, L1 is a substituted or unsubstituted C6 to C60 arylene group; or a substituted or unsubstituted C2 to C60 heteroarylene group, Z1 is selected from the group consisting of hydrogen; deuterium; halogen; a cyano group; a substituted or unsubstituted C1 to C60 alkyl group; a substituted or unsubstituted C2 to C60 heteroaryl group; and a substituted or unsubstituted amine group, m and n are an integer of 1 to 4, and s is an integer of 0 to 3, and R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In the organic light emitting device provided in one embodiment of the present application, the organic material layer comprising the heterocyclic compound of Chemical Formula 1 further comprises a heterocyclic compound represented by the following Chemical Formula 2.

[Chemical Formula 2]

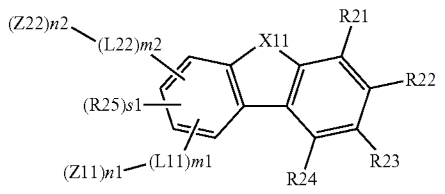

In Chemical Formula 2,

X11 is O; or S,

R21 to R25 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, L11 and L22 are the same as or different from each other, and each independently a direct bond; a substituted or unsubstituted C6 to C60 arylene group; or a substituted or unsubstituted C2 to C60 heteroarylene group, Z11 and Z22 are the same as or different from each other, and each independently selected from the group consisting of a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group, R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group, m1 and m2 are an integer of 0 to 4, s1 is an integer of 0 to 2, and n1 and n2 are an integer of 1 to 6.

In addition, another embodiment of the present application provides a composition for an organic material layer of an organic light emitting device, the composition comprising the heterocyclic compound represented by Chemical Formula 1, and the heterocyclic compound represented by Chemical Formula 2.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as a light emitting material of the organic light emitting device. For example, the compound can be used alone as a light emitting material, or two of the compounds can be used together as a light emitting material, and can be used as a host material of a light emitting layer.

Particularly, the compound of Chemical Formula 1 exhibits excellent thermal stability by introducing substituents at different positions around the skeleton of the core structure, and thereby expands the conjugation range. Particularly, as a host material of a light emitting layer with strong hole properties, superior device properties are obtained compared to existing technologies.

In addition, the compound of Chemical Formula 1 has low T1 energy and more readily transfers triplet exciton energy to a dopant, and particularly, an amine-based substituent increases a HOMO value of the compound, which lowers a hole injection barrier and resolves hole trap of the red dopant resulting in high light emission efficiency.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, a cyano group may mean —CN.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium such as a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as $T2/T1 \times 100 = T$ % when the total number of substituents that a basic compound may have is defined as T1, and the number of specific substituents among these is defined as T2.

In other words, in one example, having a deuterium content of 20% in a phenyl group represented by

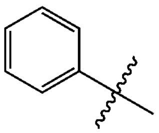 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

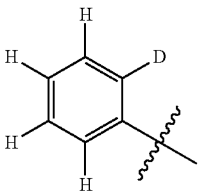

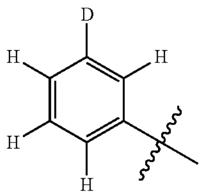

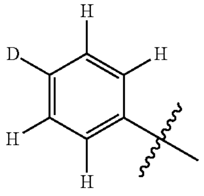

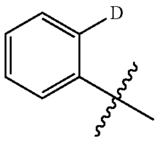

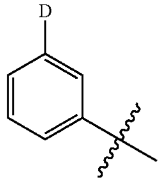

-continued

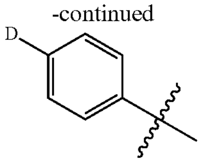

In addition, in one embodiment of the present application, "a phenyl group having a deuterium content of 0%" may mean a phenyl group that does not comprise a deuterium atom, that is, a phenyl group that has 5 hydrogen atoms.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, an indenyl group, an acenaphthylenyl group, a 2,3-dihydro-1H-indenyl group, a fused ring group thereof, and the like, but are not limited thereto.

In the present specification, a fluorenyl group may be substituted, and adjacent substituents may bond to each other to form a ring.

When the fluorenyl group is substituted, the following structural formulae and the like may be included, however, the structure is not limited thereto.

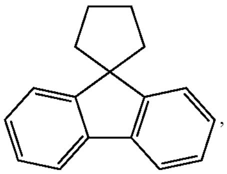
,
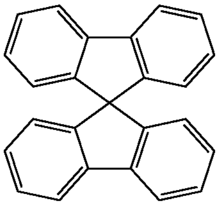
,

-continued

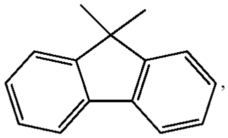
,
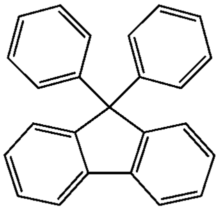
,

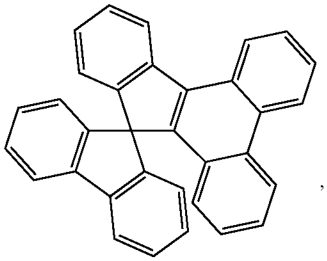
,

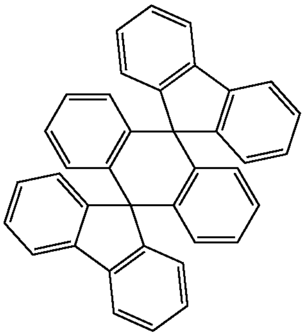

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]

carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido [1,2-a]imidazo[1,2-e]indolinyl group, a 5,11-dihydroindeno [1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, the phosphine oxide group is represented by —P(═O)$R_{101}R_{102}$, and $R_{101}$ and $R_{102}$ are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures illustrated as the cycloalkyl group, the cycloheteroalkyl group, the aryl group and the heteroaryl group described above may be used except for those that are not a monovalent group.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(═O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted, and R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group.

One embodiment of the present application provides a compound represented by Chemical Formula 1.

In one embodiment of the present application, Chemical Formula 1 may be represented by the following Chemical Formula [1-A] or [1-B].

[Chemical Formula 1-A]

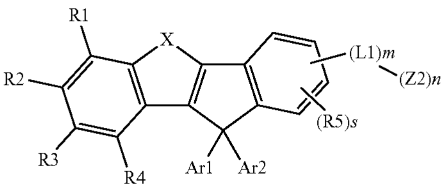

[Chemical Formula 1-B]

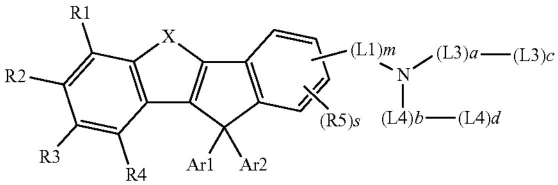

In Chemical Formulae 1-A and 1-B,

R1 to R5, X, Ar1, Ar2, L1, m, n and s have the same definitions as in Chemical Formula 1, Z2 is selected from the group consisting of hydrogen; deuterium; halogen; a cyano group; a substituted or unsubstituted C1 to C60 alkyl group; and a substituted or unsubstituted C2 to C60 heteroaryl group, L3 and L4 are the same as or different from each other, and each independently a direct bond; a substituted or unsubstituted C6 to C60 arylene group; or a substituted or unsubstituted C2 to C60 heteroarylene group, Z3 and Z4 are the same as or different from each other, and each independently selected from the group consisting of hydrogen; deuterium; halogen; a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group, a and b are an integer of 0 to 5, and c and d are an integer of 1 to 6.

In one embodiment of the present application, Chemical Formula 1-A may be represented by any one of the following Chemical Formulae 1-1-A to 1-4-A.

[Chemical Formula 1-1-A]

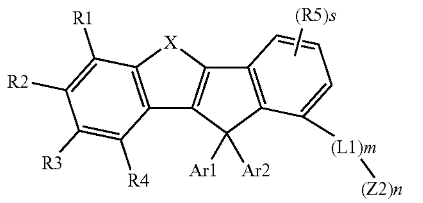

[Chemical Formula 1-2-A]

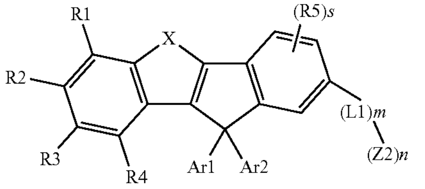

[Chemical Formula 1-3-A]

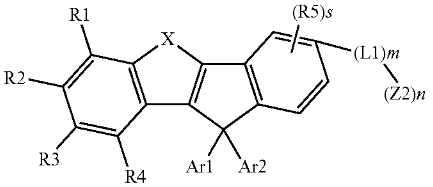

[Chemical Formula 1-4-A]

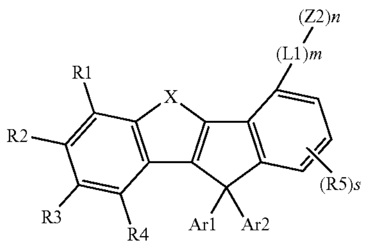

In Chemical Formulae 1-1-A to 1-4-A,

R1 to R5, X, Ar1, Ar2, L1, Z2, m, n and s have the same definitions as in Chemical Formula 1-A.

In one embodiment of the present application, Chemical Formula 1-B may be represented by any one of the following Chemical Formulae 1-1-B to 1-4-B.

[Chemical Formula 1-1-B]

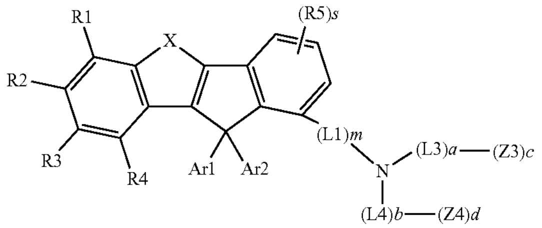

[Chemical Formula 1-2-B]

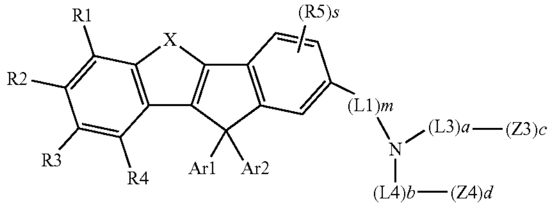

[Chemical Formula 1-3-B]

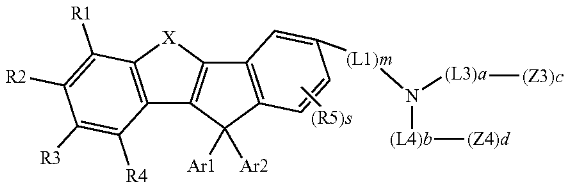

[Chemical Formula 1-4-B]

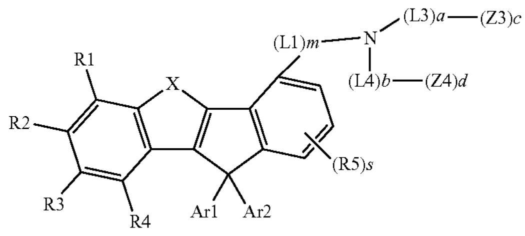

In Chemical Formulae 1-1-B to 1-4-B,

R1 to R5, X, Ar1, Ar2, L1, L3, L4, Z3, Z4, m, a, b, c, d and s have the same definitions as in Chemical Formula 1-B.

In one embodiment of the present application, X may be O.

In one embodiment of the present application, X may be S.

In one embodiment of the present application, R1 to R5 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; —SiRR'R" and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R1 to R5 are the same as or different from each other, and may be each independently selected from the group consisting of hydrogen; a substituted or unsubstituted C6 to C60 aryl group; a substituted or unsubstituted C2 to C60 heteroaryl group; —P(═O)RR'; —SiRR'R" and —NRR'.

In another embodiment, R1 to R5 may be hydrogen.

In one embodiment of the present application, Ar1 and Ar2 are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, Ar1 and Ar2 are the same as or different from each other, and may be each independently a substituted or unsubstituted C1 to C40 alkyl group; a substituted or unsubstituted C6 to C40 aryl group; or a substituted or unsubstituted C2 to C40 heteroaryl group.

In another embodiment, Ar1 and Ar2 are the same as or different from each other, and may be each independently a C1 to C40 alkyl group; a C6 to C40 aryl group; or a C2 to C40 heteroaryl group.

In another embodiment, Ar1 and Ar2 are the same as or different from each other, and may be each independently a C1 to C40 alkyl group; or a C6 to C40 aryl group.

In another embodiment, Ar1 and Ar2 are the same as or different from each other, and may be each independently a C1 to C20 linear alkyl group; or a C6 to C20 monocyclic aryl group.

In another embodiment, Ar1 and Ar2 are the same as or different from each other, and may be each independently a methyl group; or a phenyl group.

In one embodiment of the present application, Ar1 and Ar2 may be the same as each other.

In one embodiment of the present application, Ar1 and Ar2 may be different from each other.

In one embodiment of the present application, L1 may be a substituted or unsubstituted C6 to C60 arylene group; or a substituted or unsubstituted C2 to C60 heteroarylene group.

In another embodiment, L1 may be a substituted or unsubstituted C6 to C40 arylene group; or a substituted or unsubstituted C2 to C40 heteroarylene group.

In another embodiment, L1 may be a substituted or unsubstituted C6 to C40 monocyclic or polycyclic arylene group; or a substituted or unsubstituted C2 to C40 monocyclic or polycyclic heteroarylene group.

In another embodiment, L1 may be a C6 to C40 monocyclic or polycyclic arylene group; or a C2 to C40 monocyclic or polycyclic heteroarylene group.

In another embodiment, L1 may be a phenylene group; a biphenylene group; a naphthalene group; a triphenylene group; a divalent dibenzofuran group; a divalent dibenzothiophene group; or a divalent naphtho[2,1-b]benzofuran group.

In one embodiment of the present application, L1 may be any one of the following structural formulae.

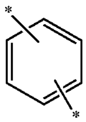
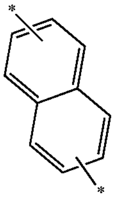
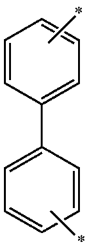
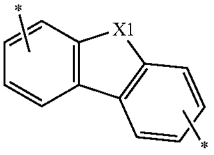

-continued

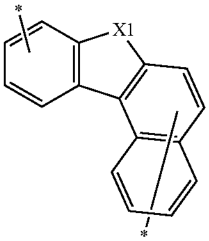
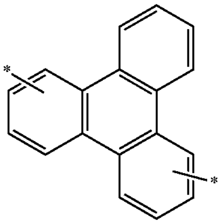

In the structural formulae,

X1 is O; or S.

In another embodiment, L1 may be any one of the following structural formulae.

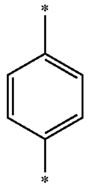
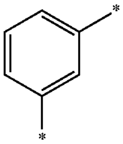
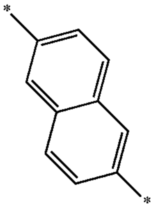
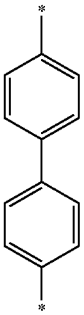
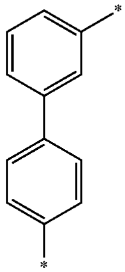
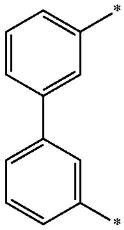
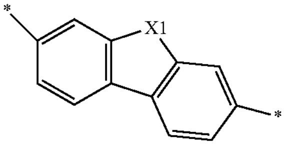
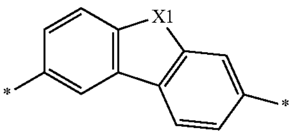
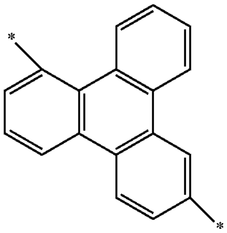
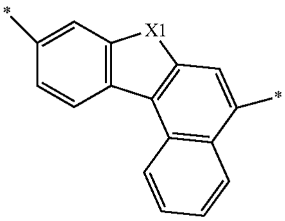

-continued

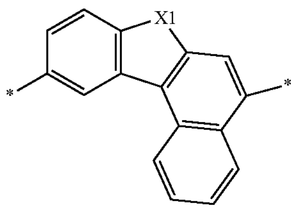

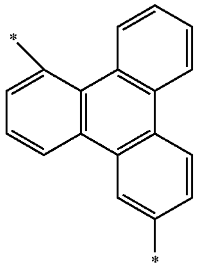

In the structural formulae,

X1 is O; or S.

In one embodiment of the present application, Z2 may be selected from the group consisting of hydrogen; deuterium; halogen; a cyano group; a substituted or unsubstituted C1 to C60 alkyl group; and a substituted or unsubstituted C2 to C60 heteroaryl group.

In another embodiment, Z2 may be selected from the group consisting of hydrogen; deuterium; halogen; a cyano group; a substituted or unsubstituted C1 to C40 alkyl group; and a substituted or unsubstituted C2 to C40 heteroaryl group.

In another embodiment, Z2 may be selected from the group consisting of a C1 to C40 alkyl group; and a C2 to C40 heteroaryl group.

In one embodiment of the present application, L3 and L4 are the same as or different from each other, and may be each independently a direct bond; a substituted or unsubstituted C6 to C60 arylene group; or a substituted or unsubstituted C2 to C60 heteroarylene group.

In another embodiment, L3 and L4 are the same as or different from each other, and may be each independently a direct bond; a substituted or unsubstituted C6 to C40 arylene group; or a substituted or unsubstituted C2 to C40 heteroarylene group.

In another embodiment, L3 and L4 are the same as or different from each other, and may be each independently a direct bond; or a C6 to C40 arylene group.

In another embodiment, L3 and L4 are the same as or different from each other, and may be each independently a direct bond; or a C6 to C40 monocyclic or polycyclic arylene group.

In another embodiment, L3 and L4 are the same as or different from each other, and may be each independently a direct bond; a C6 to C10 monocyclic arylene group; or a C10 to C40 polycyclic arylene group.

In another embodiment, L3 and L4 are the same as or different from each other, and may be each independently a direct bond; a phenylene group; or a biphenylene group.

In one embodiment of the present application, Z3 and Z4 are the same as or different from each other, and may be each independently selected from the group consisting of hydrogen; deuterium; halogen; a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group.

In another embodiment, Z3 and Z4 are the same as or different from each other, and may be each independently selected from the group consisting of a substituted or unsubstituted C1 to C60 alkyl group; a substituted or unsubstituted C6 to C60 aryl group; a substituted or unsubstituted C2 to C60 heteroaryl group; and a substituted or unsubstituted amine group.

In another embodiment, Z3 and Z4 are the same as or different from each other, and may be each independently selected from the group consisting of a substituted or unsubstituted C1 to C40 alkyl group; a substituted or unsubstituted C6 to C40 aryl group; a substituted or unsubstituted C2 to C40 heteroaryl group; and a substituted or unsubstituted amine group.

In another embodiment, Z3 and Z4 are the same as or different from each other, and may be each independently selected from the group consisting of a substituted or unsubstituted C1 to C40 alkyl group; a substituted or unsubstituted C2 to C40 heteroaryl group; and a substituted or unsubstituted C6 to C40 aryl group.

In another embodiment, Z3 and Z4 are the same as or different from each other, and may be each independently selected from the group consisting of a C1 to C40 alkyl group; a C2 to C40 heteroaryl group; and a C6 to C40 aryl group unsubstituted or substituted with a C1 to C40 alkyl group or a C6 to C40 aryl group.

In another embodiment, Z3 and Z4 are the same as or different from each other, and may be each independently a phenyl group; a biphenyl group; a dimethylfluorenyl group; a diphenylfluorenyl group; a triphenylenyl group; a spirobifluorenyl group; a dibenzofuran group; a dibenzothiophene group; or a methyl group.

In one embodiment of the present application, R, R' and R" are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C60 monocyclic or polycyclic aryl group.

In another embodiment, R, R' and R" are the same as or different from each other, and may be each independently a substituted or unsubstituted C6 to C40 monocyclic aryl group.

In another embodiment, R, R' and R" are the same as or different from each other, and may be each independently a C6 to C20 monocyclic aryl group.

In another embodiment, R, R' and R" may be a phenyl group.

According to one embodiment of the present application, Chemical Formula 1 may be represented by any one of the following compounds, but is not limited thereto.

-continued
1
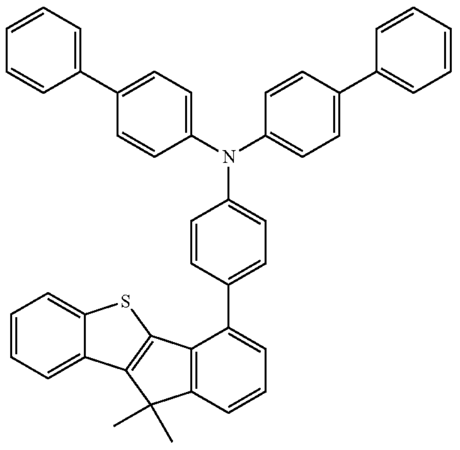
2
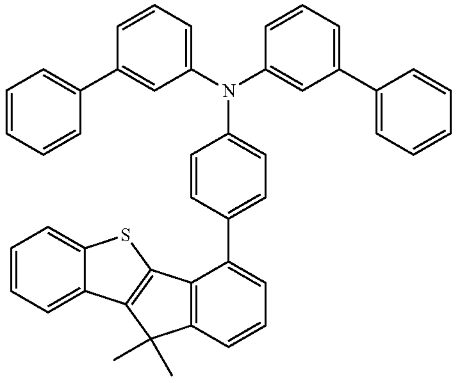
3
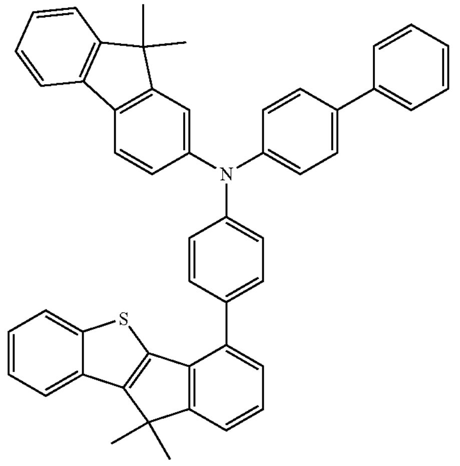
4
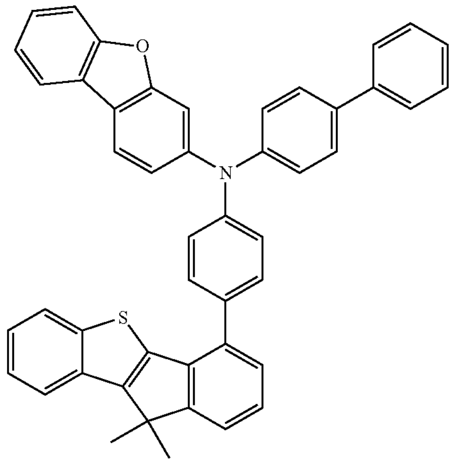
5
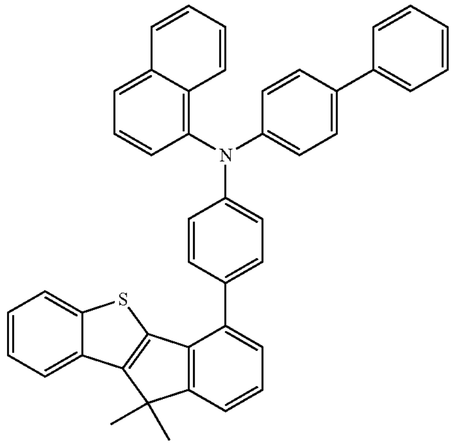
6
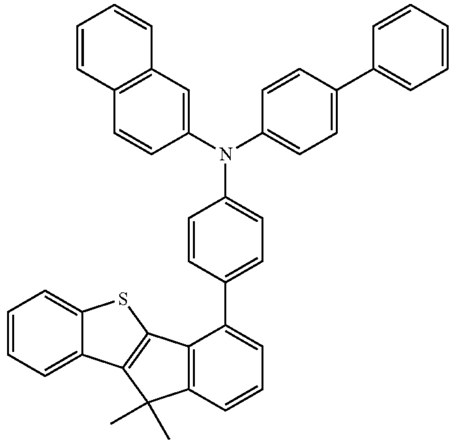

-continued
7
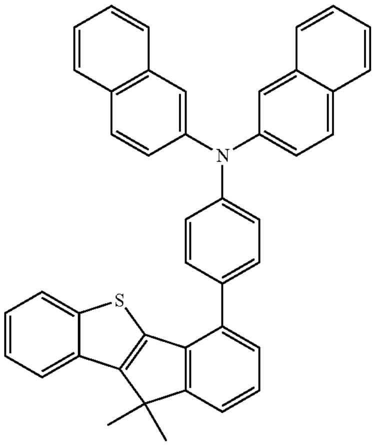
8
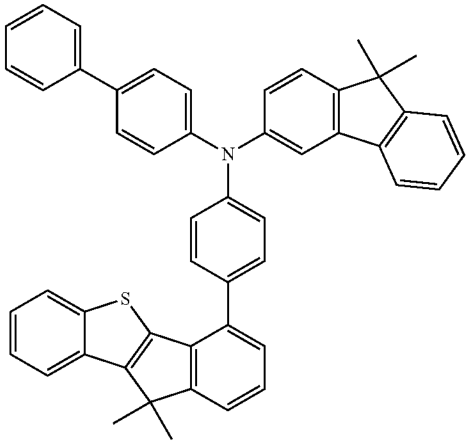
9
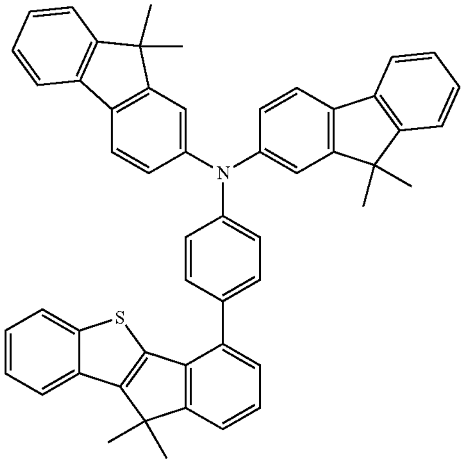
-continued
10
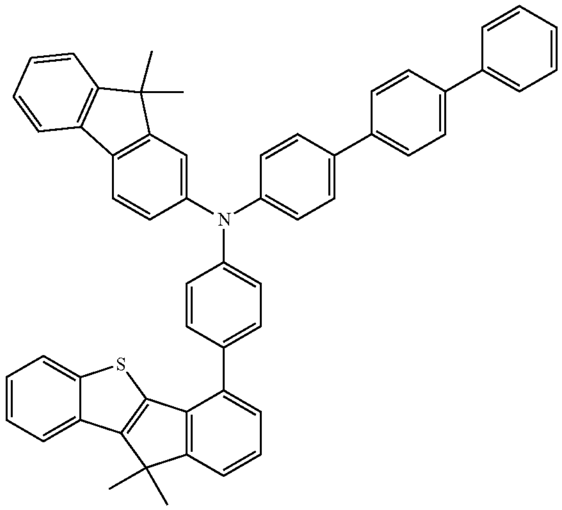
11
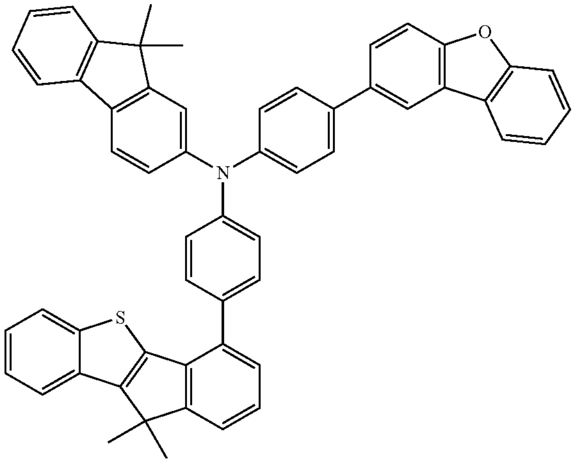
12
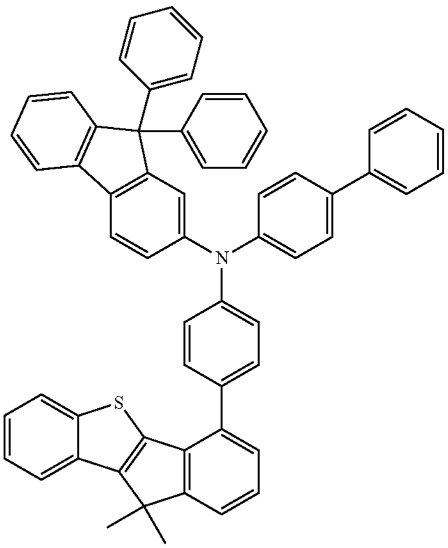

-continued
13
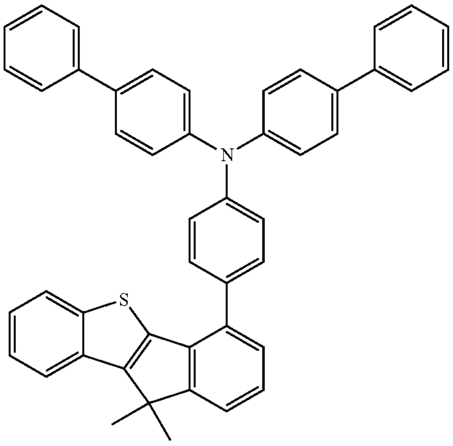
14
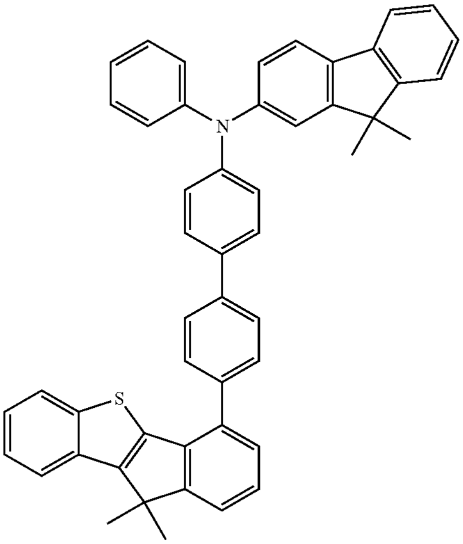
15
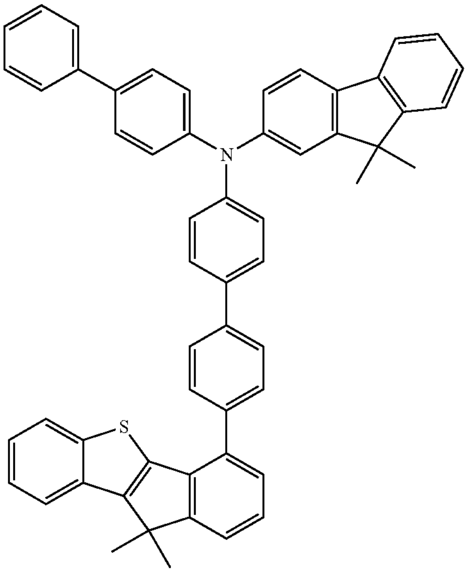
-continued
16
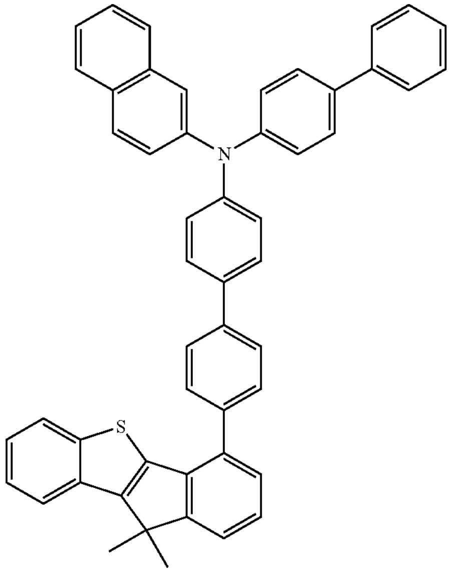
17
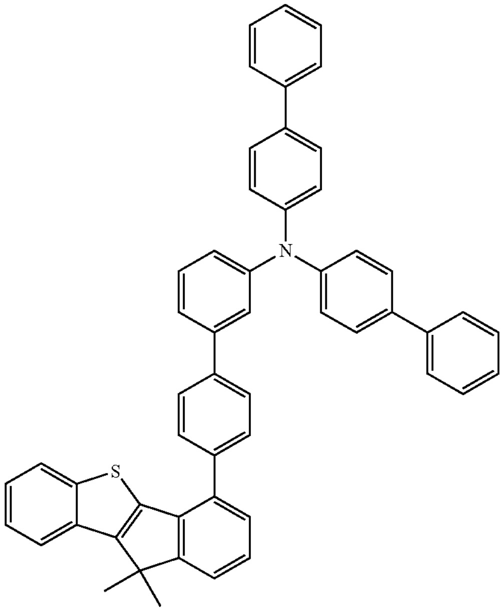

-continued
18
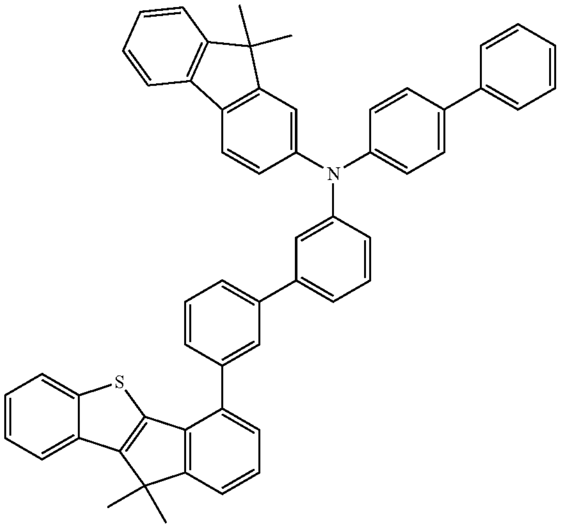
19
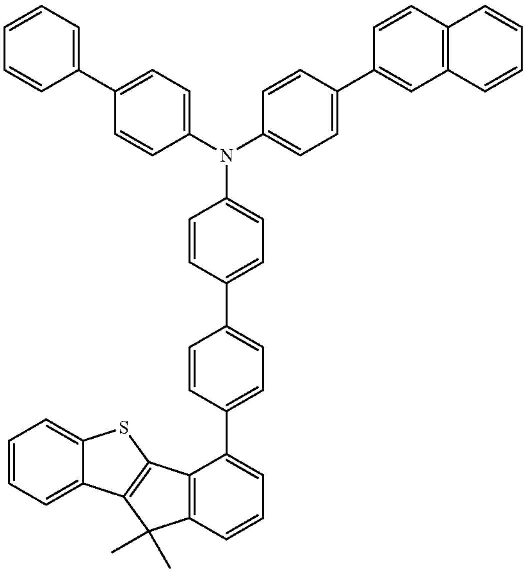
20
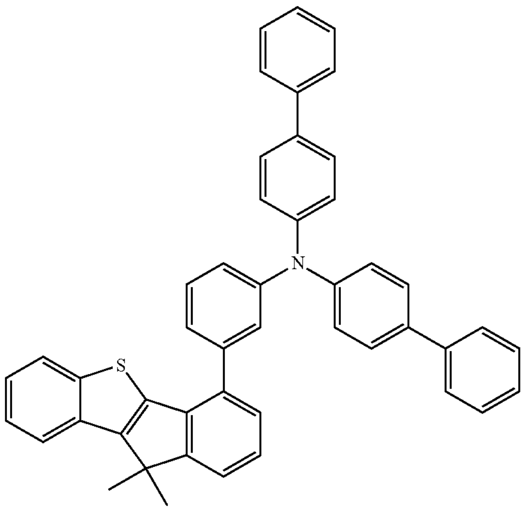
-continued
21
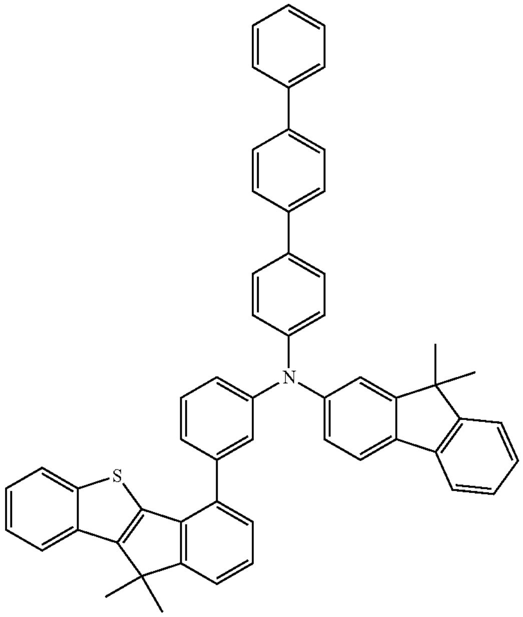
22
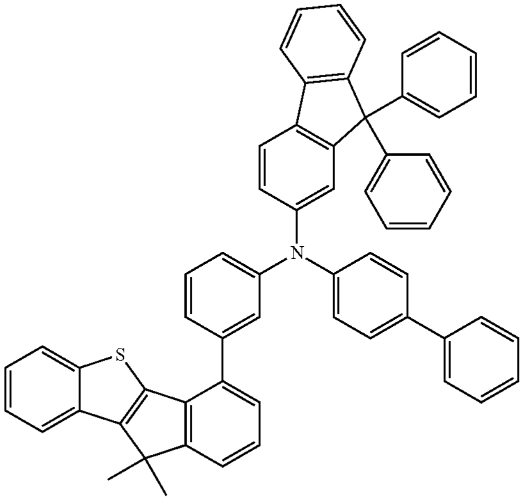
23
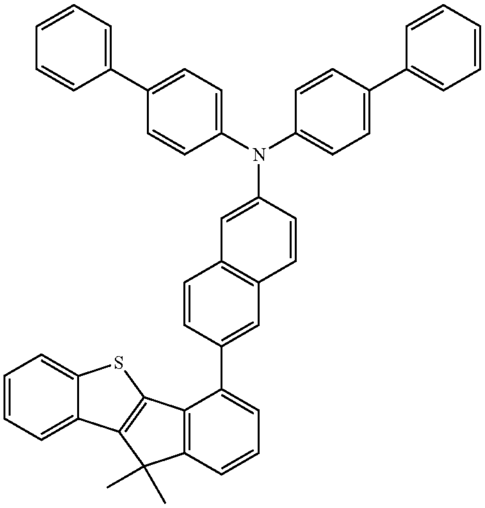

24
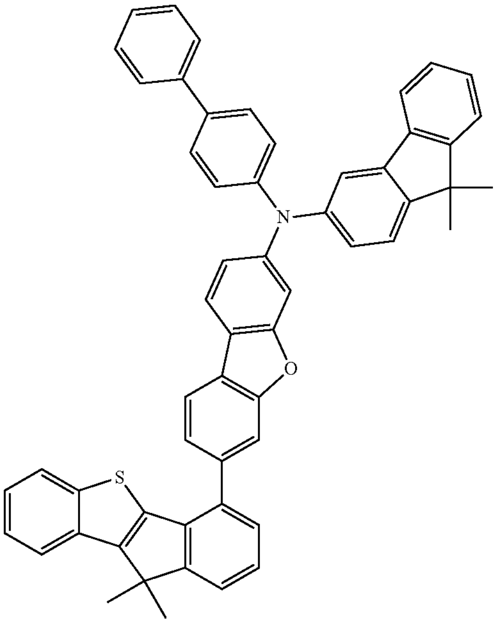
25
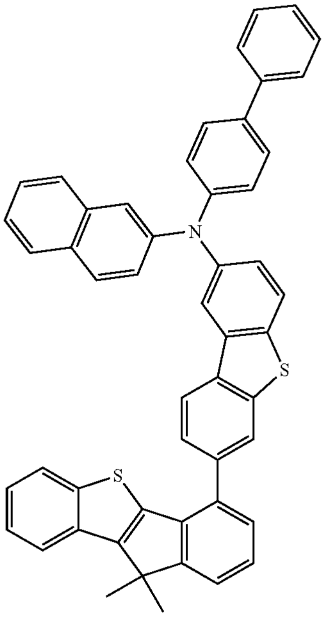
26
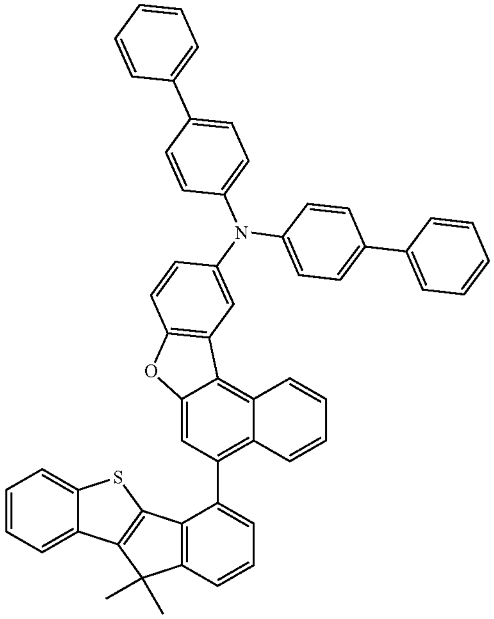
27
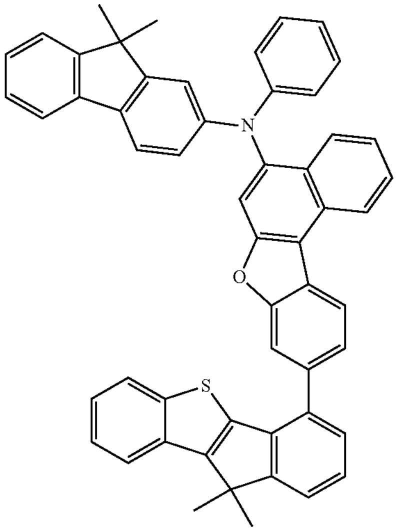
28
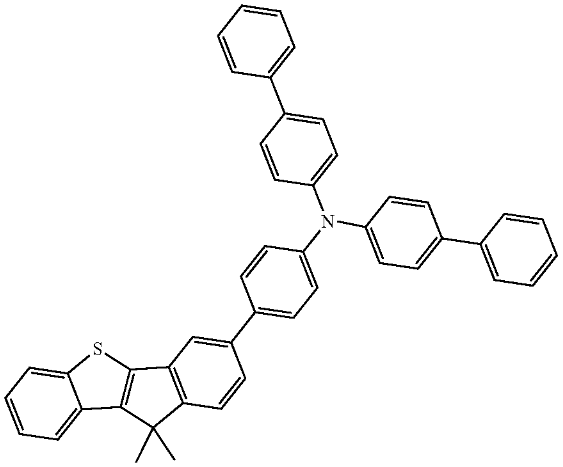

-continued
29
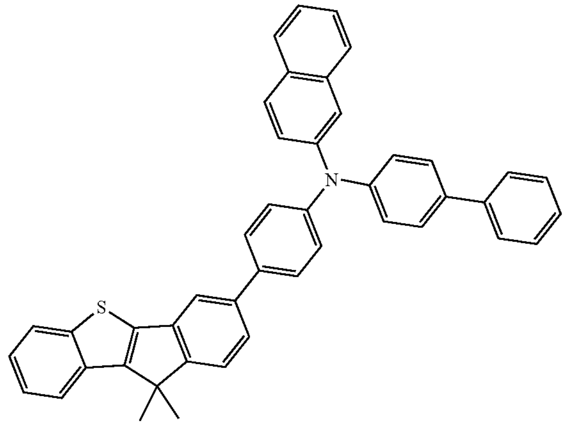
30
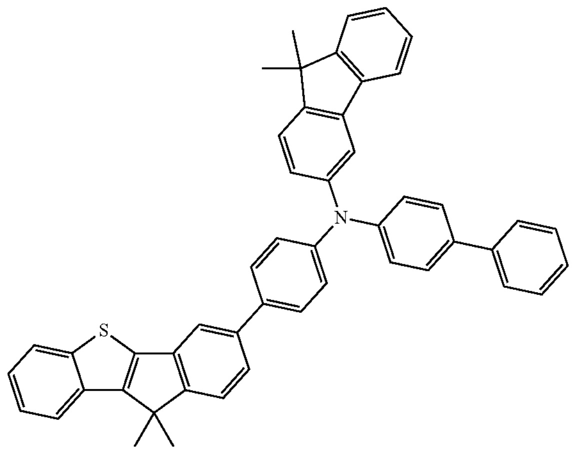
31
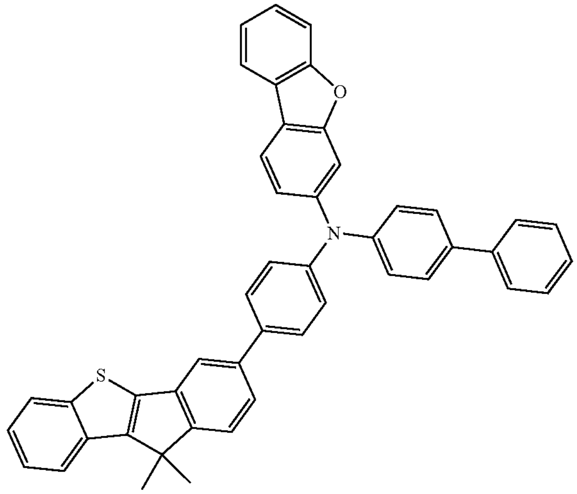
-continued
32
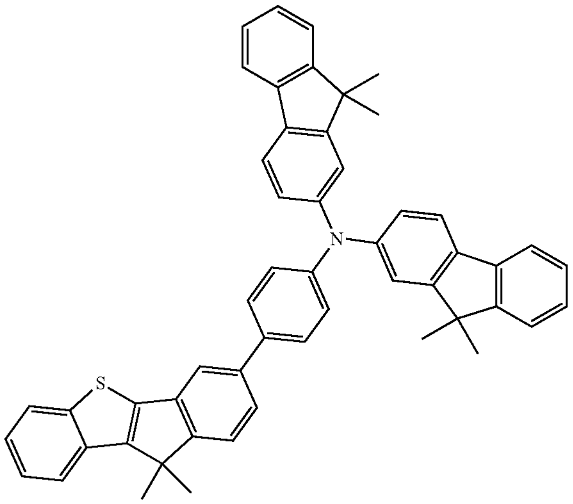
33
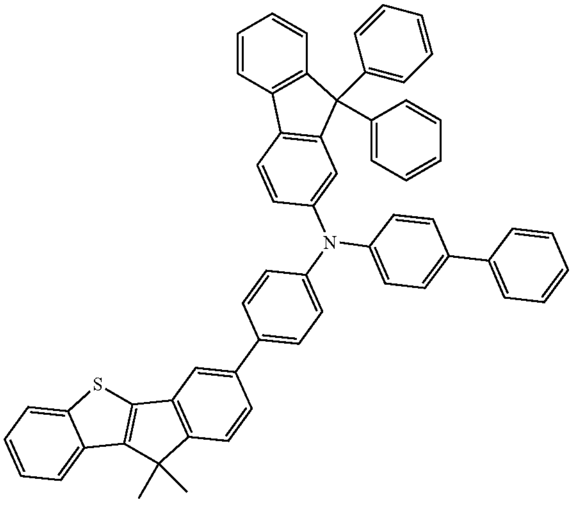
34
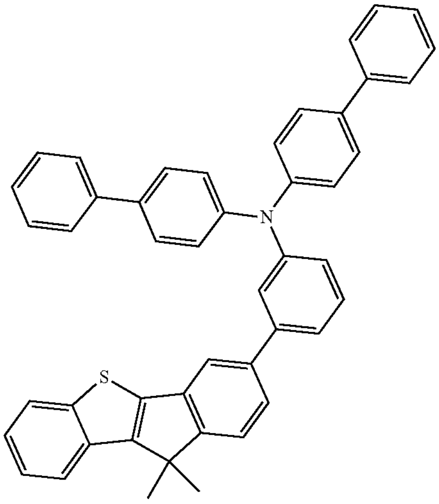

-continued
35
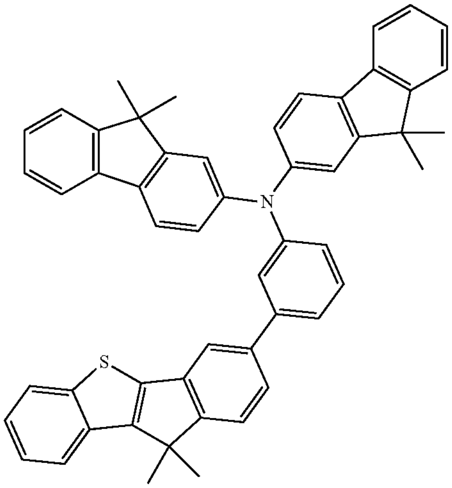
36
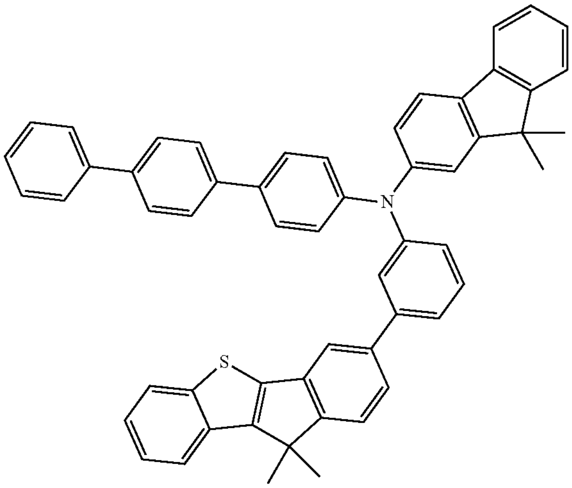
37
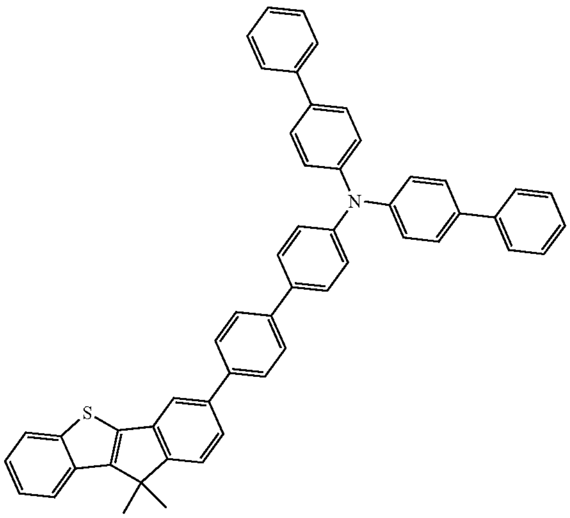
-continued
38
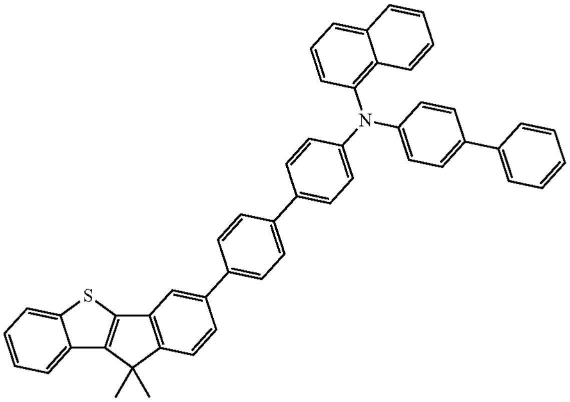
39
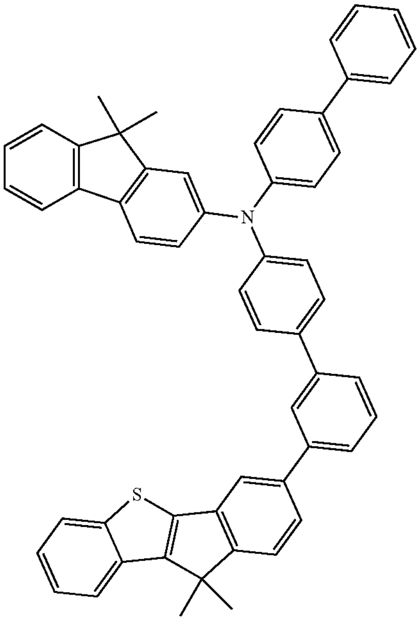
40
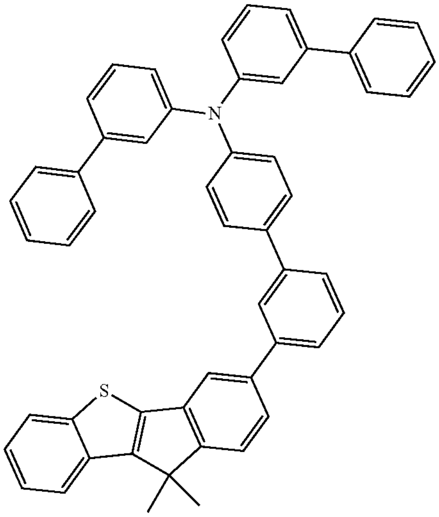

-continued
41
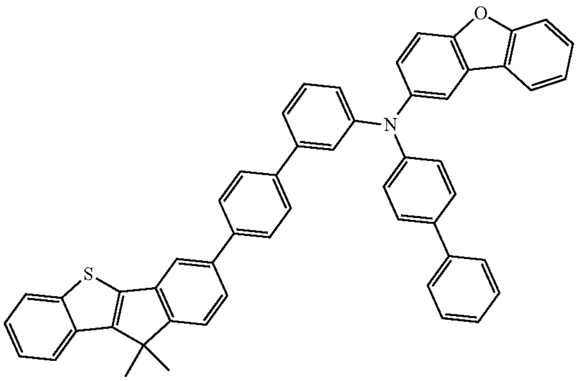
42
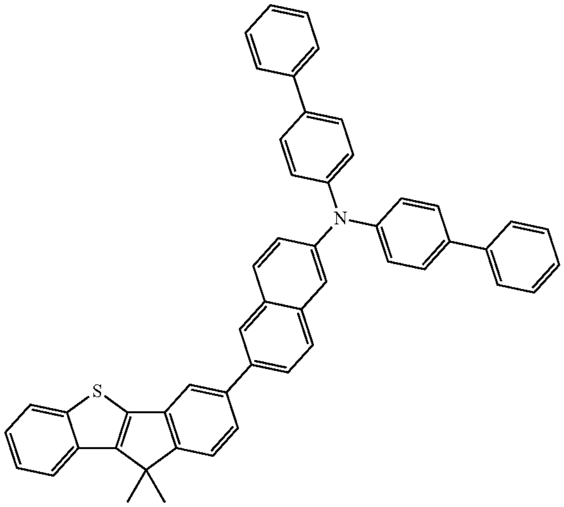
43
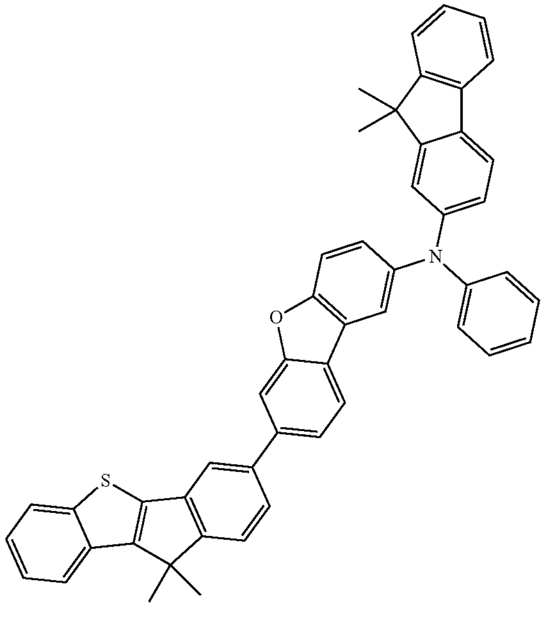
-continued
44
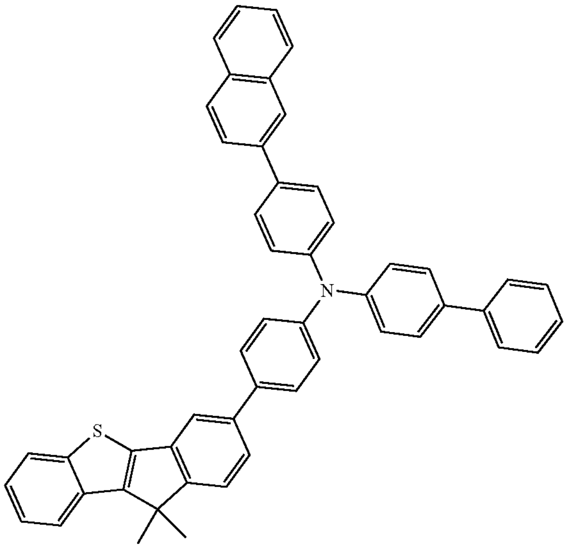
45
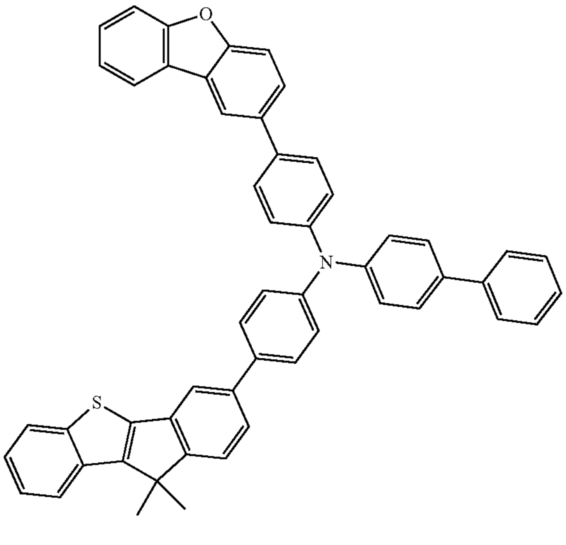

-continued
46
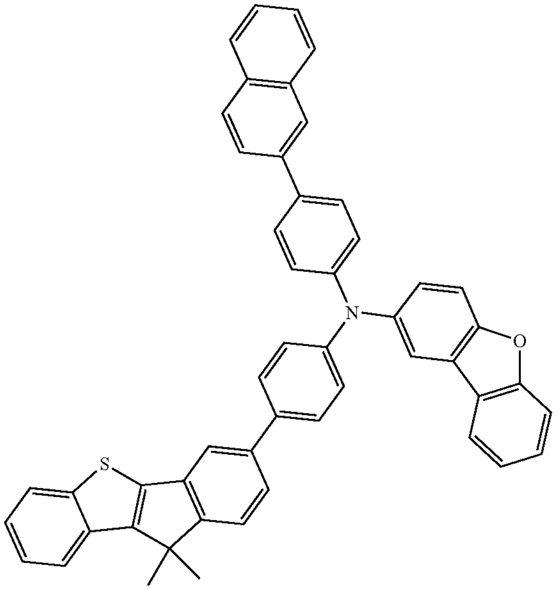
47
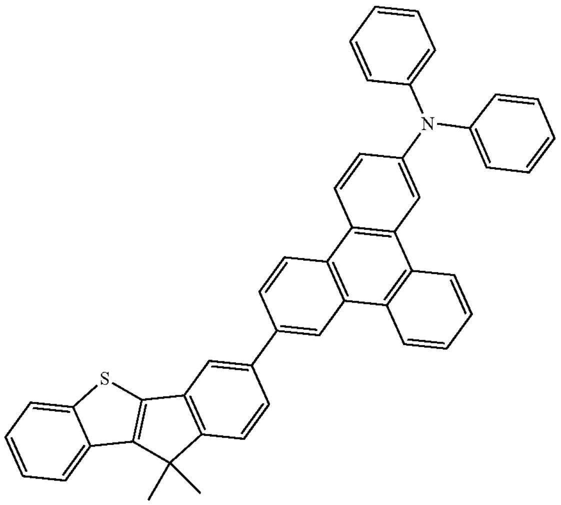
48
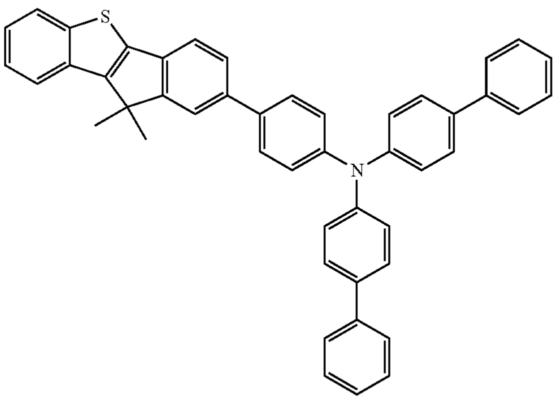
-continued
49
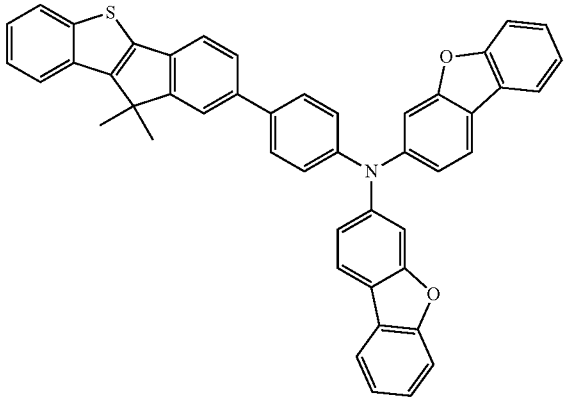
50
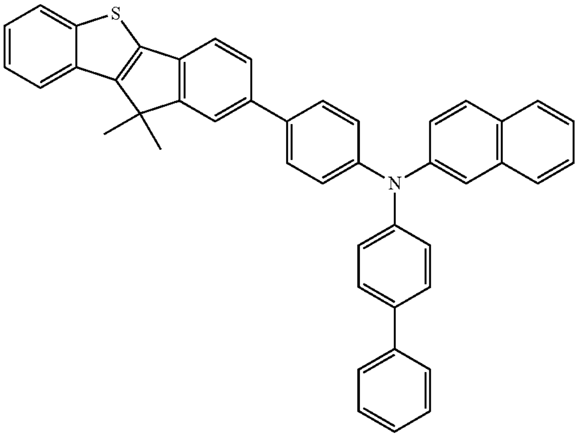
51
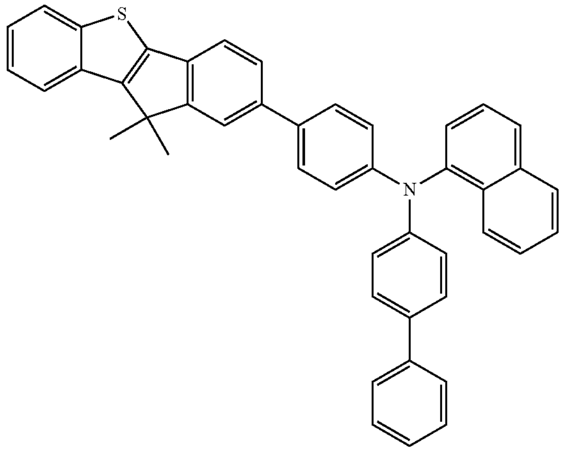

-continued
52
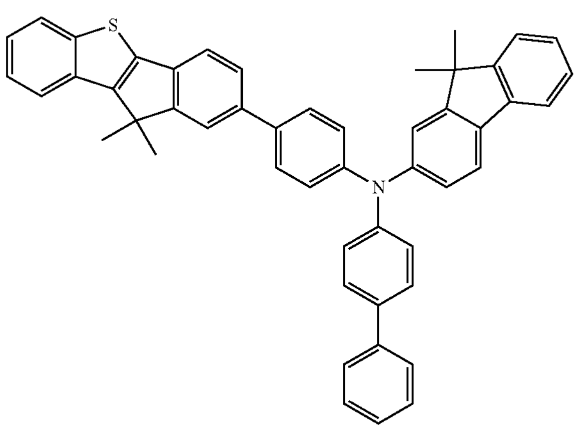
53
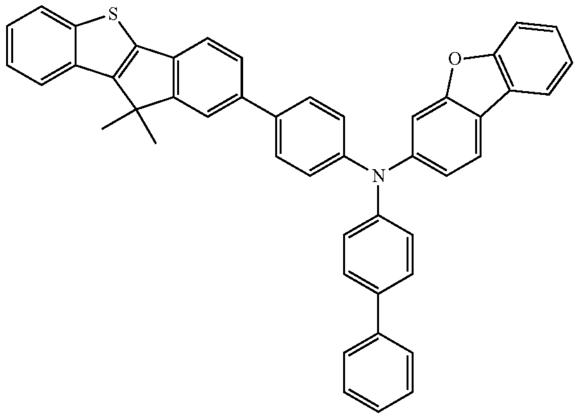
54
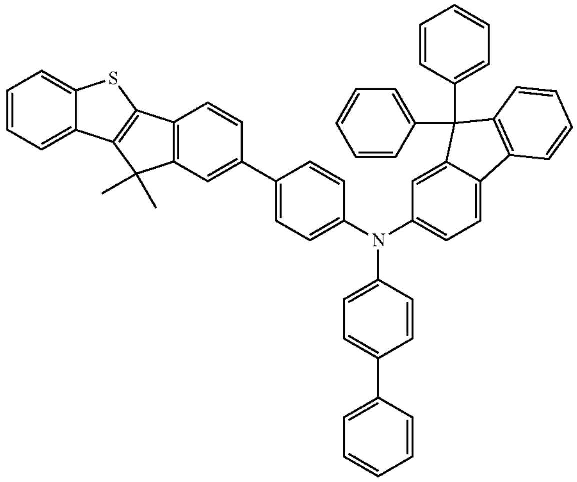
-continued
55
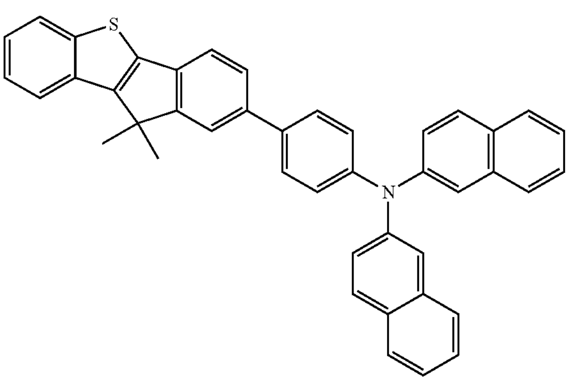
56
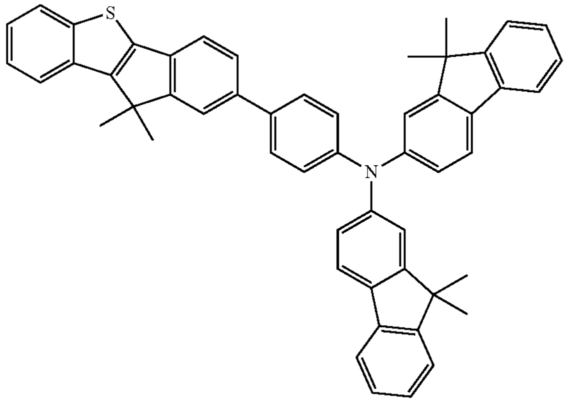
57
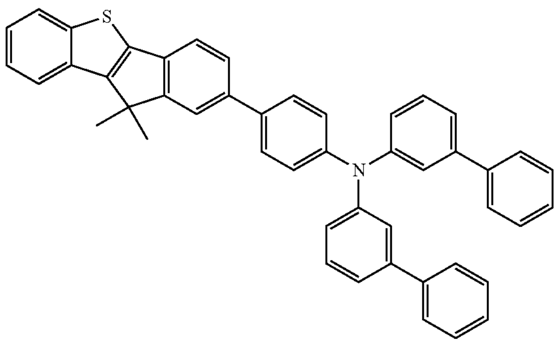
58
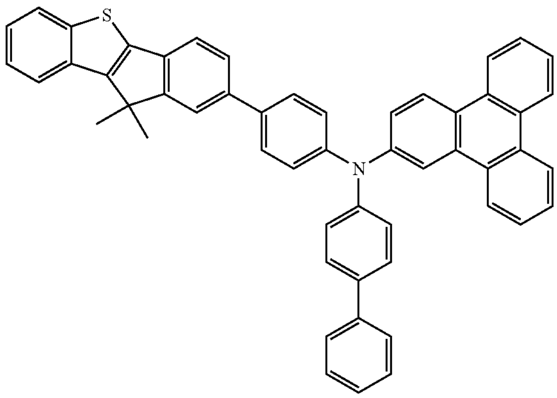

-continued
59
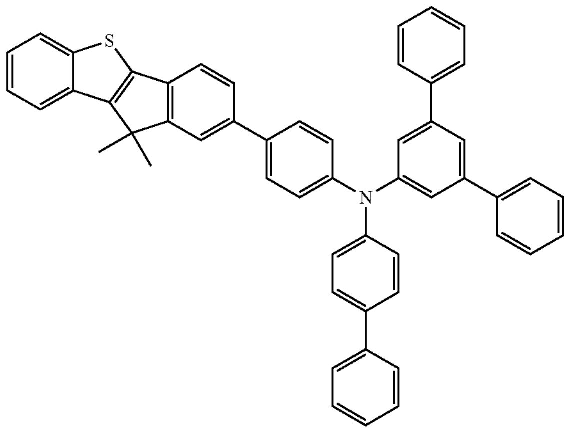
60
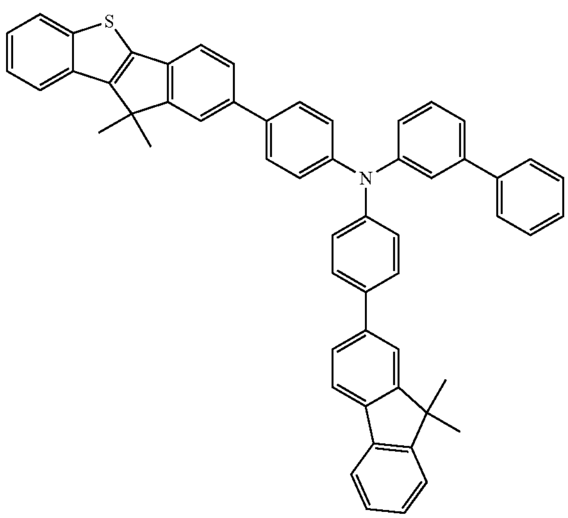
61
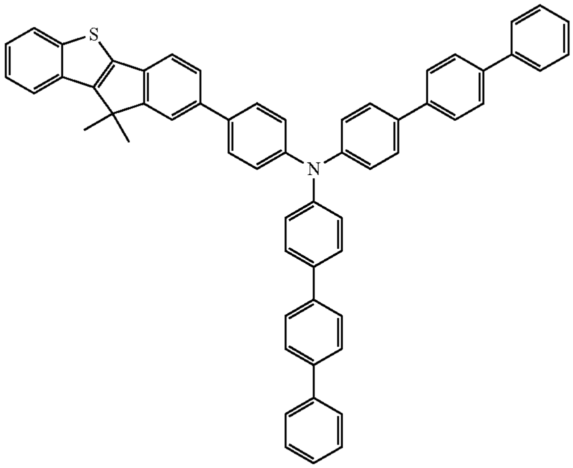
-continued
62
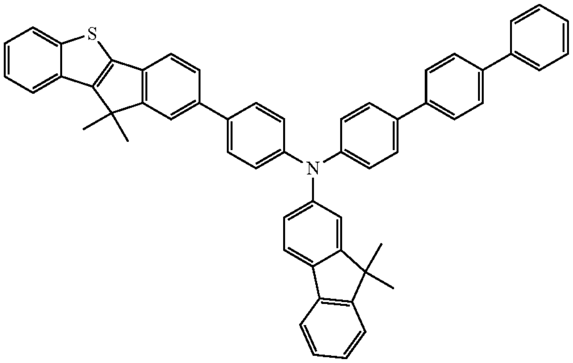
63
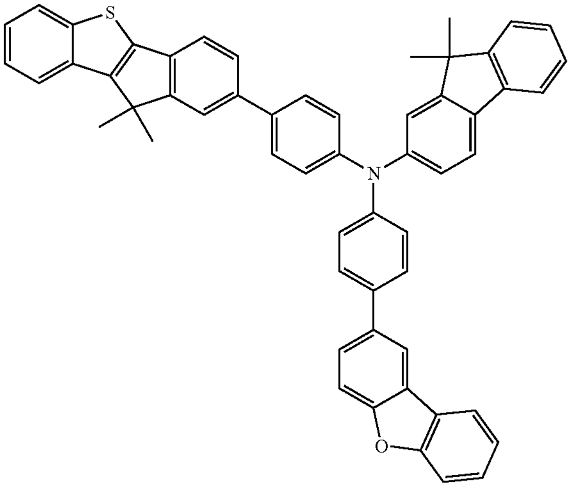
64
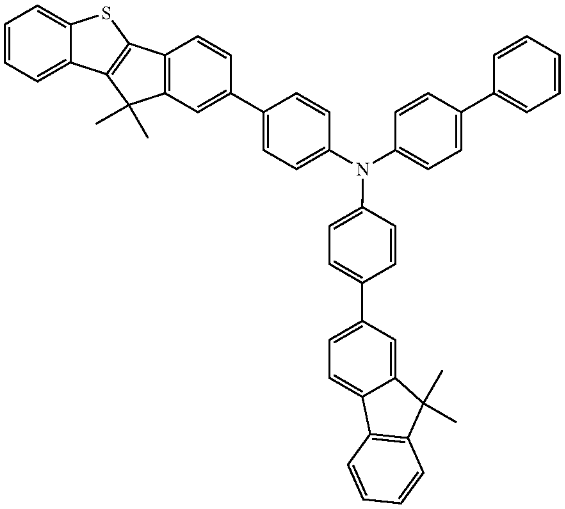

-continued
65
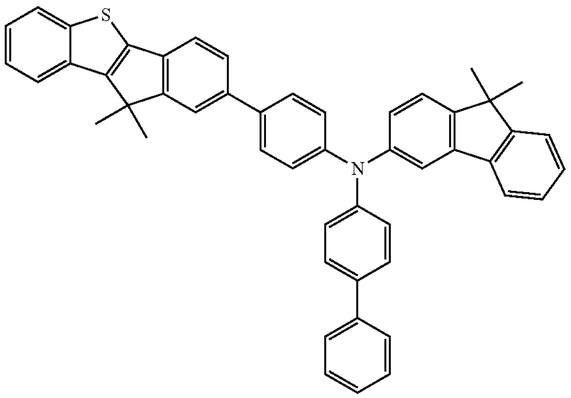
66
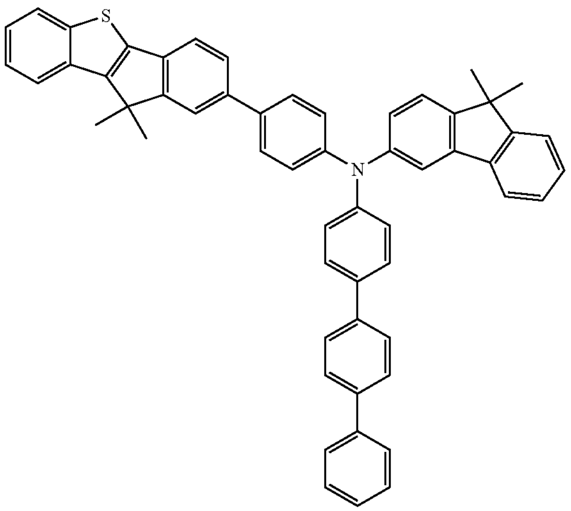
67
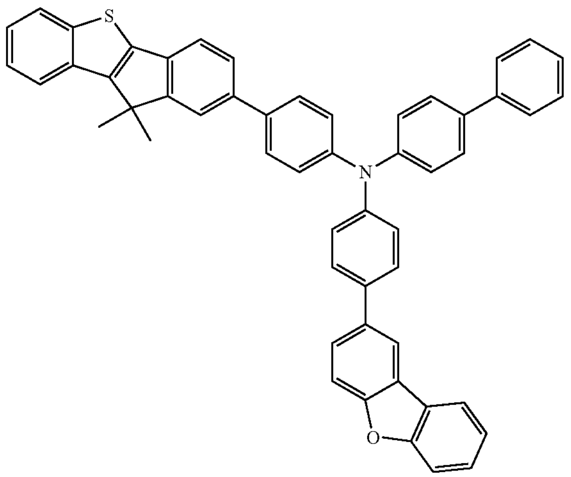
-continued
68
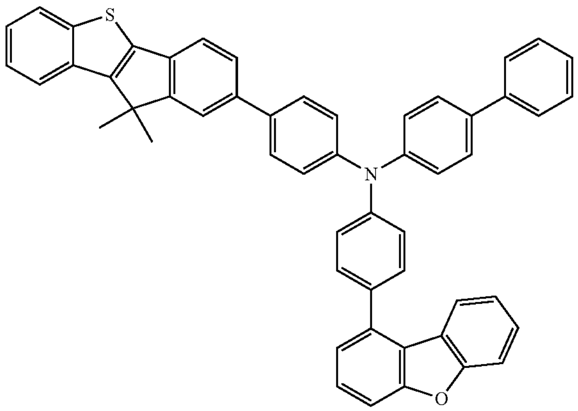
69
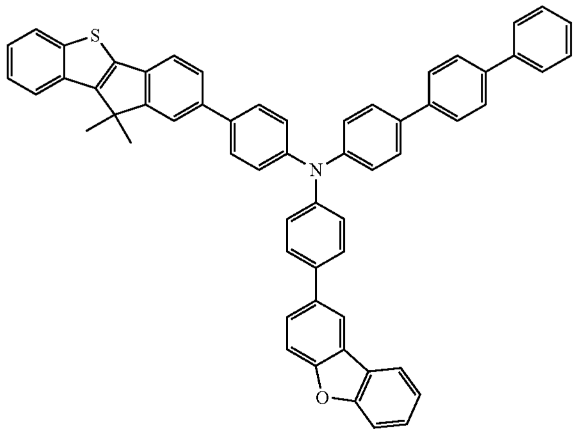
70
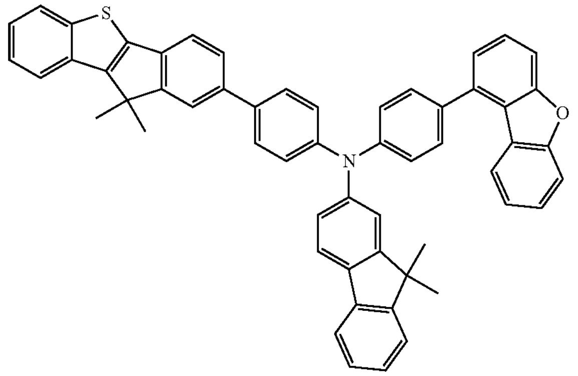

-continued
71
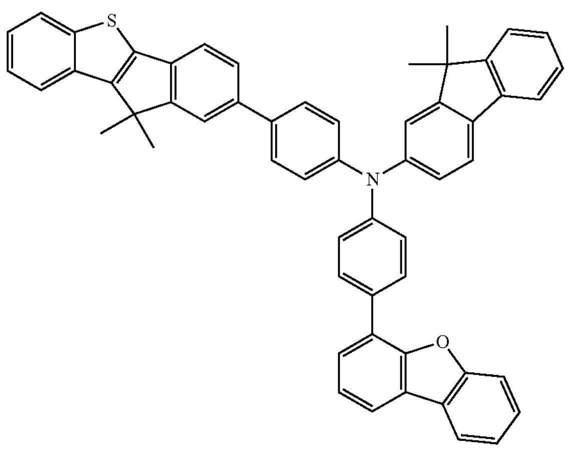
72
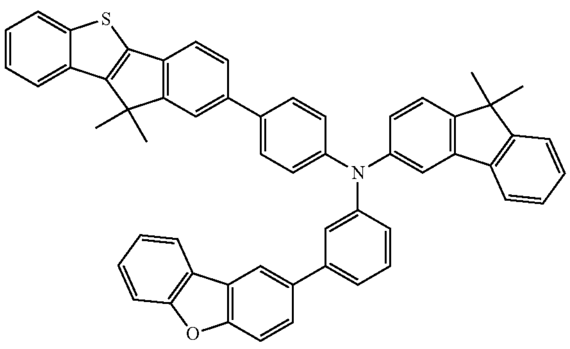
73
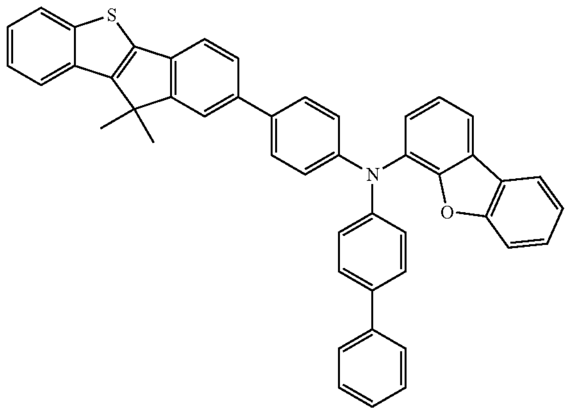
-continued
74
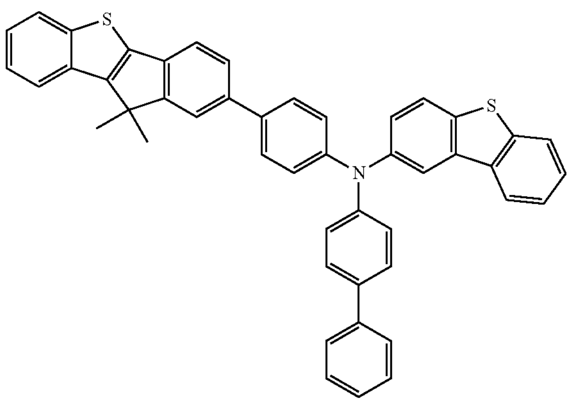
75
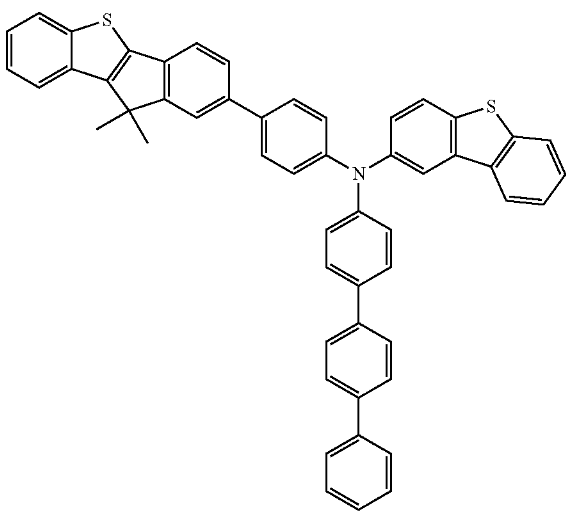
76
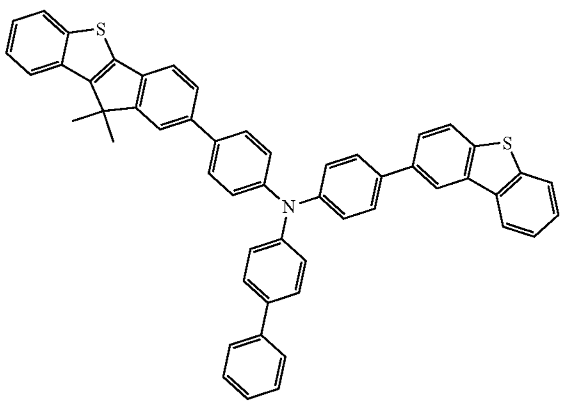

-continued
77
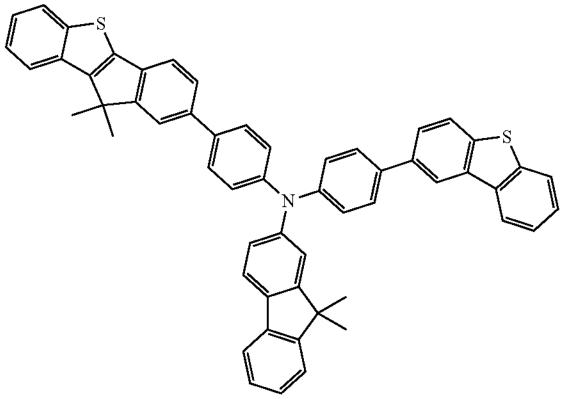
78
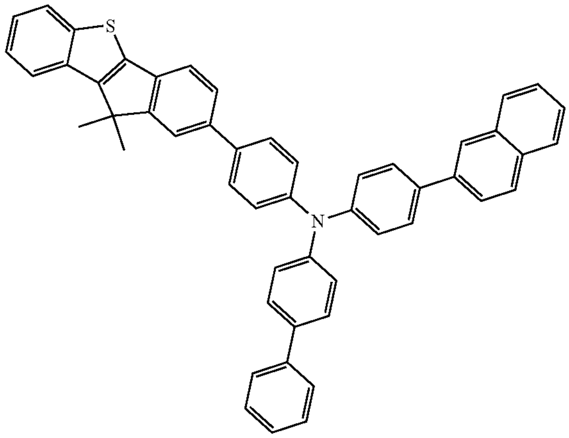
79
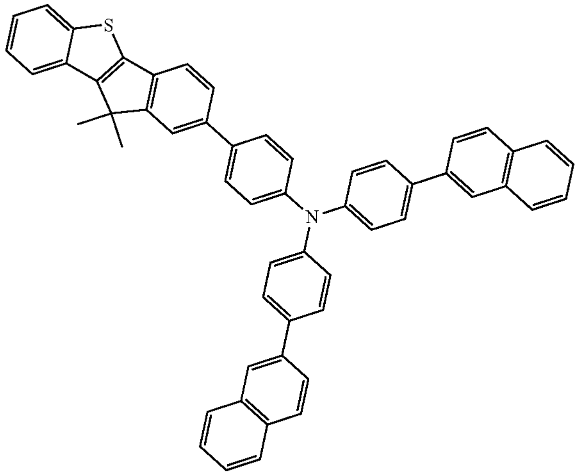
-continued
80
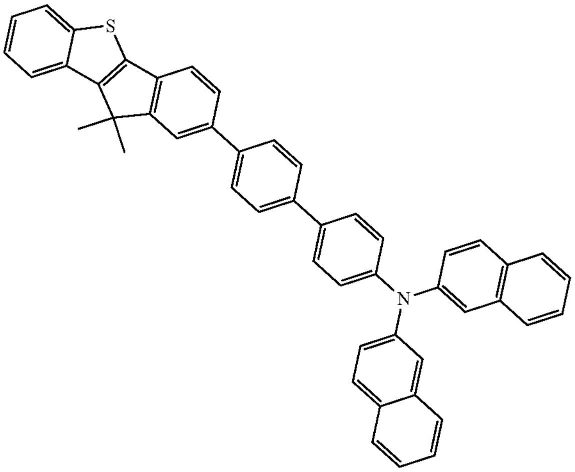
81
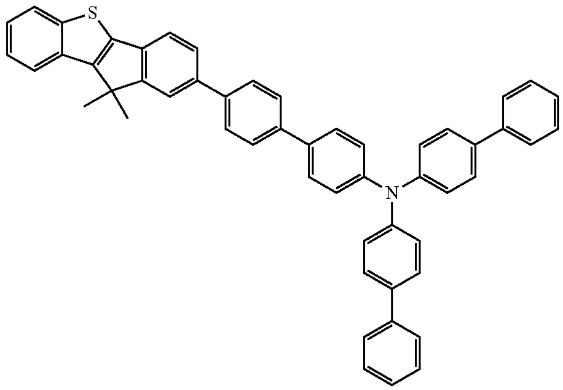
82
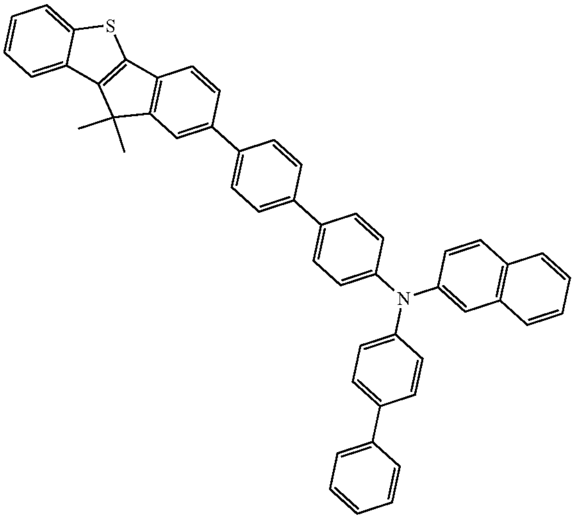

-continued
83
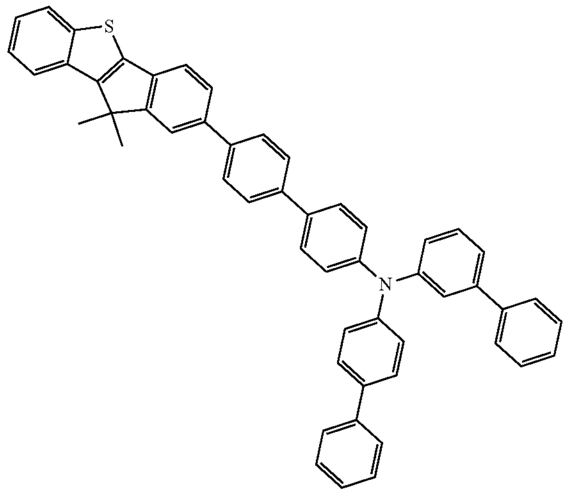
84
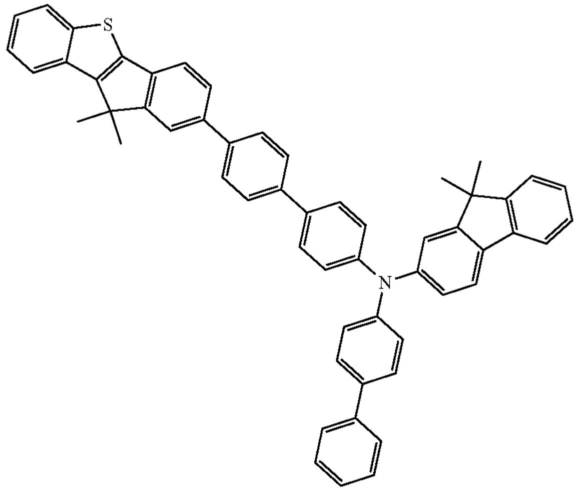
85
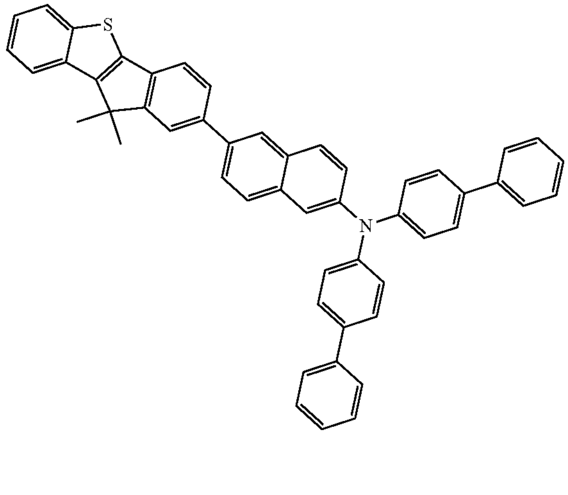
-continued
86
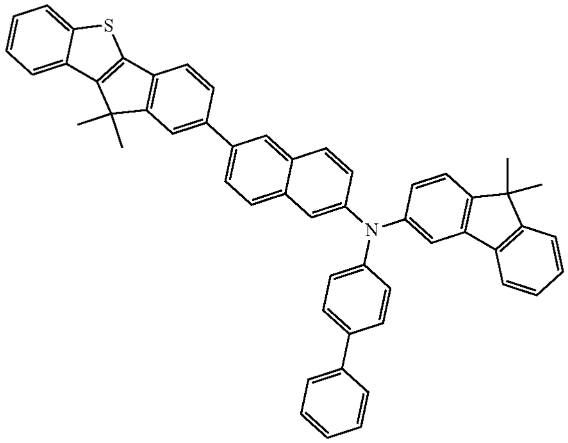
87
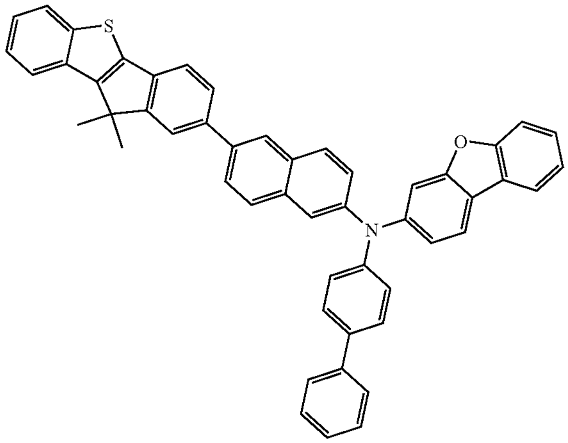
88
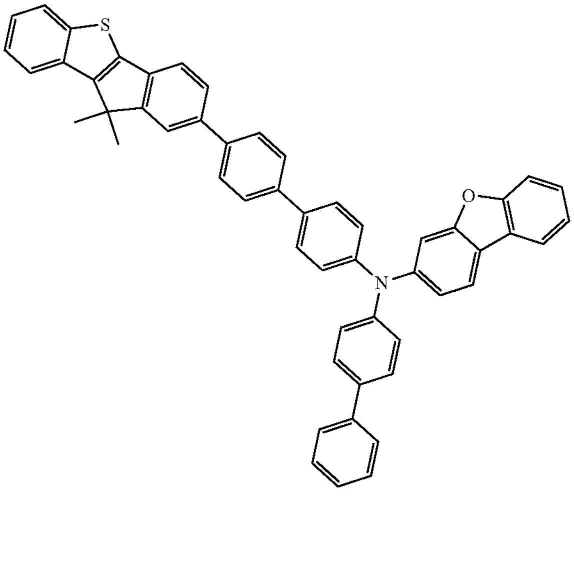

-continued
89
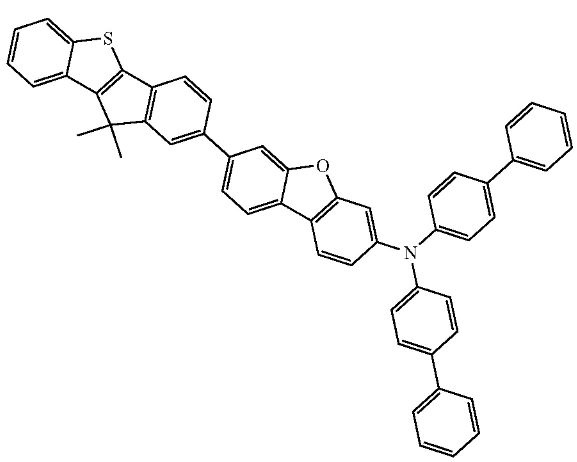
90
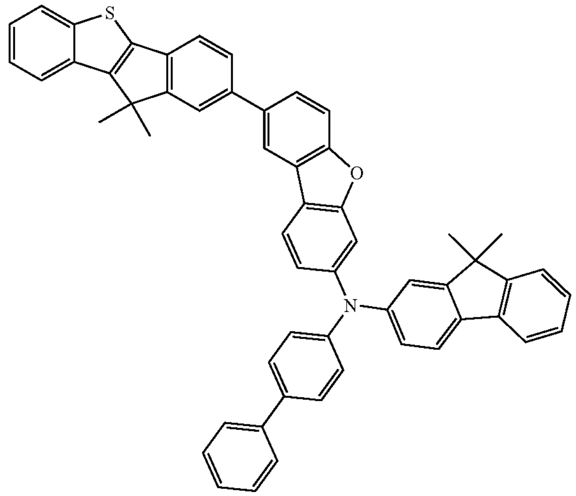
91
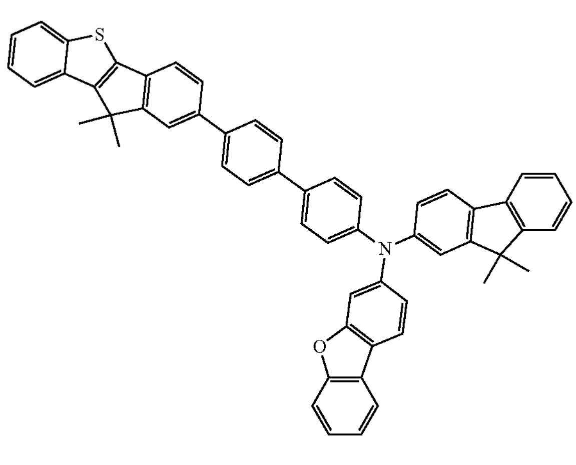
-continued
92
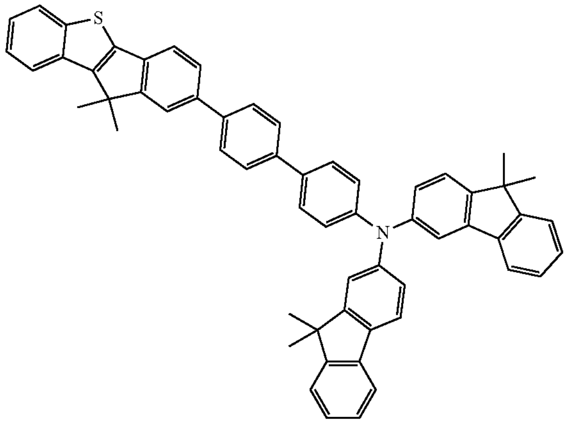
93
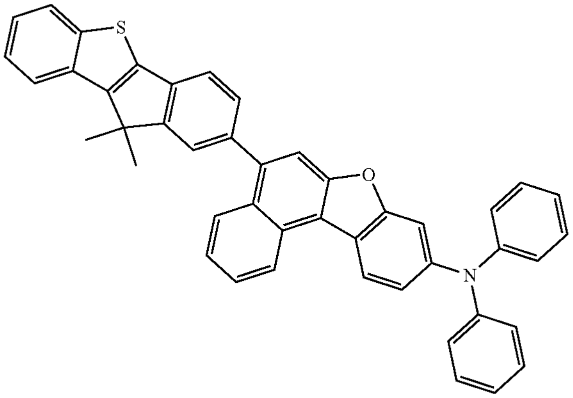
94
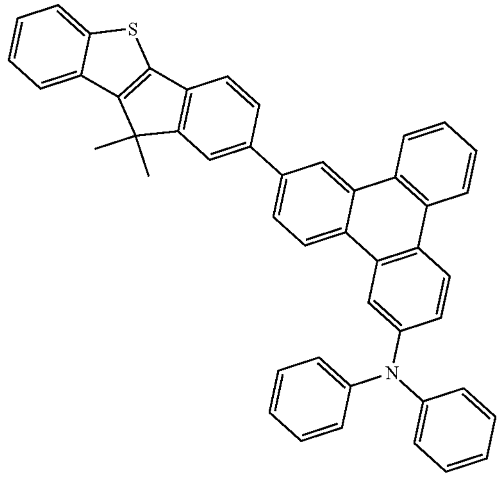

-continued
95
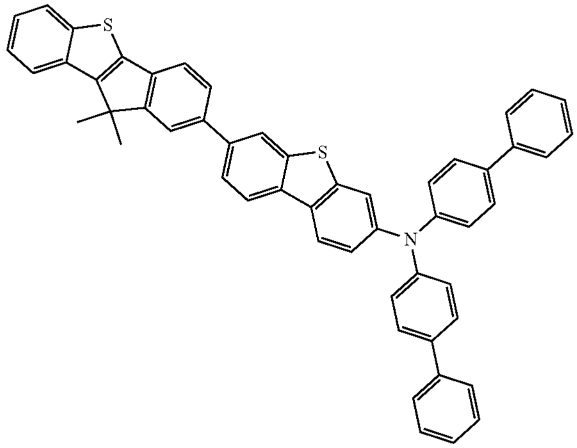
96
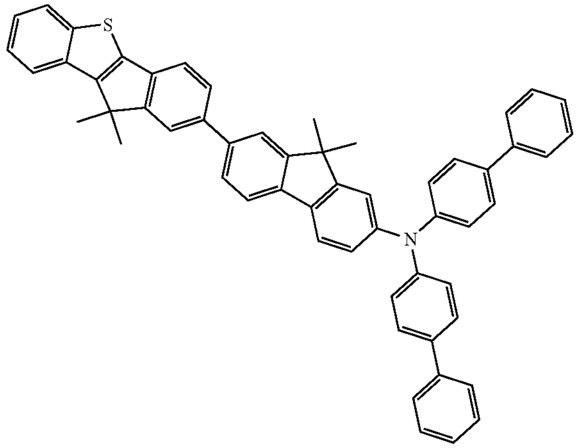
97
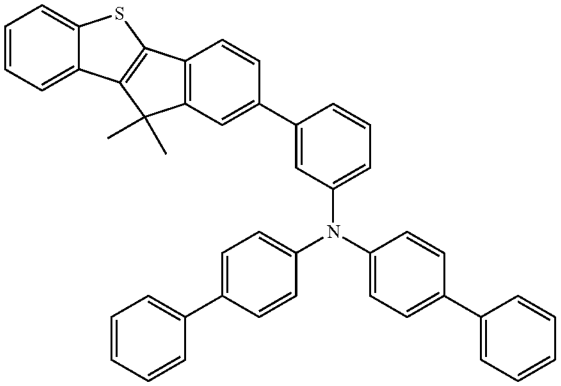
-continued
98
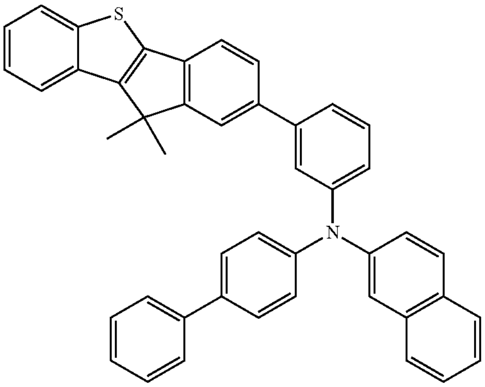
99
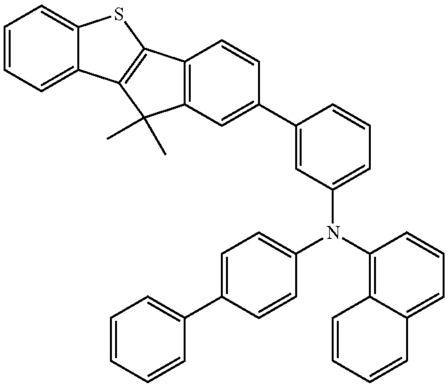
100
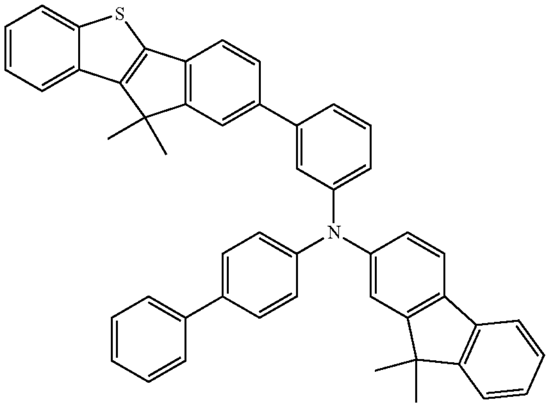
101
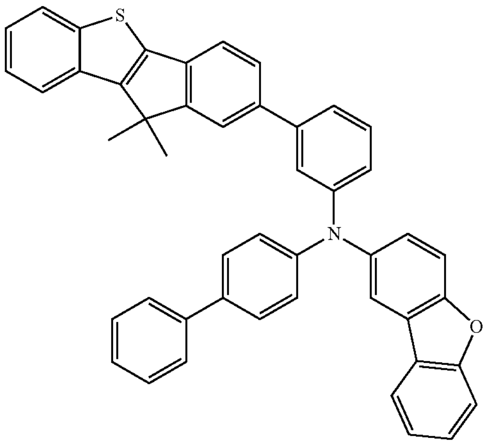

-continued
102
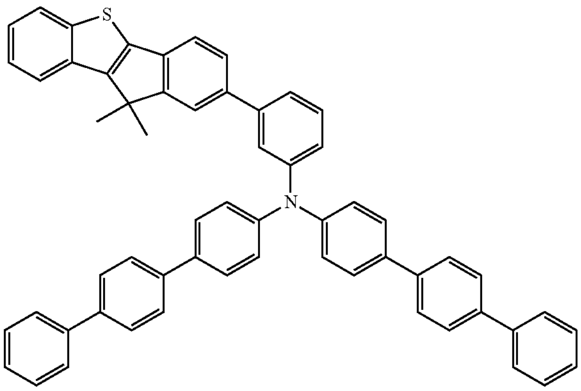
103
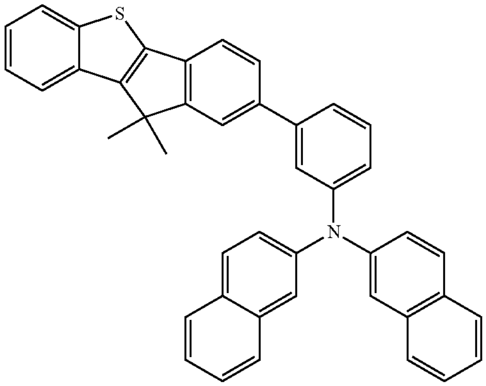
104
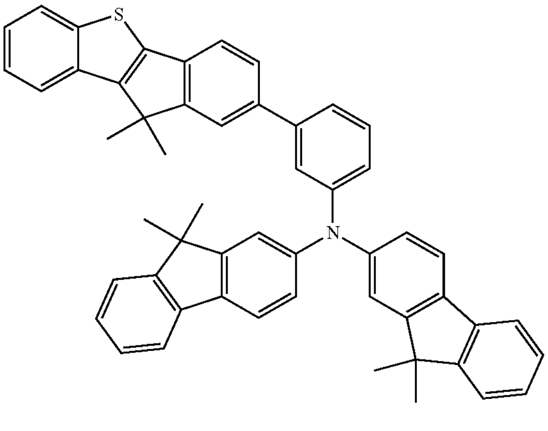
-continued
105
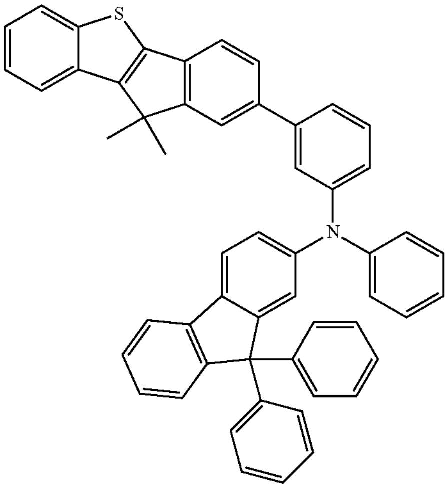
106
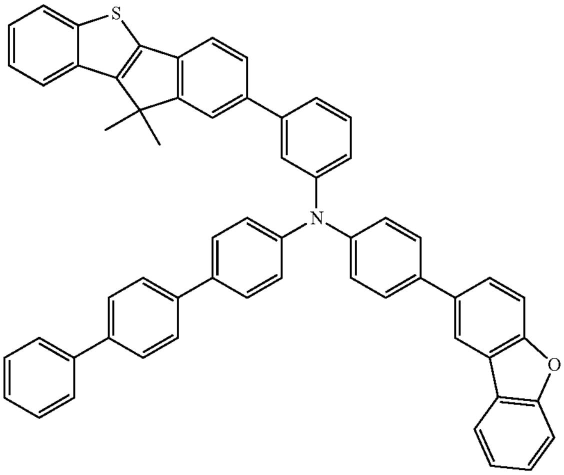
107
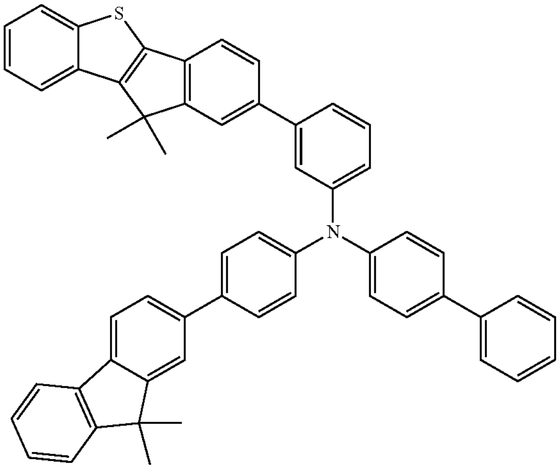

-continued
108
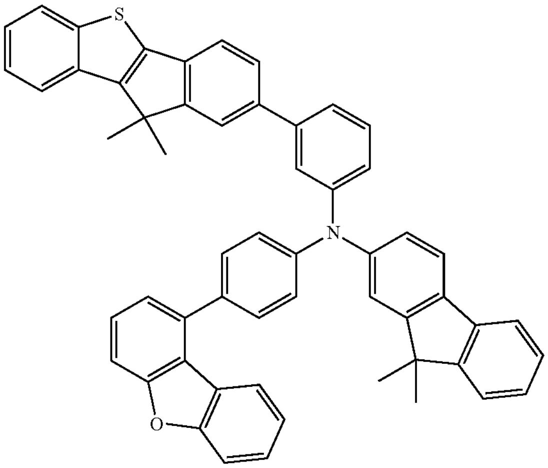
109
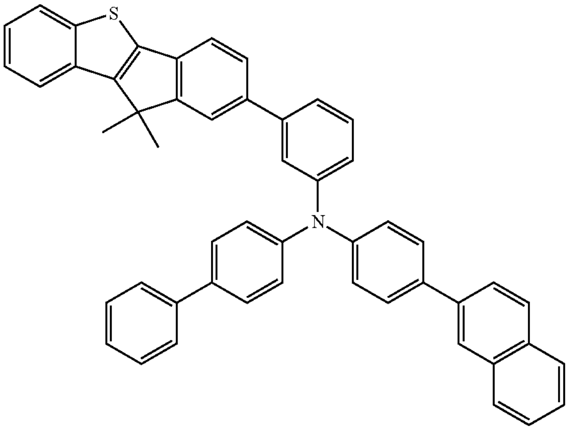
110
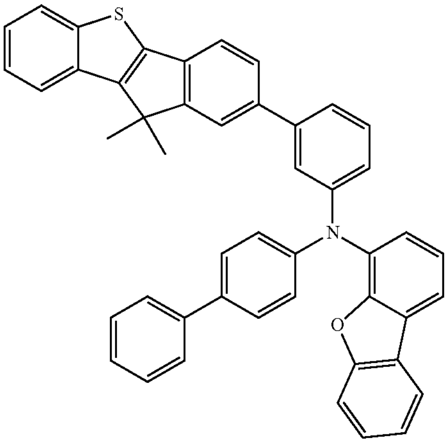
-continued
111
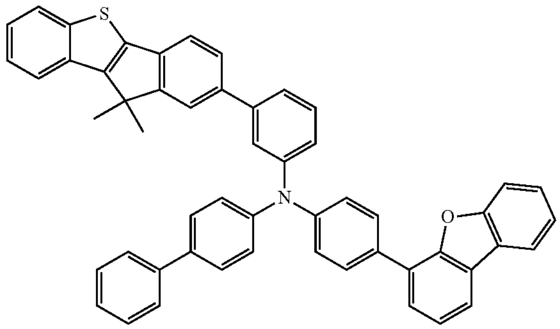
112
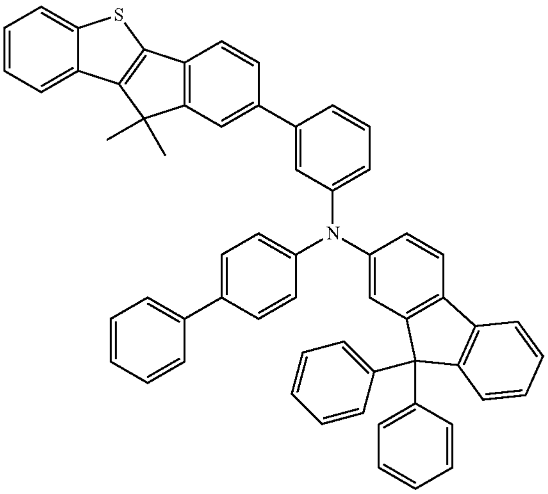
113
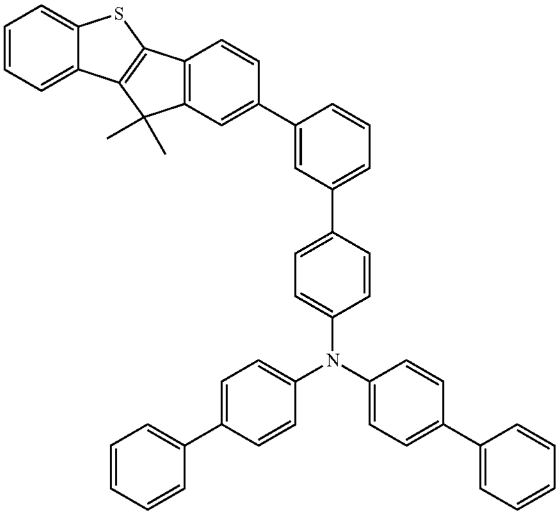

-continued
114
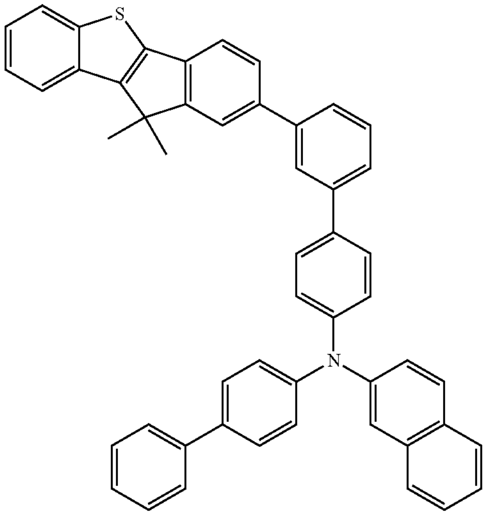
115
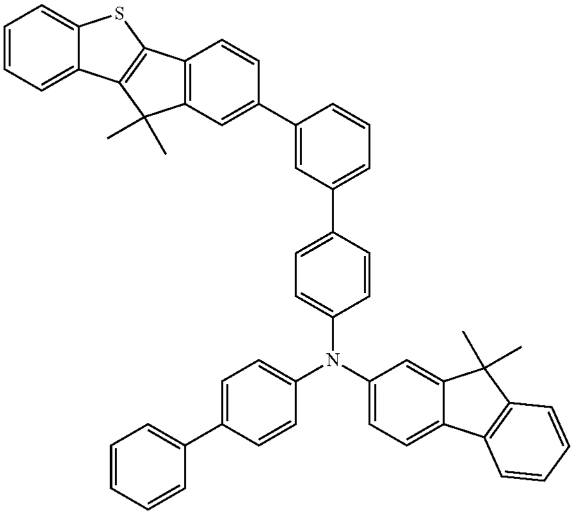
116
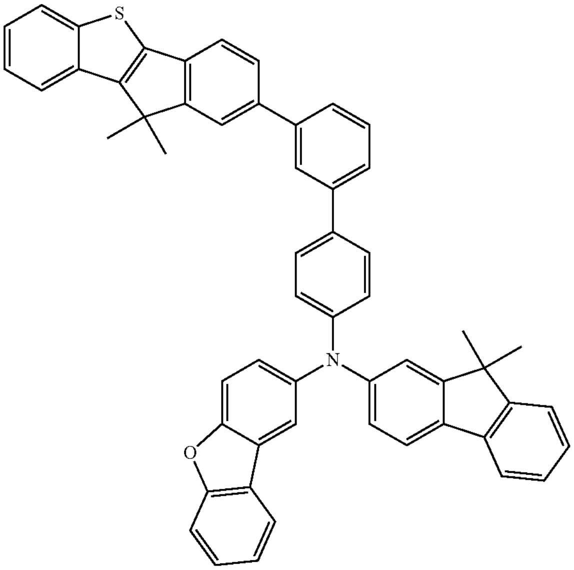
-continued
117
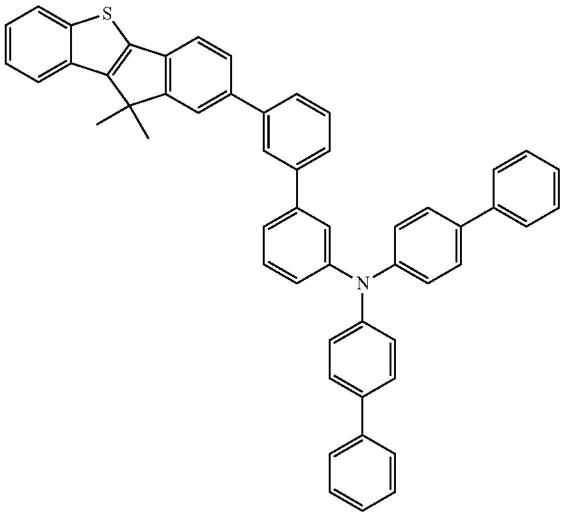
118
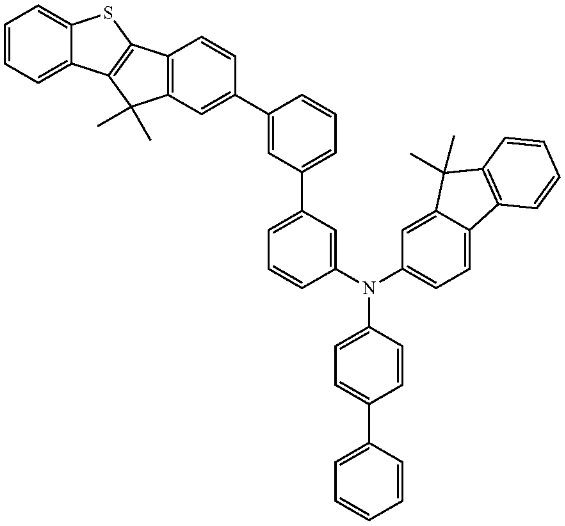
119
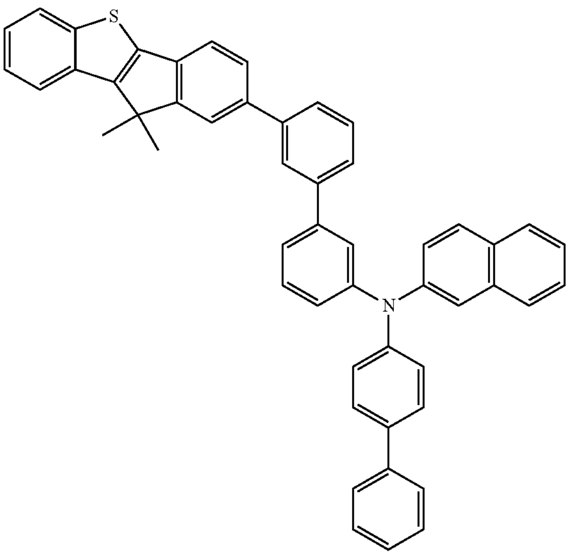

-continued
120
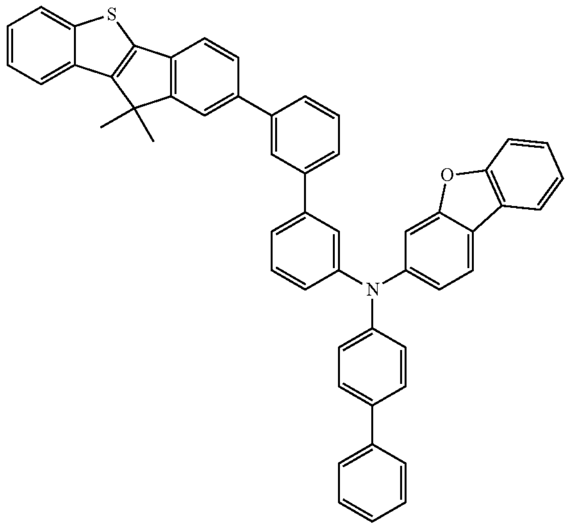
121
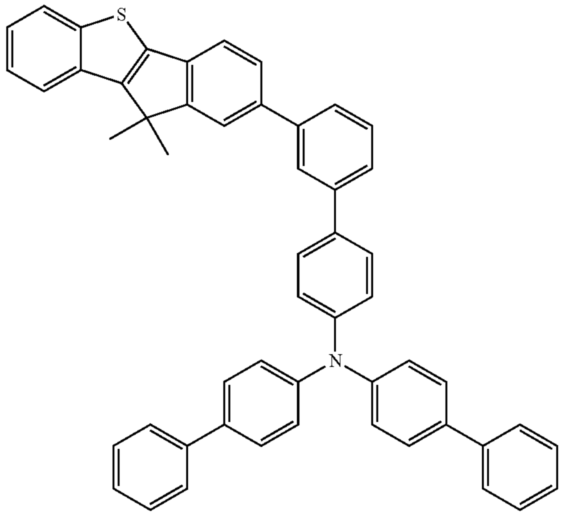
122
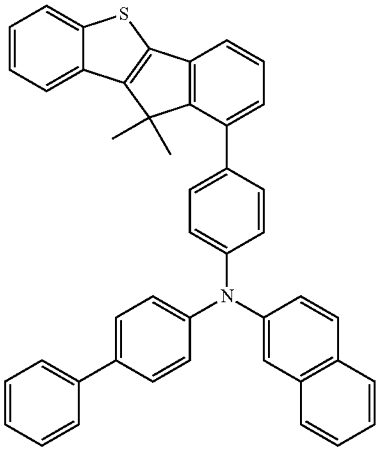
-continued
123
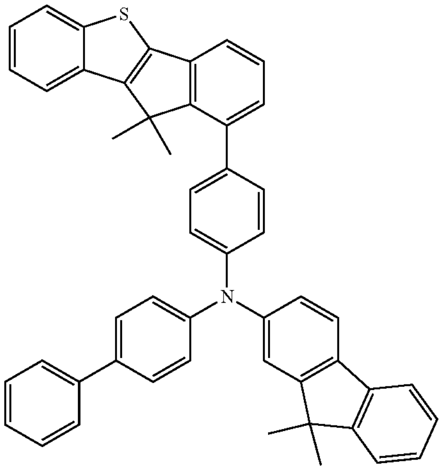
124
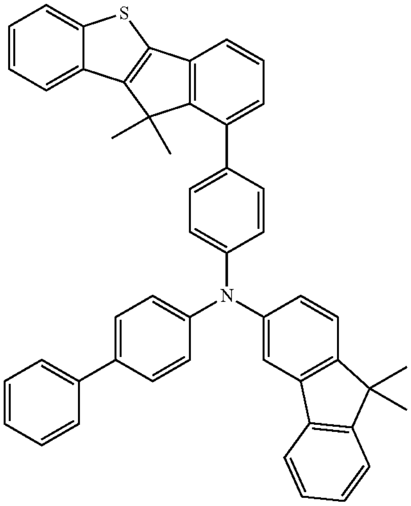
125
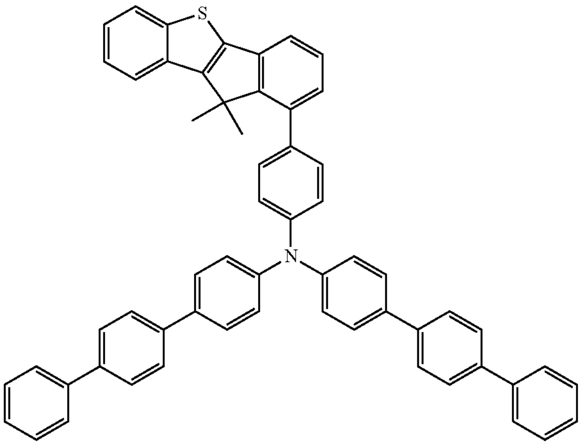

-continued
126
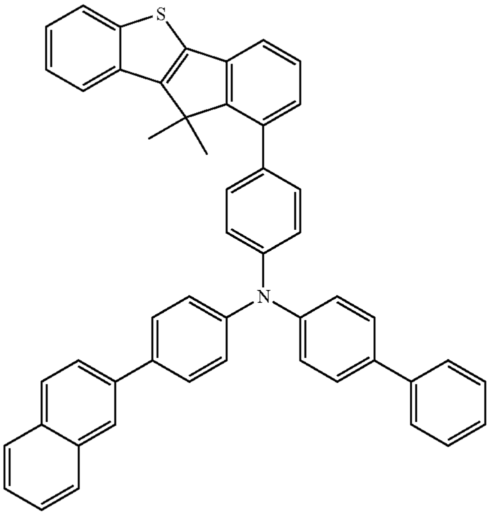
127
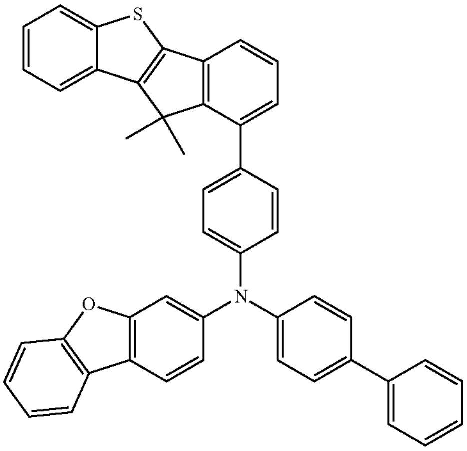
128
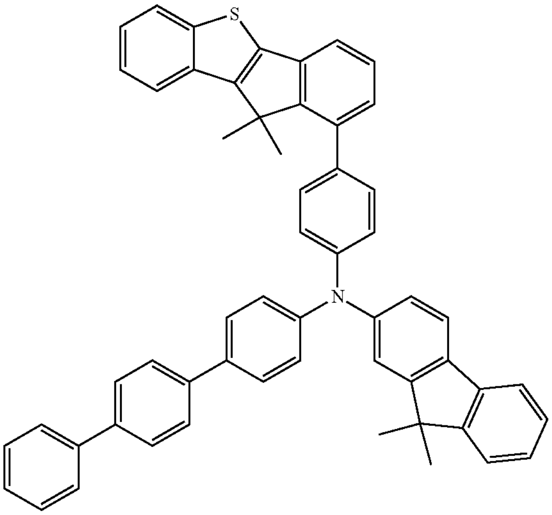
-continued
129
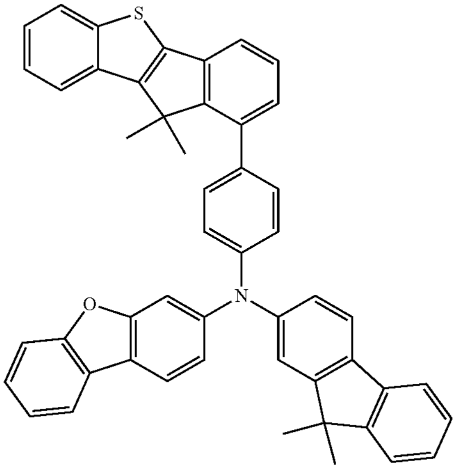
130
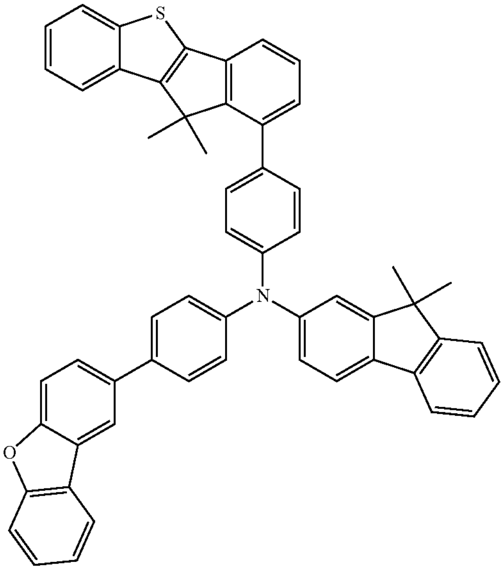
131
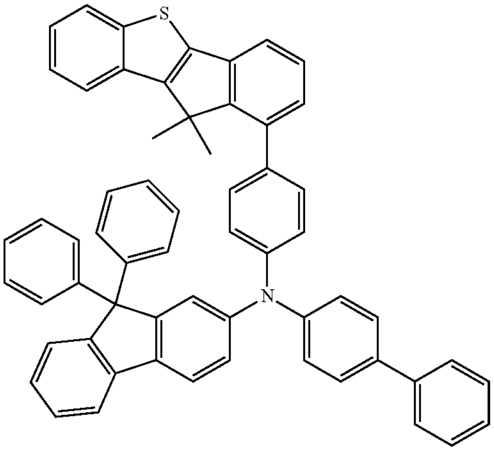

-continued
132
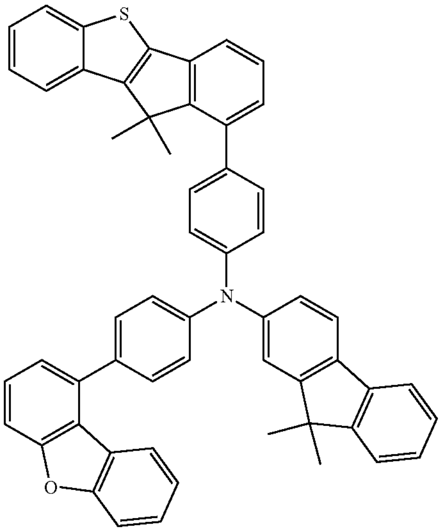
133
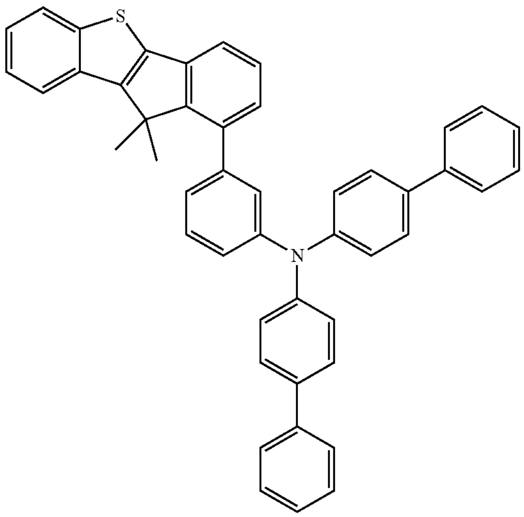
-continued
134
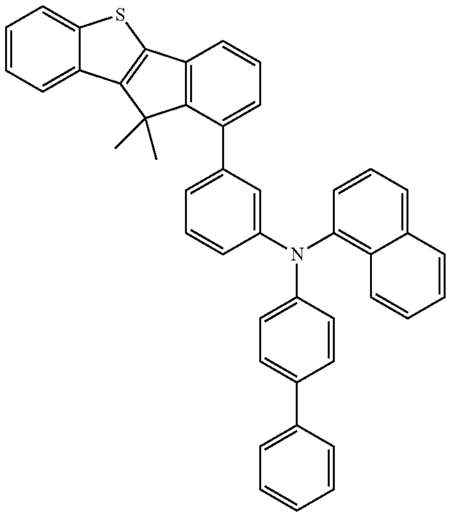
135
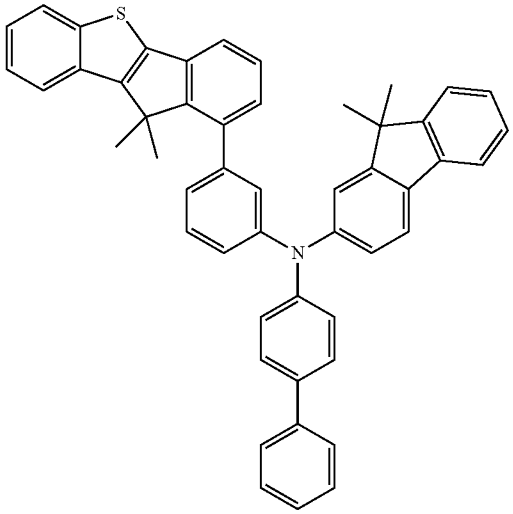
136
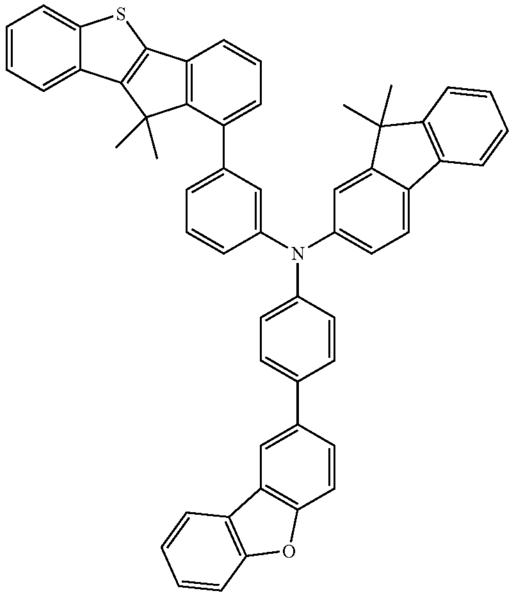

-continued
137
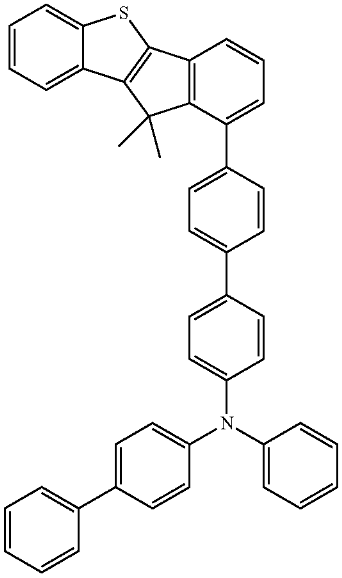
138
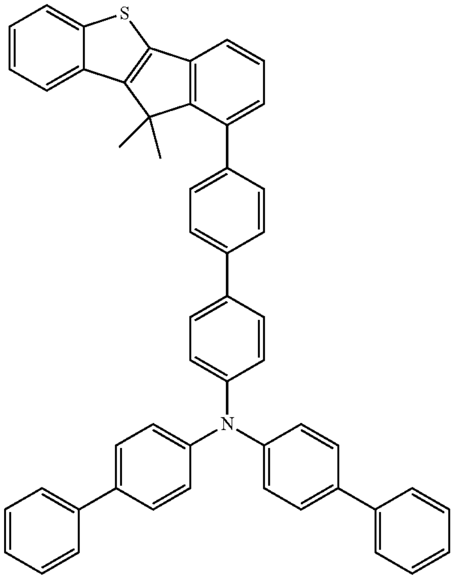
-continued
139
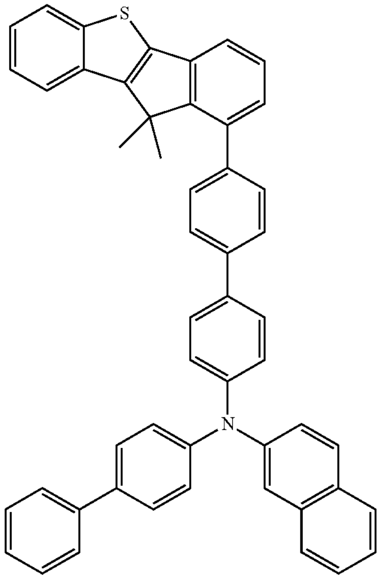
140
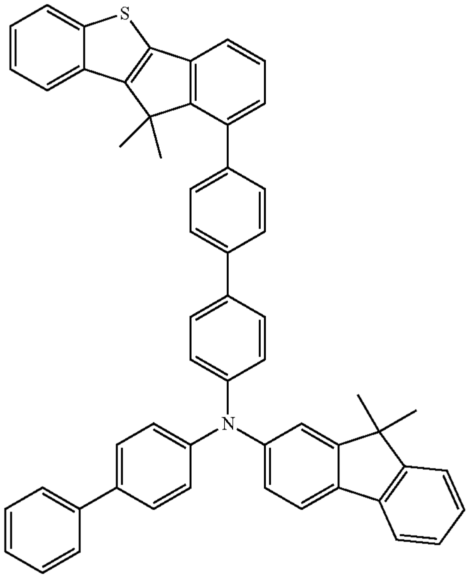

-continued
141
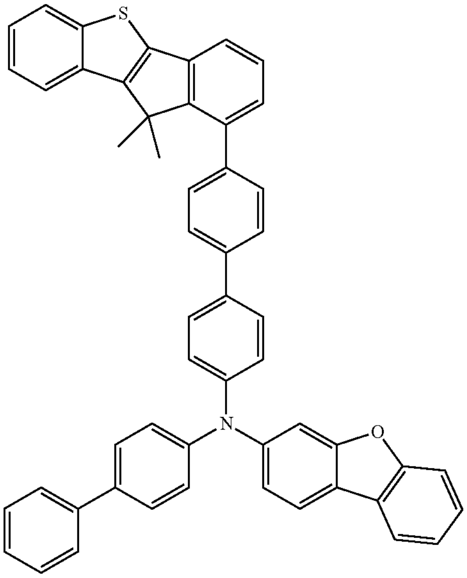
142
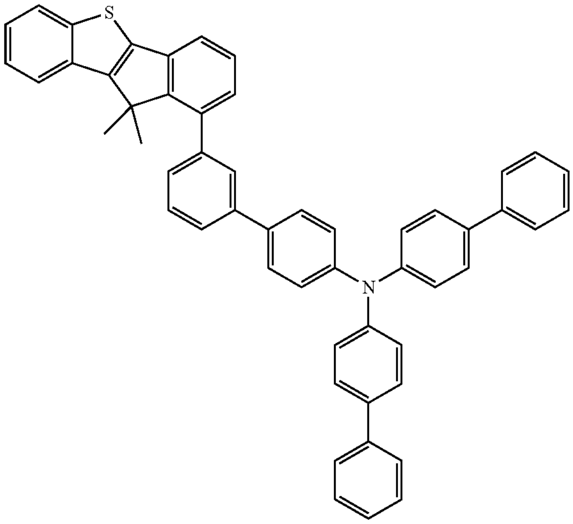
-continued
143
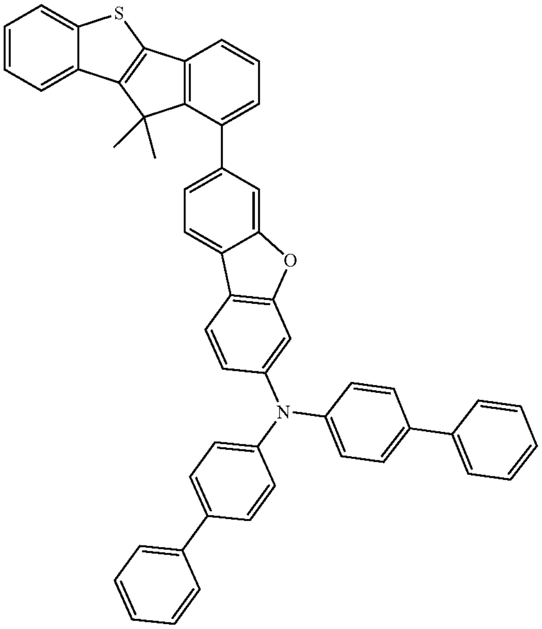
144
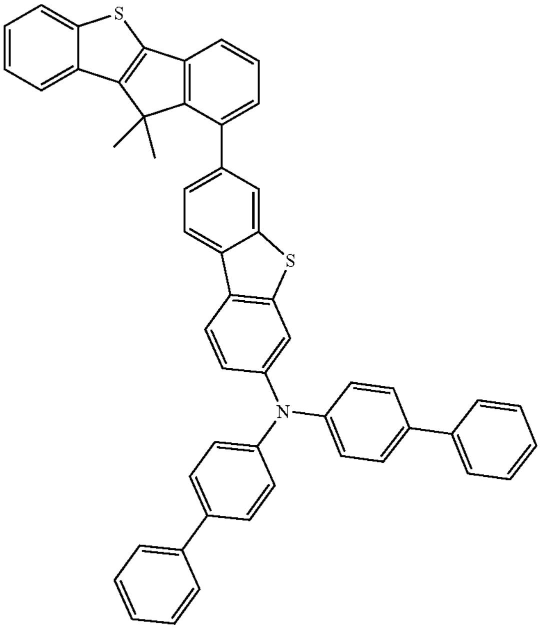

-continued
145
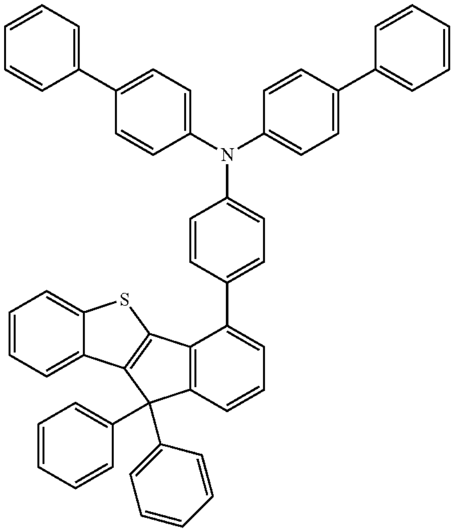
146
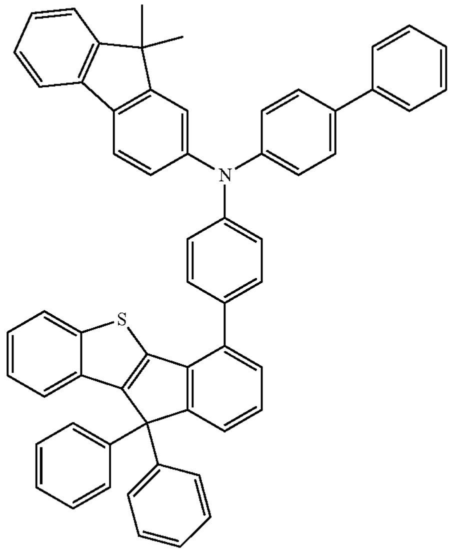
147
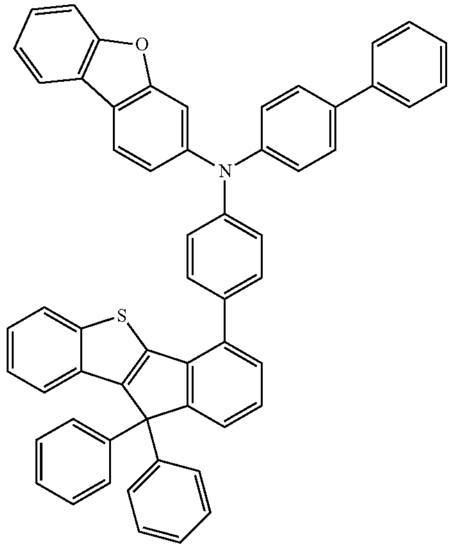
-continued
148
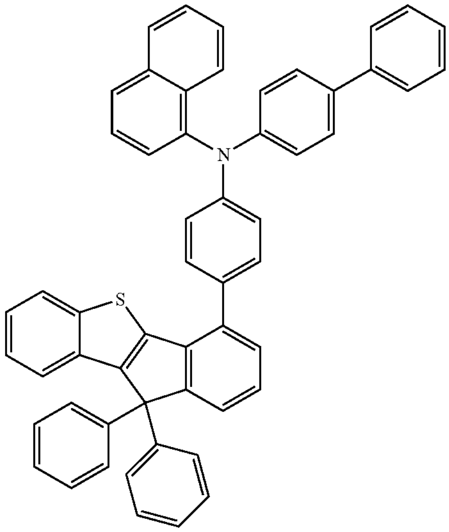
149
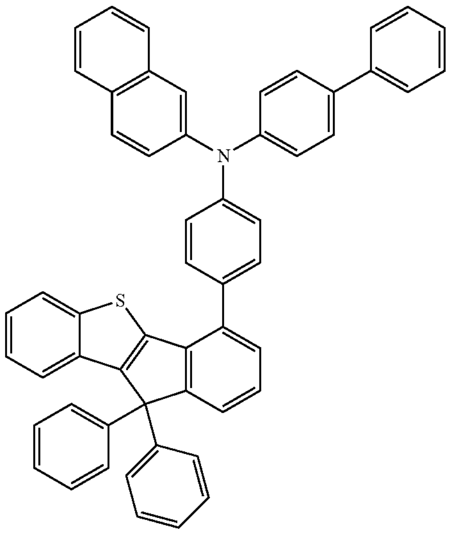
150
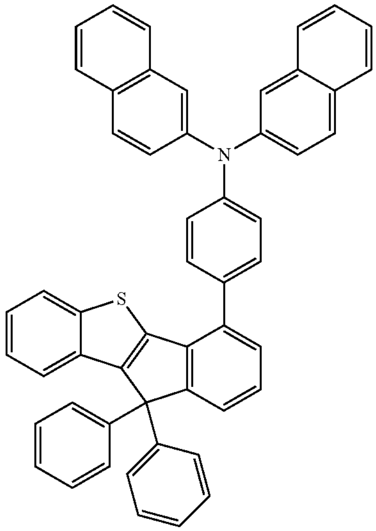

-continued
151
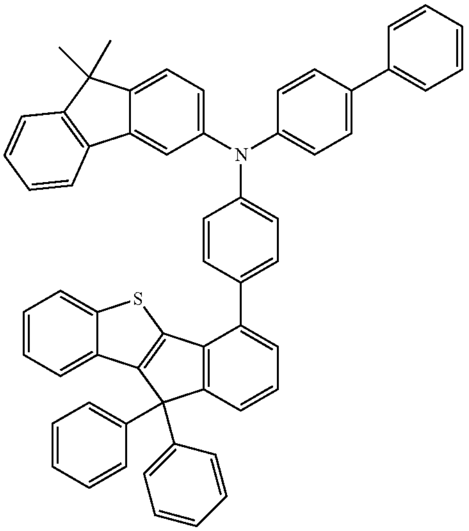
152
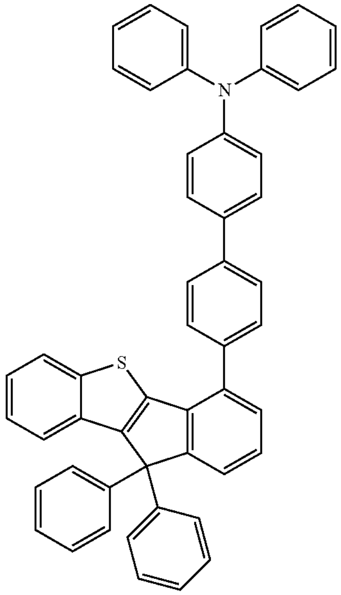
-continued
153
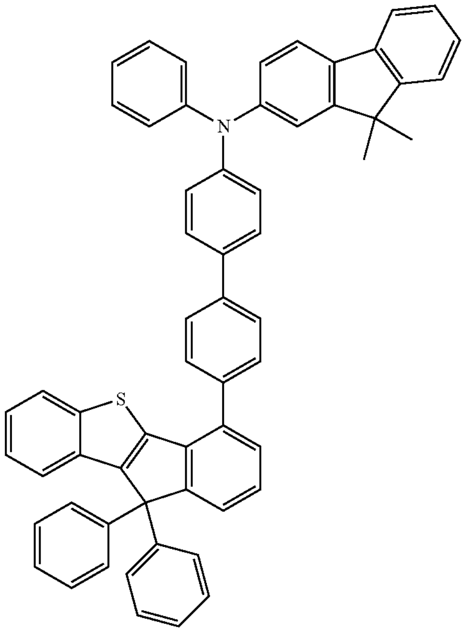
154
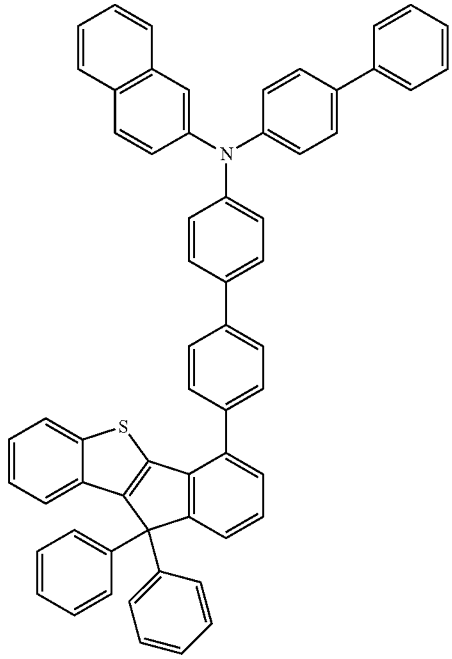

-continued
155
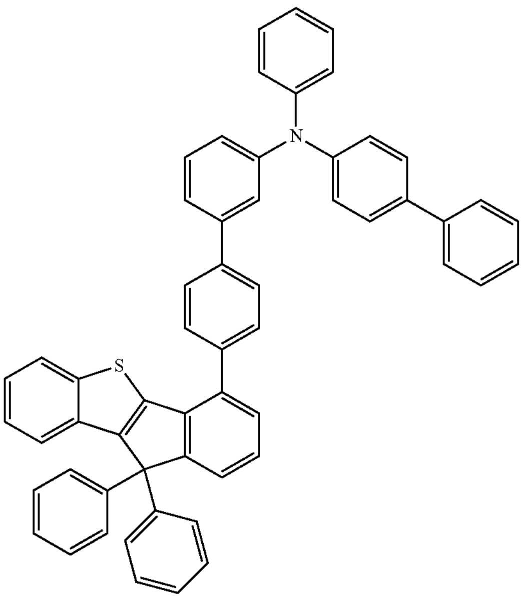
156
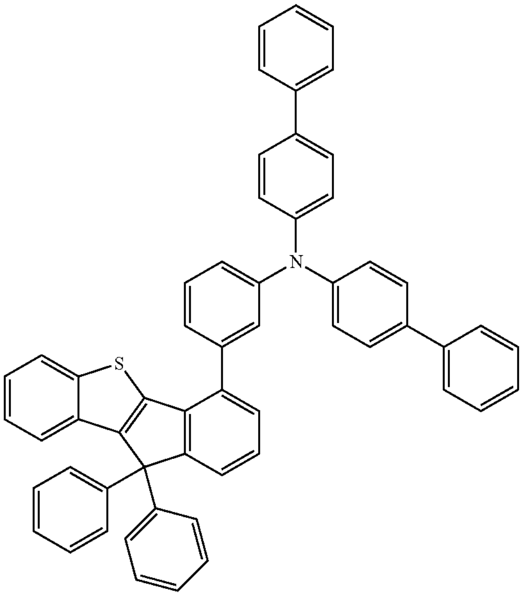
-continued
157
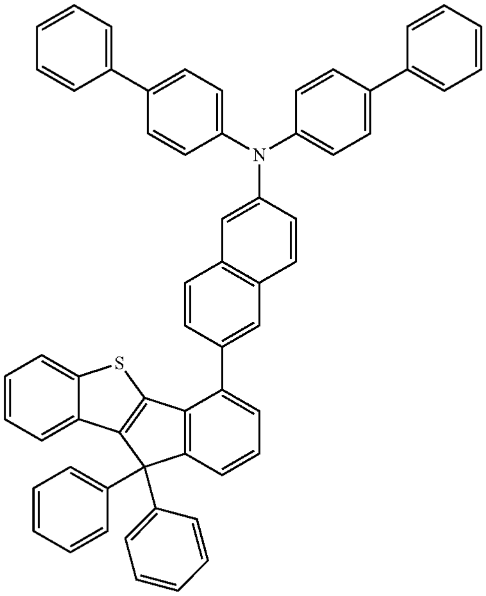
158
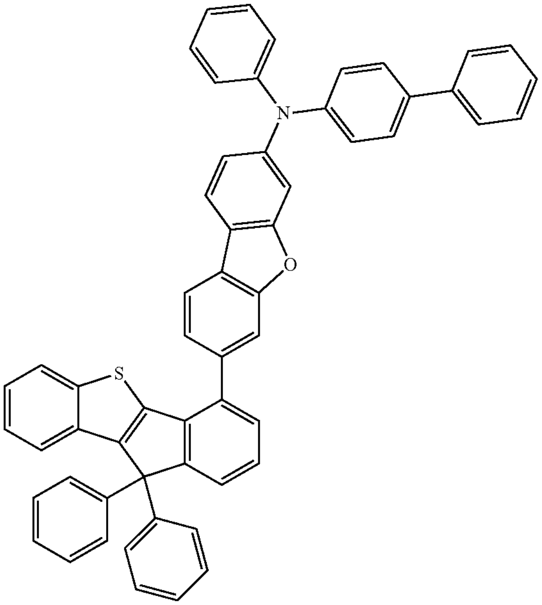

-continued
159
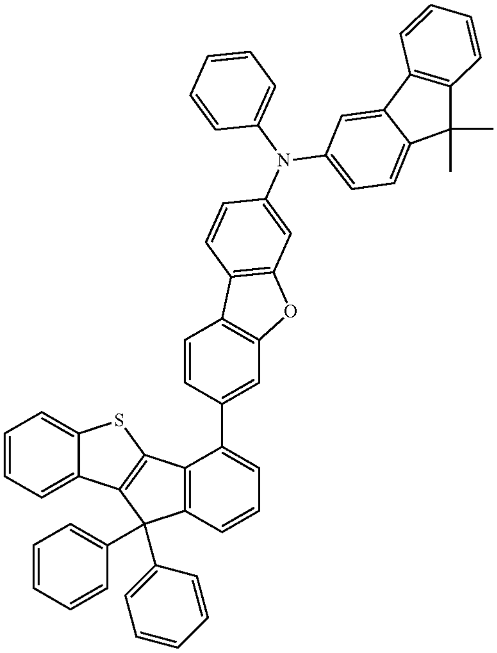
160
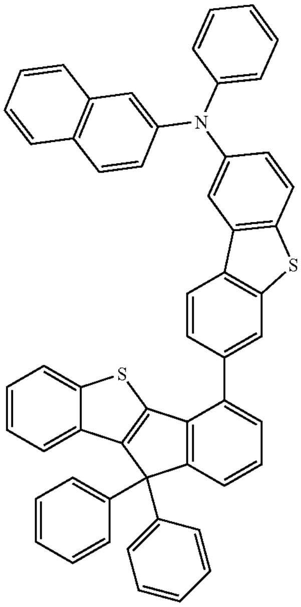
-continued
161
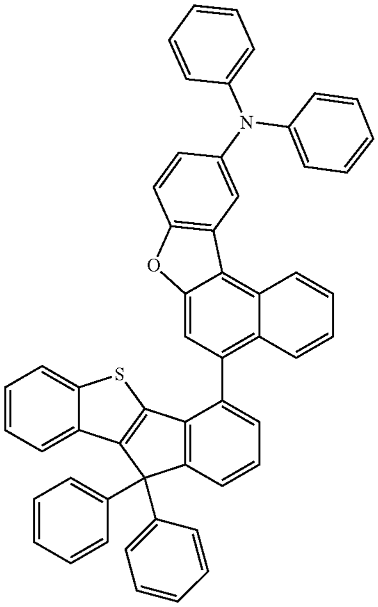
162
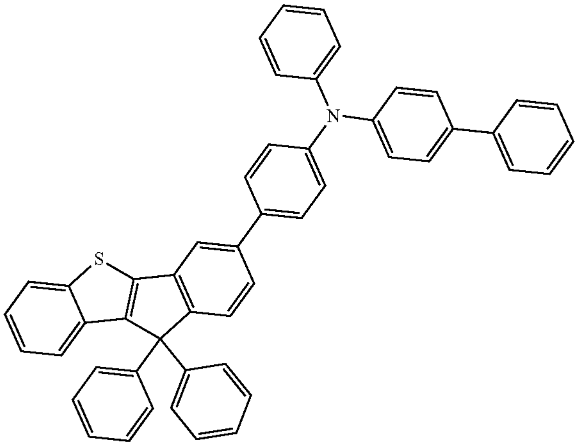
163
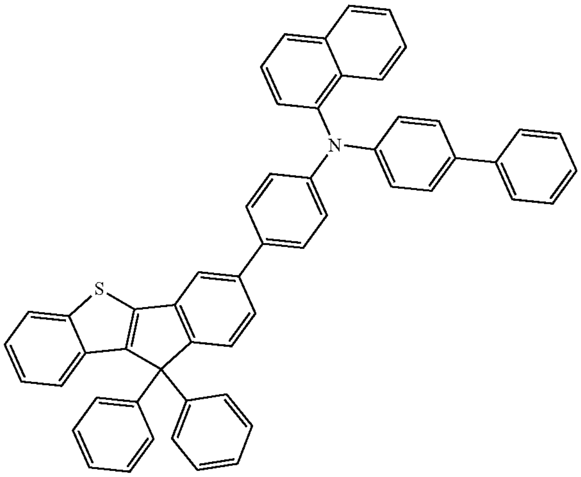

164
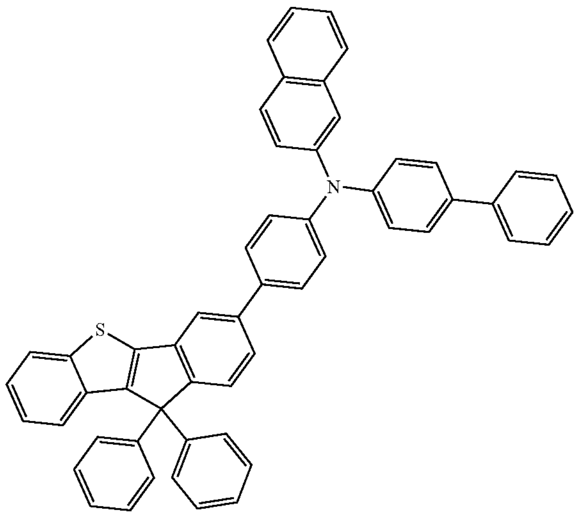
165
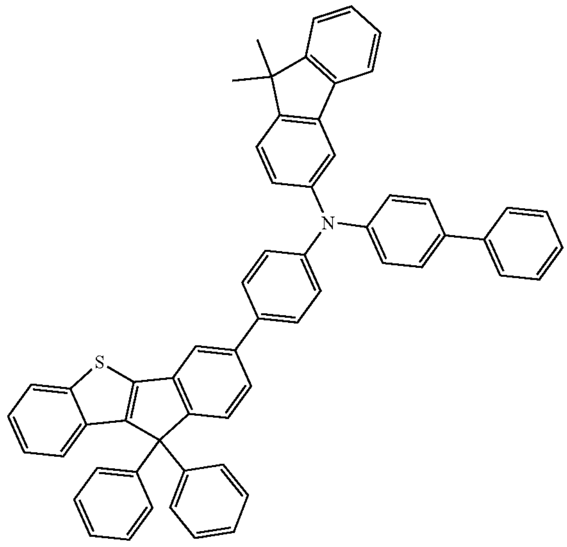
166
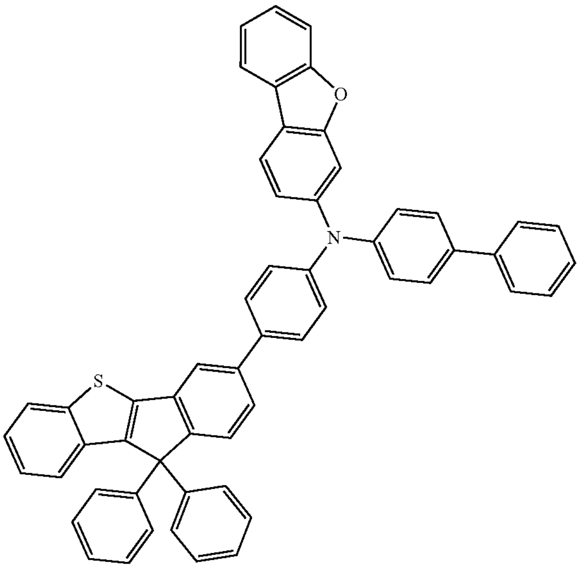
167
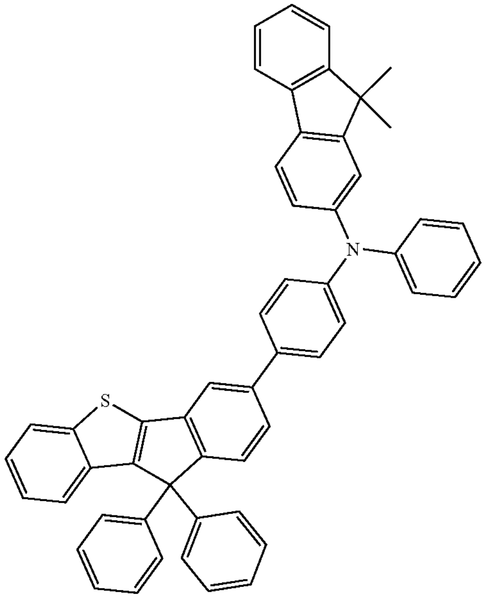

-continued
168
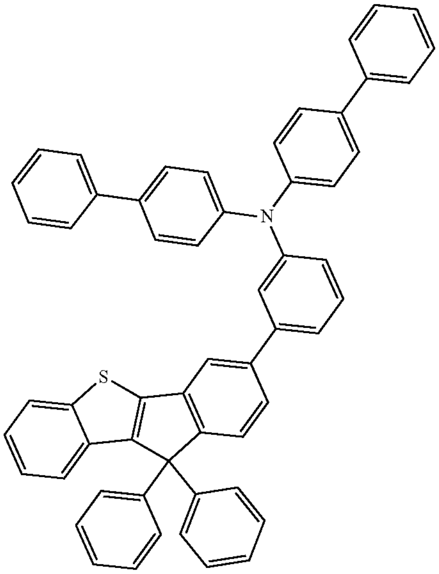
169
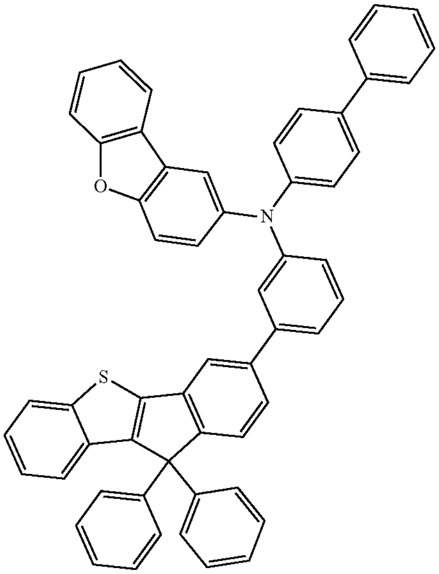
-continued
170
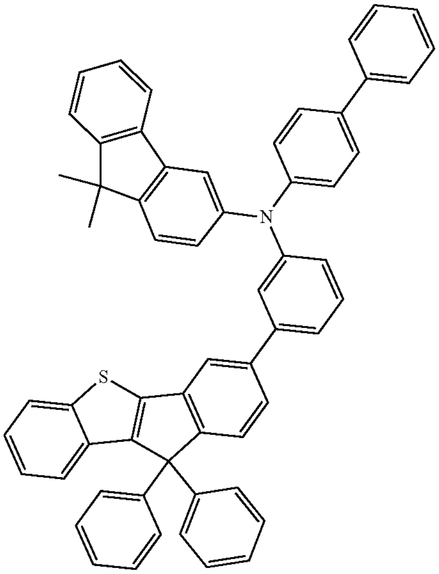
171
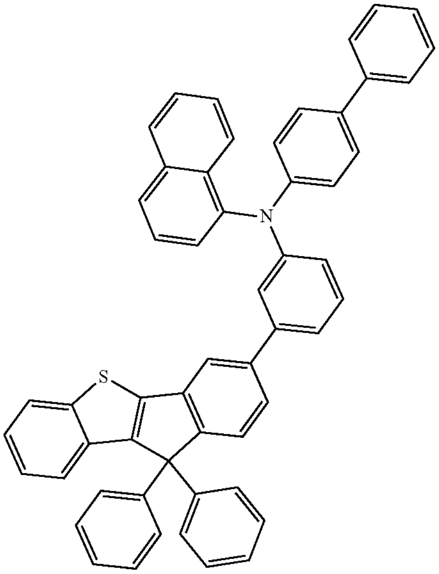
172
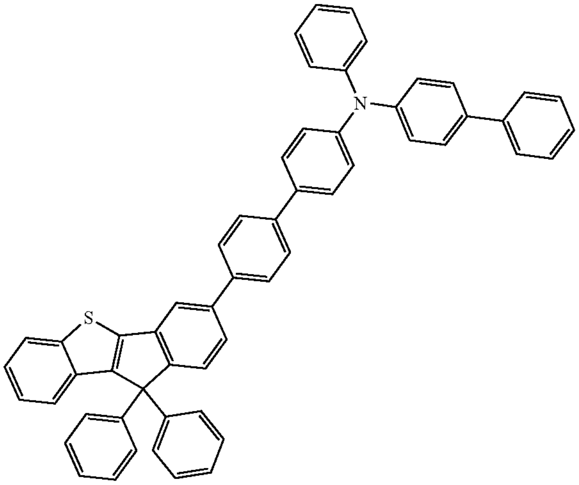

-continued
173
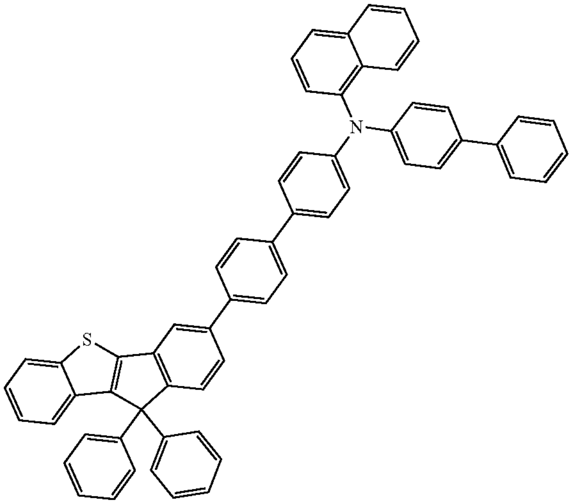
174
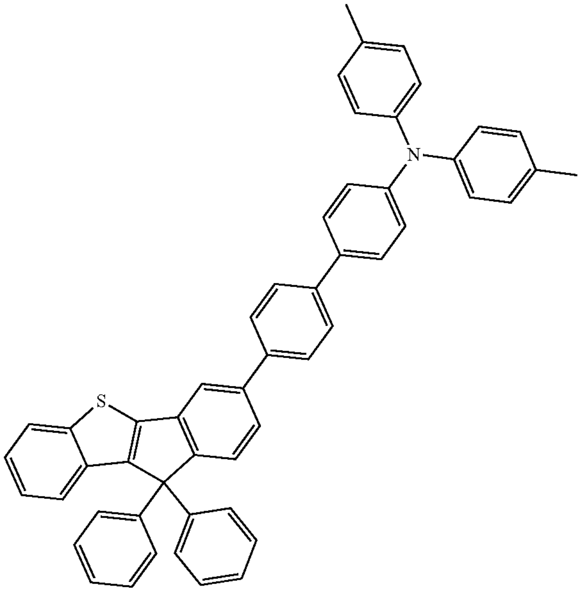
-continued
175
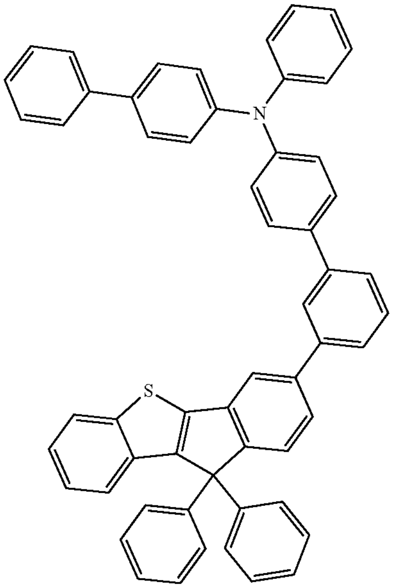
176
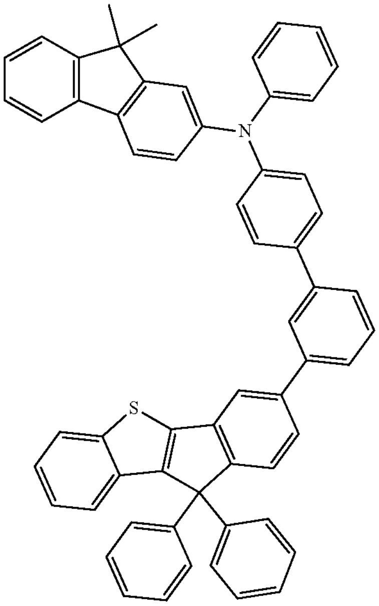

-continued
177
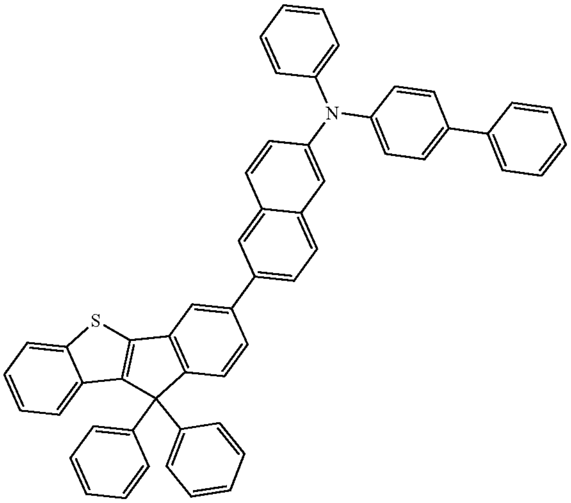
178
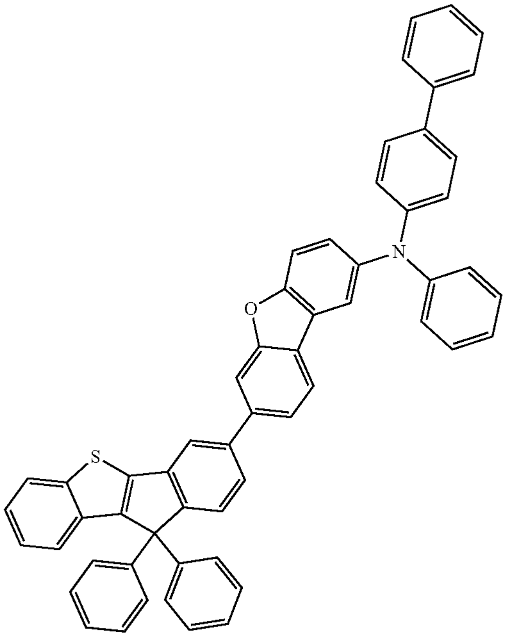
-continued
179
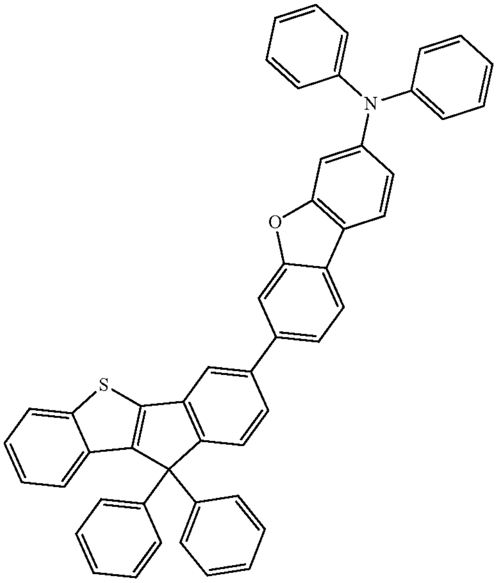
180
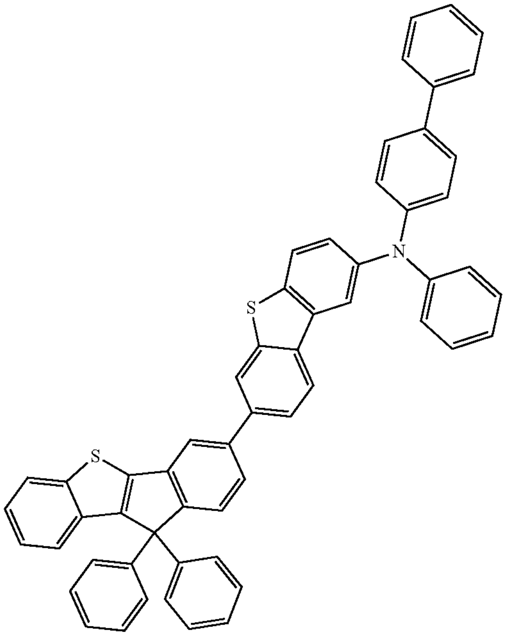
181
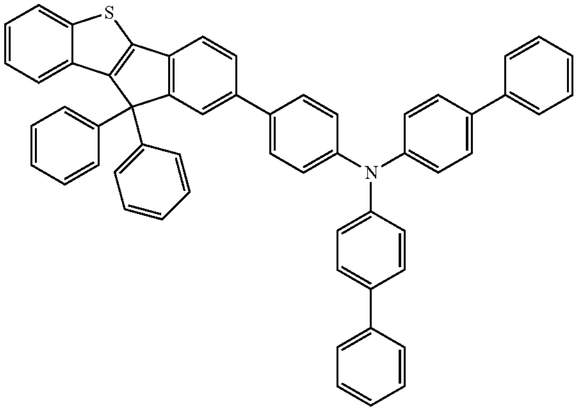

-continued
182
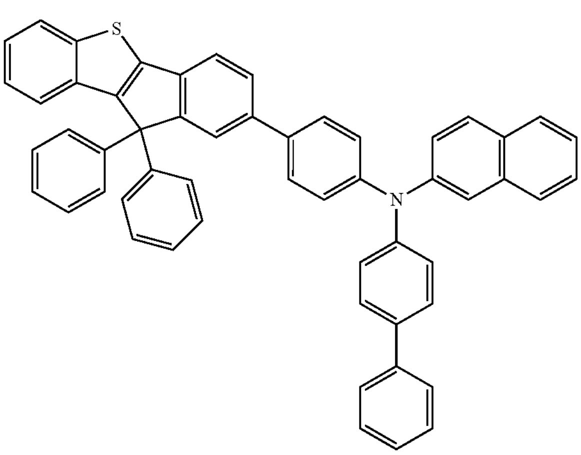
183
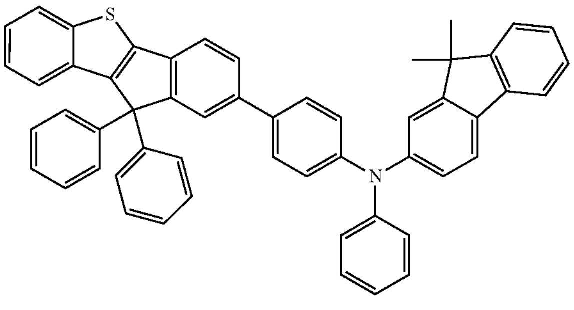
184
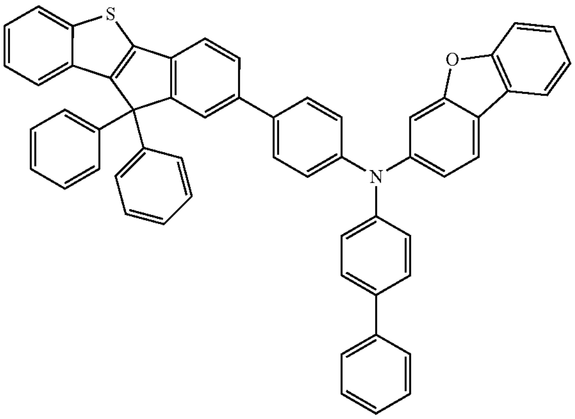
185
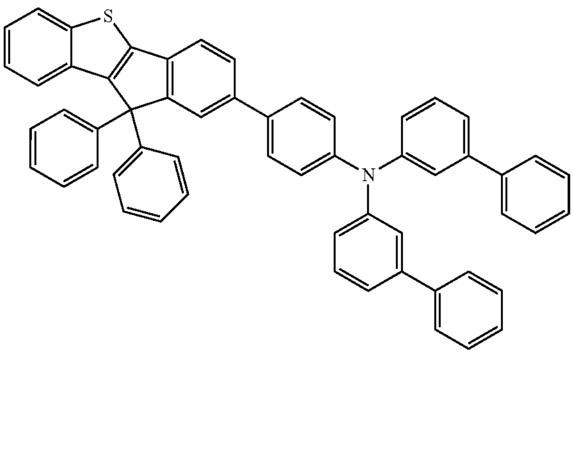
-continued
186
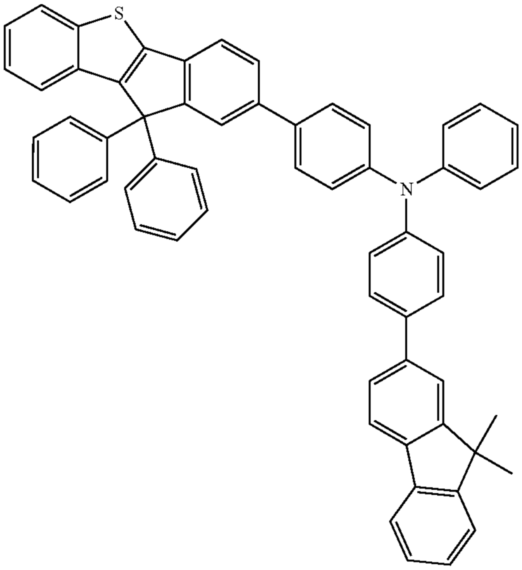
187
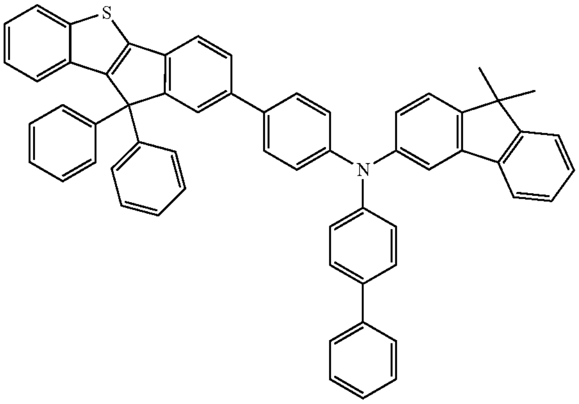
188
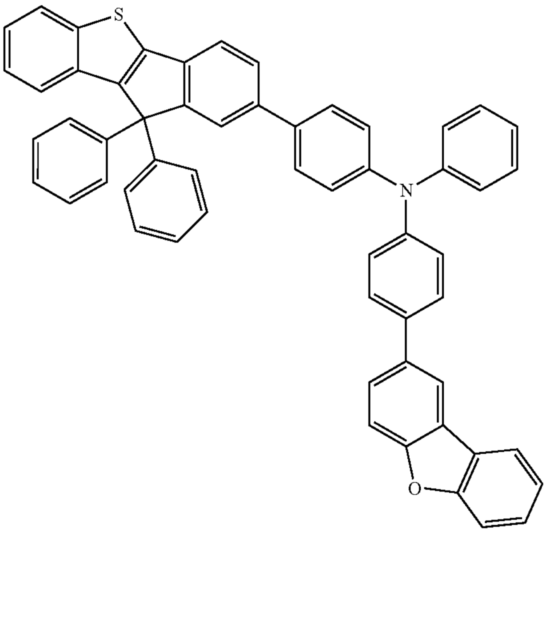

-continued
189
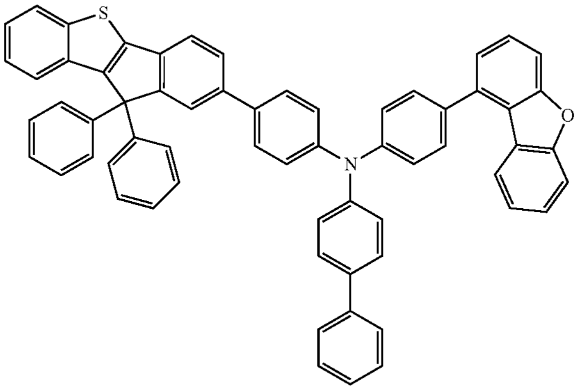
190
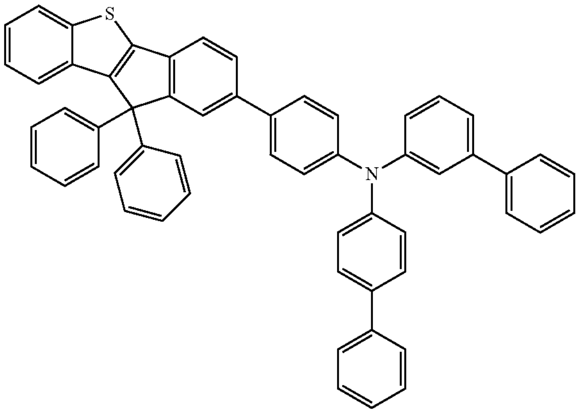
191
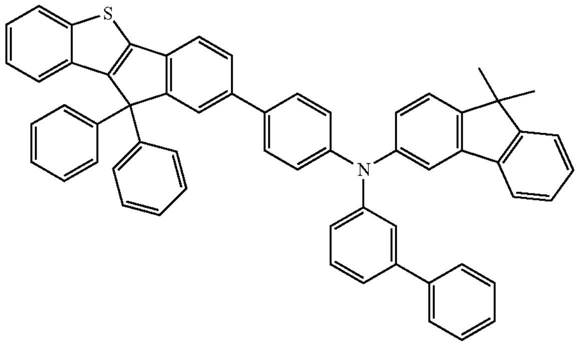
192
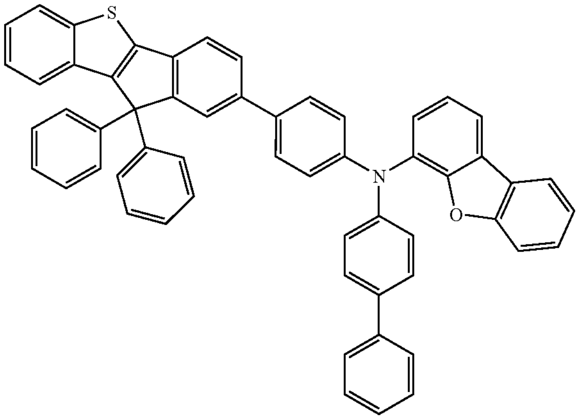
-continued
193
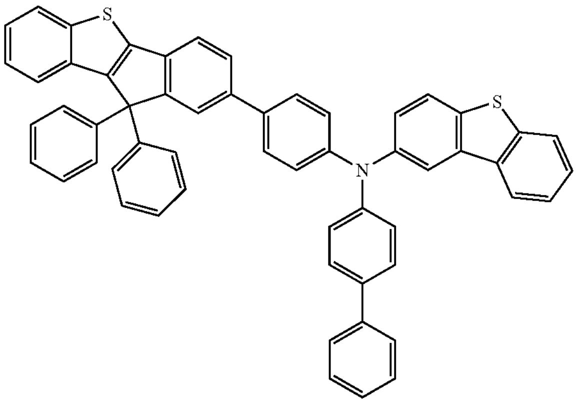
194
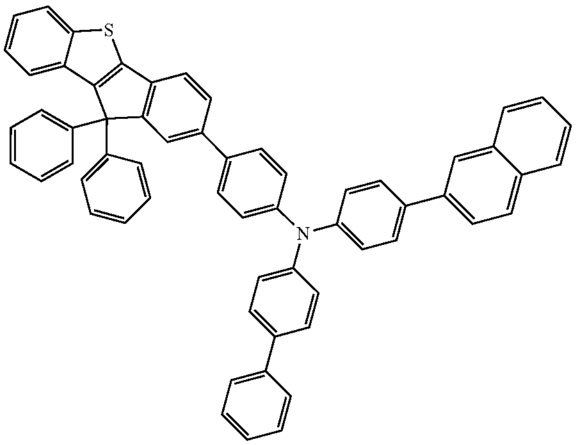
195
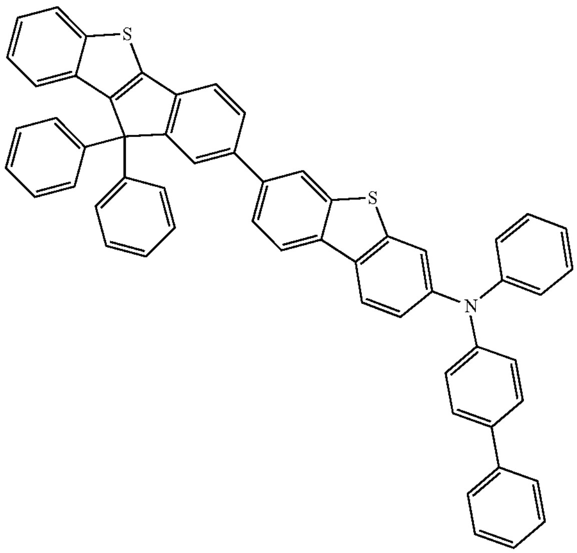

-continued
196
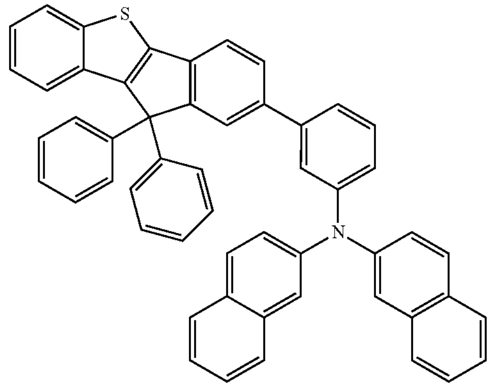
197
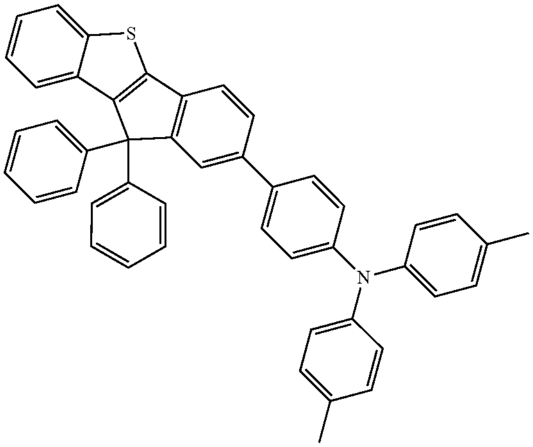
198
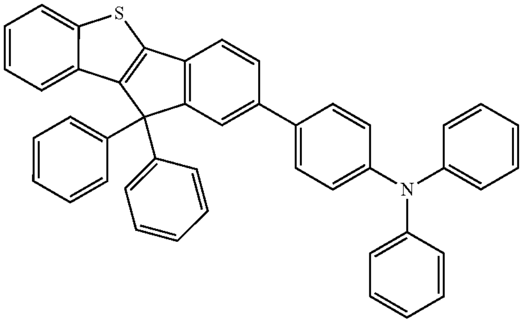
-continued
199
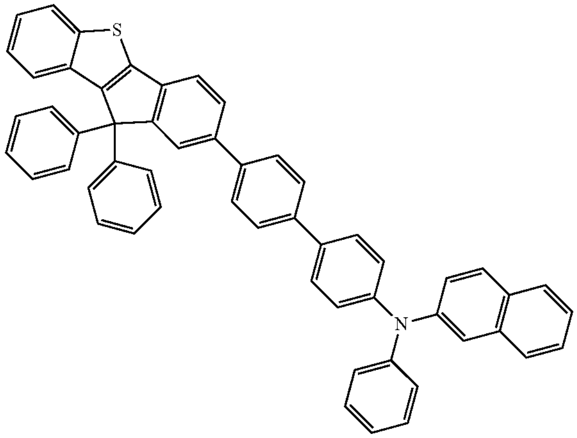
200
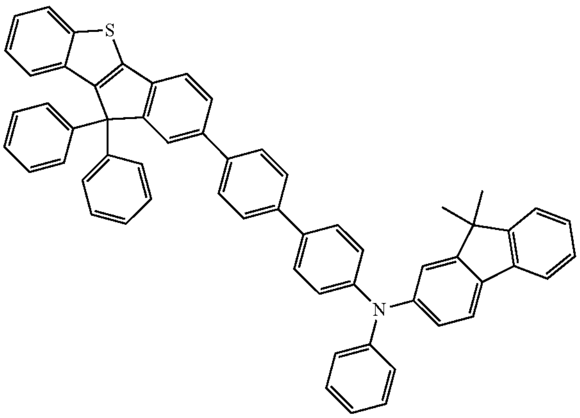
201
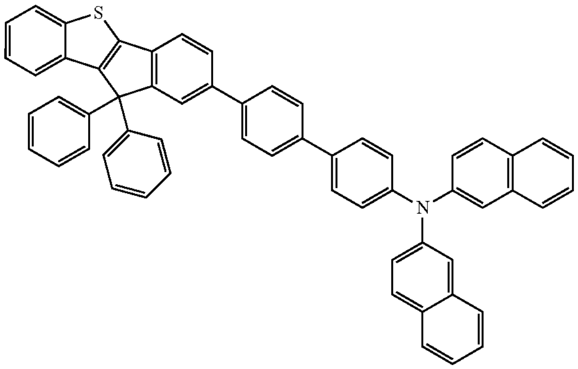

-continued
202
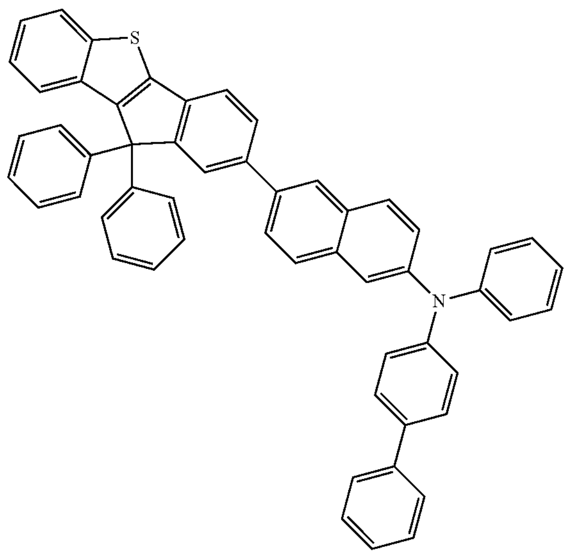
203
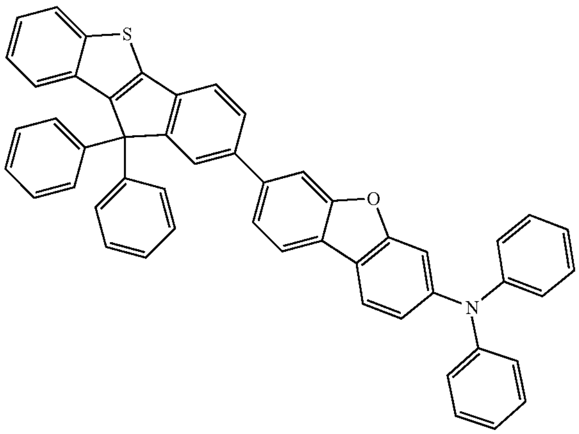
204
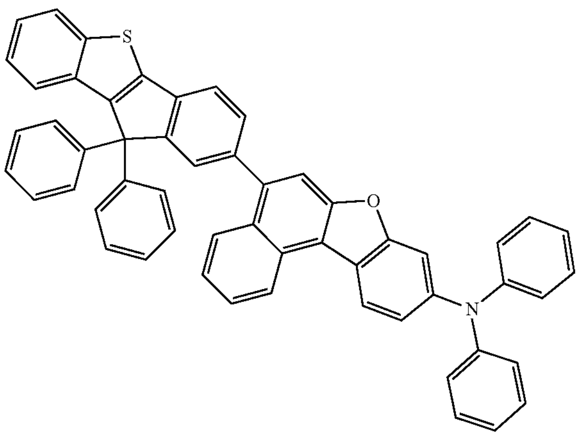
-continued
205
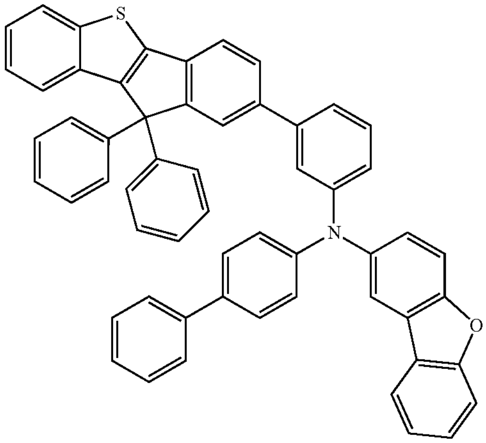
206
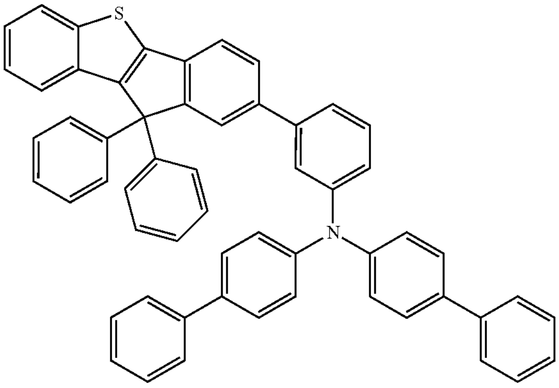
207
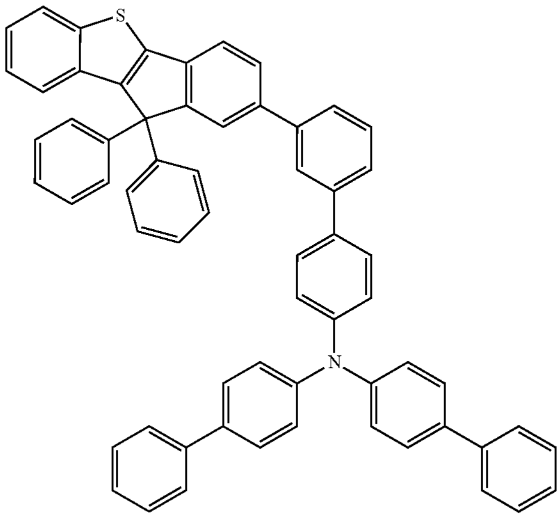

-continued
208
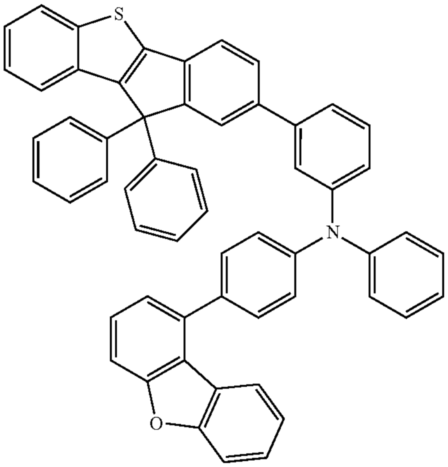
209
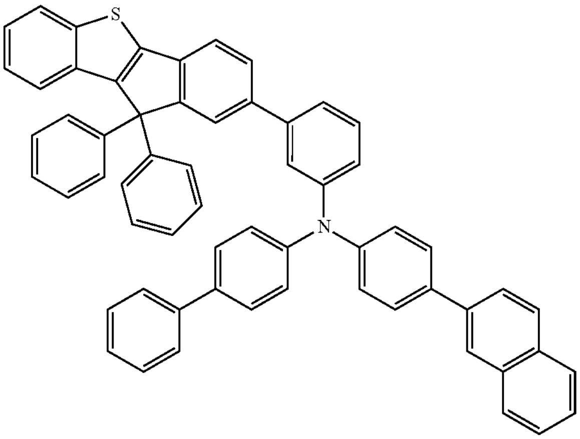
210
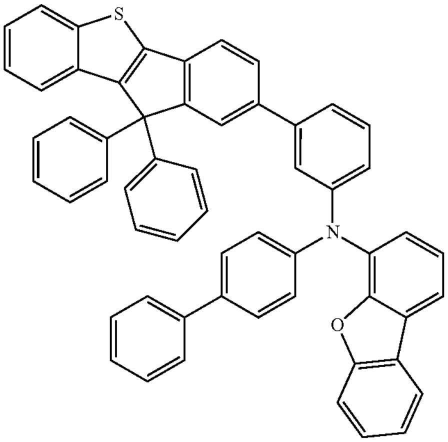
-continued
211
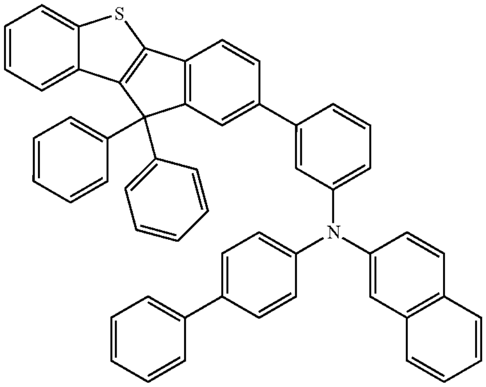
212
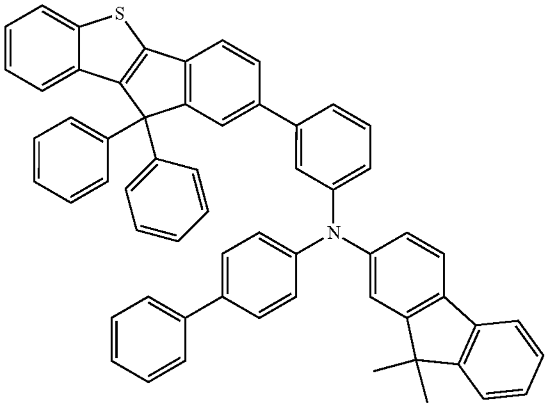
213
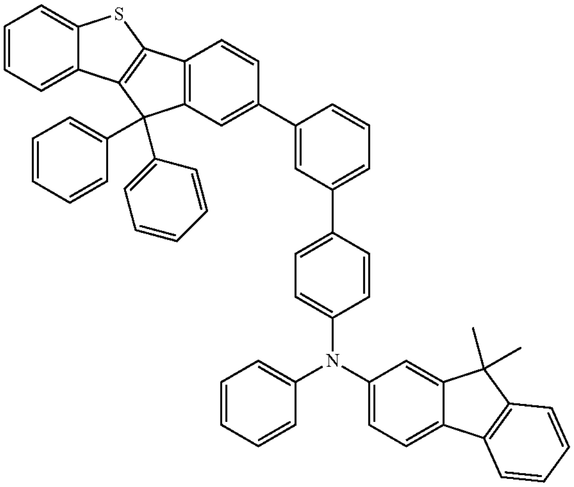

-continued
214
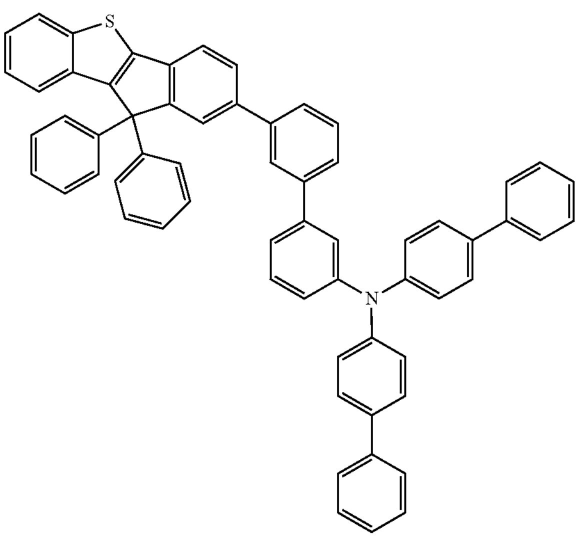
215
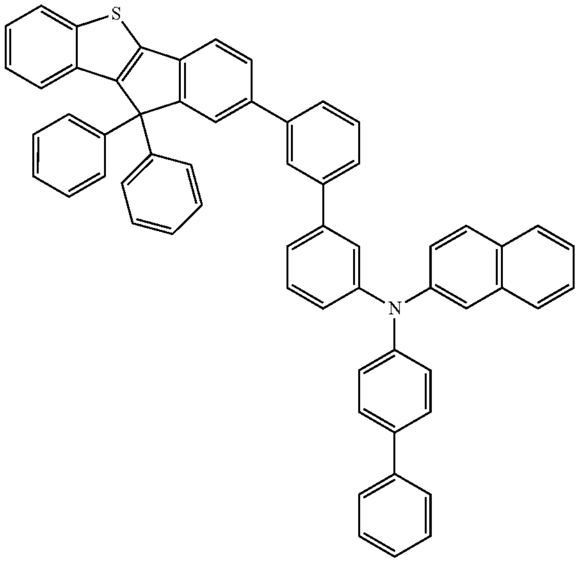
216
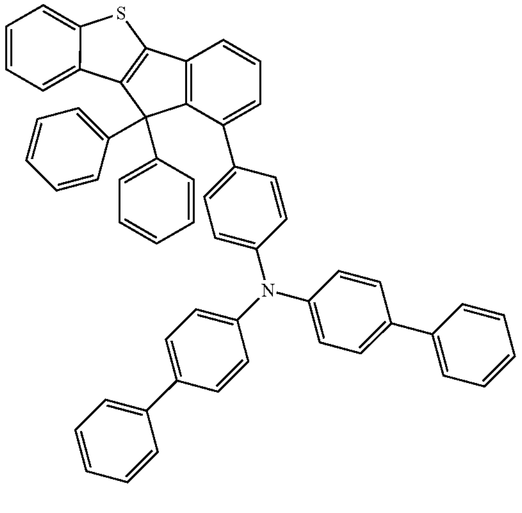
-continued
217
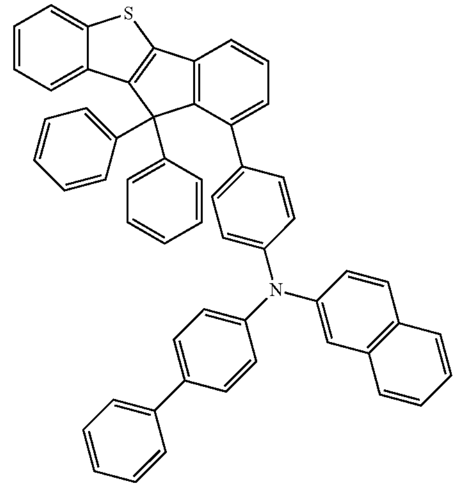
218
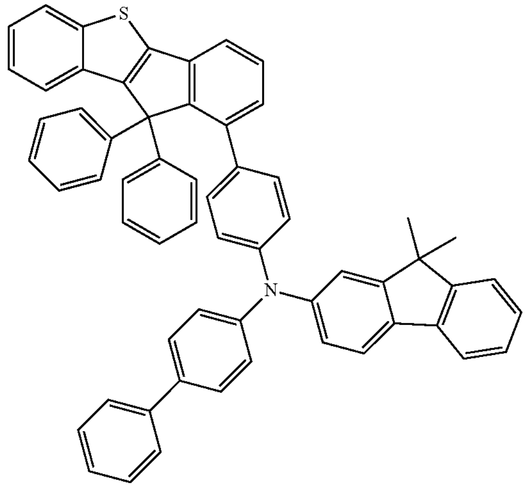
219
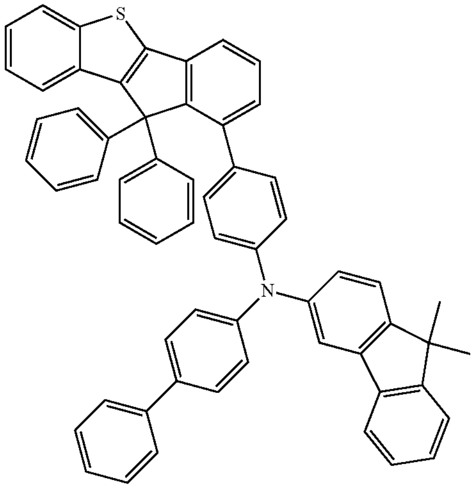

-continued
220
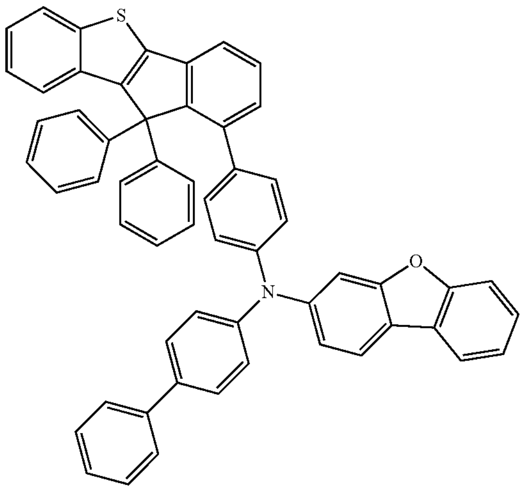
221
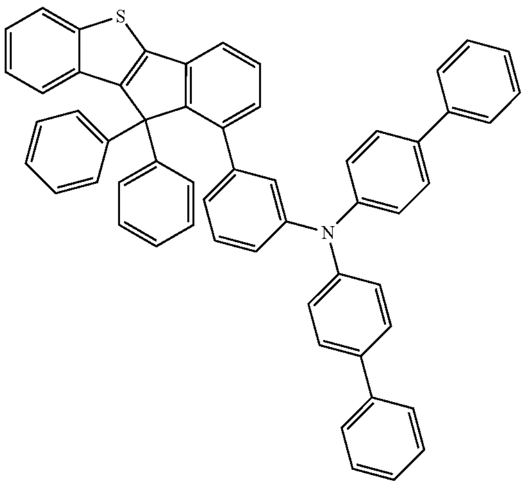
222
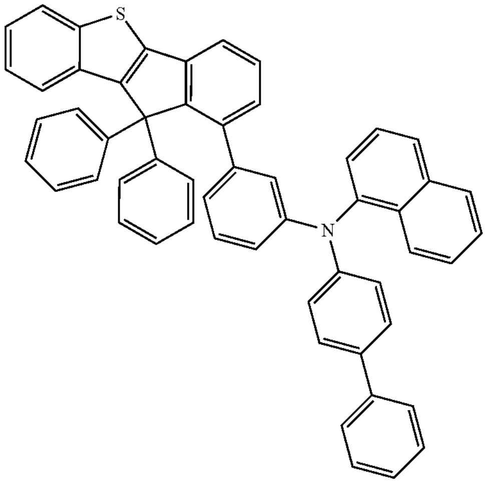
-continued
223
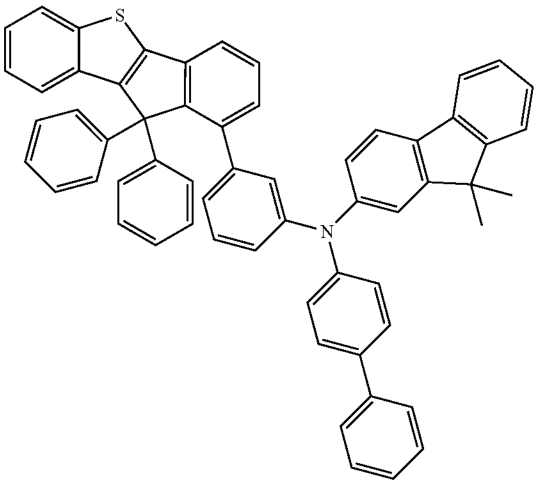
224
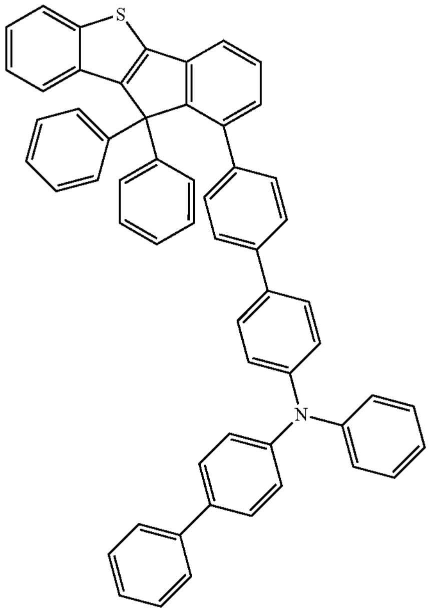
225
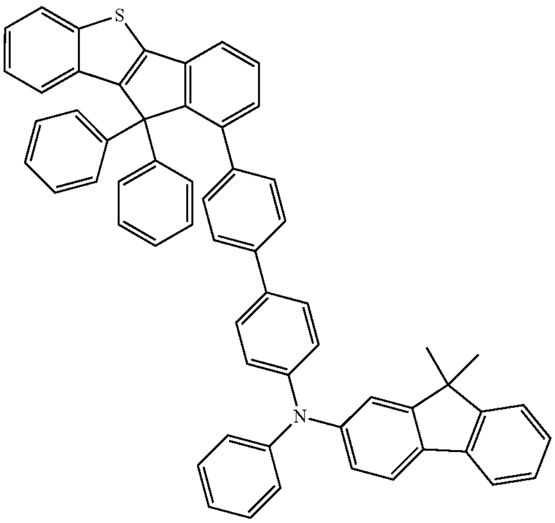

-continued
226
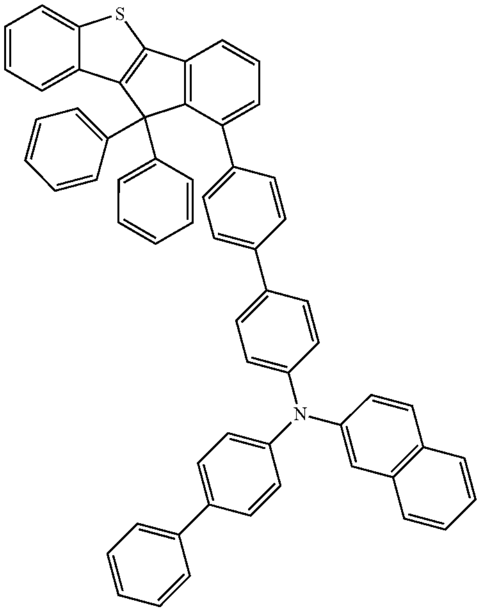
227
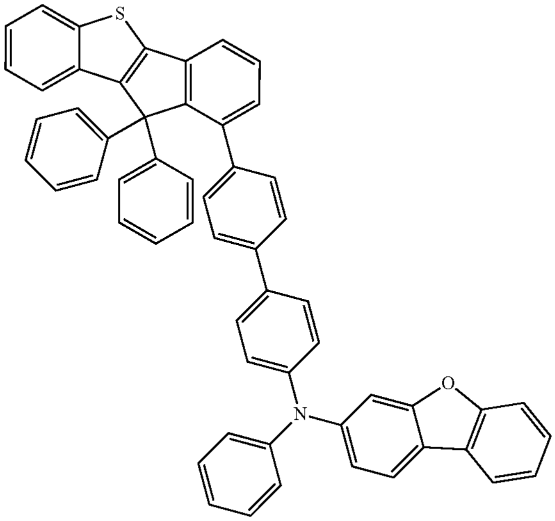
-continued
228
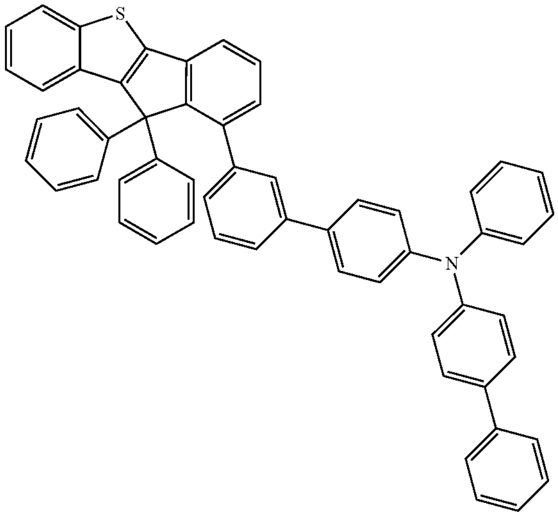
229
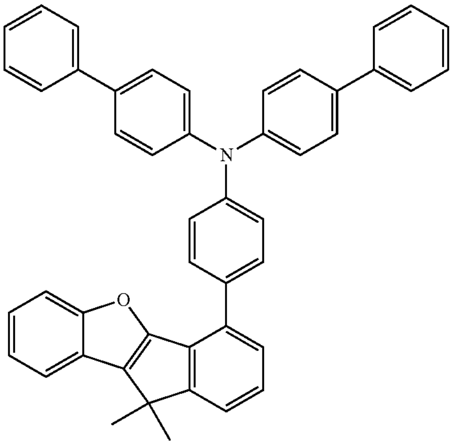
230
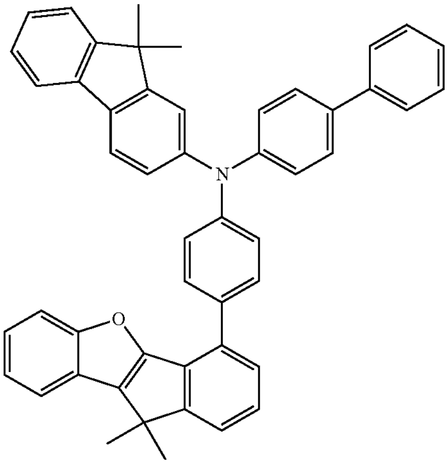

-continued
231
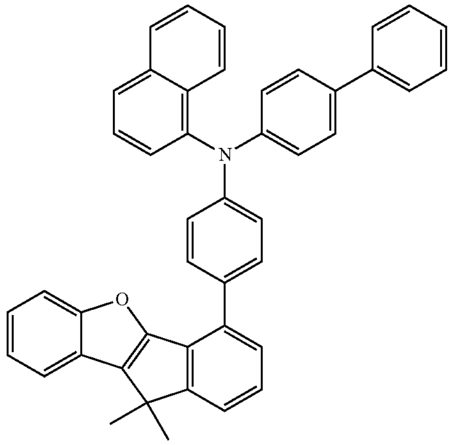
232
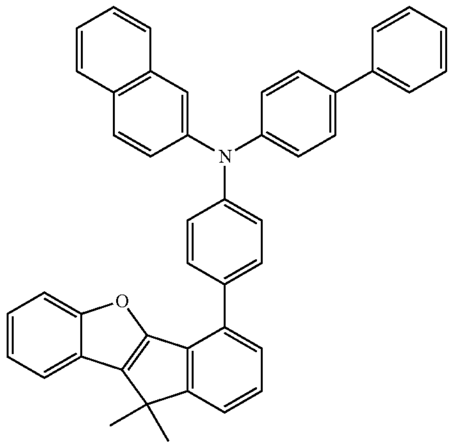
233
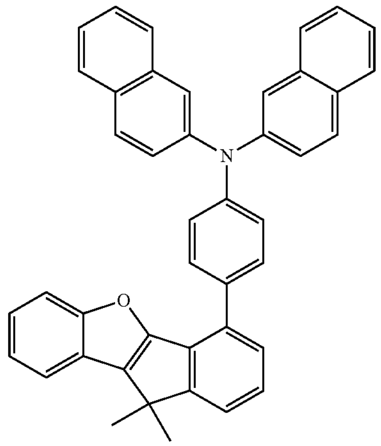
-continued
234
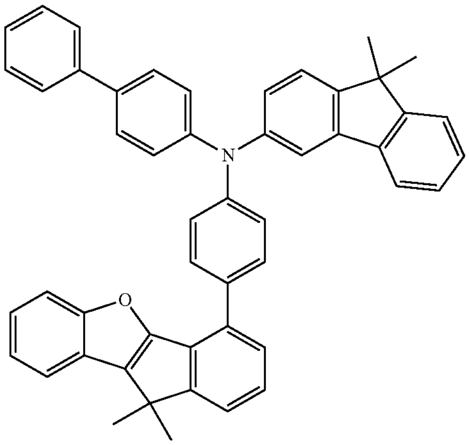
235
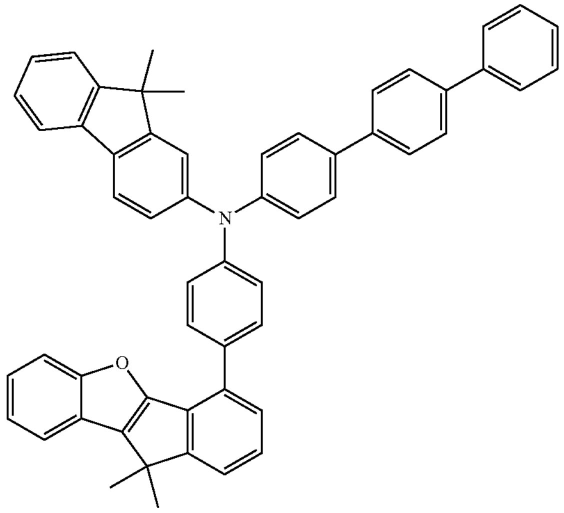
236
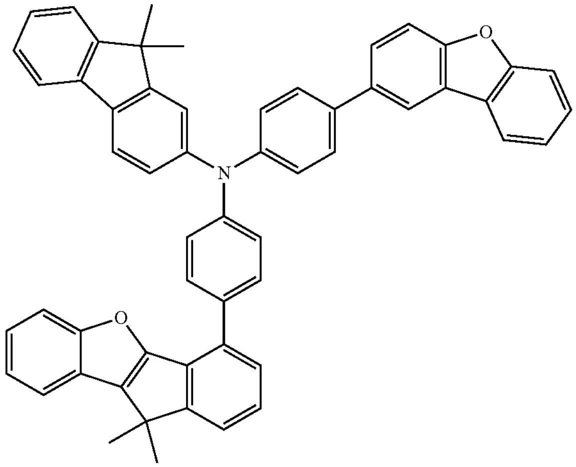

-continued
237
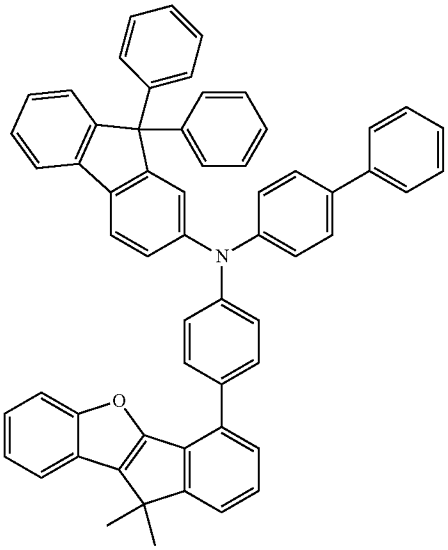
238
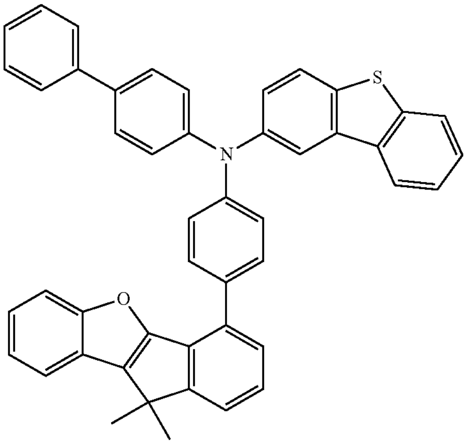
239
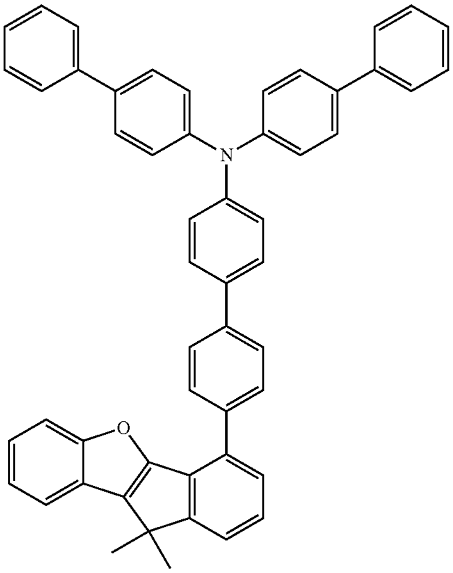
-continued
240
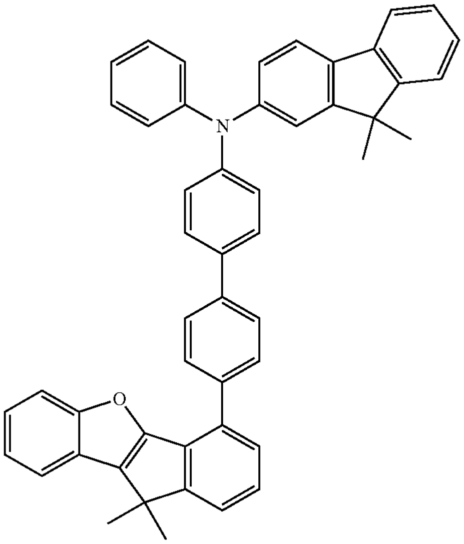
241
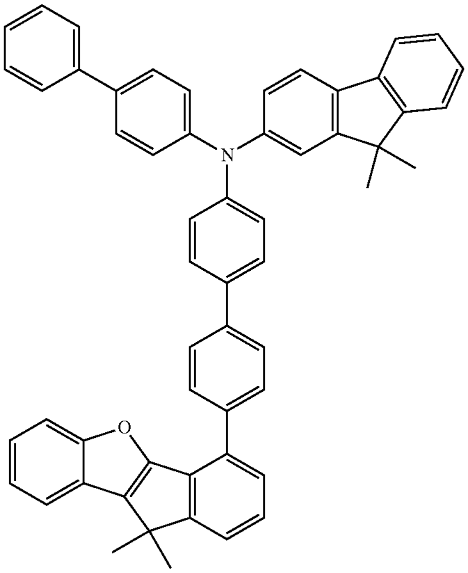

-continued
242
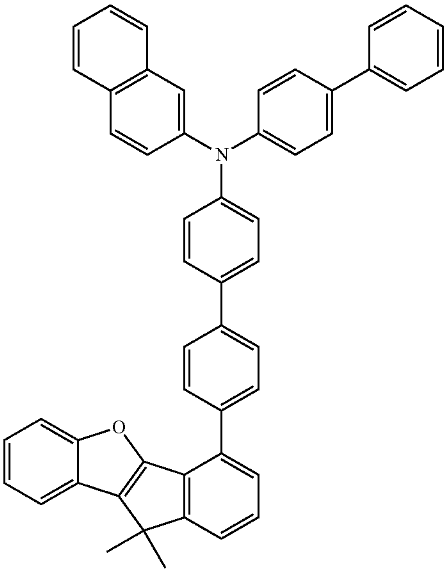
243
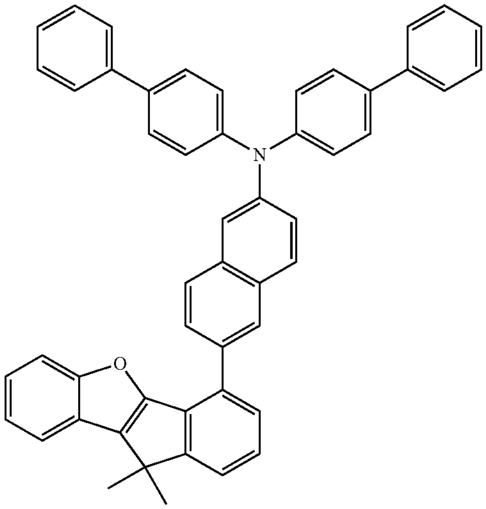
244
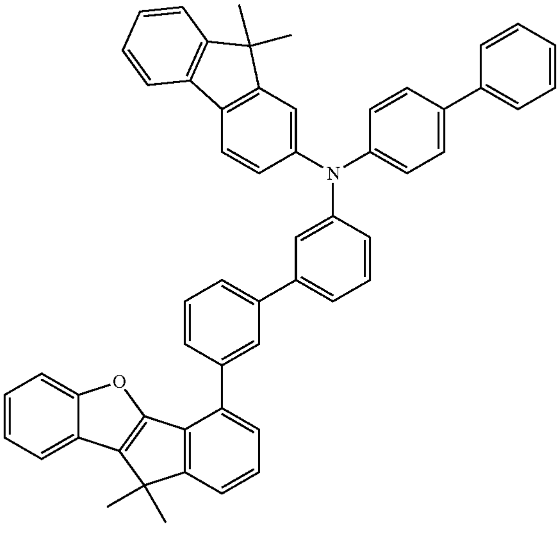
-continued
245
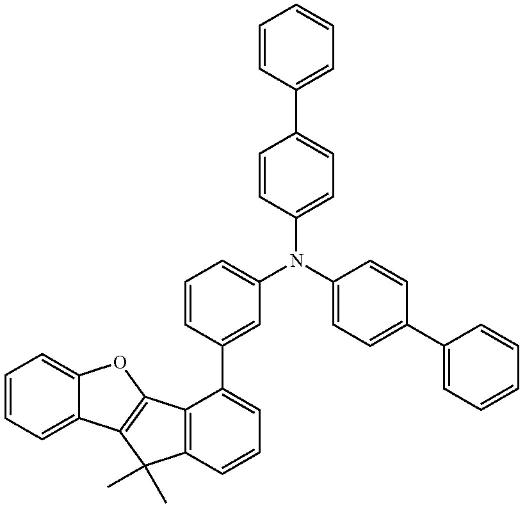
246
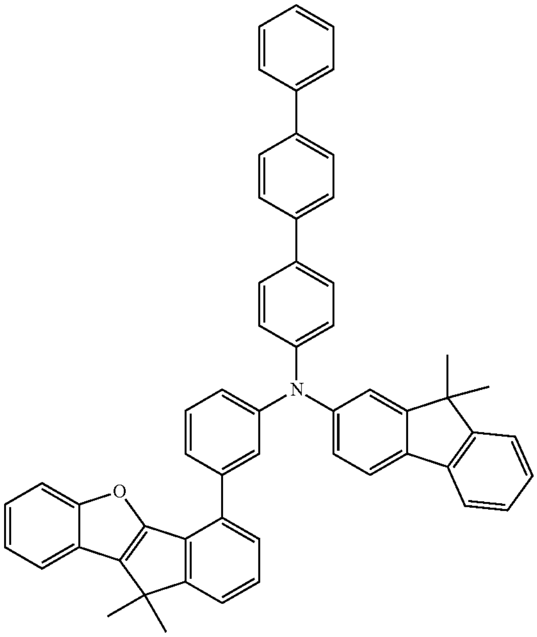
247
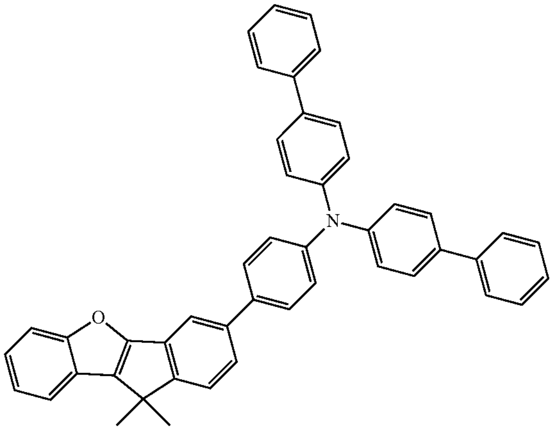

-continued
248
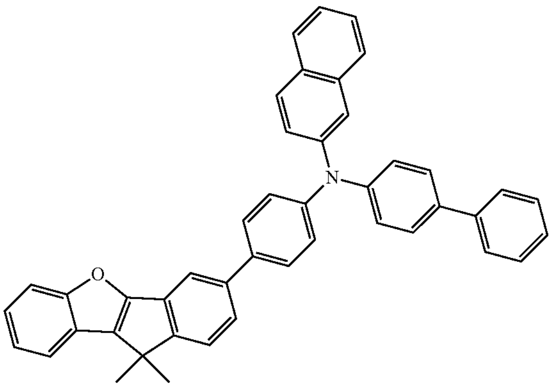
249
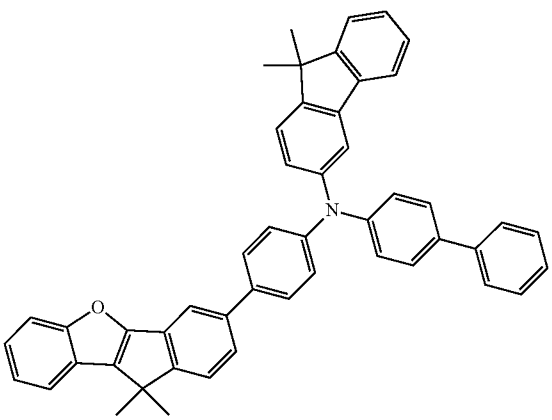
250
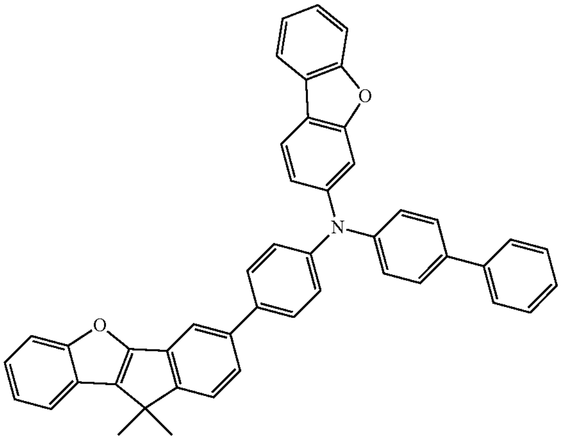
-continued
251
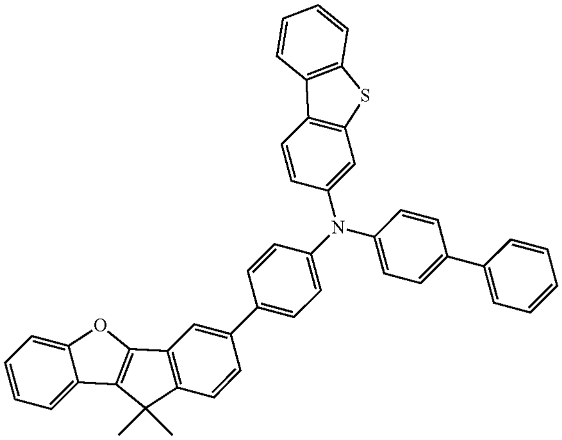
252
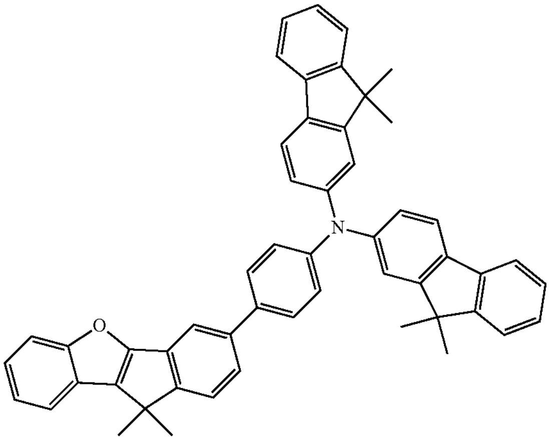
253
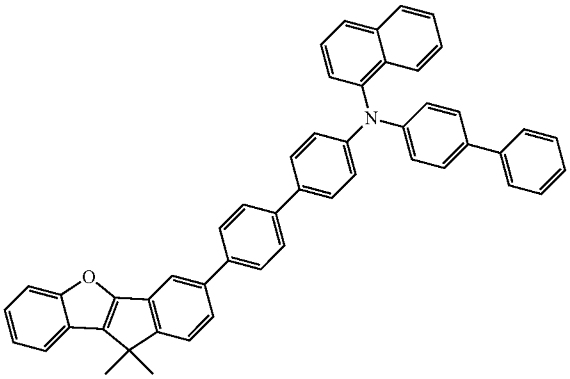

-continued
254
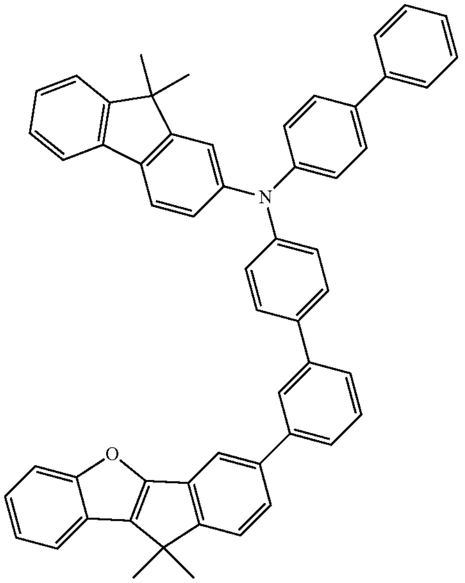
255
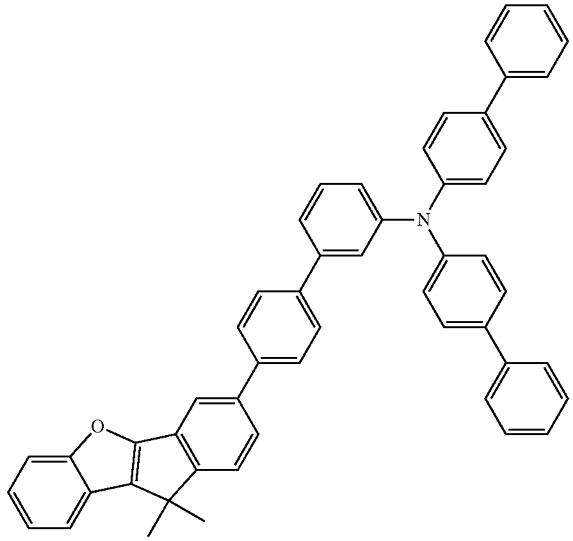
256
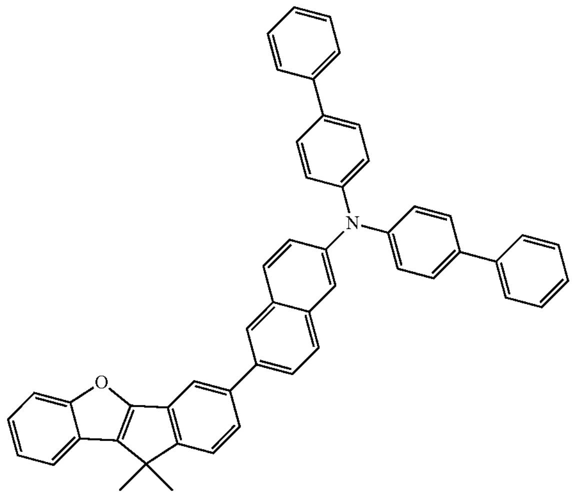
-continued
257
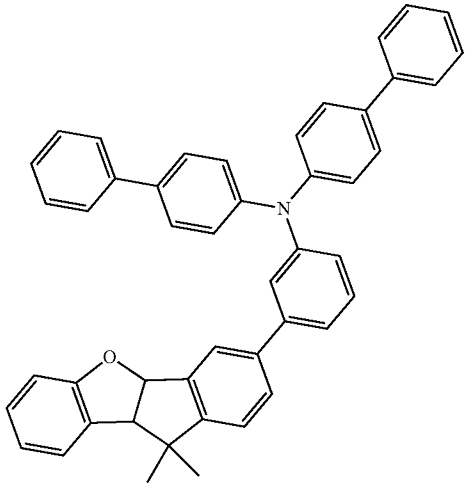
258
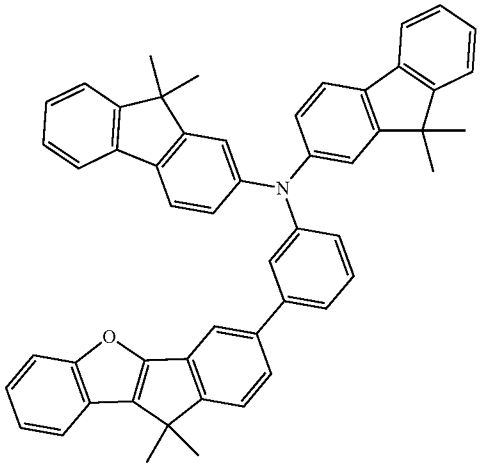
259
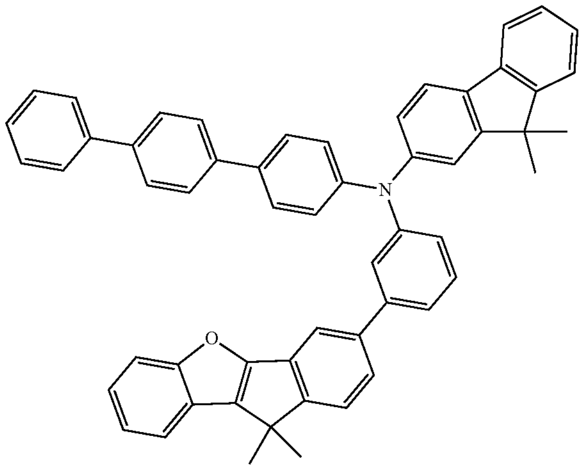

-continued
260
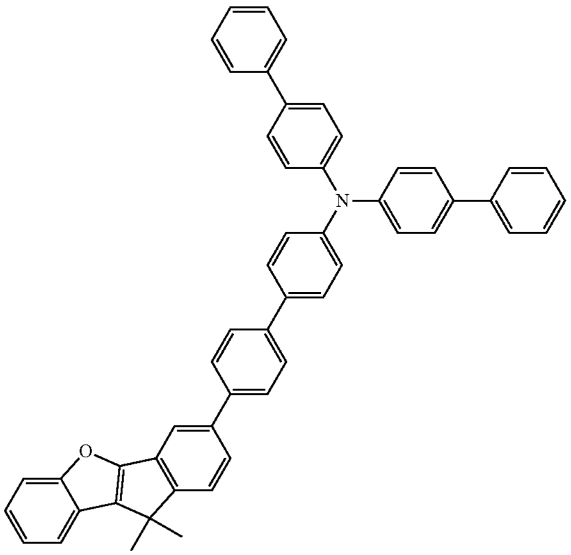
261
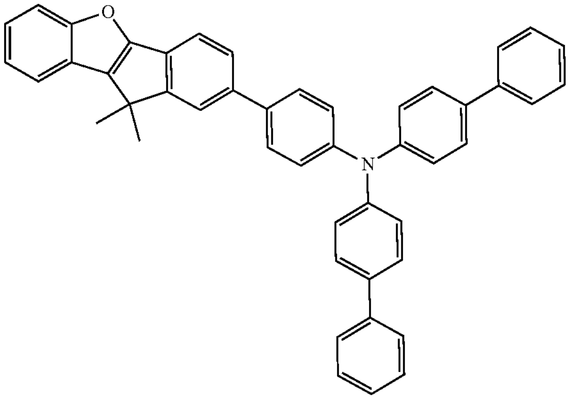
262
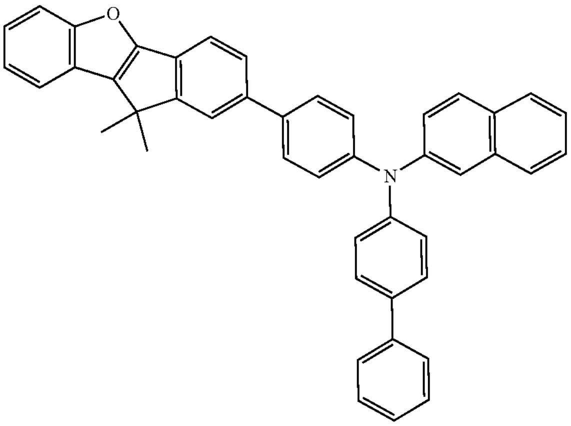
-continued
263
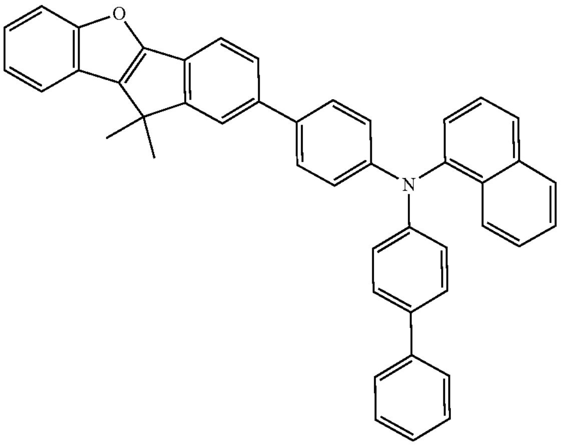
264
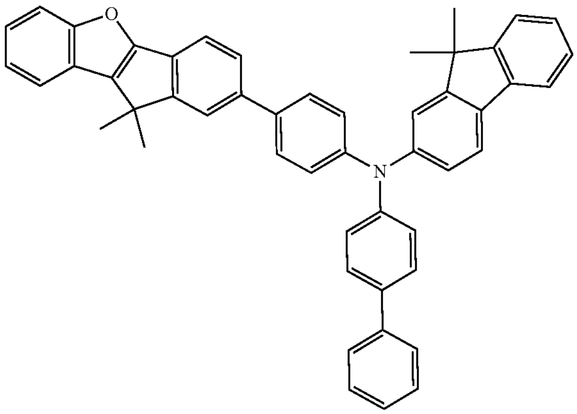
265
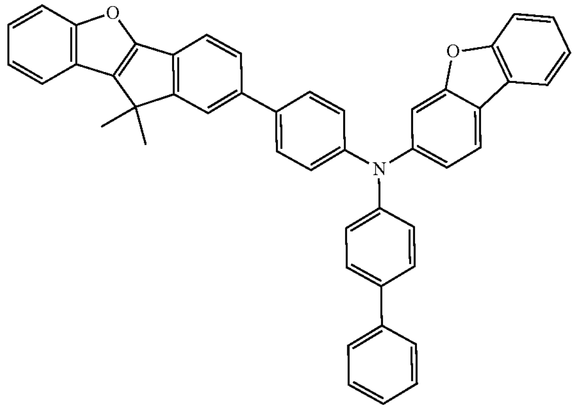

-continued
266
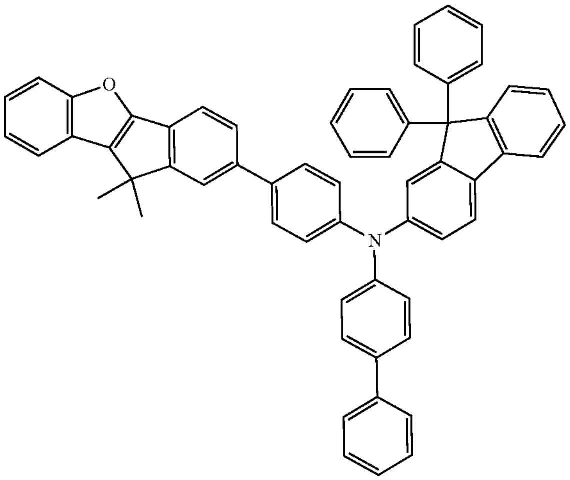
267
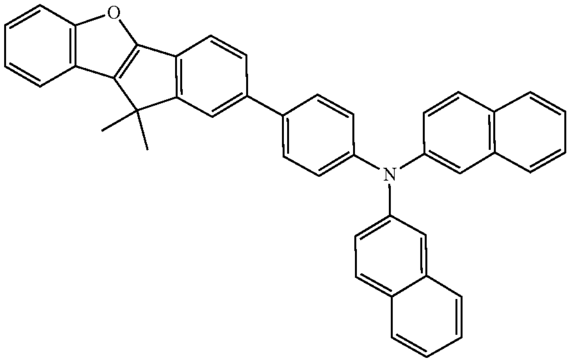
268
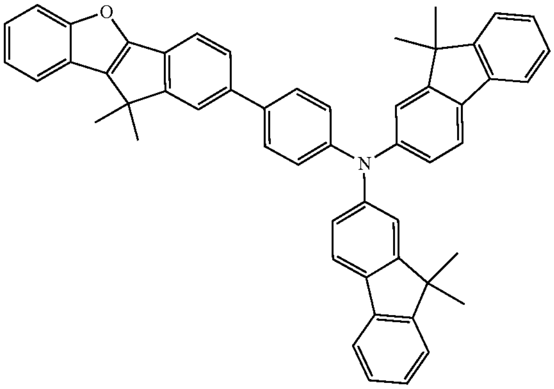
-continued
269
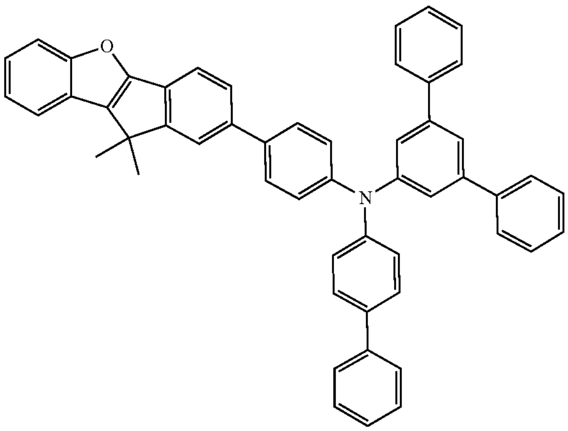
270
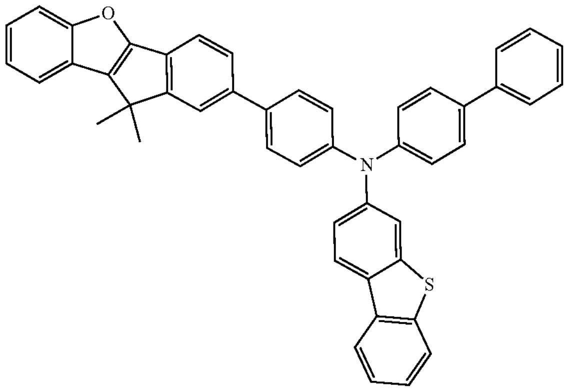
271
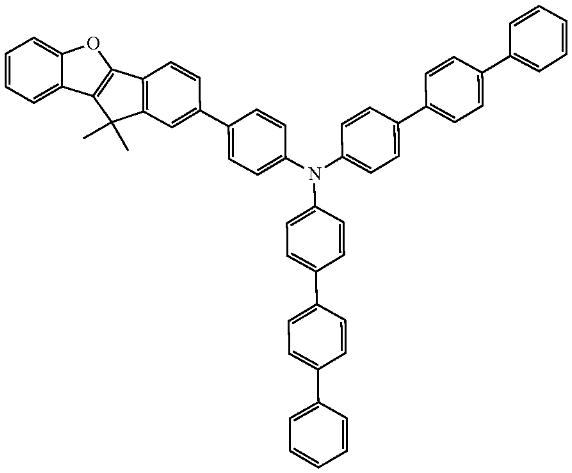

-continued
272
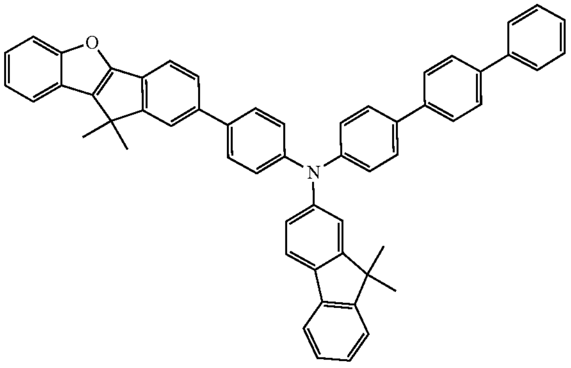
273
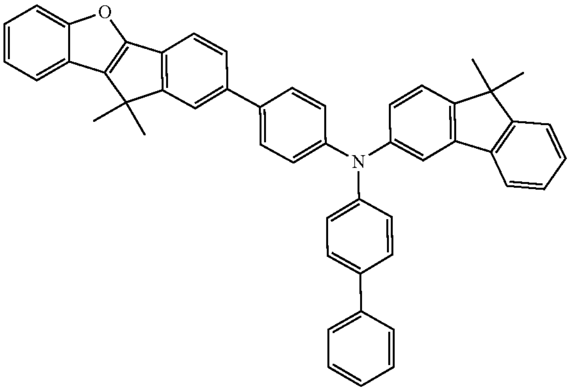
274
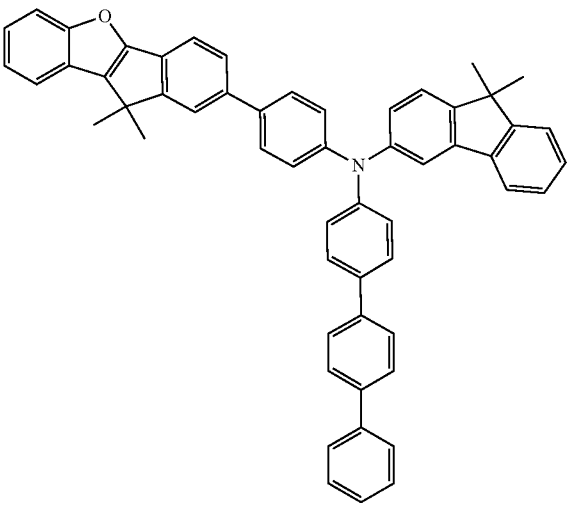
-continued
275
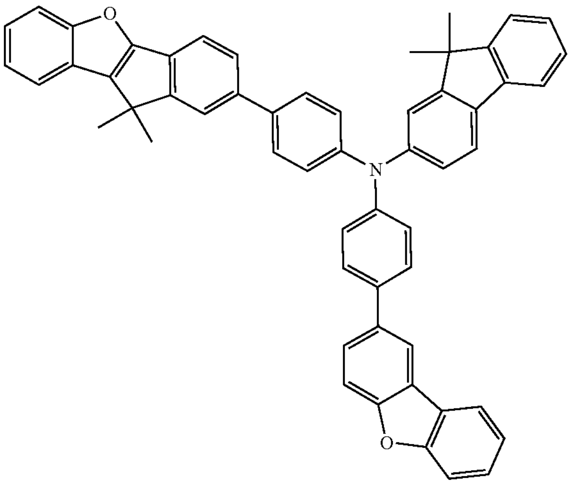
276
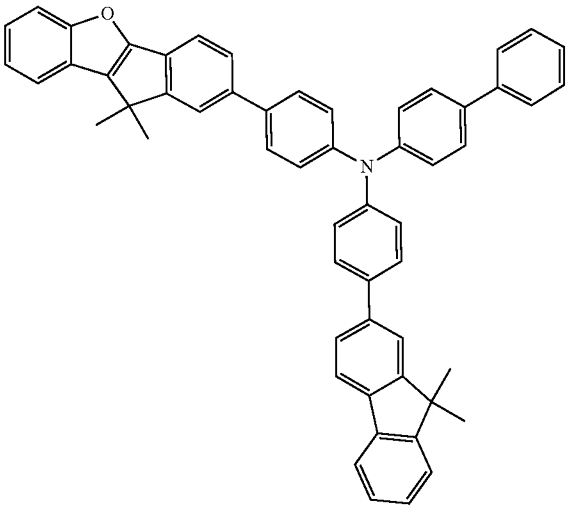
277
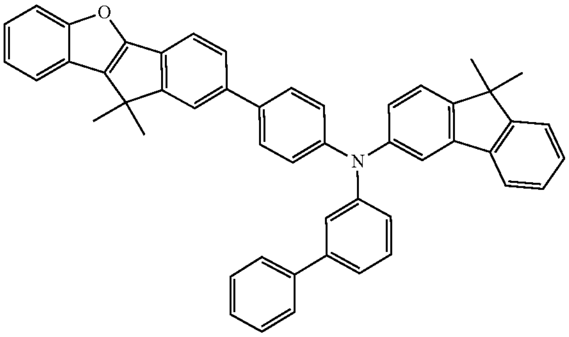

-continued
278
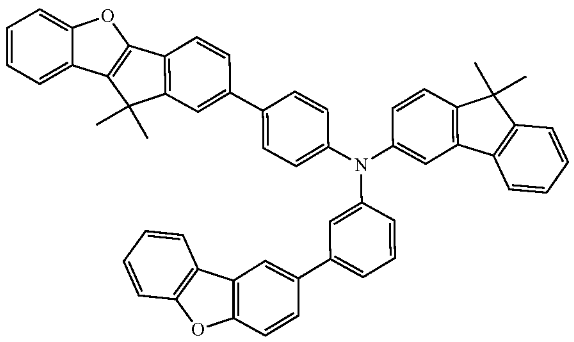
279
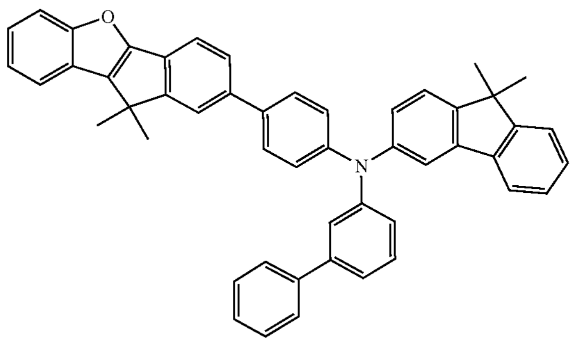
280
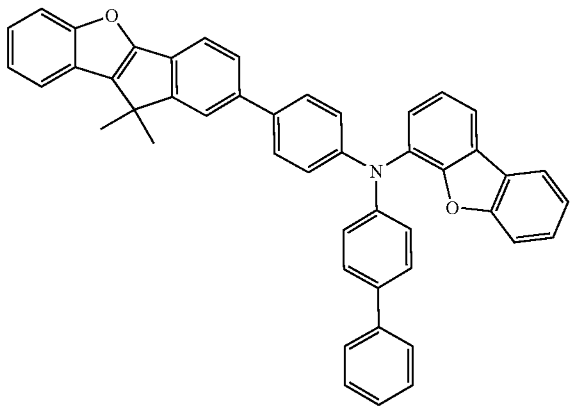
281
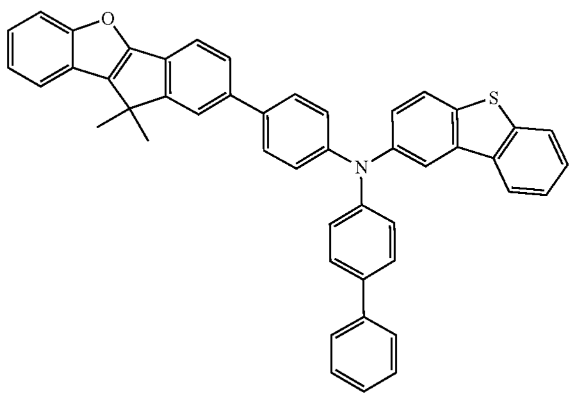
-continued
282
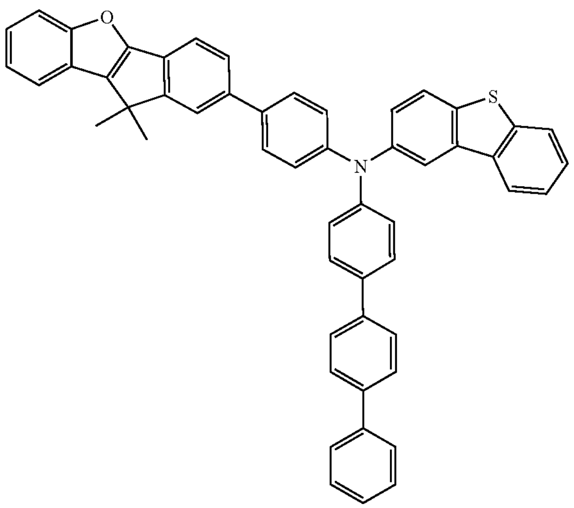
283
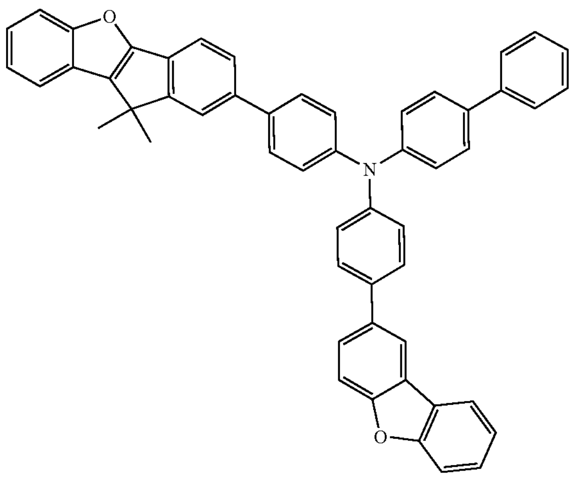
284
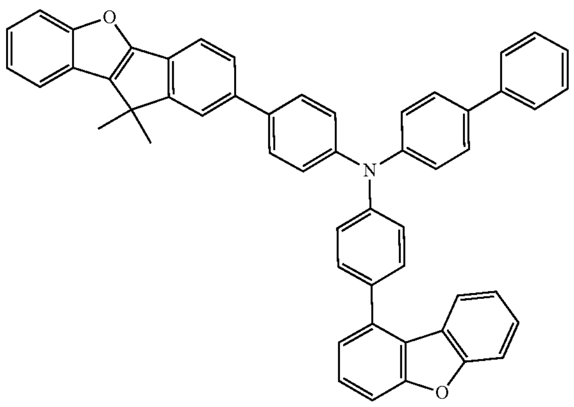

-continued
285
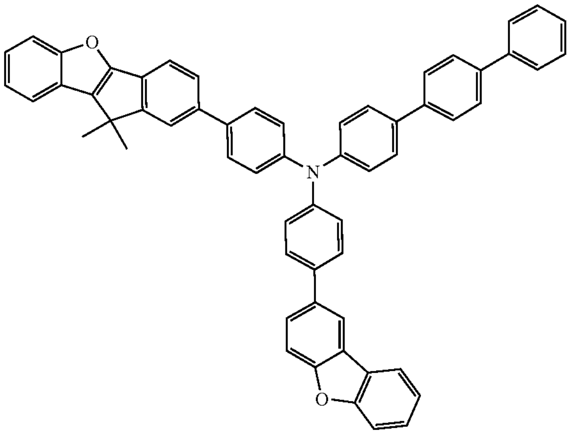
286
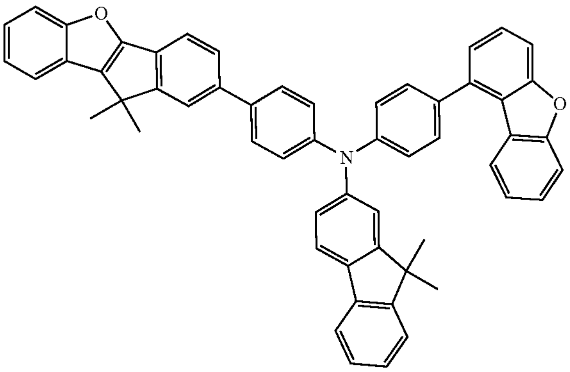
287
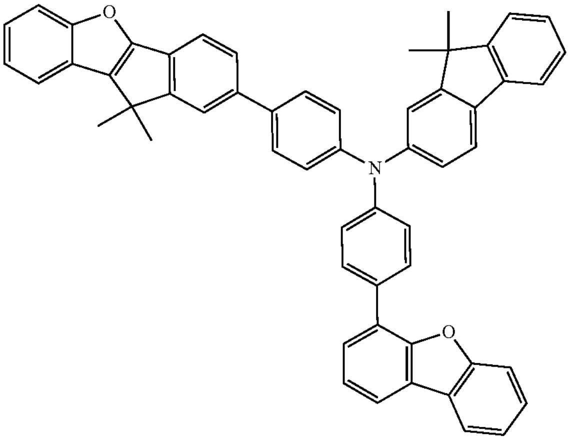
-continued
288
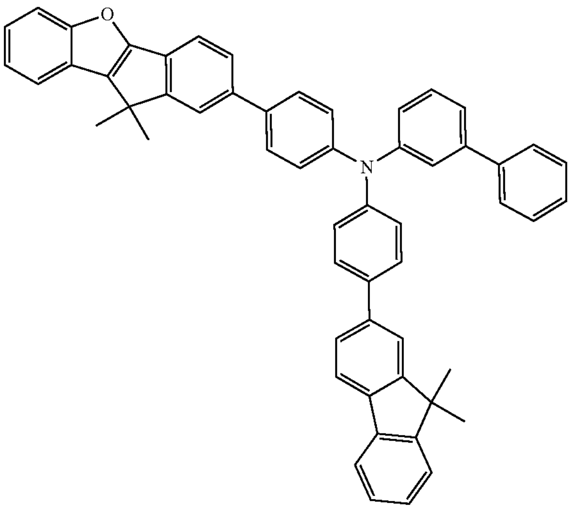
289
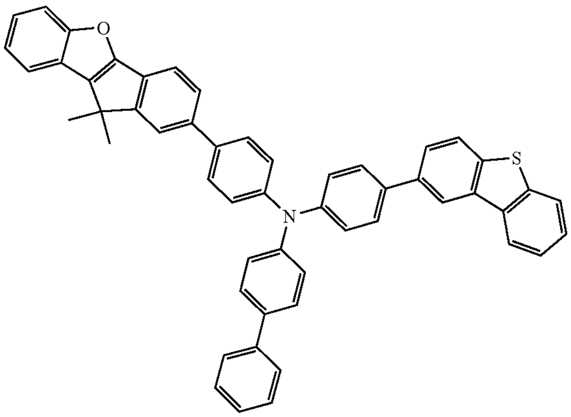
290
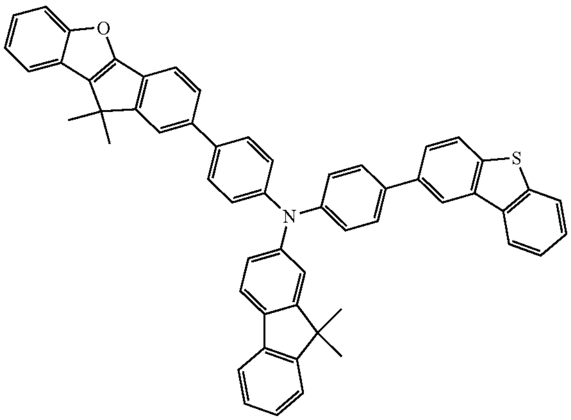

-continued
291
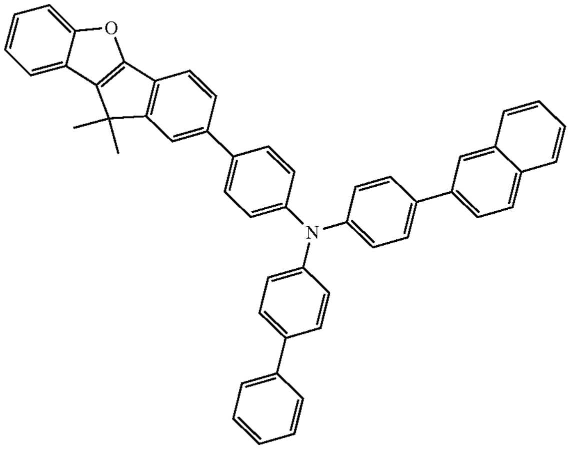
292
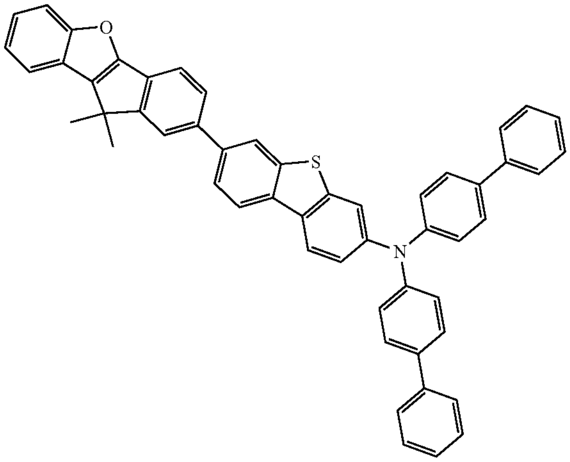
293
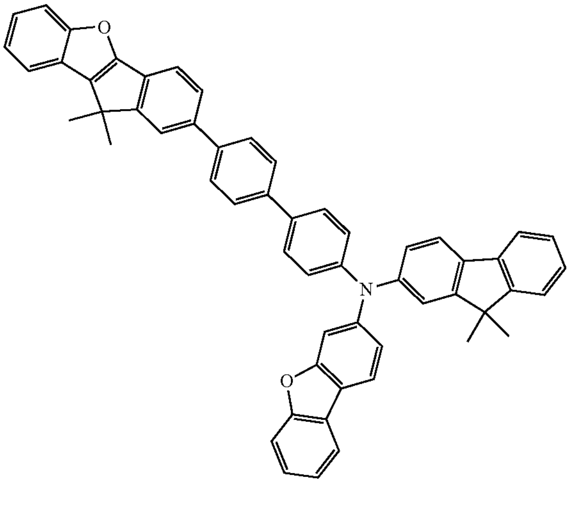
-continued
294
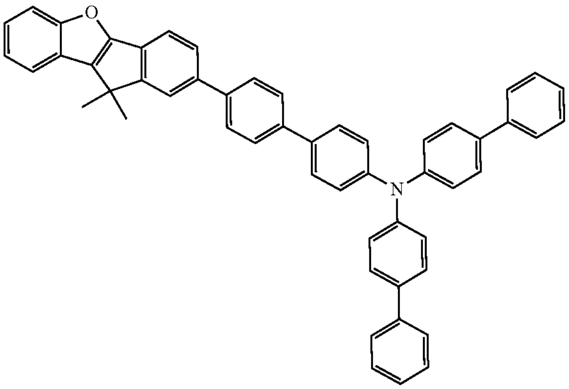
295
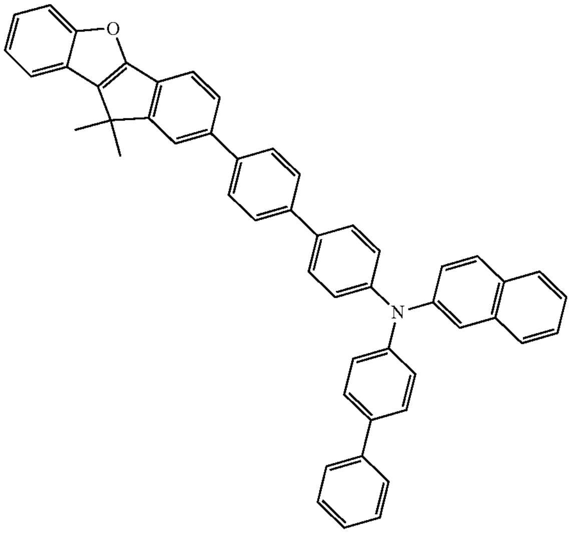
296
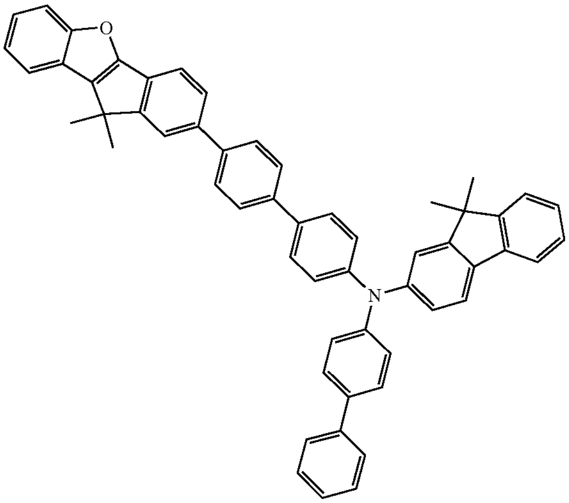

-continued
297
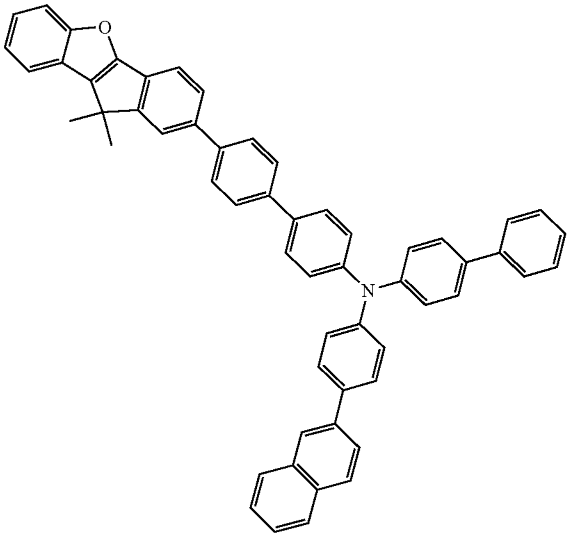
298
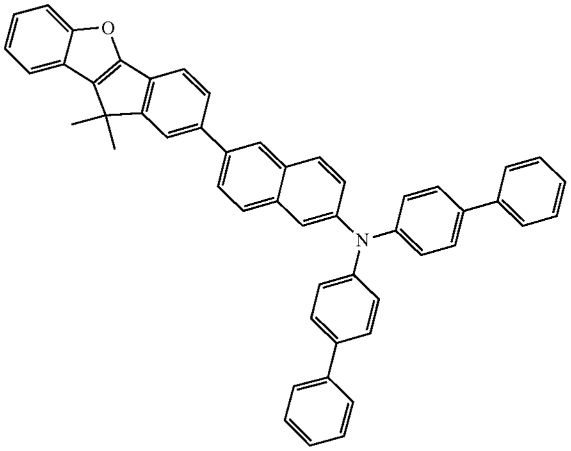
299
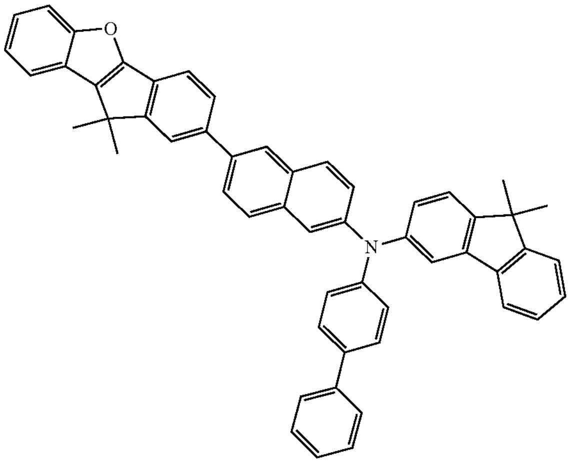
-continued
300
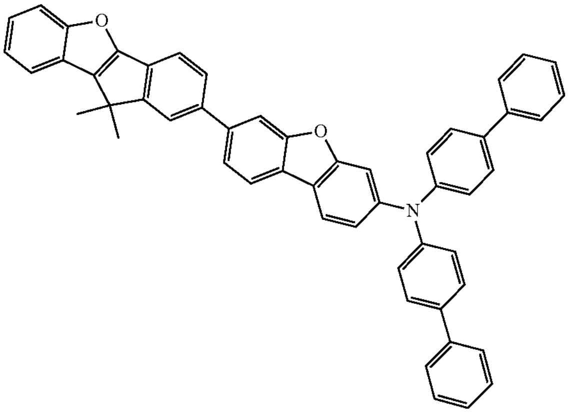
301
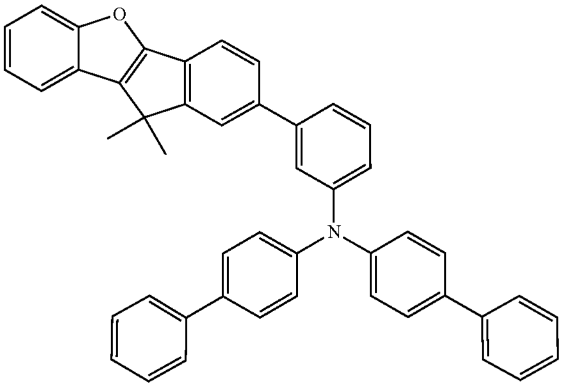
302
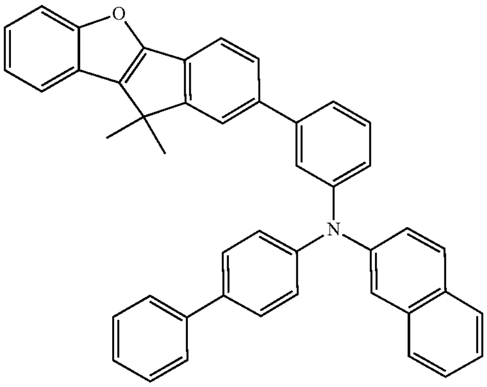

-continued
303
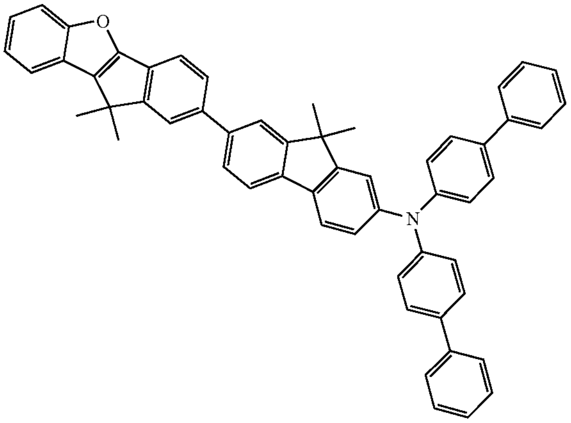
304
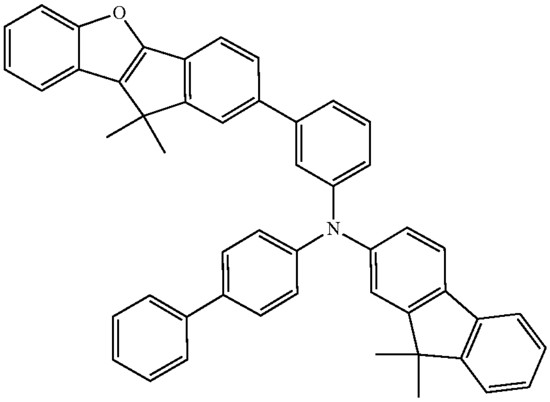
305
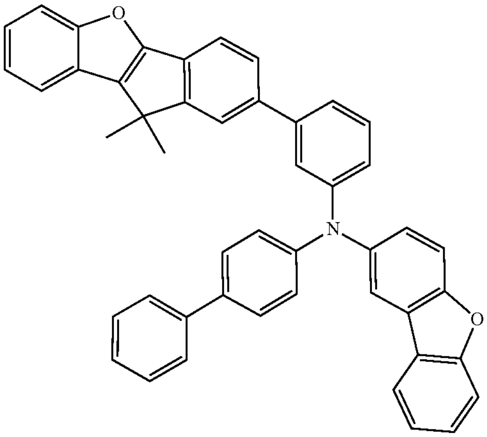
-continued
306
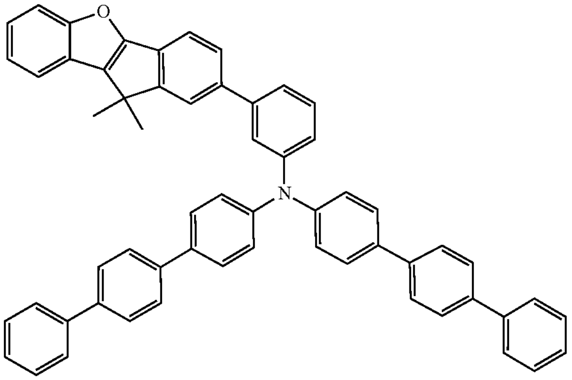
307
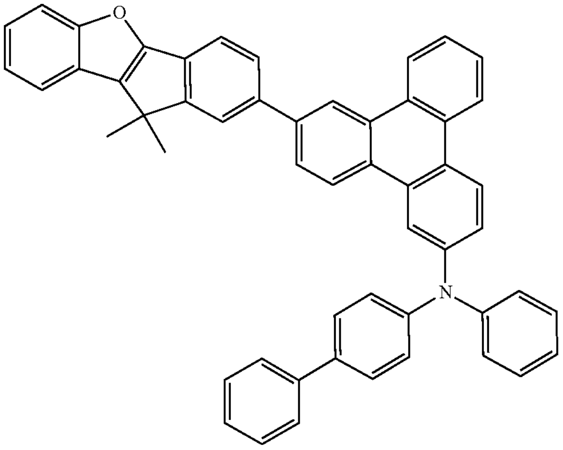
308
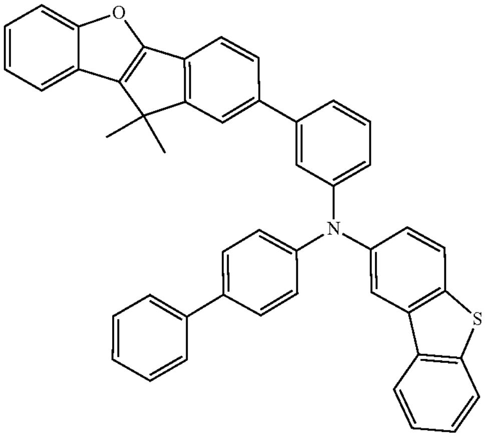

-continued
309
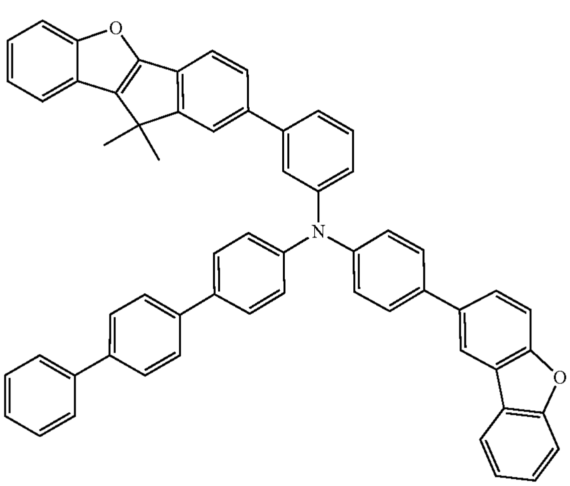
310
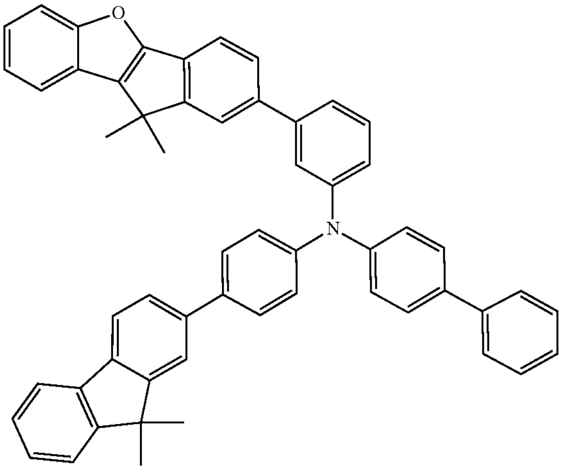
311
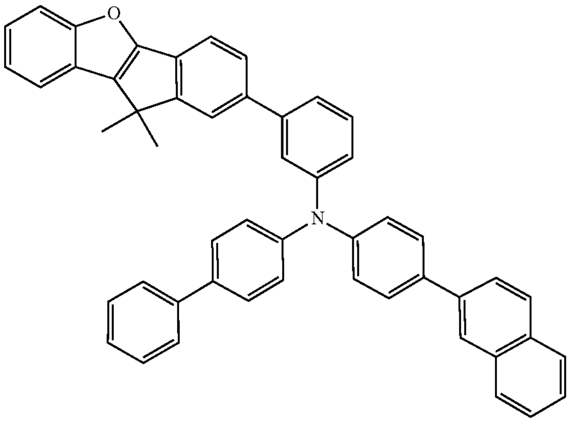
-continued
312
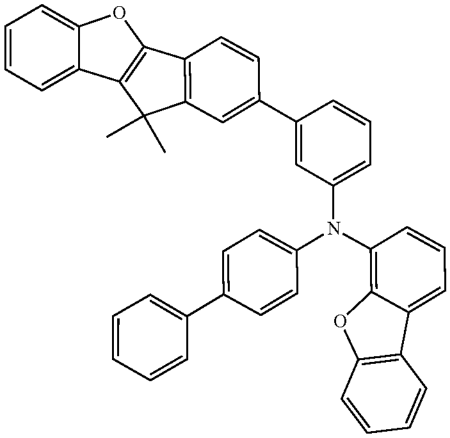
313
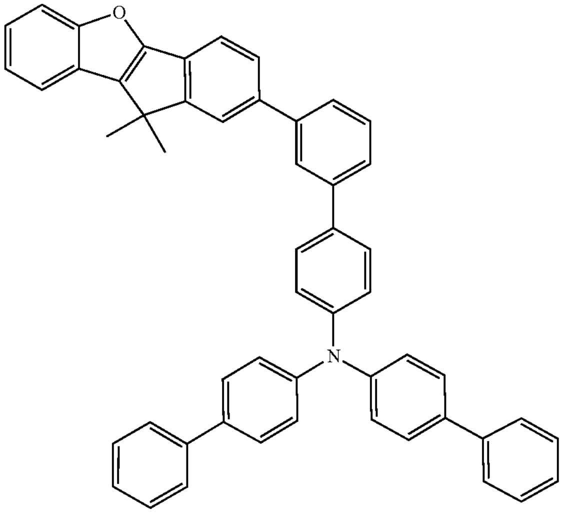
314
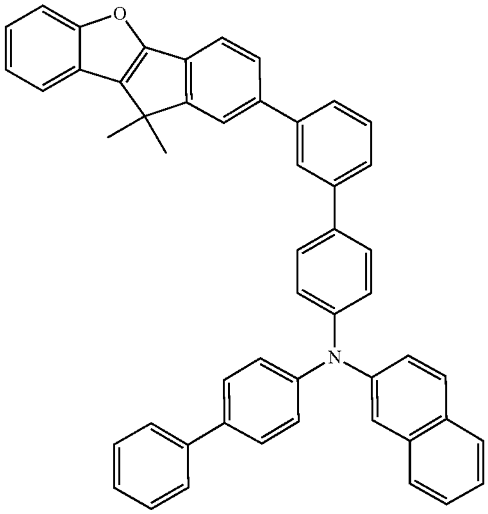

-continued
315
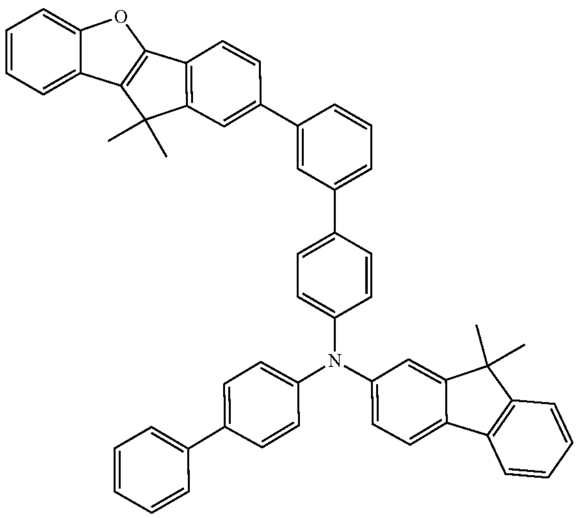
316
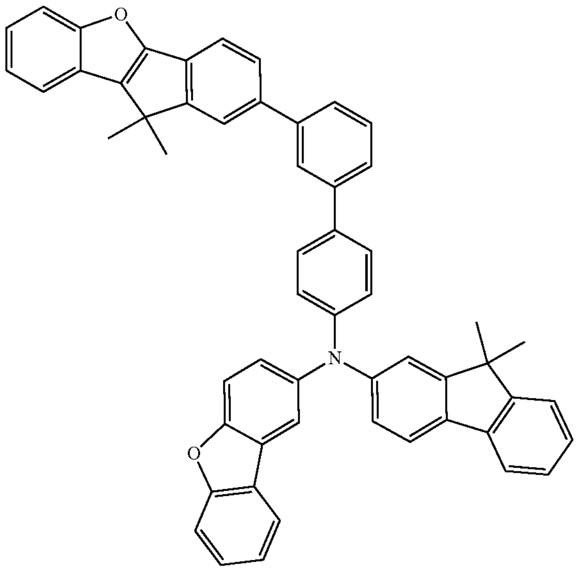
317
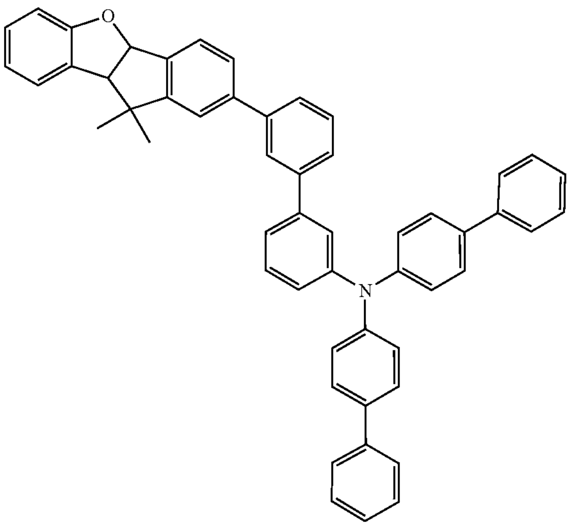
-continued
318
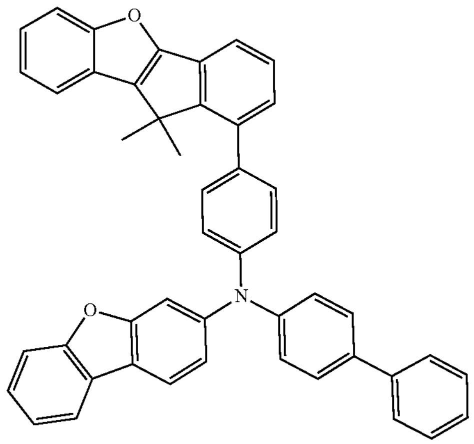
319
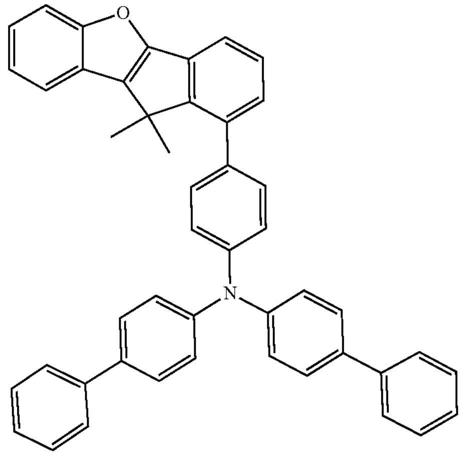
320
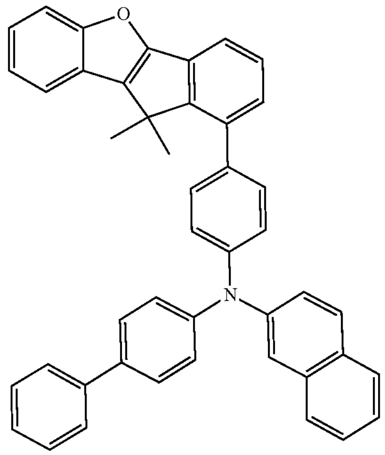

-continued
321
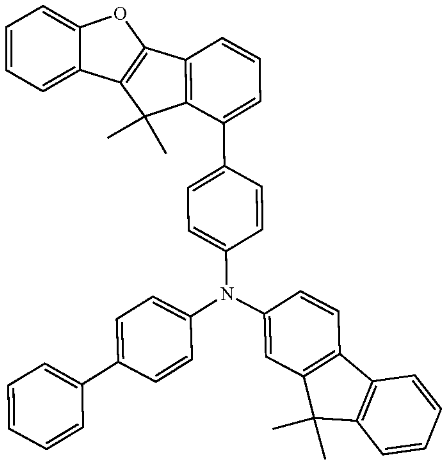
322
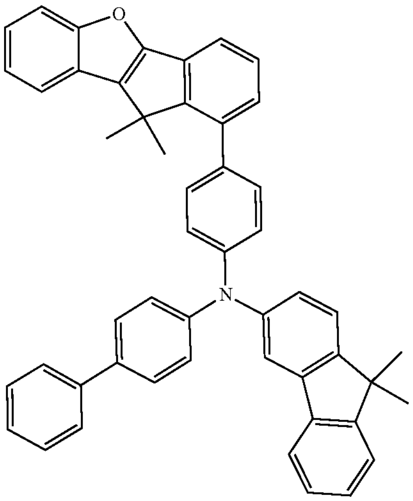
323
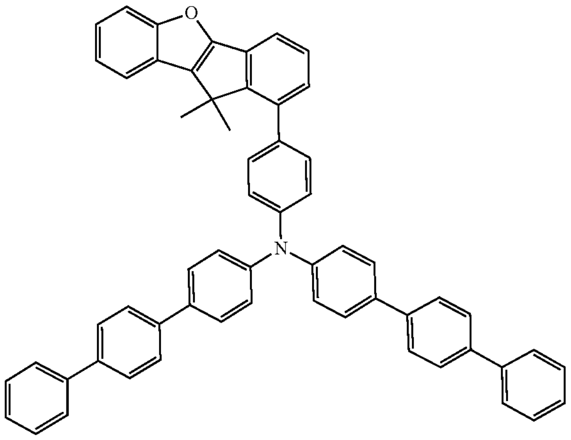
-continued
324
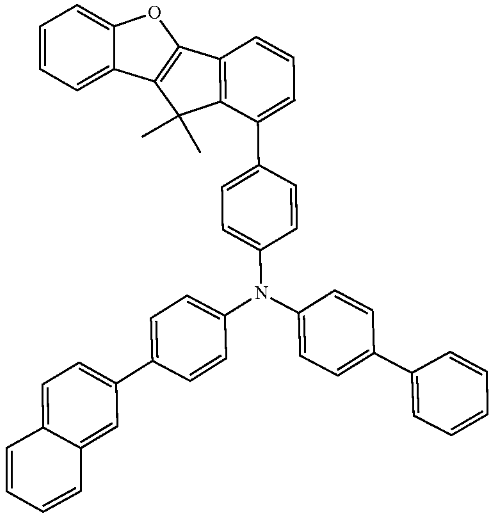
325
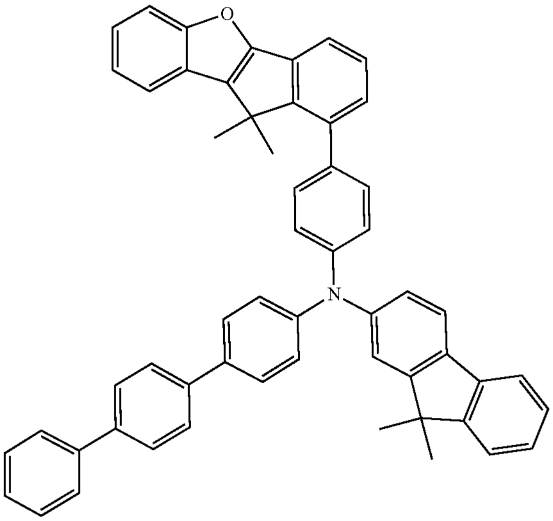
326
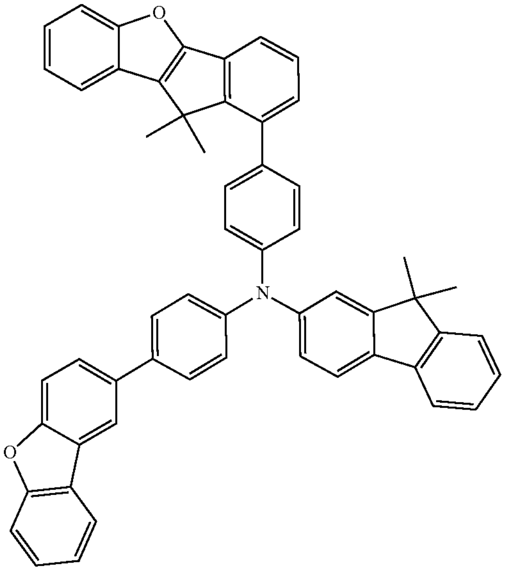

-continued
327
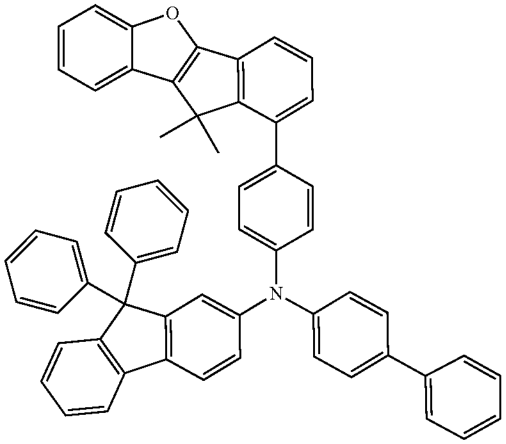
328
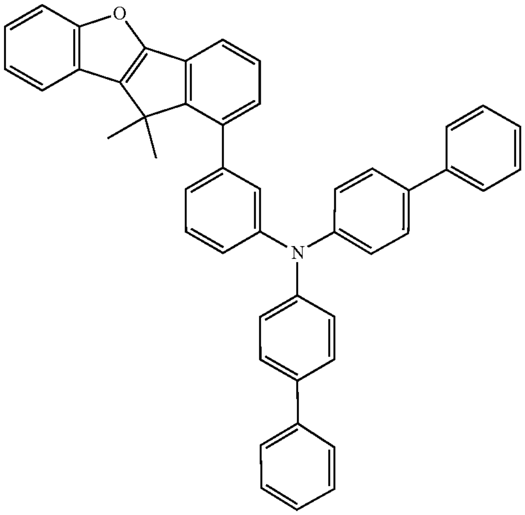
329
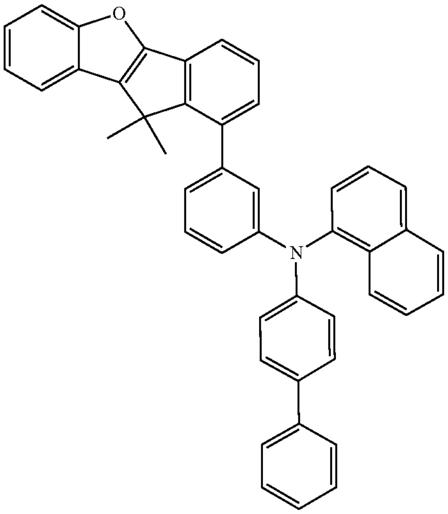
-continued
330
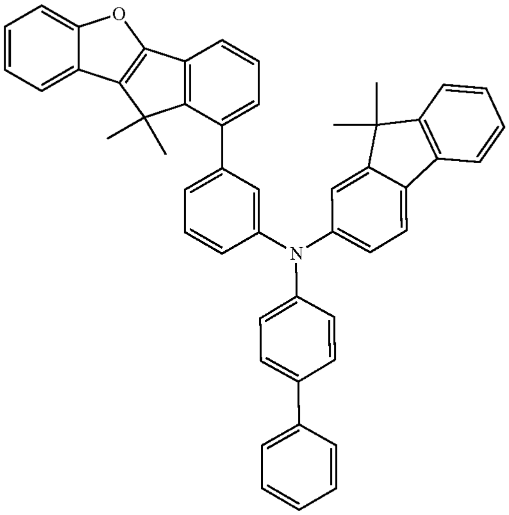
331
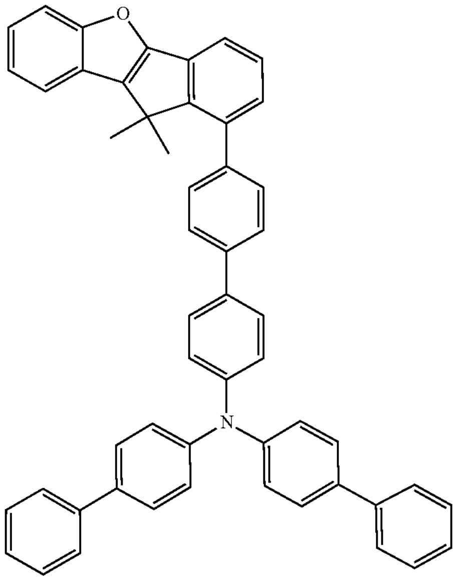

-continued
332
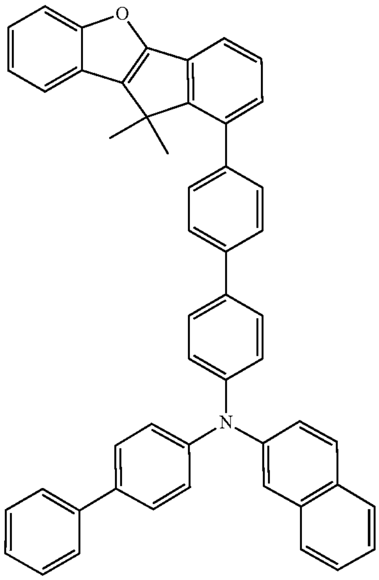
333
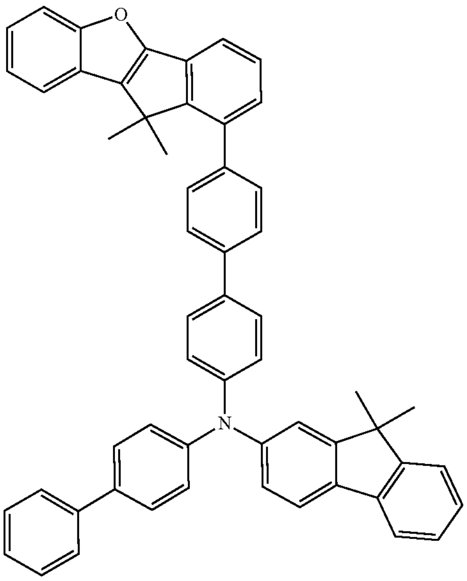
-continued
334
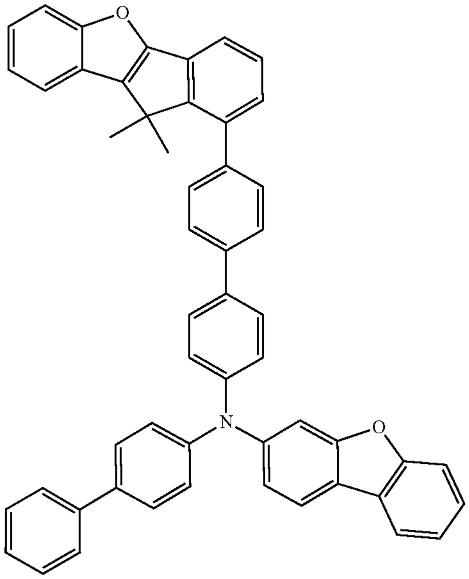
335
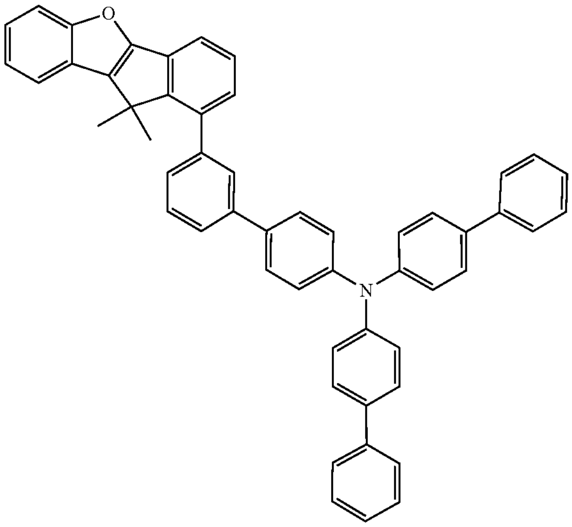

-continued
336
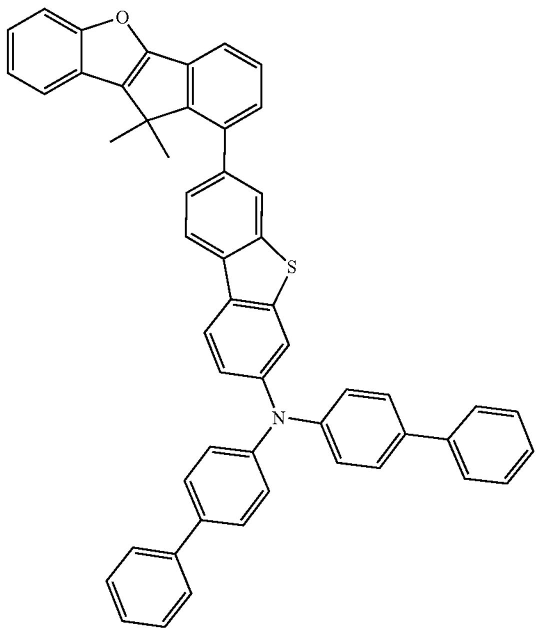
337
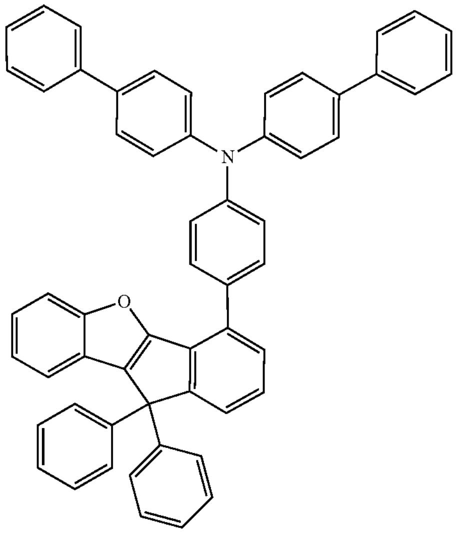
-continued
338
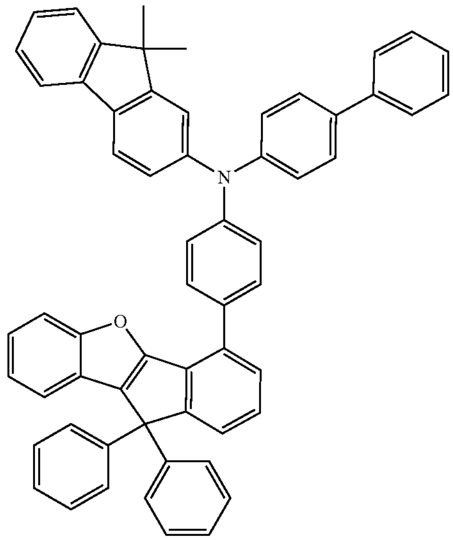
339
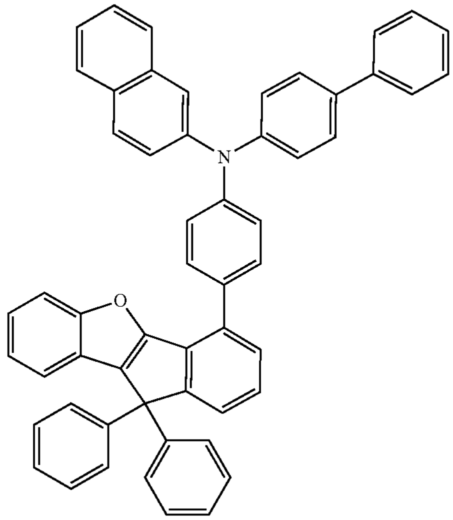
340
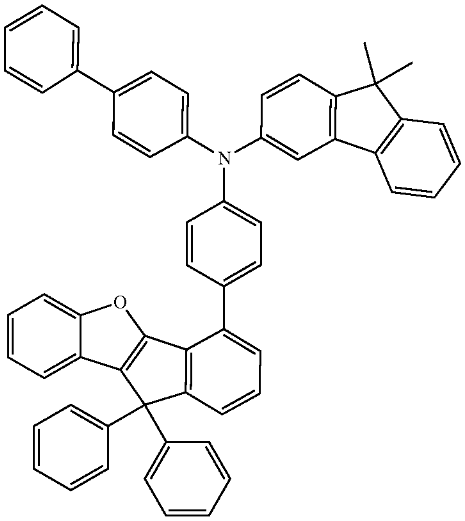

-continued
341
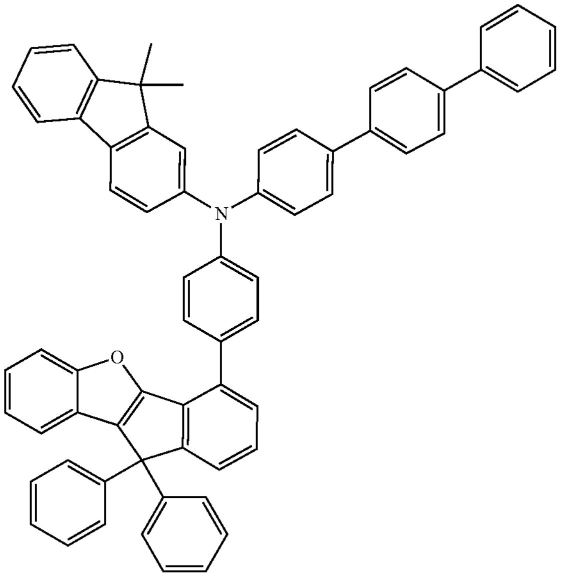
342
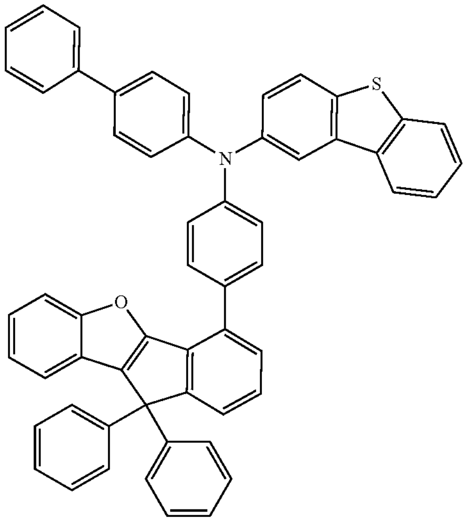
-continued
343
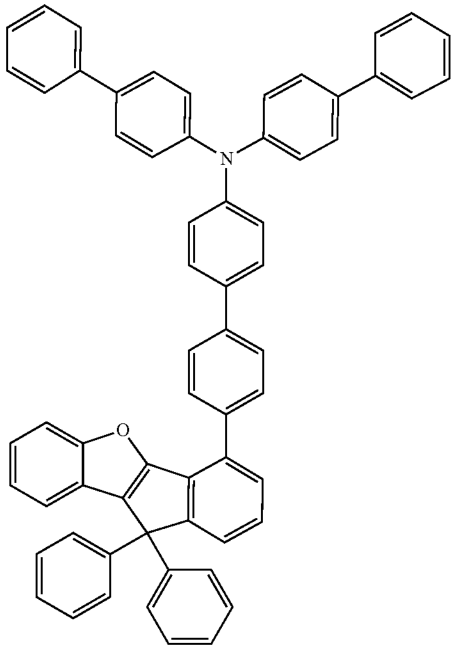
344
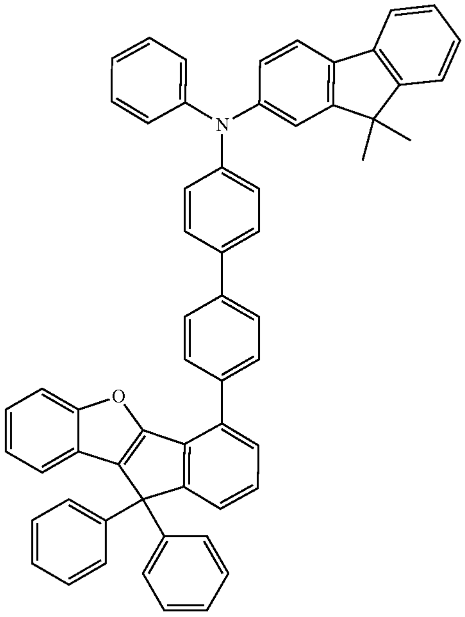

-continued
345
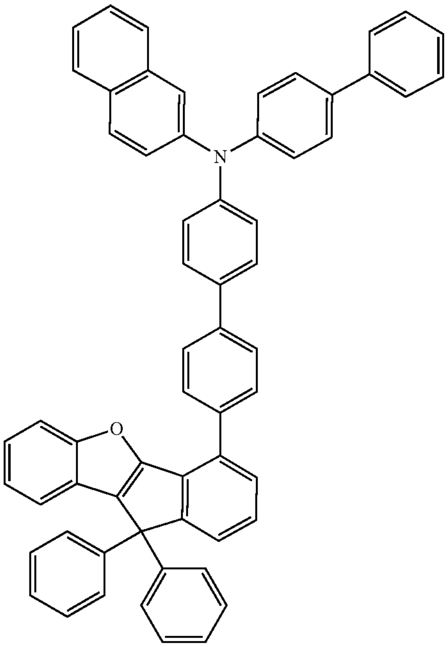
346
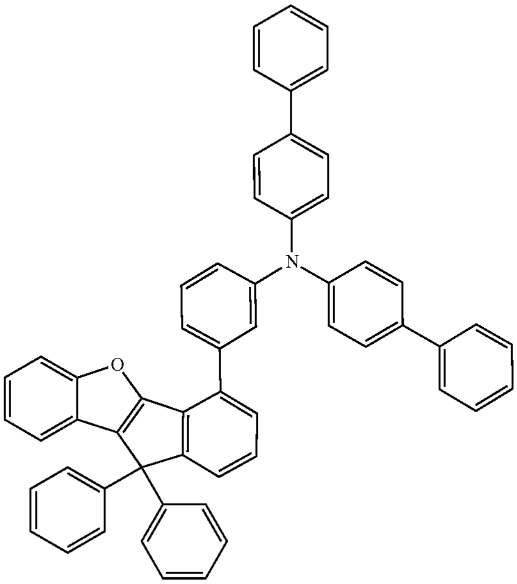
-continued
347
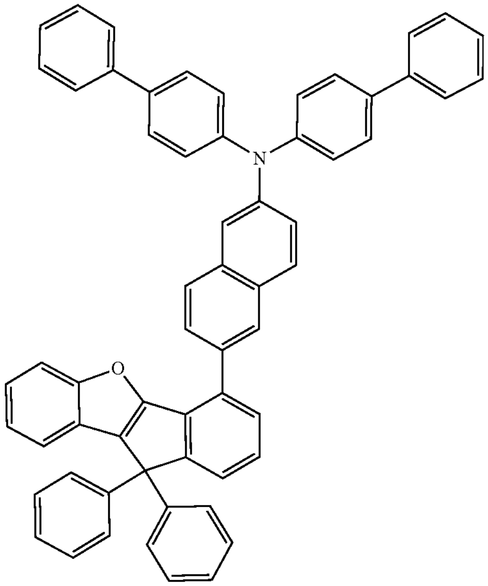
348
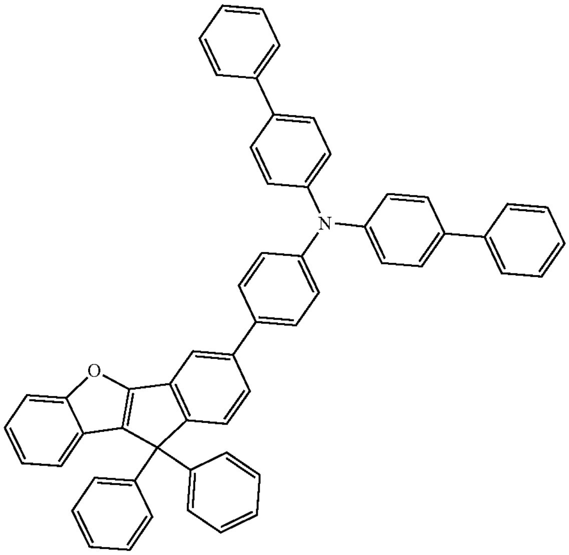

-continued
349
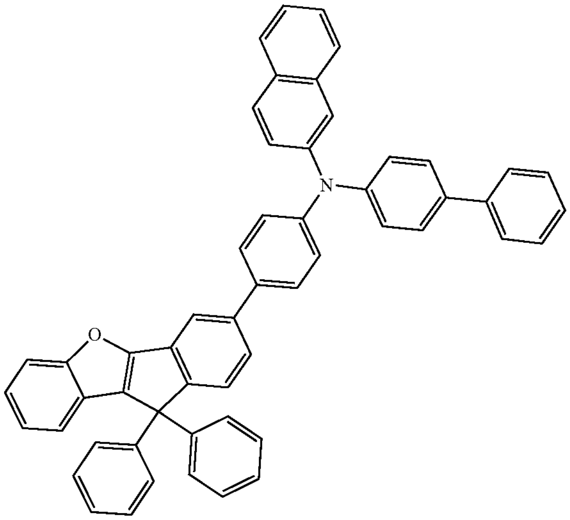
350
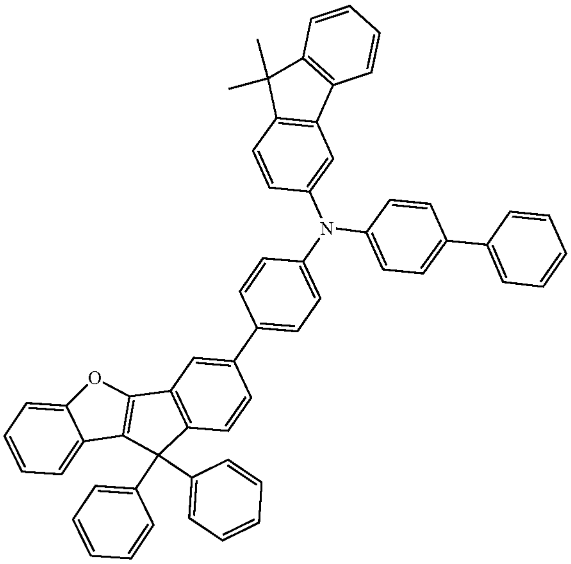
-continued
351
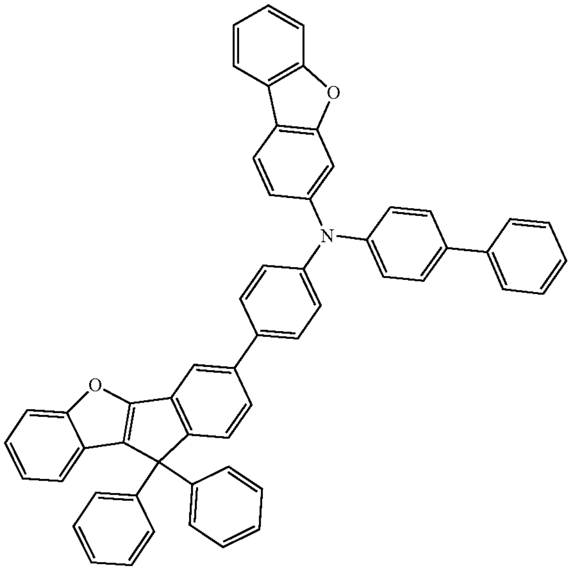
352
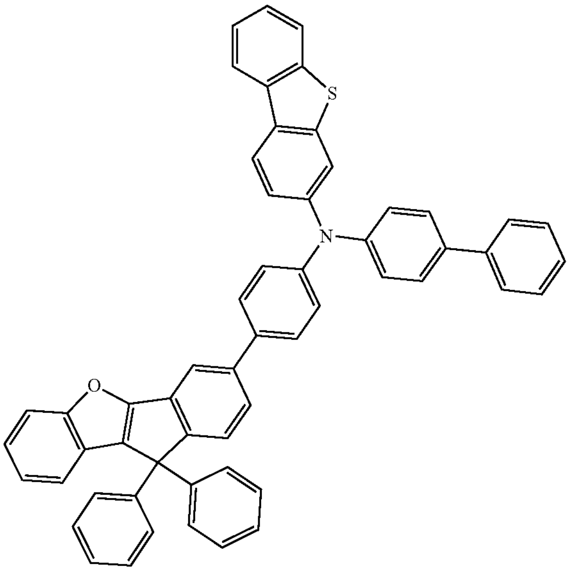

-continued
353
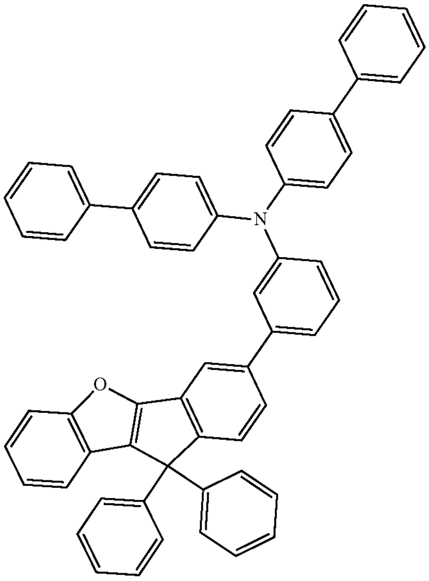
354
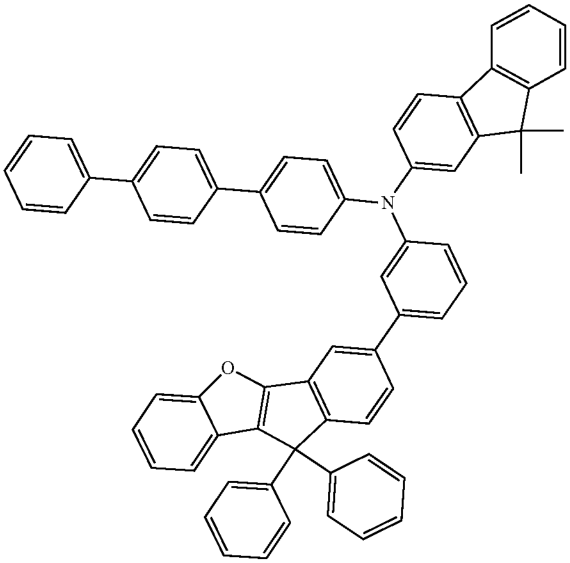
-continued
355
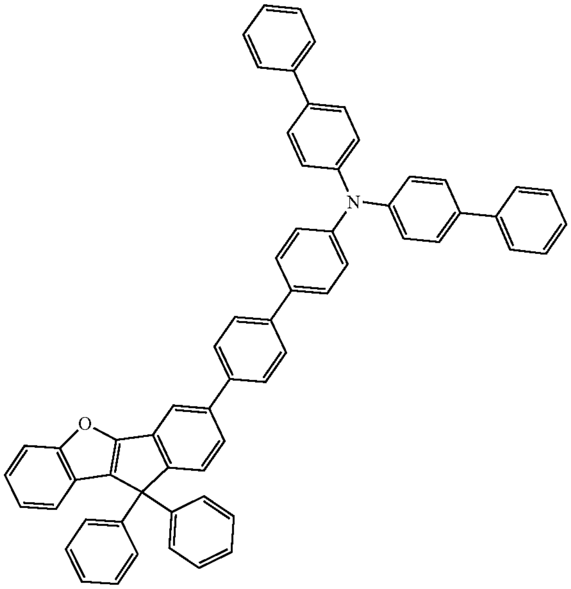
356
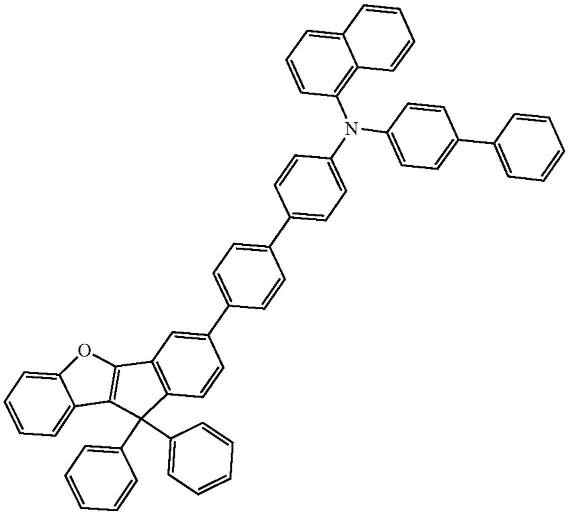
357
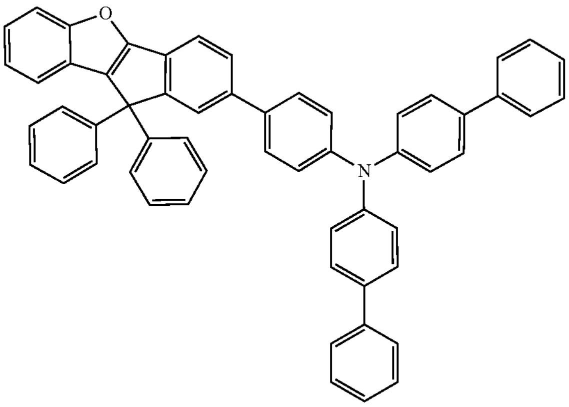

-continued
358
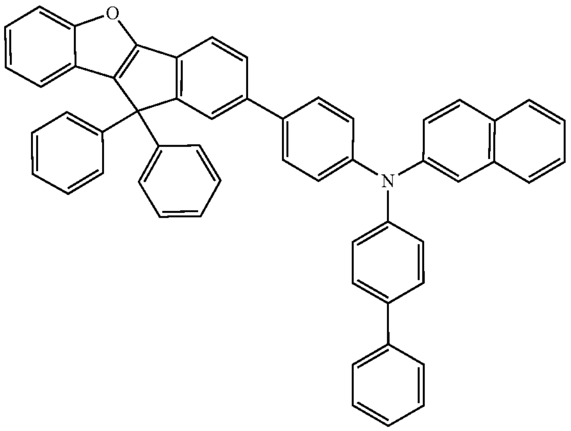
359
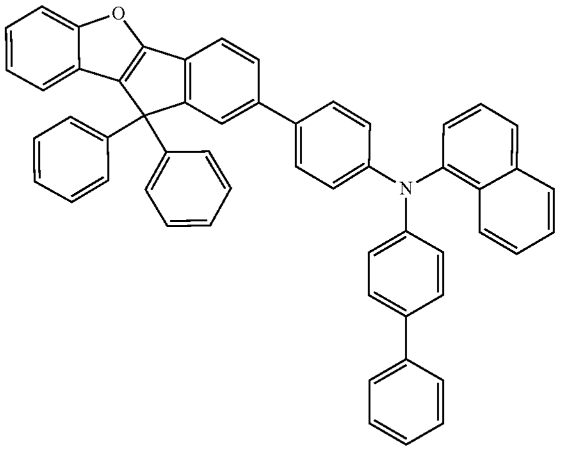
360
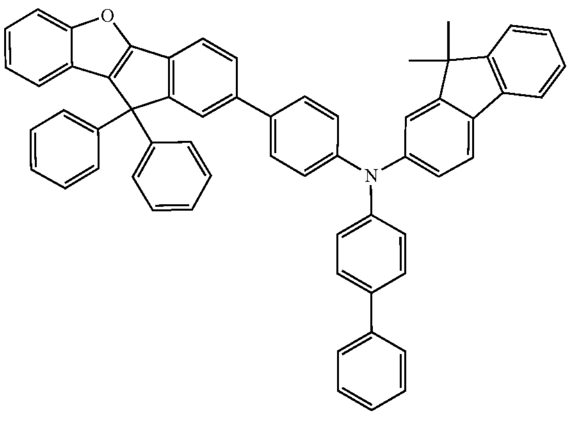
-continued
361
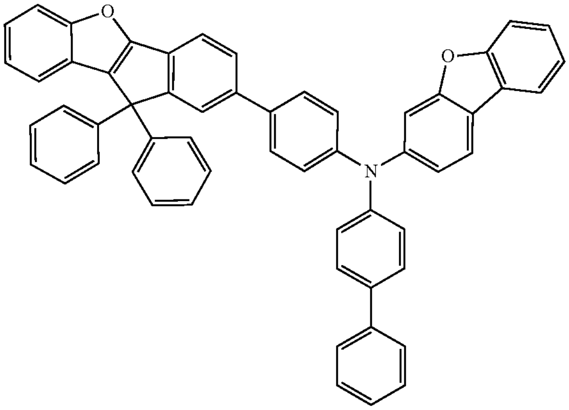
362
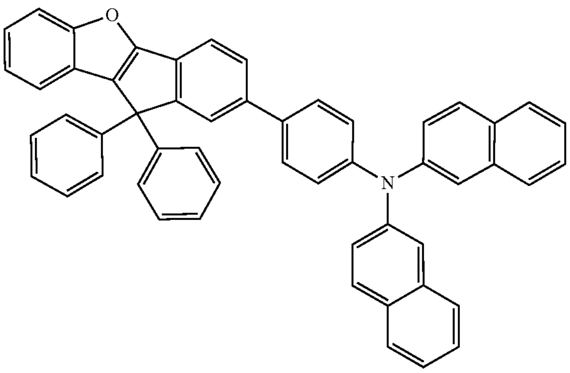
363
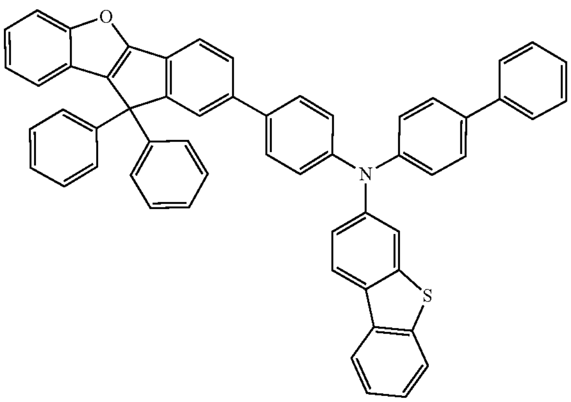

-continued
364
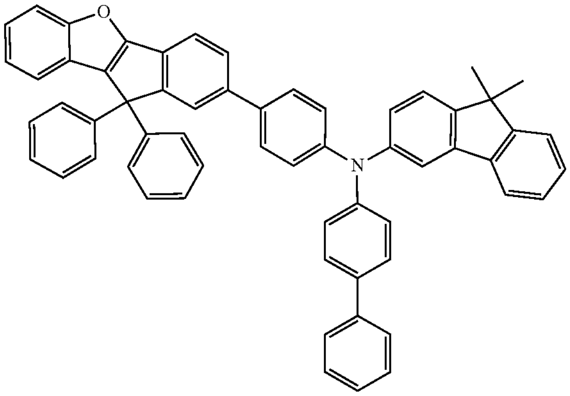
365
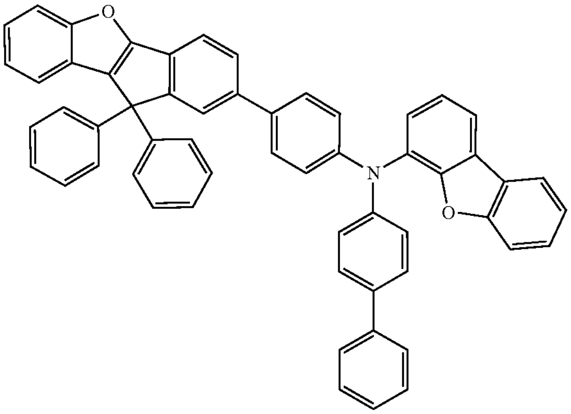
366
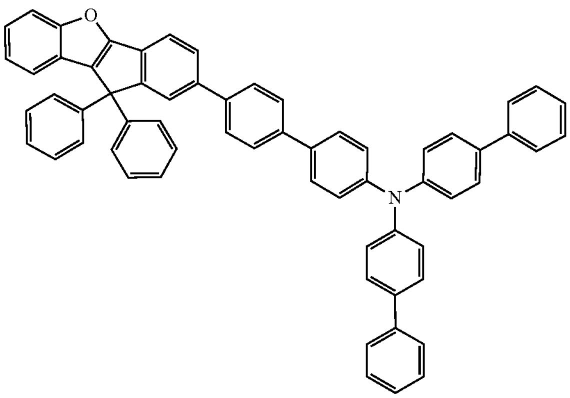
-continued
367
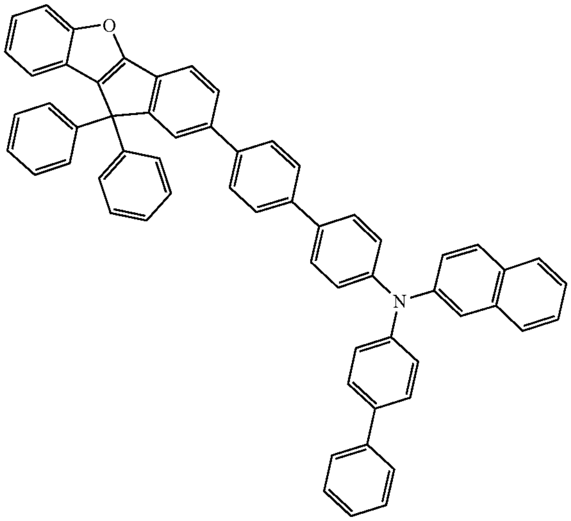
368
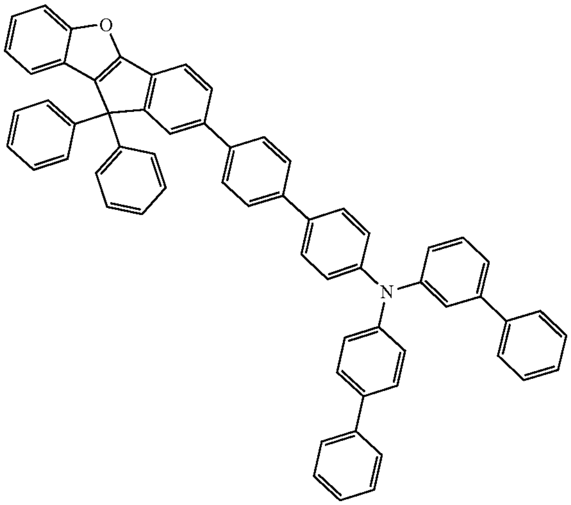
369
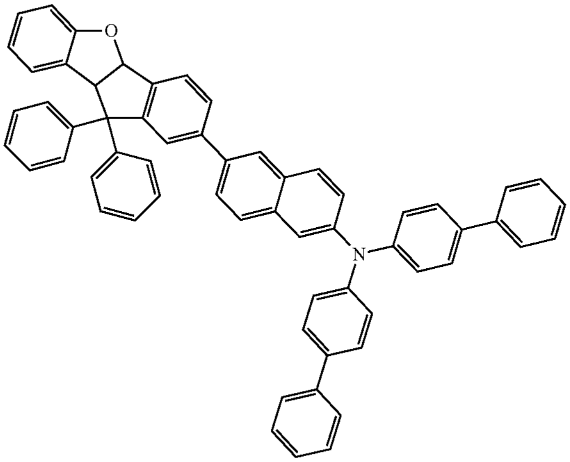

-continued
370
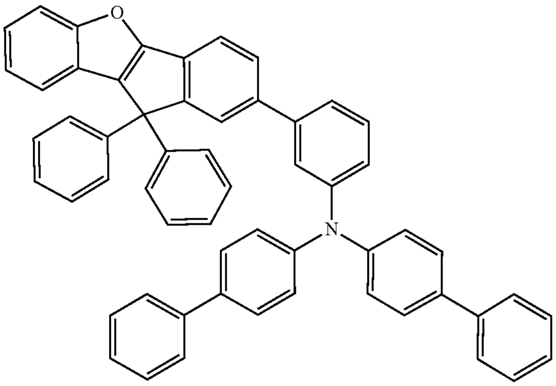
371
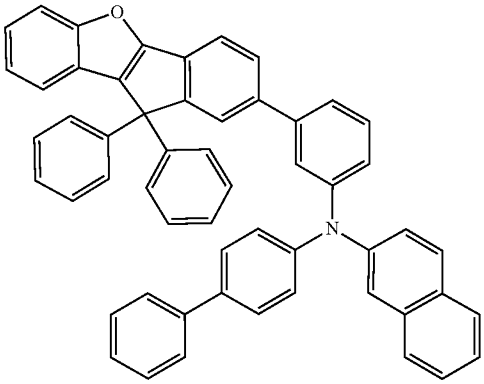
372
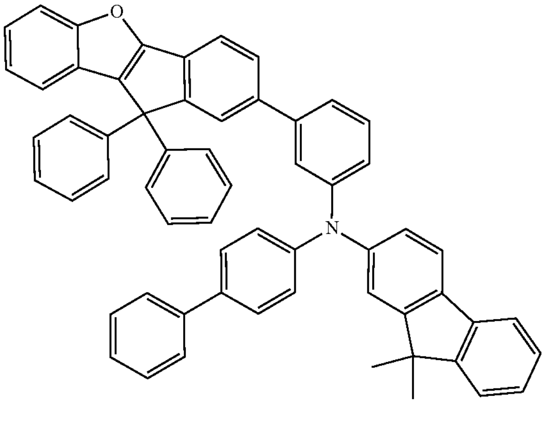
-continued
373
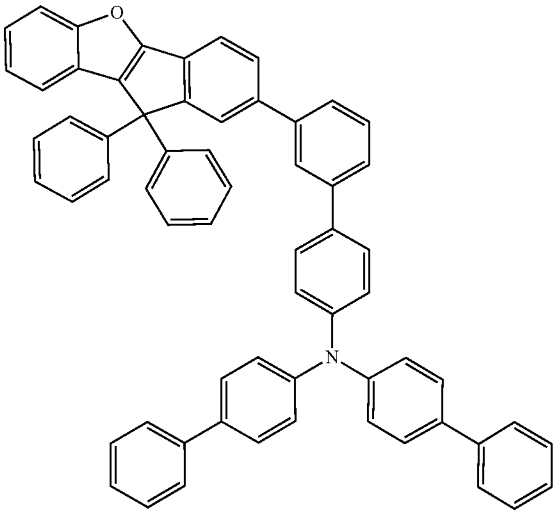
374
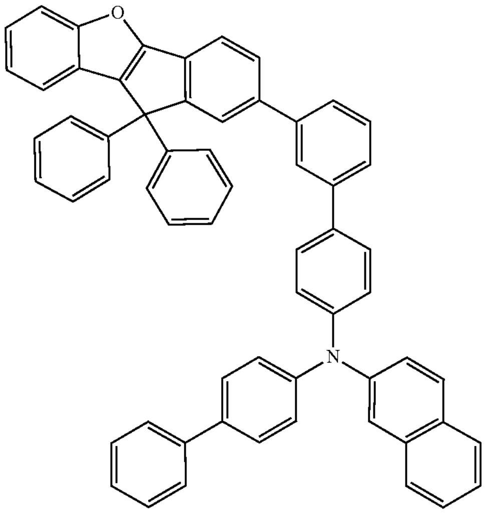
375
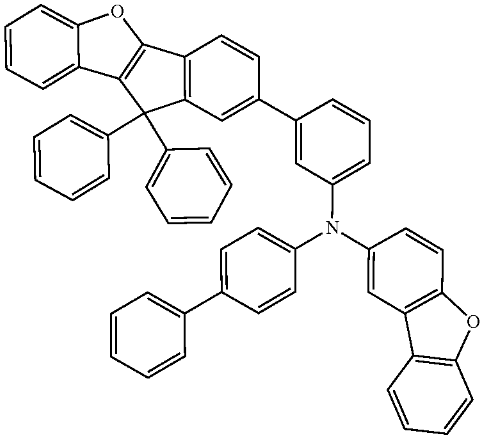

-continued
376
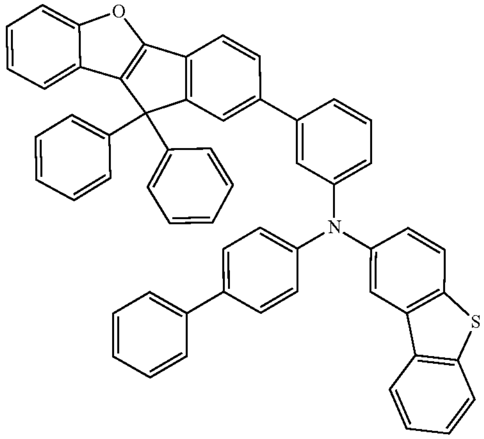
377
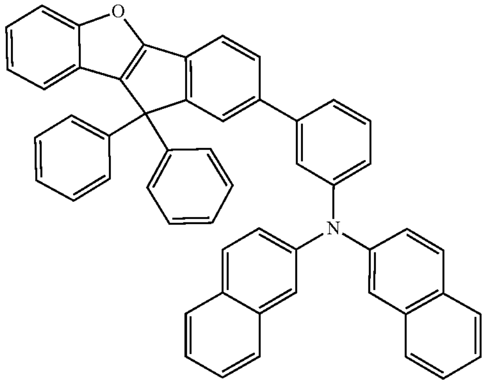
378
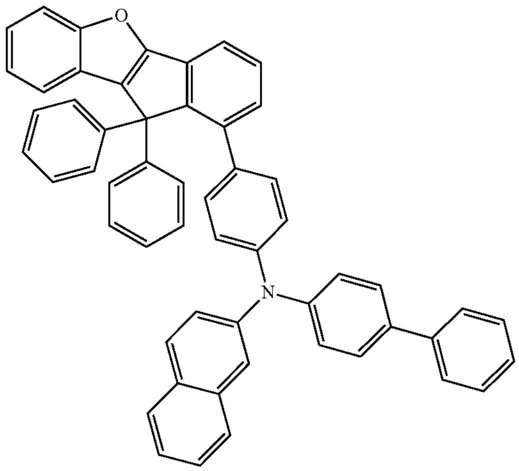
-continued
379
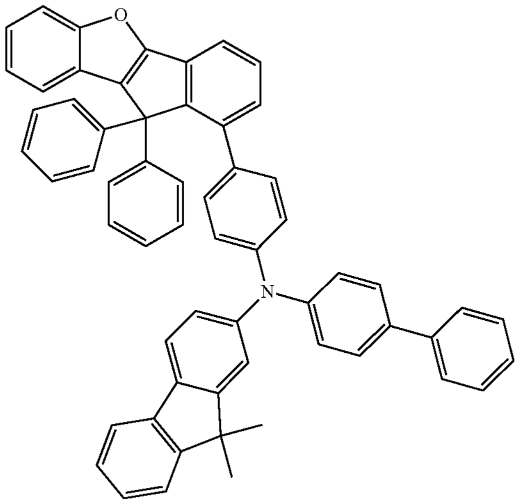
380
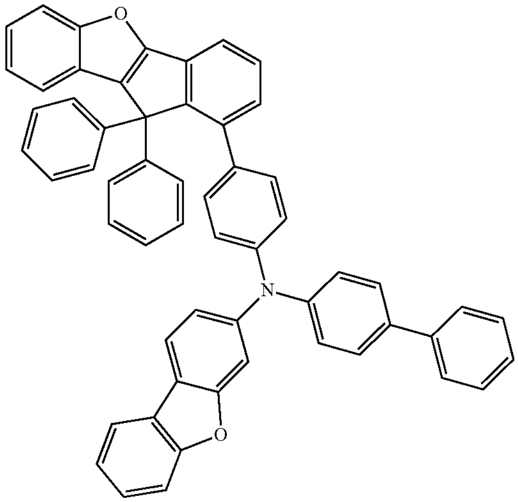
381
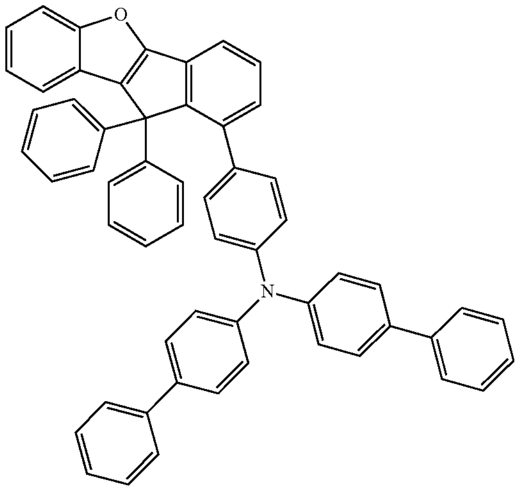

-continued

382

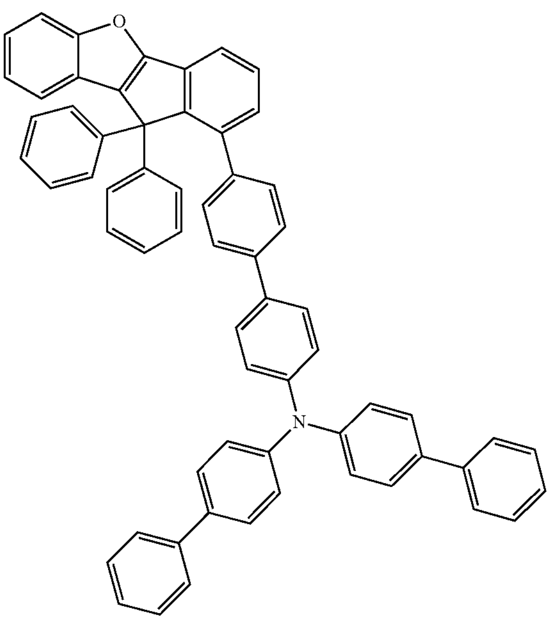

383

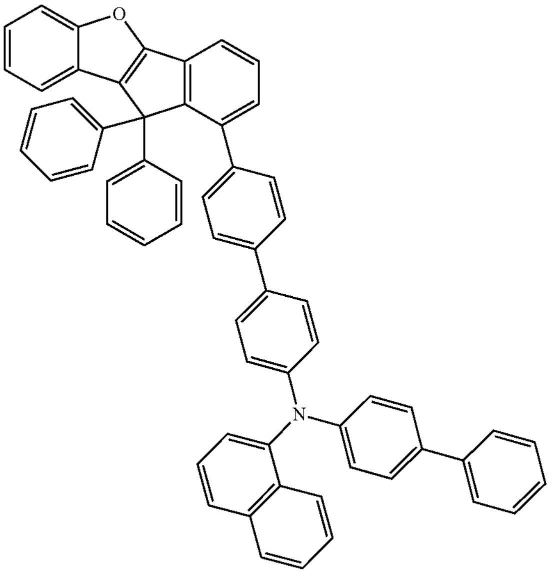

-continued

384

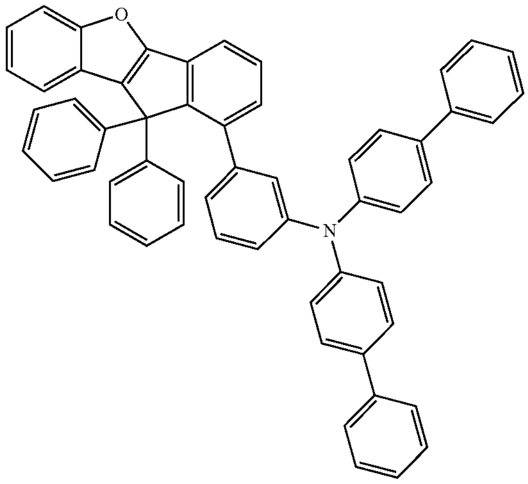

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise one heterocyclic compound according to Chemical Formula 1.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise two types of the heterocyclic compound according to Chemical Formula 1.

Specific descriptions on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a green light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a red light emitting layer of the red organic light emitting device.

The organic light emitting device of the present disclosure may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In addition, in the organic light emitting device provided in one embodiment of the present application, the organic material layer comprising the heterocyclic compound of Chemical Formula 1 further comprises a heterocyclic compound represented by the following Chemical Formula 2.

[Chemical Formula 2]

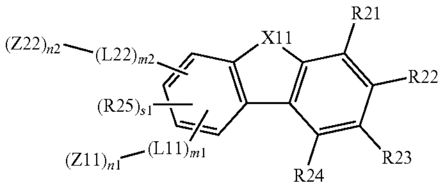

In Chemical Formula 2,

X11 is O; or S,

R21 to R25 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and a substituted or unsubstituted amine group, or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, L11 and L22 are the same as or different from each other, and each independently a direct bond; a substituted or unsubstituted C6 to C60 arylene group; or a substituted or unsubstituted C2 to C60 heteroarylene group, Z11 and Z22 are the same as or different from each other, and each independently selected from the group consisting of a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group, R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group, m1 and m2 are an integer of 0 to 4, s1 is an integer of 0 to 2, and n1 and n2 are an integer of 1 to 6.

In one embodiment of the present application, Chemical Formula 2 may be represented by any one of the following Chemical Formulae 3 to 5.

[Chemical Formula 3]

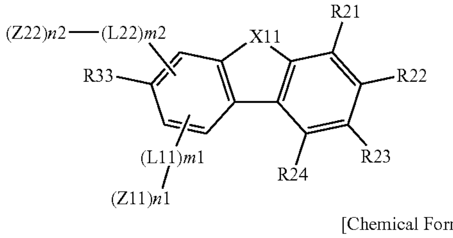

[Chemical Formula 4]

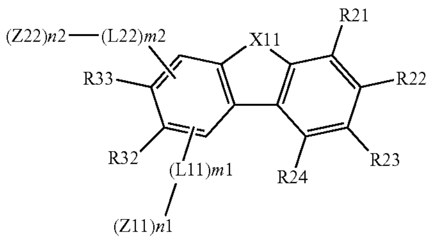

-continued

[Chemical Formula 5]

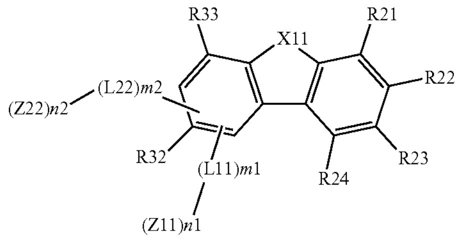

In Chemical Formulae 3 to 5,

X11, L11, L22, Z11, Z22, R21 to R24, m1, m2, n1 and n2 have the same definitions as in Chemical Formula 2, and R32 and R33 are selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR'.

In one embodiment of the present application, X11 is O.

In one embodiment of the present application, X11 is S.

In one embodiment of the present application, R21 to R25 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R21 to R25 are the same as or different from each other, and each independently selected from the group consisting of hydrogen; a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R21 to R25 are the same as or different from each other, and each independently selected from the group consisting of hydrogen; a substituted or unsubstituted C6 to C40 aryl group; and a substituted or unsubstituted C2 to C40 heteroaryl group, or two or more groups adjacent to each other may bond to each other to form a substituted or unsubstituted C6 to C40 aliphatic or aromatic hydrocarbon ring.

In another embodiment, R21 to R25 may be hydrogen.

In one embodiment of the present application, L11 and L22 are the same as or different from each other, and may be each independently a direct bond; a substituted or unsubstituted C6 to C60 arylene group; or a substituted or unsubstituted C2 to C60 heteroarylene group.

In another embodiment, L11 and L22 are the same as or different from each other, and may be each independently a direct bond; a substituted or unsubstituted C6 to C40 arylene group; or a substituted or unsubstituted C2 to C40 heteroarylene group.

In another embodiment, L11 and L22 are the same as or different from each other, and may be each independently a direct bond; a substituted or unsubstituted C6 to C20 arylene group; or a substituted or unsubstituted C2 to C20 heteroarylene group.

In another embodiment, L11 and L22 are the same as or different from each other, and may be each independently a direct bond; a C6 to C20 arylene group; or a C2 to C20 heteroarylene group.

In another embodiment, L11 and L22 are the same as or different from each other, and may be each independently a direct bond; a phenylene group; a biphenylene group; a naphthalene group; a divalent pyridine group; or a divalent dibenzothiophene group.

In one embodiment of the present application, R32 and R33 may be hydrogen.

In one embodiment of the present application, Z11 and Z22 are the same as or different from each other, and may be each independently selected from the group consisting of a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group.

In another embodiment, Z11 and Z22 are the same as or different from each other, and may be each independently selected from the group consisting of a cyano group; a substituted or unsubstituted C1 to C40 alkyl group; a substituted or unsubstituted C6 to C40 aryl group; a substituted or unsubstituted C2 to C40 heteroaryl group; and a substituted or unsubstituted amine group.

In another embodiment, Z11 and Z22 are the same as or different from each other, and may be each independently selected from the group consisting of a cyano group; a C6 to C40 aryl group unsubstituted or substituted with one or more substituents selected from the group consisting of a cyano group, a C1 to C40 alkyl group and a C6 to C40 aryl group; a C2 to C40 heteroaryl group unsubstituted or substituted with one or more substituents selected from the group consisting of a C1 to C40 alkyl group, a C6 to C40 aryl group and a C2 to C40 heteroaryl group; and an amine group unsubstituted or substituted with one or more substituents selected from the group consisting of a C6 to C40 aryl group and a C2 to C40 heteroaryl group.

In another embodiment, Z11 may be a C2 to C40 heteroaryl group unsubstituted or substituted with one or more substituents selected from the group consisting of a C1 to C40 alkyl group, a C6 to C40 aryl group and a C2 to C40 heteroaryl group.

In another embodiment, Z22 may be selected from the group consisting of a cyano group; a C6 to C40 aryl group unsubstituted or substituted with one or more substituents selected from the group consisting of a cyano group, a C1 to C40 alkyl group and a C6 to C40 aryl group; a C2 to C40 heteroaryl group unsubstituted or substituted with one or more substituents selected from the group consisting of a C1 to C40 alkyl group, a C6 to C40 aryl group and a C2 to C40 heteroaryl group; and an amine group unsubstituted or substituted with one or more substituents selected from the group consisting of a C6 to C40 aryl group and a C2 to C40 heteroaryl group.

In another embodiment, Z11 may be a triazine group unsubstituted or substituted with one or more substituents selected from the group consisting of a phenyl group, a biphenyl group, a naphthyl group, a triphenylenyl group, a diphenylfluorenyl group, a dimethylfluorenyl group, a dibenzothiophene group and a dibenzofuran group; a pyrimidine group unsubstituted or substituted with a phenyl group; a pyridine group unsubstituted or substituted with a phenyl group; a quinoline group unsubstituted or substituted with a phenyl group; a quinazoline group unsubstituted or substituted with a phenyl group; a phenanthroline group; a benzothiazole group; a benzimidazole group unsubstituted or substituted with a phenyl group; a benzo[b]naphtho[1,2-d]thiophene group; benzo[4,5]thieno[3,2-d]pyrimidine unsubstituted or substituted with a phenyl group; or benzofuro[3,2-d]pyrimidine unsubstituted or substituted with a phenyl group.

In another embodiment, Z22 may be a cyano group; a carbazole group unsubstituted or substituted with a phenyl group; a fused carbazole group unsubstituted or substituted with a phenyl group or a methyl group; a dimethylfluorenyl group; a diphenylfluorenyl group; a spirobifluorenyl group; a phenyl group unsubstituted or substituted with a cyano group; a biphenyl group; a triphenylenyl group; a dibenzothiophene group unsubstituted or substituted with a phenyl group or a triphenylenyl group; a fused dibenzothiophene group; a dibenzofuran group; or an amine group unsubstituted or substituted with one or more substituents selected from the group consisting of a phenyl group, a biphenyl group, a dibenzofuran group, a dibenzothiophene group and a naphthyl group.

In one embodiment of the present application, the fused carbazole group means that a fused ring bonds to a substituent of the carbazole group, and the fused ring may be a phenyl ring, a naphthyl ring, a benzofuran ring or an indole ring.

In one embodiment of the present application, the fused dibenzofuran group means that a fused ring bonds to a substituent of the dibenzofuran, and the fused ring may be a phenyl ring, a naphthyl ring, a benzofuran ring or an indole ring.

Effects of more superior efficiency and lifetime are obtained when comprising the heterocyclic compound of Chemical Formula 1 and the heterocyclic compound of Chemical Formula 2 in the organic material layer of the organic light emitting device. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

In one embodiment of the present application, Chemical Formula 2 may be any one of the following compounds.

2-1

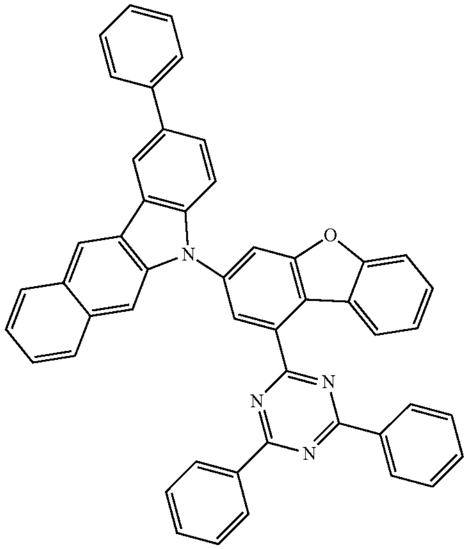

2-2

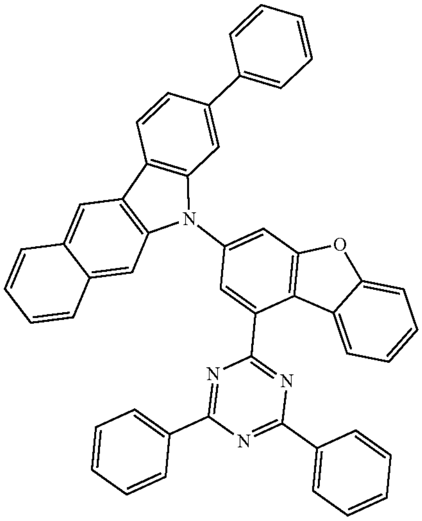

2-3

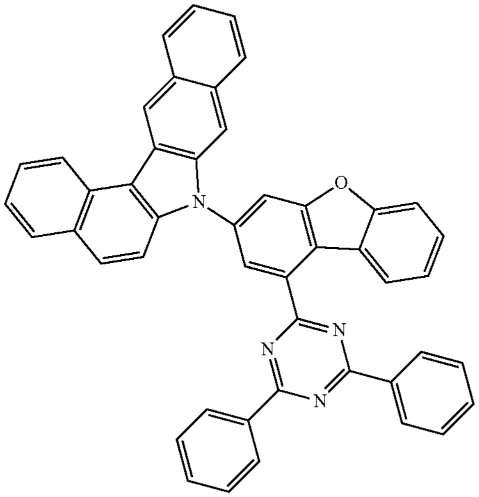

-continued
2-4
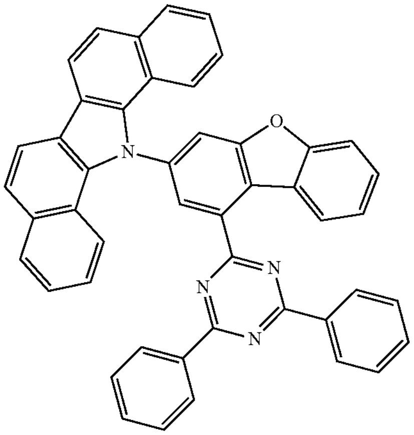
2-5
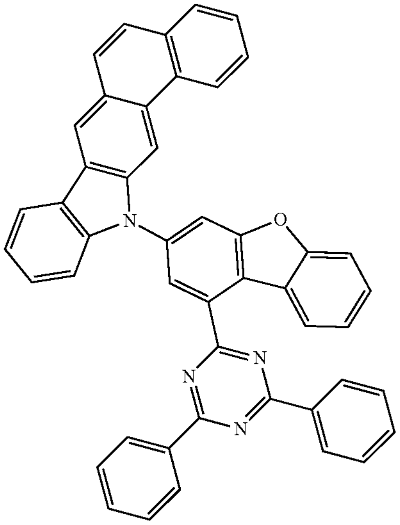
2-6
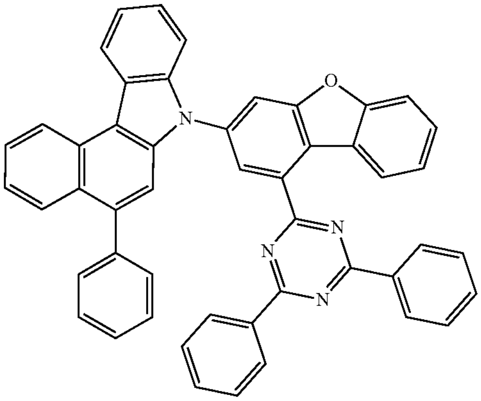
-continued
2-7
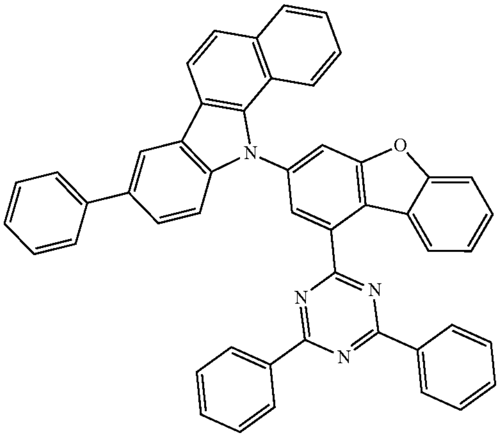
2-8
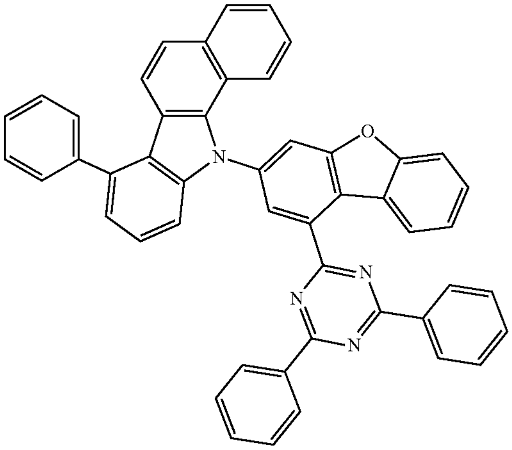
2-9
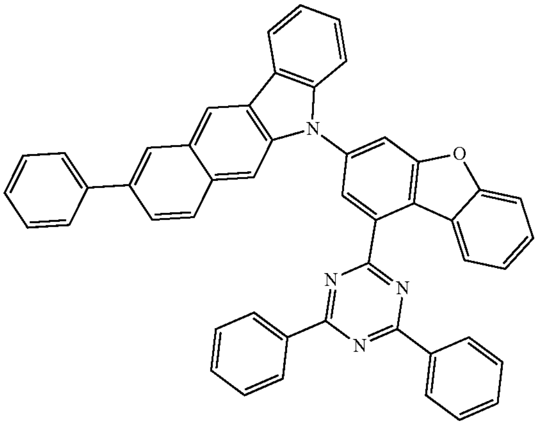

-continued
2-10
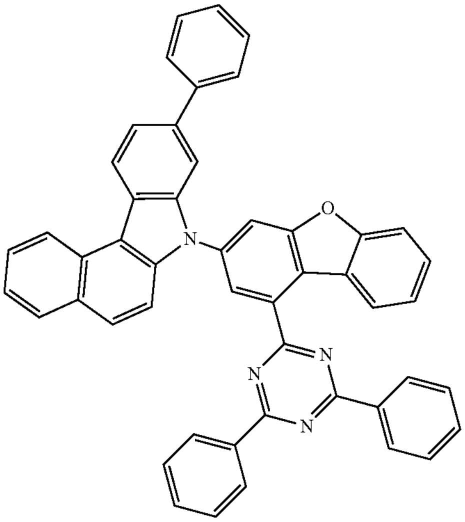
2-11
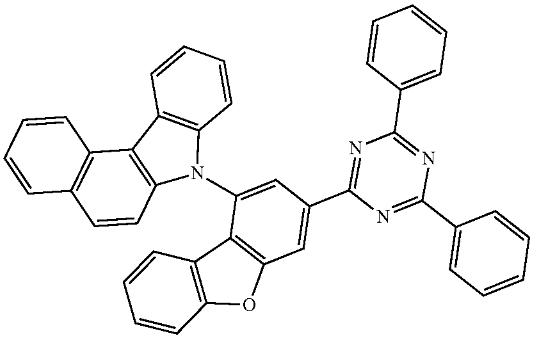
2-12
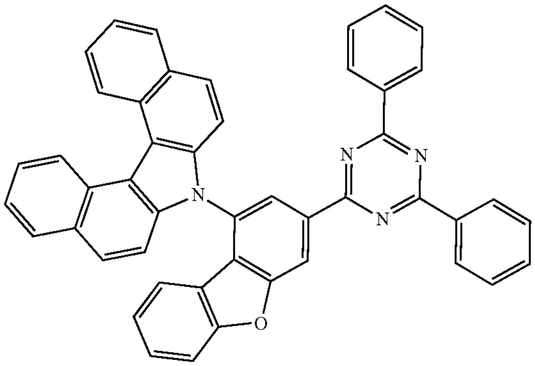
2-13
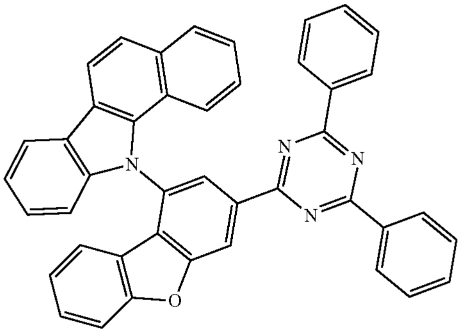
-continued
2-14
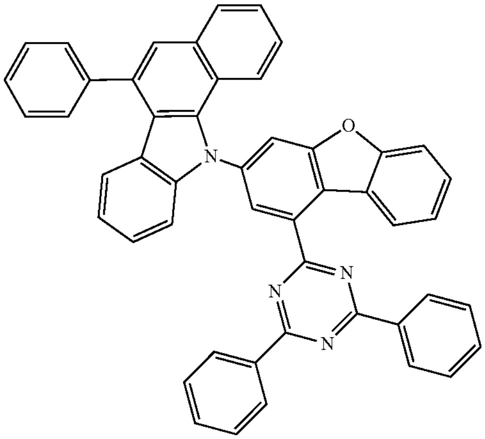
2-15
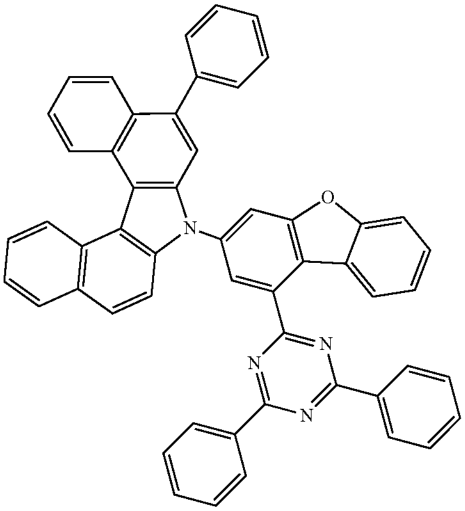
2-16
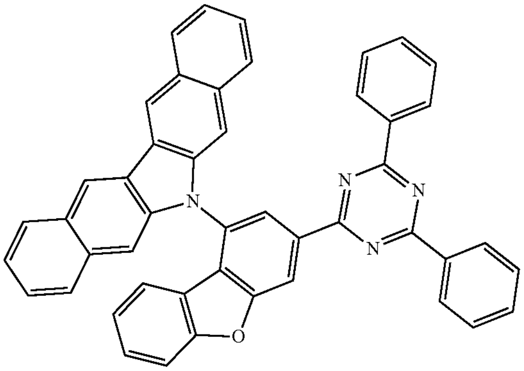

-continued
2-17
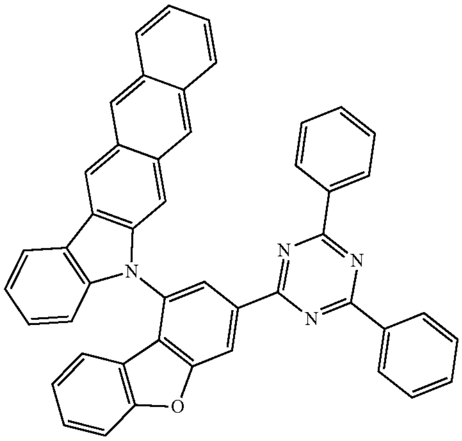
2-18
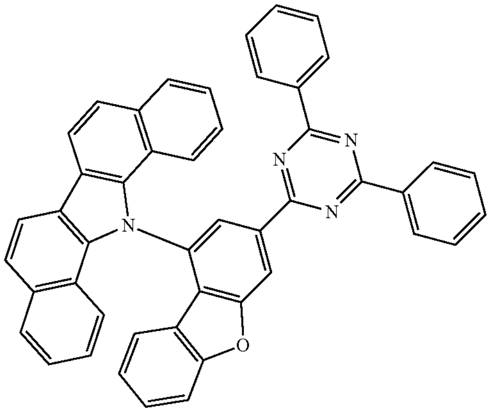
2-19
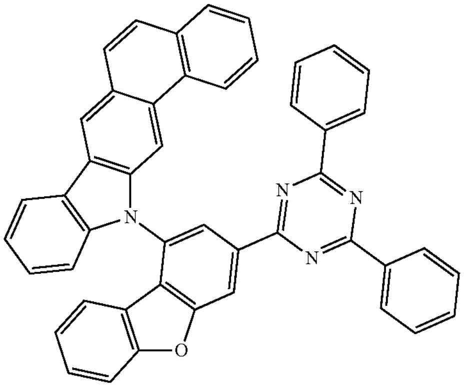
2-20
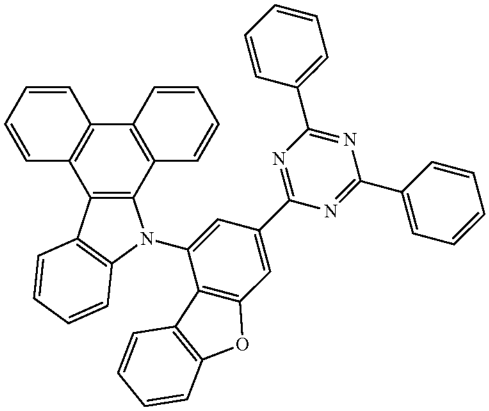
-continued
2-21
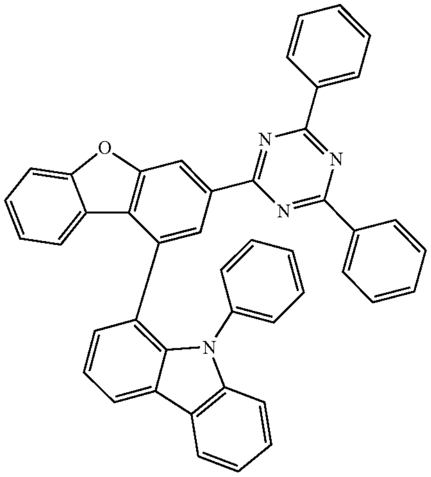
2-22
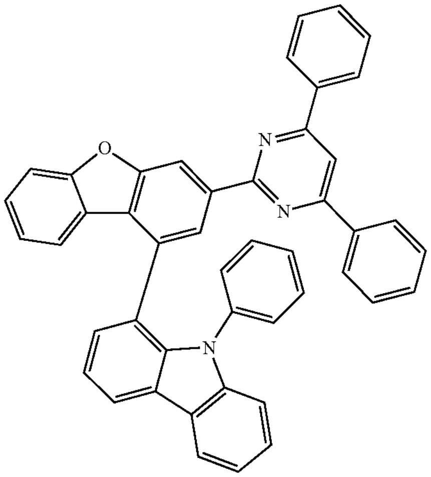
2-23
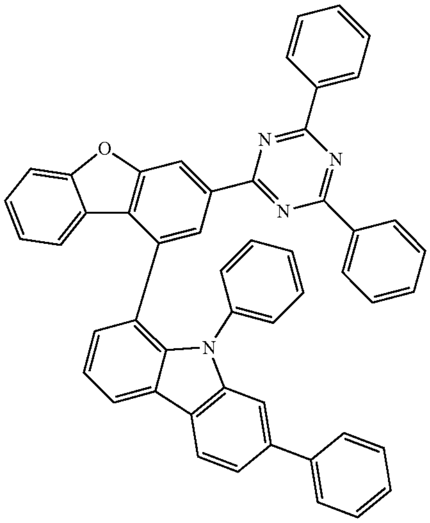

-continued
2-24
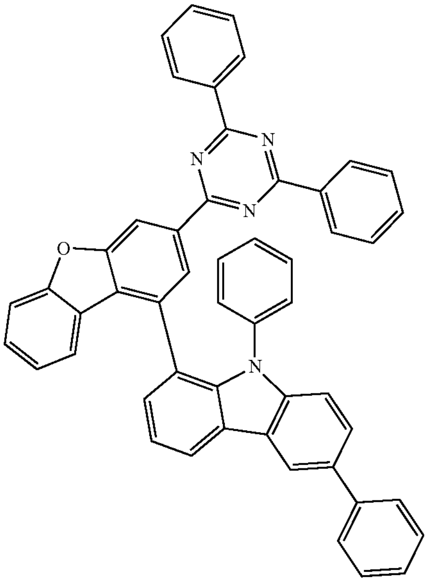
2-25
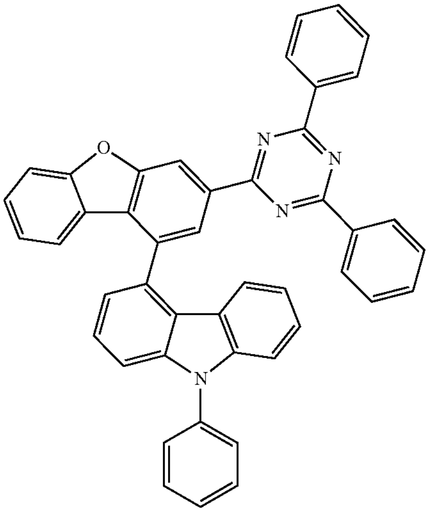
2-26
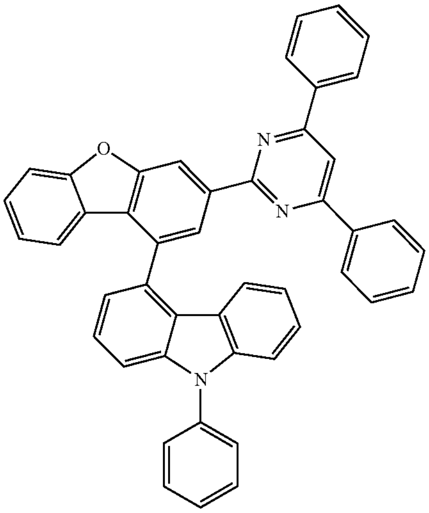
-continued
2-27
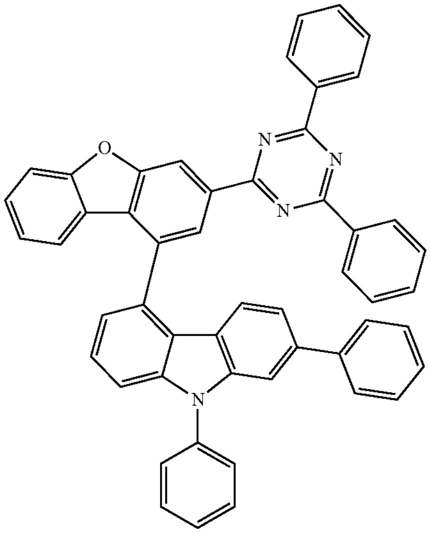
2-28
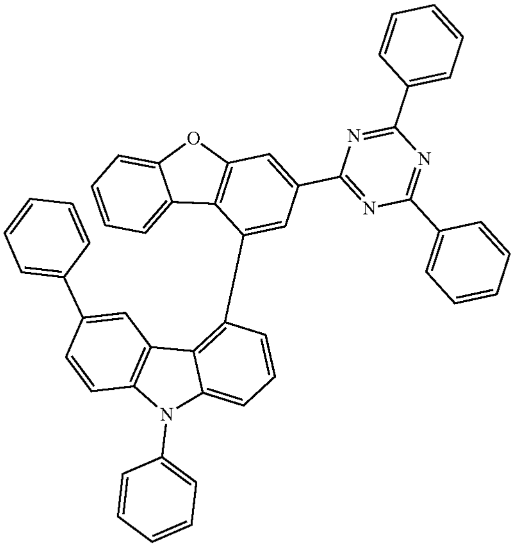
2-29
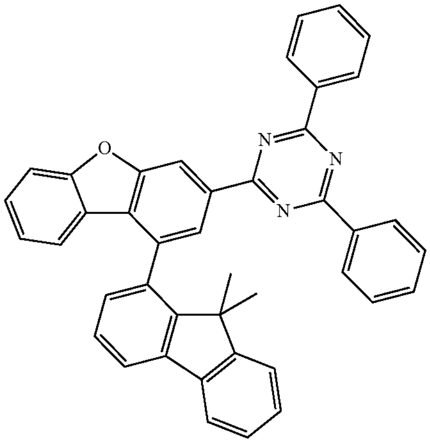

-continued
2-30
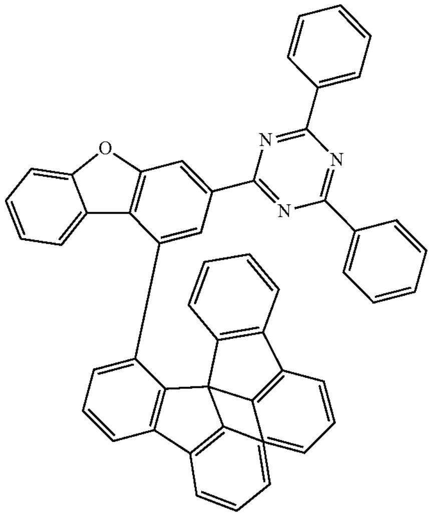
2-31
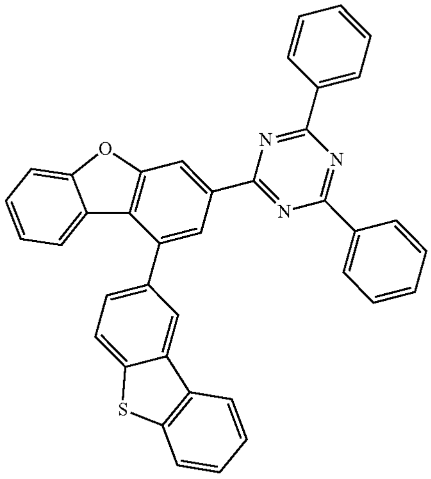
2-32
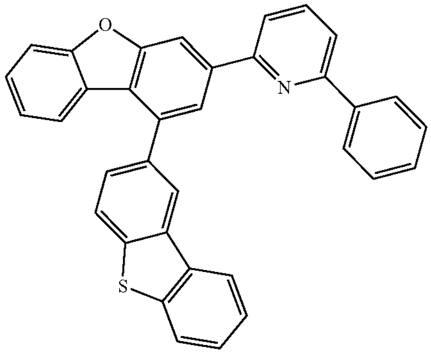
-continued
2-33
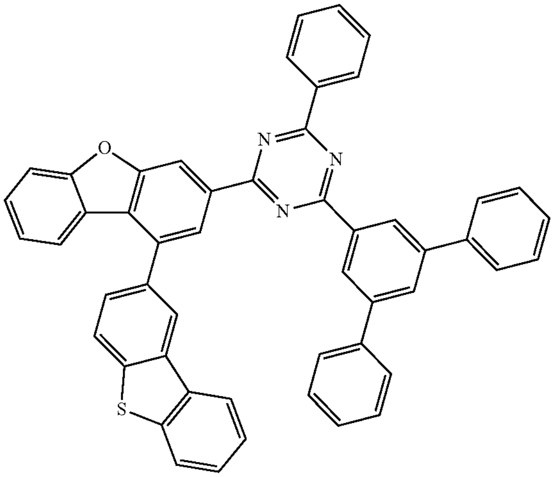
2-34
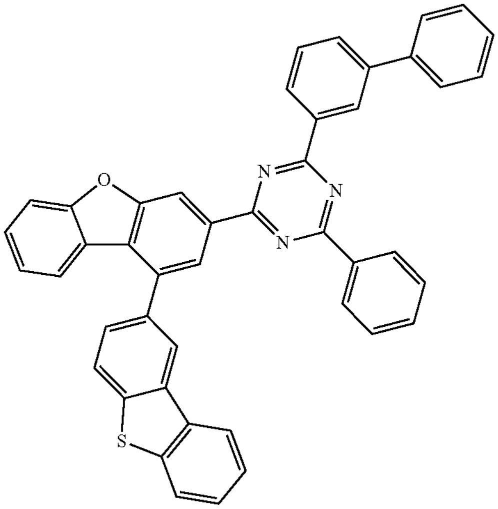
2-35
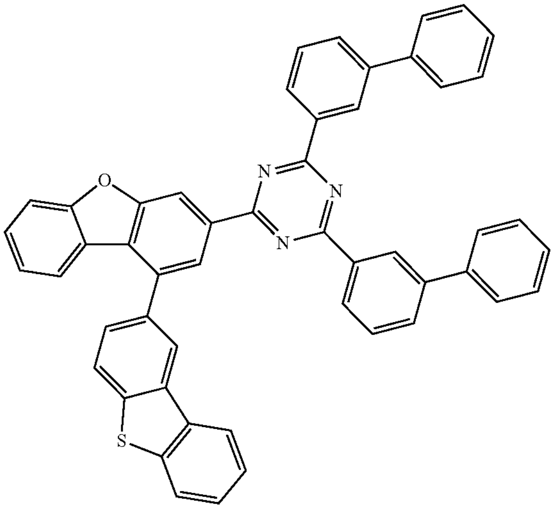

-continued
2-36
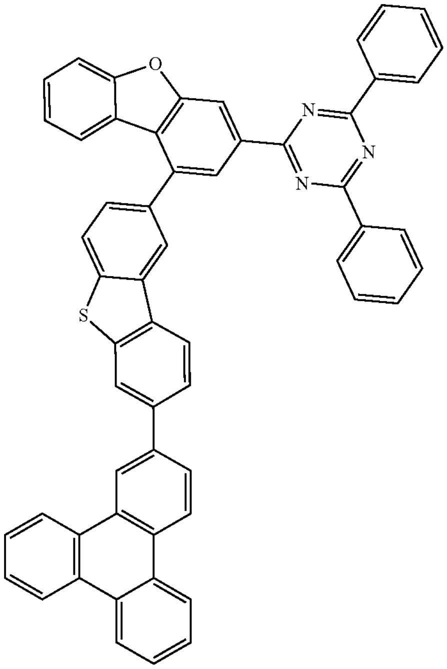
2-37
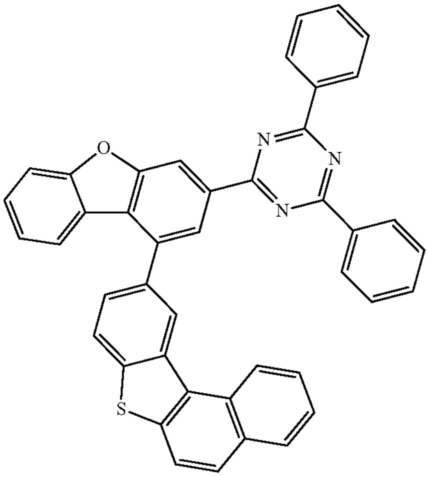
2-38
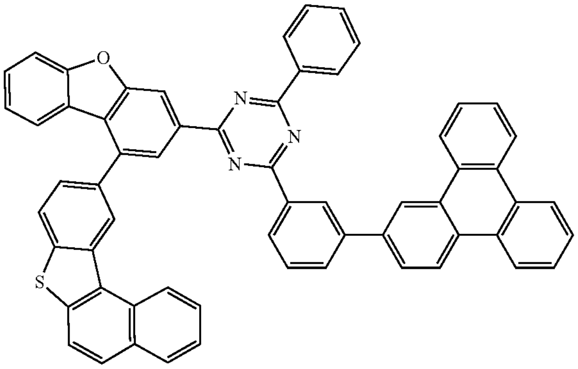
-continued
2-39
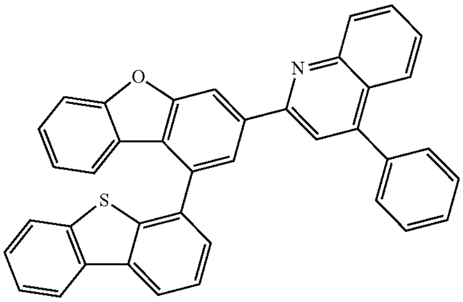
2-40
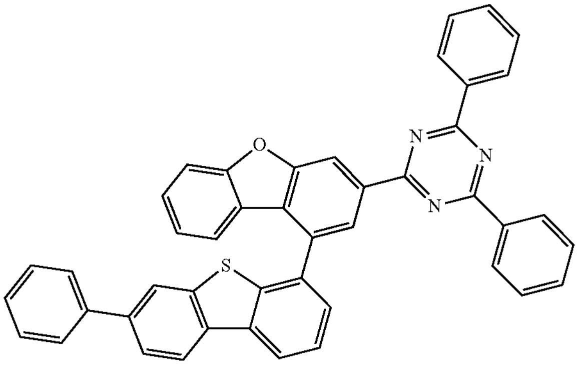
2-41
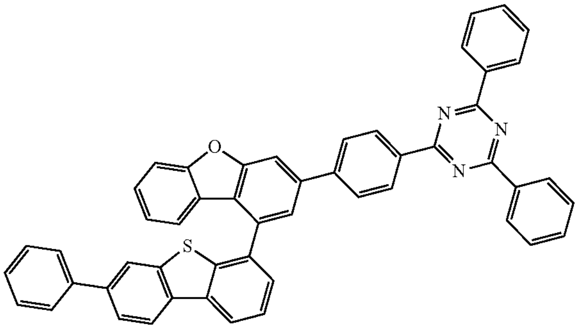
2-42
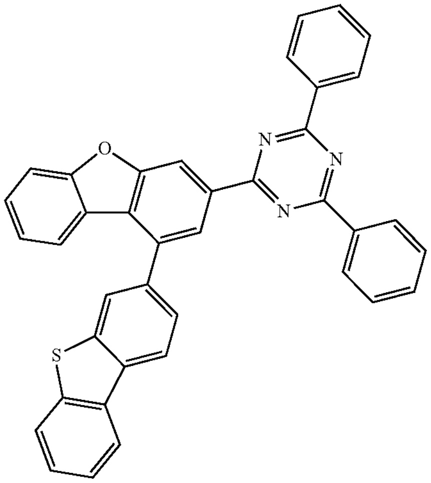

-continued
2-43
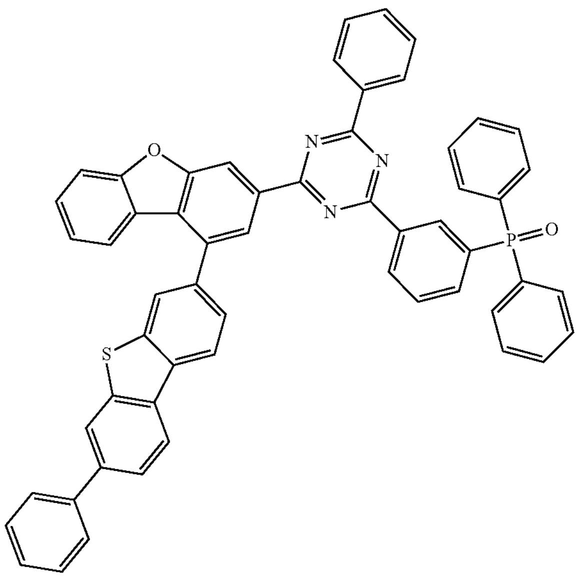
2-44
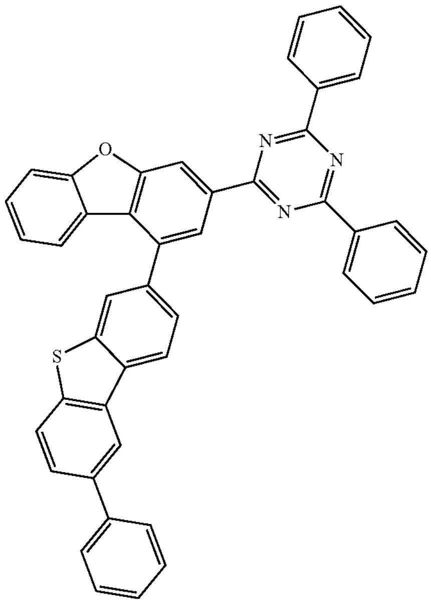
-continued
2-45
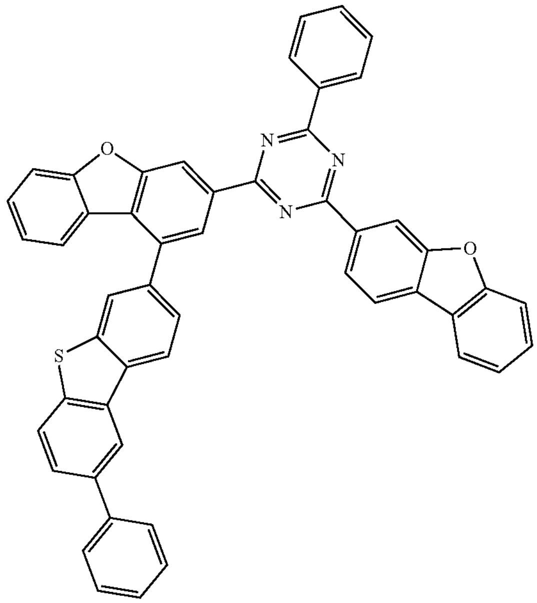
2-46
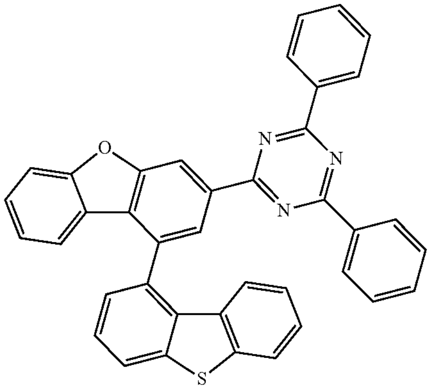
2-47
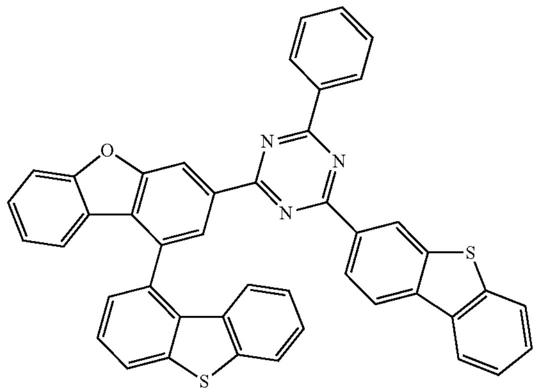

-continued
2-48
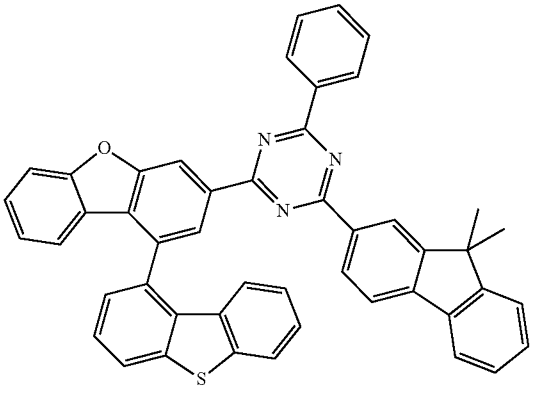
2-49
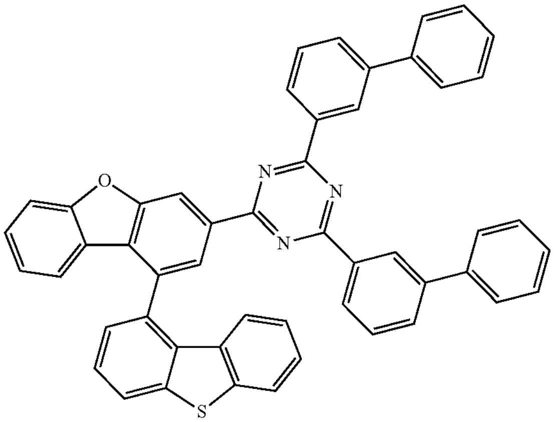
2-50
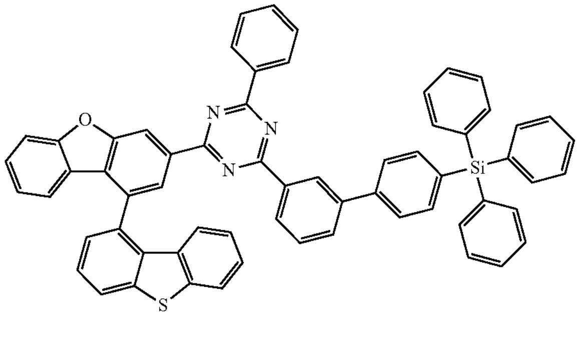
-continued
2-51
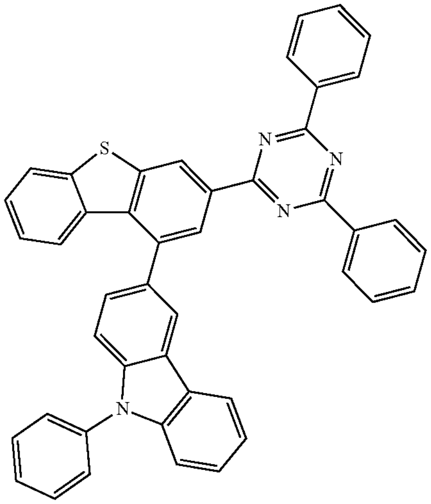
2-52
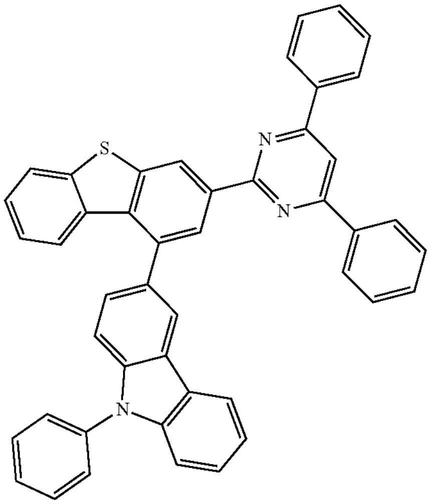
2-53
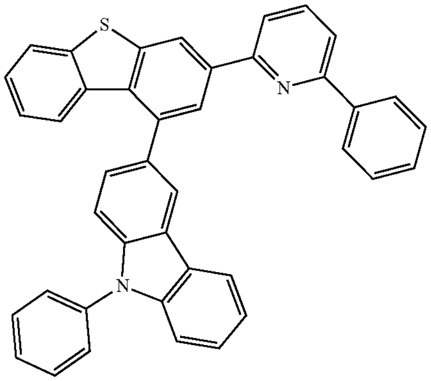

-continued
2-54
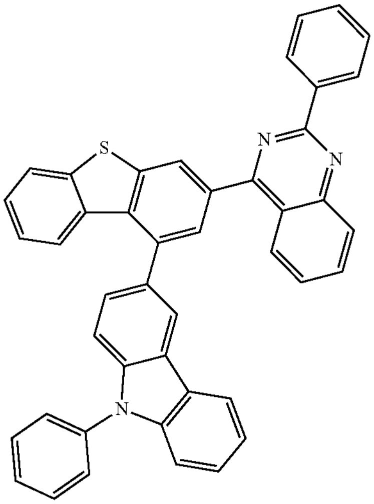
2-55
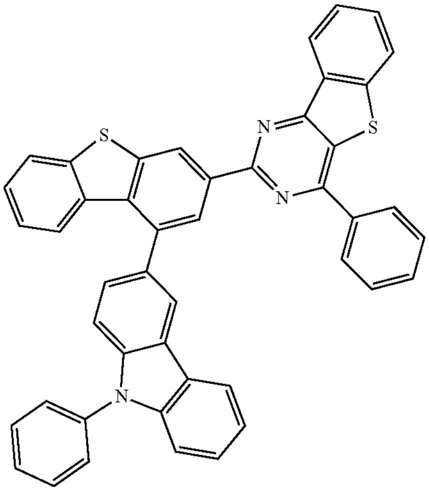
2-56
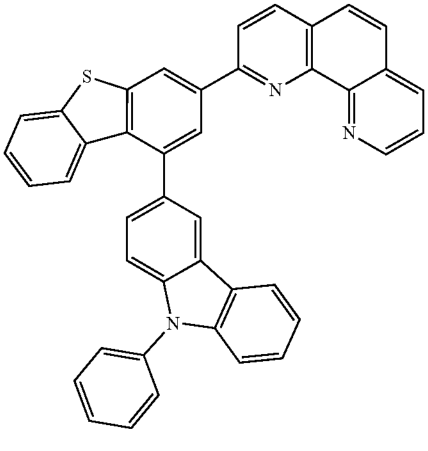
-continued
2-57
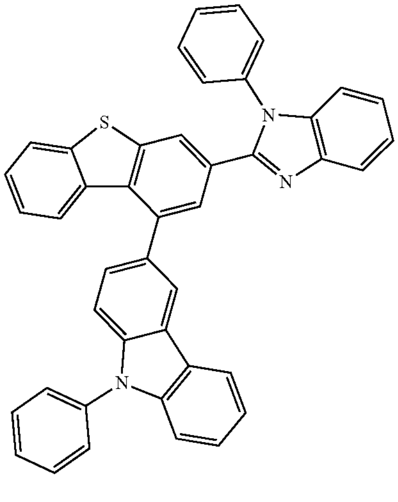
2-58
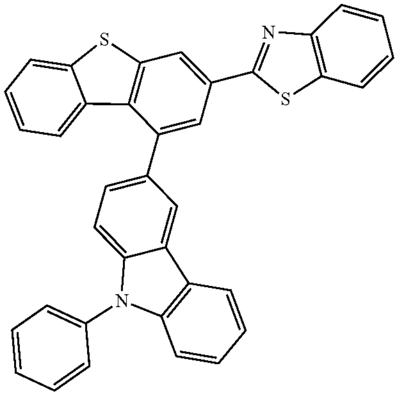
2-59
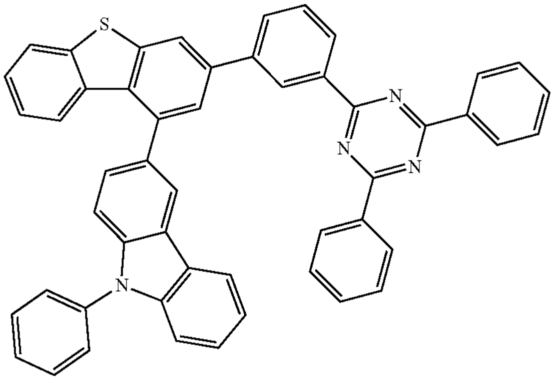

-continued
2-60
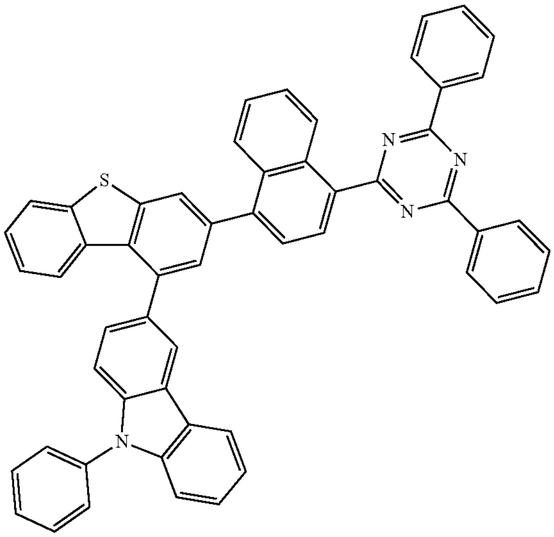
2-61
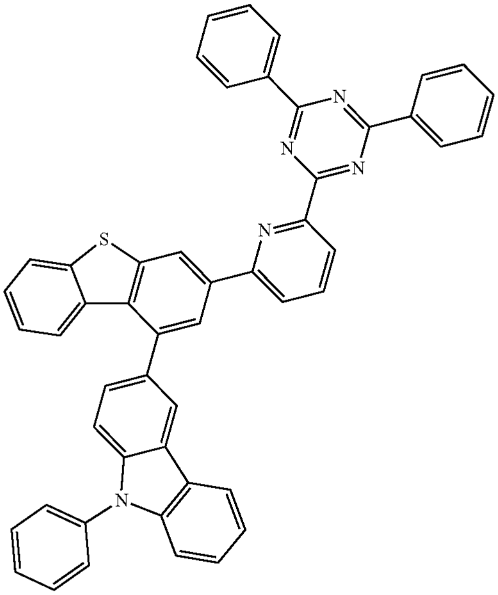
2-62
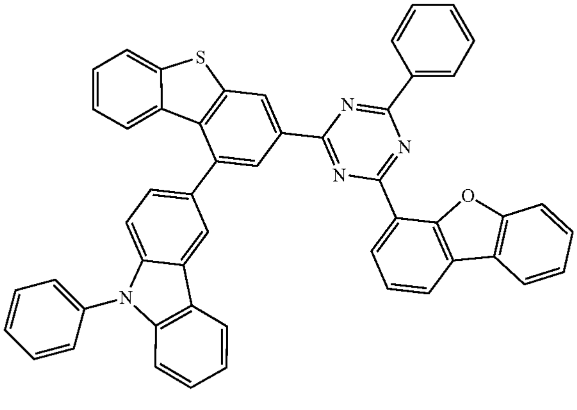
-continued
2-63
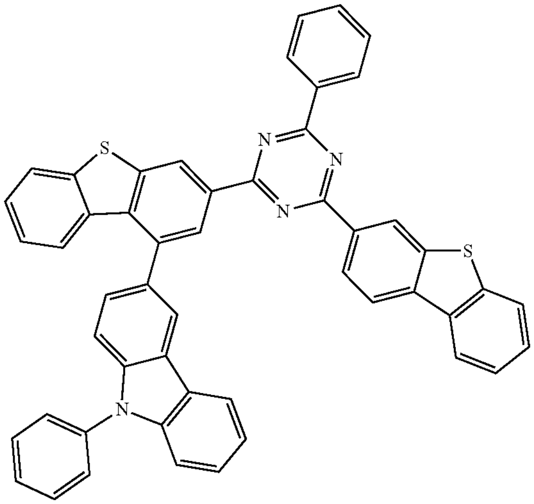
2-64
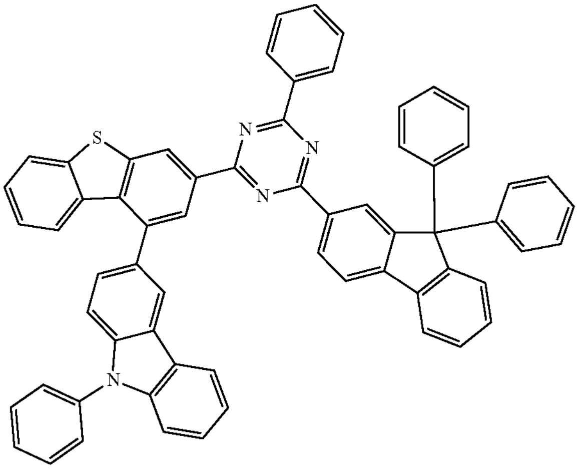
2-65
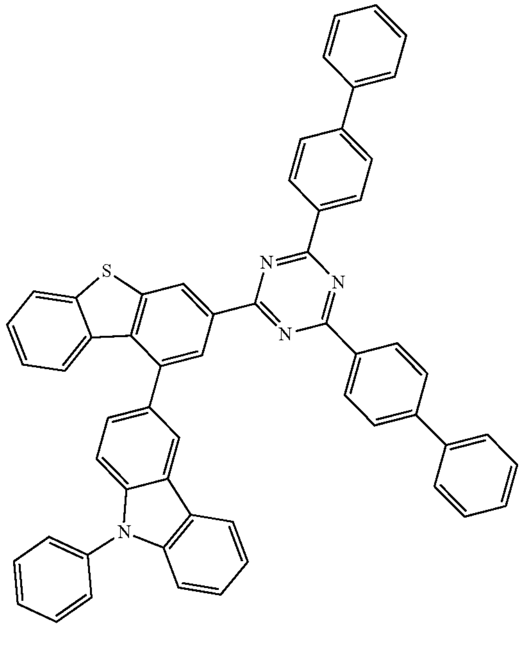

-continued
2-66
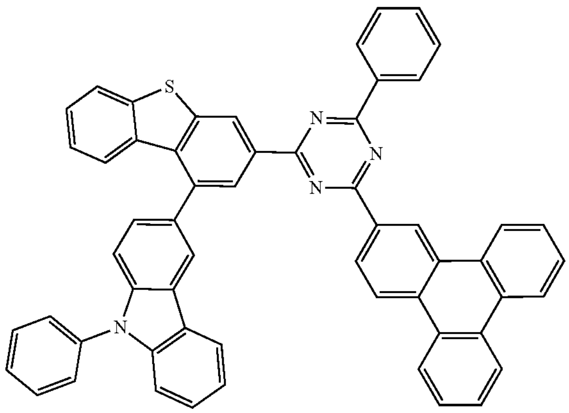
2-67
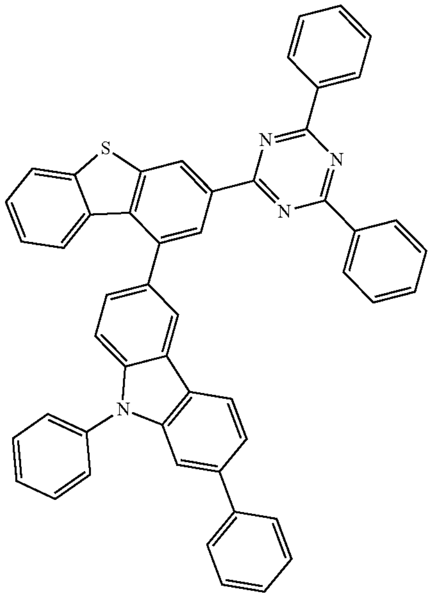
2-68
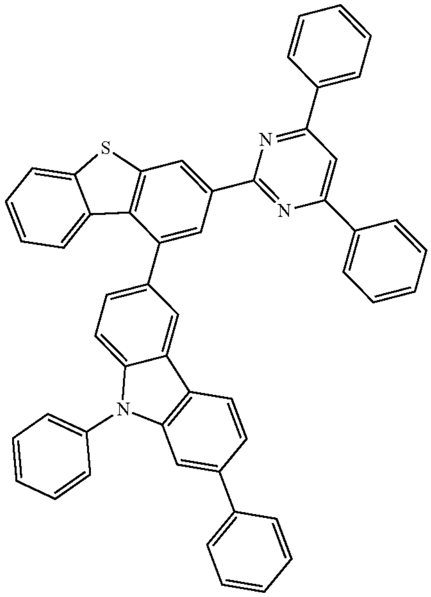
-continued
2-69
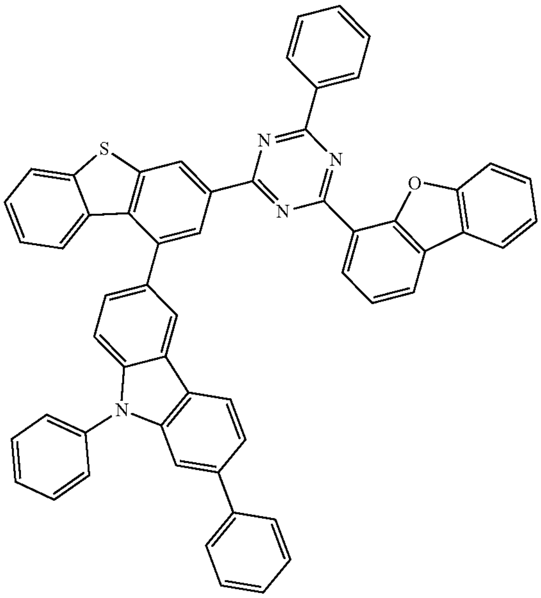
2-70
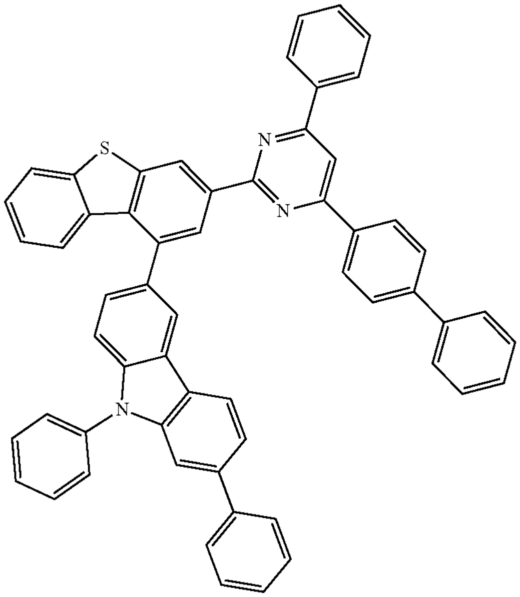

-continued
2-71
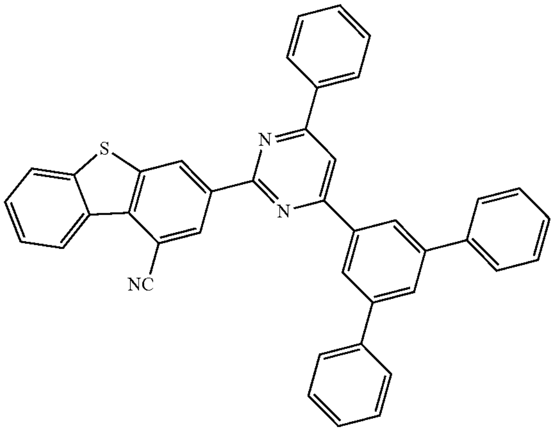
2-72
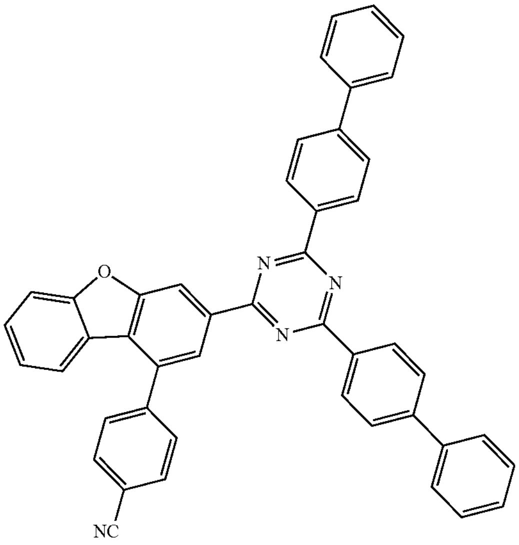
2-73
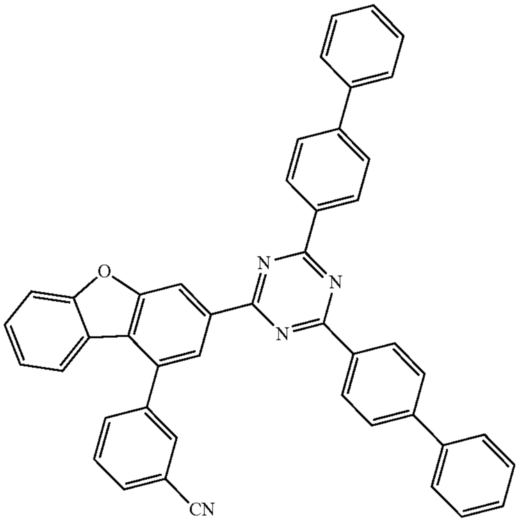
-continued
2-74
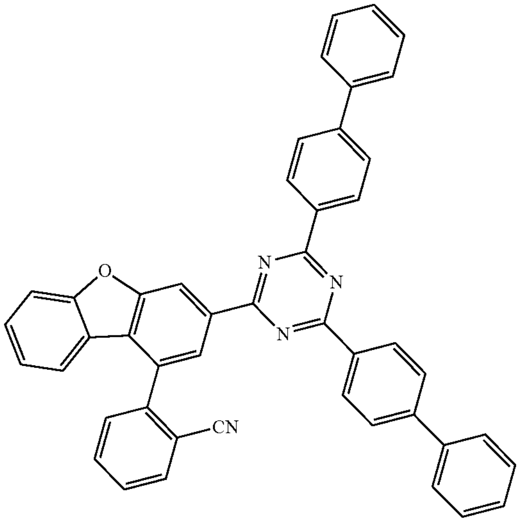
2-75
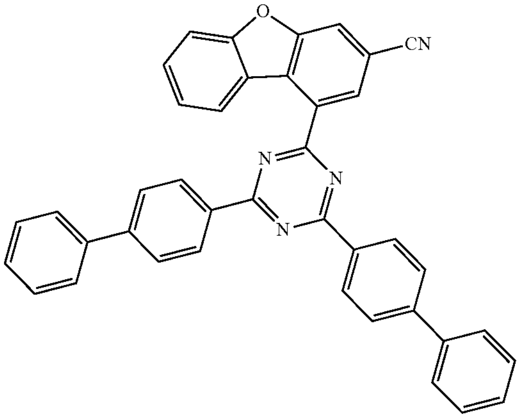
2-76
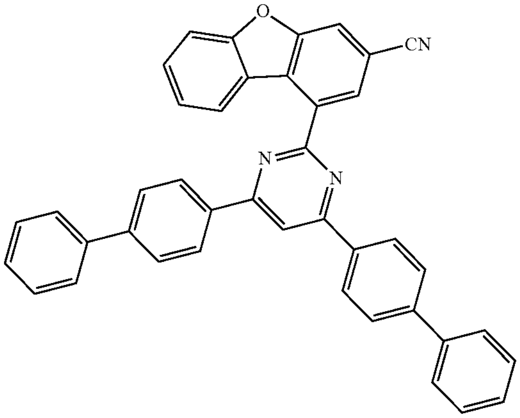

-continued
2-77
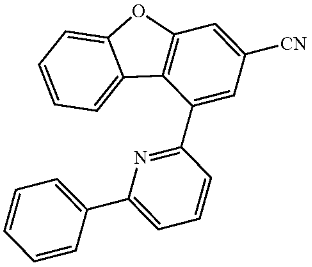
2-78
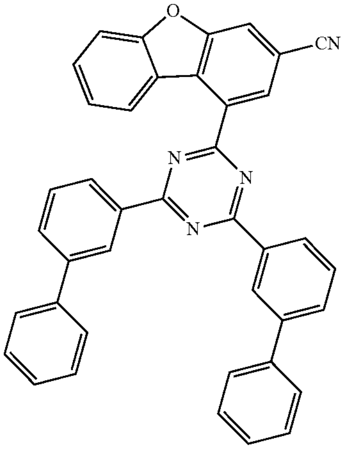
2-79
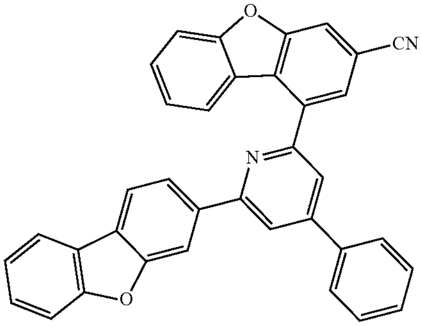
2-80
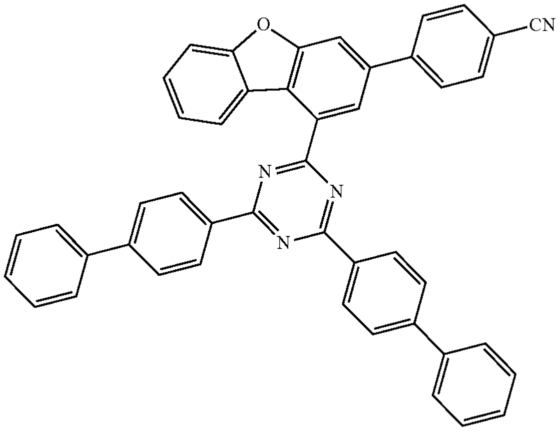
-continued
2-81
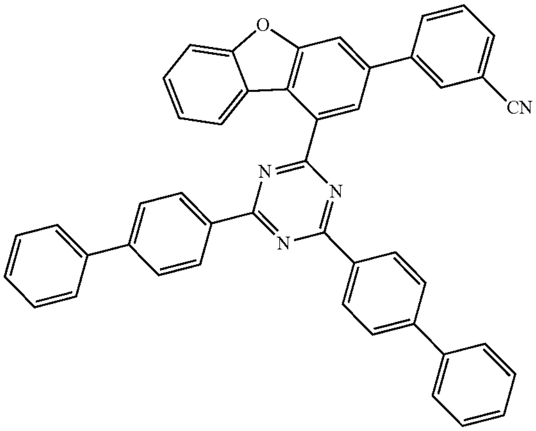
2-82
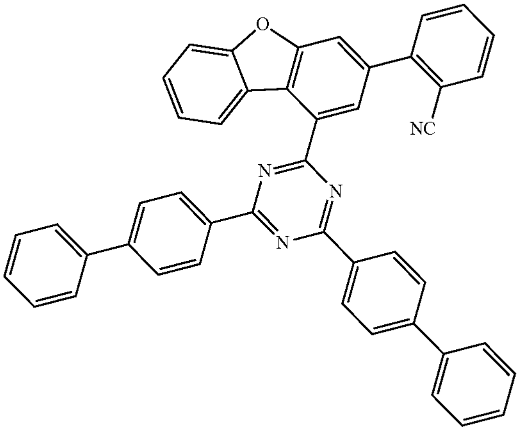
2-83
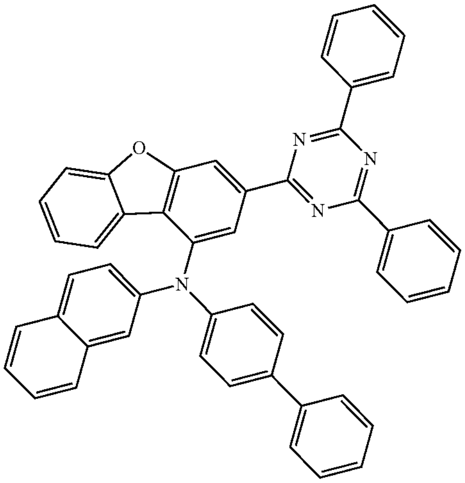

-continued
2-84
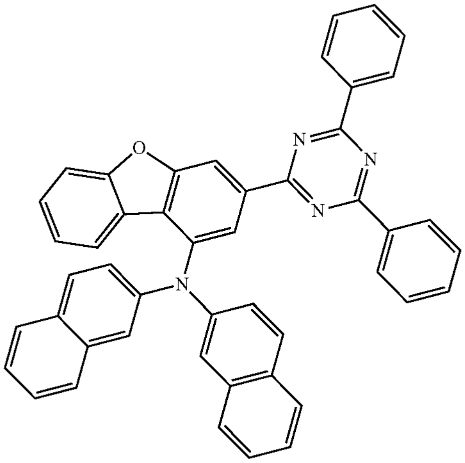
2-85
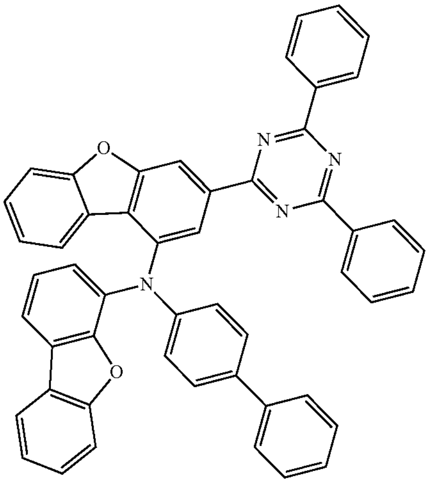
2-86
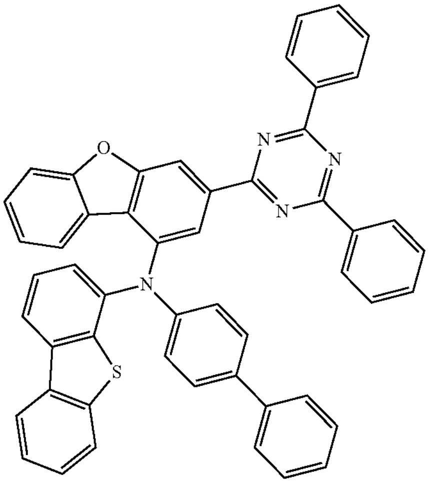
-continued
2-87
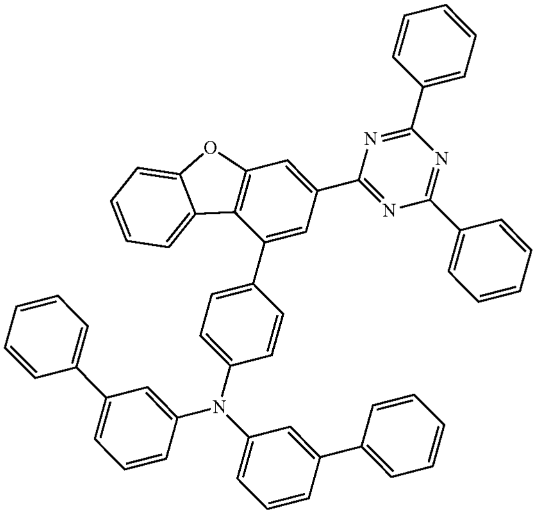
2-88
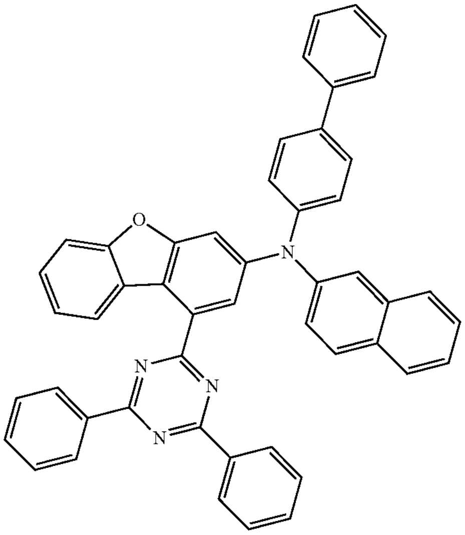
2-89
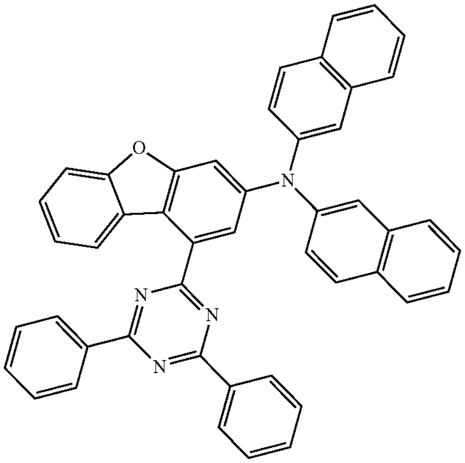

-continued 2-90

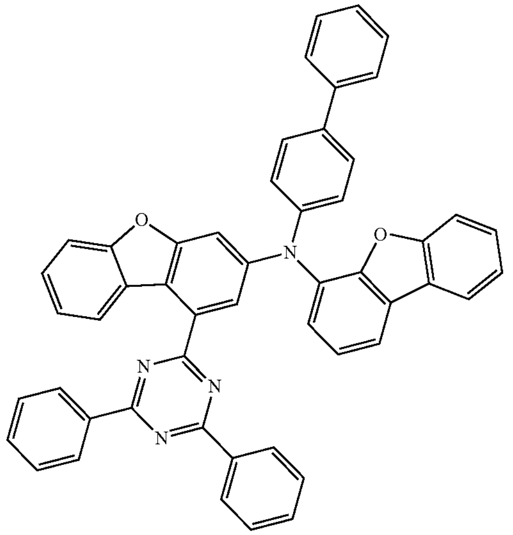

Another embodiment of the present application provides a composition for an organic material layer of an organic light emitting device, the composition comprising the heterocyclic compound represented by Chemical Formula 1, and the heterocyclic compound represented by Chemical Formula 2.

Specific descriptions on the heterocyclic compound represented by Chemical Formula 1 and the heterocyclic compound represented by Chemical Formula 2 are the same as the descriptions provided above.

In the composition, the heterocyclic compound represented by Chemical Formula 1:the heterocyclic compound represented by Chemical Formula 2 may have a weight ratio of 1:10 to 10:1, 1:8 to 8:1, 1:5 to 5:1, or 1:2 to 2:1, however, the weight ratio is not limited thereto.

The composition may be used when forming an organic material of an organic light emitting device, and may be more preferably used when forming a host of a light emitting layer.

In one embodiment of the present application, the organic material layer comprises the heterocyclic compound represented by Chemical Formula 1 and the heterocyclic compound represented by Chemical Formula 2, and a phosphorescent dopant may be used therewith.

In one embodiment of the present application, the organic material layer comprises the heterocyclic compound represented by Chemical Formula 1 and the heterocyclic compound represented by Chemical Formula 2, and an iridium-based dopant may be used therewith.

As a material of the phosphorescent dopant, those known in the art may be used.

For example, phosphorescent dopant materials represented by LL'MX', LL'L"M, LMX'X", L2MX' and L3M may be used, however, the scope of the present disclosure is not limited to these examples.

Herein, L, L', L", X' and X" are a bidentate ligand different from each other, and M is a metal forming an octahedral complex.

M may comprise iridium, platinum, osmium and the like.

L is an anionic bidentate ligand coordinated to M as the iridium-based dopant by sp2 carbon and heteroatom, and X may function to trap electrons or holes. Nonlimiting examples of L may comprise 2-(1-naphthyl)benzoxazole, (2-phenylbenzoxazole), (2-phenylbenzothiazole), (2-phenylbenzothiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X' and X" may comprise acetylacetonate (acac), hexafluoroacetylacetonate, salicylidene, picolinate, 8-hydroxyquinolinate and the like.

More specific examples of the phosphorescent dopant are described below, however, the phosphorescent dopant is not limited to these examples.

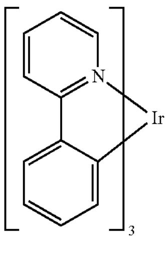
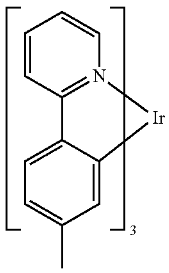
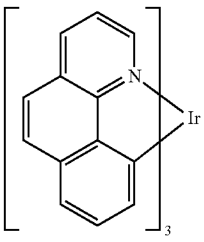

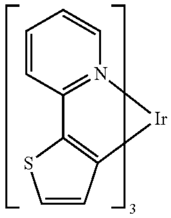
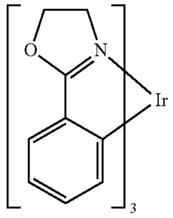
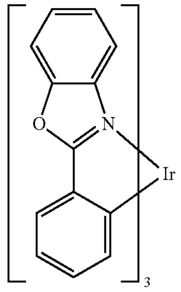

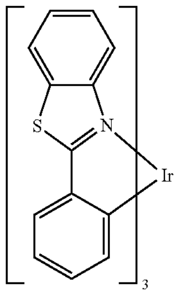
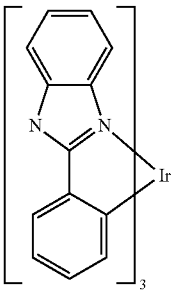

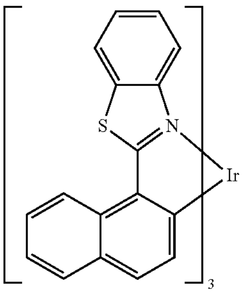
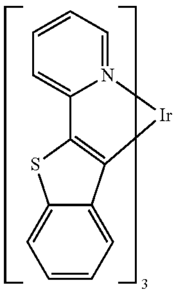

-continued

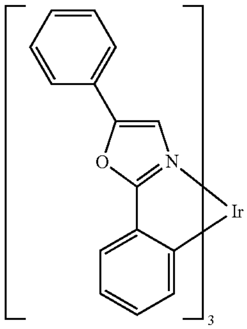

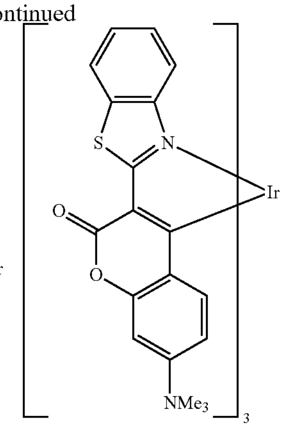

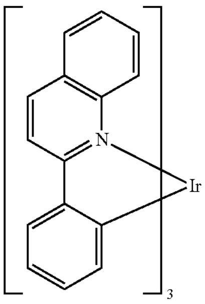

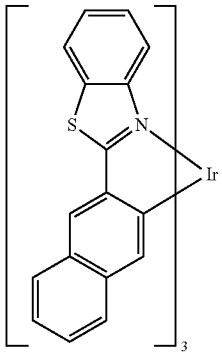

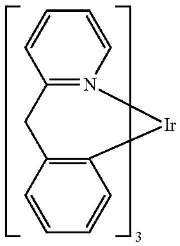

In one embodiment of the present application, as the iridium-based dopant, $Ir(ppy)_3$ may be used as a green phosphorescent dopant.

In one embodiment of the present application, a content of the dopant may be from 1% to 15%, preferably from 3% to 10% and more preferably from 5% to 10% based on the whole light emitting layer.

In the organic light emitting device of the present disclosure, the organic material layer may comprise a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

In the organic light emitting device of the present disclosure, the organic material layer comprises an electron injection layer or an electron transfer layer, and the electron injection layer or the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In the method for manufacturing an organic light emitting device provided in one embodiment of the present application, the forming of organic material layers is forming the heterocyclic compound of Chemical Formula 1 and the heterocyclic compound of Chemical Formula 2 using a thermal vacuum deposition method after pre-mixing.

The pre-mixing means first mixing the heterocyclic compound of Chemical Formula 1 and the heterocyclic compound of Chemical Formula 2 in one source of supply before depositing on the organic material layer.

The premixed material may be referred to as the composition for an organic material layer according to one embodiment of the present application.

The organic material layer comprising Chemical Formula 1 may further comprise other materials as necessary.

The organic material layer comprising both Chemical Formula 1 and Chemical Formula 2 may further comprise other materials as necessary.

In the organic light emitting device according to one embodiment of the present application, materials other than the compound of Chemical Formula 1 or Chemical Formula 2 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

<Preparation Example 1> Preparation of Compound 1-1(C)

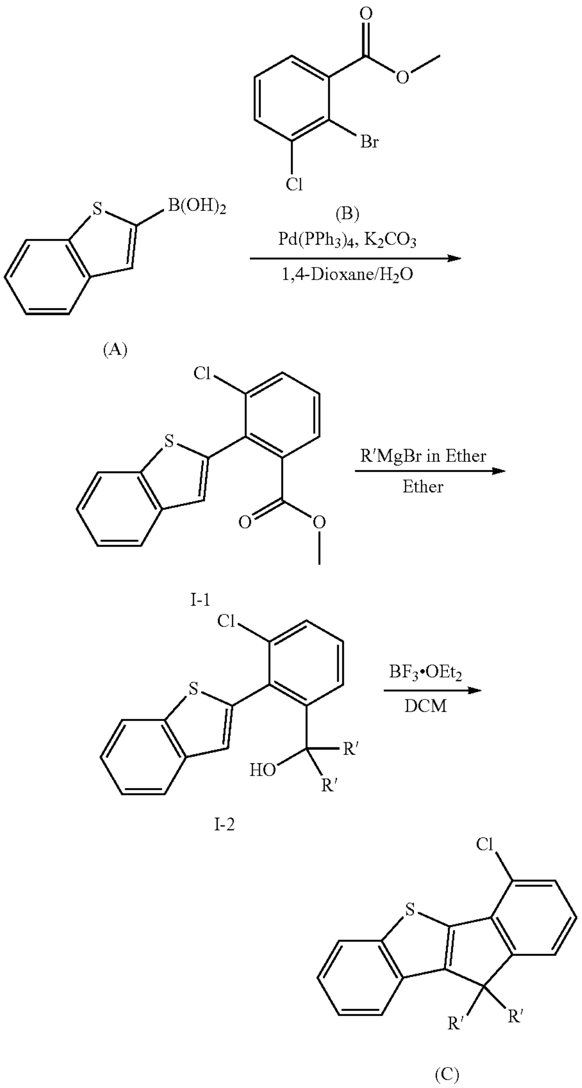

(A) (B) I-1 I-2 (C)

Preparation of Compound I-1

After dissolving benzo[b]thiophen-2-ylboronic acid (20 g, 112.35 mmol), methyl-2-bromo-3-chlorobenzoate (28 g, 112.35 mmol), $Pd(PPh_3)_4$ (6.5 g, 5.62 mmol) and $K_2CO_3$ (31 g, 224.71 mmol) in 1,4-dioxane/$H_2O$ (200 mL/50 mL), the mixture was stirred for 4 hours at 100° C. The mixture solution completed with the reaction was dissolved in methylene chloride (MC), and extracted with water. The organic layer was dried with anhydrous $MgSO_4$, and then silica gel filtered. For the filtered filtrate, the solvent was removed using a rotary evaporator, and the result went through column chromatography <MC/Hex=1/3> to obtain yellow oil I-1 (21 g) in a 62% yield.

Preparation of Compound 1-2

Compound I-1 (21 g, 69.31 mmol) was dissolved in ether (200 mL), and 3 M methylmagnesium bromide (or phenylmagnesium bromide) in ether (57 mL, 173.26 mmol) was slowly added dropwise thereto. The mixture was stirred for 16 hours at a reaction temperature of 80° C., and then a 1 M aqueous $NH_4Cl$ solution (200 mL) was slowly added dropwise to the mixture solution completed with the reaction at 0° C. to terminate the reaction. The mixture solution was dissolved in an excess amount of ethyl acetate (EA), and extracted with water. The organic layer was dried with anhydrous $MgSO_4$, and then silica gel filtered. For the filtered filtrate, the solvent was removed using a rotary evaporator, and the result went through column chromatography <MC/Hex=1/1> to obtain colorless oil 1-2 (14 g) in a 68% yield.

Preparation of Compound C

After dissolving Compound 1-2 (14 g, 46.36 mmol) in dichloromethane (DCM) (150 mL), $BF_3OEt_2$ (5.7 mL, 46.36 mmol) was added thereto at 0° C., and the mixture was stirred for 1 hour. The mixture solution completed with the reaction was dissolved in MC, and extracted with $NaHCO_3$ (aq.). The organic layer was dried with anhydrous $MgSO_4$, and then silica gel filtered. For the filtered filtrate, the solvent was removed using a rotary evaporator, and the result went through column chromatography <MC/Hex=1/2> to obtain yellow oil C (12.5 g) in a 95% yield.

The following Compound C was synthesized in the same manner as in Preparation Example 1 except that A and B of the following Table 1 were used as the intermediates.

TABLE 1

| Compound No. | Intermediate A | Intermediate B | C |
|---|---|---|---|
| 1 | 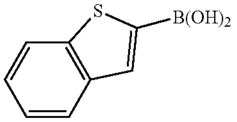 | 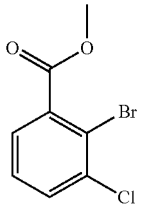 | 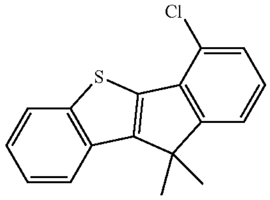 |
| 28 | 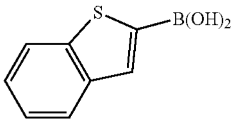 [SMILES: OB(O)c1cc2ccccc2s1] | 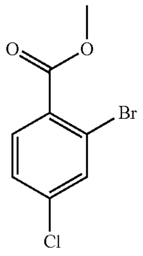 | 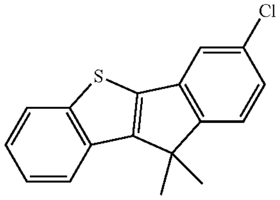 |
| 48 | 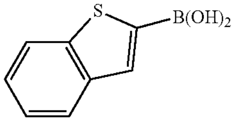 [SMILES: OB(O)c1cc2ccccc2s1] | 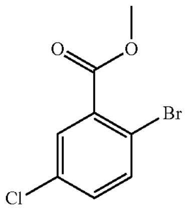 | 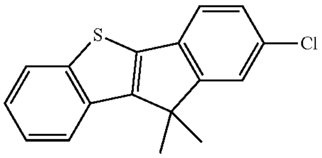 |
| 121 | 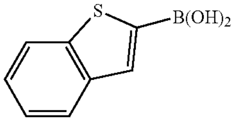 [SMILES: OB(O)c1cc2ccccc2s1] | 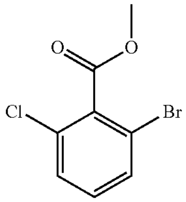 | 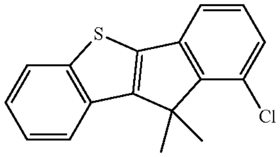 |

TABLE 1-continued
| Compound No. | Intermediate A | Intermediate B | C |
|---|---|---|---|
| 145 | 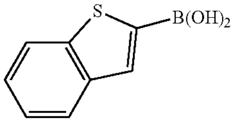 [SMILES: OB(O)c1cc2ccccc2s1] | 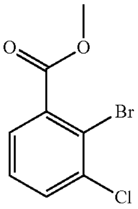 | 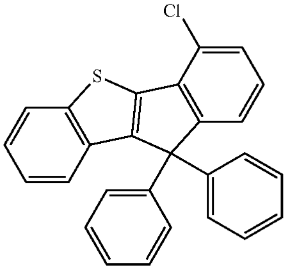 |
| 162 | 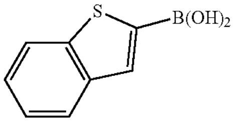 [SMILES: OB(O)c1cc2ccccc2s1] | 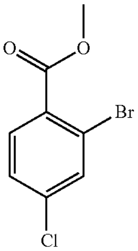 | 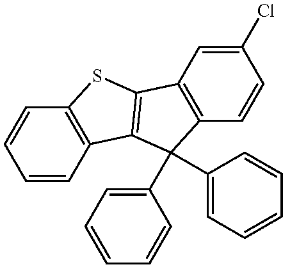 |
| 181 | 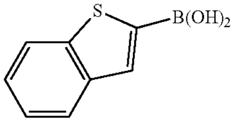 [SMILES: OB(O)c1cc2ccccc2s1] | 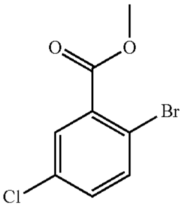 | 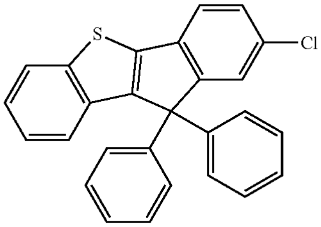 |
| 216 | 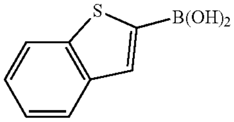 [SMILES: OB(O)c1cc2ccccc2s1] | 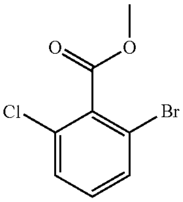 | 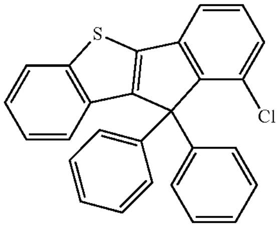 |
| 229 | 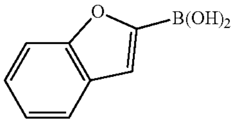 [SMILES: OB(O)c1cc2ccccc2o1] | 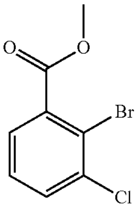 | 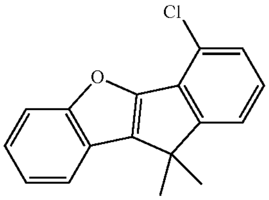 |
| 247 | 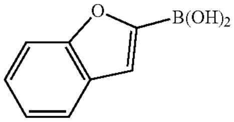 [SMILES: OB(O)c1cc2ccccc2o1] | 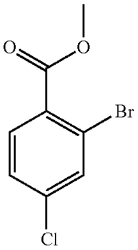 | 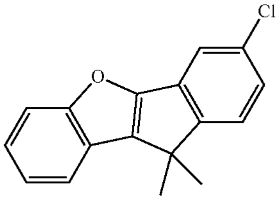 |

TABLE 1-continued
| Compound No. | Intermediate A | Intermediate B | C |
|---|---|---|---|
| 261 | 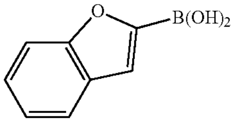 [SMILES: OB(O)c1cc2ccccc2o1] | 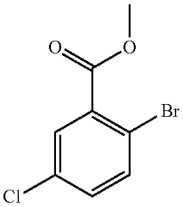 | 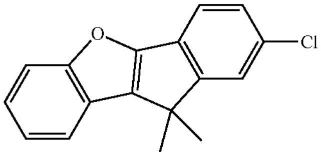 |
| 319 | 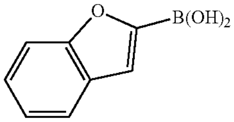 [SMILES: OB(O)c1cc2ccccc2o1] | 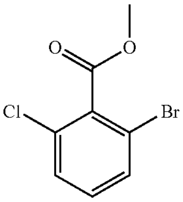 | 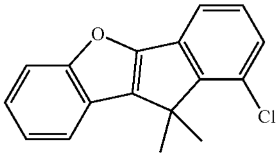 |
| 337 | 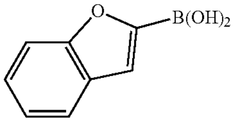 [SMILES: OB(O)c1cc2ccccc2o1] | 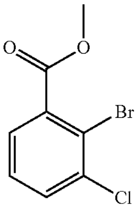 | 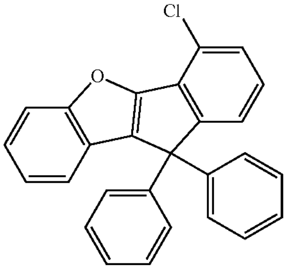 |
| 348 | 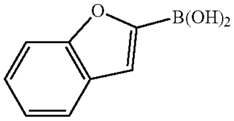 [SMILES: OB(O)c1cc2ccccc2o1] | 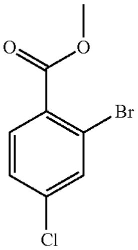 | 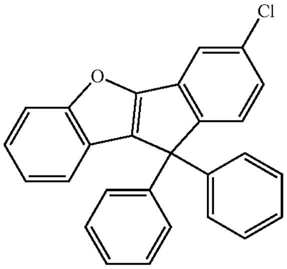 |
| 357 | 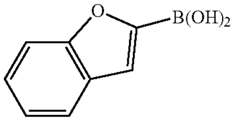 [SMILES: OB(O)c1cc2ccccc2o1] | 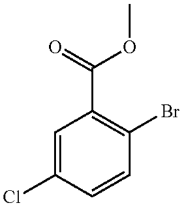 | 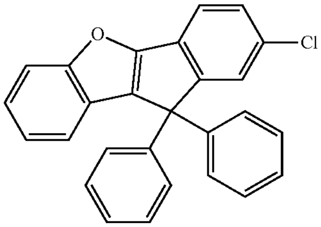 |
| 381 | 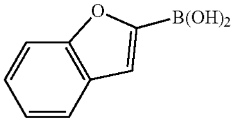 [SMILES: OB(O)c1cc2ccccc2o1] | 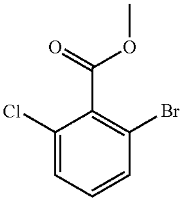 | 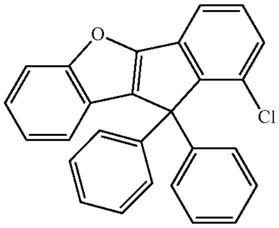 |

<Preparation Example 2> Preparation of Target Compound

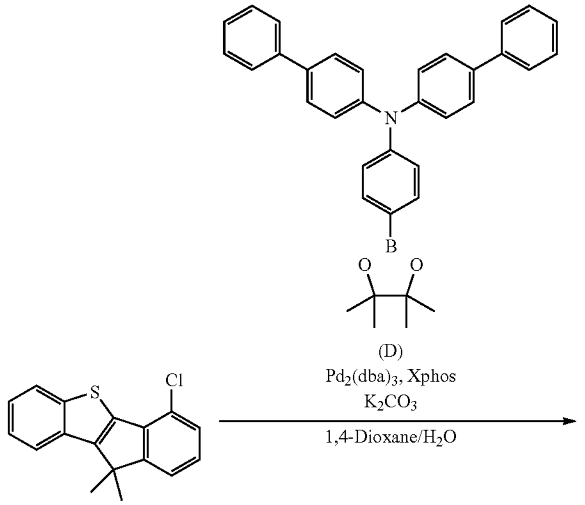

(C)

-continued

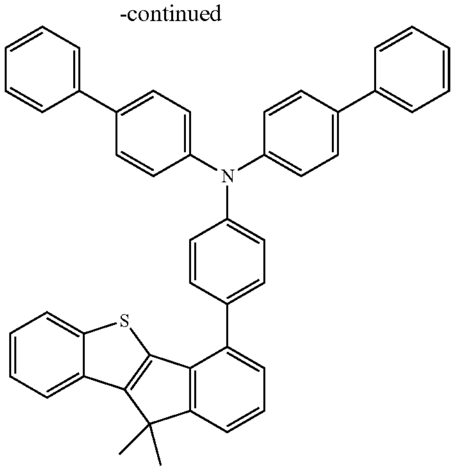

1

After dissolving Compound C (5 g, 17.56 mmol), N-([1,1'-biphenyl]-4-yl)-N-(4-(4,4,5,5-tetramethyl-1,3,2-dioxaborolan-2-yl)phenyl)-[1,1'-biphenyl]-4-amine (9 g, 17.56 mmol), $Pd_2(dba)_3$ (1.6 g, 1.75 mmol), XPhos (1.7 g, 3.52 mmol) and $K_2CO_3$ (5 g, 35.12 mmol) in 1,4-dioxane/$H_2O$ (70 mL/15 mL), the mixture was stirred for 15 hours at 100° C. The mixture solution completed with the reaction was dissolved in an excess amount of DCM, and extracted with water. The organic layer was dried with anhydrous $MgSO_4$, and then silica gel filtered. For the filtered filtrate, the solvent was removed using a rotary evaporator, and the result went through column chromatography <MC/Hex=1/2> to obtain yellow solid target Compound 1 (5.6 g) in a 50% yield.

The following target compounds were synthesized in the same manner as in Preparation Example 2 except that C and D of the following Table 2 were used as the intermediates.

TABLE 2
| Compound No. | Intermediate C | Intermediate D | Target Compound | Yield |
|---|---|---|---|---|
| 1 | 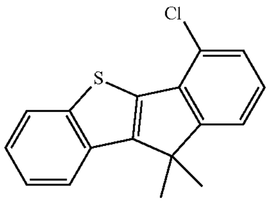 | 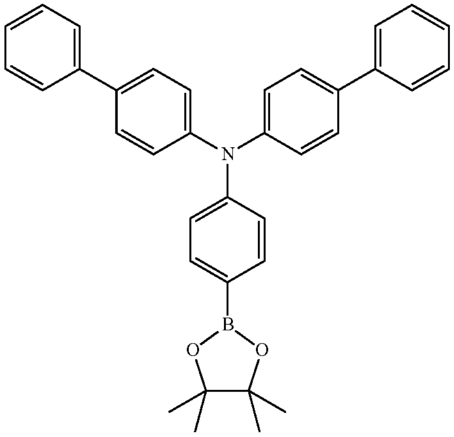 [SMILES: CC1(C)OB(c2ccc(N(c3ccc(-c4ccccc4)cc3)c3ccc(-c4ccccc4)cc3)cc2)OC1(C)C] | 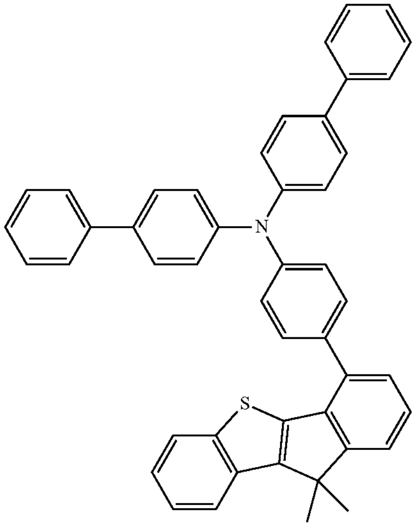 [SMILES: CC1(C)c2cccc(-c3ccc(N(c4ccc(-c5ccccc5)cc4)c4ccc(-c5ccccc5)cc4)cc3)c2-c2sc3ccccc3c21] | 50% |

TABLE 2-continued
| Compound No. | Intermediate C | Intermediate D | Target Compound | Yield |
|---|---|---|---|---|
| 28 | 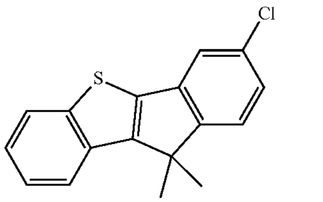 [SMILES: CC1(C)c2ccc(Cl)cc2-c2sc3ccccc3c21] | 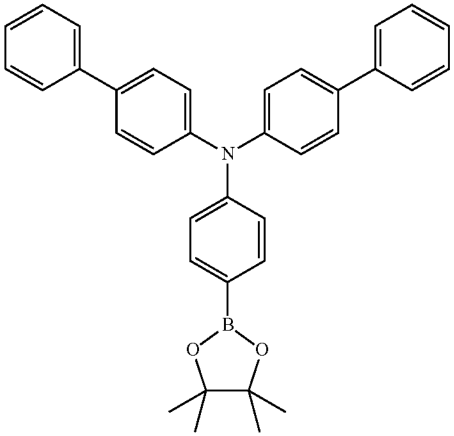 [SMILES: CC1(C)OB(c2ccc(N(c3ccc(-c4ccccc4)cc3)c3ccc(-c4ccccc4)cc3)cc2)OC1(C)C] | 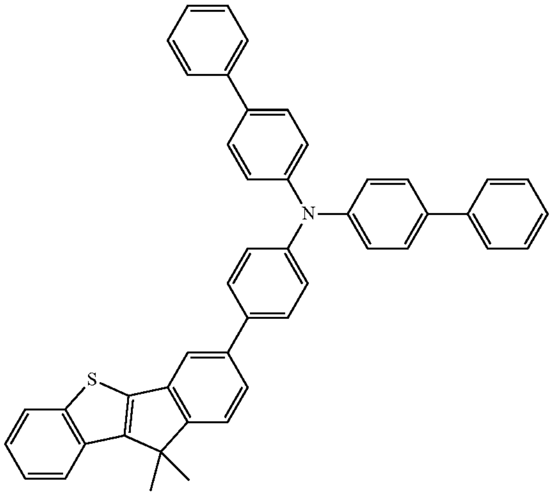 | 57% |
| 48 | 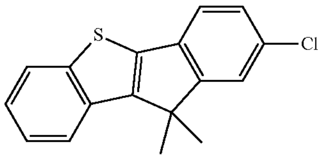 [SMILES: CC1(C)c2cc(Cl)ccc2-c2sc3ccccc3c21] | 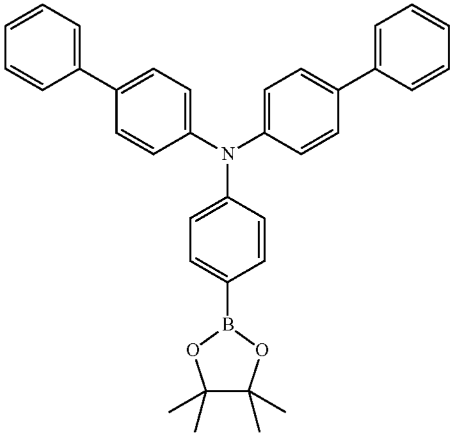 [SMILES: CC1(C)OB(c2ccc(N(c3ccc(-c4ccccc4)cc3)c3ccc(-c4ccccc4)cc3)cc2)OC1(C)C] | 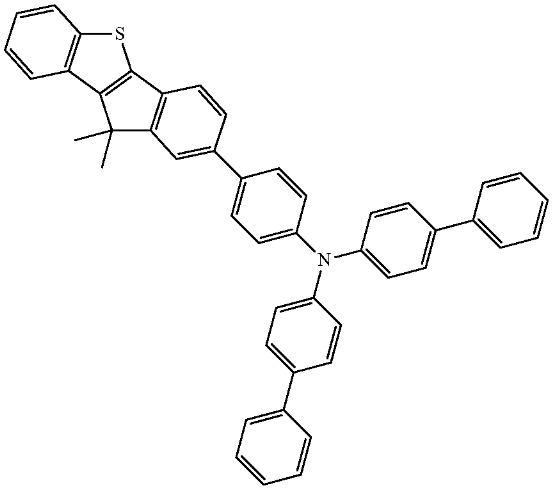 [SMILES: CC1(C)c2cc(-c3ccc(N(c4ccc(-c5ccccc5)cc4)c4ccc(-c5ccccc5)cc4)cc3)ccc2-c2sc3ccccc3c21] | 70% |

TABLE 2-continued
| Compound No. | Intermediate C | Intermediate D | Target Compound | Yield |
| --- | --- | --- | --- | --- |
| 50 | 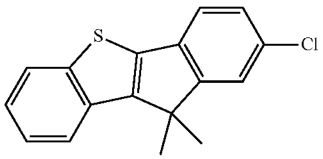 [SMILES: CC1(C)c2cc(Cl)ccc2-c2sc3ccccc3c21] | 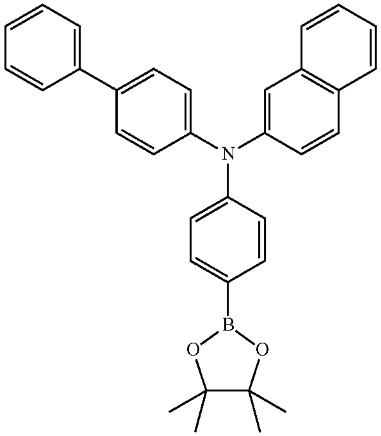 [SMILES: CC1(C)OB(c2ccc(N(c3ccc(-c4ccccc4)cc3)c3ccc4ccccc4c3)cc2)OC1(C)C] | 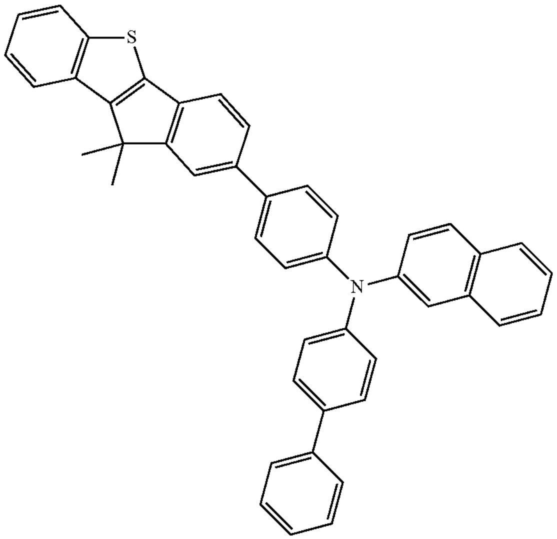 [SMILES: CC1(C)c2cc(-c3ccc(N(c4ccc(-c5ccccc5)cc4)c4ccc5ccccc5c4)cc3)ccc2-c2sc3ccccc3c21] | 65% |
| 52 | 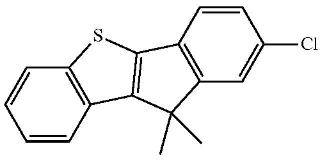 [SMILES: CC1(C)c2cc(Cl)ccc2-c2sc3ccccc3c21] | 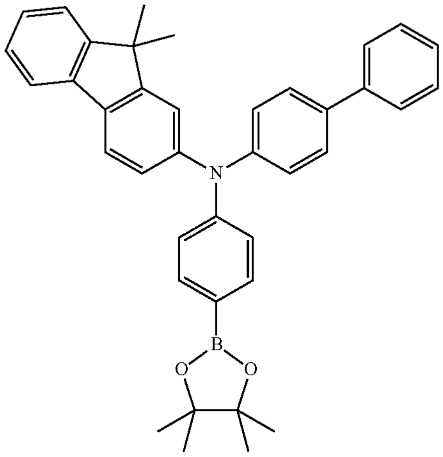 [SMILES: CC1(C)c2ccccc2-c2ccc(N(c3ccc(B4OC(C)(C)C(C)(C)O4)cc3)c3ccc(-c4ccccc4)cc3)cc21] | 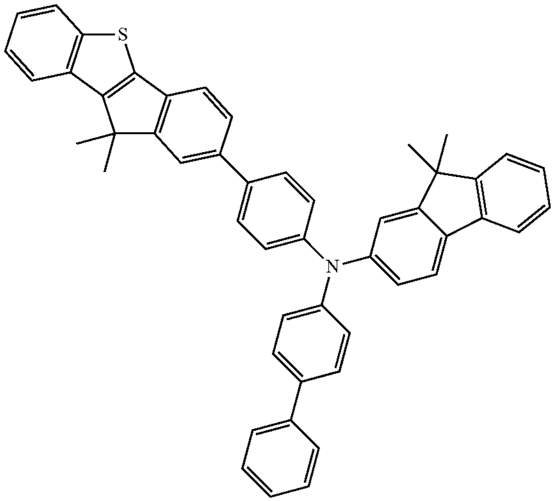 [SMILES: CC1(C)c2ccccc2-c2ccc(N(c3ccc(-c4ccccc4)cc3)c3ccc(-c4ccc5c(c4)C(C)(C)c4c-5sc5ccccc45)cc3)cc21] | 59% |

TABLE 2-continued
| Compound No. | Intermediate C | Intermediate D | Target Compound | Yield |
|---|---|---|---|---|
| 61 | 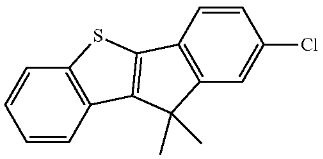 [SMILES: CC1(C)c2cc(Cl)ccc2-c2sc3ccccc3c21] | 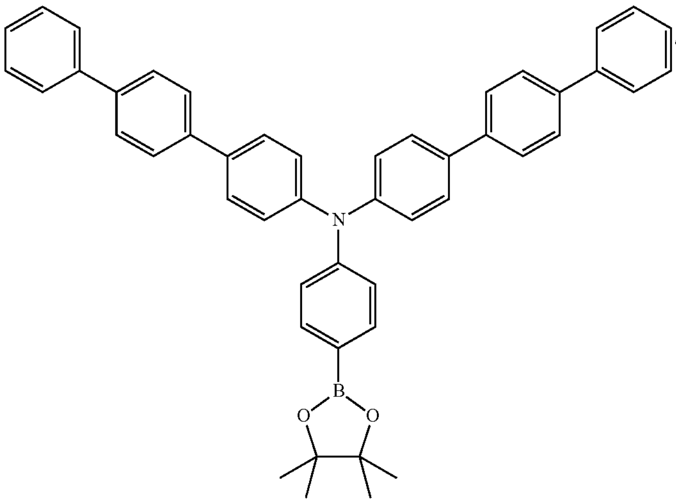 [SMILES: CC1(C)OB(c2ccc(N(c3ccc(-c4ccc(-c5ccccc5)cc4)cc3)c3ccc(-c4ccc(-c5ccccc5)cc4)cc3)cc2)OC1(C)C] | 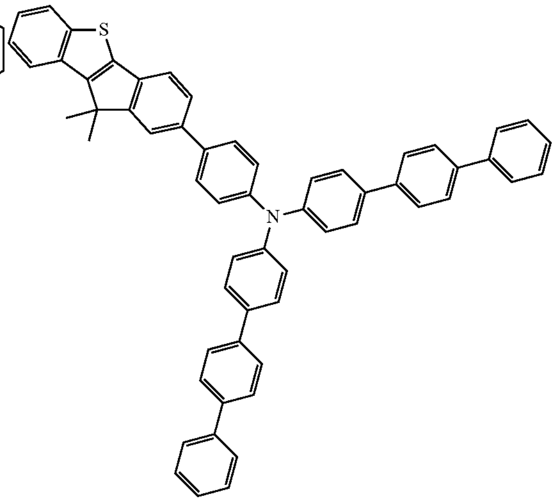 | 55% |

TABLE 2-continued
| Compound No. | Intermediate C | Intermediate D | Target Compound | Yield |
| --- | --- | --- | --- | --- |
| 62 | 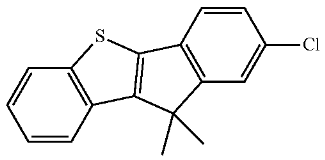 [SMILES: CC1(C)c2cc(Cl)ccc2-c2sc3ccccc3c21] | 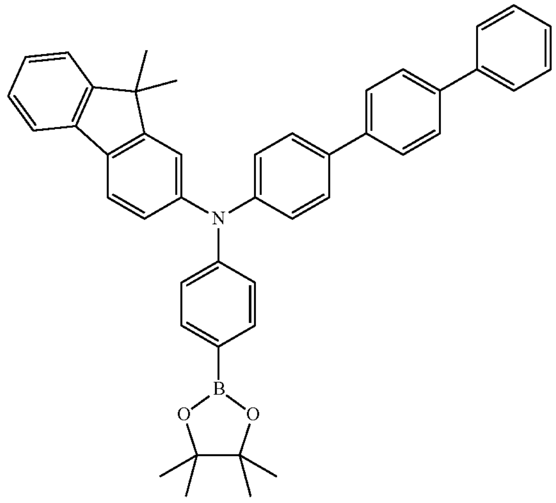 [SMILES: CC1(C)c2ccccc2-c2ccc(N(c3ccc(B4OC(C)(C)C(C)(C)O4)cc3)c3ccc(-c4ccc(-c5ccccc5)cc4)cc3)cc21] | 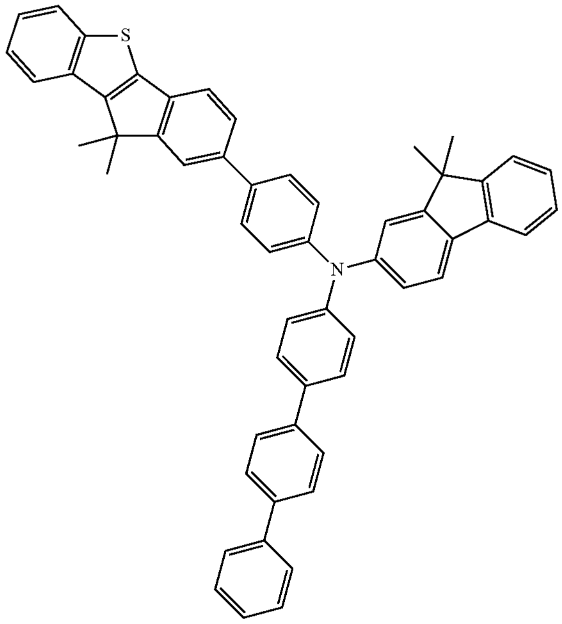 [SMILES: CC1(C)c2ccccc2-c2ccc(N(c3ccc(-c4ccc(-c5ccccc5)cc4)cc3)c3ccc(-c4ccc5c(c4)C(C)(C)c4c-5sc5ccccc45)cc3)cc21] | 66% |

TABLE 2-continued
| Compound No. | Intermediate C | Intermediate D | Target Compound | Yield |
|---|---|---|---|---|
| 63 | 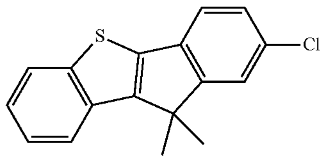 [SMILES: CC1(C)c2cc(Cl)ccc2-c2sc3ccccc3c21] | 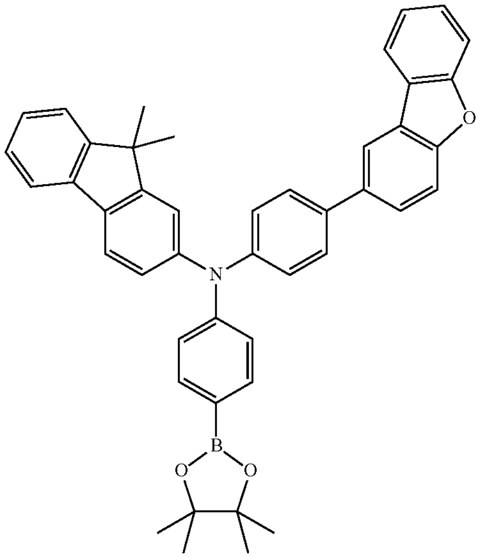 [SMILES: CC1(C)c2ccccc2-c2ccc(N(c3ccc(B4OC(C)(C)C(C)(C)O4)cc3)c3ccc(-c4ccc5oc6ccccc6c5c4)cc3)cc21] | 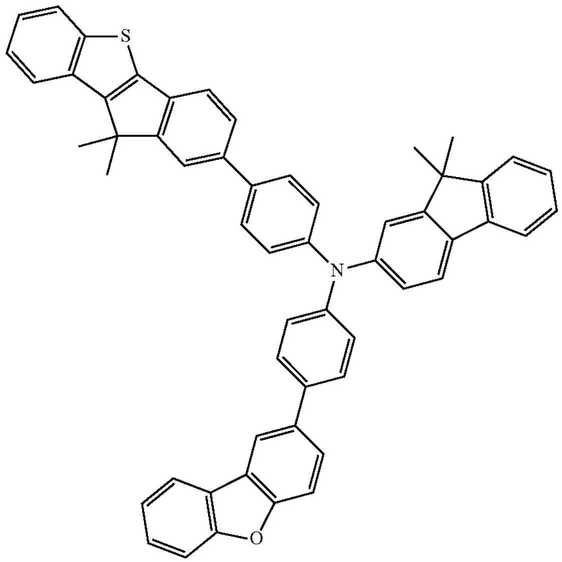 [SMILES: CC1(C)c2ccccc2-c2ccc(N(c3ccc(-c4ccc5c(c4)C(C)(C)c4c-5sc5ccccc45)cc3)c3ccc(-c4ccc5oc6ccccc6c5c4)cc3)cc21] | 55% |

TABLE 2-continued
| Compound No. | Intermediate C | Intermediate D | Target Compound | Yield |
|---|---|---|---|---|
| 78 | 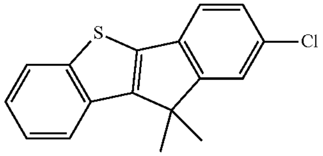 [SMILES: CC1(C)c2cc(Cl)ccc2-c2sc3ccccc3c21] | 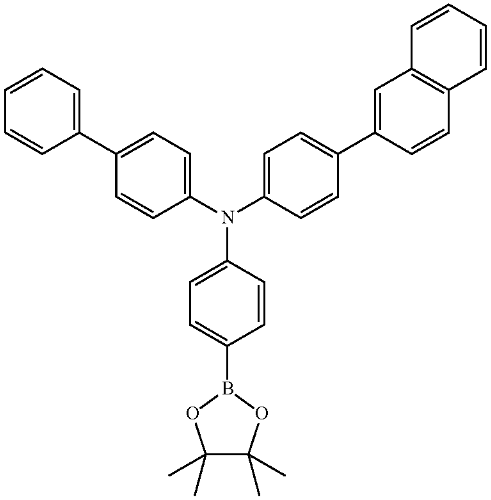 [SMILES: CC1(C)OB(c2ccc(N(c3ccc(-c4ccccc4)cc3)c3ccc(-c4ccc5ccccc5c4)cc3)cc2)OC1(C)C] | 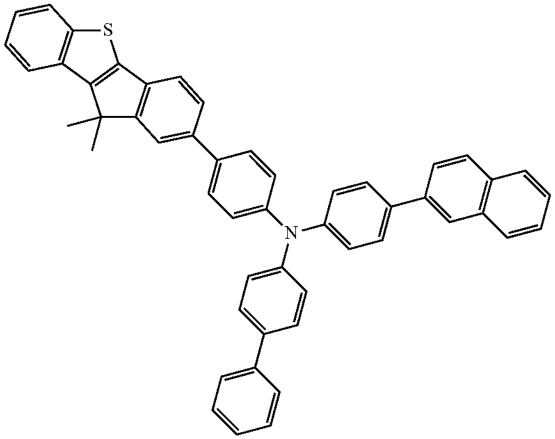 [SMILES: CC1(C)c2cc(-c3ccc(N(c4ccc(-c5ccccc5)cc4)c4ccc(-c5ccc6ccccc6c5)cc4)cc3)ccc2-c2sc3ccccc3c21] | 45% |
| 97 | 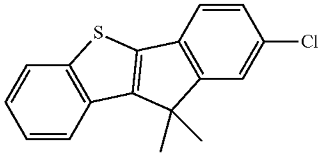 [SMILES: CC1(C)c2cc(Cl)ccc2-c2sc3ccccc3c21] | 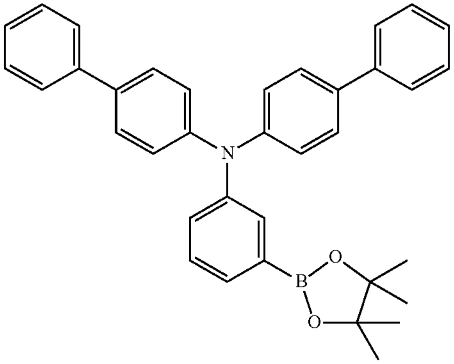 [SMILES: CC1(C)OB(c2cccc(N(c3ccc(-c4ccccc4)cc3)c3ccc(-c4ccccc4)cc3)c2)OC1(C)C] | 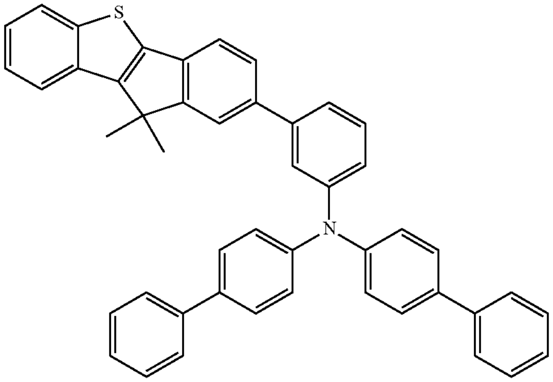 [SMILES: CC1(C)c2cc(-c3cccc(N(c4ccc(-c5ccccc5)cc4)c4ccc(-c5ccccc5)cc4)c3)ccc2-c2sc3ccccc3c21] | 59% |

TABLE 2-continued
| Compound No. | Intermediate C | Intermediate D | Target Compound | Yield |
|---|---|---|---|---|
| 121 | 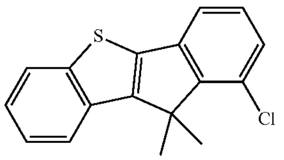 [SMILES: CC1(C)c2c(Cl)cccc2-c2sc3ccccc3c21] | 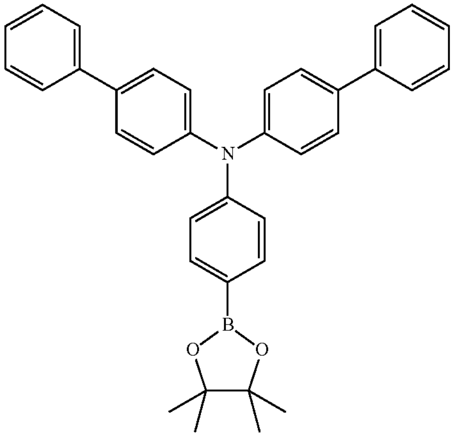 [SMILES: CC1(C)OB(c2ccc(N(c3ccc(-c4ccccc4)cc3)c3ccc(-c4ccccc4)cc3)cc2)OC1(C)C] | 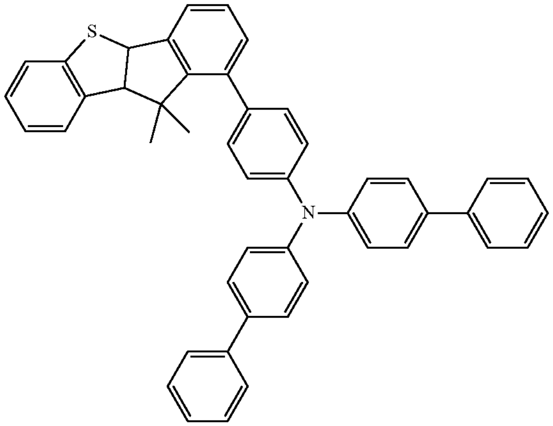 | 66% |
| 145 | 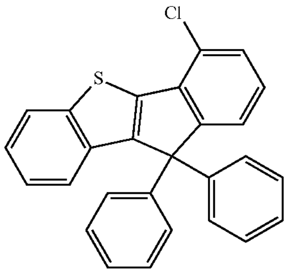 | 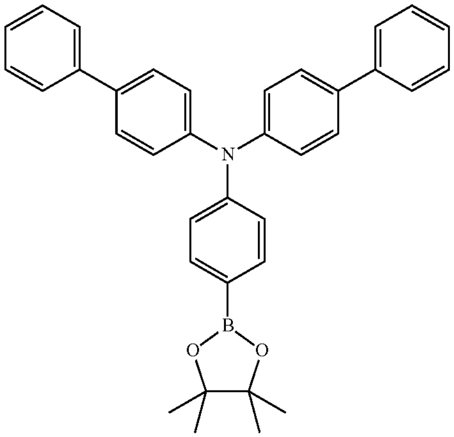 [SMILES: CC1(C)OB(c2ccc(N(c3ccc(-c4ccccc4)cc3)c3ccc(-c4ccccc4)cc3)cc2)OC1(C)C] | 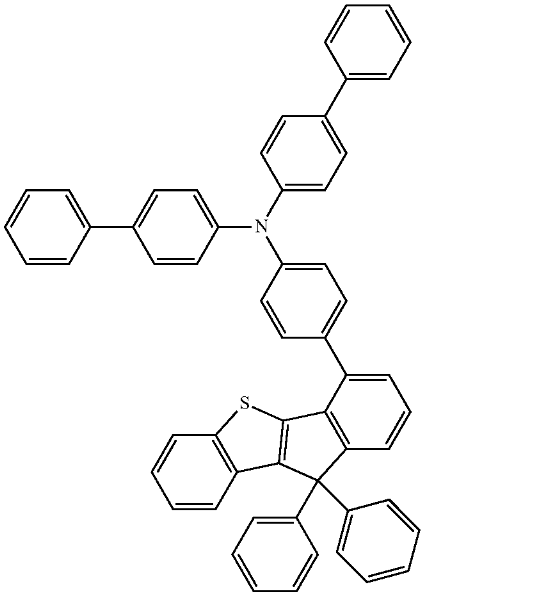 [SMILES: c1ccc(-c2ccc(N(c3ccc(-c4ccccc4)cc3)c3ccc(-c4cccc5c4-c4sc6ccccc6c4C5(c4ccccc4)c4ccccc4)cc3)cc2)cc1] | 57% |

TABLE 2-continued
| Compound No. | Intermediate C | Intermediate D | Target Compound | Yield |
| --- | --- | --- | --- | --- |
| 162 | 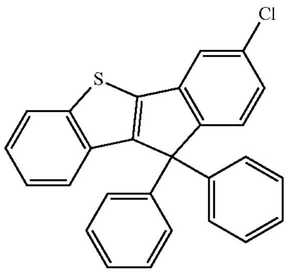 [SMILES: Clc1ccc2c(c1)-c1sc3ccccc3c1C2(c1ccccc1)c1ccccc1] | 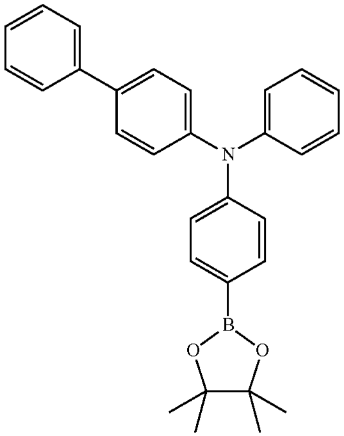 [SMILES: CC1(C)OB(c2ccc(N(c3ccccc3)c3ccc(-c4ccccc4)cc3)cc2)OC1(C)C] | 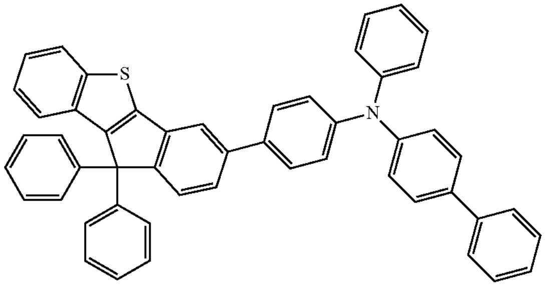 [SMILES: c1ccc(-c2ccc(N(c3ccccc3)c3ccc(-c4ccc5c(c4)-c4sc6ccccc6c4C5(c4ccccc4)c4ccccc4)cc3)cc2)cc1] | 62% |
| 181 | 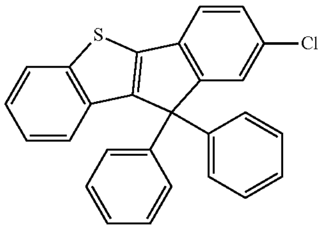 | 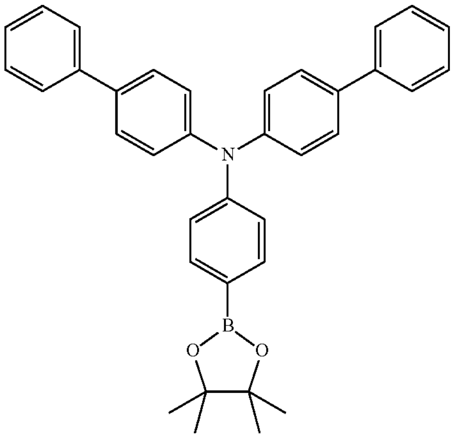 [SMILES: CC1(C)OB(c2ccc(N(c3ccc(-c4ccccc4)cc3)c3ccc(-c4ccccc4)cc3)cc2)OC1(C)C] | 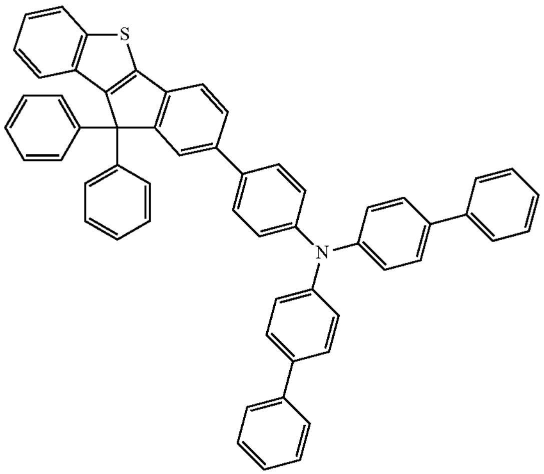 [SMILES: c1ccc(-c2ccc(N(c3ccc(-c4ccccc4)cc3)c3ccc(-c4ccc5c(c4)C(c4ccccc4)(c4ccccc4)c4c-5sc5ccccc45)cc3)cc2)cc1] | 45% |

TABLE 2-continued
| Compound No. | Intermediate C | Intermediate D | Target Compound | Yield |
| --- | --- | --- | --- | --- |
| 182 | 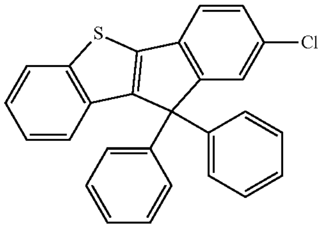 | 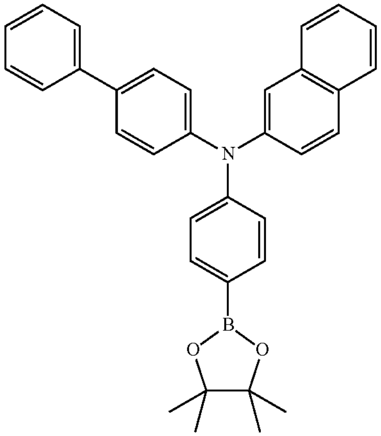 [SMILES: CC1(C)OB(c2ccc(N(c3ccc(-c4ccccc4)cc3)c3ccc4ccccc4c3)cc2)OC1(C)C] | 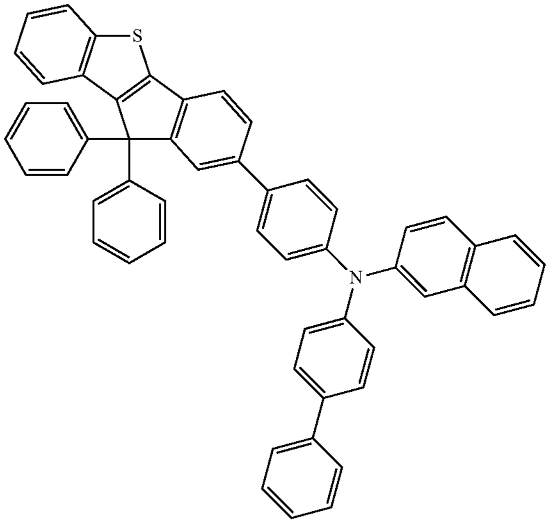 [SMILES: c1ccc(-c2ccc(N(c3ccc(-c4ccc5c(c4)C(c4ccccc4)(c4ccccc4)c4c-5sc5ccccc45)cc3)c3ccc4ccccc4c3)cc2)cc1] | 51% |
| 216 | 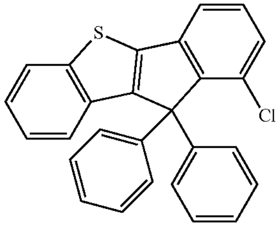 | 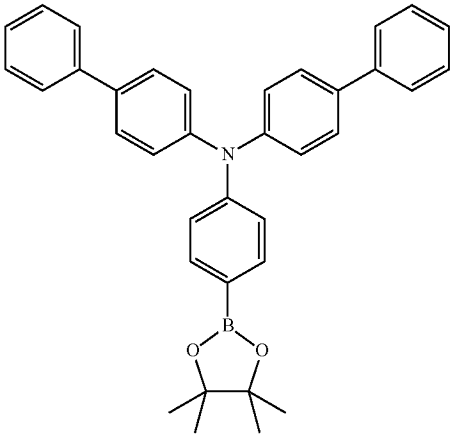 [SMILES: CC1(C)OB(c2ccc(N(c3ccc(-c4ccccc4)cc3)c3ccc(-c4ccccc4)cc3)cc2)OC1(C)C] | 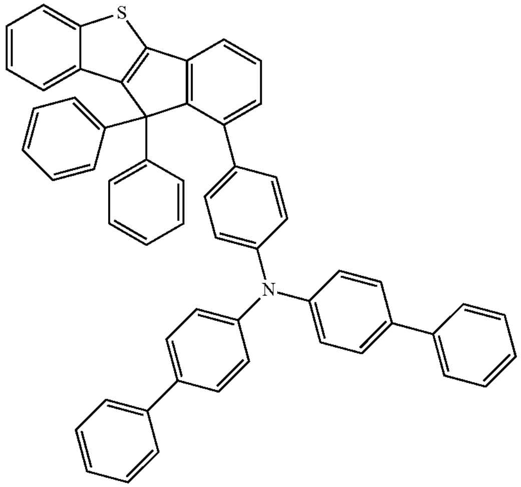 [SMILES: c1ccc(-c2ccc(N(c3ccc(-c4ccccc4)cc3)c3ccc(-c4cccc5c4C(c4ccccc4)(c4ccccc4)c4c-5sc5ccccc45)cc3)cc2)cc1] | 52% |

TABLE 2-continued
| Compound No. | Intermediate C | Intermediate D | Target Compound | Yield |
| --- | --- | --- | --- | --- |
| 229 | 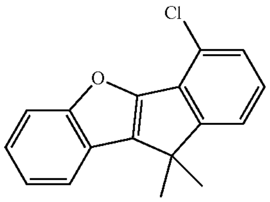 [SMILES: CC1(C)c2cccc(Cl)c2-c2oc3ccccc3c21] | 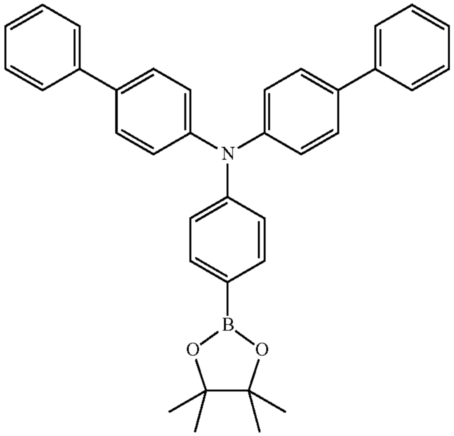 [SMILES: CC1(C)OB(c2ccc(N(c3ccc(-c4ccccc4)cc3)c3ccc(-c4ccccc4)cc3)cc2)OC1(C)C] | 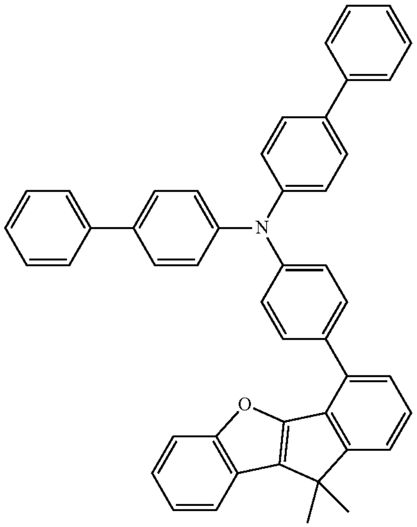 [SMILES: CC1(C)c2cccc(-c3ccc(N(c4ccc(-c5ccccc5)cc4)c4ccc(-c5ccccc5)cc4)cc3)c2-c2oc3ccccc3c21] | 48% |
| 247 | 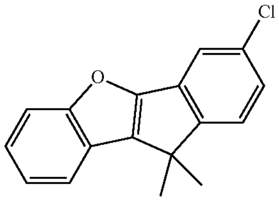 | 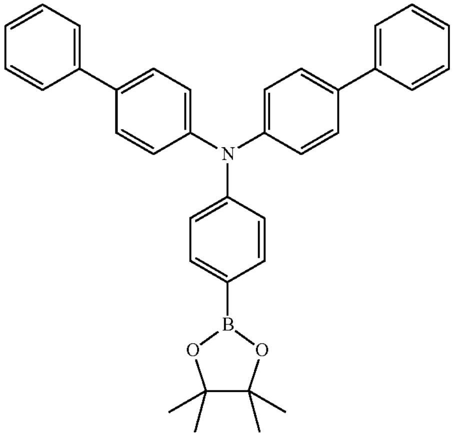 [SMILES: CC1(C)OB(c2ccc(N(c3ccc(-c4ccccc4)cc3)c3ccc(-c4ccccc4)cc3)cc2)OC1(C)C] | 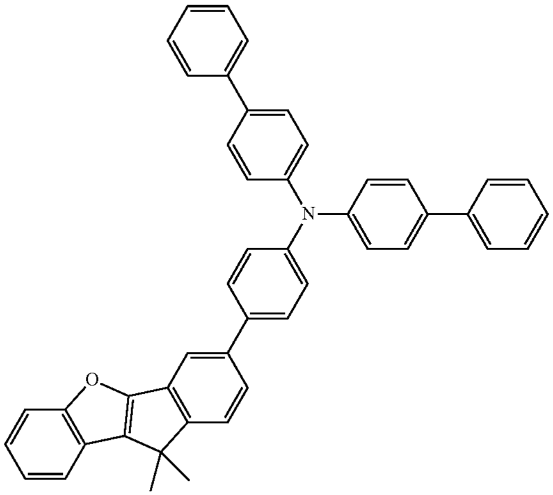 [SMILES: CC1(C)c2ccc(-c3ccc(N(c4ccc(-c5ccccc5)cc4)c4ccc(-c5ccccc5)cc4)cc3)cc2-c2oc3ccccc3c21] | 61% |

TABLE 2-continued
| Compound No. | Intermediate C | Intermediate D | Target Compound | Yield |
|---|---|---|---|---|
| 261 | 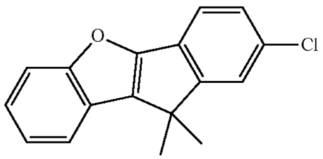 [SMILES: CC1(C)c2cc(Cl)ccc2-c2oc3ccccc3c21] | 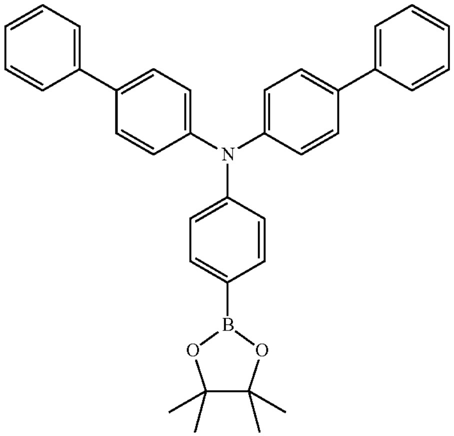 [SMILES: CC1(C)OB(c2ccc(N(c3ccc(-c4ccccc4)cc3)c3ccc(-c4ccccc4)cc3)cc2)OC1(C)C] | 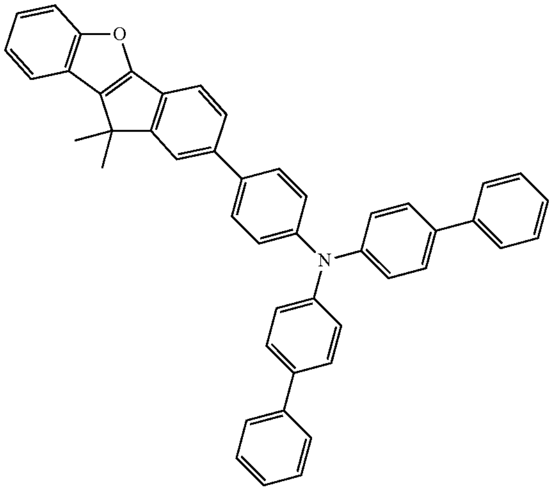 [SMILES: CC1(C)c2cc(-c3ccc(N(c4ccc(-c5ccccc5)cc4)c4ccc(-c5ccccc5)cc4)cc3)ccc2-c2oc3ccccc3c21] | 55% |
| 264 | 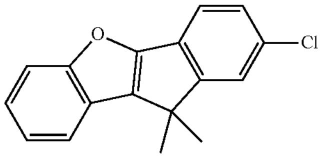 [SMILES: CC1(C)c2cc(Cl)ccc2-c2oc3ccccc3c21] | 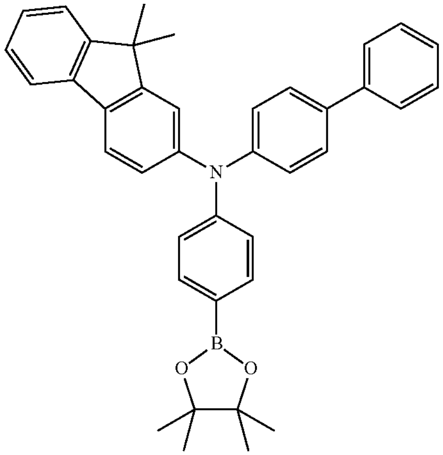 [SMILES: CC1(C)c2ccccc2-c2ccc(N(c3ccc(B4OC(C)(C)C(C)(C)O4)cc3)c3ccc(-c4ccccc4)cc3)cc21] | 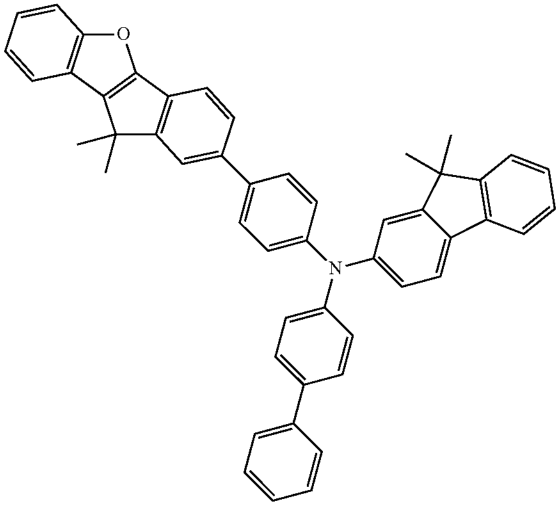 [SMILES: CC1(C)c2ccccc2-c2ccc(N(c3ccc(-c4ccccc4)cc3)c3ccc(-c4ccc5c(c4)C(C)(C)c4c-5oc5ccccc45)cc3)cc21] | 59% |

TABLE 2-continued
| Compound No. | Intermediate C | Intermediate D | Target Compound | Yield |
|---|---|---|---|---|
| 276 | 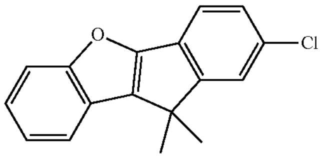 [SMILES: CC1(C)c2cc(Cl)ccc2-c2oc3ccccc3c21] | 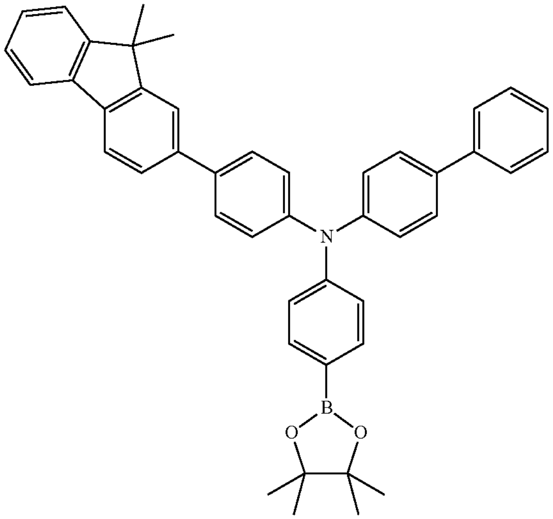 [SMILES: CC1(C)c2ccccc2-c2ccc(-c3ccc(N(c4ccc(B5OC(C)(C)C(C)(C)O5)cc4)c4ccc(-c5ccccc5)cc4)cc3)cc21] | 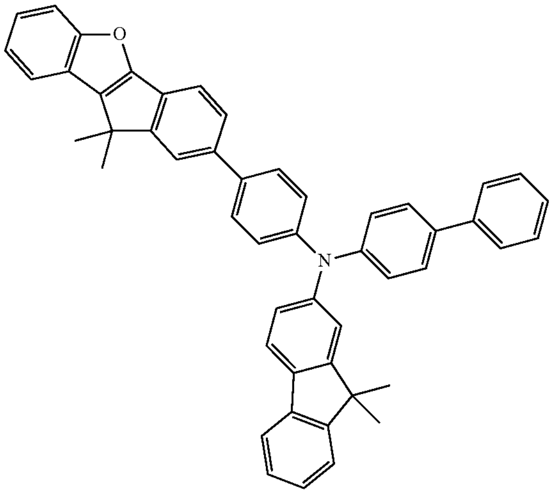 [SMILES: CC1(C)c2ccccc2-c2ccc(N(c3ccc(-c4ccccc4)cc3)c3ccc(-c4ccc5c(c4)C(C)(C)c4c-5oc5ccccc45)cc3)cc21] | 58% |

TABLE 2-continued
| Compound No. | Intermediate C | Intermediate D | Target Compound | Yield |
|---|---|---|---|---|
| 294 | 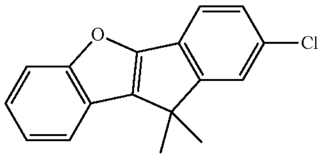 [SMILES: CC1(C)c2cc(Cl)ccc2-c2oc3ccccc3c21] | 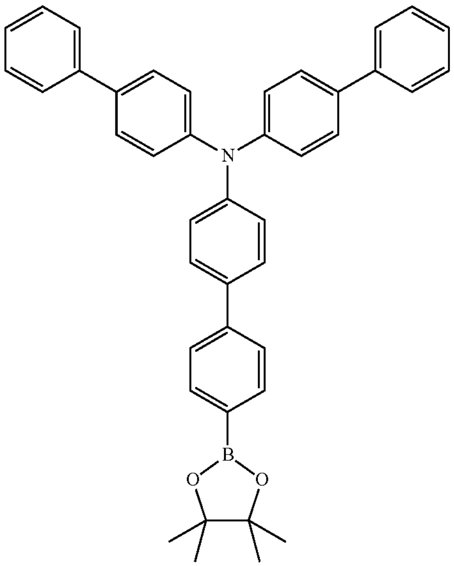 [SMILES: CC1(C)OB(c2ccc(-c3ccc(N(c4ccc(-c5ccccc5)cc4)c4ccc(-c5ccccc5)cc4)cc3)cc2)OC1(C)C] | 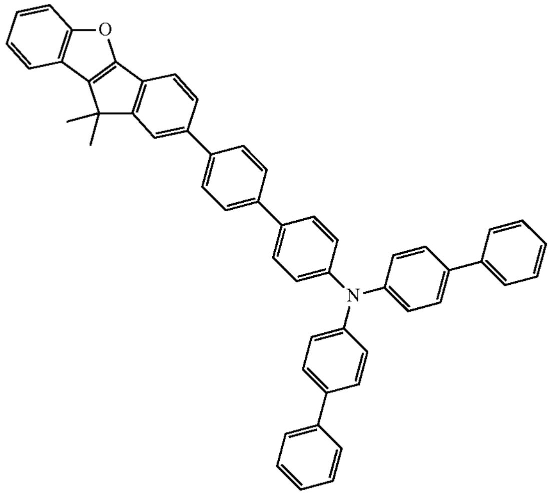 [SMILES: CC1(C)c2cc(-c3ccc(-c4ccc(N(c5ccc(-c6ccccc6)cc5)c5ccc(-c6ccccc6)cc5)cc4)cc3)ccc2-c2oc3ccccc3c21] | 60% |
| 319 | 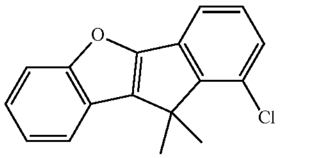 [SMILES: CC1(C)c2c(Cl)cccc2-c2oc3ccccc3c21] | 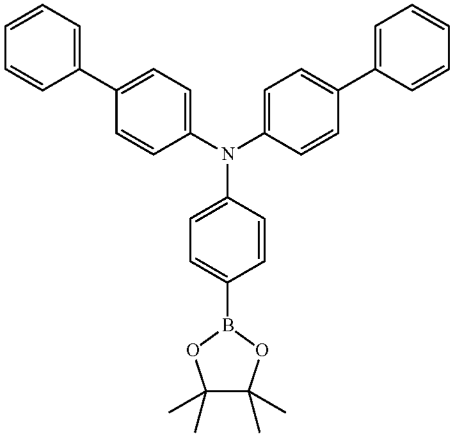 [SMILES: CC1(C)OB(c2ccc(N(c3ccc(-c4ccccc4)cc3)c3ccc(-c4ccccc4)cc3)cc2)OC1(C)C] | 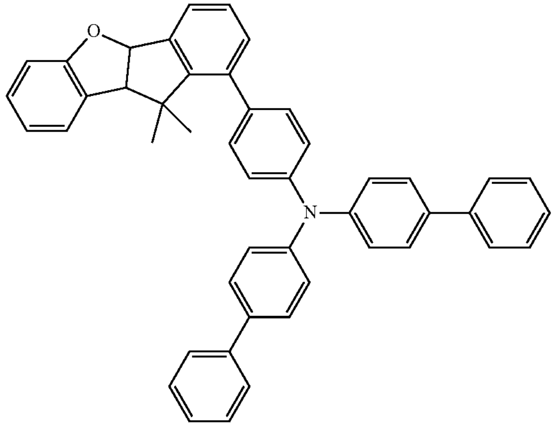 [SMILES: CC1(C)c2c(-c3ccc(N(c4ccc(-c5ccccc5)cc4)c4ccc(-c5ccccc5)cc4)cc3)cccc2C2Oc3ccccc3C21] | 44% |

TABLE 2-continued
| Compound No. | Intermediate C | Intermediate D | Target Compound | Yield |
| --- | --- | --- | --- | --- |
| 337 | 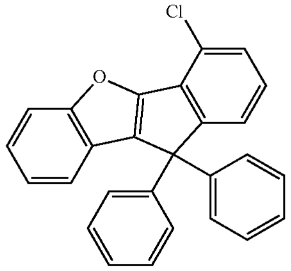 | 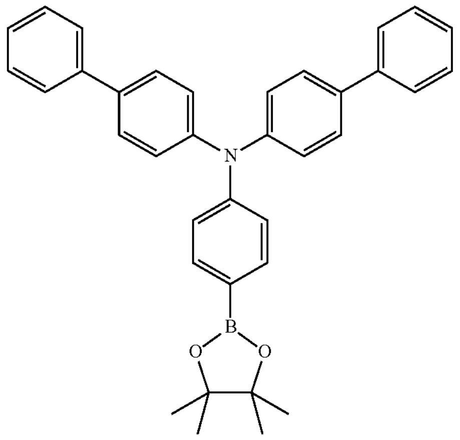 [SMILES: CC1(C)OB(c2ccc(N(c3ccc(-c4ccccc4)cc3)c3ccc(-c4ccccc4)cc3)cc2)OC1(C)C] | 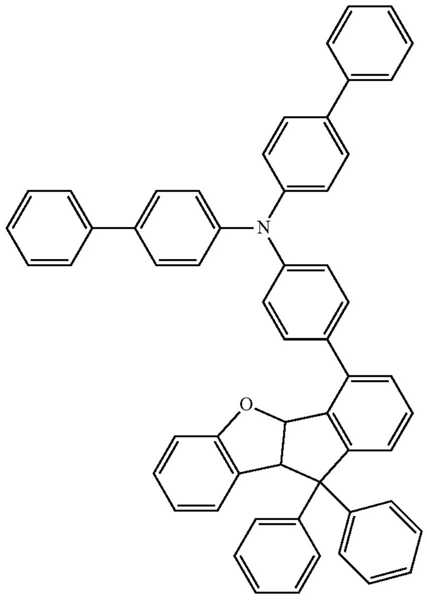 [SMILES: c1ccc(-c2ccc(N(c3ccc(-c4ccccc4)cc3)c3ccc(-c4cccc5c4C4Oc6ccccc6C4C5(c4ccccc4)c4ccccc4)cc3)cc2)cc1] | 50% |
| 348 | 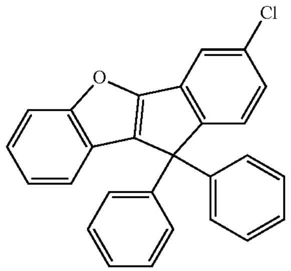 [SMILES: Clc1ccc2c(c1)-c1oc3ccccc3c1C2(c1ccccc1)c1ccccc1] | 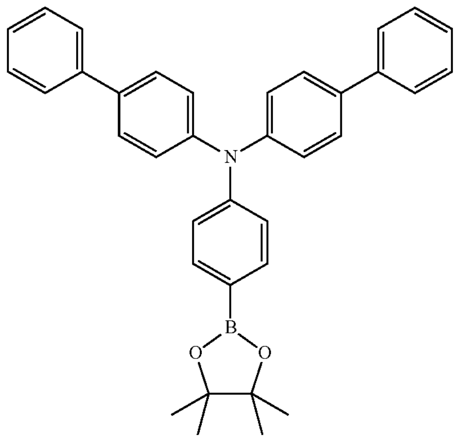 [SMILES: CC1(C)OB(c2ccc(N(c3ccc(-c4ccccc4)cc3)c3ccc(-c4ccccc4)cc3)cc2)OC1(C)C] | 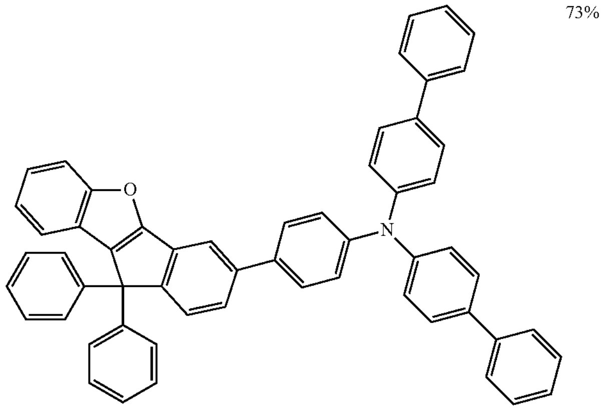 | 73% |

TABLE 2-continued
| Compound No. | Intermediate C | Intermediate D | Target Compound | Yield |
|---|---|---|---|---|
| 357 | 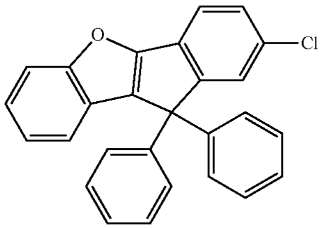 [SMILES: Clc1ccc2c(c1)C(c1ccccc1)(c1ccccc1)c1c-2oc2ccccc12] | 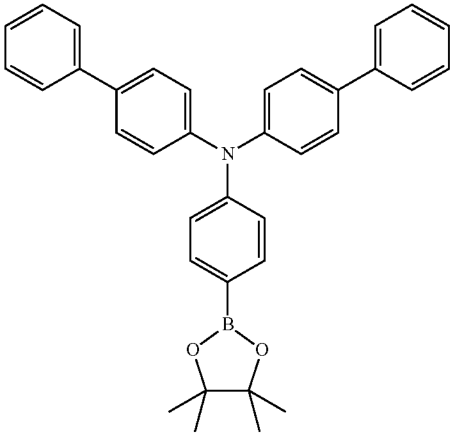 [SMILES: CC1(C)OB(c2ccc(N(c3ccc(-c4ccccc4)cc3)c3ccc(-c4ccccc4)cc3)cc2)OC1(C)C] | 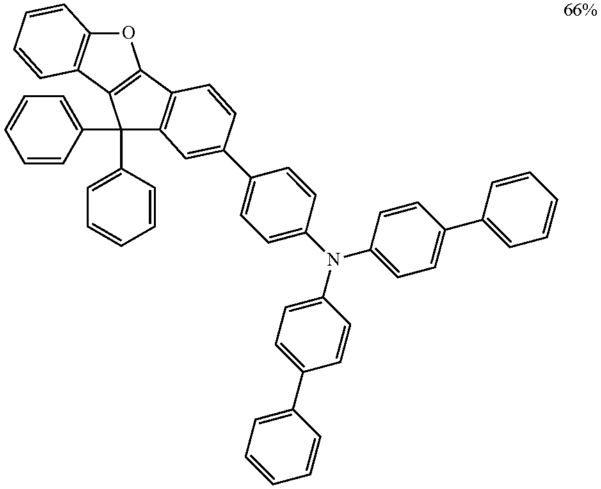 | 66% |
| 378 | 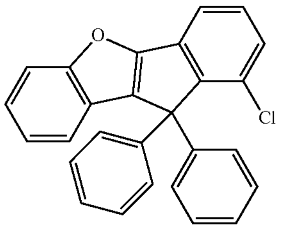 [SMILES: Clc1cccc2c1C(c1ccccc1)(c1ccccc1)c1c-2oc2ccccc12] | 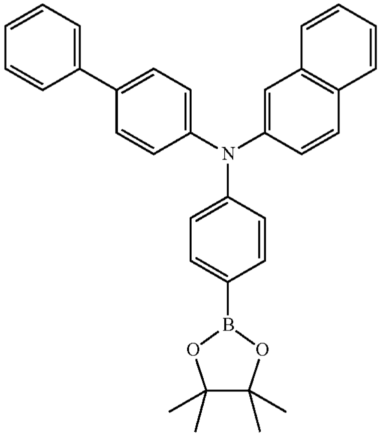 [SMILES: CC1(C)OB(c2ccc(N(c3ccc(-c4ccccc4)cc3)c3ccc4ccccc4c3)cc2)OC1(C)C] | 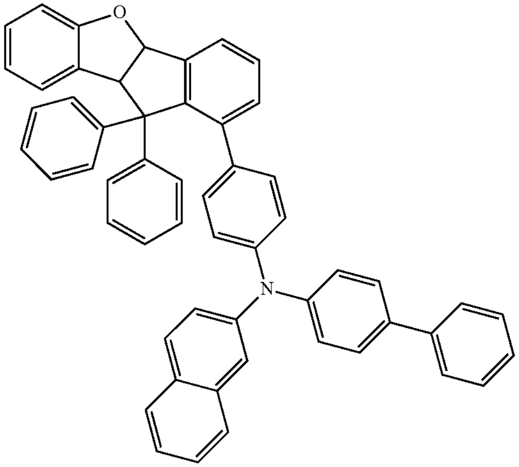 [SMILES: c1ccc(-c2ccc(N(c3ccc(-c4cccc5c4C(c4ccccc4)(c4ccccc4)C4c6ccccc6OC54)cc3)c3ccc4ccccc4c3)cc2)cc1] | 41% |

TABLE 2-continued
| Compound No. | Intermediate C | Intermediate D | Target Compound | Yield |
|---|---|---|---|---|
| 381 | 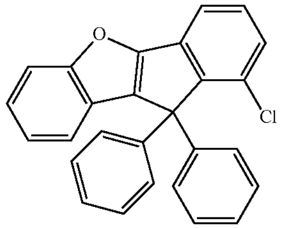 [SMILES: Clc1cccc2c1C(c1ccccc1)(c1ccccc1)c1c-2oc2ccccc12] | 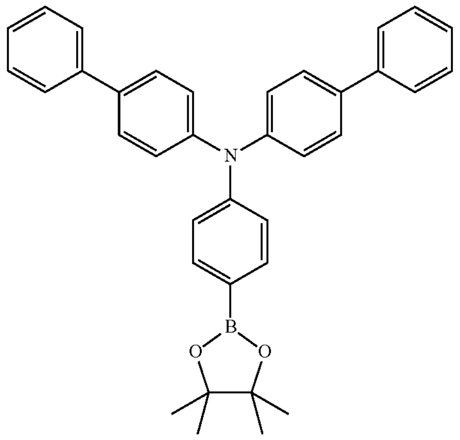 [SMILES: CC1(C)OB(c2ccc(N(c3ccc(-c4ccccc4)cc3)c3ccc(-c4ccccc4)cc3)cc2)OC1(C)C] | 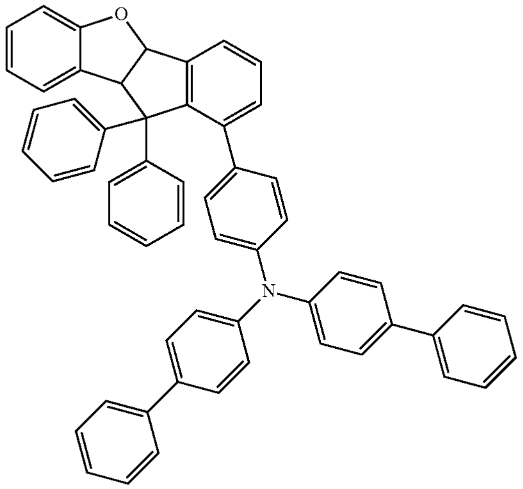 [SMILES: c1ccc(-c2ccc(N(c3ccc(-c4ccccc4)cc3)c3ccc(-c4cccc5c4C(c4ccccc4)(c4ccccc4)C4c6ccccc6OC54)cc3)cc2)cc1] | 40% |

Heterocyclic compounds corresponding to Chemical Formula 1 other than the compounds described in Preparation Examples 1 and 2, and Table 1 and Table 2 were also prepared in the same manner as in the preparation examples described above.

Synthesis identification data of the compounds prepared above are as described in the following [Table 3] and [Table 4]

TABLE 3

| NO | $^1$H NMR ($CDCl_3$, 300 Mz) |
|---|---|
| 1 | 1.72 (s, 6H), 6.70 (m, 6H), 7.07-7.10 (m, 4H), 7.20-7.23 (m, 8H), 7.33-7.39 (m, 8H), 7.66 (d, 2H), 7.89 (d, 1H) |
| 28 | 1.72 (s, 6H), 6.70 (m, 6H), 7.07-7.10 (m, 4H), 7.20-7.23 (m, 8H), 7.33-7.39 (m, 5H), 7.41 (t, 2H), 7.62 (s, 1H), 7.66 (d, 2H), 7.88 (d, 1H) |
| 48 | 1.70 (s, 6H), 6.70 (m, 6H), 7.08 (d, 1H), 7.33-7.39 (m, 7H), 7.41-7.55 (m, 9H), 7.62 (s, 1H), 7.73 (d, 2H), 7.77 (d, 1H), 7.92 (s, 1H), 7.98 (d, 1H) |
| 50 | 1.70 (s, 6H), 6.69 (m, 6H), 7.07 (d, 1H), 7.40-7.59 (m, 11H), 7.75-7.88 (m, 8H), 7.98 (d, 1H) |
| 52 | 1.70 (s, 6H), 1.75 (s, 6H), 6.58 (d, 1H), 6.65-6.67(m, 4H), 6.75 (s, 1H), 7.07 (d, 1H), 7.29 (t, 1H), 7.38-7.40 (m, 5H), 7.51-7.56 (m, 8H), 7.62 (d, 1H), 7.74 (d, 1H), 7.76 (d, 1H), 7.87 (d, 1H), 7.93 (s, 1H), 7.98 (d, 1H) |
| 61 | 1.71 (s, 6H), 6.70 (m, 6H), 7.08 (d, 1H), 7.25 (dd, 8H), 7.41 (t, 2H), 7.44-7.49 (m, 6H) , 7.51-7.55 (m, 9H), 7.73 (d, 2H), 7.78 (d, 1H), 7.90 (s, 1H), 7.99 (d, 1H) |
| 62 | 1.70 (s, 6H), 1.75 (s, 6H), 6.58 (d, 1H), 6.65-6.67 (m, 4H), 6.75 (s, 1H), 7.07 (d, 1H), 7.25-7 26 (dd, 8H), 7.28 (t, 1H), 7.42-7.48 (m, 3H), 7.51-7.54 (m, 6H), 7.62 (d, 1H), 7.74 (d, 1H), 7.78 (d, 1H), 7.87 (d, 1H), 7.91 (s, 1H), 7.98 (d, 1H) |
| 63 | 1.70 (s, 6H), 1.77 (s, 6H), 6.58 (d, 1H), 6.66-6.69 (m, 4H), 6.75 (s, 1H), 7.07 (d, 1H), 7.28-7.30 (m, 4H), 7.51-7.54 (m, 8H), 7.71-7.88 (m, 10H) |
| 78 | 1.70 (s, 6H), 6.66-6.69 (m, 6H), 6.75 (s, 1H), 7.05 (d, 1H), 7.42 (t, 1H), 7.51-7.54 (m, 7H), 7.60-7.65 (m, 10H), 7.73-7.80 (m, 3H), 8.00-8.10 (m, 2H) |
| 97 | 1.72 (s, 6H), 6.58 (d, 1H), 6.65-6.67 (m, 4H), 6.88-6.89 (m, 2H), 7.07 (d, 1H), 7.44-7.48 (m, 5H), 7.50-7.59 (m, 12H), 7.73-7.76 (m, 2H), 7.93 (s, 1H), 7.98 (d, 1H) |
| 121 | 1.70 (s, 6H), 6.66-6.69 (m, 6H), 7.44 (t, 2H), 7.51-7.54 (m, 7H), 7.60-7.65 (m, 9H), 7.67-7.77 (m, 3H), 8.00 (d, 2H) |
| 145 | 6.67-6.70 (m, 6H), 7.09-7.12 (m, 5H), 7.20-7.23 (m, 4H), 7.33-7.39 (m, 7H), 7.42-7.60 (m, 13H), 7.73 (d, 2H), 7.90 (s, 1H), 8.12 (d, 1H) |
| 162 | 6.65-6.69 (m, 6H), 6.81 (t, 1H), 7.20-7.23 (m, 4H), 7.38-7.40 (m, 8H), 7.45-7.60 (m, 14H), 7.75 (d, 1H), 7.95 (s, 1H), |
| 181 | 6.69-6.71 (m, 6H) , 7.06-7.11 (m, 5H) , 7.20-7.23 (m, 4H) , 7.33-7.39 (m, 7H) , 7.42-7.60 (m, 13H) , 7.73 (d, 2H) , 7.89 (s, 1H) , 7.98 (d, 1H) |
| 182 | 6.69-6.71 (d, 4H), 7.06-7.12 (m, 5H), 7.25-7.27 (m, 4H), 7.34-7.39 (m, 7H), 7.40-7.61 (m, 9H), 7.73-7.77 (m, 4H), 7.87-7.89 (m, 3H), 7.98 (d, 1H) |
| 216 | 6.70 (m, 6H), 7.06-7.11 (m, 4H), 7.20-7.23 (m, 5H), 7.33-7.39 (m, 7H), 7.42-7.60 (m, 13H), 7.63 (d, 2H), 7.73 (d, 1H), 7.98 (d, 1H) |
| 229 | 1.72 (s, 6H), 6.70 (m, 6H), 7.06-7.10 (m, 5H), 7.20-7.23 (m, 7H), 7.33-7.39 (m, 8H), 7.66 (d, 2H), 7.89 (d, 1H) |
| 247 | 1.72 (s, 6H), 6.70 (m, 6H), 7.05-7.08 (m, 4H), 7.21-7.30 (m, 6H), 7.38-7.45 (m, 8H), 7.51-7.55 (m, 2H), 7.62 (s, 1H), 7.65 (d, 1H), 7.90 (d, 1H) |
| 261 | 1.70 (s, 6H), 6.68 (m, 6H), 7.07 (d, 1H), 7.32-7.45 (m, 12H), 7.51-7.55 (m, 6H), 7.66 (d, 1H), 7.77 (d, 1H), 7.89 (d, 1H), 7.92 (s, 1H) |
| 264 | 1.70 (s, 6H), 1.75 (s, 6H), 6.58 (d, 1H), 6.65-6.67 (m, 4H), 6.75 (s, 1H), 7.07 (d, 1H), 7.28-7.40 (m, 8H), 7.51-7.56 (m, 6H), 7.62-7.66 (m, 3H), 7.77 (d, 1H), 7.87-7.89 (m, 2H) |
| 276 | 1.70 (s, 6H), 1.75 (s, 6H), 6.67-6.68 (m, 6H), 6.75 (s, 1H), 7.07 (d, 1H), 7.30-7.41 (m, 7H), 7.51-7.57 (m, 9H), 7.62-7.66 (m, 2H), 7.77 (d, 2H), 7.87-7.92 (m, 4H) |
| 294 | 1.72 (s, 6H), 6.70 (m, 6H), 7.08 (d, 1H), 7.25 (m, 6H), 7.38-7.41 (m, 10H), 7.48-7.52 (m, 6H), 7.65 (d, 1H), 7.77 (d, 1H), 7.90 (d, 1H), 7.93 (s, 1H) |
| 319 | 1.73 (s, 6H), 6.69 (m, 6H), 7.38-7.41 (m, 10H), 7.50-7.55 (m, 8H), 7.65-7.67 (d, 3H), 7.90 (d, 1H) |
| 337 | 6.70 (m, 6H), 7.09-7.11 (m, 4H), 7.26-7.30 (m, 5H), 7.35-7.40 (m, 8H), 7.42-7.59 (m, 13H), 7.66 (d, 2H), 7.90 (d, 1H) |
| 348 | 6.70 (m, 6H), 7.11-7.12 (m, 4H), 7.28-7.32 (m, 8H), 7.38-7.40 (m, 6H), 7.48-7.59 (m, 13H), 7.66 (d, 1H), 7.90 (d, 1H) |
| 357 | 6.69 (m, 6H), 7.06 (d, 1H), 7.11-7.12 (m, 4H), 7.29-7.32 (m, 8H), 7.37-7.41 (m, 4H), 7.48-7.59 (m, 12H), 7.66 (d, 1H), 7.73 (d, 1H), 7.88 (s, 1H), 7.90 (d, 1H) |
| 378 | 6.69 (m, 6H), 7.11-7.12 (m, 4H), 7.29-7.33 (m, 6H), 7.37-7.41 (m, 4H), 7.48-7.59 (m, 9H), 7.63-7.66 (m, 3H), 7.77-7.88 (m, 5H) |
| 381 | 6.71 (m, 6H), 7.10-7.12 (m, 4H), 7.29-7.32 (m, 9H), 7.37-7.41 (m, 4H), 7.48-7.59 (m, 12H), 7.62-7.65 (m, 3H), 7.90 (d, 1H) |

TABLE 4

| Compound | FD-MS |
|---|---|
| 1 | m/z = 645.25 ($C_{47}H_{35}NS$ = 645.85) |
| 2 | m/z = 645.25 ($C_{47}H_{35}NS$ = 645. 85) |
| 3 | m/z = 685.28 ($C_{50}H_{39}NS$ = 685.92) |
| 4 | m/z = 659.23 ($C_{47}H_{33}NOS$ = 659.84) |
| 5 | m/z = 619.82 ($C_{45}H_{33}NS$ = 619.23) |
| 6 | m/z = 619.82 ($C_{45}H_{33}NS$ = 619. 23) |
| 7 | m/z = 593.22 ($C_{43}H_{31}NS$ = 593.78) |
| 8 | m/z = 685.28 ($C_{50}H_{39}NS$ = 685. 92) |
| 9 | m/z = 725.31 ($C_{53}H_{43}NS$ = 725.98) |
| 10 | m/z = 761.31 ($C_{56}H_{43}NS$ = 762. 01) |
| 11 | m/z = 775.29 ($C_{56}H_{41}NOS$ = 776.00) |
| 12 | m/z = 809.31 ($C_{60}H_{43}NS$ = 810. 06) |
| 13 | m/z = 721.28 ($C_{53}H_{39}NS$ = 721.95) |
| 14 | m/z = 685.28 ($C_{50}H_{39}NS$ = 685. 92) |
| 15 | m/z = 761.31 ($C_{56}H_{43}NS$ = 762. 01) |
| 16 | m/z = 695.26 ($C_{51}H_{37}NS$ = 695. 91) |
| 17 | m/z = 721.28 ($C_{53}H_{39}NS$ = 721.95) |
| 18 | m/z = 761.31 ($C_{56}H_{43}NS$ = 762.01) |
| 19 | m/z = 771.30 ($C_{57}H_{41}NS$ = 772. 01) |
| 20 | m/z = 645.25 ($C_{47}H_{33}NS$ = 645.85) |
| 21 | m/z = 761.31 ($C_{56}H_{43}NS$ = 762.01) |
| 22 | m/z = 809.31 ($C_{60}H_{43}NS$ = 810.06) |
| 23 | m/z = 695.26 ($C_{51}H_{37}NS$ = 695.91) |
| 24 | m/z = 775.29 ($C_{56}H_{41}NOS$ = 776.00) |
| 25 | m/z = 725.22 ($C_{51}H_{35}NS_2$ = 725.96) |
| 26 | m/z = 785.28 ($C_{57}H_{39}NOS$ = 785.99) |
| 27 | m/z = 749.28 ($C_{54}H_{39}NOS$ = 749. 96) |
| 28 | m/z = 645.25 ($C_{47}H_{33}NS$ = 645.85) |
| 29 | m/z = 619.82 ($C_{45}H_{33}NS$ = 619.23) |
| 30 | m/z = 685.28 ($C_{50}H_{39}NS$ = 685.92) |
| 31 | m/z = 659.23 ($C_{47}H_{33}NOS$ = 659.84) |
| 32 | m/z = 725.31 ($C_{53}H_{43}NS$ = 725.98) |
| 33 | m/z = 809.31 ($C_{60}H_{43}NS$ = 810.06) |
| 34 | m/z = 645.25 ($C_{47}H_{35}NS$ = 645.85) |
| 35 | m/z = 725.31 ($C_{53}H_{43}NS$ = 725.98) |
| 36 | m/z = 761.31 ($C_{56}H_{43}NS$ = 762. 01) |
| 37 | m/z = 721.28 ($C_{53}H_{39}NS$ = 721.95) |
| 38 | m/z = 695.26 ($C_{51}H_{37}NS$ = 695.91) |
| 39 | m/z = 761.31 ($C_{56}H_{43}NS$ = 762.01) |
| 40 | m/z = 721.28 ($C_{53}H_{39}NS$ = 721.95) |
| 41 | m/z = 735.26 ($C_{53}H_{37}NOS$ = 735.93) |
| 42 | m/z = 695.26 ($C_{51}H_{37}NS$ = 695.91) |
| 43 | m/z = 699.26 ($C_{50}H_{37}NOS$ = 699.90) |
| 44 | m/z = 695.26 ($C_{51}H_{37}NS$ = 695.91) |
| 45 | m/z = 735.26 ($C_{53}H_{37}NOS$ = 735.93) |
| 46 | m/z = 709.24 ($C_{51}H_{35}NOS$ = 709.89) |
| 47 | m/z = 643.23 ($C_{47}H_{33}NS$ = 643.84) |
| 48 | m/z = 645.25 ($C_{47}H_{35}NS$ = 645.85) |
| 49 | m/z = 673.21 ($C_{47}H_{31}NO_2S$ = 673.82) |
| 50 | m/z = 619.82 ($C_{45}H_{33}NS$ = 619.23) |
| 51 | m/z = 619.82 ($C_{45}H_{33}NS$ = 619.23) |
| 52 | m/z = 685.28 ($C_{50}H_{39}NS$ = 685.92) |
| 53 | m/z = 659.23 ($C_{47}H_{33}NOS$ = 659.84) |
| 54 | m/z = 809.31 ($C_{60}H_{43}NS$ = 810.06) |
| 55 | m/z = 593.22 ($C_{43}H_{31}NS$ = 593.78) |
| 56 | m/z = 725.22 ($C_{51}H_{35}NS_2$ = 725.96) |
| 57 | m/z = 645.25 ($C_{47}H_{35}NS$ = 645.85) |
| 58 | m/z = 719.26 ($C_{53}H_{37}NS$ = 719.93) |
| 59 | m/z = 721.28 ($C_{53}H_{39}NS$ = 721.95) |
| 60 | m/z = 761.31 (C56H43NS = 762. 01) |
| 61 | m/z = 797.31 ($C_{59}H_{38}N_4O_2$ = 798.04) |

TABLE 4-continued

| Compound | FD-MS |
|---|---|
| 62 | m/z = 761.31 ($C_{56}H_{4}NS$ = 762. 01) |
| 63 | m/z = 775.29 ($C_{56}H_{41}NOS$ = 776.00) |
| 64 | m/z = 761.31 ($C_{56}H_{43}NS$ = 762. 01) |
| 65 | m/z = 685.28 ($C_{50}H_{39}NS$ = 685.92) |
| 66 | m/z = 761.31 ($C_{56}H_{43}NS$ = 762. 01) |
| 67 | m/z = 735.26 ($C_{53}H_{37}NOS$ = 735.93) |
| 68 | m/z = 735.26 ($C_{53}H_{37}NOS$ = 735.93) |
| 69 | m/z = 811.29 ($C_{59}H_{41}NOS$ = 812.03) |
| 70 | m/z = 775.29 ($C_{56}H_{41}NOS$ = 776.00) |
| 71 | m/z = 775.29 ($C_{56}H_{41}NOS$ = 776.00) |
| 72 | m/z = 775.29 ($C_{56}H_{41}NOS$ = 776.00) |
| 73 | m/z = 659.23 ($C_{47}H_{33}NOS$ = 659.84) |
| 74 | m/z = 675.21 ($C_{44}H_{33}NS_{2}$ = 675.90) |
| 75 | m/z = 751.24 ($C_{53}H_{37}NS_{2}$ = 752.00) |
| 76 | m/z = 751.24 ($C_{53}H_{37}NS_{2}$ = 752.00) |
| 77 | m/z = 791.27 ($C_{56}H_{41}NS_{2}$ = 792.06) |
| 78 | m/z = 695.26 ($C_{51}H_{37}NS$ = 695.91) |
| 79 | m/z = 745.28 ($C_{55}H_{39}NS$ = 745.99) |
| 80 | m/z = 669.25 ($C_{49}H_{35}NS$ = 669.87) |
| 81 | m/z = 721.28 ($C_{53}H_{39}NS$ = 721.95) |
| 82 | m/z = 695.26 ($C_{51}H_{37}NS$ = 695.91) |
| 83 | m/z = 721.28 ($C_{33}H_{39}NS$ = 721.95) |
| 84 | m/z = 761.31 ($C_{56}H_{43}NS$ = 762. 01) |
| 85 | m/z = 695.26 ($C_{51}H_{37}NS$ = 695.91) |
| 86 | m/z = 735.26 ($C_{53}H_{37}NOS$ = 735.93) |
| 87 | m/z = 709.24 ($C_{51}H_{35}NOS$ = 709.89) |
| 88 | m/z = 735.26 ($C_{53}H_{37}NOS$ = 735.93) |
| 89 | m/z = 735.26 ($C_{53}H_{37}NOS$ = 735.93) |
| 90 | m/z = 775.29 ($C_{56}H_{41}NOS$ = 776.00) |
| 91 | m/z = 775.29 ($C_{56}H_{41}NOS$ = 776.00) |
| 92 | m/z = 801.34 ($C_{59}H_{47}NO$ = 801.08) |
| 93 | m/z = 633.21 ($C_{45}H_{31}NOS$ = 633.80) |
| 94 | m/z = 643.24 ($C_{47}H_{33}NS$ = 643. 84) |
| 95 | m/z = 751.24 ($C_{53}H_{37}NS_{2}$ = 752.00) |
| 96 | m/z = 761.31 ($C_{56}H_{43}NS$ = 762. 01) |
| 97 | m/z = 645.25 ($C_{47}H_{35}NS$ = 645.85) |
| 98 | m/z = 619.82 ($C_{45}H_{33}NS$ = 619. 23) |
| 99 | m/z = 619.82 ($C_{45}H_{33}NS$ = 619.23) |
| 100 | m/z = 685.28 ($C_{50}H_{39}NS$ = 685. 92) |
| 101 | m/z = 659.23 ($C_{47}H_{33}NOS$ = 659.84) |
| 102 | m/z = 797.31 ($C_{49}H_{43}NS$ = 798.04) |
| 103 | m/z = 593.22 ($C_{43}H_{31}NS$ = 593.78) |
| 104 | m/z = 725.22 ($C_{51}H_{35}NS_{2}$ = 725.96) |
| 105 | m/z = 733.28 ($C_{54}H_{39}NS$ = 733.96) |
| 106 | m/z = 811.29 ($C_{59}H_{41}NOS$ = 812.03) |
| 107 | m/z = 761.31 ($C_{56}H_{43}NS$ = 762. 01) |
| 108 | m/z = 775.29 ($C_{56}H_{41}NOS$ = 776.00) |
| 109 | m/z = 695.26 ($C_{51}H_{37}NS$ = 695.91) |
| 110 | m/z = 659.23 ($C_{47}H_{33}NOS$ = 659.84) |
| 111 | m/z = 735.26 ($C_{53}H_{37}NOS$ = 735.93) |
| 112 | m/z = 809.31 ($C_{60}H_{43}NS$ = 810.06) |
| 113 | m/z = 721.28 ($C_{53}H_{39}NS$ = 721.95) |
| 114 | m/z = 695.26 ($C_{51}H_{37}NS$ = 695.91) |
| 115 | m/z = 761.31 ($C_{56}H_{43}NS$ = 762. 01) |
| 116 | m/z = 775.29 ($C_{56}H_{41}NOS$ = 776.00) |
| 117 | m/z = 721.28 ($C_{53}H_{39}NS$ = 721.95) |
| 118 | m/z = 761.31 ($C_{56}H_{43}NS$ = 762. 01) |
| 119 | m/z = 695.26 ($C_{51}H_{37}NS$ = 695.91) |
| 120 | m/z = 735.26 ($C_{53}H_{37}NOS$ = 735.93) |
| 121 | m/z = 645.25 ($C_{47}H_{35}NS$ = 645.85) |
| 122 | m/z = 619.82 ($C_{45}H_{33}NS$ = 619.23) |
| 123 | m/z = 685.28 ($C_{50}H_{39}NS$ = 685.92) |
| 124 | m/z = 685.28 ($C_{50}H_{39}NS$ = 685.92) |
| 125 | m/z = 797.31 ($C_{49}H_{43}NS$ = 798.04) |
| 126 | m/z = 695.26 ($C_{51}H_{37}NS$ = 695.91) |
| 127 | m/z = 659.23 ($C_{47}H_{33}NOS$ = 659.84) |
| 128 | m/z = 761.31 ($C_{56}H_{43}NS$ = 762. 01) |
| 129 | m/z = 669.25 ($C_{49}H_{35}NS$ = 669.87) |
| 130 | m/z = 775.29 ($C_{56}H_{41}NOS$ = 776.00) |
| 131 | m/z = 809.31 ($C_{60}H_{43}NS$ = 810. 06) |
| 132 | m/z = 775.29 ($C_{56}H_{41}NOS$ = 776.00) |
| 133 | m/z = 645.25 ($C_{47}H_{35}NS$ = 645.85) |
| 134 | m/z = 619.82 ($C_{45}H_{33}NS$ = 619.23) |
| 135 | m/z = 685.28 ($C_{50}H_{39}NS$ = 685.92) |
| 136 | m/z = 775.29 ($C_{56}H_{41}NOS$ = 776.00) |
| 137 | m/z = 645.25 ($C_{47}H_{35}NS$ = 645.85) |
| 138 | m/z = 721.28 ($C_{53}H_{39}NS$ = 721.95) |
| 139 | m/z = 695.26 ($C_{51}H_{37}NS$ = 695.91) |

TABLE 4-continued

| Compound | FD-MS |
|---|---|
| 140 | m/z = 761.31 ($C_{56}H_{43}NS$ = 762. 01) |
| 141 | m/z = 735.26 ($C_{53}H_{37}NOS$ = 735.93) |
| 142 | m/z = 721.28 ($C_{53}H_{39}NS$ = 721.95) |
| 143 | m/z = 735.26 ($C_{53}H_{37}NOS$ = 735.93) |
| 144 | m/z = 751.24 ($C_{53}H_{37}NS_{2}$ = 752.00) |
| 145 | m/z = 769.28 ($C_{57}H_{39}NS$ = 769.99) |
| 146 | m/z = 809.31 ($C_{60}H_{43}NS$ = 810.06) |
| 147 | m/z = 783.26 ($C_{57}H_{37}NOS$ = 783.97) |
| 148 | m/z = 743.26 ($C_{55}H_{37}NS$ = 743.95) |
| 149 | m/z = 743.26 ($C_{55}H_{37}NS$ = 743.95) |
| 150 | m/z = 717.25 ($C_{53}H_{35}NS$ = 717.92) |
| 151 | m/z = 809.31 ($C_{60}H_{43}NS$ = 810. 06) |
| 152 | m/z = 693.25 ($C_{51}H_{35}NS$ = 693.90) |
| 153 | m/z = 809.31 ($C_{60}H_{43}NS$ = 810. 06) |
| 154 | m/z = 819.30 ($C_{61}H_{41}NS$ = 820.05) |
| 155 | m/z = 769.28 ($C_{57}H_{39}NS$ = 769.99) |
| 156 | m/z = 769.28 ($C_{57}H_{39}NS$ = 769.99) |
| 157 | m/z = 819.30 ($C_{61}H_{41}NS$ = 820. 05) |
| 158 | m/z = 783.26 ($C_{57}H_{37}NOS$ = 783.97) |
| 159 | m/z = 823.29 ($C_{60}H_{41}NOS$ = 824.04) |
| 160 | m/z = 773.22 ($C_{55}H_{35}NS_{2}$ = 774.00) |
| 161 | m/z = 757.24 ($C_{55}H_{35}NOS$ = 757.94) |
| 162 | m/z = 693.25 ($C_{51}H_{35}NS$ = 693.90) |
| 163 | m/z = 743.26 ($C_{55}H_{37}NS$ = 743.95) |
| 164 | m/z = 743.26 ($C_{55}H_{37}NS$ = 743.95) |
| 165 | m/z = 809.31 ($C_{60}H_{43}NS$ = 810.06) |
| 166 | m/z = 783.26 ($C_{57}H_{37}NOS$ = 783.97) |
| 167 | m/z = 743.26 ($C_{55}H_{37}NS$ = 743.95) |
| 168 | m/z = 769.28 ($C_{57}H_{39}NS$ = 769.99) |
| 169 | m/z = 783.26 ($C_{57}H_{37}NOS$ = 783.97) |
| 170 | m/z = 809.31 ($C_{60}H_{43}NS$ = 810. 06) |
| 171 | m/z = 743.26 ($C_{55}H_{37}NS$ = 743.95) |
| 172 | m/z = 769.28 ($C_{57}H_{39}NS$ = 769. 99) |
| 173 | m/z = 819.30 ($C_{61}H_{41}NS$ = 820.05) |
| 174 | m/z = 721.28 ($C_{53}H_{39}NS$ = 721.96) |
| 175 | m/z = 769.28 ($C_{57}H_{39}NS$ = 769.99) |
| 176 | m/z = 809.31 ($C_{60}H_{43}NS$ = 810.06) |
| 177 | m/z = 743.26 ($C_{55}H_{37}NS$ = 743.95) |
| 178 | m/z = 783.26 ($C_{57}H_{37}NOS$ = 783.97) |
| 179 | m/z = 707.23 ($C_{51}H_{33}NOS$ = 707.88) |
| 180 | m/z = 799.24 ($C_{57}H_{37}NS_{2}$ = 800.04) |
| 181 | m/z = 769.28 ($C_{57}H_{39}NS$ = 769.99) |
| 182 | m/z = 743.26 ($C_{55}H_{37}NS$ = 743. 95) |
| 183 | m/z = 743.26 ($C_{55}H_{37}NS$ = 743.95) |
| 184 | m/z = 783.26 ($C_{57}H_{37}NOS$ = 783.97) |
| 185 | m/z = 769.28 ($C_{57}H_{39}NS$ = 769.99) |
| 186 | m/z = 809.31 ($C_{60}H_{43}NS$ = 810.06) |
| 187 | m/z = 809.31 ($C_{60}H_{43}NS$ = 810.06) |
| 188 | m/z = 783.26 ($C_{57}H_{37}NOS$ = 783.97) |
| 189 | m/z = 859.29 ($C_{63}H_{41}NOS$ = 860.07) |
| 190 | m/z = 769.28 ($C_{57}H_{39}NS$ = 769.99) |
| 191 | m/z = 809.31 ($C_{60}H_{43}NS$ = 810.06) |
| 192 | m/z = 783.26 ($C_{57}H_{37}NOS$ = 783.97) |
| 193 | m/z = 799.24 ($C_{57}H_{37}NS_{2}$ = 800.04) |
| 194 | m/z = 819.30 ($C_{61}H_{41}NS$ = 820.05) |
| 195 | m/z = 799.24 ($C_{57}H_{37}NS_{2}$ = 800.04) |
| 196 | m/z = 717.25 ($C_{53}H_{35}NS$ = 717.92) |
| 197 | m/z = 645.25 ($C_{47}H_{35}NS$ = 645.85) |
| 198 | m/z = 693.25 ($C_{51}H_{35}NS$ = 693.90) |
| 199 | m/z = 743.26 ($C_{55}H_{37}NS$ = 743.95) |
| 200 | m/z = 809.31 ($C_{60}H_{43}NS$ = 810.06) |
| 201 | m/z = 793.28 ($C_{59}H_{39}NS$ = 794.01) |
| 202 | m/z = 743.26 ($C_{55}H_{37}NS$ = 743.95) |
| 203 | m/z = 707.23 ($C_{51}H_{33}NOS$ = 707.88) |
| 204 | m/z = 757.24 ($C_{55}H_{35}NOS$ = 757.94) |
| 205 | m/z = 783.26 ($C_{57}H_{37}NOS$ = 783.97) |
| 206 | m/z = 769.28 ($C_{57}H_{39}NS$ = 769. 99) |
| 207 | m/z = 845.31 ($C_{63}H_{43}NS$ = 846.09) |
| 208 | m/z = 783.26 ($C_{57}H_{37}NOS$ = 783.97) |
| 209 | m/z = 819.30 ($C_{61}H_{41}NS$ = 820. 05) |
| 210 | m/z = 783.26 ($C_{57}H_{37}NOS$ = 783.97) |
| 211 | m/z = 743.26 ($C_{55}H_{37}NS$ = 743.95) |
| 212 | m/z = 809.31 ($C_{60}H_{43}NS$ = 810. 06) |
| 213 | m/z = 809.31 ($C_{60}H_{43}NS$ = 810. 06) |
| 214 | m/z = 845.31 ($C_{63}H_{43}NS$ = 846. 09) |
| 215 | m/z = 769.28 ($C_{57}H_{39}NS$ = 769.99) |
| 216 | m/z = 769.28 ($C_{57}H_{39}NS$ = 769.99) |
| 217 | m/z = 743.26 ($C_{55}H_{37}NS$ = 743.95) |

TABLE 4-continued

| Compound | FD-MS |
|---|---|
| 218 | m/z = 809.31 ($C_{60}H_{43}NS$ = 810.06) |
| 219 | m/z = 809.31 ($C_{60}H_{43}NS$ = 810.06) |
| 220 | m/z = 783.26 ($C_{57}H_{37}NOS$ = 783.97) |
| 221 | m/z = 769.28 ($C_{57}H_{39}NS$ = 769.99) |
| 222 | m/z = 743.26 ($C_{55}H_{37}NS$ = 743.95) |
| 223 | m/z = 769.28 ($C_{57}H_{39}NS$ = 769.99) |
| 224 | m/z = 769.28 ($C_{57}H_{39}NS$ = 769.99) |
| 225 | m/z = 769.28 ($C_{57}H_{39}NS$ = 769.99) |
| 226 | m/z = 783.26 ($C_{57}H_{37}NOS$ = 783.97) |
| 227 | m/z = 783.26 ($C_{57}H_{37}NOS$ = 783.97) |
| 228 | m/z = 769.28 ($C_{57}H_{39}NS$ = 769.99) |
| 229 | m/z = 629.27 ($C_{47}H_{395}NO$ = 629.79) |
| 230 | m/z = 669.30 ($C_{50}H_{39}NO$ = 669. 85) |
| 231 | m/z = 603.26 ($C_{45}H_{33}NO$ = 603.75) |
| 232 | m/z = 603.26 ($C_{45}H_{33}NO$ = 603.75) |
| 233 | m/z = 577.24 ($C_{43}H_{31}NO$ = 577.71) |
| 234 | m/z = 669.30 ($C_{50}H_{39}NO$ = 669.85) |
| 235 | m/z = 745.33 ($C_{56}H_{43}NO$ = 745.95) |
| 236 | m/z = 759.31 ($C_{56}H_{41}NO_2$ = 759.93) |
| 237 | m/z = 793.33 ($C_{60}H_{43}NO$ = 793.99) |
| 238 | m/z = 659.23 ($C_{47}H_{33}NOS$ = 659.84) |
| 239 | m/z = 705.30 ($C_{53}H_{39}NO$ = 705.88) |
| 240 | m/z = 669.30 ($C_{50}H_{39}NO$ = 669.85) |
| 241 | m/z = 745.33 ($C_{56}H_{43}NO$ = 745.95) |
| 242 | m/z = 679.29 ($C_{51}H3_{7}NO$ = 679.85) |
| 243 | m/z = 679.29 ($C_{51}H_{37}NO$ = 679.85) |
| 244 | m/z = 679.29 ($C_{51}H_{37}NO$ = 679.85) |
| 245 | m/z = 629.27 ($C_{47}H_{395}NO$ = 629.79) |
| 246 | m/z = 745.33 ($C_{56}H_{43}NO$ = 745.95) |
| 247 | m/z = 629.27 ($C_{47}H_{395}NO$ = 629.79) |
| 248 | m/z = 603.26 ($C_{45}H_{33}NO$ = 603.75) |
| 249 | m/z = 669.30 ($C_{50}H_{39}NO$ = 669.85) |
| 250 | m/z = 643.25 ($C_{50}H_{39}NO_2$ = 643.77) |
| 251 | m/z = 659.23 ($C_{47}H_{33}NOS$ = 659.84) |
| 252 | m/z = 709.33 ($C_{53}H_{43}NO$ = 709.97) |
| 253 | m/z = 679.29 ($C_{51}H_{37}NO$ = 679.85) |
| 254 | m/z = 745.33 ($C_{56}H_{43}NO$ = 745.95) |
| 255 | m/z=705.30 ($C_{53}H_{39}NO$ = 705.88) |
| 256 | m/z = 679.29 ($C_{51}H_{37}NO$ = 679.85) |
| 257 | m/z = 629.27 ($C_{47}H_{395}NO$ = 629.79) |
| 258 | m/z = 709.33 ($C_{53}H_{43}NO$ = 709.97 |
| 259 | m/z = 745.33 ($C_{56}H_{43}NO$ = 745.95) |
| 260 | m/z = 705.30 ($C_{53}H_{39}NO$ = 705.88) |
| 261 | m/z = 629.27 ($C_{47}H_{395}NO$ = 629.79) |
| 262 | m/z = 603.26 ($C_{45}H_{33}NO$ = 603.75) |
| 263 | m/z = 603.26 ($C_{45}H_{33}NO$ = 603.75) |
| 264 | m/z = 669.30 ($C_{50}H_{39}NO$ = 669.85) |
| 265 | m/z = 643.25 ($C_{50}H_{39}NO_2$ = 643.77) |
| 266 | m/z = 793.33 ($C_{60}H_{43}NO$ = 793. 99) |
| 267 | m/z = 577.24 ($C_{43}H_{31}NO$ = 577.71) |
| 268 | m/z = 709.33 ($C_{53}H_{43}NO$ = 709.97) |
| 269 | m/z = 705.30 ($C_{53}H_{39}NO$ = 705.88) |
| 270 | m/z = 659.23 ($C_{47}H_{33}NOS$ = 659.84) |
| 271 | m/z = 781.33 ($C_{59}H_{43}NO$ = 781.98) |
| 272 | m/z = 745.33 ($C_{56}H_{43}NO$ = 745.95) |
| 273 | m/z = 669.30 ($C_{50}H_{39}NO$ = 669.85) |
| 274 | m/z = 745.33 ($C_{56}H_{43}NO$ = 745.95) |
| 275 | m/z = 759.31 ($C_{56}H_{41}NO_2$ = 759.93) |
| 276 | m/z = 745.33 ($C_{56}H_{43}NO$ = 745.95) |
| 277 | m/z = 669.30 ($C_{50}H_{39}NO$ = 669.85) |
| 278 | m/z = 759.31 ($C_{56}H_{41}NO_2$ = 759.93) |
| 279 | m/z = 643.25 ($C_{50}H_{39}NO_2$ = 643.77) |
| 280 | m/z = 643.25 ($C_{50}H_{39}NO_2$ = 643.77) |
| 281 | m/z = 659.23 ($C_{47}H_{33}NOS$ = 659.84) |
| 282 | m/z = 735.26 ($C_{53}H_{37}NOS$ = 735.93) |
| 283 | m/z = 719.28 ($C_{53}H_{37}NO_2$ = 719.87) |
| 284 | m/z = 719.28 ($C_{53}H_{37}NO_2$ = 719.87) |
| 285 | m/z = 795.31 ($C_{50}H_{39}NO_2$ = 795.96) |
| 286 | m/z = 759.31 ($C_{56}H_{41}NO_2$ = 759.93) |
| 287 | m/z = 759.31 ($C_{56}H_{41}NO_2$ = 759.93) |
| 288 | m/z = 745.33 ($C_{56}H_{43}NO$ = 745.95) |
| 289 | m/z = 735.26 ($C_{53}H_{37}NOS$ = 735.93) |
| 290 | m/z = 775.29 ($C_{56}H_{41}NOS$ = 776.00) |
| 291 | m/z = 679.29 ($C_{51}H_{37}NO$ = 679.85) |
| 292 | m/z = 735.26 ($C_{53}H_{37}NOS$ = 735.93) |
| 293 | m/z = 759.31 ($C_{56}H_{41}NO_2$ = 759.93) |
| 294 | m/z = 705.30 ($C_{53}H_{39}NO$ = 705.88) |
| 295 | m/z = 679.29 ($C_{51}H_{37}NO$ = 679.85) |

TABLE 4-continued

| Compound | FD-MS |
|---|---|
| 296 | m/z = 745.33 ($C_{56}H_{43}NO$ = 745.95) |
| 297 | m/z = 755.32 ($C_{57}H_{41}NO$ = 755.94) |
| 298 | m/z = 679.29 ($C_{51}H_{37}NO$ = 679.85) |
| 299 | m/z = 719.28 ($C_{53}H_{37}NO_2$ = 719.87) |
| 300 | m/z = 719.28 ($C_{53}H_{37}NO_2$ = 719.87) |
| 301 | m/z = 629.27 ($C_{47}H_{395}NO$ = 629.79) |
| 302 | m/z = 603.26 ($C_{45}H_{33}NO$ = 603.75) |
| 303 | m/z = 745.33 ($C_{56}H_{43}NO$ = 745.95) |
| 304 | m/z = 669.30 ($C_{50}H_{39}NO$ = 669.85) |
| 305 | m/z = 643.25 ($C_{50}H_{39}NO_2$ = 643.77) |
| 306 | m/z = 781.33 ($C_{59}H_{43}NO$ = 781.98) |
| 307 | m/z = 703.29 ($C_{53}H_{37}NO$ = 703.87) |
| 308 | m/z = 659.23 ($C_{47}H_{33}NOS$ = 659.84) |
| 309 | m/z = 795.31 ($C_{59}H_{41}NO_2$ = 795.96) |
| 310 | m/z = 745.33 ($C_{56}H_{43}NO$ = 745.95) |
| 311 | m/z = 679.29 ($C_{51}H_{37}NO$ = 679.85) |
| 312 | m/z = 643.25 ($C_{50}H_{39}NO_2$ = 643.77) |
| 313 | m/z = 705.30 ($C_{53}H_{39}NO$ = 705.88) |
| 314 | m/z = 679.29 ($C_{51}H_{37}NO$ = 679.85) |
| 315 | m/z = 745.33 ($C_{56}H_{43}NO$ = 745.95) |
| 316 | m/z = 759.31 ($C_{56}H_{41}NO_2$ = 759.93) |
| 317 | m/z = 705.30 ($C_{53}H_{39}NO$ = 705.88) |
| 318 | m/z = 643.25 ($C_{50}H_{39}NO_2$ = 643.77) |
| 319 | m/z = 629.27 ($C_{47}H_{395}NO$ = 629.79) |
| 320 | m/z = 603.26 ($C_{45}H_{33}NO$ = 603.75) |
| 321 | m/z = 669.30 ($C_{50}H_{39}NO$ = 669.85) |
| 322 | m/z = 669.30 ($C_{50}H_{39}NO$ = 669.85) |
| 323 | m/z = 781.33 ($C_{59}H_{43}NO$ = 781.98) |
| 324 | m/z = 679.29 ($C_{51}H_{37}NO$ = 679.85) |
| 325 | m/z = 745.33 ($C_{56}H_{43}NO$ = 745.95) |
| 326 | m/z = 759.31 ($C_{56}H_{41}NO_2$ = 759.93) |
| 327 | m/z = 793.33 ($C_{60}H_{43}NO$ = 793.99) |
| 328 | m/z = 629.27 ($C_{47}H_{395}NO$ = 629.79) |
| 329 | m/z = 603.26 ($C_{45}H_{33}NO$ = 603.75) |
| 330 | m/z = 669.30 ($C_{50}H_{39}NO$ = 669.85) |
| 331 | m/z = 705.30 ($C_{53}H_{39}NO$ = 705.88) |
| 332 | m/z = 679.29 ($C_{51}H_{37}NO$ = 679.85) |
| 333 | m/z = 745.33 ($C_{56}H_{43}NO$ = 745.95) |
| 334 | m/z = 719.28 ($C_{53}H_{37}NO_2$ = 719.87) |
| 335 | m/z = 705.30 ($C_{53}H_{39}NO$ = 705.88) |
| 336 | m/z = 735.26 ($C_{53}H_{37}NOS$ = 735.93) |
| 337 | m/z = 753.30 ($C_{57}H_{39}NO$ = 753.93) |
| 338 | m/z = 793.33 ($C_{60}H_{43}NO$ = 793.99) |
| 339 | m/z = 727.29 ($C_{55}H_{37}NO$ = 727.89) |
| 340 | m/z = 793.33 ($C_{60}H_{43}NO$ = 793.99) |
| 341 | m/z = 869.37 ($C_{66}H_{47}NO$ = 870.09) |
| 342 | m/z = 783.26 ($C_{57}H_{37}NOS$ = 783.97) |
| 343 | m/z = 829.33 ($C_{63}H_{43}NO$ = 830.02) |
| 344 | m/z = 793.33 ($C_{60}H_{43}NO$ = 793.99) |
| 345 | m/z = 803.32 ($C_{61}H_{41}NO$ = 803.98) |
| 346 | m/z = 753.30 ($C_{57}H_{39}NO$ = 753.93) |
| 347 | m/z = 803.32 ($C_{61}H_{41}NO$ = 803.98) |
| 348 | m/z = 753.30 ($C_{57}H_{39}NO$ = 753.93) |
| 349 | m/z = 727.29 ($C_{55}H_{37}NO$ = 727.89) |
| 350 | m/z = 793.33 ($C_{60}H_{43}NO$ = 793.99) |
| 351 | m/z = 767.28 ($C_{57}H_{37}NO_2$ = 767.91) |
| 352 | m/z = 783.26 ($C_{57}H_{37}NOS$ = 783.97) |
| 353 | m/z = 753.30 ($C_{57}H_{39}NO$ = 753.93) |
| 354 | m/z = 869.37 ($C_{66}H_{47}NO$ = 870.09) |
| 355 | m/z = 829.33 ($C_{63}H_{43}NO$ = 830.02) |
| 356 | m/z = 803.32 ($C_{61}H_{41}NO$ = 803.98) |
| 357 | m/z = 753.30 ($C_{57}H_{39}NO$ = 753.93) |
| 358 | m/z = 727.29 ($C_{55}H_{37}NO$ = 727.89) |
| 359 | m/z = 727.29 ($C_{55}H_{37}NO$ = 727.89) |
| 360 | m/z = 793.33 ($C_{60}H_{43}NO$ = 793.99) |
| 361 | m/z = 767.28 ($C_{57}H_{37}NO_2$ = 767.91) |
| 362 | m/z = 701.27 ($C_{53}H_{35}NO$ = 701.85) |
| 363 | m/z = 783.26 ($C_{57}H_{37}NOS$ = 783.97) |
| 364 | m/z = 793.33 ($C_{60}H_{43}NO$ = 793.99) |
| 365 | m/z = 767.28 ($C_{57}H_{37}NO_2$ = 767.91) |
| 366 | m/z = 829.33 ($C_{63}H_{43}NO$ = 830.02) |
| 367 | m/z = 803.32 ($C_{61}H_{41}NO$ = 803.98) |
| 368 | m/z = 829.33 ($C_{63}H_{43}NO$ = 830.02) |
| 369 | m/z = 803.32 ($C_{61}H_{41}NO$ = 803.98) |
| 370 | m/z = 753.30 ($C_{57}H_{39}NO$ = 753.93) |
| 371 | m/z = 727.29 ($C_{55}H_{37}NO$ = 727.89) |
| 372 | m/z = 793.33 ($C_{60}H_{43}NO$ = 793.99) |
| 373 | m/z = 829.33 ($C_{63}H_{43}NO$ = 830.02) |

TABLE 4-continued

| Compound | FD-MS |
|---|---|
| 374 | m/z = 803.32 ($C_{61}H_{41}NO$ = 803. 98) |
| 375 | m/z = 767.28 ($C_{57}H_{37}NO$ = 767.91) |
| 376 | m/z = 783.26 ($C5_{7}H_{37}NOS$ = 783.97) |
| 377 | m/z = 701.27 ($C_{53}H_{35}NO$ = 701.85) |
| 378 | m/z = 727.29 ($C_{55}H_{37}NO$ = 727.89) |
| 379 | m/z = 793.33 ($C_{60}H_{43}NO$ = 793.99) |
| 380 | m/z = 767.28 ($C_{57}H_{37}NO_2$ = 767.91) |
| 381 | m/z = 753.30 ($C_{57}H_{39}NO$ = 753.93) |
| 382 | m/z = 829.33 ($C_{63}H_{43}NO$ = 830.02) |
| 383 | m/z=803.32 ($C_{61}H_{41}NO$ = 803.98) |
| 384 | m/z = 753.30 ($C_{57}H_{39}NO$ = 753.93) |

<Experimental Example 1>—Manufacture of Organic Light Emitting Device

1) Manufacture of Organic Light Emitting Device (Red Single Host)

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treatment was conducted for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 500 Å using a compound described in the following Table 5 as a red host and $(piq)_2(Ir)$ (acac) as a red phosphorescent dopant and by doping the $(piq)_2(Ir)$ (acac) to the host by 3%. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/m$^2$ through a lifetime measurement system (M6000) manufactured by McScience Inc. Properties of the organic electroluminescent devices of the present disclosure are as shown in the following Table 5.

TABLE 5

| | Compound | Driving Voltage (V) | Efficiency (cd/A) | Color Coordinate (x, y) | Lifetime ($T_{90}$) |
|---|---|---|---|---|---|
| Comparative Example 1 | Comparative Compound A | 6.35 | 12.5 | 0.690, 0.310 | 60 |
| Comparative Example 2 | Comparative Compound B | 5.90 | 13.2 | 0.688, 0.312 | 45 |
| Comparative Example 3 | Comparative Compound C | 6.20 | 13.7 | 0.689, 0.311 | 57 |
| Comparative Example 4 | Comparative Compound D | 6. 03 | 12.5 | 0.69, 0 0.310 | 55 |
| Comparative Example 5 | Comparative Compound E | 6.45 | 13.2 | 0.672, 0.327 | 45 |
| Comparative Example 6 | Comparative Compound F | 5.98 | 11.9 | 0.691, 0.309 | 50 |
| Example 1 | 1 | 4.75 | 15.2 | 0.676, 0.324 | 99 |
| Example 2 | 28 | 5.09 | 16.7 | 0.678, 0.322 | 102 |
| Example 3 | 48 | 4.58 | 18.7 | 0.691, 0.309 | 99 |
| Example 4 | 50 | 5.27 | 17.0 | 0.681, 0.319 | 100 |
| Example 5 | 52 | 4.69 | 19.7 | 0.683, 0.317 | 80 |
| Example 6 | 61 | 4.78 | 15.2 | 0.678, 0.321 | 89 |
| Example 7 | 62 | 4.60 | 21.0 | 0.678, 0.321 | 104 |
| Example 8 | 63 | 4.90 | 22.7 | 0.679, 0.321 | 107 |
| Example 9 | 78 | 4.06 | 17.2 | 0.685, 0.314 | 100 |
| Example 10 | 97 | 5.05 | 15.2 | 0.674, 0.325 | 89 |
| Example 11 | 121 | 5.10 | 18.6 | 0.689, 0.310 | 109 |
| Example 12 | 145 | 4.18 | 18.0 | 0.689, 0.310 | 103 |
| Example 13 | 162 | 4.94 | 16.8 | 0.689, 0.310 | 89 |
| Example 14 | 181 | 5.19 | 18.4 | 0.676, 0.324 | 120 |
| Example 15 | 182 | 4.96 | 17.9 | 0.684, 0.315 | 129 |
| Example 16 | 216 | 4.99 | 15.2 | 0.685, 0.314 | 122 |
| Example 17 | 229 | 4.91 | 14.8 | 0.688, 0.312 | 86 |
| Example 18 | 247 | 4.89 | 17.1 | 0.691, 0.309 | 98 |
| Example 19 | 261 | 4.92 | 18.0 | 0.687, 0.313 | 96 |
| Example 20 | 264 | 4.97 | 16.5 | 0.682, 0.317 | 108 |
| Example 21 | 276 | 5.10 | 19.0 | 0.684, 0.316 | 94 |
| Example 22 | 294 | 4.93 | 16.7 | 0.681, 0.319 | 129 |
| Example 23 | 319 | 5.09 | 17.9 | 0.687, 0.313 | 89 |
| Example 24 | 337 | 4.98 | 19.8 | 0.681, 0.319 | 101 |

TABLE 5-continued
| | Compound | Driving Voltage (V) | Efficiency (cd/A) | Color Coordinate (x, y) | Lifetime ($T_{90}$) |
|---|---|---|---|---|---|
| Example 25 | 348 | 5.08 | 17.7 | 0.682, 0.318 | 109 |
| Example 26 | 357 | 4.80 | 16.9 | 0.684, 0.316 | 102 |
| Example 27 | 378 | 4.92 | 15.9 | 0.682, 0.317 | 125 |
| Example 28 | 381 | 5.02 | 16.6 | 0.682, 0.317 | 115 |
Comparative Compound A
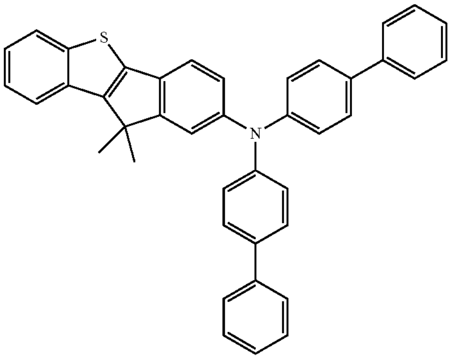
Comparative Compound B
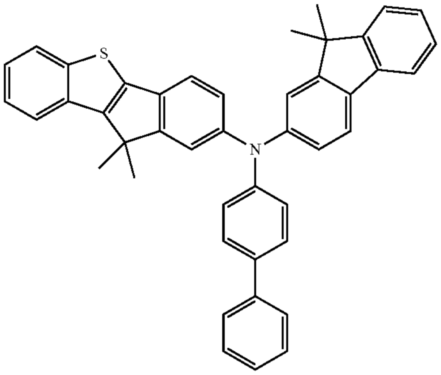
Comparative Compound C
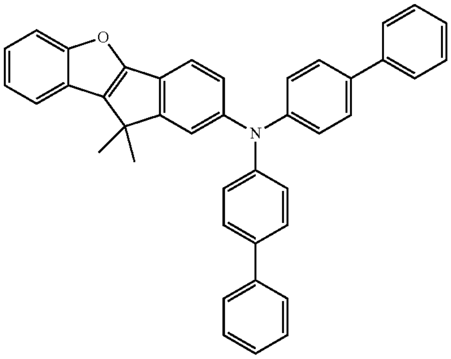 [SMILES: CC1(C)c2cc(N(c3ccc(-c4ccccc4)cc3)c3ccc(-c4ccccc4)cc3)ccc2-c2sc3ccccc3c21]
Comparative Compound D
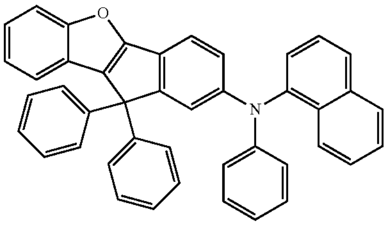 [SMILES: c1ccc(N(c2ccc3c(c2)C(c2ccccc2)(c2ccccc2)c2c-3oc3ccccc23)c2cccc3ccccc23)cc1]

TABLE 5-continued

| Compound | Driving Voltage (V) | Efficiency (cd/A) | Color Coordinate (x, y) | Lifetime ($T_{90}$) |
|---|---|---|---|---|
| 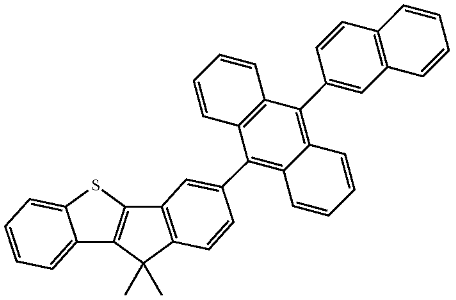 [SMILES: CC1(C)c2ccc(-c3c4ccccc4c(-c4ccc5ccccc5c4)c4ccccc34)cc2-c2sc3ccccc3c21] Comparative Compound E | | | | |
| 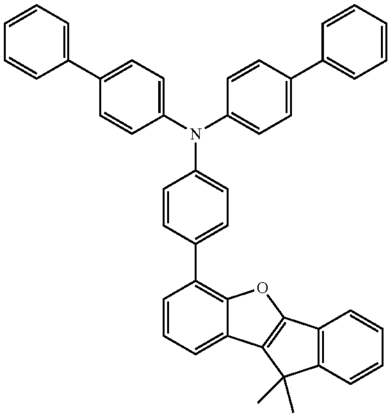 [SMILES: CC1(C)c2ccccc2-c2oc3c(-c4ccc(N(c5ccc(-c6ccccc6)cc5)c5ccc(-c6ccccc6)cc5)cc4)cccc3c21] Comparative Compound F | | | | |

As seen from Table 5, it was identified that, when using the compound corresponding to Chemical Formula 1 in the light emitting layer of the organic light emitting device, superior effects were obtained in terms of properties of lifetime, efficiency and driving voltage compared to when the compound was not used.

Particularly, Comparative Compounds A to D are cases in which an amine group directly bonds to the core structure without a linker, and it was identified that driving and efficiency were not favorable in this case, and lifetime properties were especially not favorable.

<Experimental Example 2>—Manufacture of Organic Light Emitting Device

1) Manufacture of Organic Light Emitting Device (Red N+P Mixed Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, one type of the compound described in Chemical Formula 1 and one type of the compound described in Chemical Formula 2 were pre-mixed as described in the following Table 6 and deposited to 400 Å in one source of supply as a red host, and (piq)2(Ir) (acac) was doped thereto by 3% as a red phosphorescent dopant and deposited. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc.

TABLE 6

| | Light Emitting Layer Compound | Ratio (N:P) | Driving Voltage (V) | Efficiency (cd/A) | Color Coordinate (x, y) | Lifetime ($T_{90}$) |
|---|---|---|---|---|---|---|
| Example 1 | 78:2-11 | 3:1 | 4.35 | 20.6 | 0.673, 0.327 | 250 |
| Example 2 | | 2:1 | 4.30 | 21.1 | 0.691, 0.309 | 246 |
| Example 3 | | 1:1 | 4.21 | 22.5 | 0.674, 0.326 | 220 |
| Example 4 | | 1:2 | 4.20 | 24.6 | 0.679, 0.321 | 249 |
| Example 5 | | 1:3 | 4.40 | 22.8 | 0.678, 0.322 | 206 |
| Example 6 | 61:2-15 | 3:1 | 4.37 | 21.5 | 0.674, 0.326 | 245 |
| Example 7 | | 2:1 | 4.28 | 22.8 | 0.687, 0.313 | 240 |
| Example 8 | | 1:1 | 4.11 | 24.1 | 0.681, 0.319 | 228 |
| Example 9 | | 1:2 | 4.12 | 24.4 | 0.681, 0.319 | 230 |
| Example 10 | | 1:3 | 4.46 | 22.9 | 0.682, 0.318 | 204 |
| Example 11 | 48:2-21 | 1:2 | 4.20 | 26.5 | 0.683, 0.317 | 255 |
| Example 12 | 63:2-28 | 1:2 | 3.88 | 25.7 | 0.674, 0.326 | 230 |
| Example 13 | 52:2-39 | 3:1 | 4.17 | 23.5 | 0.678, 0.322 | 256 |
| Example 14 | | 2:1 | 4.22 | 24.8 | 0.679, 0.321 | 240 |
| Example 15 | | 1:1 | 3.89 | 26. 0 | 0.681, 0.319 | 255 |
| Example 16 | | 1:2 | 4.49 | 25.3 | 0.678, 0.322 | 218 |
| Example 17 | | 1:3 | 4.64 | 27.6 | 0.674, 0.326 | 190 |
| Example 18 | 97:2-50 | 1:1 | 4.09 | 27.7 | 0.683, 0.317 | 245 |
| Example 19 | 61:2-50 | 1:1 | 4.21 | 29.9 | 0.681, 0.319 | 260 |
| Example 20 | 161:2-5 | 2:1 | 4.28 | 26.2 | 0.685, 0.315 | 293 |
| Example 21 | 294:2-16 | 2:1 | 3.88 | 25.9 | 0.676, 0.324 | 271 |
| Example 22 | 28:2-29 | 2:1 | 4.18 | 24.3 | 0.678, 0.322 | 222 |
| Example 23 | 182:2-33 | 1:1 | 4.20 | 25.8 | 0.681, 0.319 | 219 |
| Example 24 | 1:2-40 | 1:1 | 4.09 | 28.6 | 0.683, 0.317 | 280 |
| Example 25 | 357:2-52 | 1:1 | 4.01 | 27.2 | 0.678, 0.322 | 241 |
| Example 26 | 181:2-20 | 2:1 | 3.88 | 25.9 | 0.676, 0.324 | 271 |
| Example 27 | 229:2-22 | 2:1 | 4.18 | 24.3 | 0.678, 0.322 | 222 |
| Example 28 | 276:2-38 | 1:1 | 4.20 | 25.8 | 0.681, 0.319 | 219 |
| Example 29 | 319:2-46 | 1:1 | 4.09 | 28.6 | 0.683, 0.317 | 280 |
| Example 30 | 378:2-56 | 1:1 | 4.01 | 27.2 | 0.678, 0.322 | 241 |

As seen from Table 6, it was identified that, when the compound corresponding to Chemical Formula 1 and the compound corresponding to Chemical Formula 2 were combined and used in the light emitting layer of the organic light emitting device, superior effects were obtained in terms of properties of lifetime, efficiency and driving voltage compared to when the compound corresponding to Chemical Formula 1 was used alone.

Particularly, as seen from Table 5, the compound of Chemical Formula 1 has one side benzene ring having an indenothiophene structure substituted with an arylamine-based compound comprising a linker, which provides proper energy level and thermal stability to the device, and it was identified that an organic light emitting device with improved lifetime, driving stability and efficiency was manufactured using the compounds of Chemical Formula 1.

When comprising the compounds of Chemical Formula 1 and Chemical Formula 2 in an organic material layer of an organic light emitting device, superior results may be obtained in efficiency and lifetime by an occurrence of an exciplex phenomenon. The exciplex phenomenon of the compounds of Chemical Formula 1 and Chemical Formula 2 is a phenomenon of releasing energy having sizes of a donor (p-host) HOMO level and an acceptor (n-host) LUMO level due to electron exchanges between two molecules. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

<Experimental Example 3>—Evaluation on Thermal Stability and Physical Properties of Compound The following Table 7 shows data obtained from a thermal stability evaluation on the compounds. In the following Table 7, Ts means an initial temperature, and when measured while increasing the temperature, it was identified that the compound according to the present application had high purity.

TABLE 7

| | | | | Ts +50 | | Ts +70 | | Ts +90 | |
|---|---|---|---|---|---|---|---|---|---|
| Compound | Ts | Time of Evaluation | Initial Purity | Temper-ature | Purity | Temper-ature | Purity | Temper-ature | Purity |
| compound (a) | 240 | 200 hr | 99.93 | 290 | 97.90 | 310 | 95.50 | 330 | 85.05 |
| compound (b) | 240 | 200 hr | 99.95 | 290 | 97.59 | 310 | 94.88 | 330 | 88.65 |
| compound (C) | 230 | 200 hr | 99.91 | 280 | 98.01 | 300 | 96. 80 | 320 | 89.11 |
| 50 | 260 | 200 hr | 99.95 | 300 | 99.90 | 320 | 99.78 | 340 | 97.55 |
| 97 | 260 | 200 hr | 99.92 | 300 | 99.86 | 320 | 99.75 | 340 | 96.99 |
| 48 | 270 | 200 hr | 99.93 | 320 | 99.86 | 340 | 99.30 | 360 | 96.04 |
| 52 | 270 | 200 hr | 99.98 | 320 | 99.89 | 340 | 99.02 | 360 | 95.80 |
| 78 | 270 | 200 hr | 99.90 | 320 | 99.84 | 340 | 99.26 | 360 | 96.85 |
| 62 | 280 | 200 hr | 99.95 | 330 | 99.88 | 350 | 99.10 | 370 | 96.05 |
| 63 | 280 | 200 hr | 99.97 | 330 | 99.87 | 350 | 99.11 | 370 | 95.97 |

TABLE 7-continued

| Compound | Ts | Time of Evaluation | Initial Purity | Ts +50 Temper-ature | Ts +50 Purity | Ts +70 Temper-ature | Ts +70 Purity | Ts +90 Temper-ature | Ts +90 Purity |
|---|---|---|---|---|---|---|---|---|---|
| 61 | 290 | 200 hr | 99.98 | 340 | 99.80 | 360 | 98.90 | 380 | 96.46 |

compound (a)

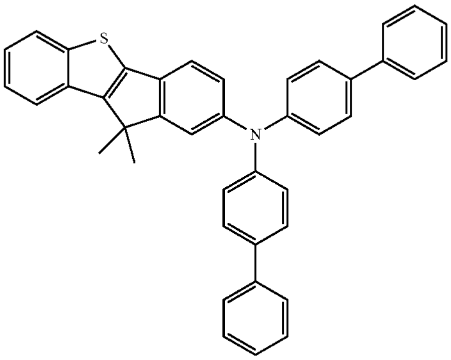

compound (b)

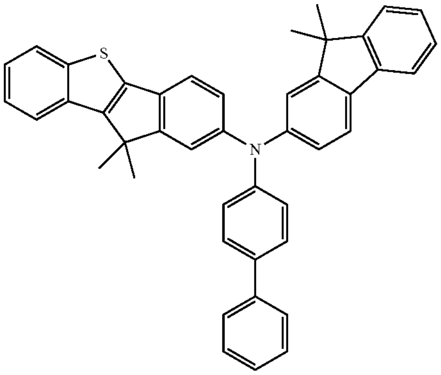

compound (C)

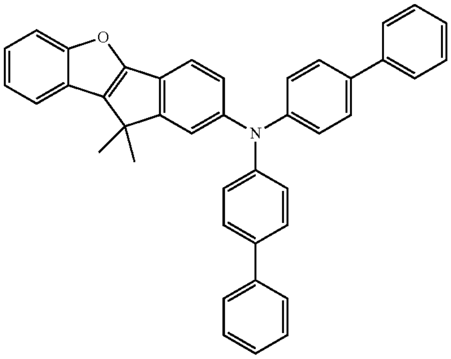 [SMILES: CC1(C)c2cc(N(c3ccc(-c4ccccc4)cc3)c3ccc(-c4ccccc4)cc3)ccc2-c2sc3ccccc3c21]

The following Table 8 shows data obtained from a physical property evaluation by a thermal analysis on the compounds.

The thermal analysis method is a method of continuously measuring physical variables of a compound as a function of temperature, and among these, a Td (thermal decomposition) value indicates a degree of decomposition of a material by heat, and Td95% means a temperature value when a mass of the compound decreases by 5%.

In other words, it is seen that, as the Td95% value increases, heat required to reduce a mass of the compound by 5% increases. The value increases as a molecular weight or a conjugation structure of the compound increases, and a deposition temperature of the material increases as well. By variously designing structures of the compound, the Td95% value may be controlled, and accordingly, the deposition temperature may be predicted.

TABLE 8
| Compound | Structure | Molecular Weight | Td | Td 95% | Tg |
|---|---|---|---|---|---|
| 48 | 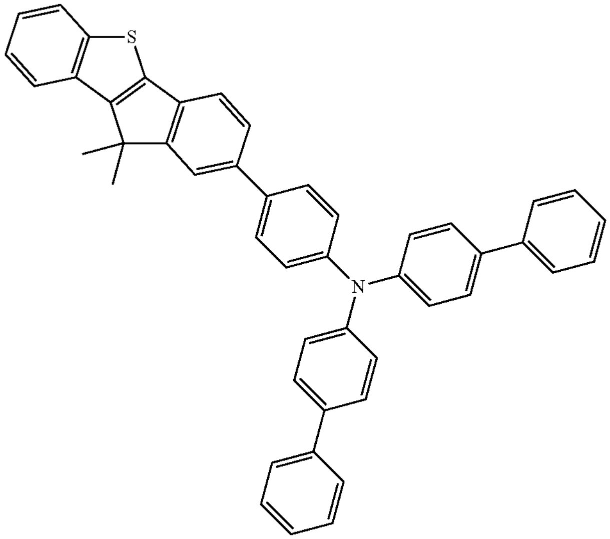 | 645.25 | 467 | 450 | ND |
| 50 | 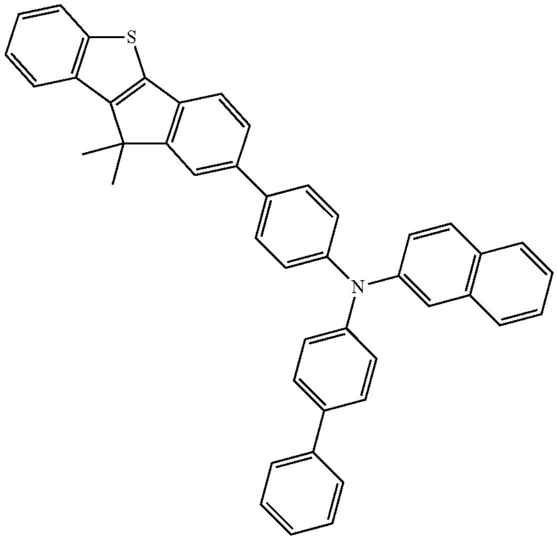 [SMILES: CC1(C)c2cc(-c3ccc(N(c4ccc(-c5ccccc5)cc4)c4ccc5ccccc5c4)cc3)ccc2-c2sc3ccccc3c21] | 619.82 | 456 | 440 | 130 |

TABLE 8-continued
| Compound | Structure | Molecular Weight | Td | Td 95% | Tg |
|---|---|---|---|---|---|
| 52 | 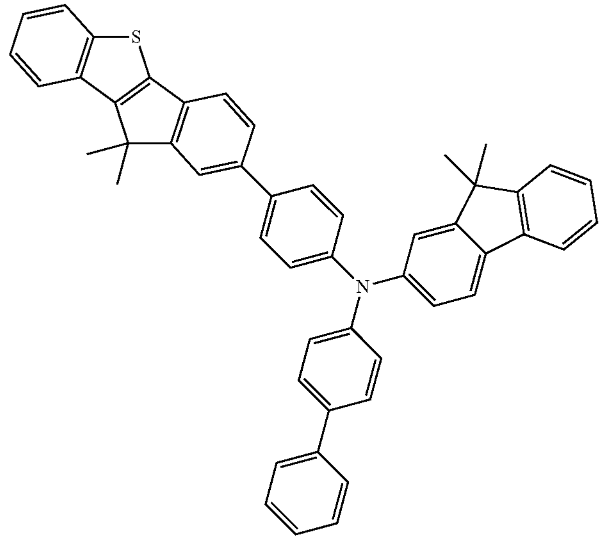 [SMILES: CC1(C)c2ccccc2-c2ccc(N(c3ccc(-c4ccccc4)cc3)c3ccc(-c4ccc5c(c4)C(C)(C)c4c-5sc5ccccc45)cc3)cc21] | 685.28 | 460 | 445 | 136 |
| 61 | 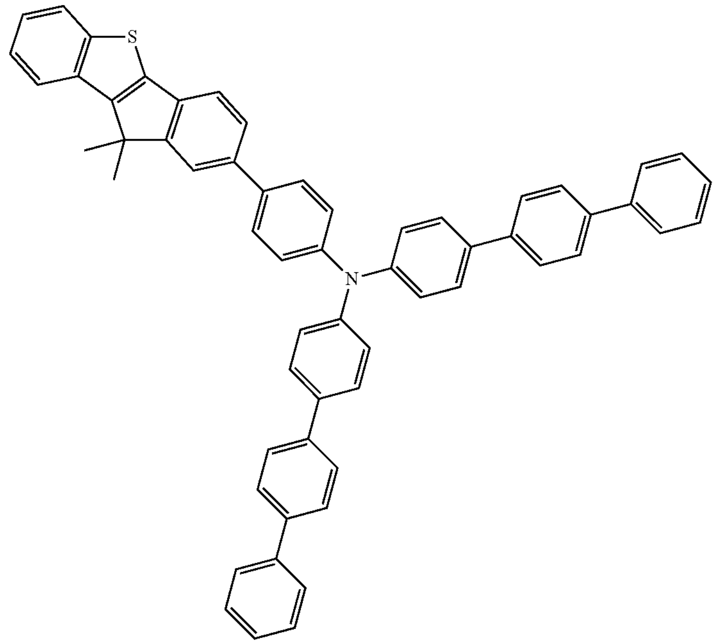 [SMILES: CC1(C)c2cc(-c3ccc(N(c4ccc(-c5ccc(-c6ccccc6)cc5)cc4)c4ccc(-c5ccc(-c6ccccc6)cc5)cc4)cc3)ccc2-c2sc3ccccc3c21] | 798.04 | 510 | 490 | ND |

TABLE 8-continued
| Compound | Structure | Molecular Weight | Td | Td 95% | Tg |
|---|---|---|---|---|---|
| 62 | 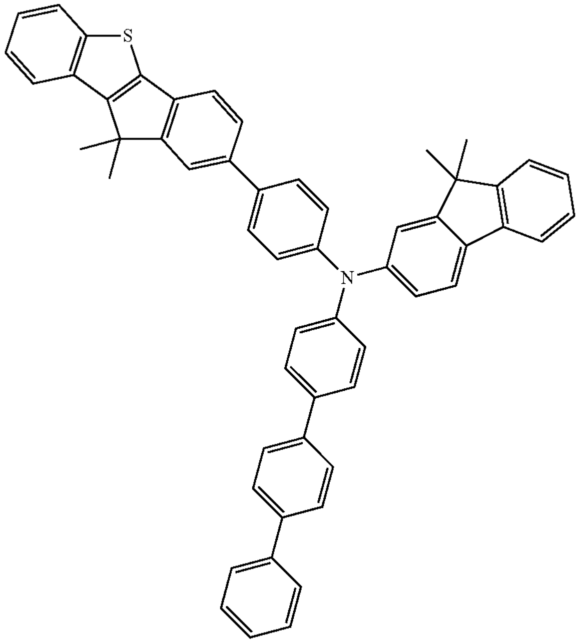 [SMILES: CC1(C)c2ccccc2-c2ccc(N(c3ccc(-c4ccc(-c5ccccc5)cc4)cc3)c3ccc(-c4ccc5c(c4)C(C)(C)c4c-5sc5ccccc45)cc3)cc21] | 761.31 | 485 | 466 | 135 |
| 63 | 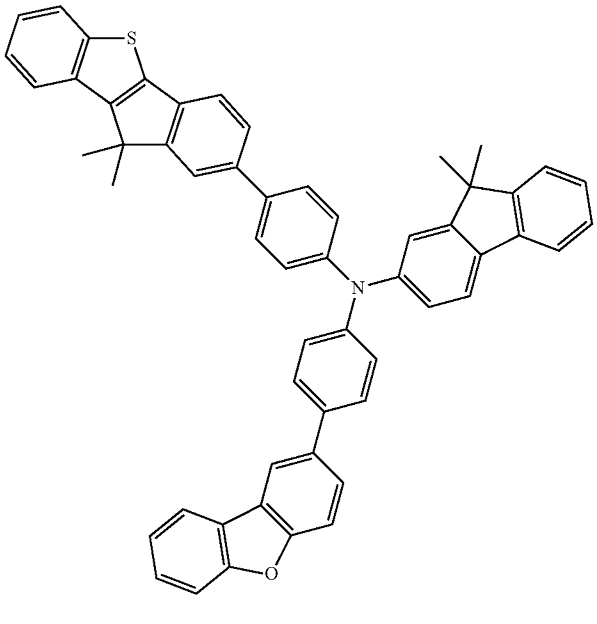 [SMILES: CC1(C)c2ccccc2-c2ccc(N(c3ccc(-c4ccc5c(c4)C(C)(C)c4c-5sc5ccccc45)cc3)c3ccc(-c4ccc5oc6ccccc6c5c4)cc3)cc21] | 776.00 | 501 | 482 | 132 |

TABLE 8-continued

| Compound | Structure | Molecular Weight | Td | Td 95% | Tg |
|---|---|---|---|---|---|
| 78 | 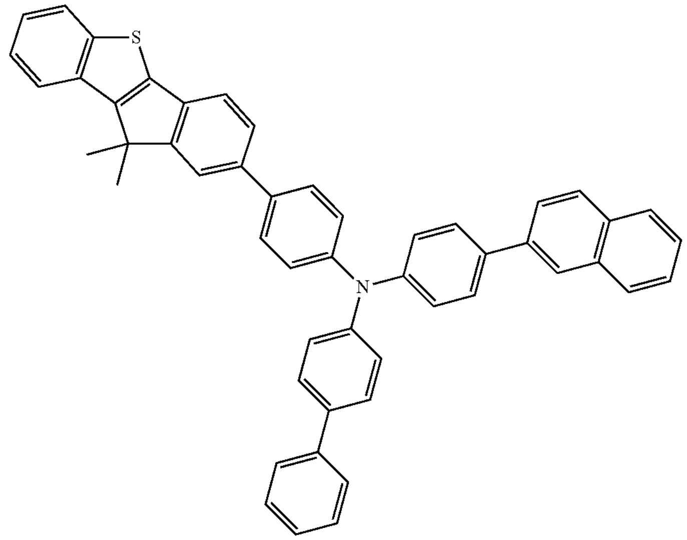 [SMILES: CC1(C)c2cc(-c3ccc(N(c4ccc(-c5ccccc5)cc4)c4ccc(-c5ccc6ccccc6c5)cc4)cc3)ccc2-c2sc3ccccc3c21] | 695.26 | 477 | 462 | ND |
| 97 | 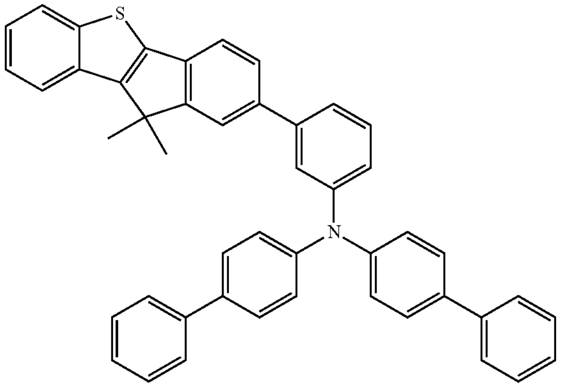 [SMILES: CC1(C)c2cc(-c3cccc(N(c4ccc(-c5ccccc5)cc4)c4ccc(-c5ccccc5)cc4)c3)ccc2-c2sc3ccccc3c21] | 645.25 | 459 | 443 | 136 |

As seen from Table 7 and Table 8, it was identified that the heterocyclic compound of Chemical Formula 1 of the present disclosure exhibited more superior thermal stability compared to the compounds of Compounds (a), (b) and (C) of Table 7.

From such results, it was identified that, when an intermediate linker (L1) such as the compound of Chemical Formula 1 of the present application was inserted instead of the arylamine functional group directly bonding to one side benzene ring of the indenothiophene, compounds having more superior thermal stability were obtained since the steric effect decreased compared to the compound having a form of direct bonding, and the molecular weight increased, the structural planarity increased and the conjugation structure was expanded. Accordingly, as seen from Table 5, it was seen that an excellent lifetime was obtained when comprising the compound of Chemical Formula 1 of the present application.

The invention claimed is:

1. A heterocyclic compound represented by the following Chemical Formula 1-B:

[Chemical Formula 1-B]

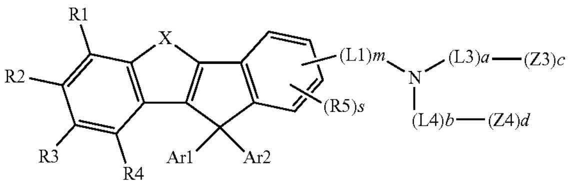

wherein, in Chemical Formula 1-B,

X is O; or S;

R1 to R5 are hydrogen;

Ar1 and Ar2 are the same as or different from each other, and each independently a substituted or unsubstituted C1 to C60 alkyl group; a substituted or unsubstituted C6 to C60 aryl group; or a substituted or unsubstituted C2 to C60 heteroaryl group;

L1 is any one of the following structural formulae:

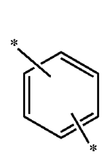

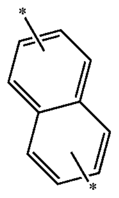

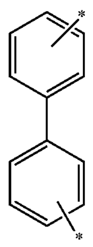

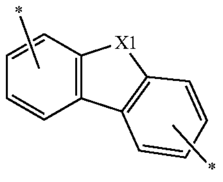

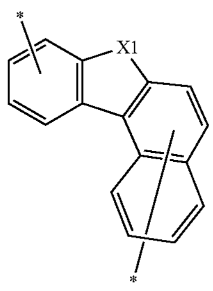

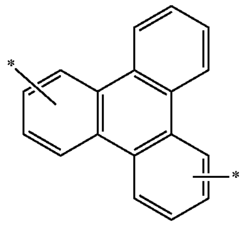

in the structural formulae,

X1 is O; or S;

L3 and L4 are the same as or different from each other, and each independently a direct bond; a substituted or unsubstituted C6 to C60 arylene group; or a substituted or unsubstituted C2 to C60 heteroarylene group;

Z3 and Z4 are the same as or different from each other, and each independently selected from the group consisting of hydrogen; deuterium; halogen; a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group;

a and b are an integer of 0 to 5;

c and d are an integer of 1 to 6;

m is an integer of 1 to 4, and s is an integer of 0 to 3.

2. The heterocyclic compound claim 1, wherein Chemical Formula 1-B is represented by any one of the following Chemical Formulae 1-1-B to 1-4-B:

[Chemical Formula 1-1-B]

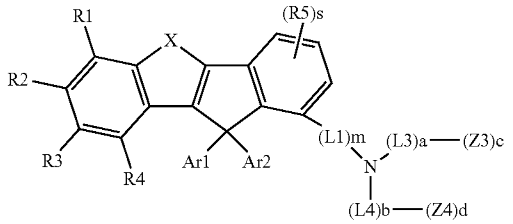

[Chemical Formula 1-2-B]

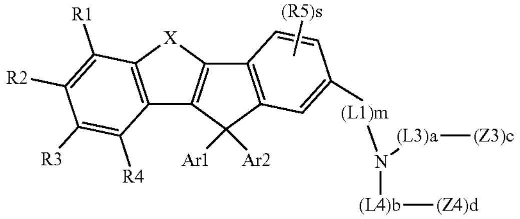

[Chemical Formula 1-3-B]

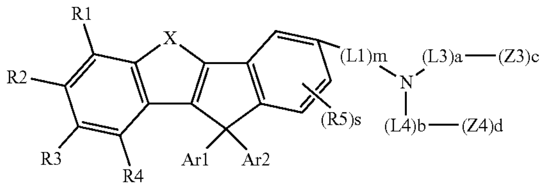

[Chemical Formula 1-4-B]

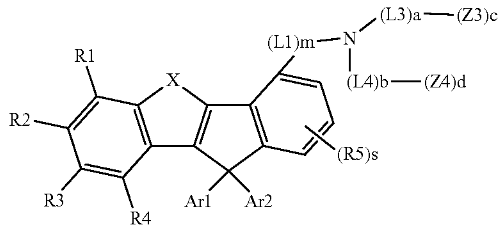

in Chemical Formulae 1-1-B to 1-4-B,

R1 to R5, X, Ar1, Ar2, L1, L3, L4, Z3, Z4, m, a, b, c, d and s have the same definitions as in Chemical Formula 1-B.

3. The heterocyclic compound of claim 1, wherein Chemical Formula 1-B is represented by any one of the following compounds:

-continued
1
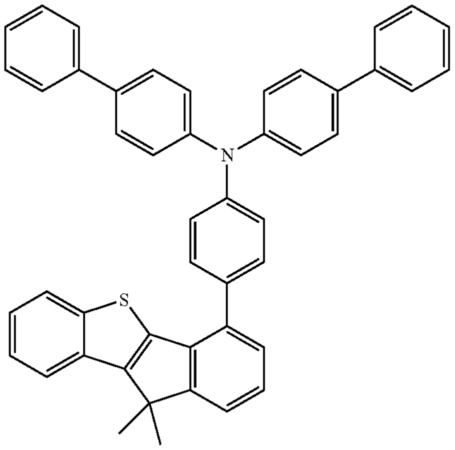
2
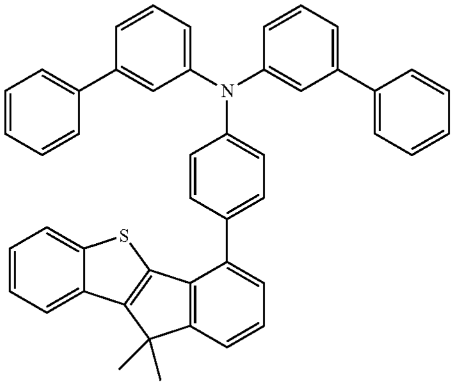
3
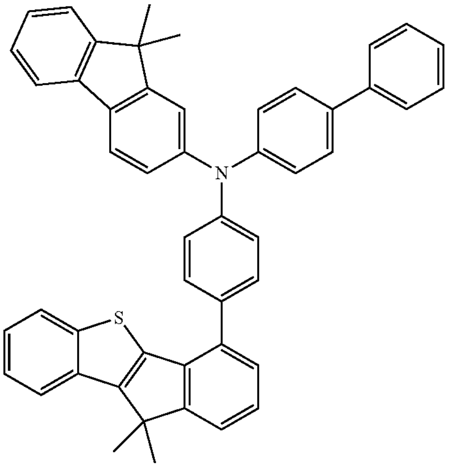
4
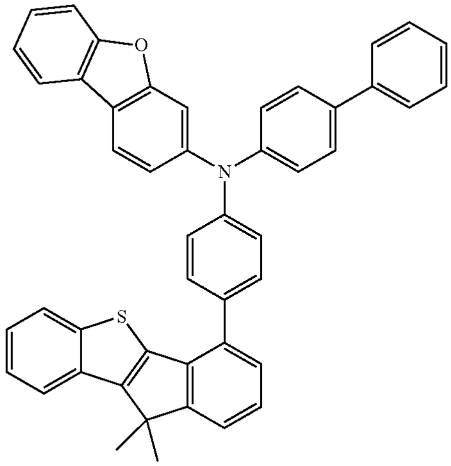
5
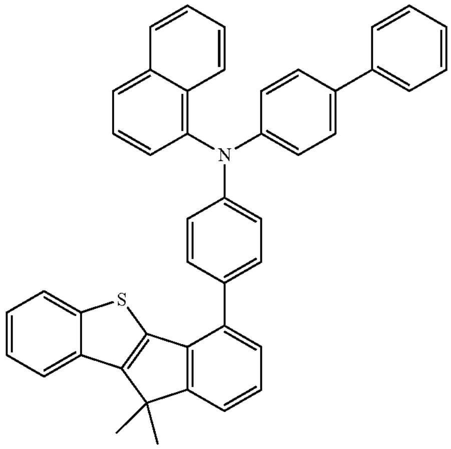
6
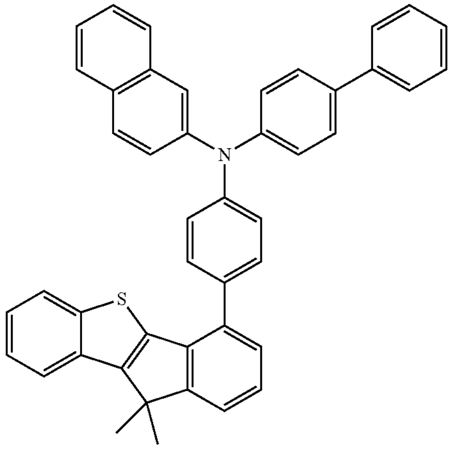

-continued
7
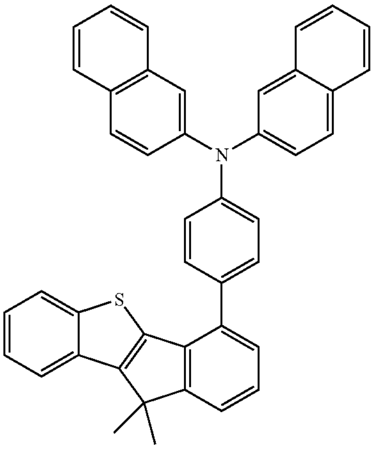
8
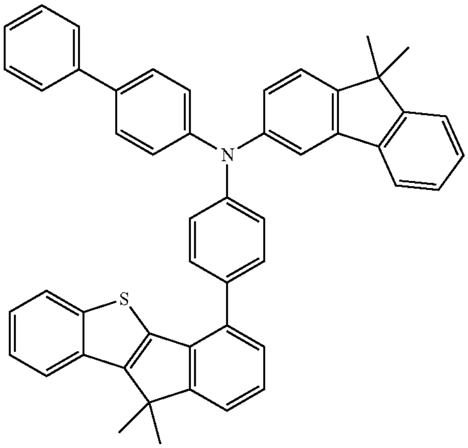
9
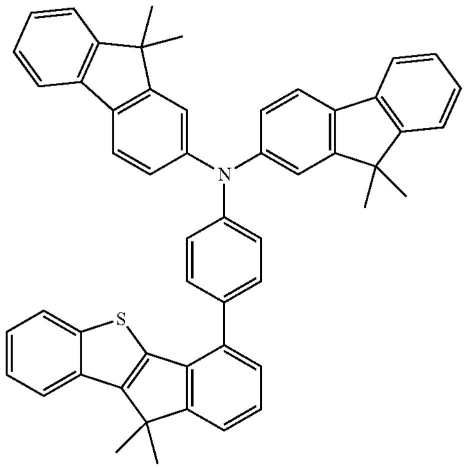
-continued
10
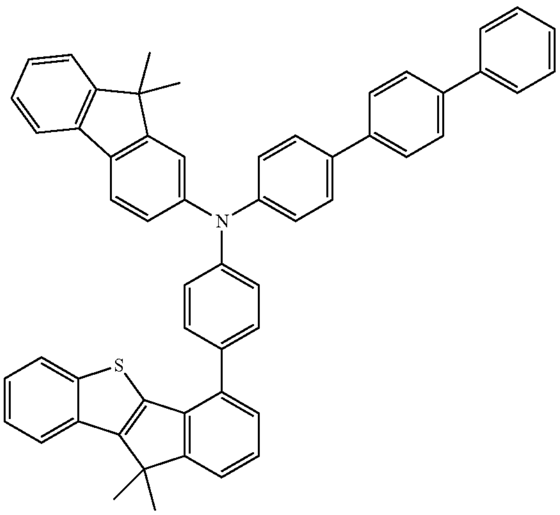
11
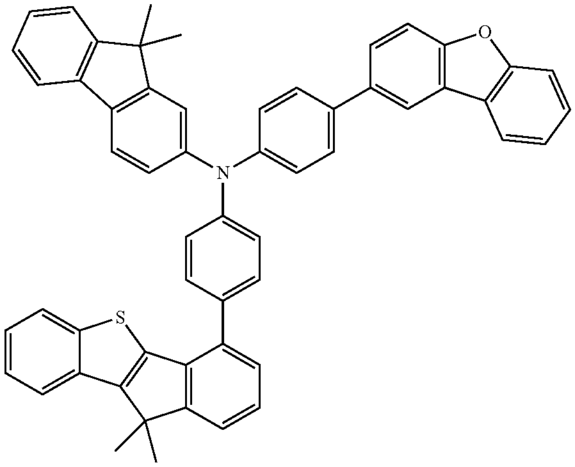
12
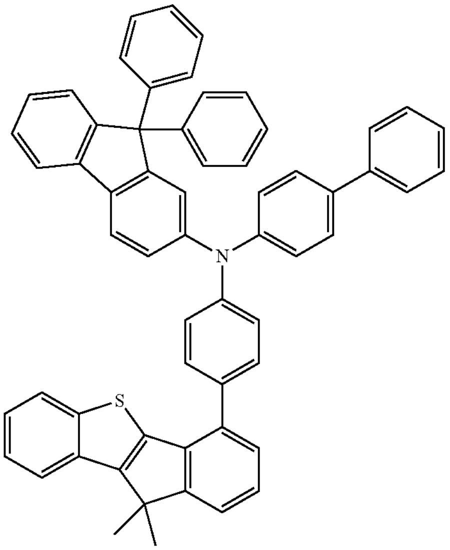

-continued
13
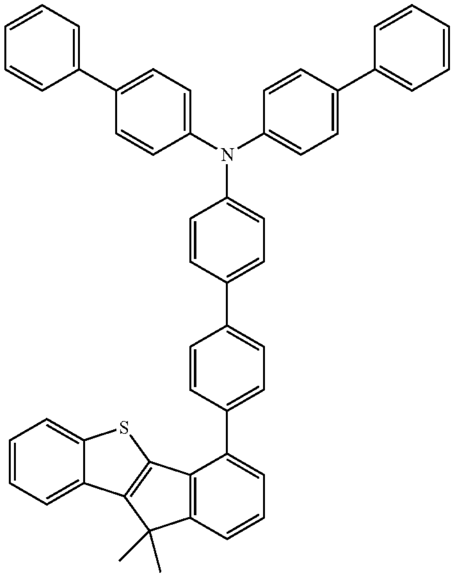
14
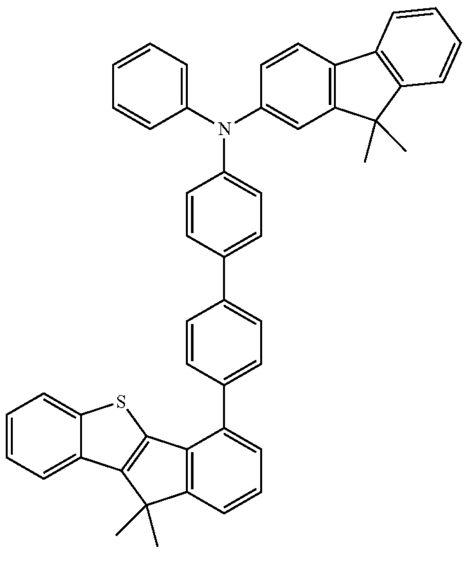
-continued
15
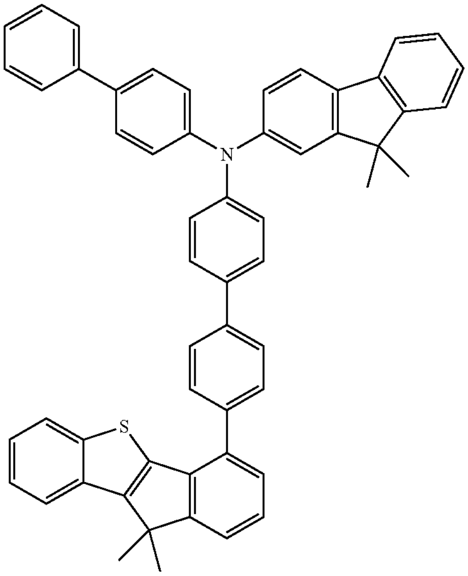
16
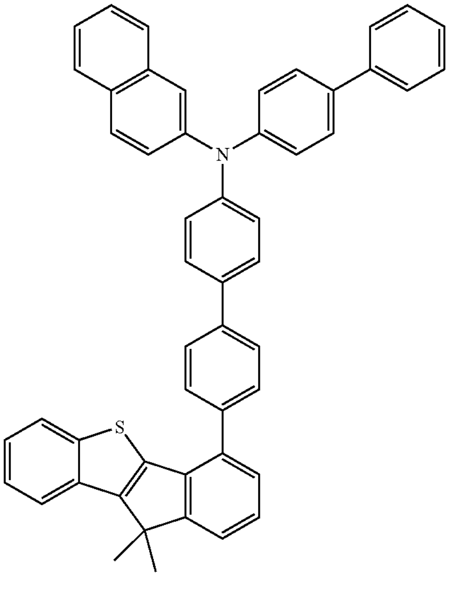

-continued
17
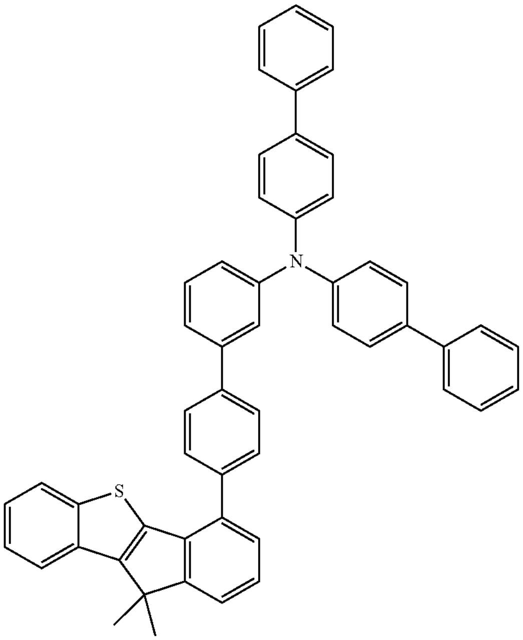
18
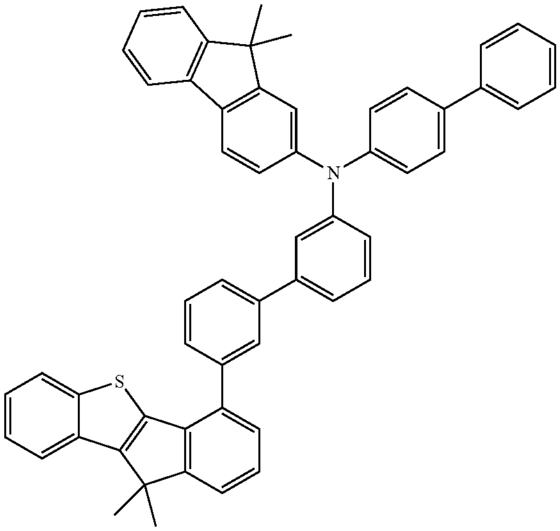
-continued
19
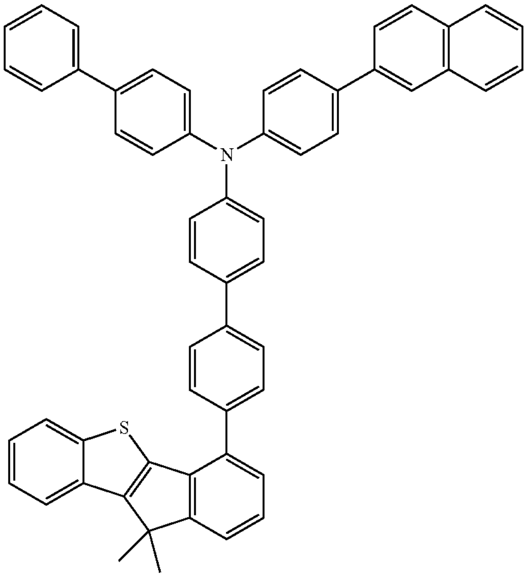
20
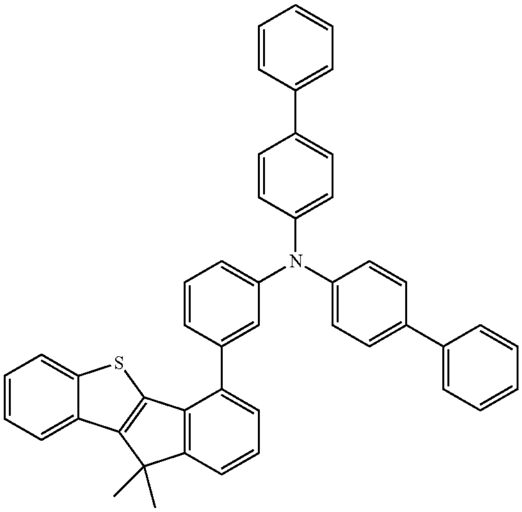

-continued
21
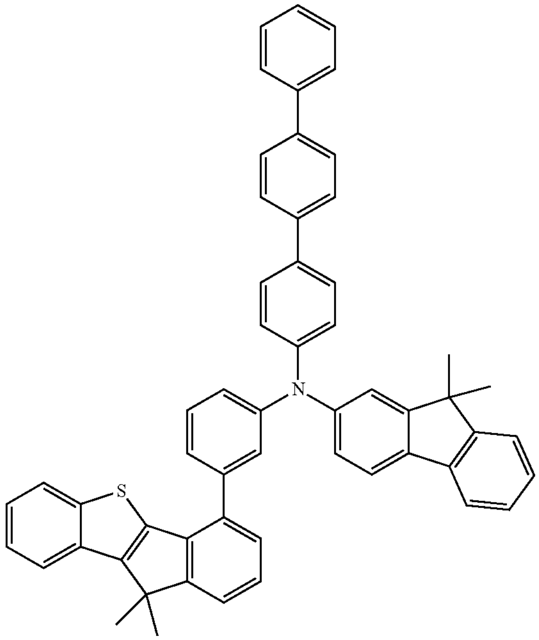
22
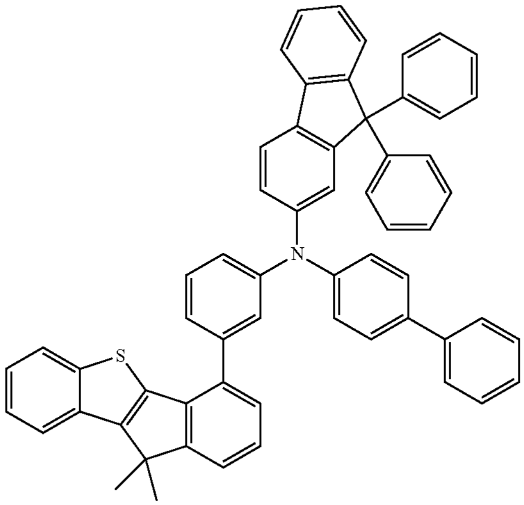
-continued
23
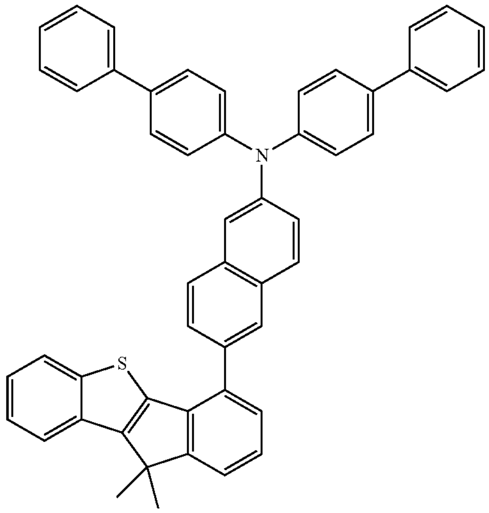
24
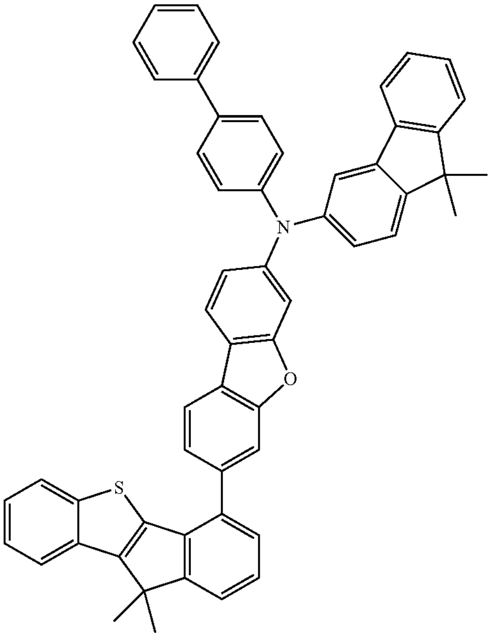

-continued
25
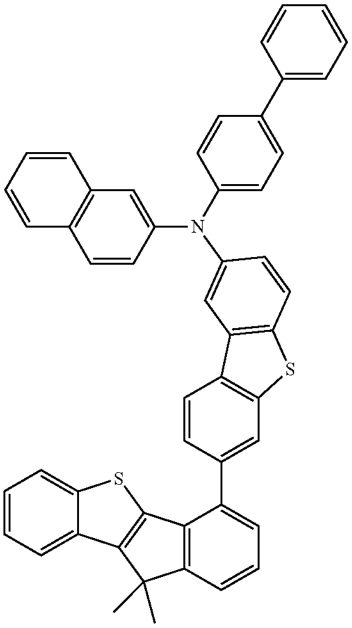
26
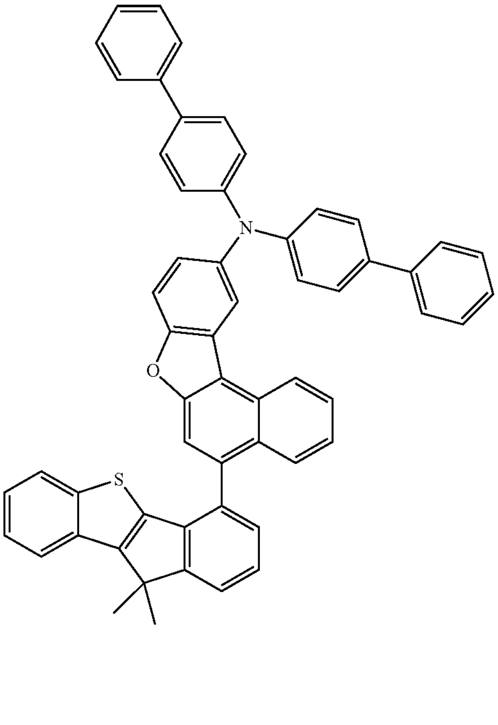
-continued
27
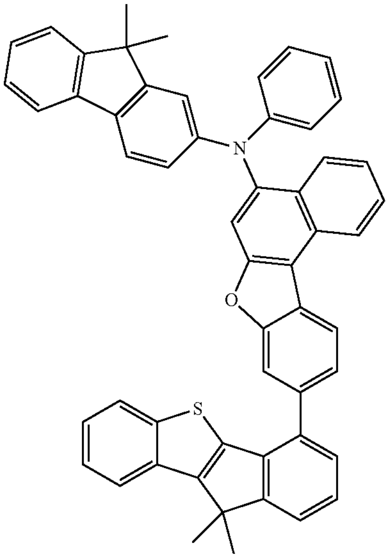
28
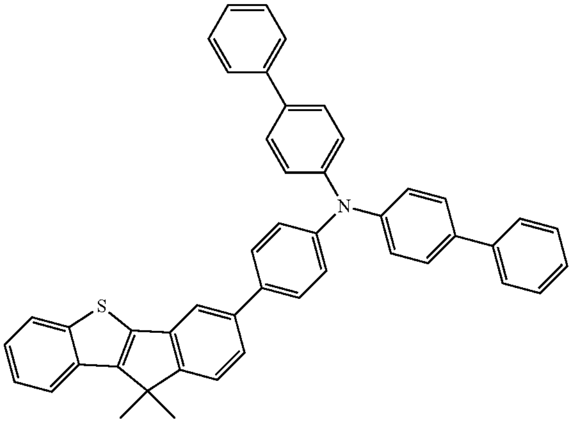
29
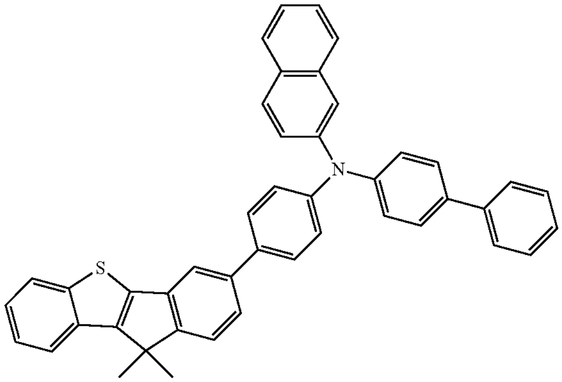

-continued
30
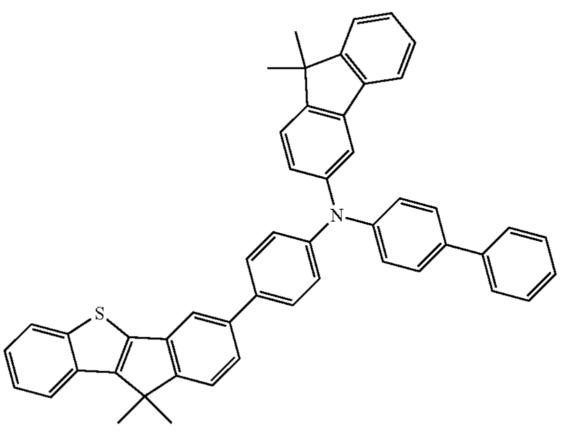
31
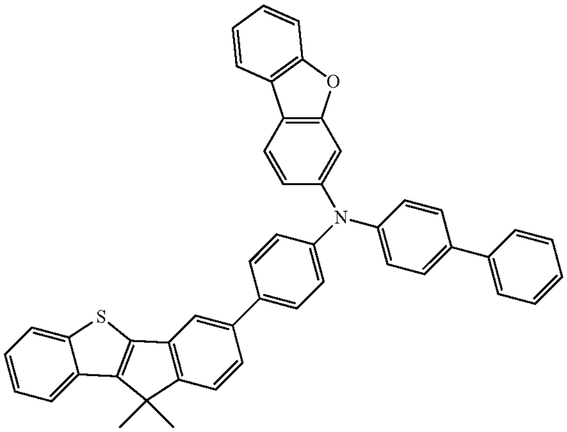
32
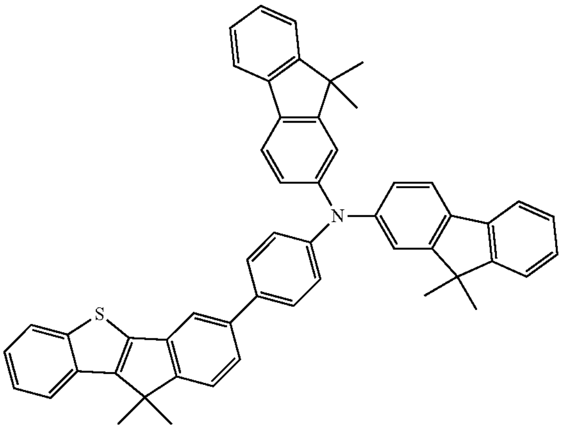
-continued
33
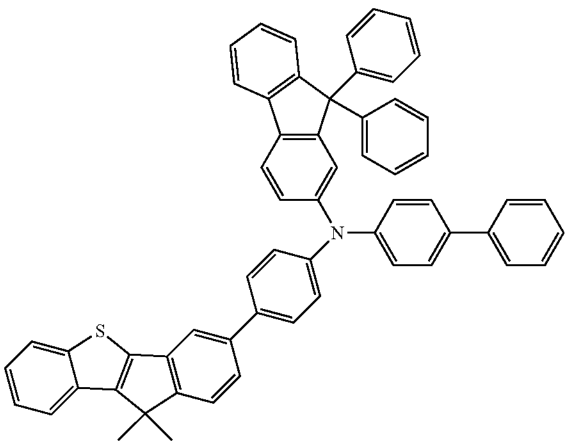
34
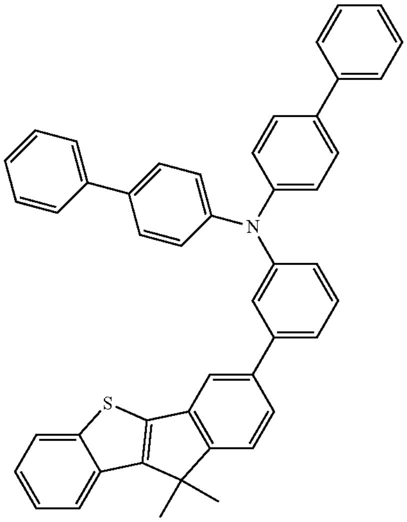
35
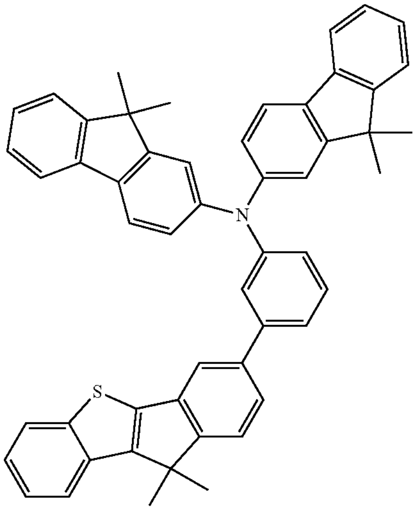

-continued
36
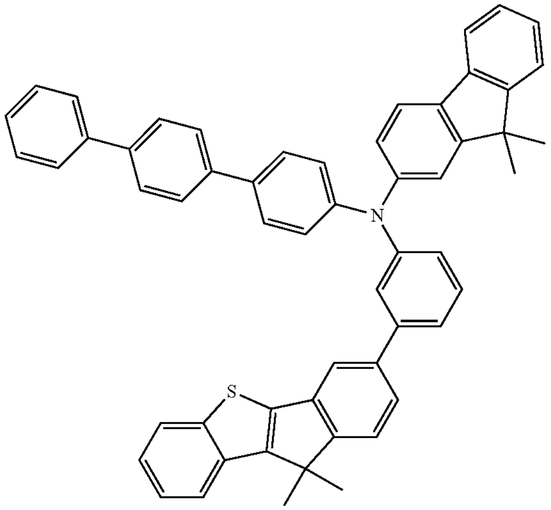
37
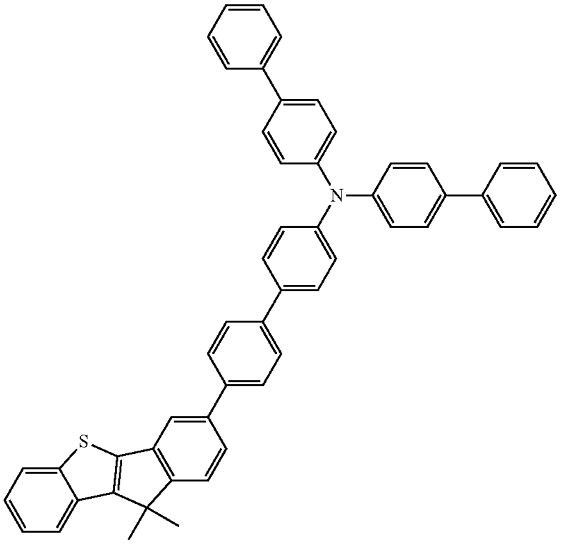
38
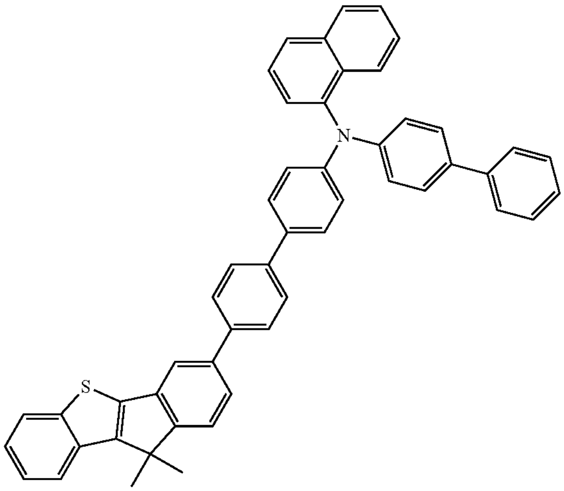
-continued
39
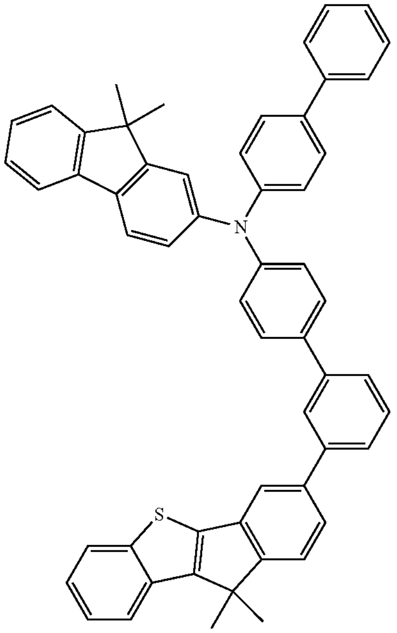
40
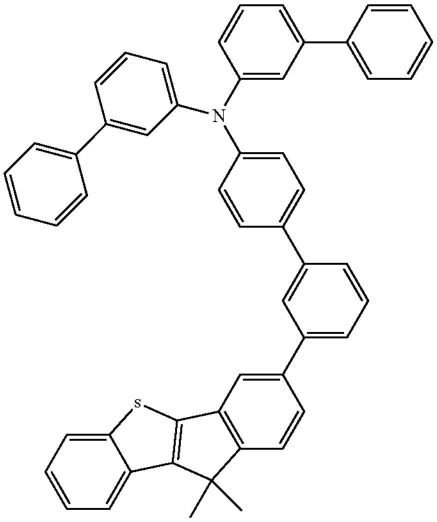
41
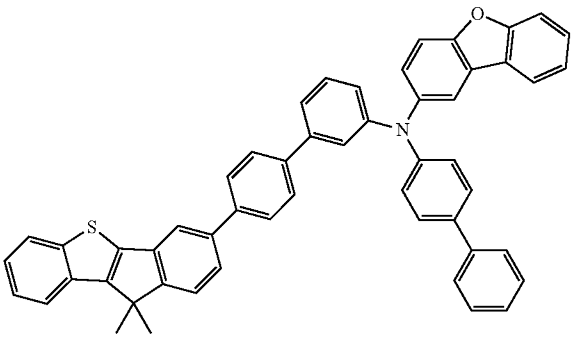

-continued
42
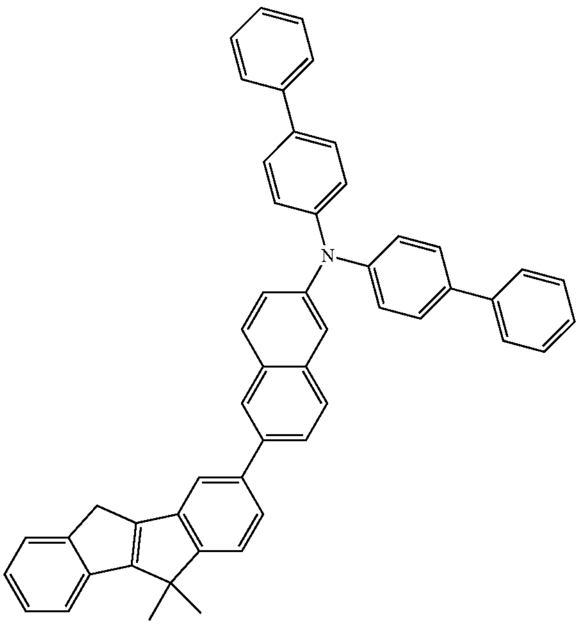
43
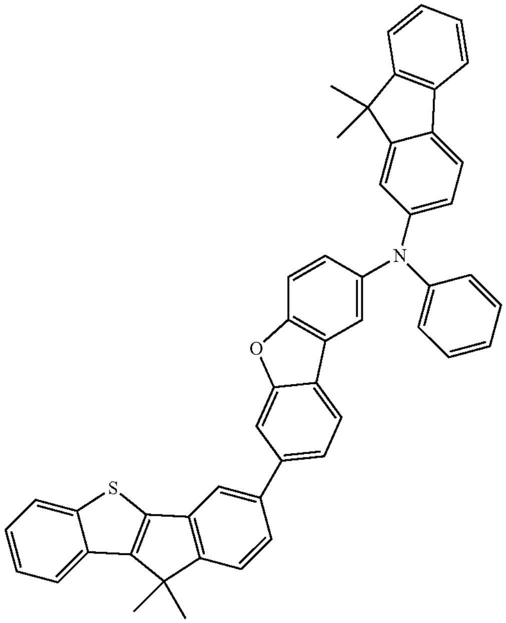
-continued
44
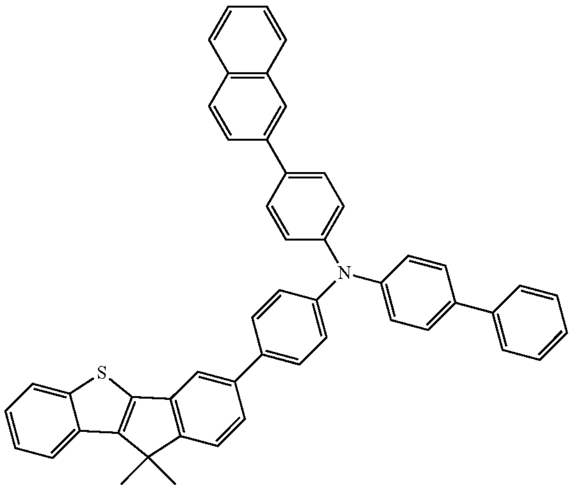
45
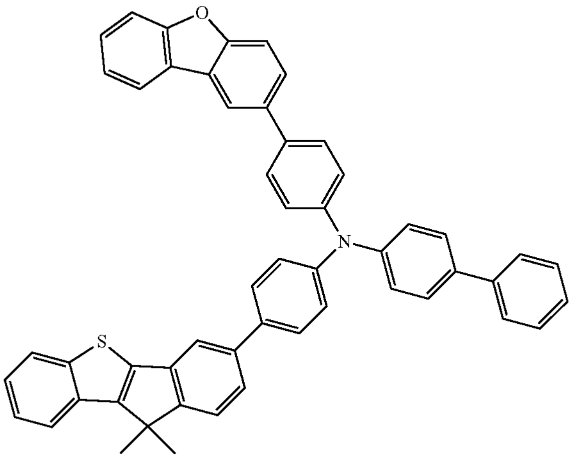
46
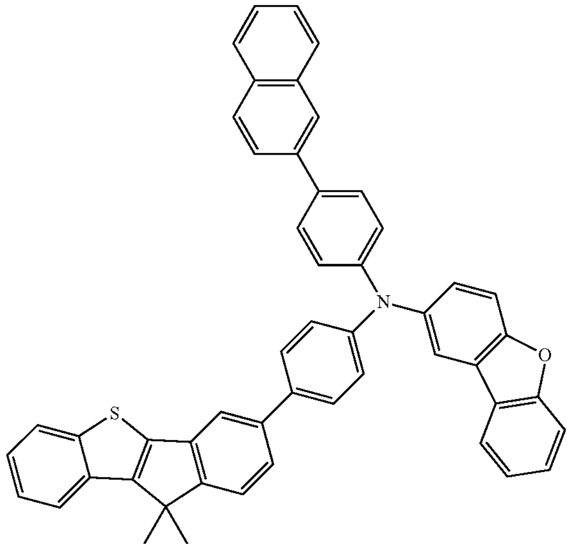

47
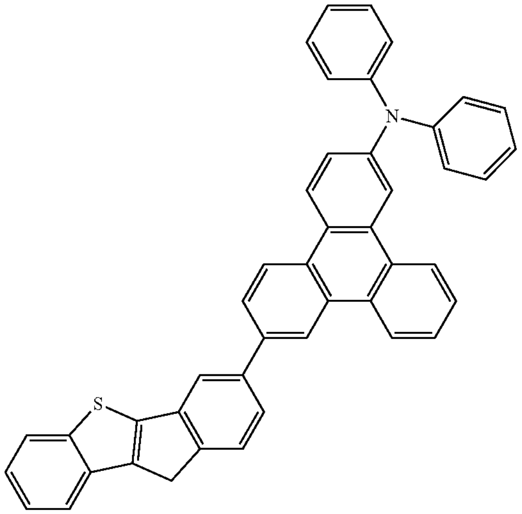
48
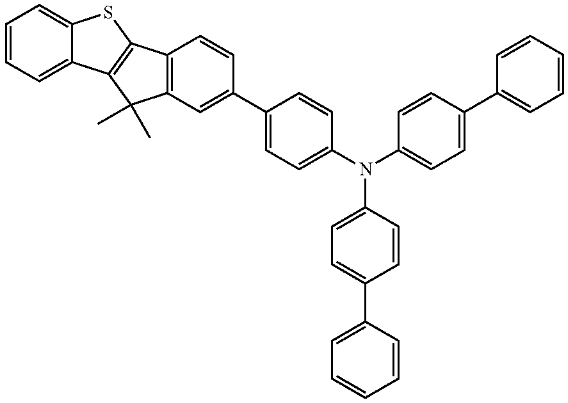
49
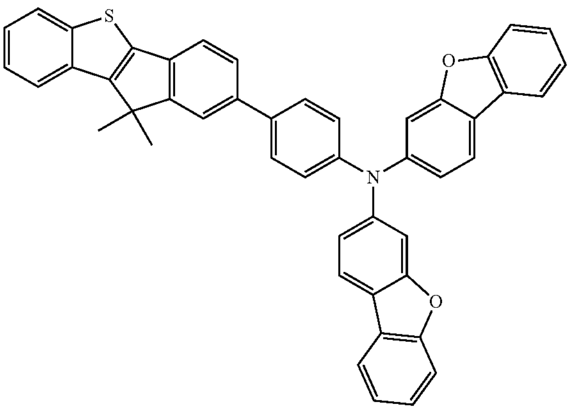
50
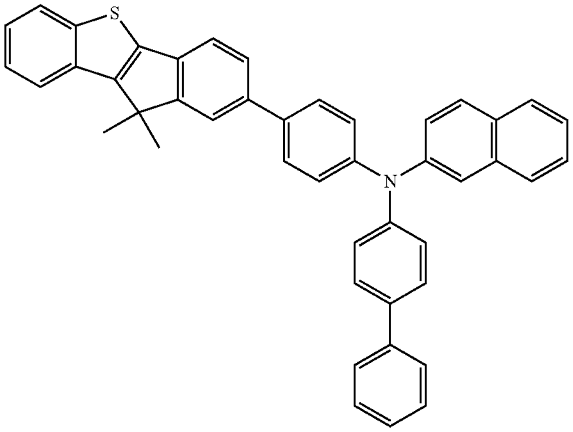
51
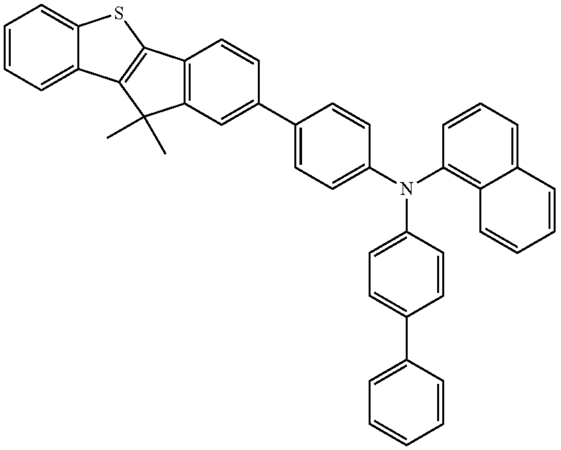
52
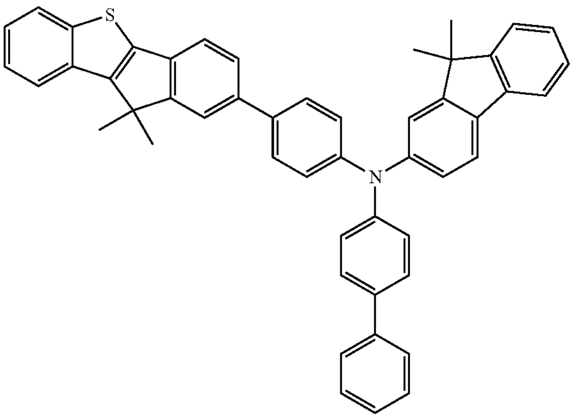

-continued
53
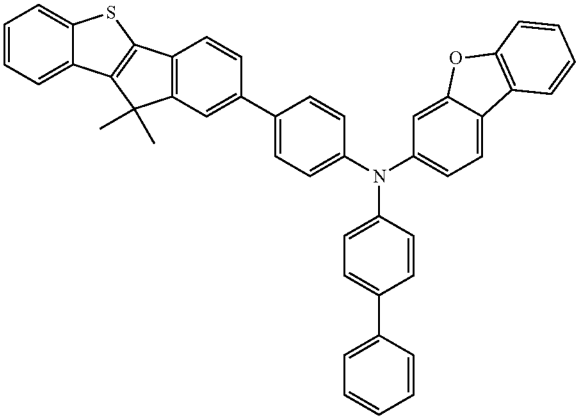
54
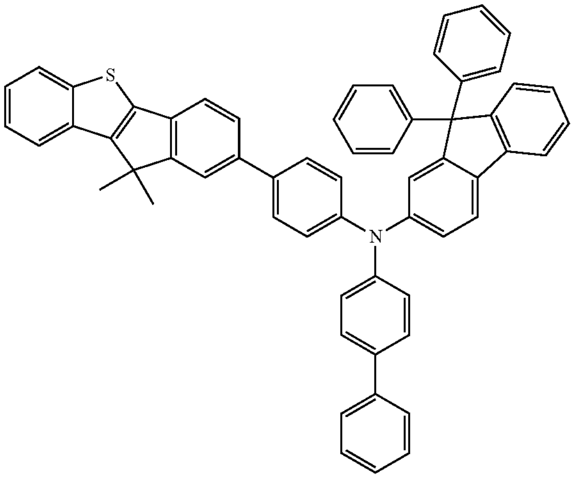
55
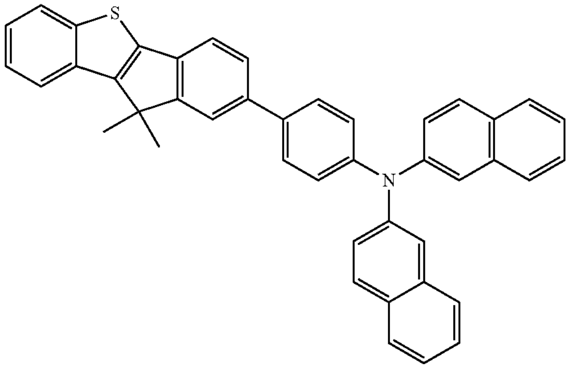
-continued
56
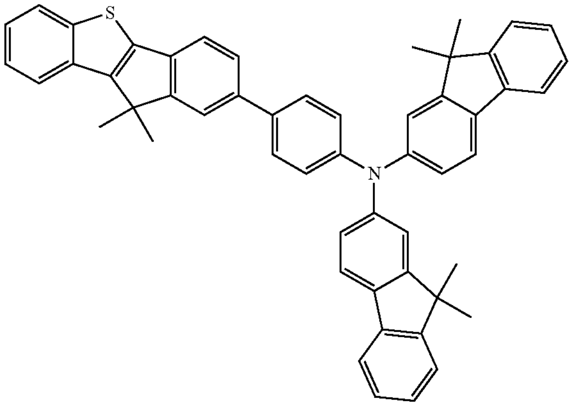
57
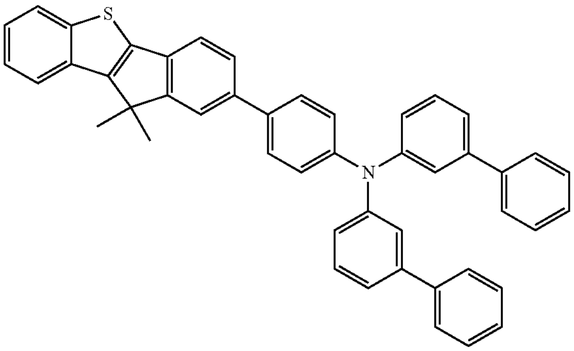
58
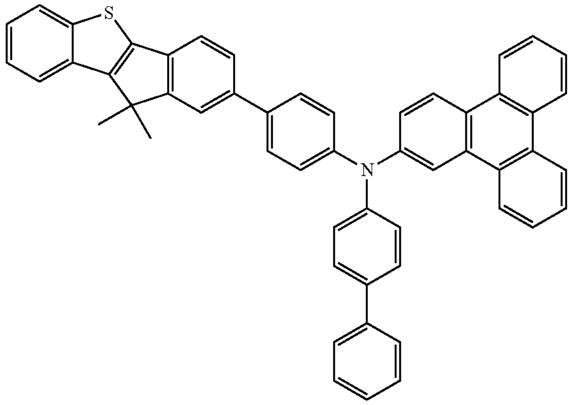

-continued
59
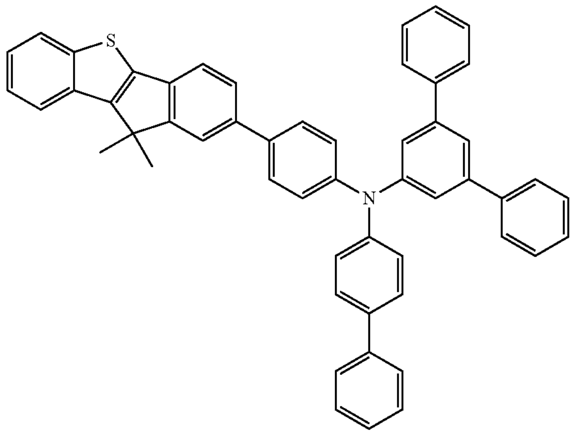
60
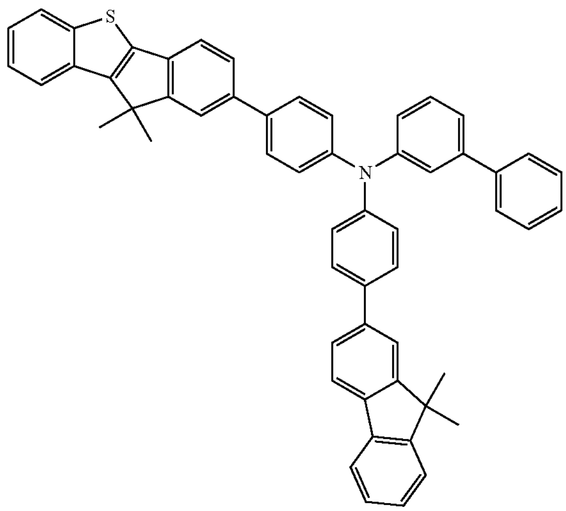
61
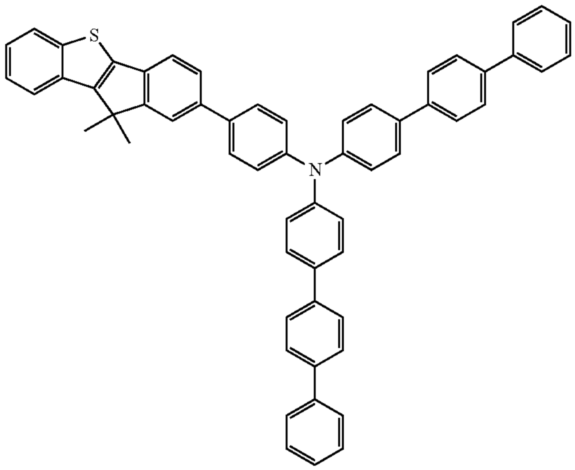
-continued
62
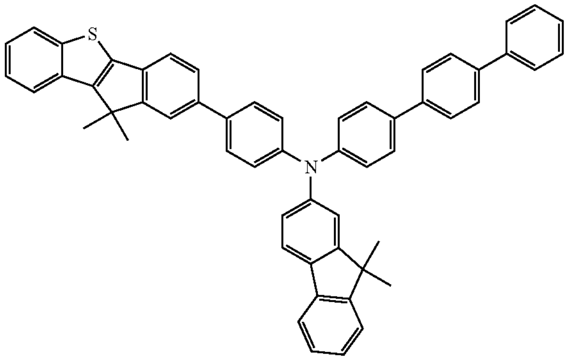
63
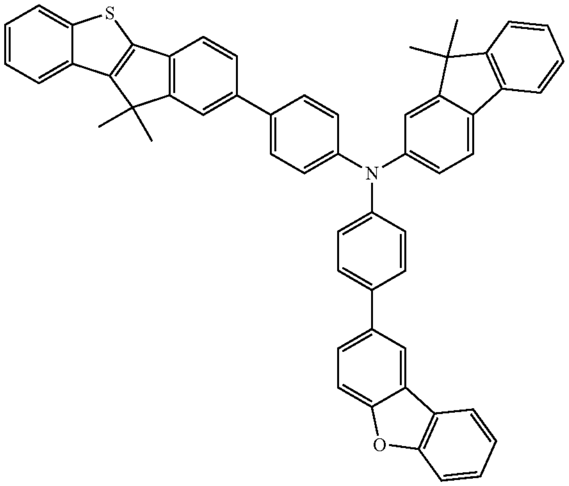
64
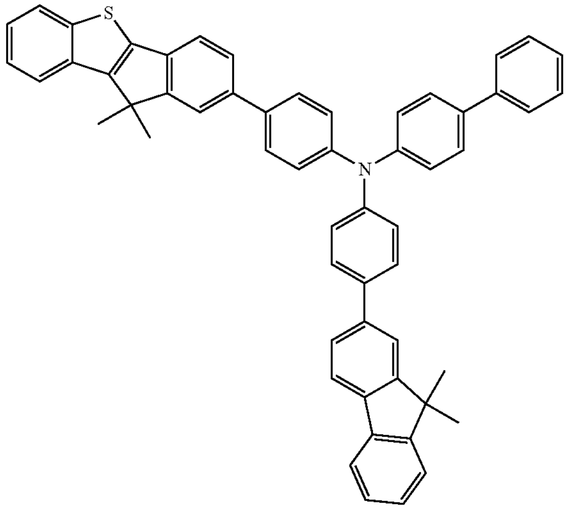

-continued
65
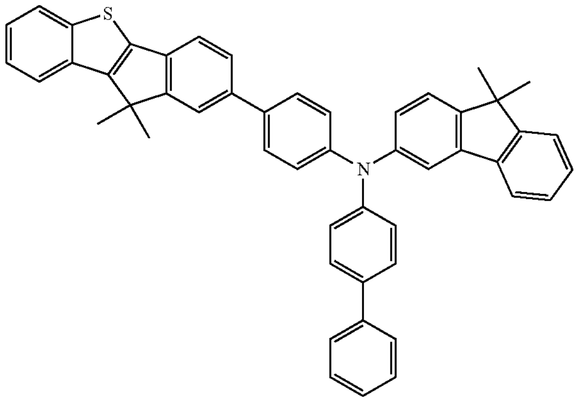
66
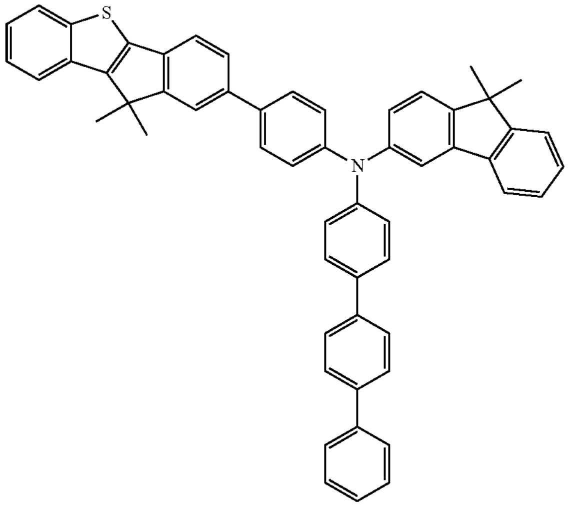
67
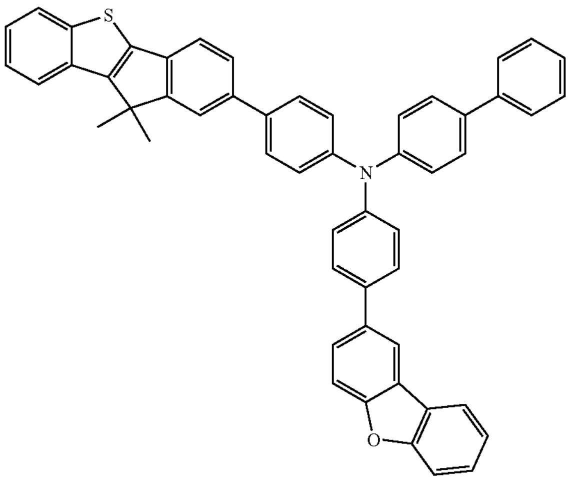
-continued
68
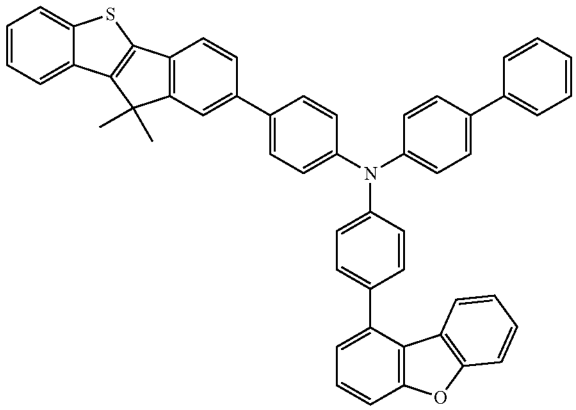
69
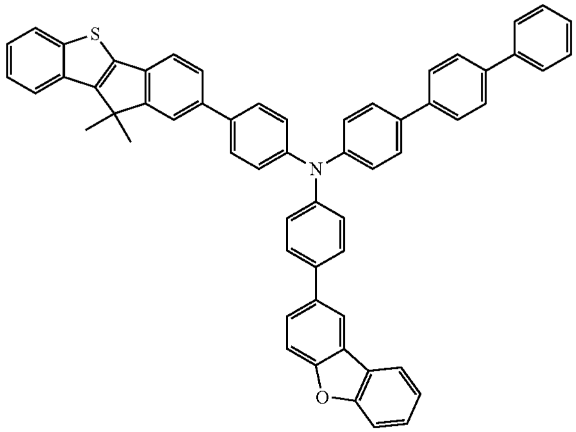
70
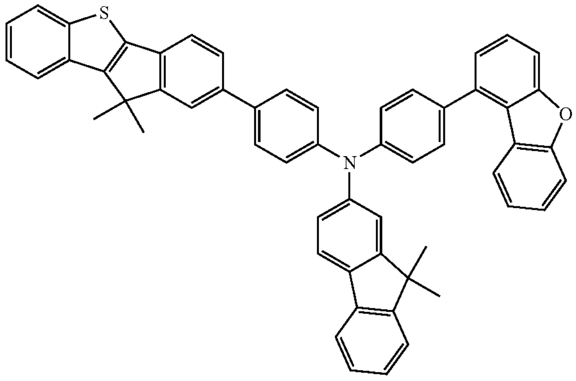

-continued
71
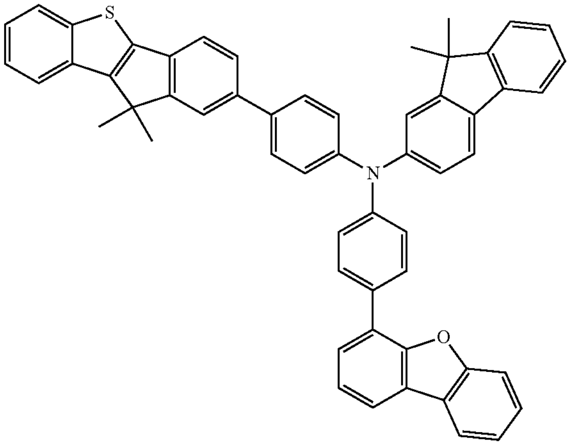
72
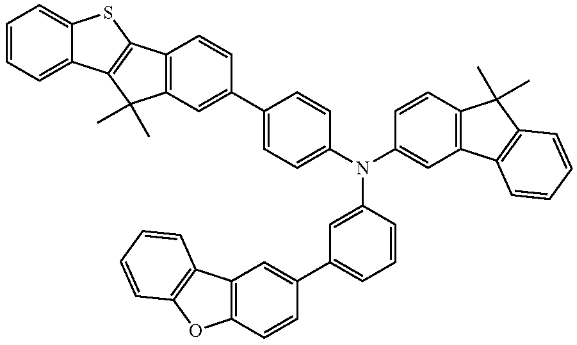
73
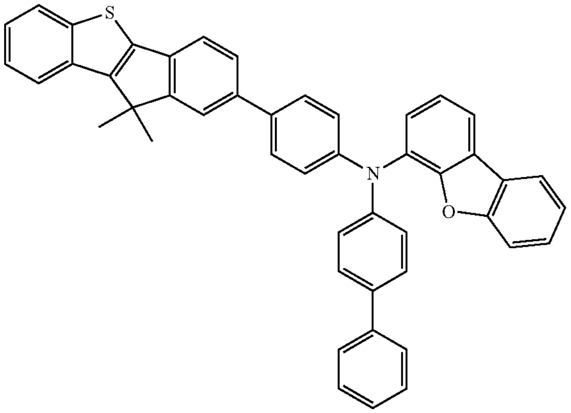
-continued
74
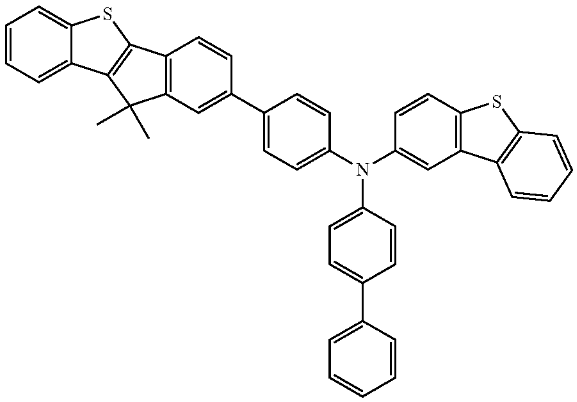
75
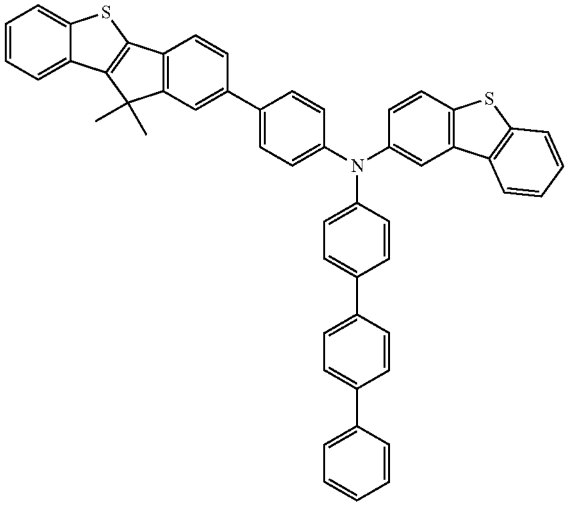
76
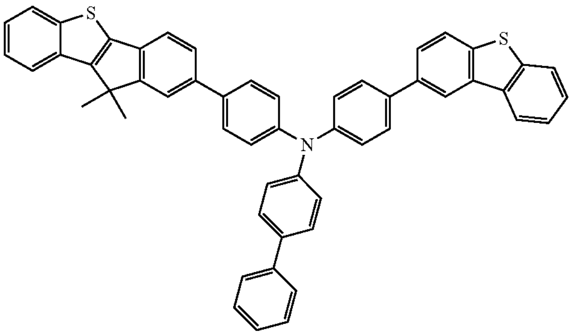

-continued
77
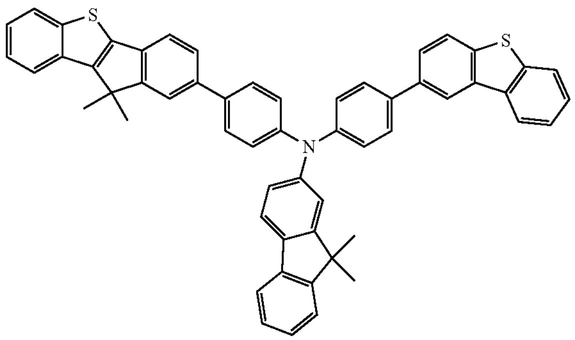
78
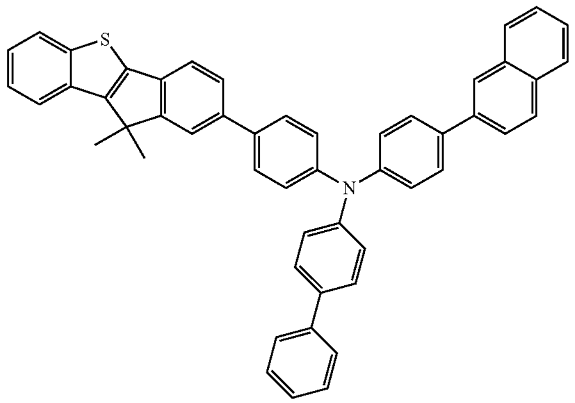
79
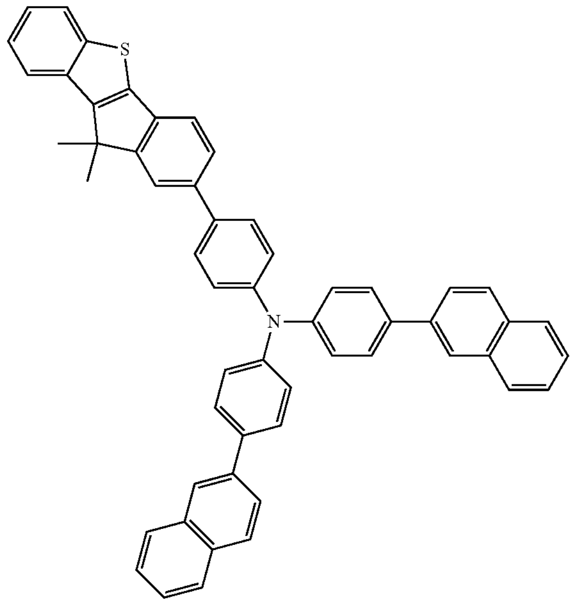
-continued
80
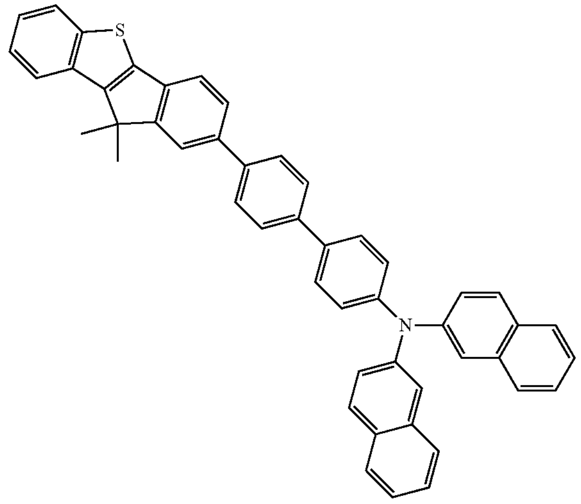
81
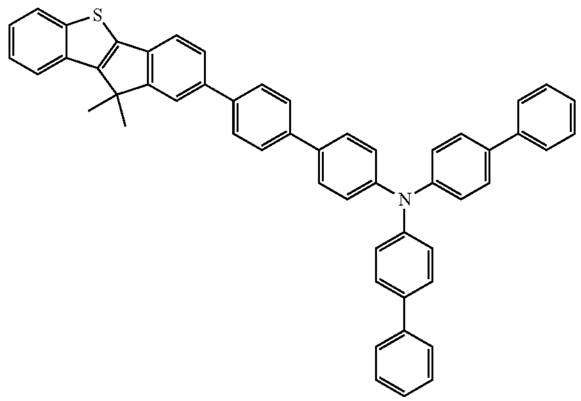
82
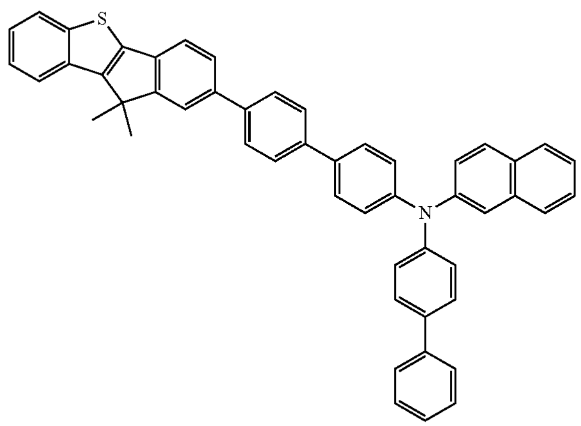

-continued
83
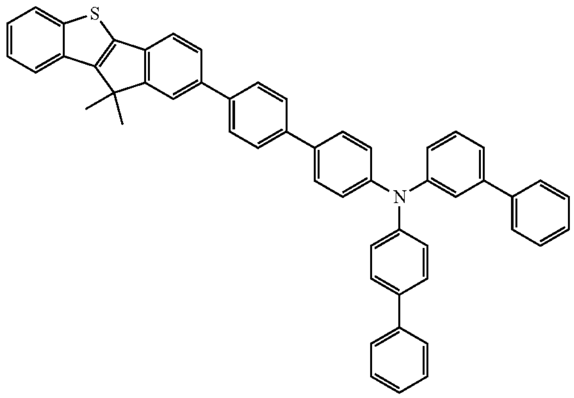
84
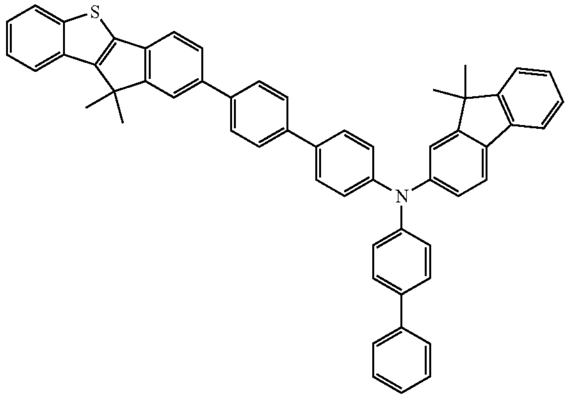
85
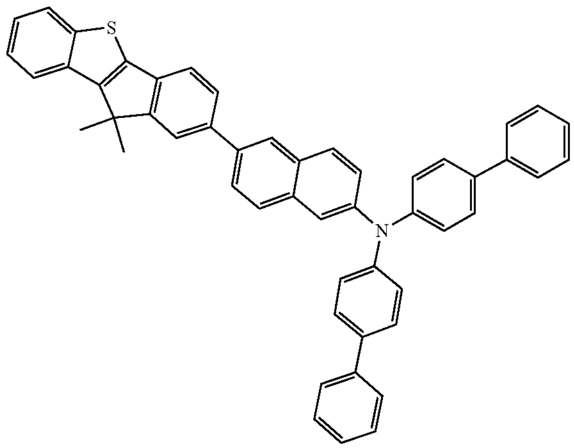
-continued
86
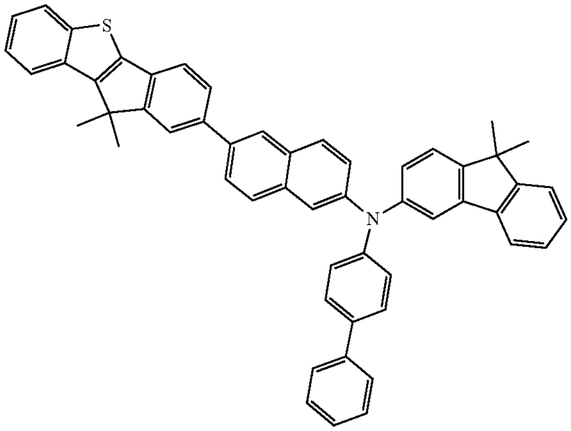
87
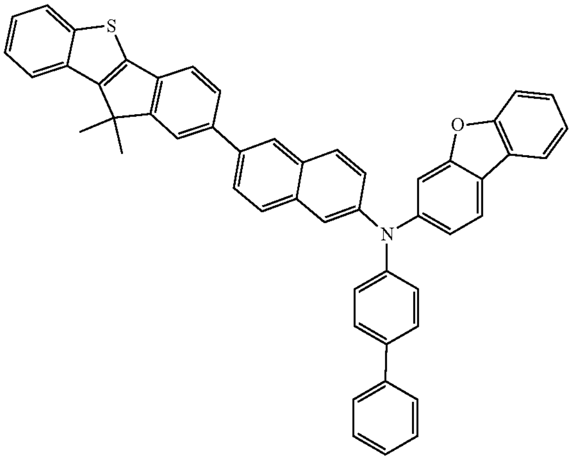
88
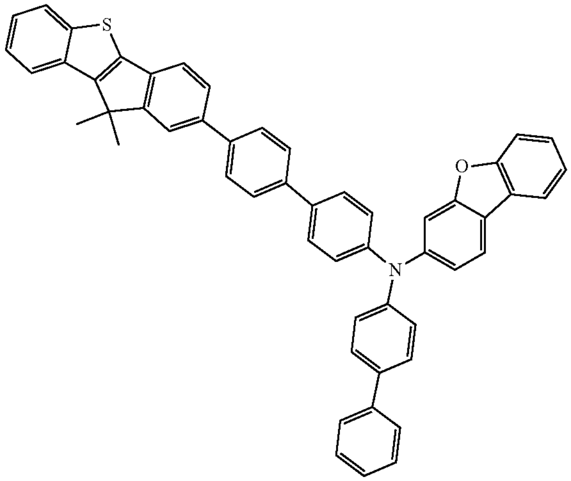

-continued
89
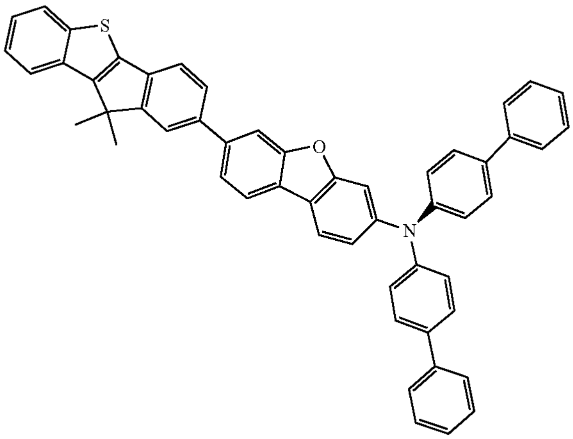
90
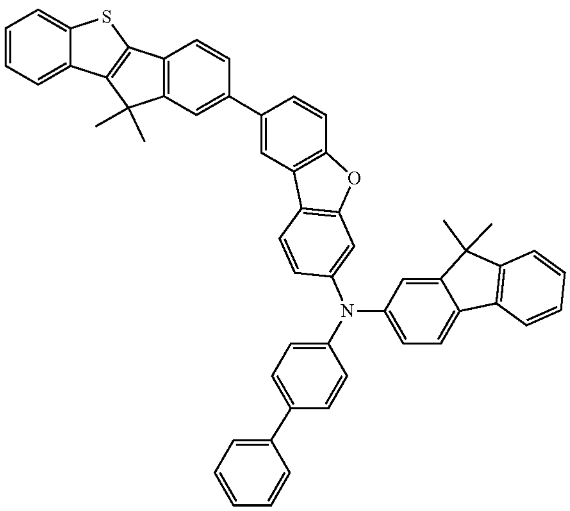
91
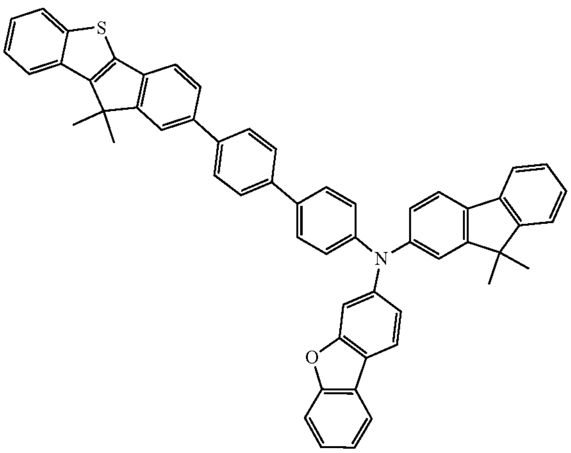
-continued
92
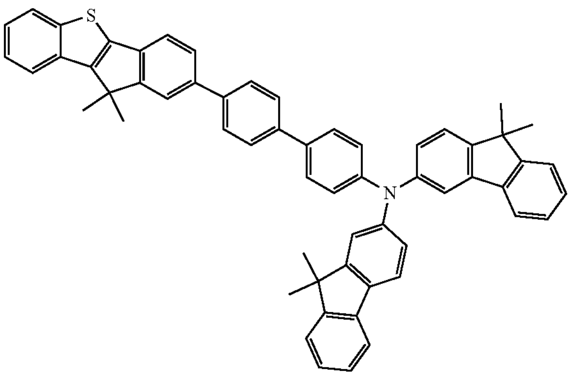
93
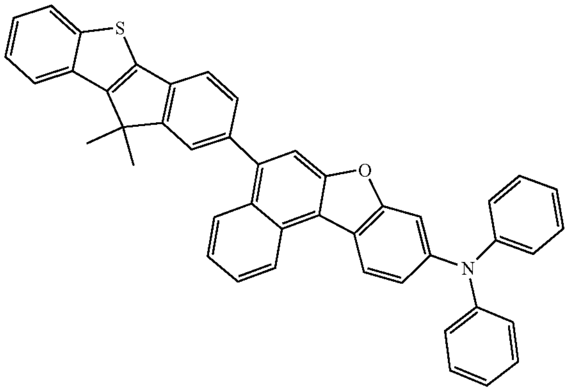
94
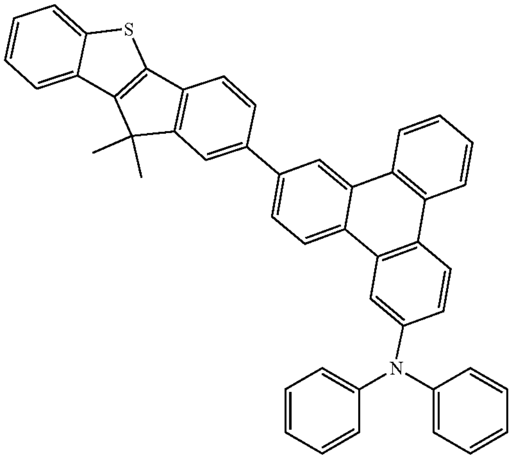

-continued
95
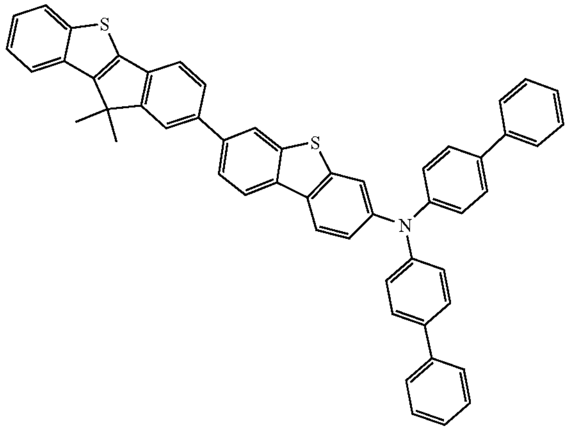
96
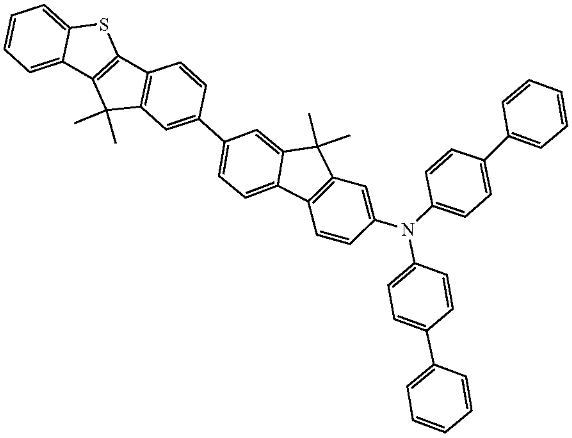
97
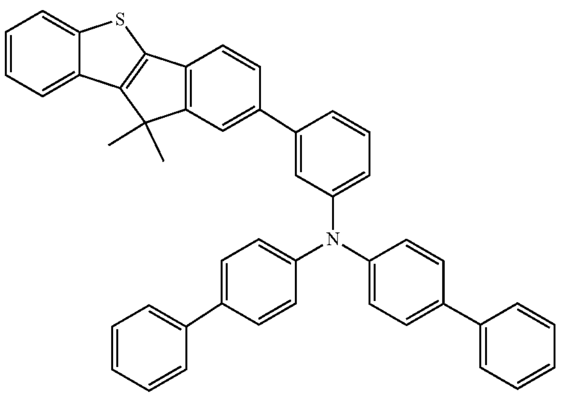
-continued
98
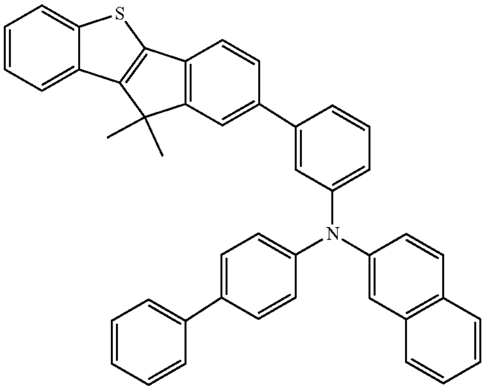
99
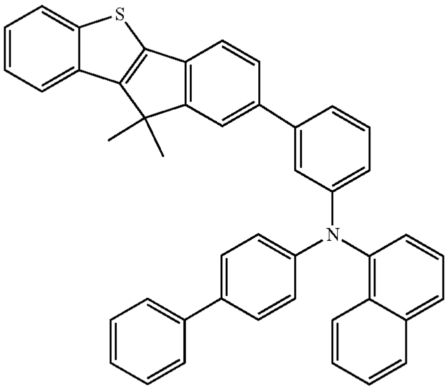
100
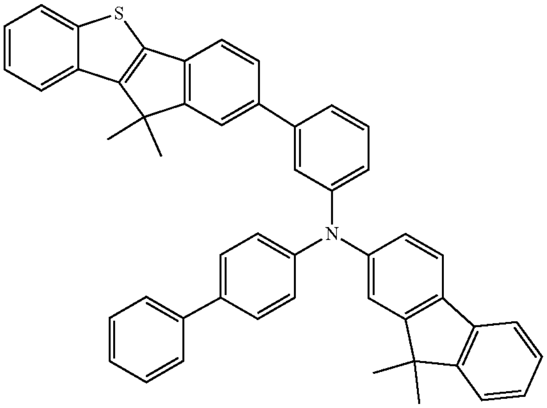

-continued
101
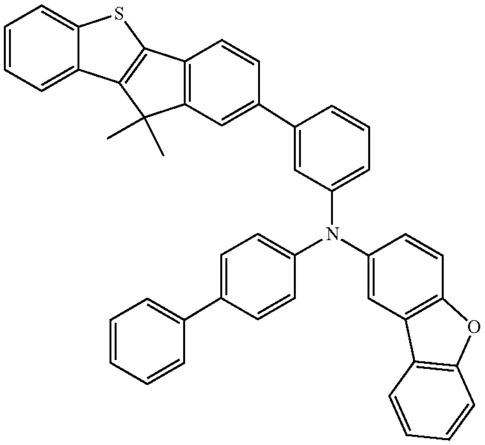
102
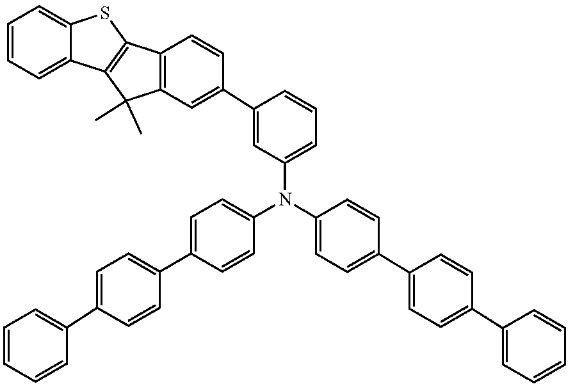
103
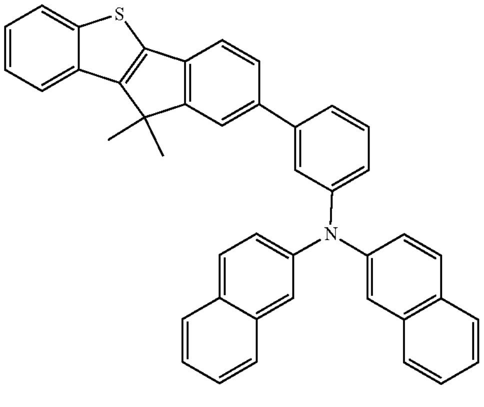
-continued
104
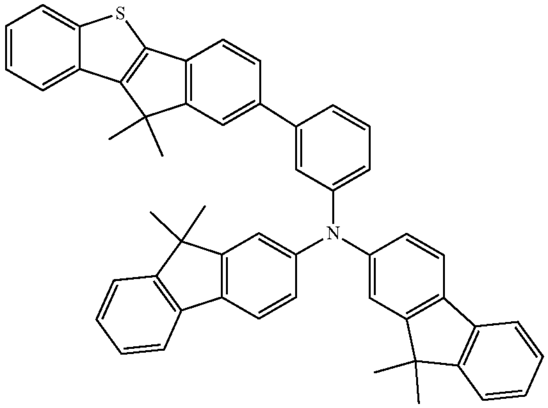
105
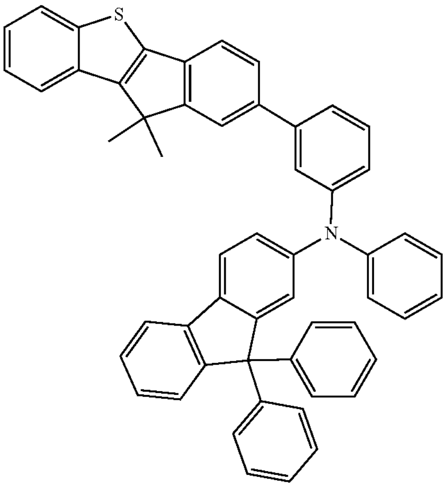
106
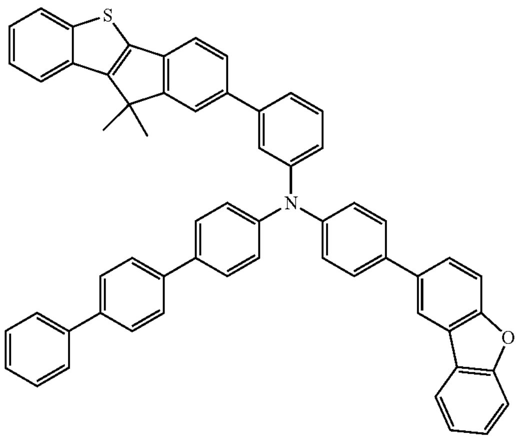

-continued
107
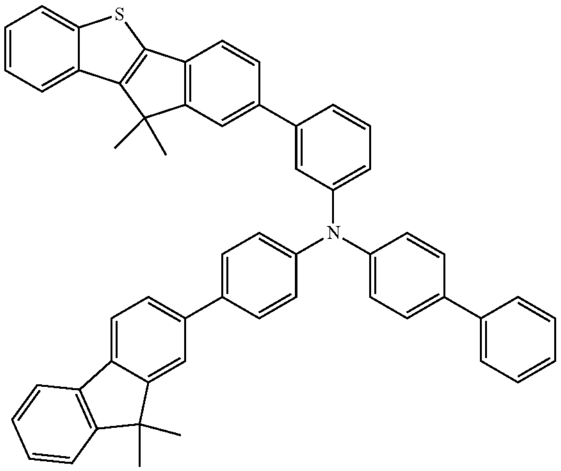
108
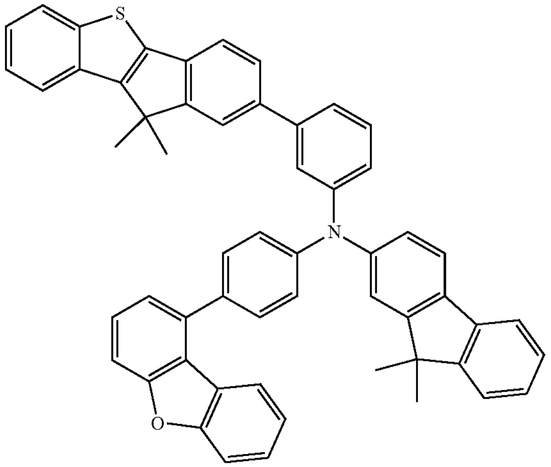
109
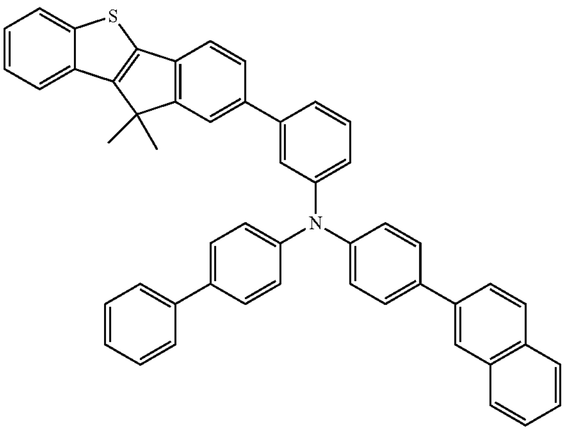
-continued
110
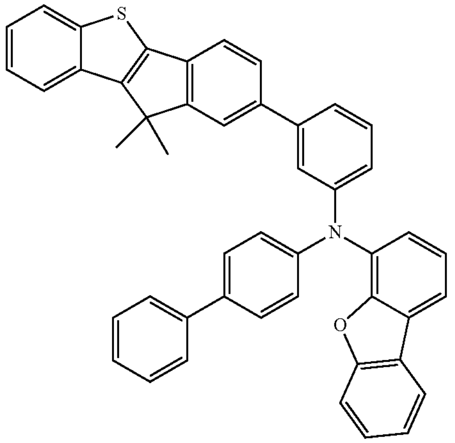
111
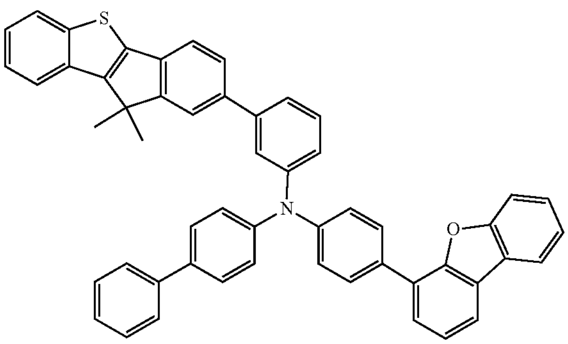
112
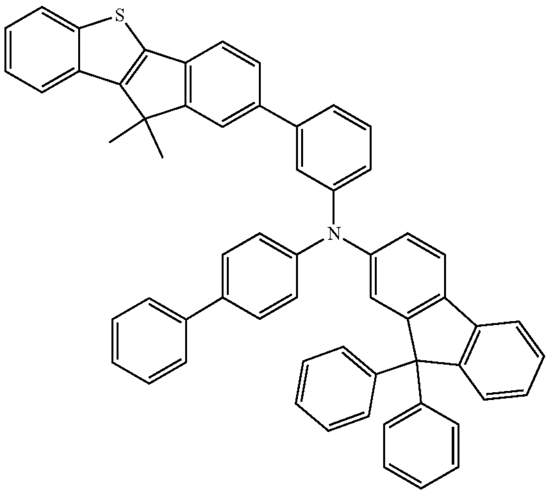

113
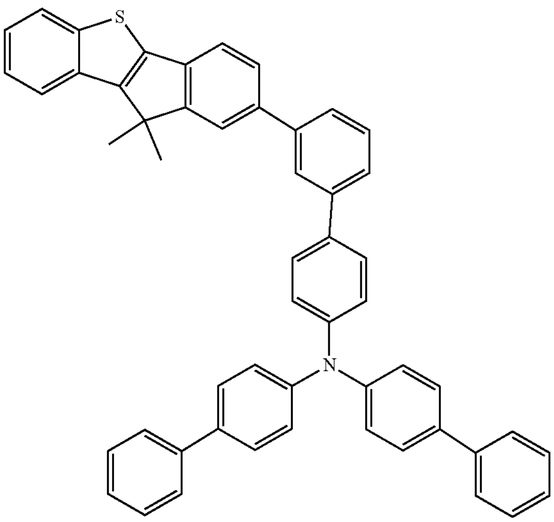
114
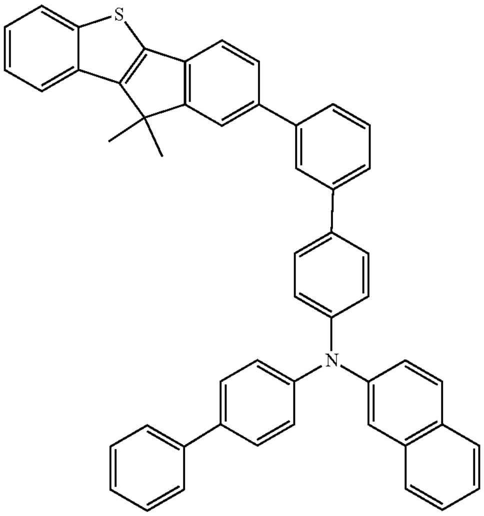
115
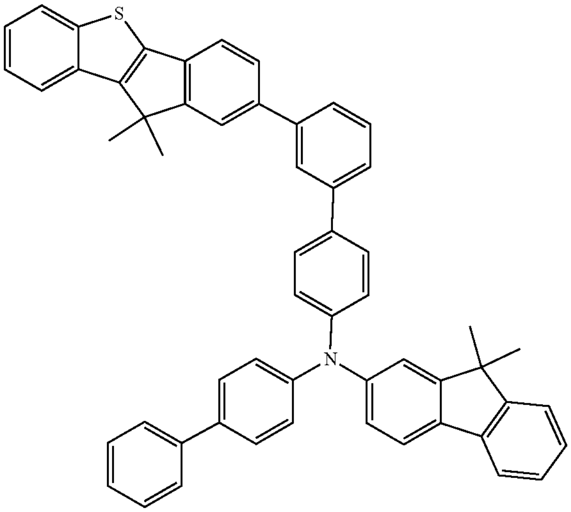
116
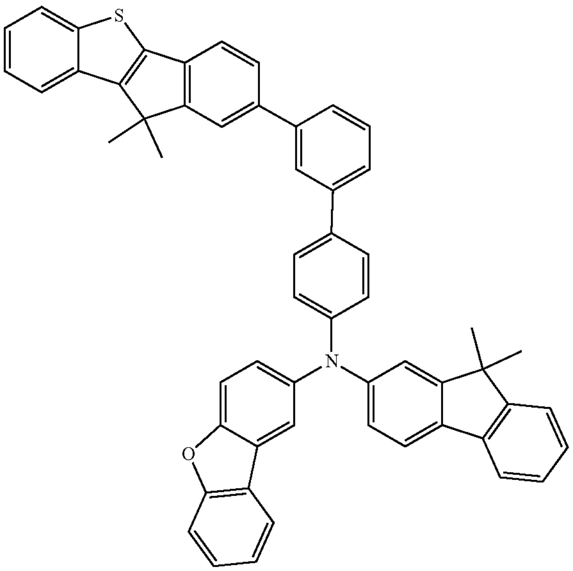
117
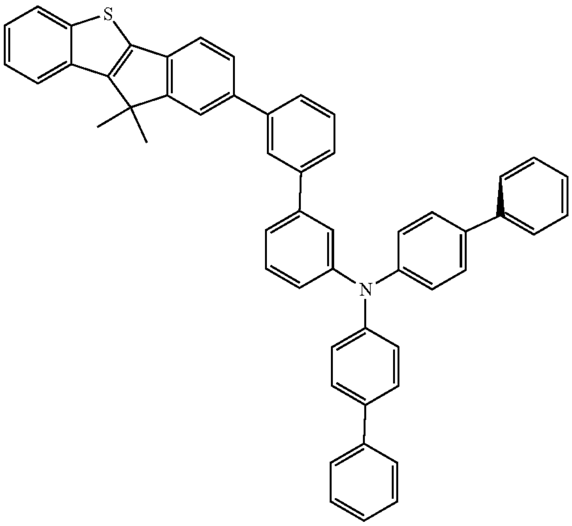

-continued
118
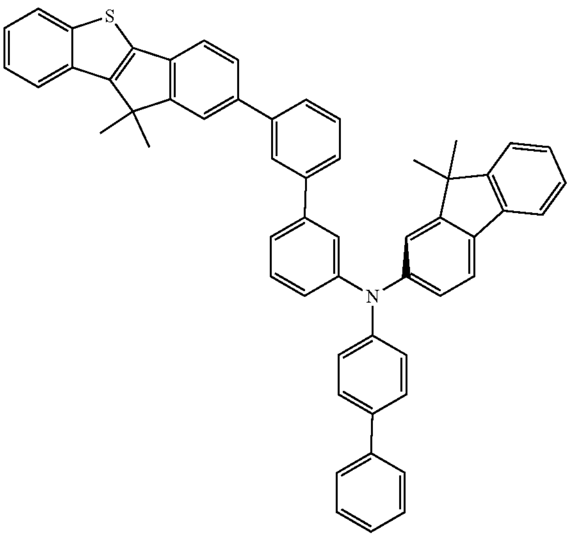
119
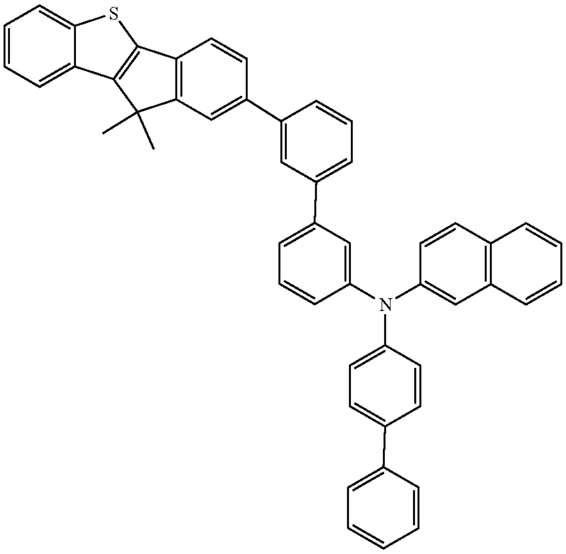
-continued
120
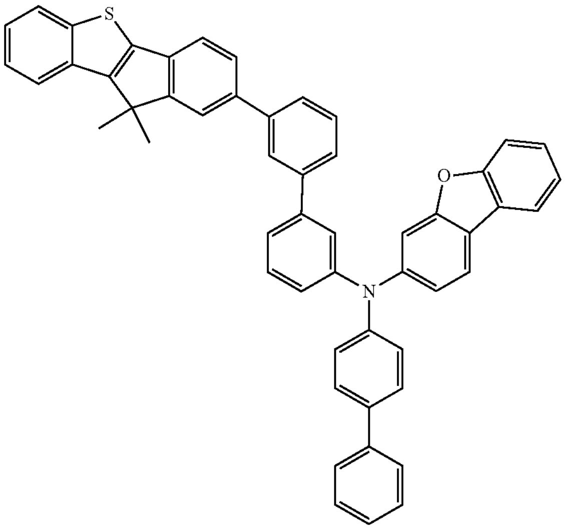
121
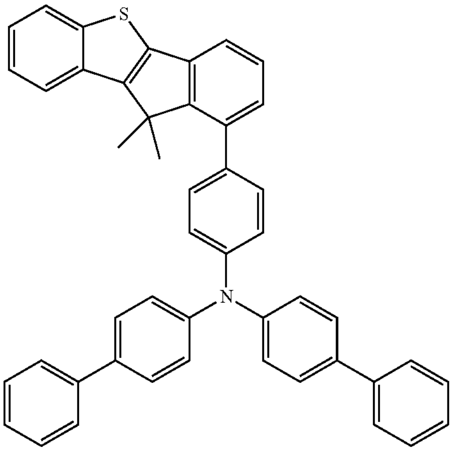
122
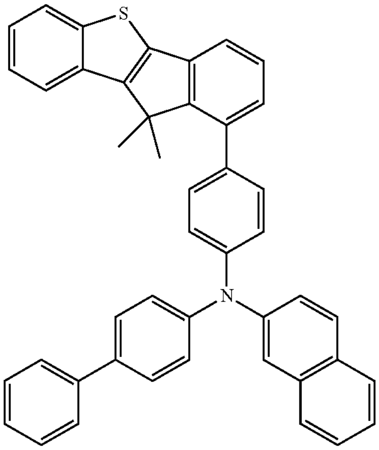

-continued
123
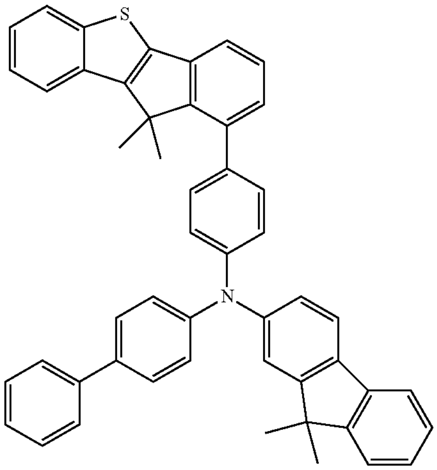
124
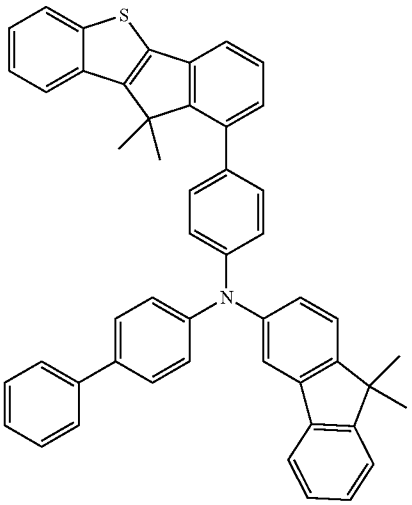
125
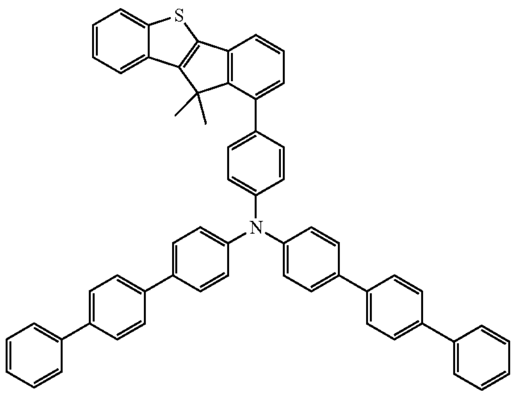
-continued
126
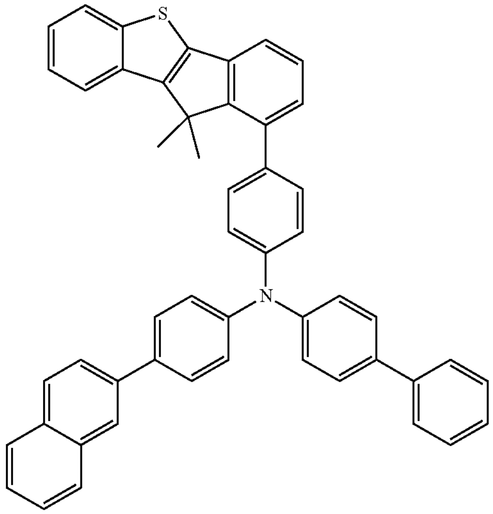
127
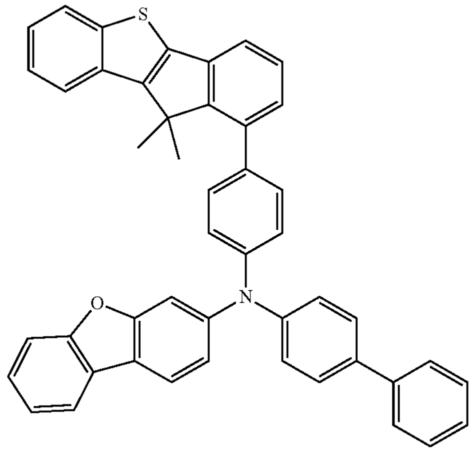
128
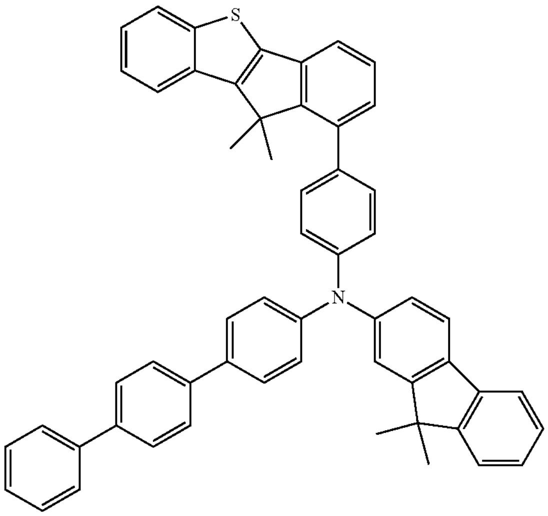

129
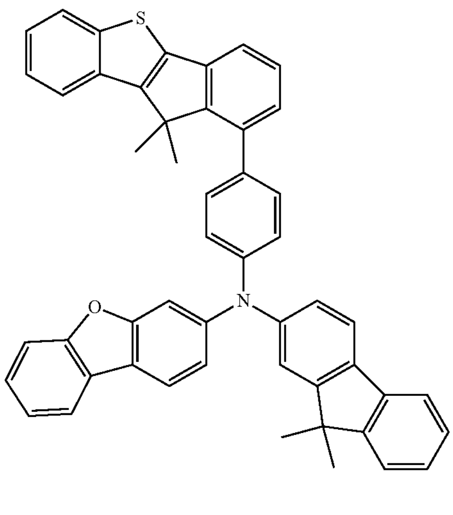
130
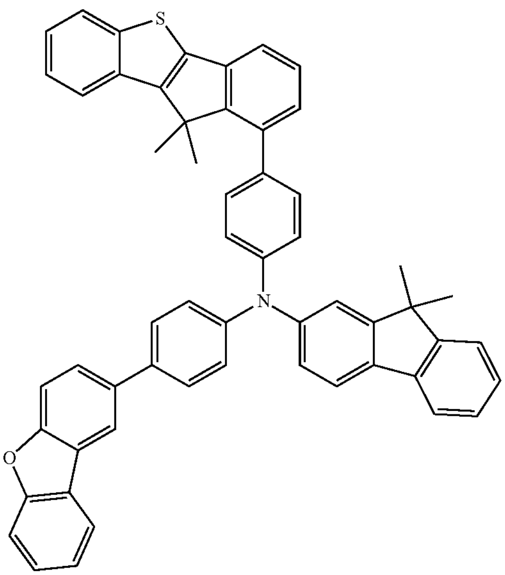
131
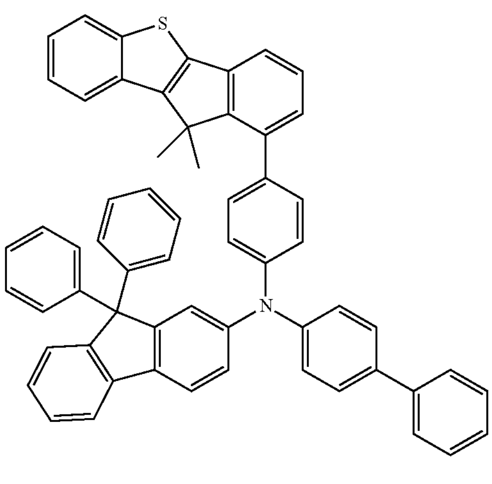
132
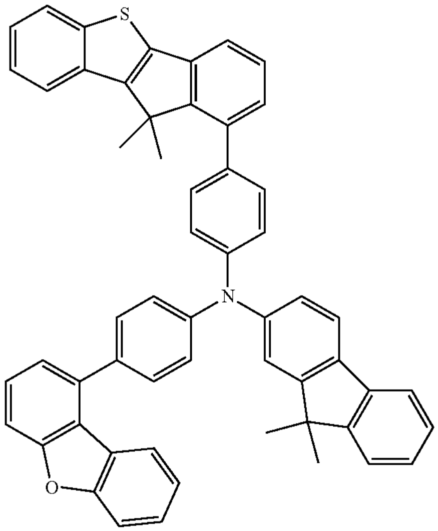
133
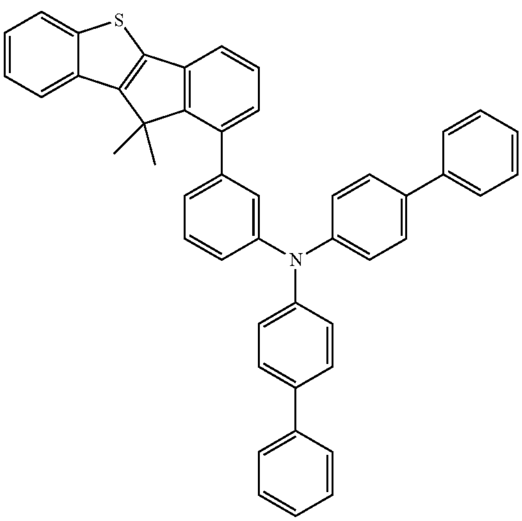
134
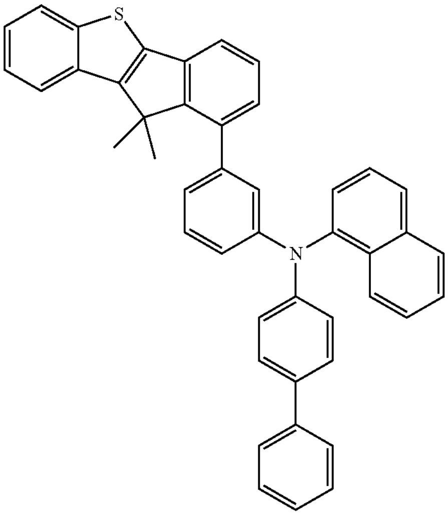

-continued
135
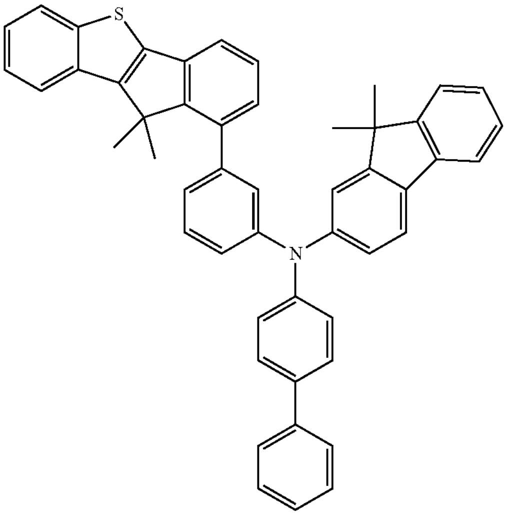
136
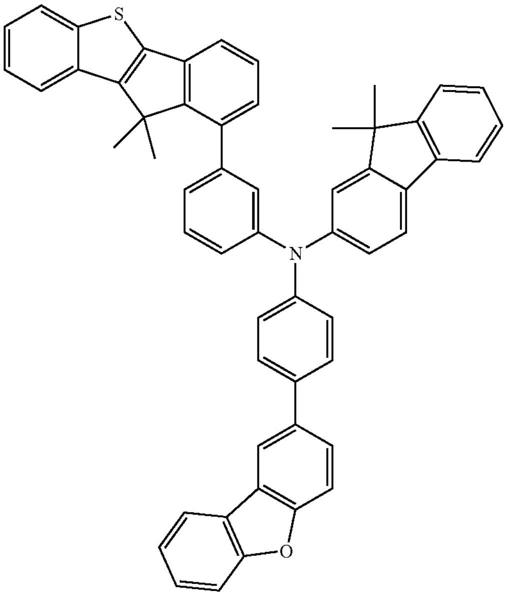
-continued
137
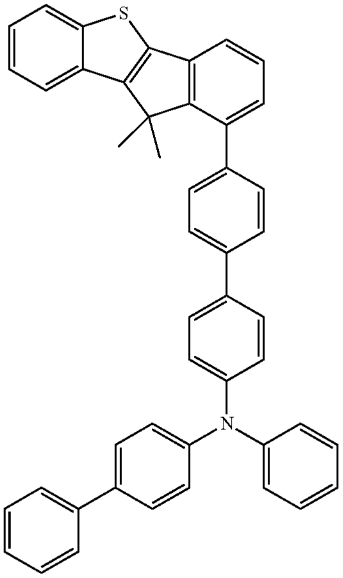
138
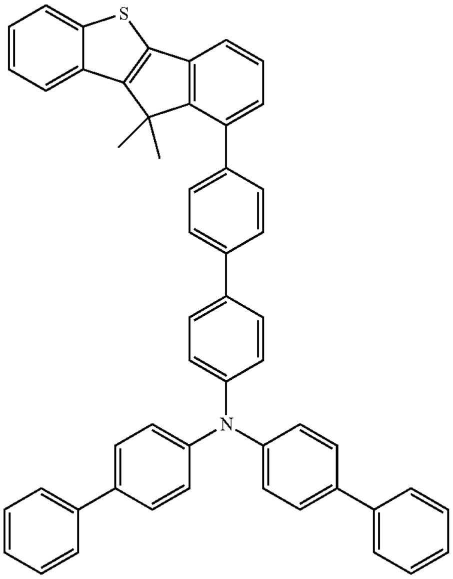

-continued
139
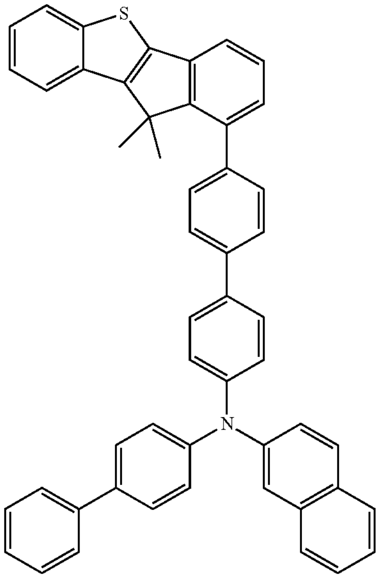
140
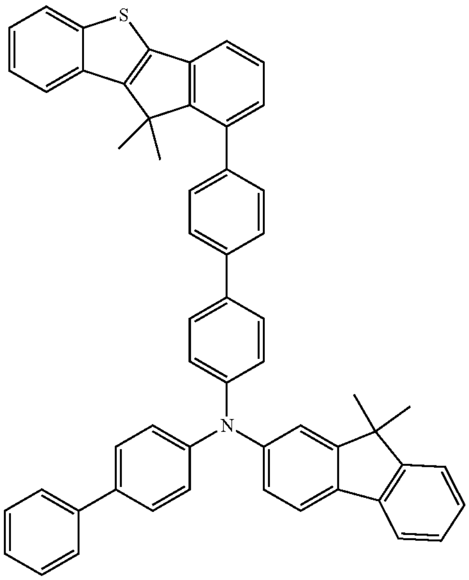
-continued
141
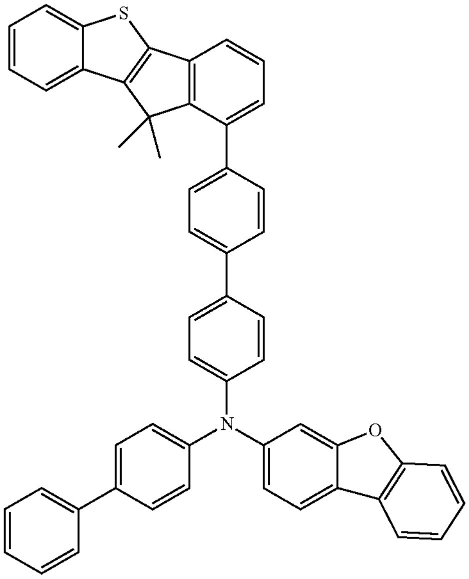
142
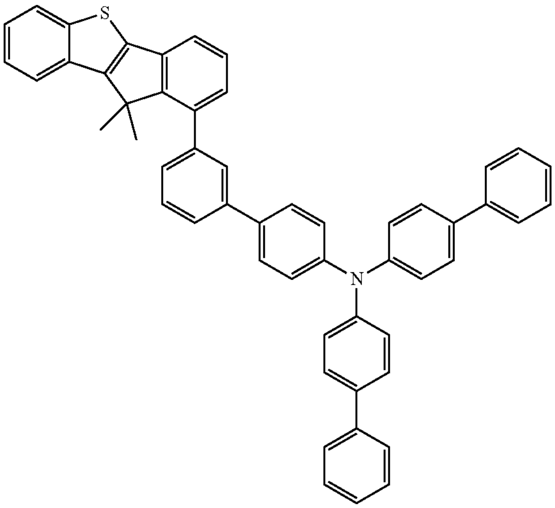
143
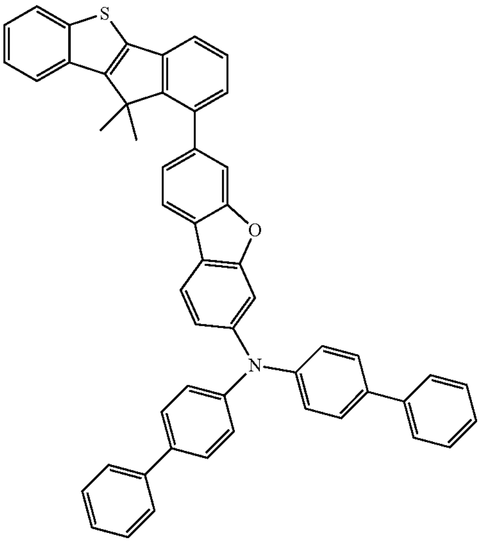

-continued
144
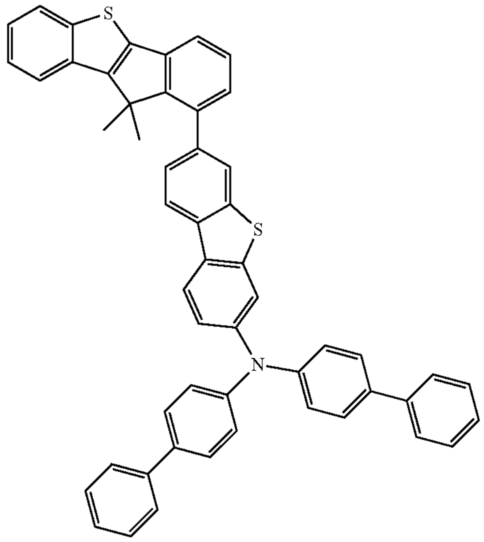
145
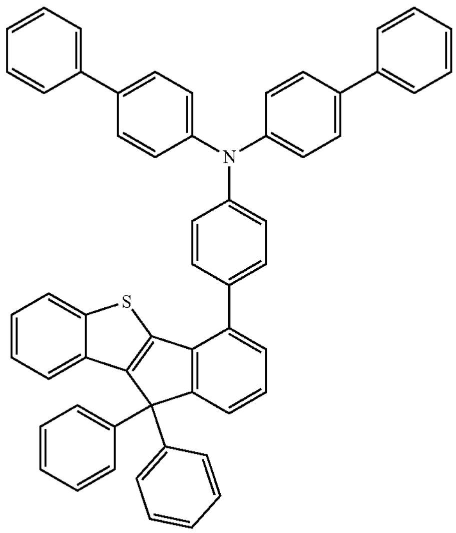
146
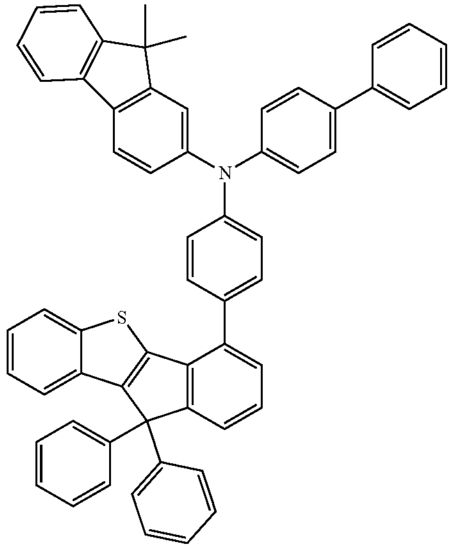
-continued
147
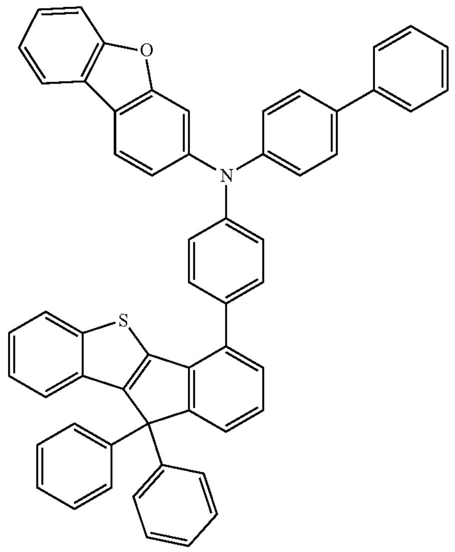
148
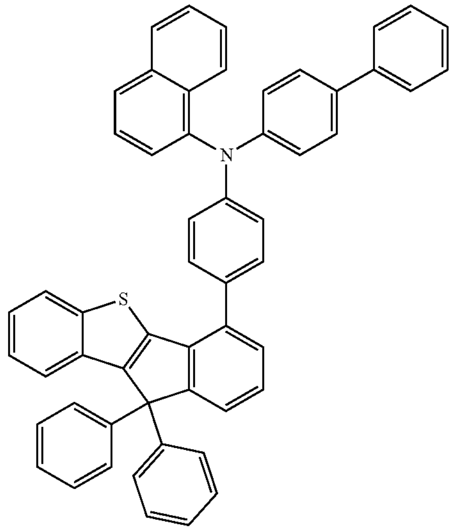
149
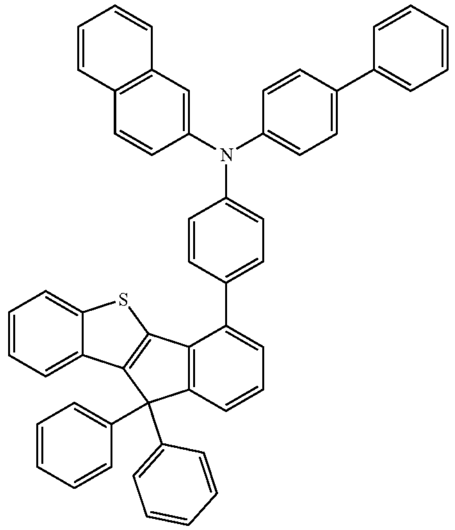

-continued
150
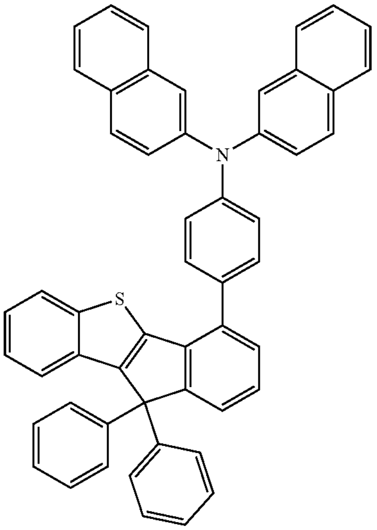
151
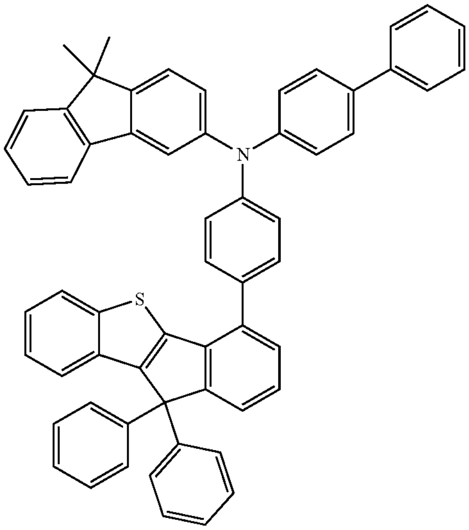
152
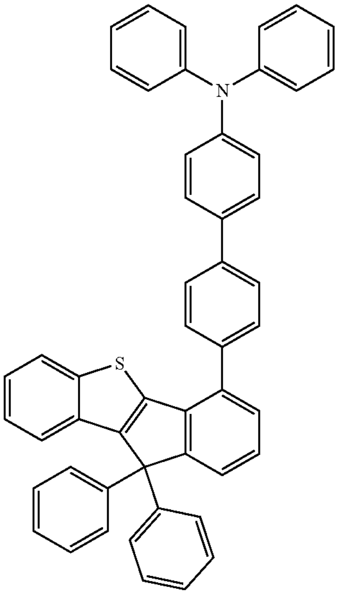
-continued
153
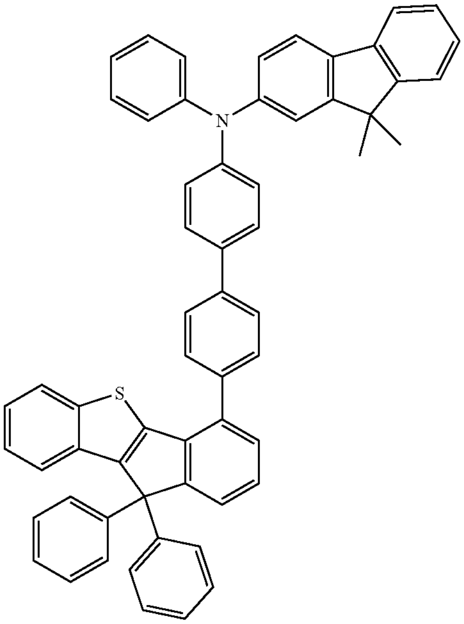
154
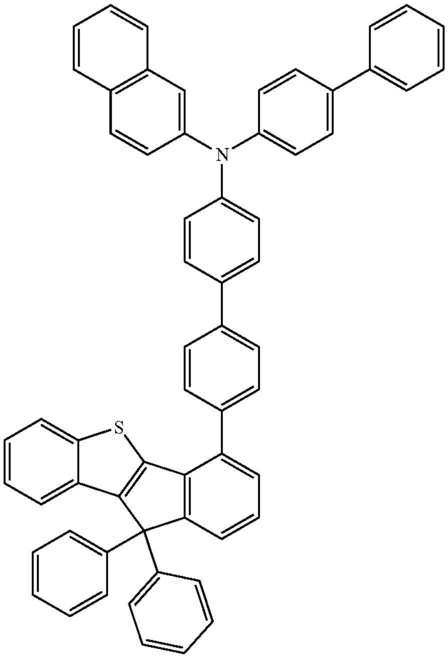

-continued
155
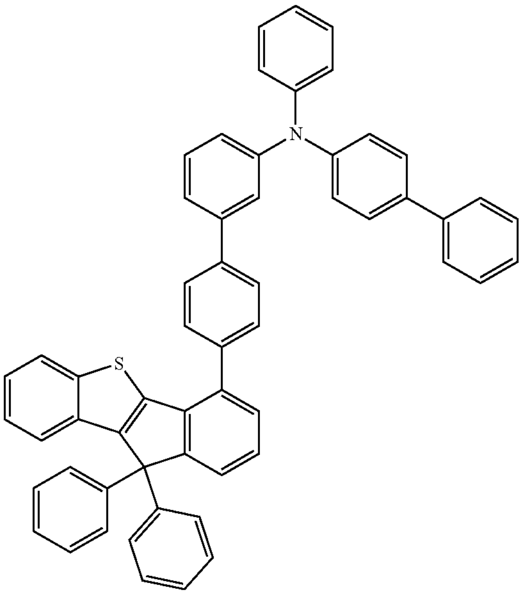
156
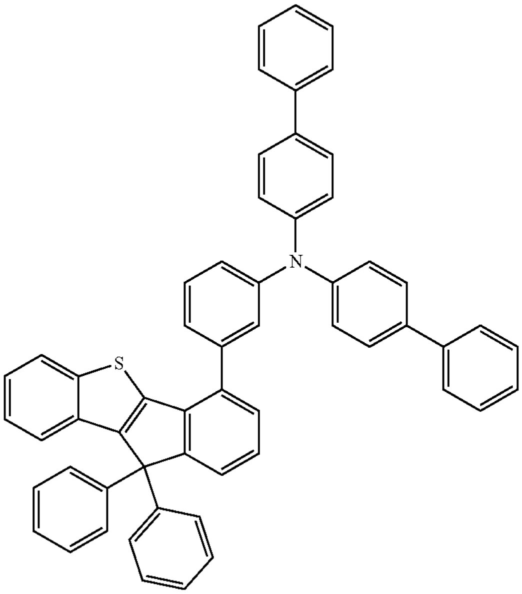
-continued
157
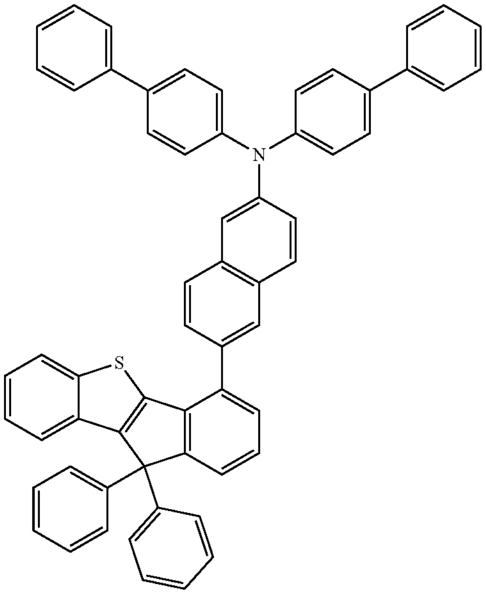
158
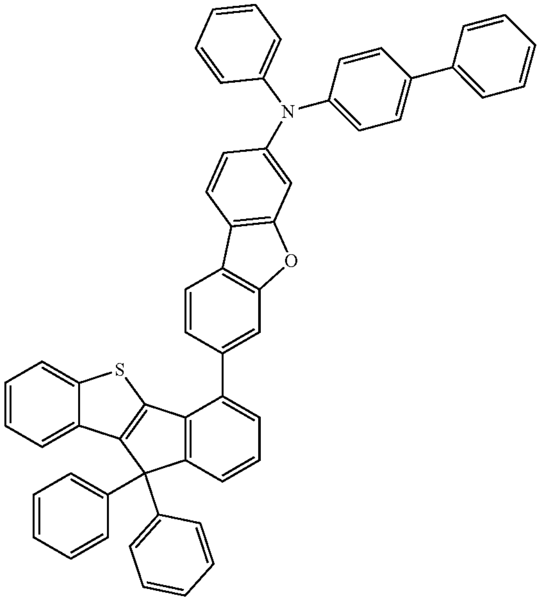

-continued
159
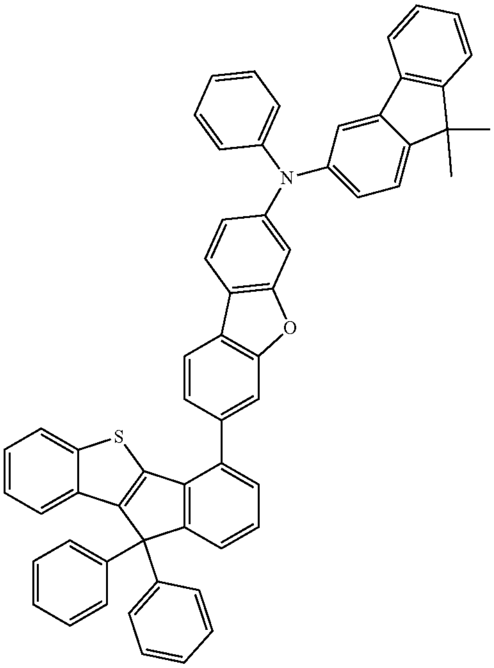
160
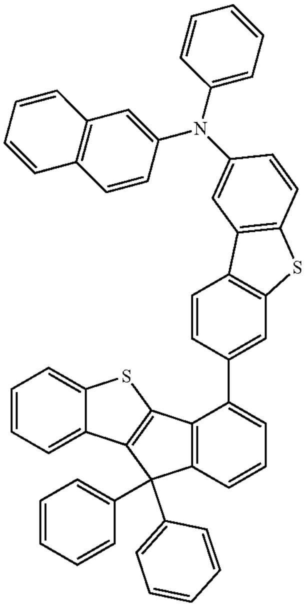
-continued
161
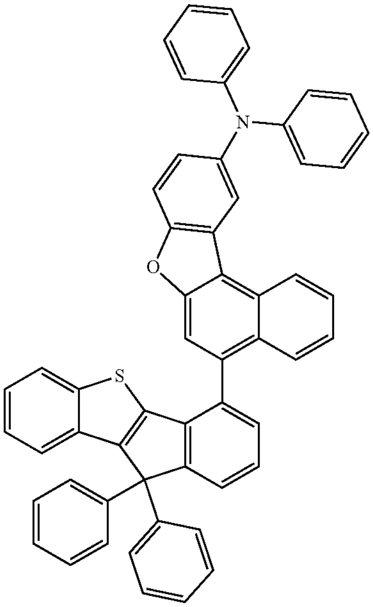
162
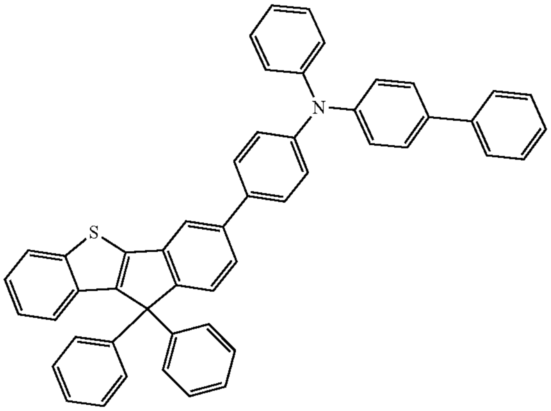
163
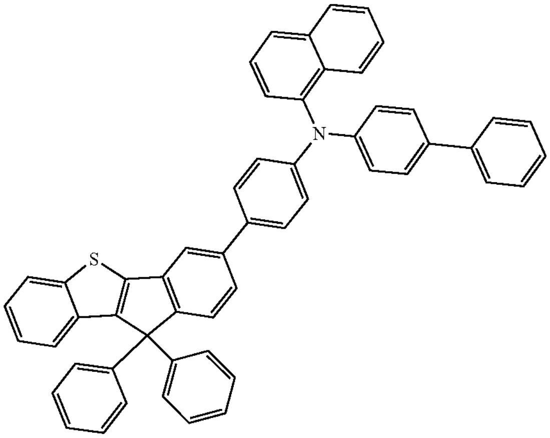

-continued
164
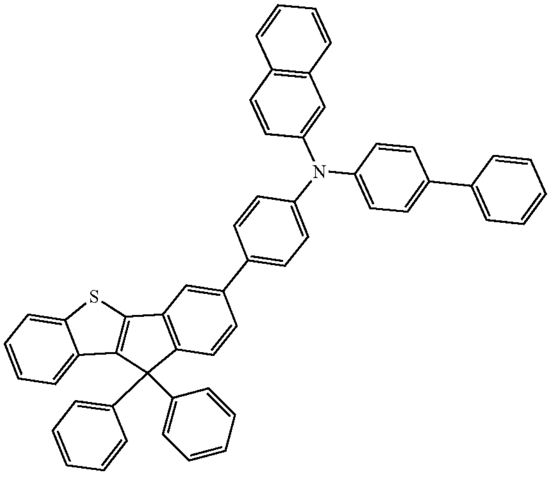
165
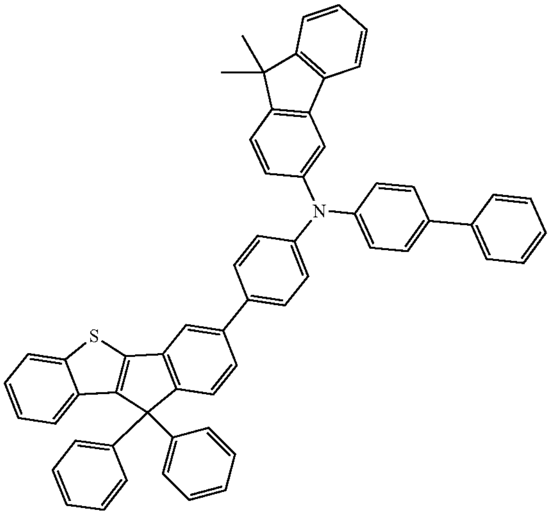
166
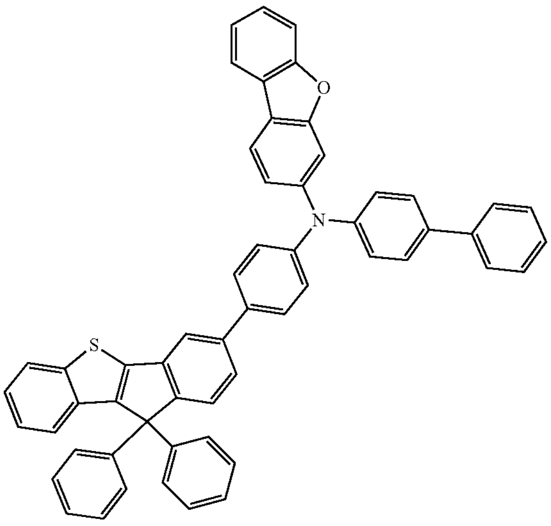
-continued
167
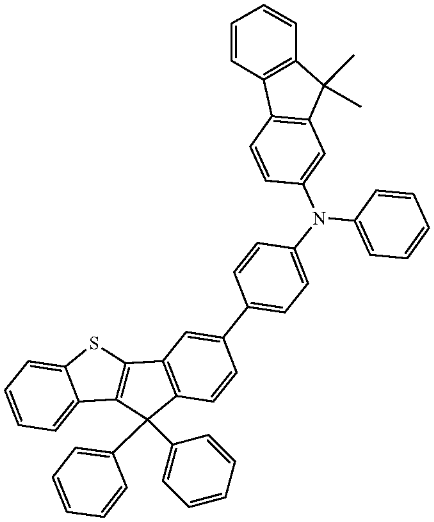
168
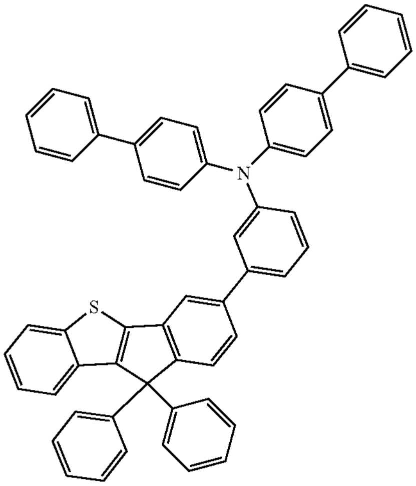
169
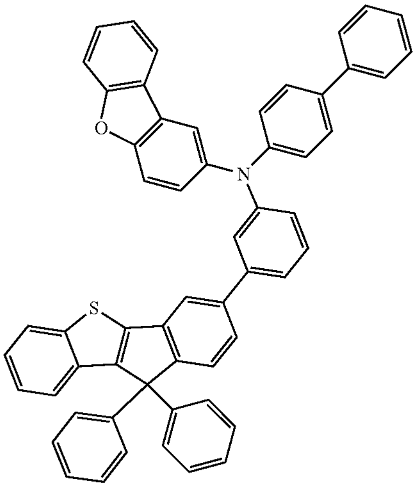

-continued
170
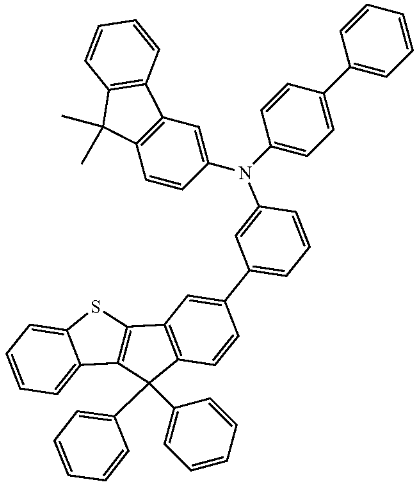
171
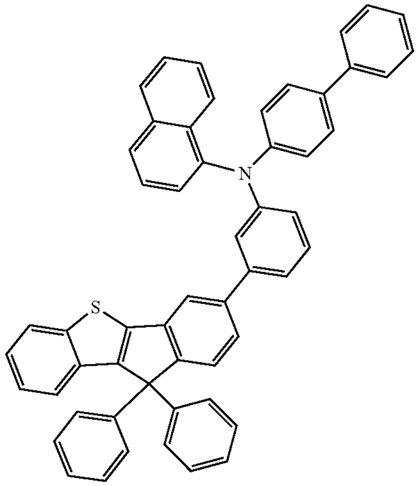
172
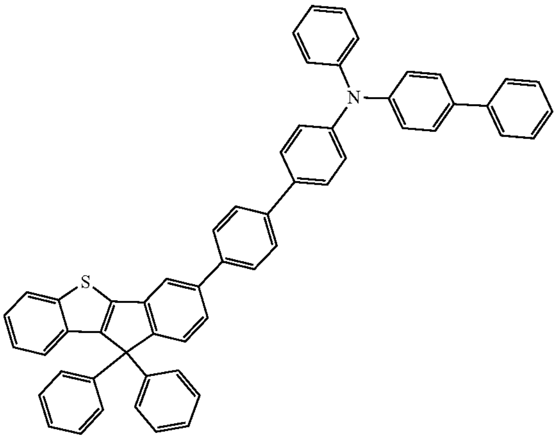
-continued
173
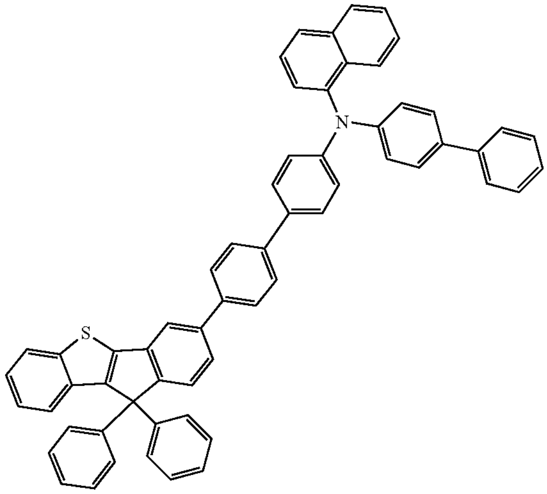
174
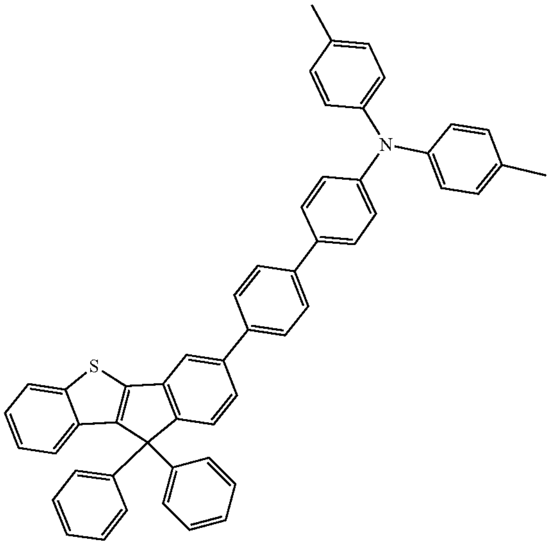
175
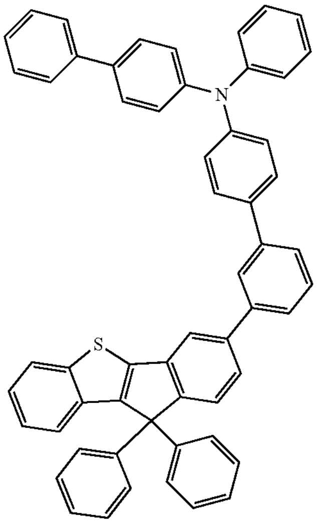

-continued
176
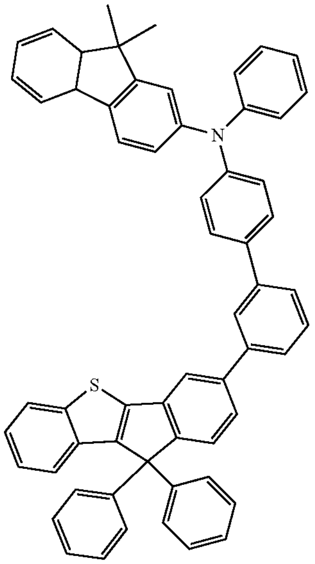
177
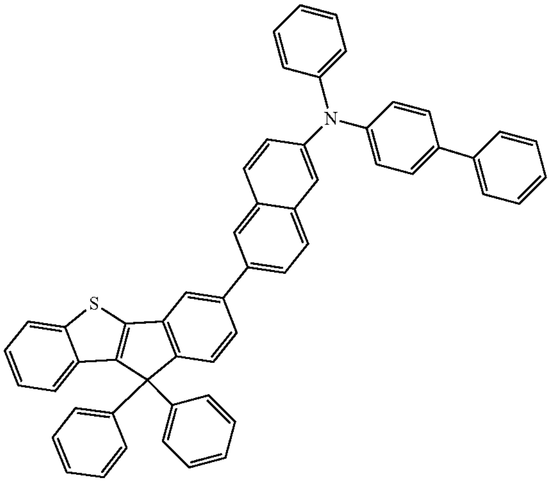
178
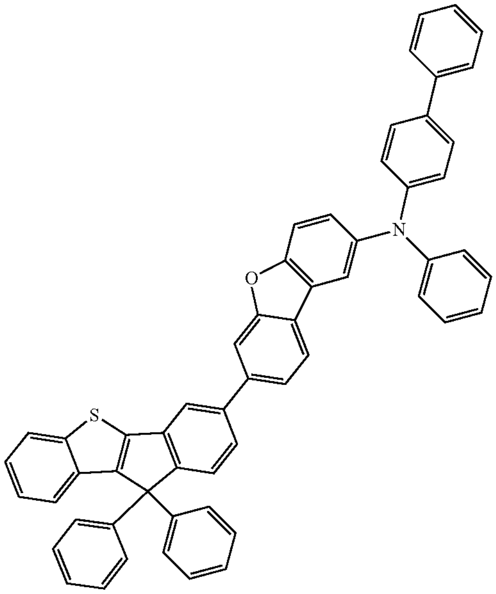
-continued
179
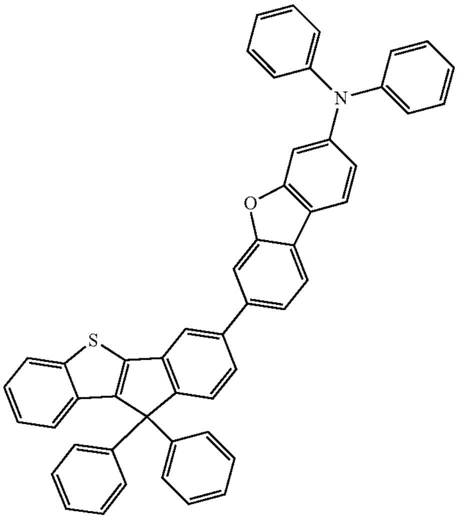
180
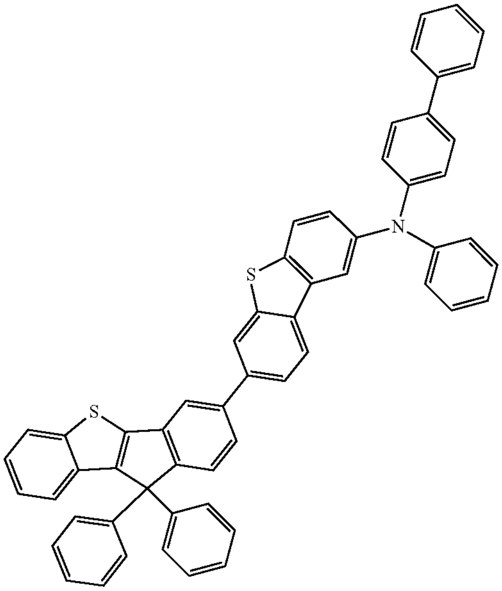
181
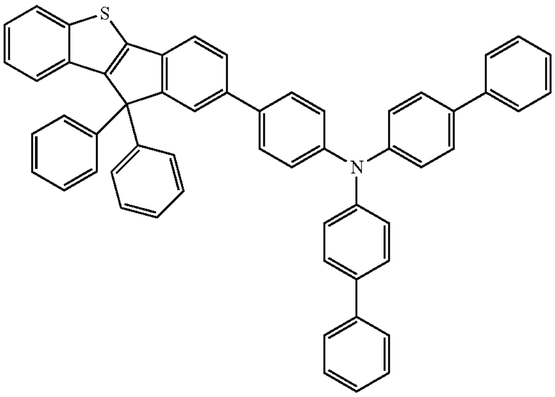

-continued
182
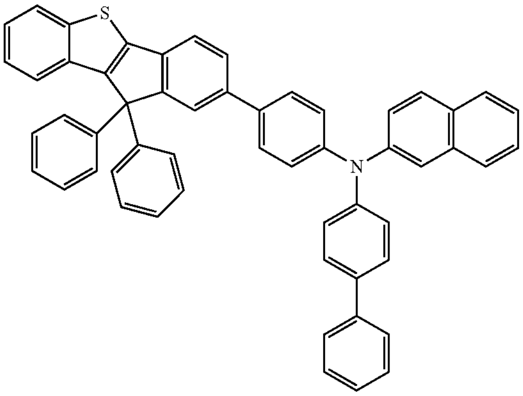
183
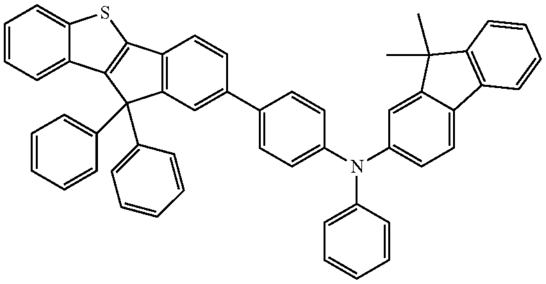
184
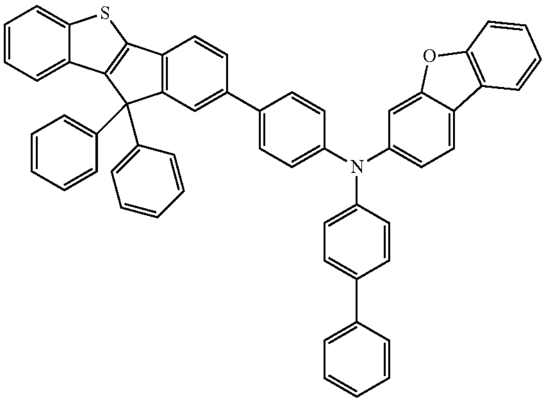
185
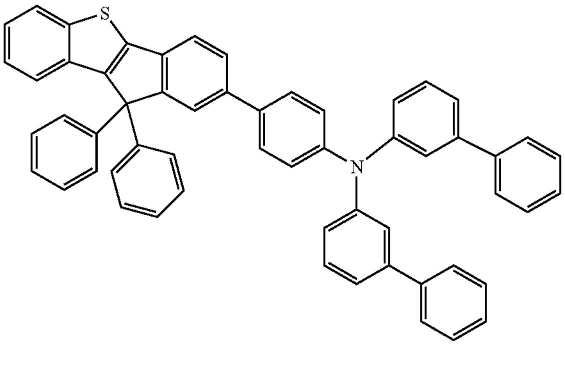
-continued
186
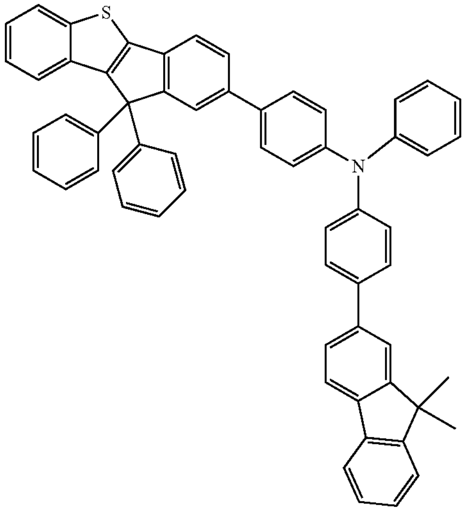
187
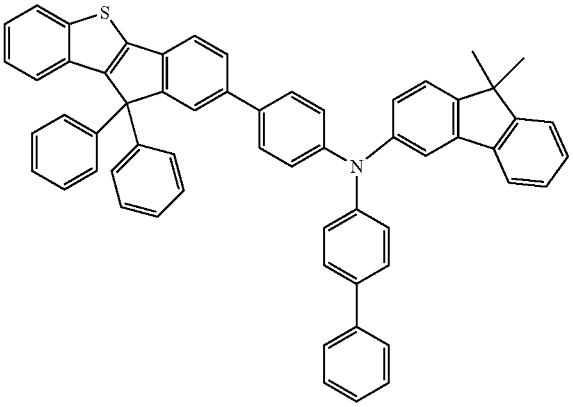
188
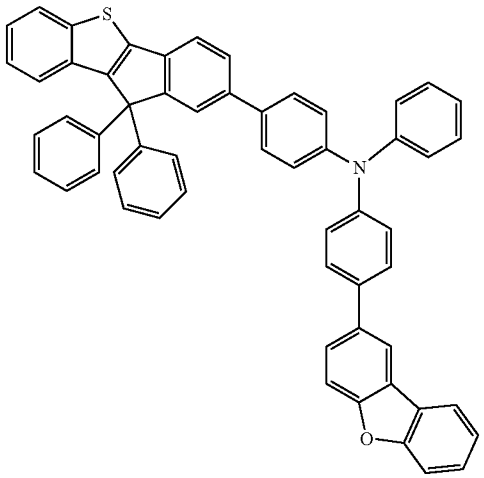

-continued
189
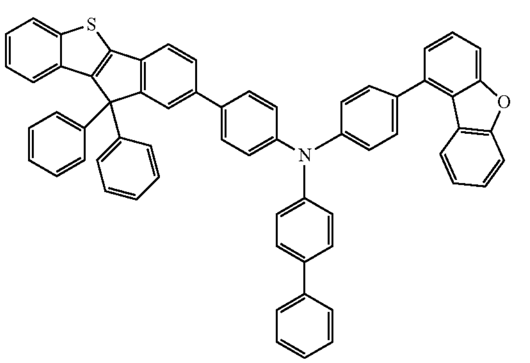
190
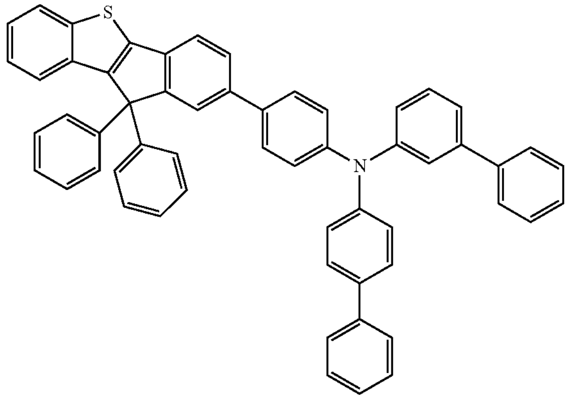
191
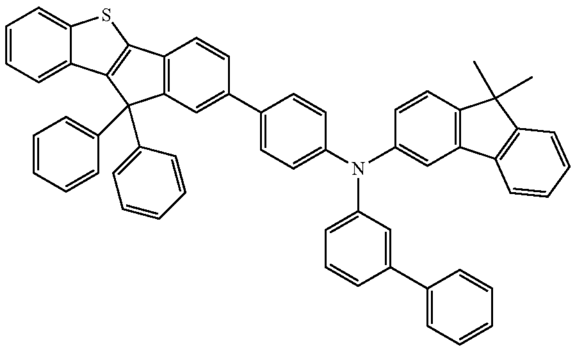
192
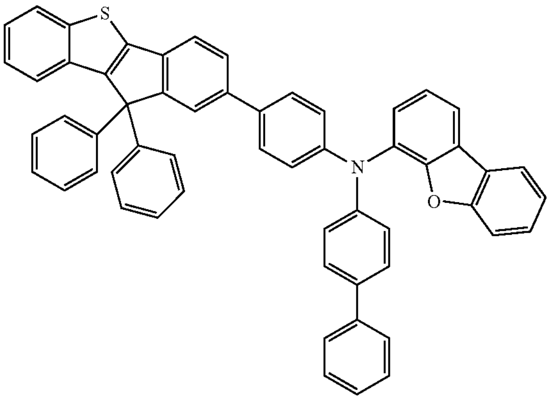
-continued
193
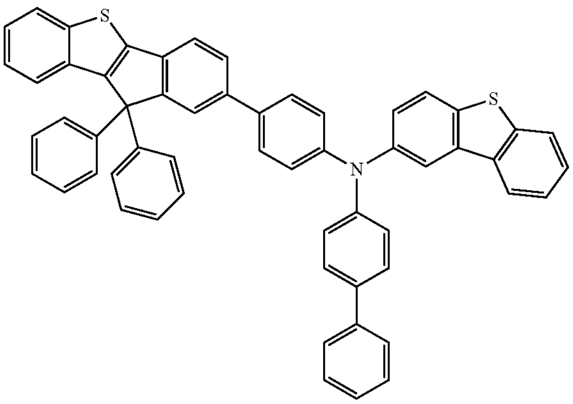
194
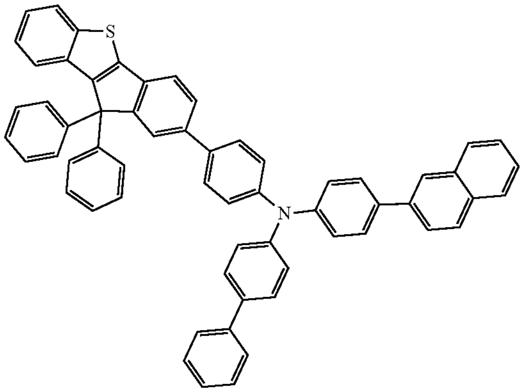
195
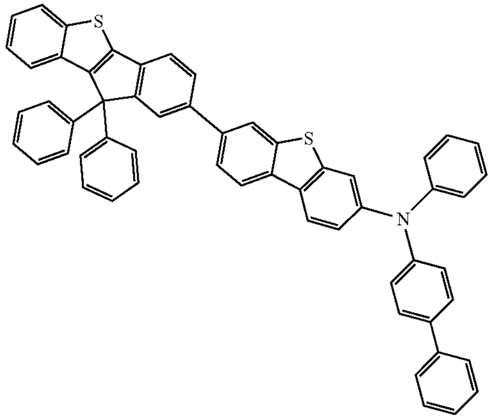
196
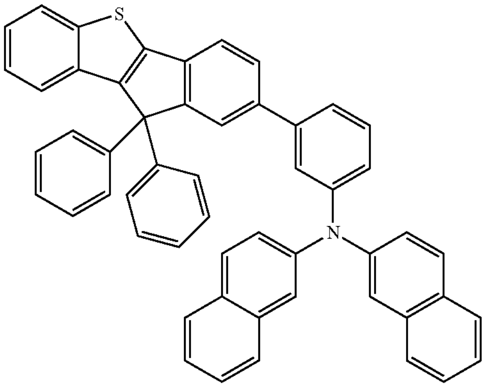

197
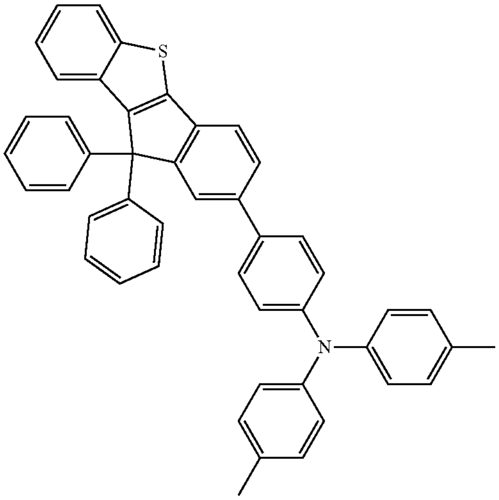
198
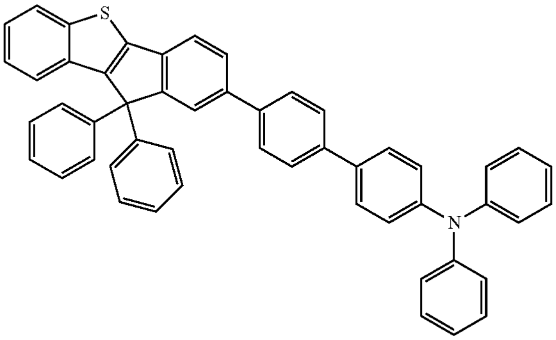
199
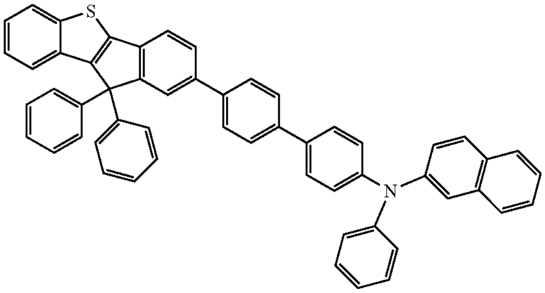
200
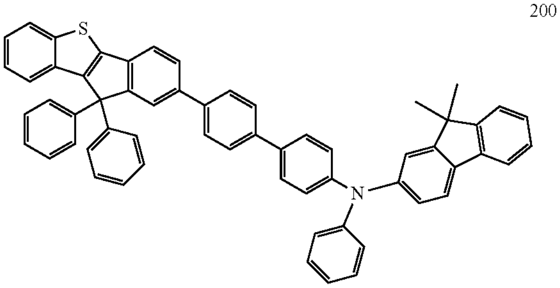
201
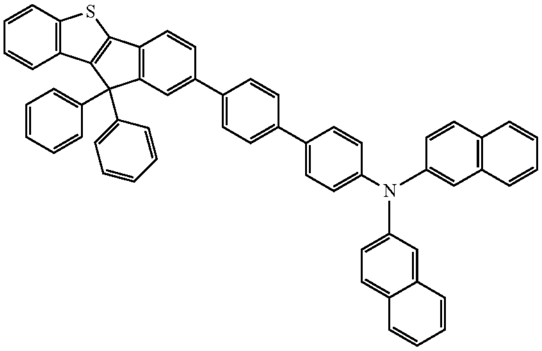
202
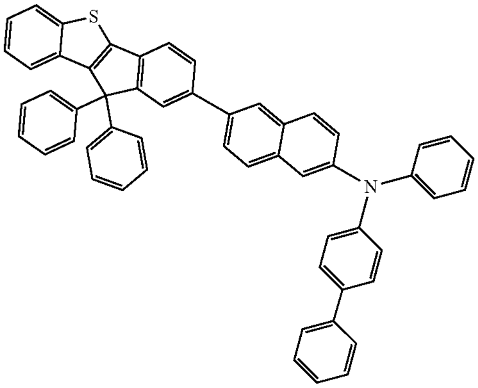
203
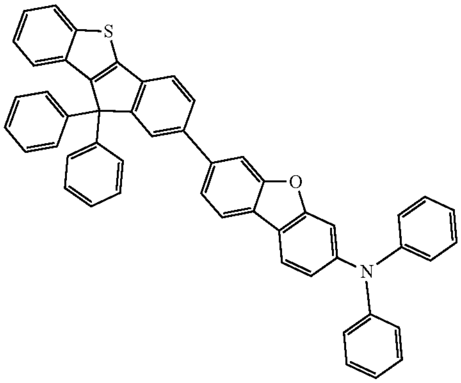
204
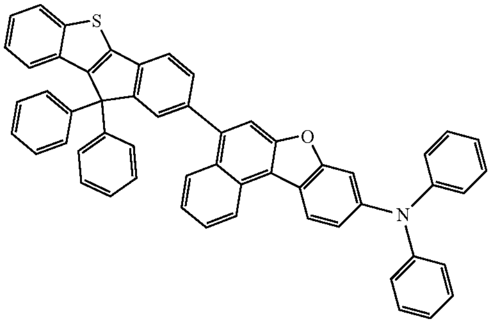

-continued
205
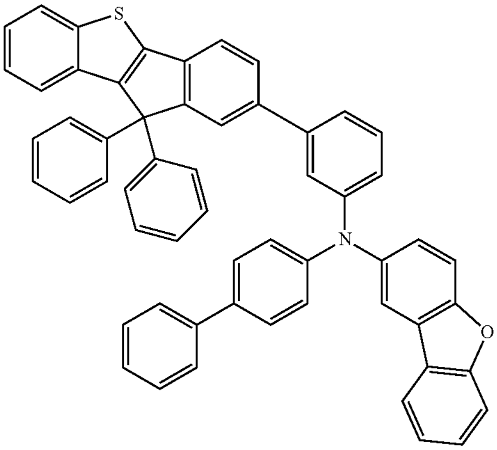
206
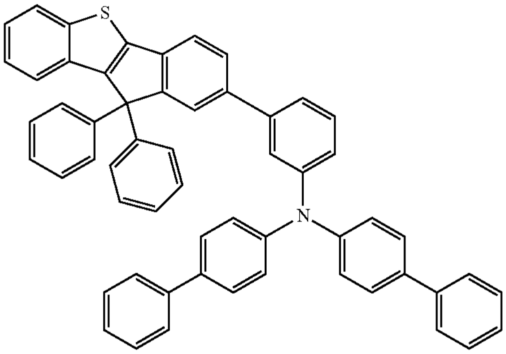
207
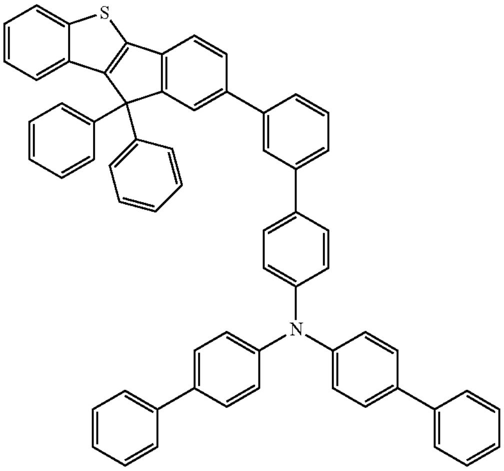
-continued
208
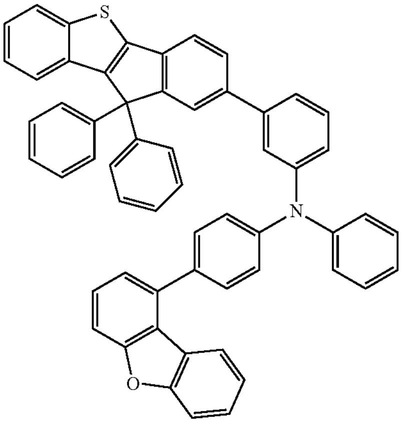
209
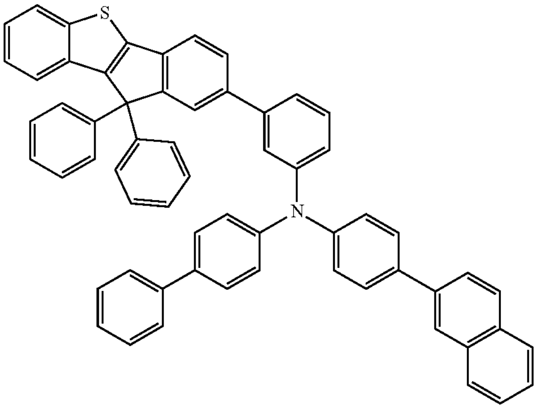
210
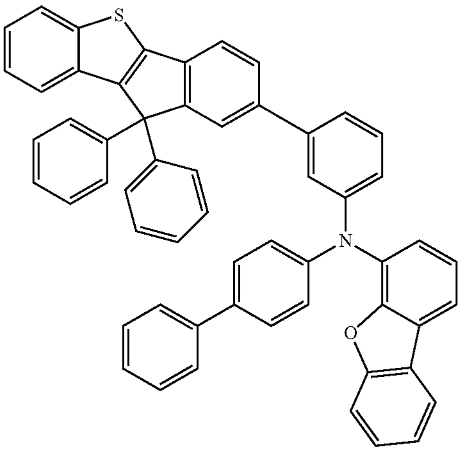

-continued
211
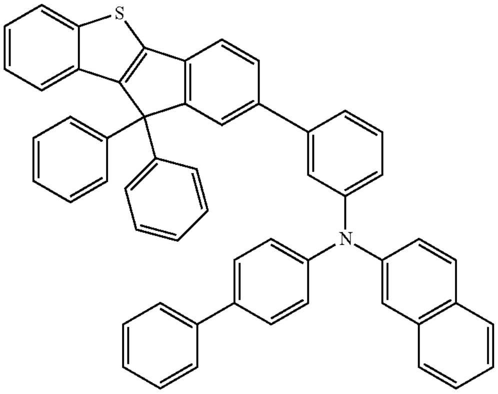
212
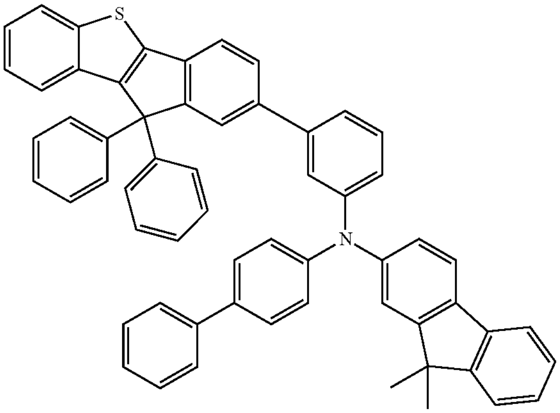
213
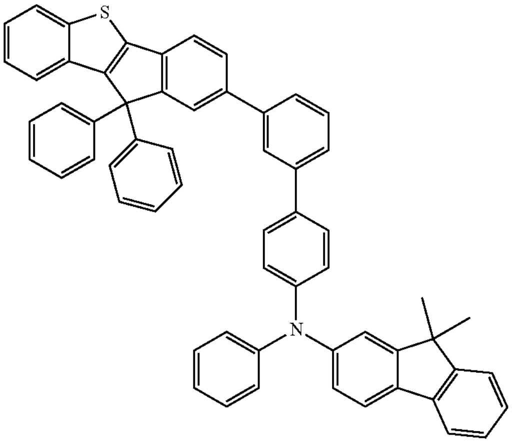
-continued
214
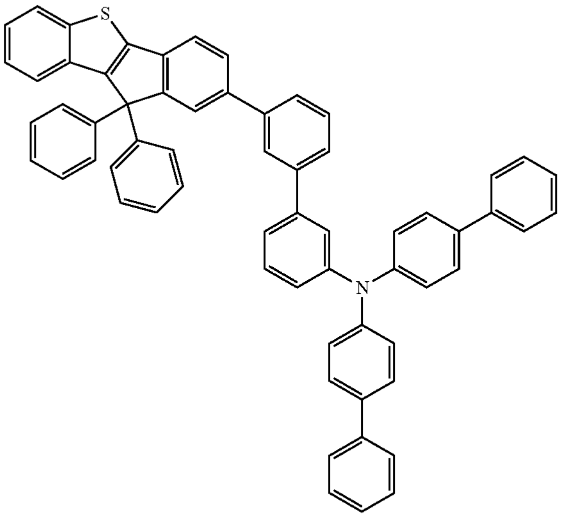
215
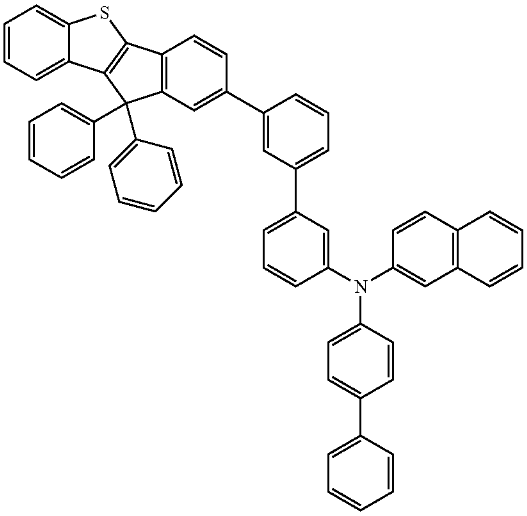
216
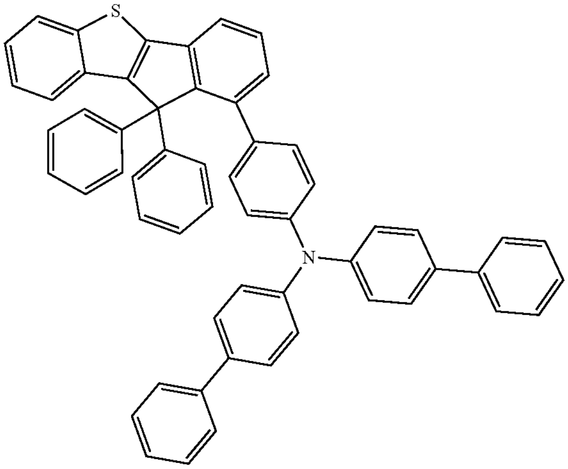

-continued
217
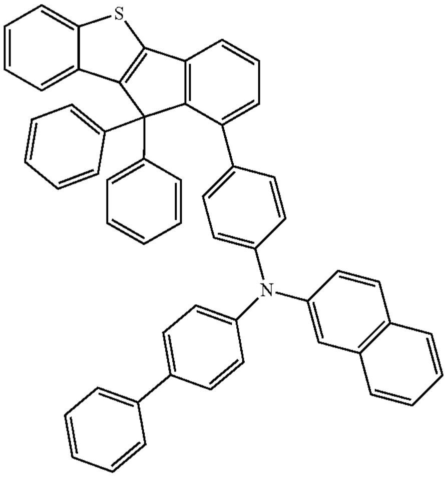
218
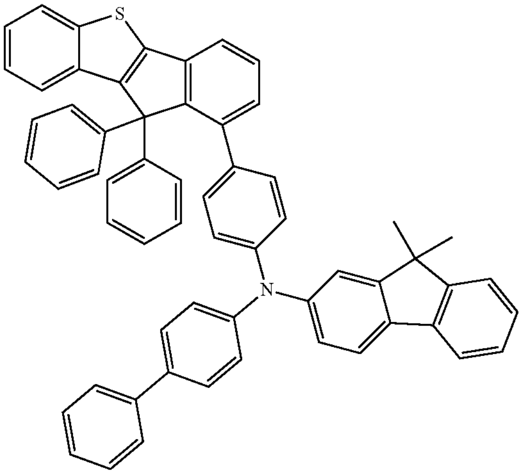
219
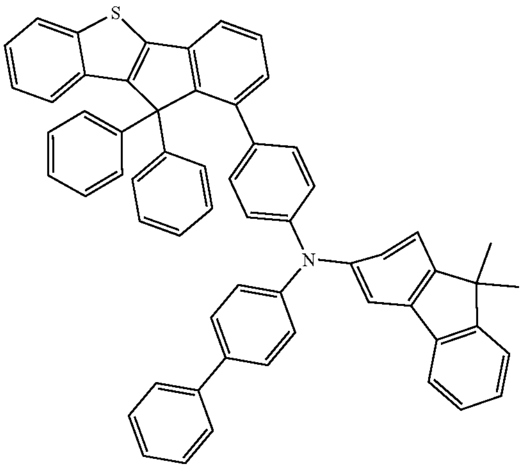
-continued
220
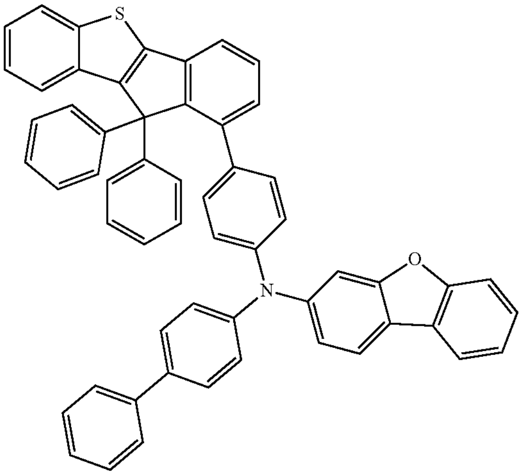
221
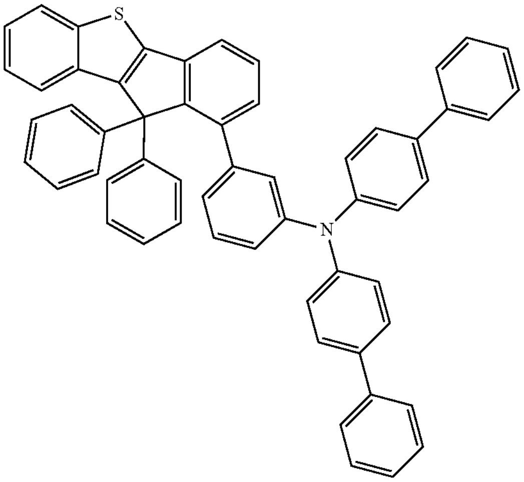
222
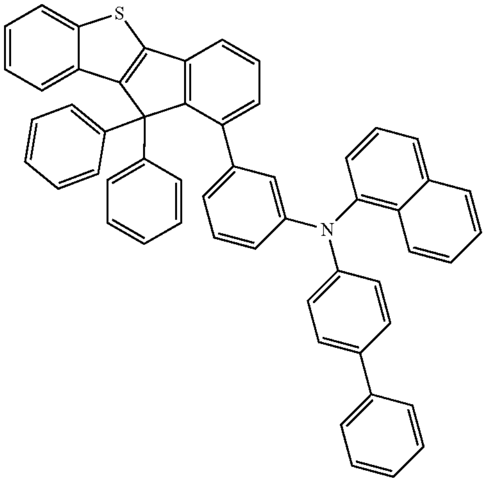

-continued
223
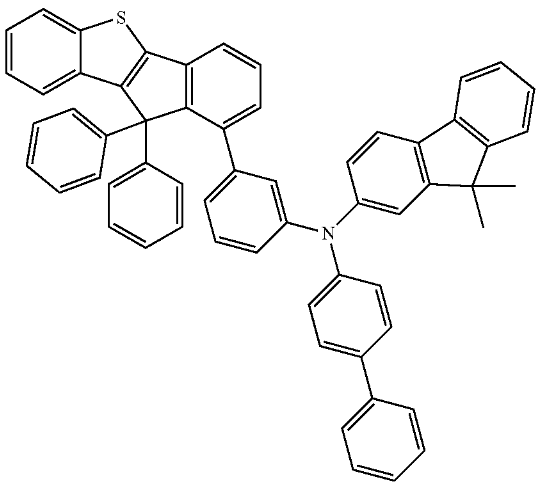
224
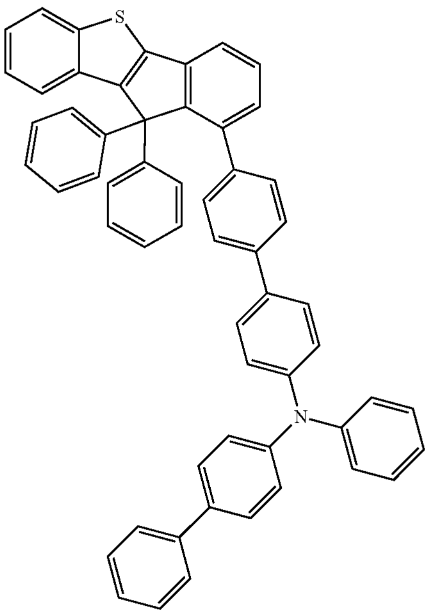
225
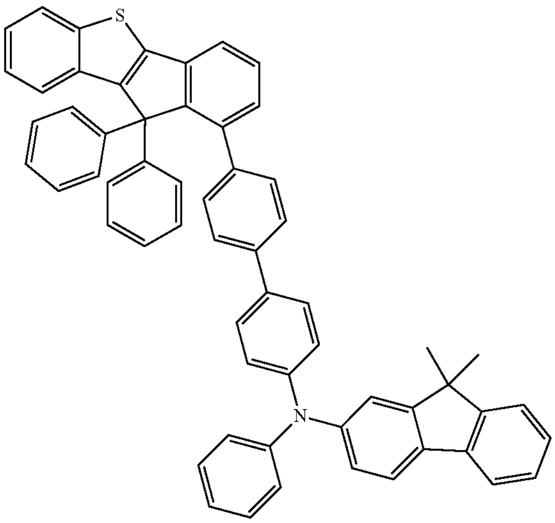
-continued
226
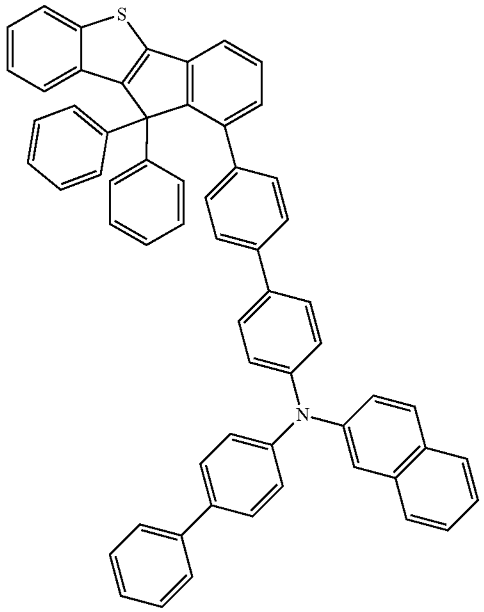
227
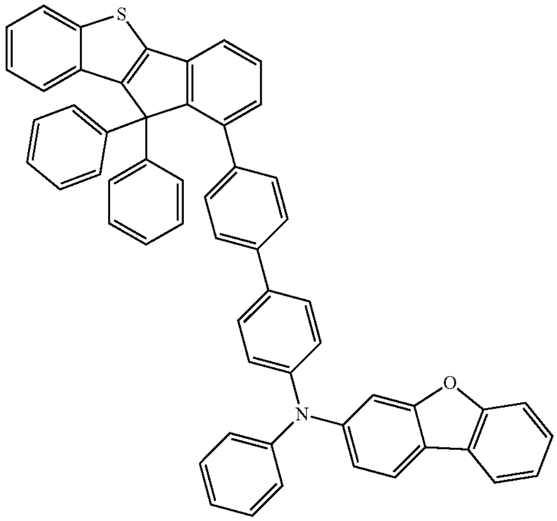

-continued
228
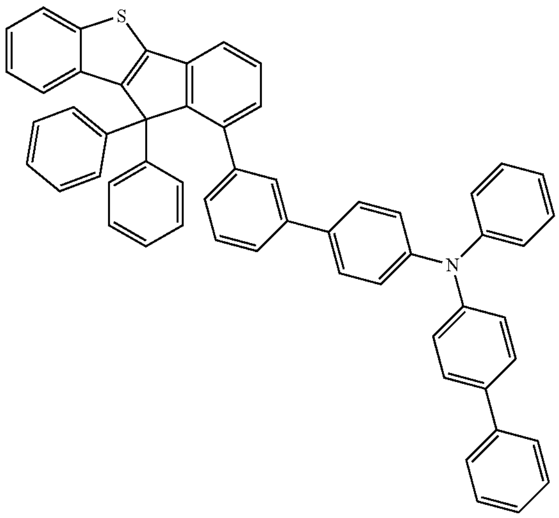
229
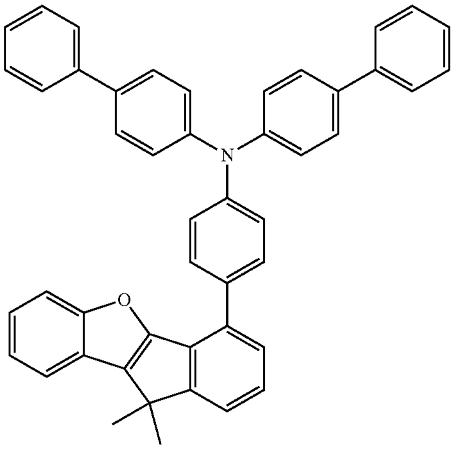
230
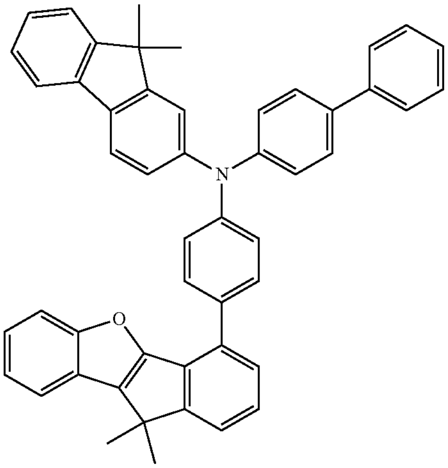
-continued
231
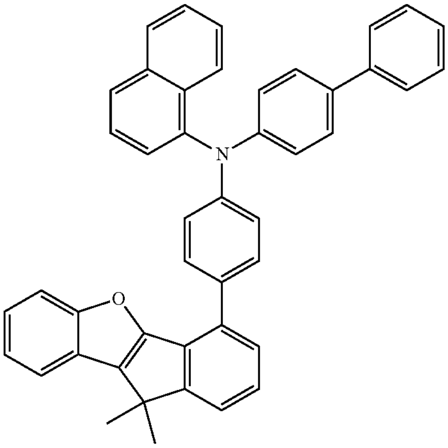
232
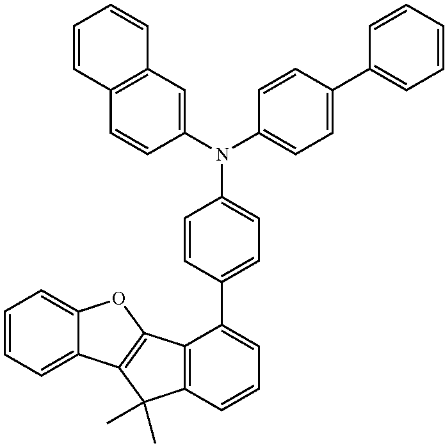
233
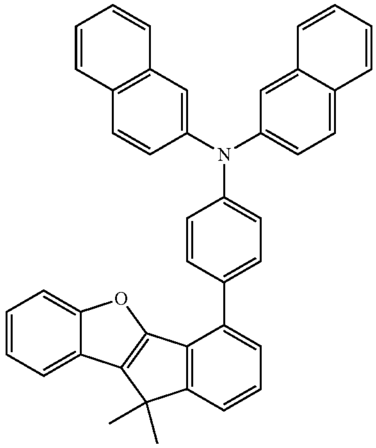

-continued
234
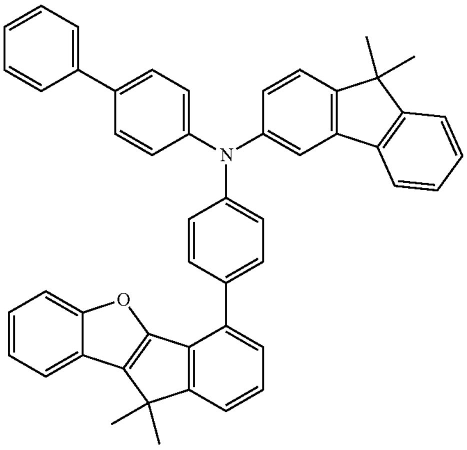
235
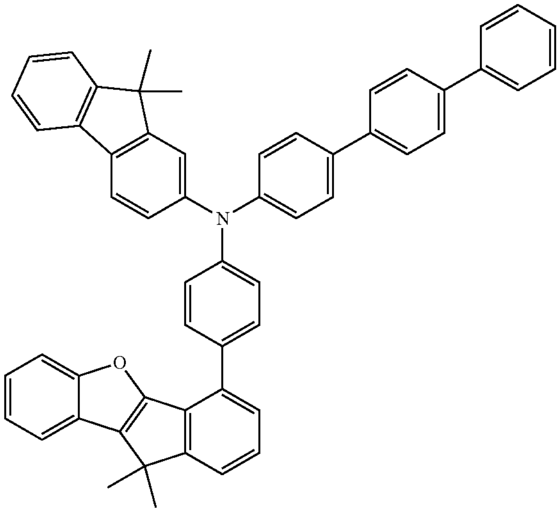
236
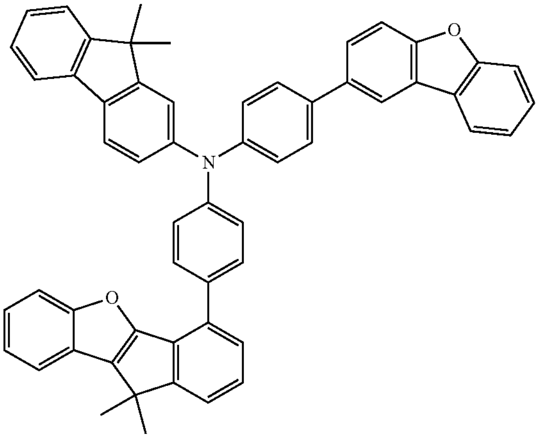
-continued
237
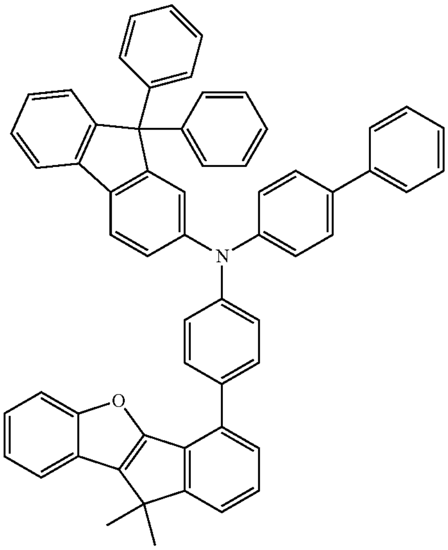
238
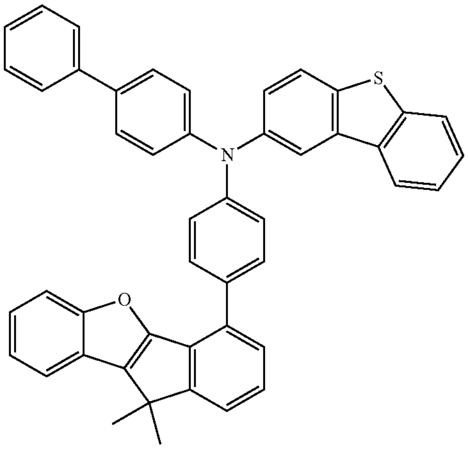
239
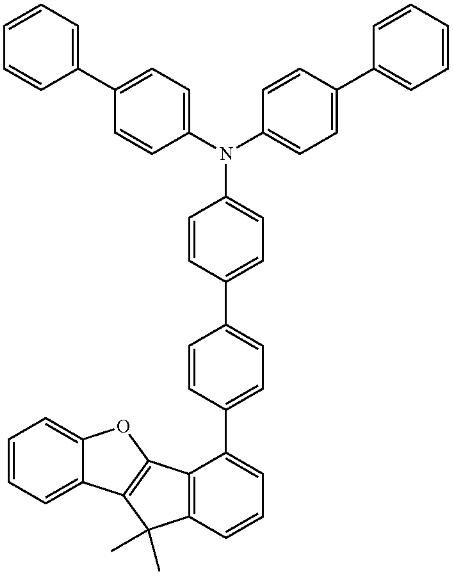

240
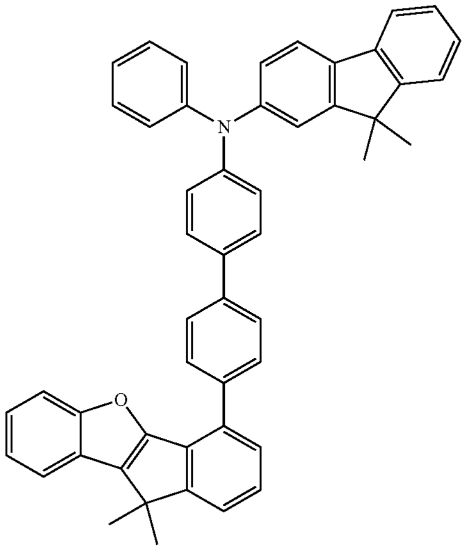
241
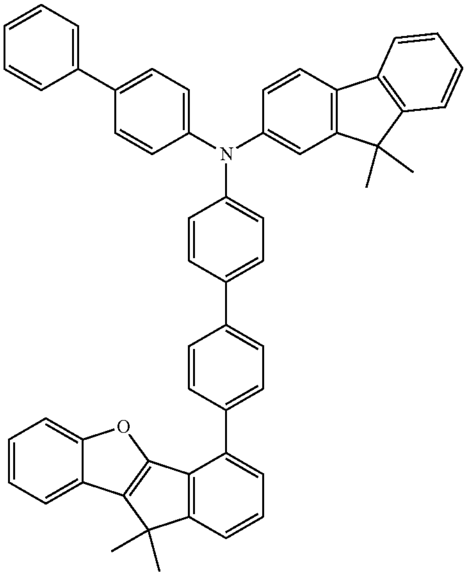
242
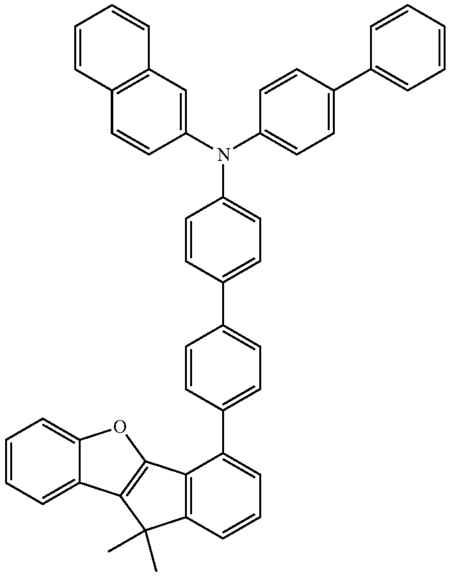
243
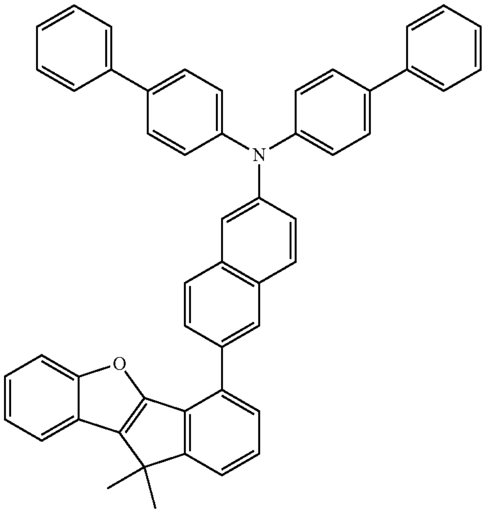
244
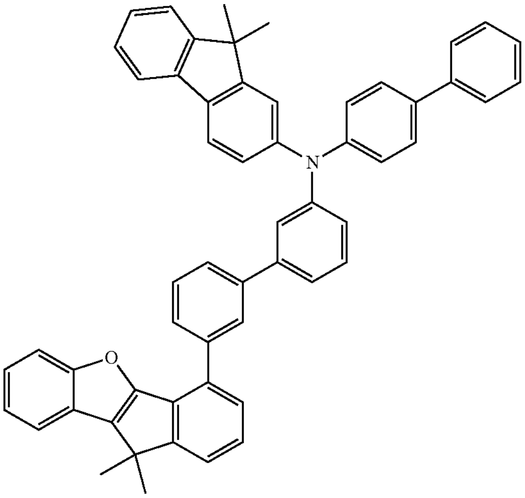

-continued
245
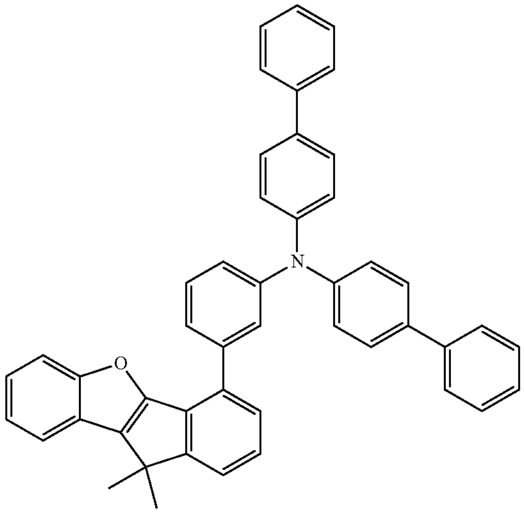
246
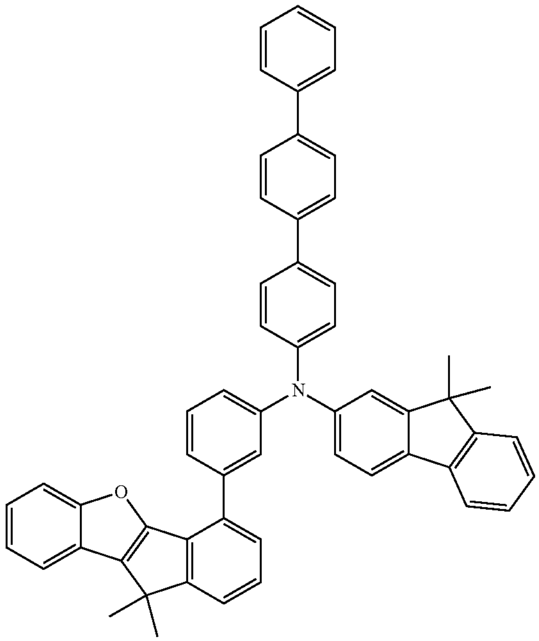
247
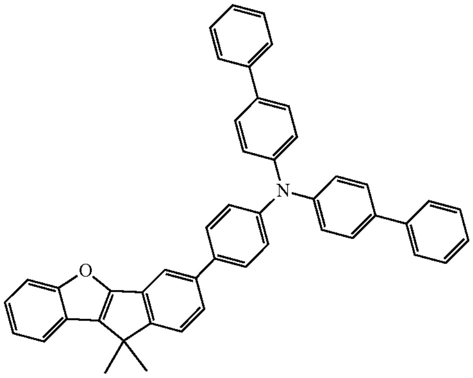
-continued
248
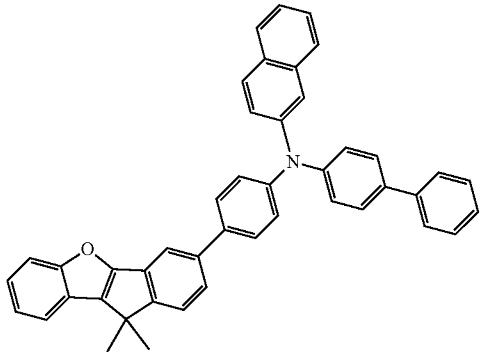
249
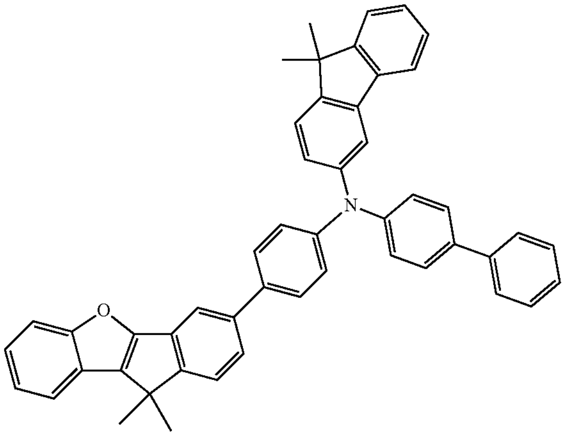
250
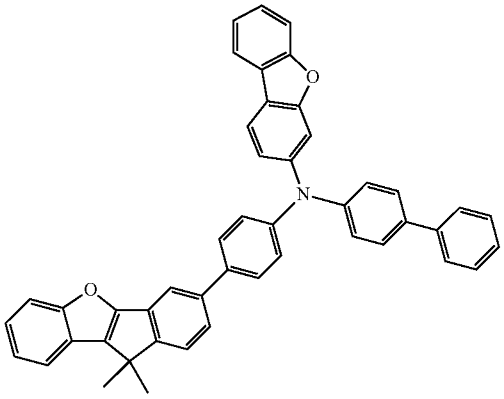
251
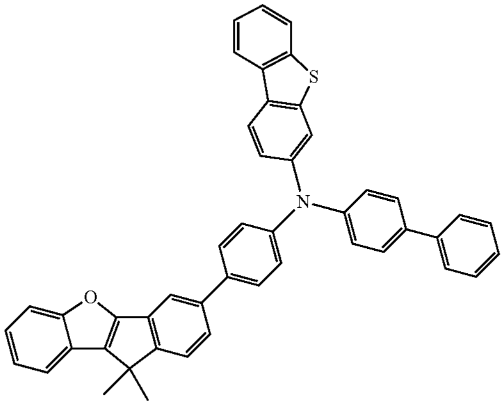

-continued
252
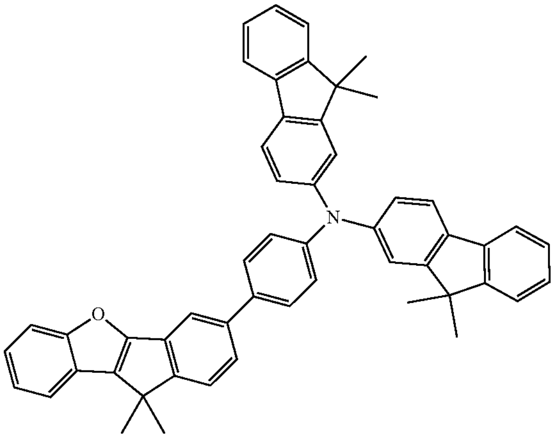
253
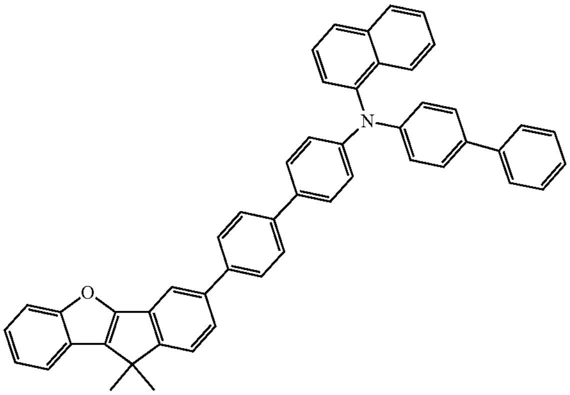
254
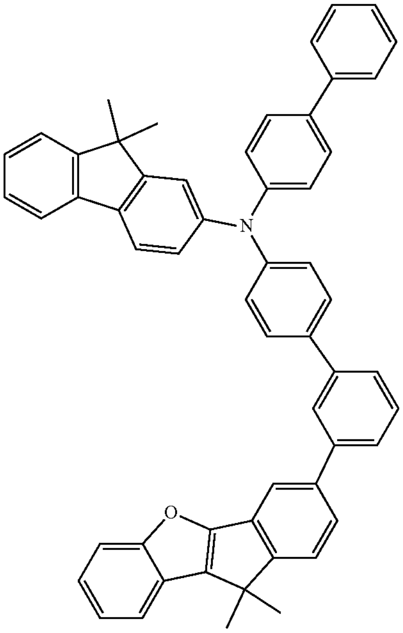
-continued
255
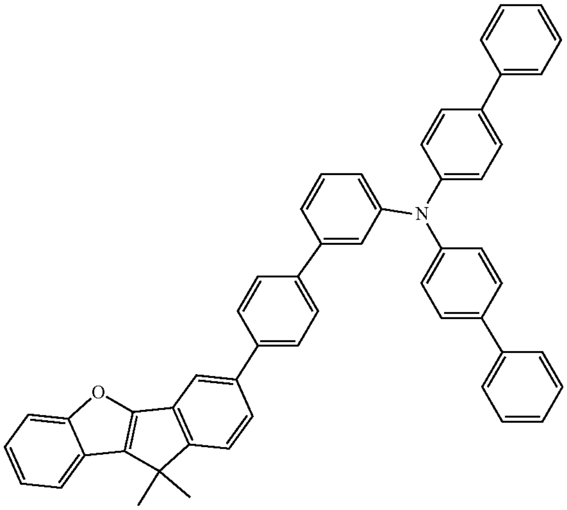
256
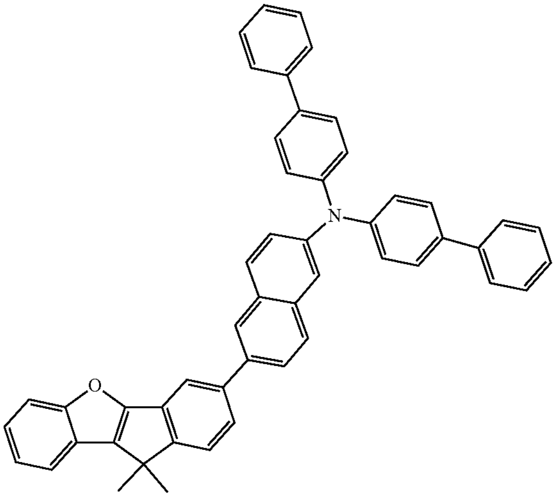
257
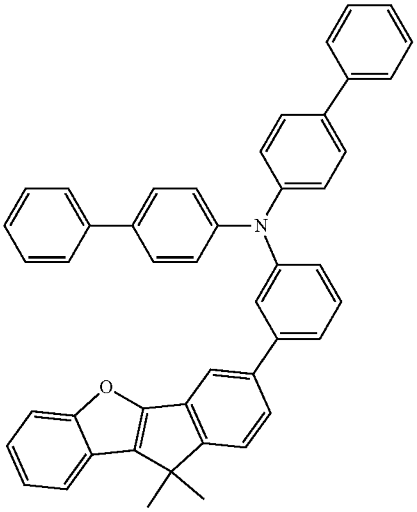

-continued
258
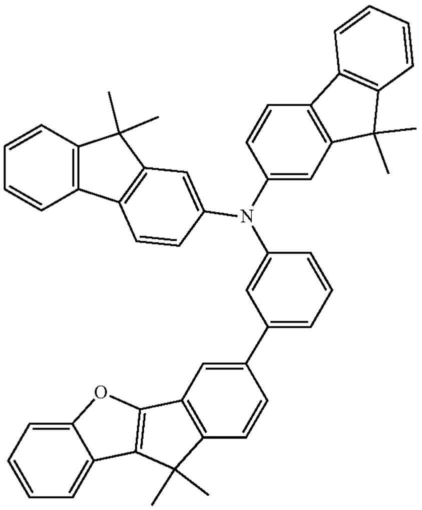
259
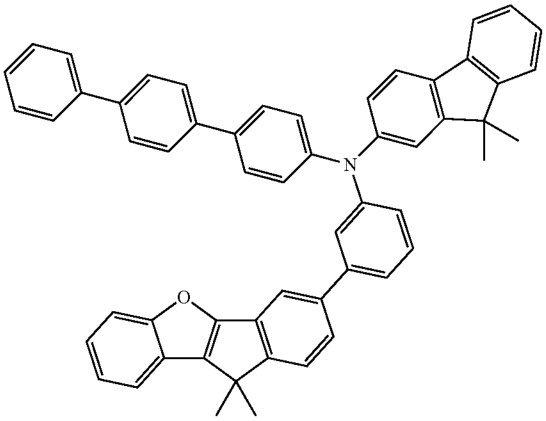
260
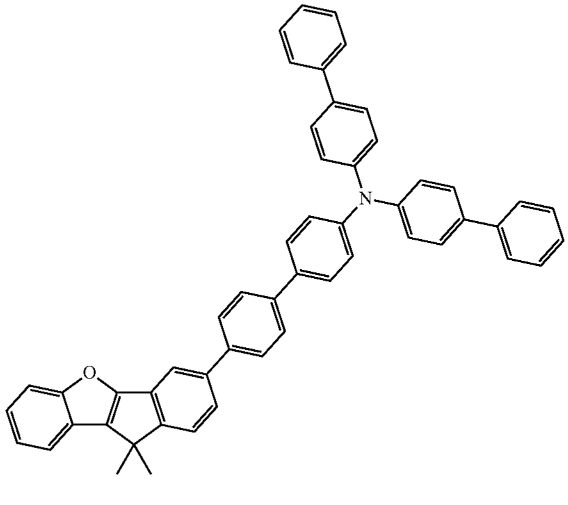
-continued
261
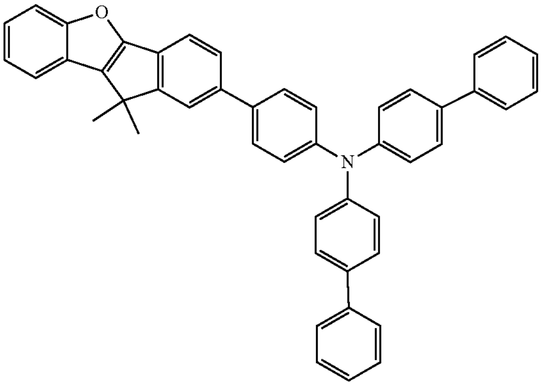
262
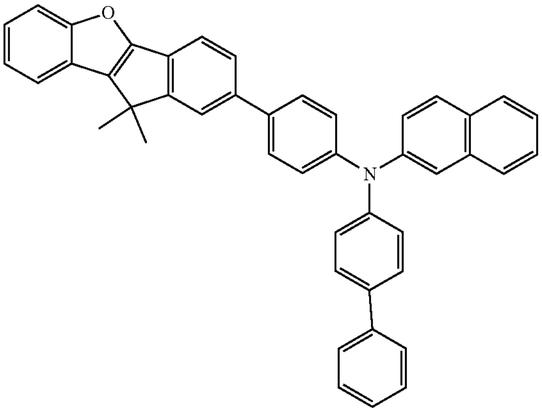
263
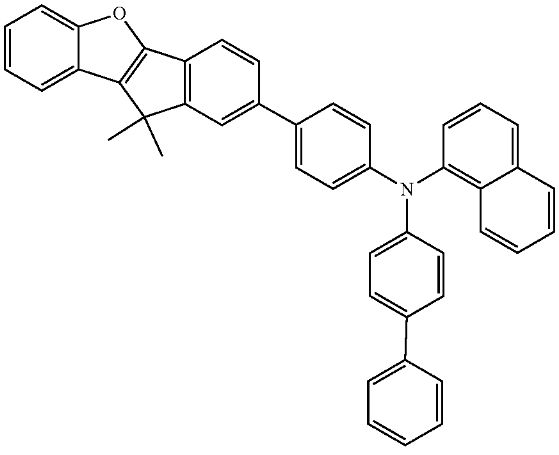

-continued
264
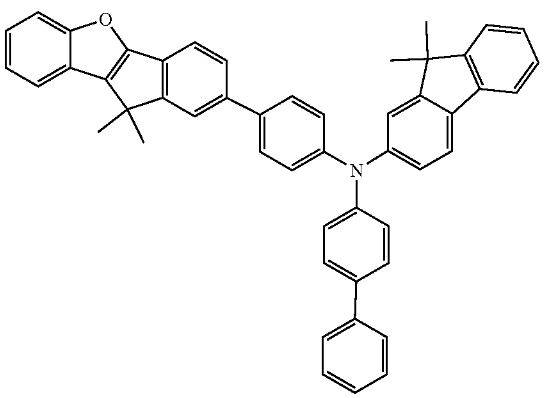
265
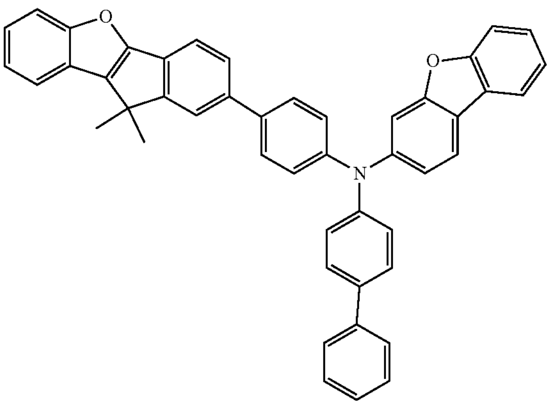
266
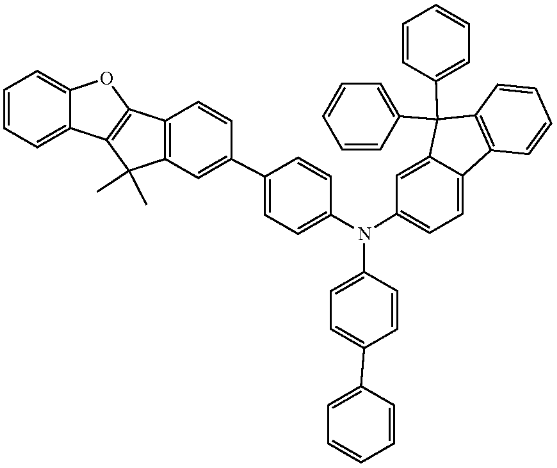
-continued
267
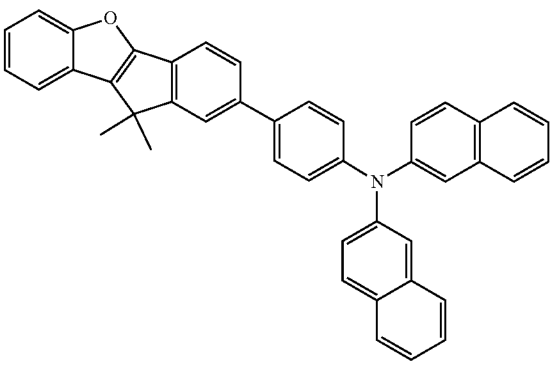
268
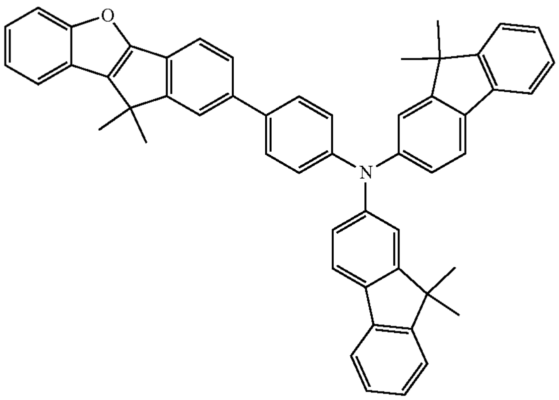
269
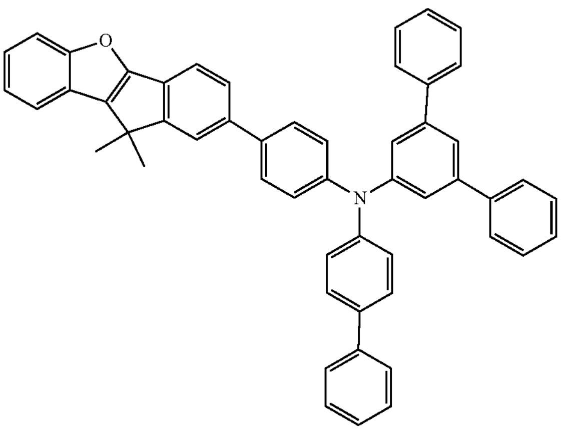

-continued
270
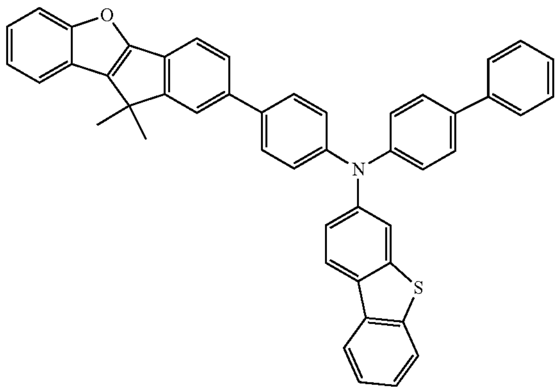
271
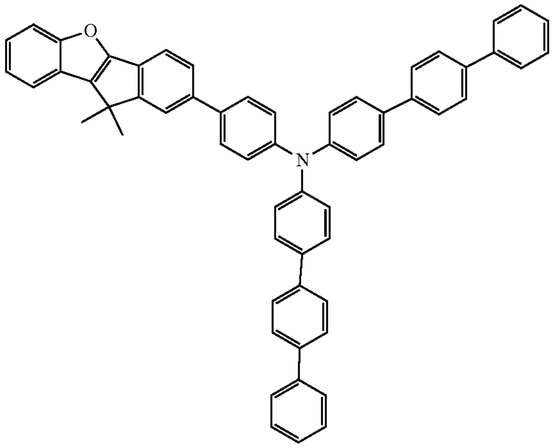
272
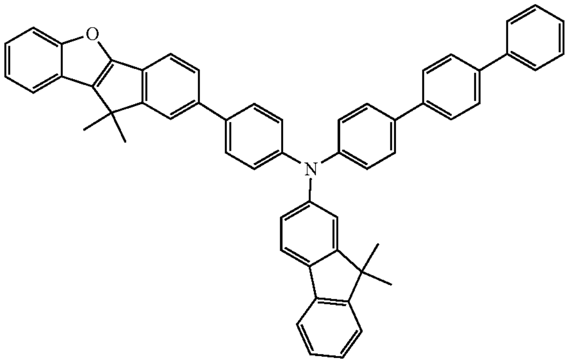
-continued
273
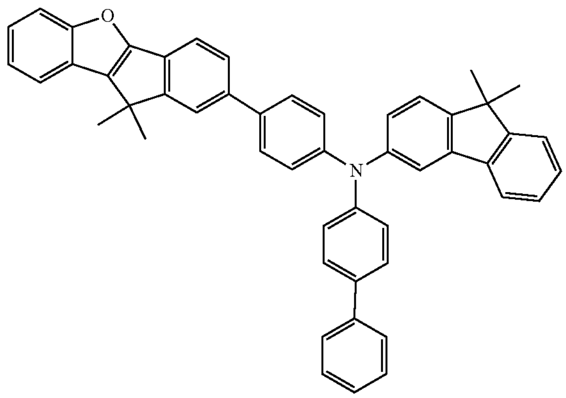
274
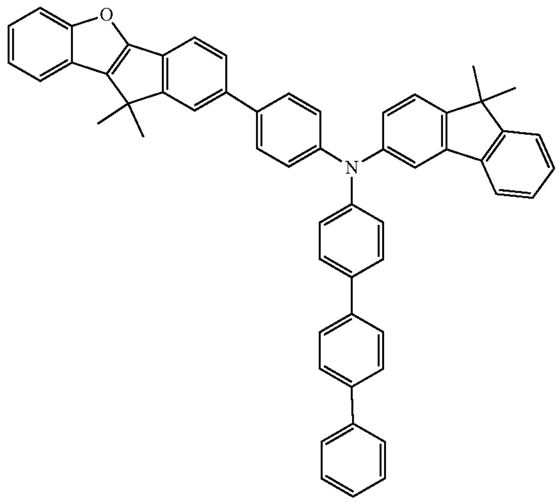
275
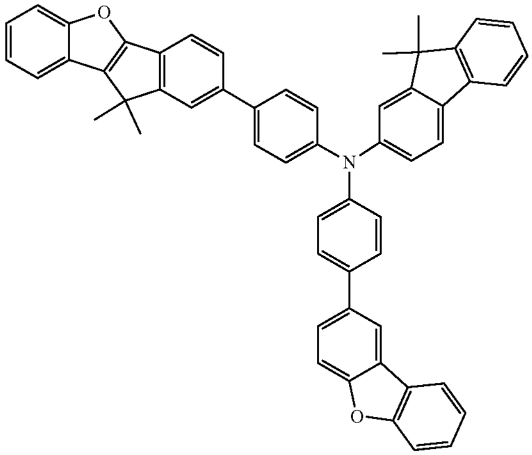

-continued
276
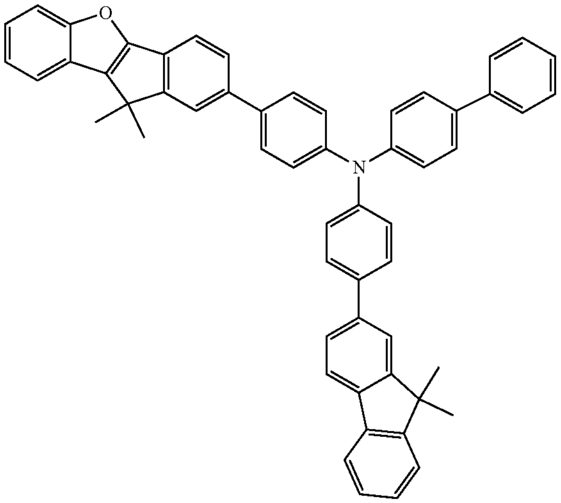
277
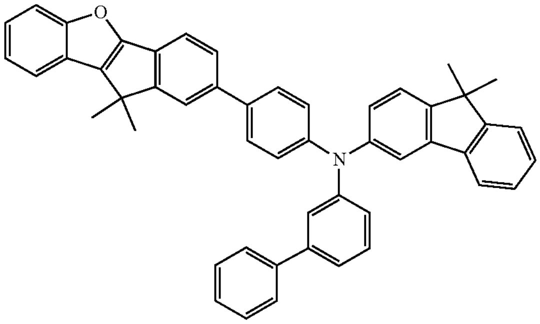
278
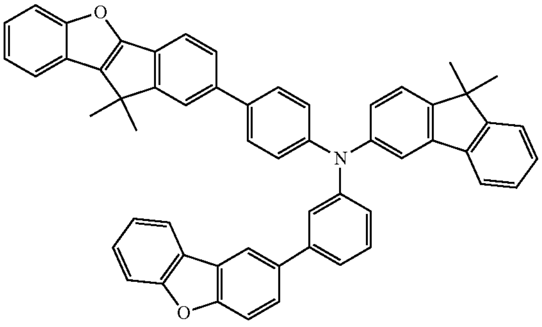
279
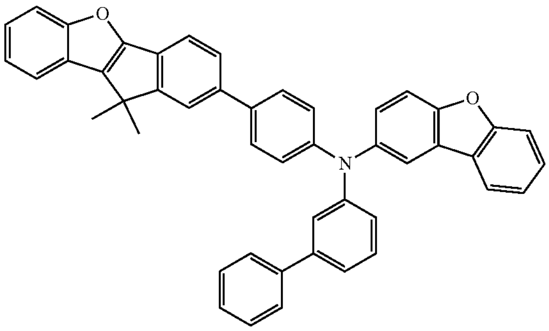
-continued
280
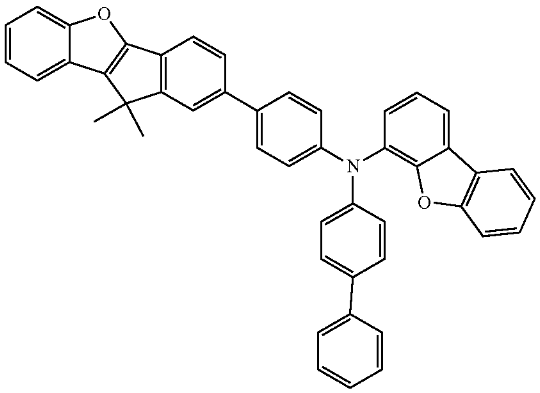
281
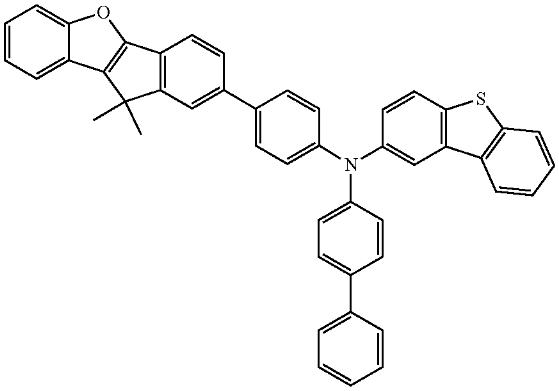
282
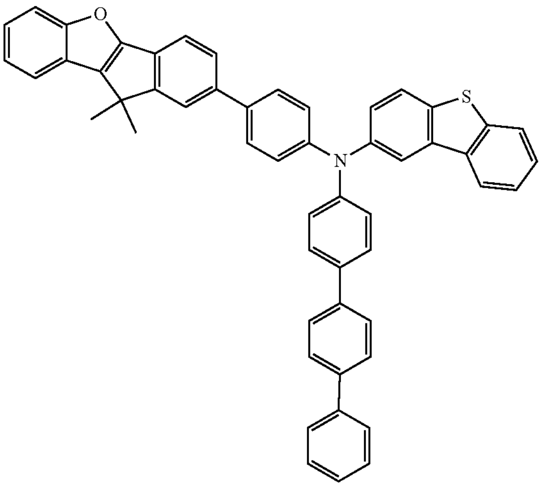

-continued
283
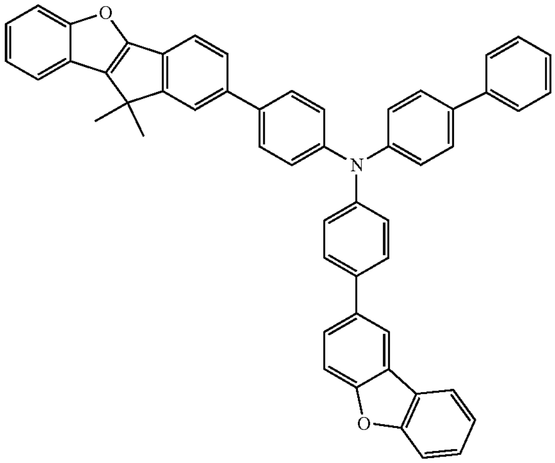
284
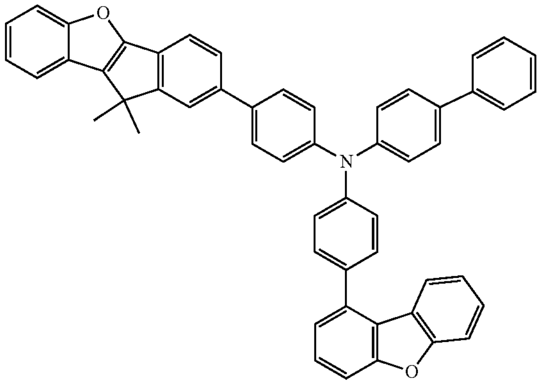
285
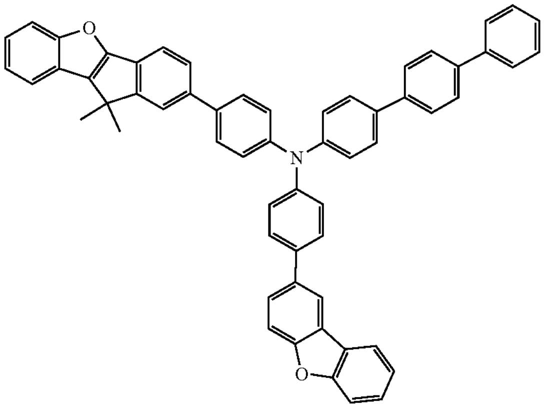
-continued
286
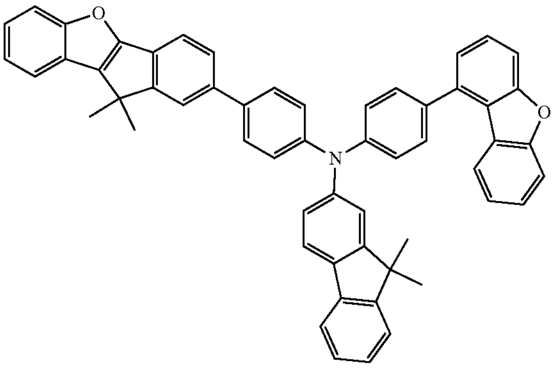
287
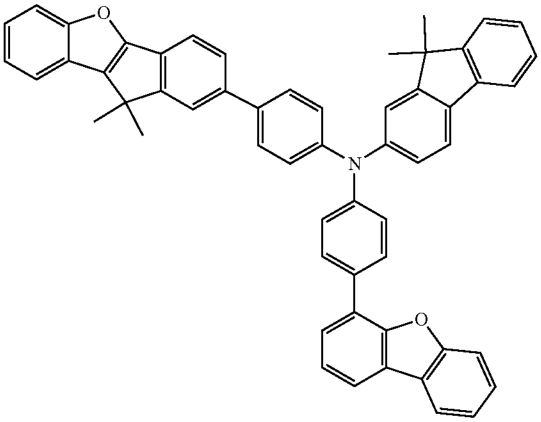
288
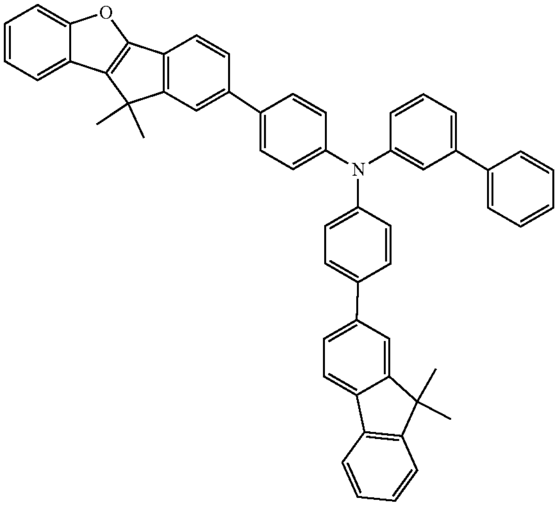

-continued
289
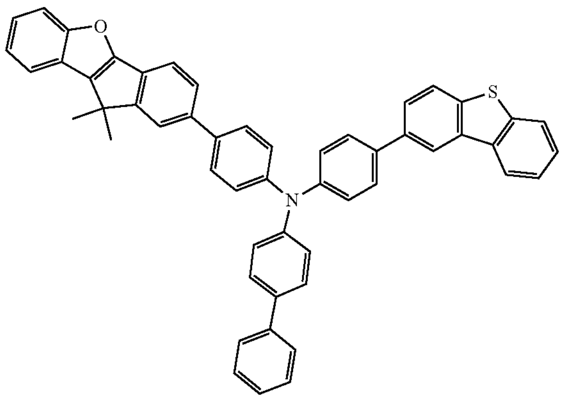
290
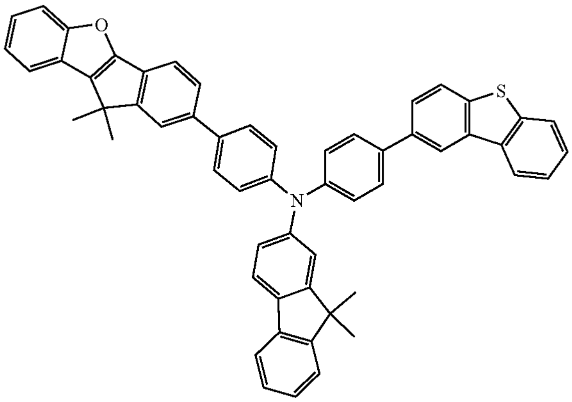
291
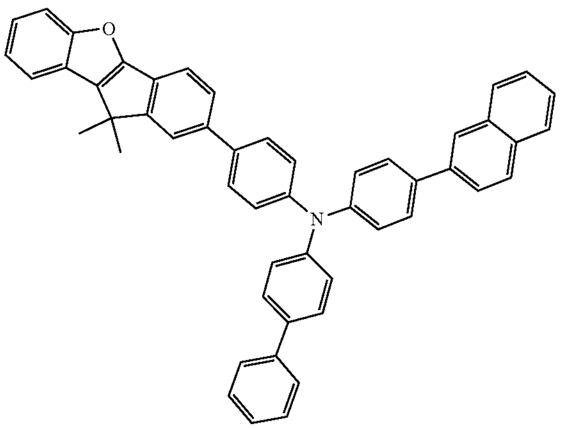
-continued
292
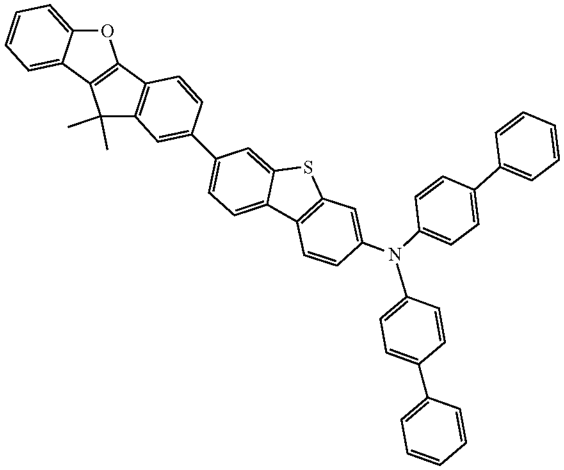
293
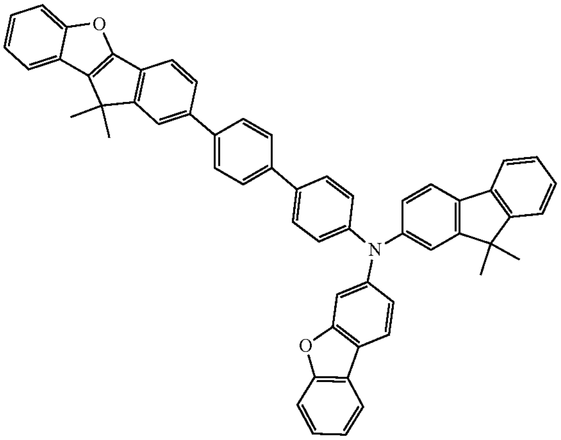
294
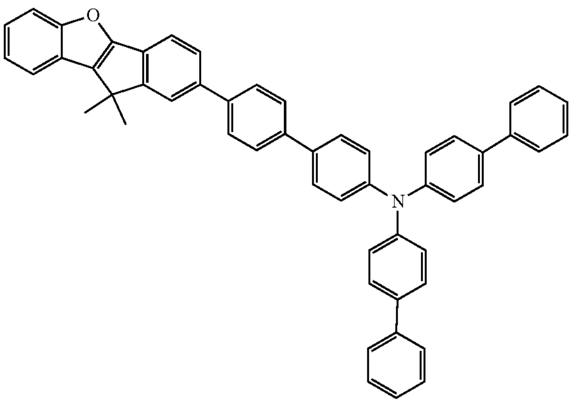

-continued
295
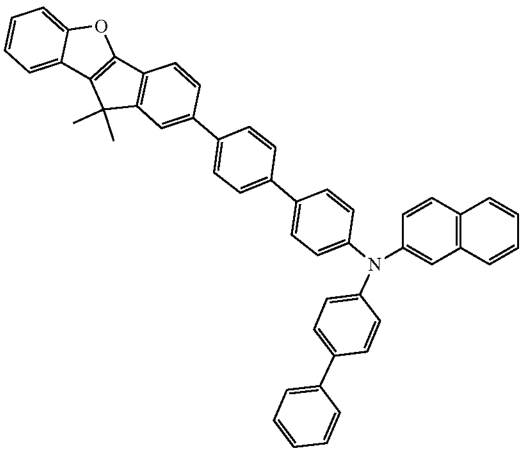
296
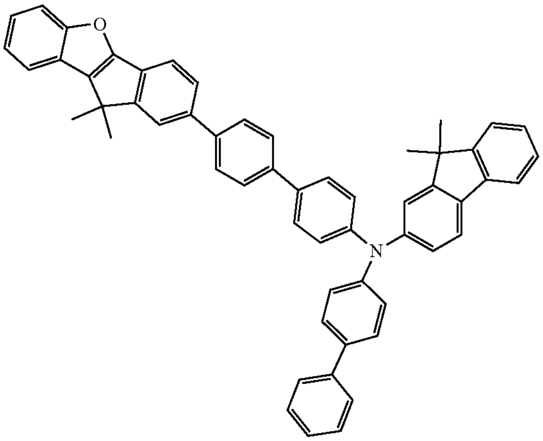
297
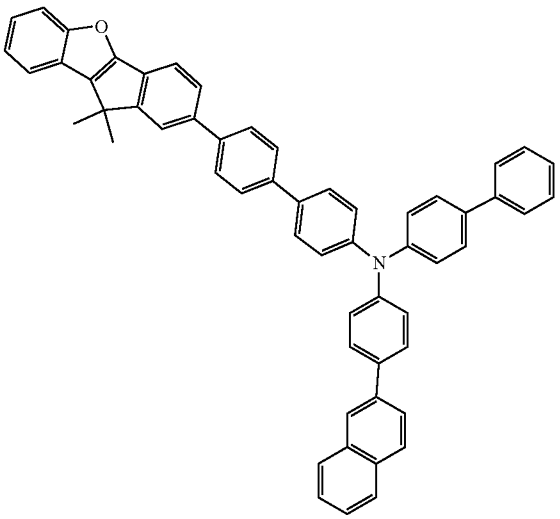
-continued
298
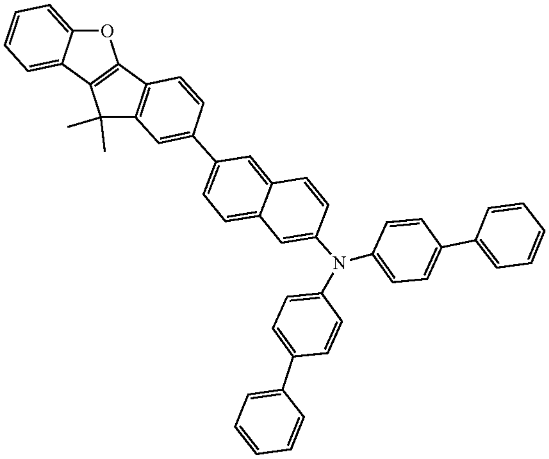
299
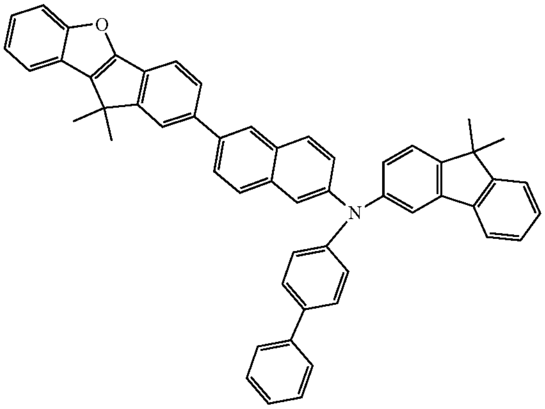
300
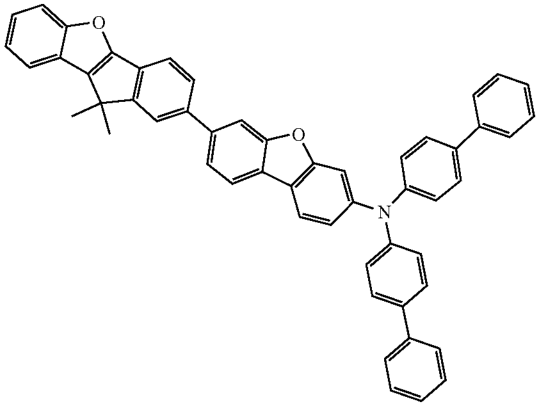

-continued
301
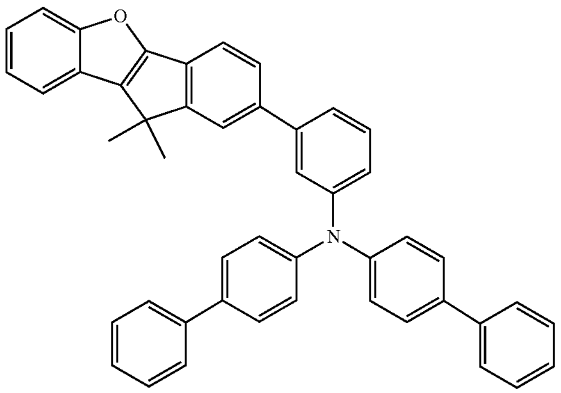
302
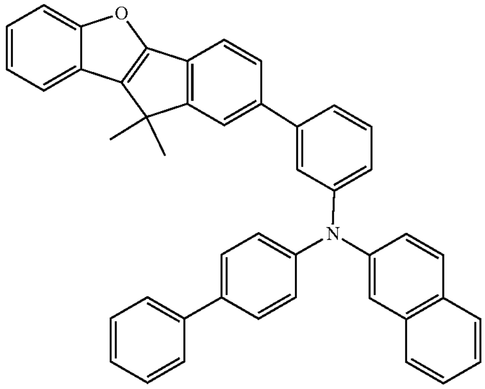
303
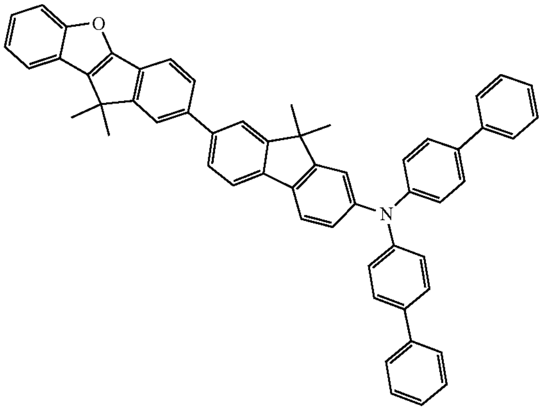
-continued
304
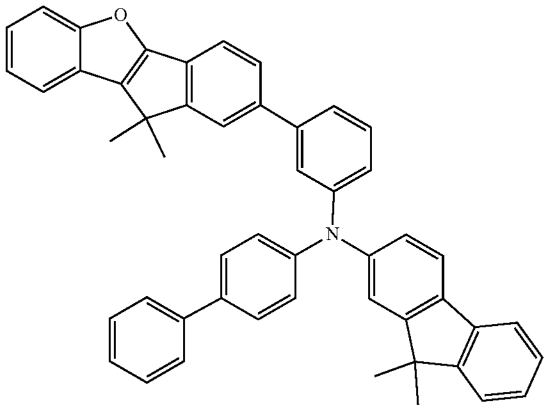
305
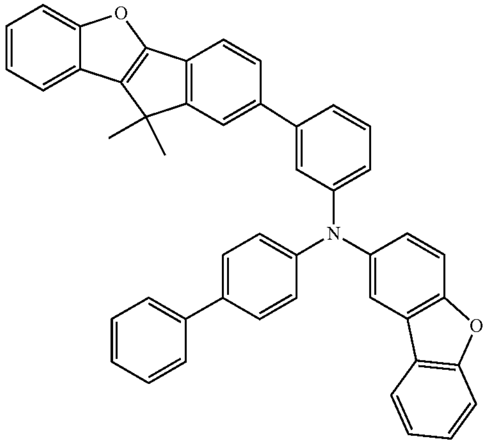
306
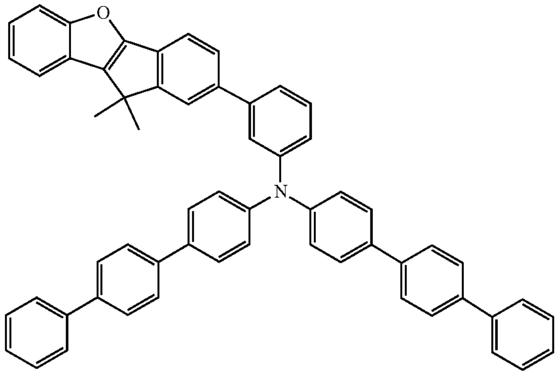

-continued
307
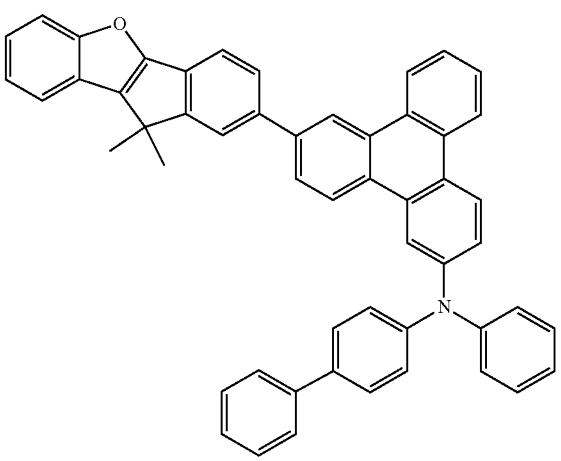
308
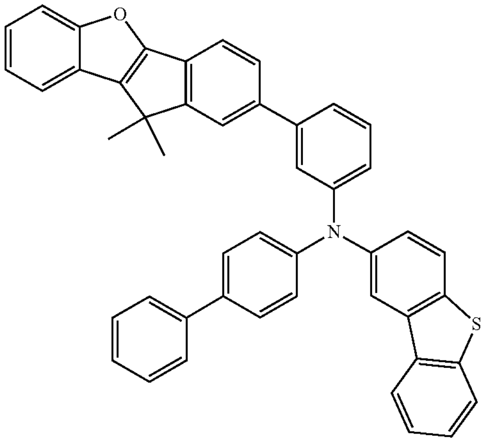
309
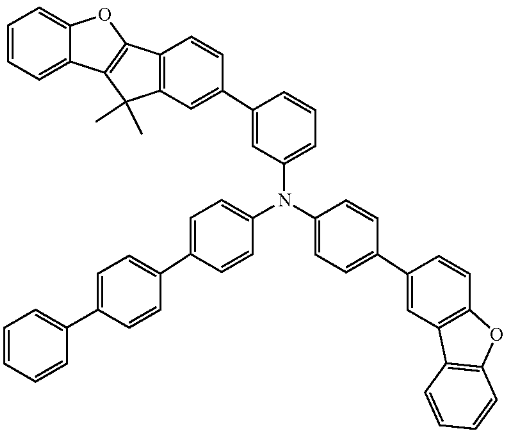
-continued
310
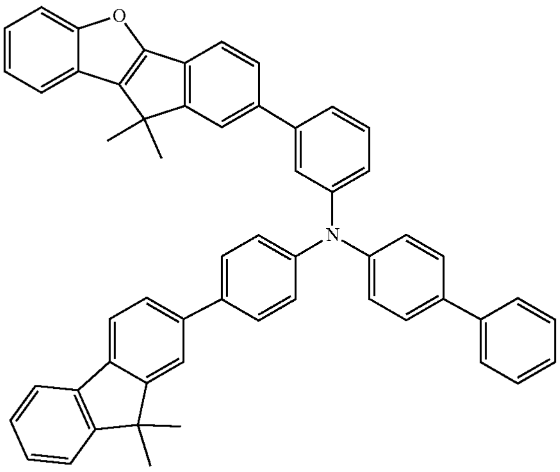
311
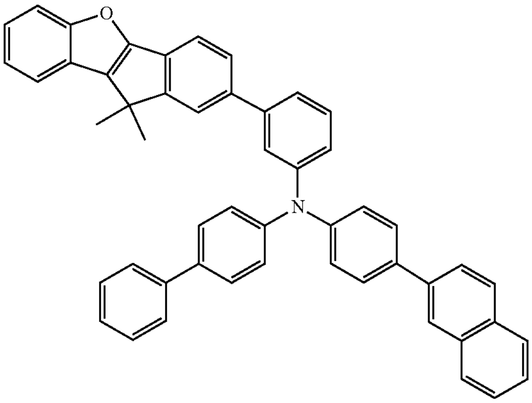
312
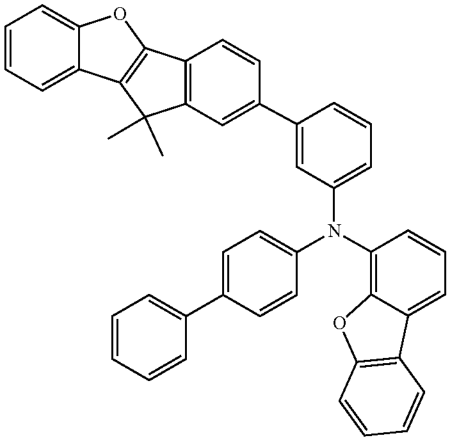

-continued
313
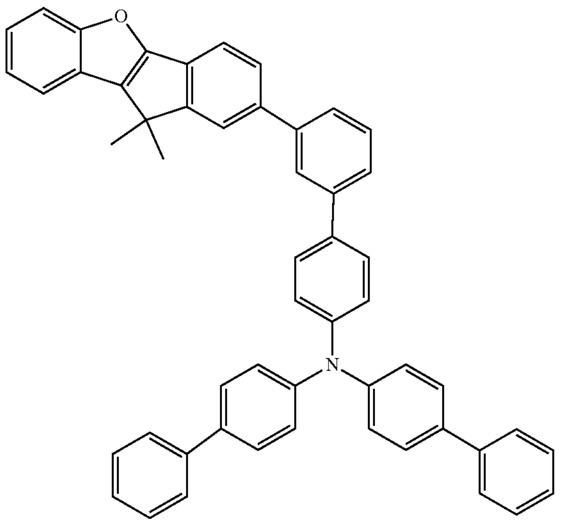
314
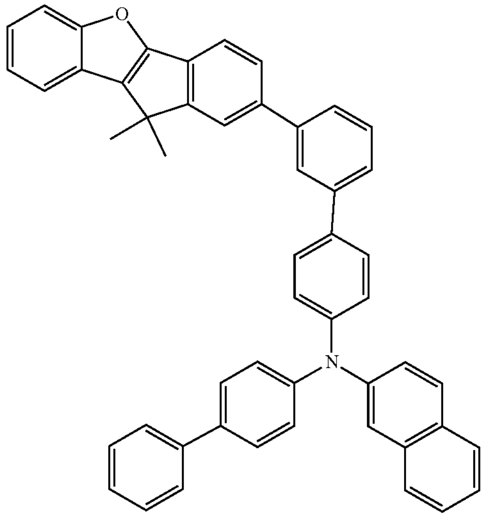
315
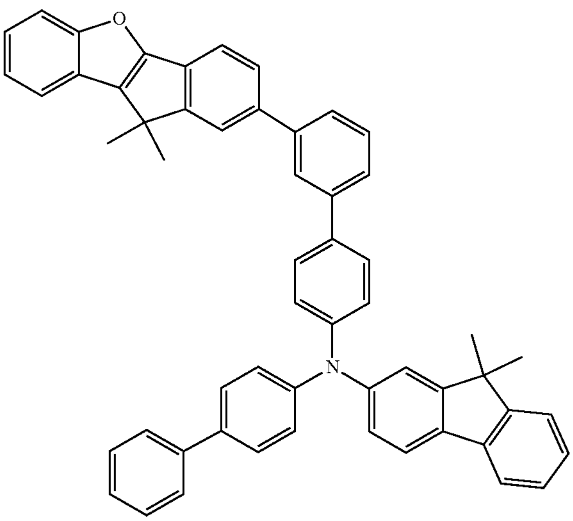
-continued
316
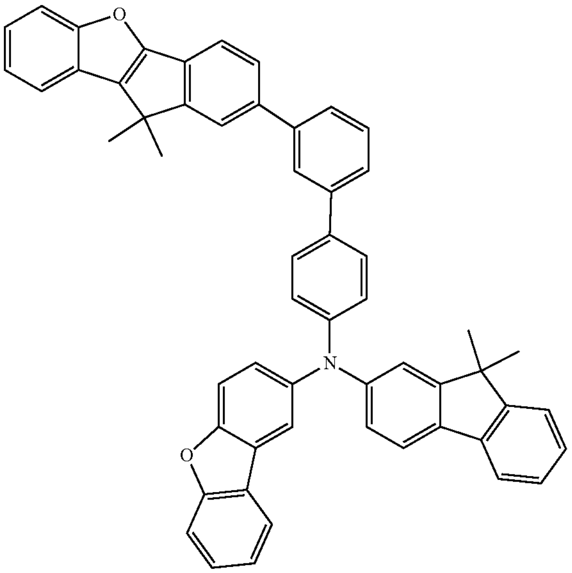
317
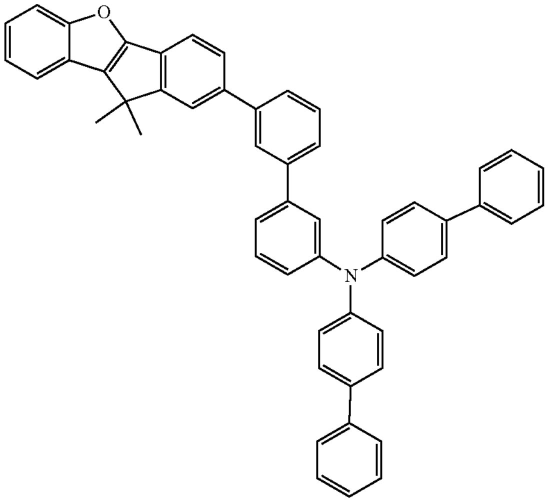
318
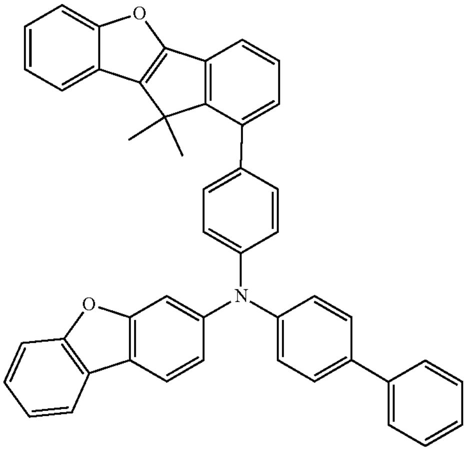

-continued
319
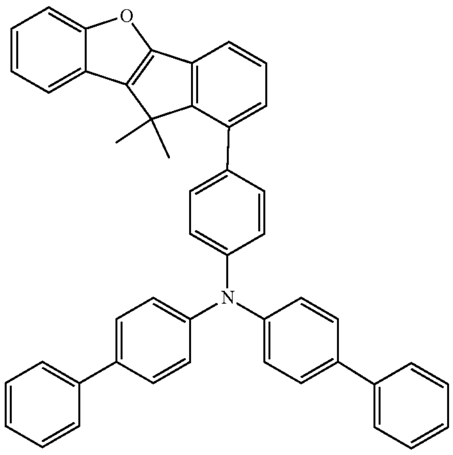
320
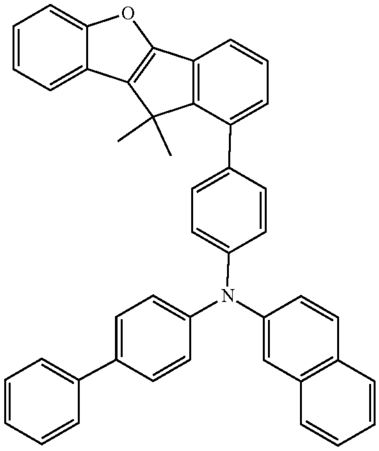
321
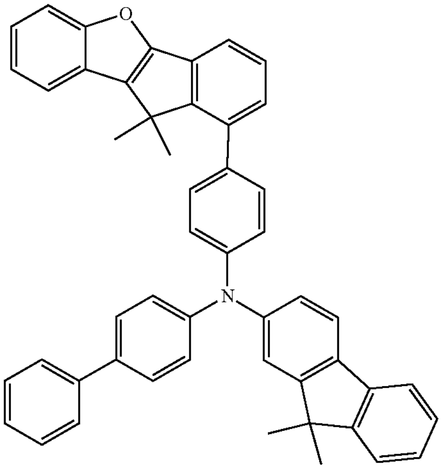
-continued
322
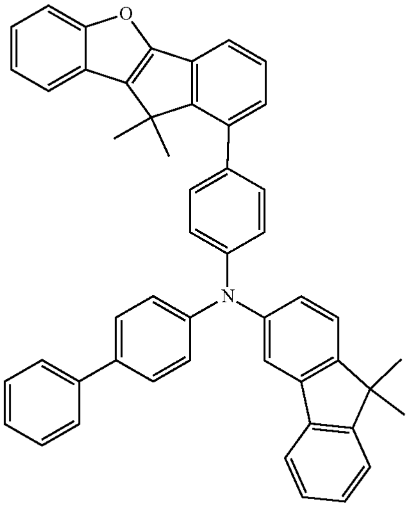
323
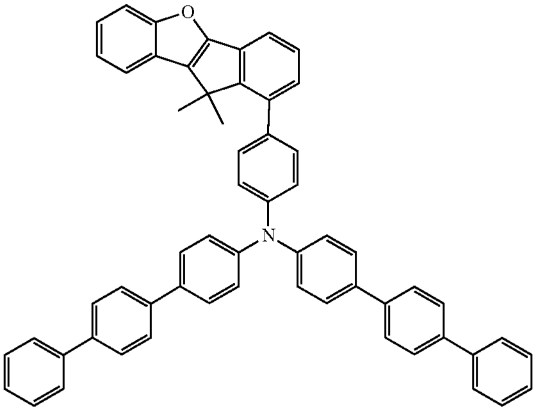
324
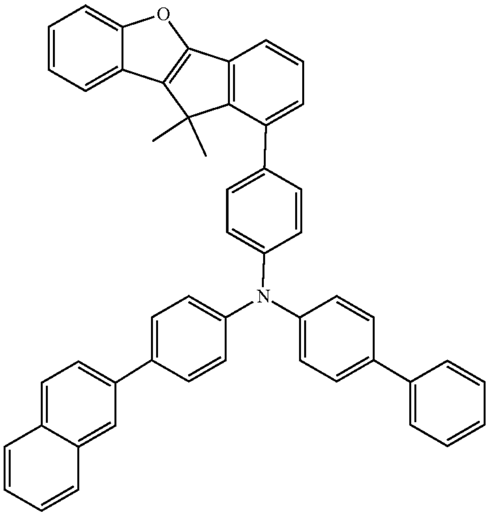

-continued
325
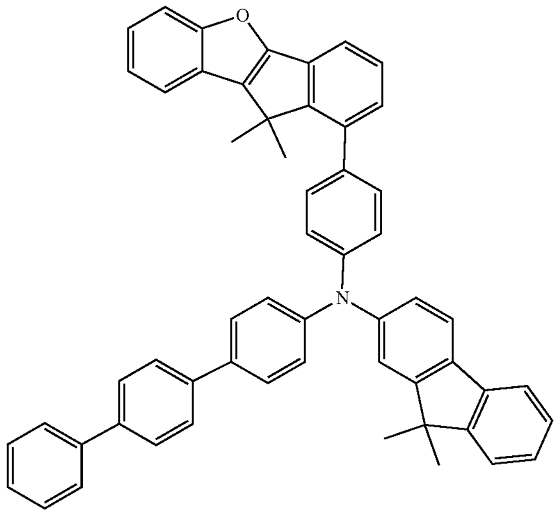
326
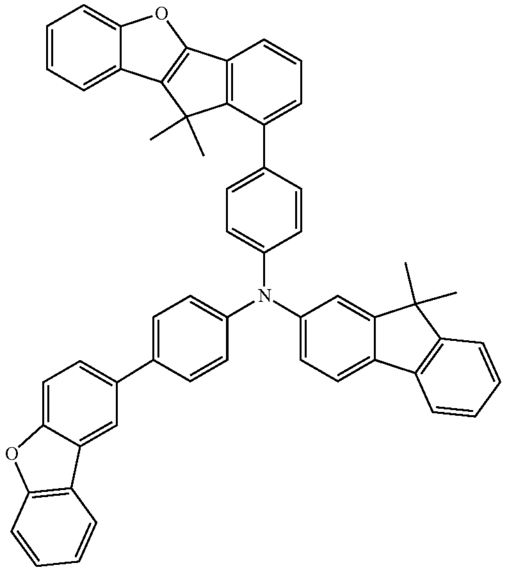
327
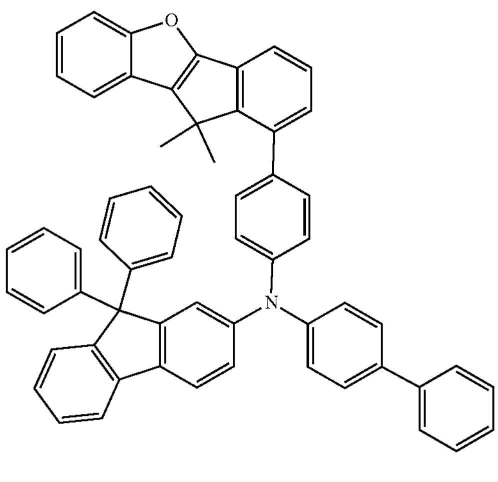
-continued
328
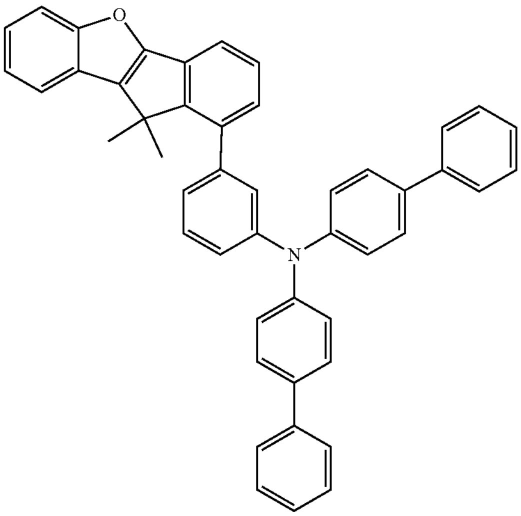
329
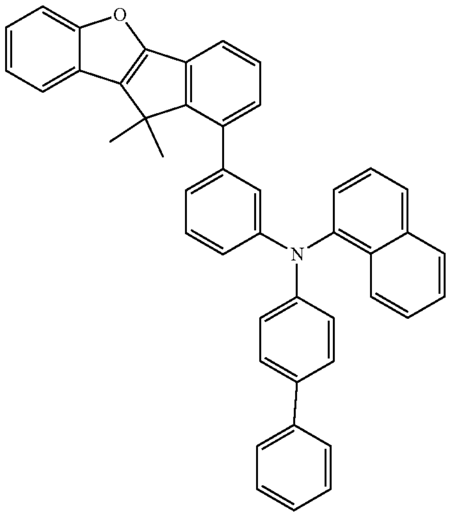
330
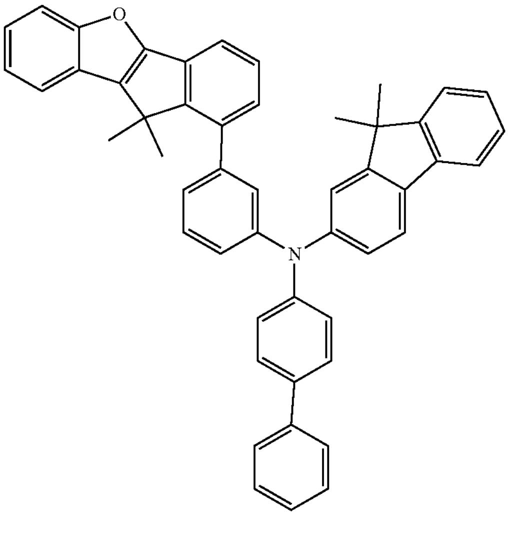

-continued
331
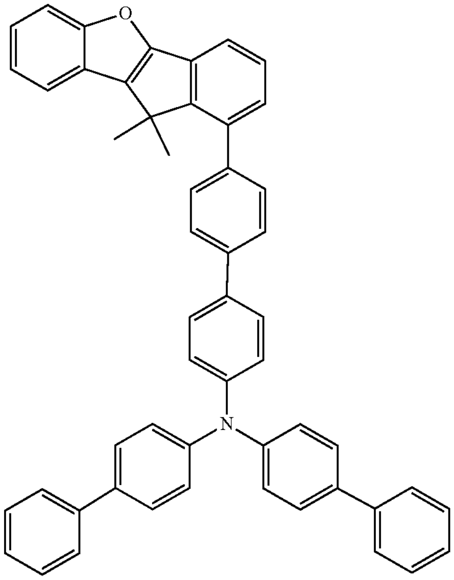
332
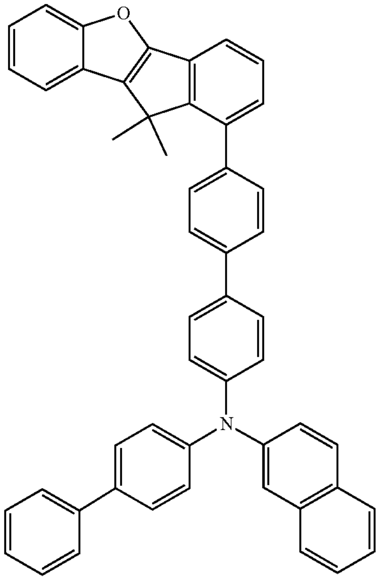
-continued
333
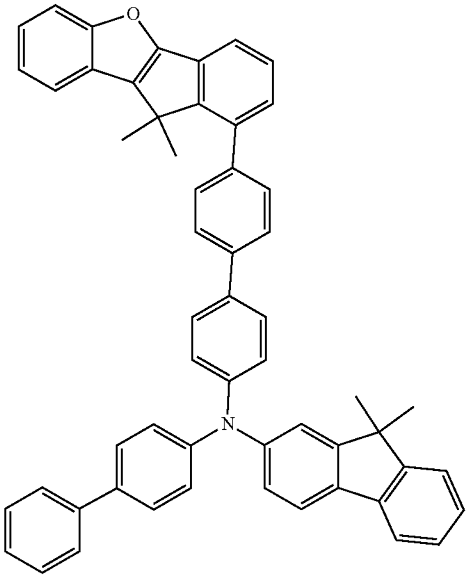
334
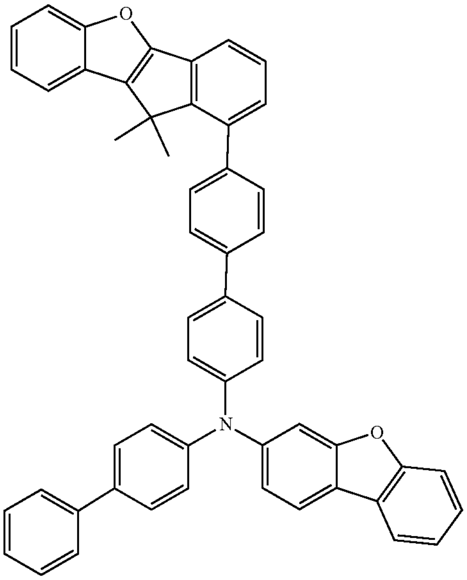
335
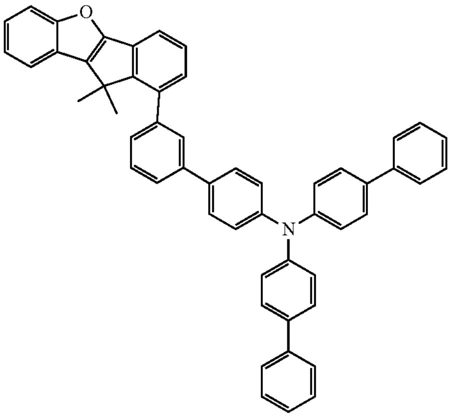

-continued
336
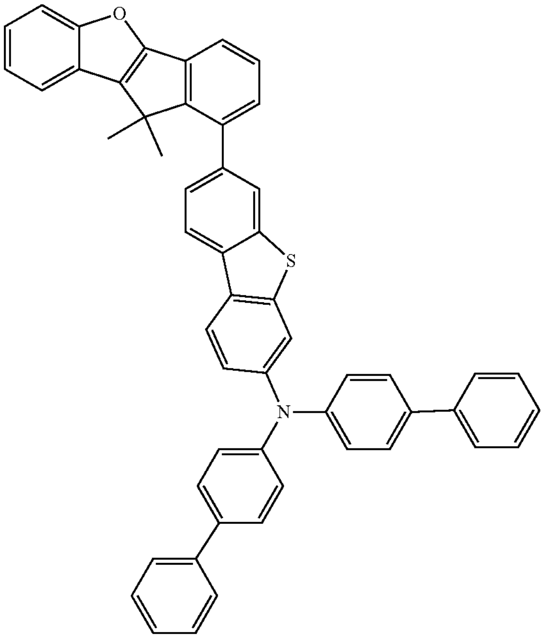
337
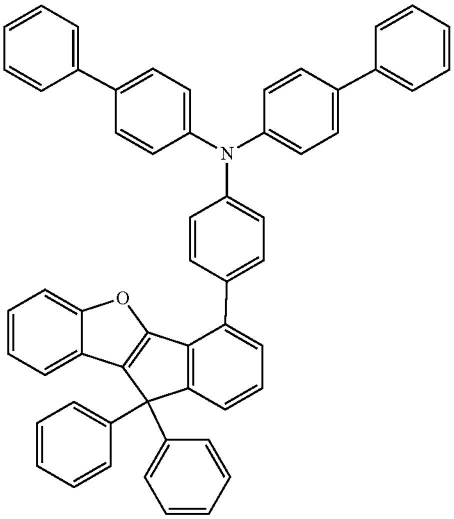
-continued
338
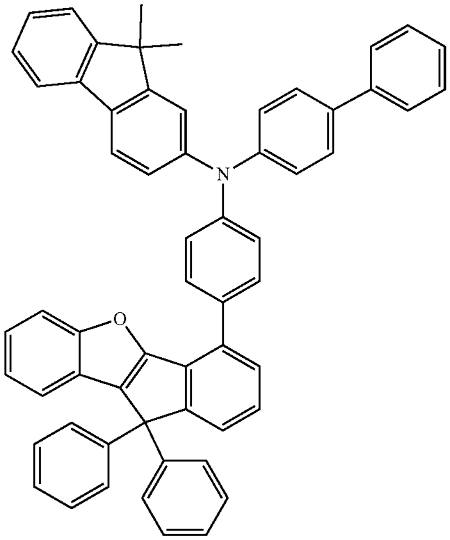
339
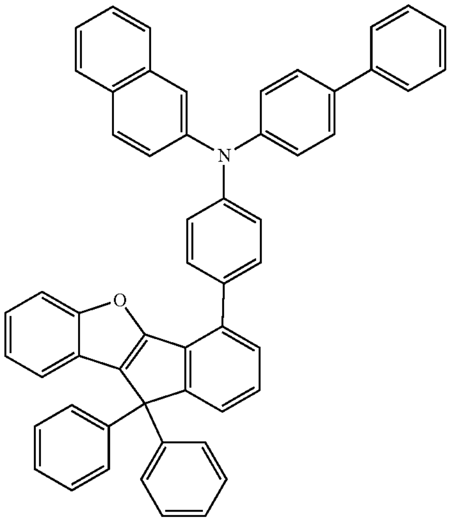
340
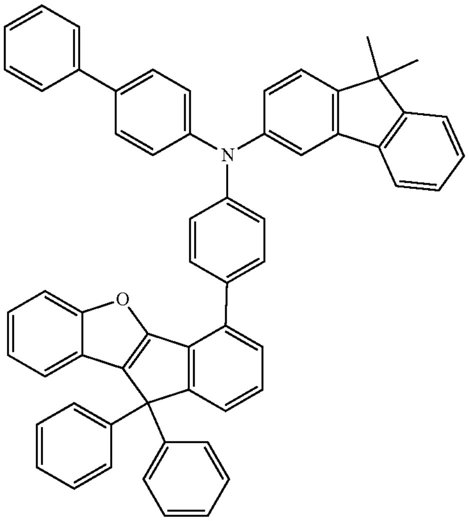

-continued
341
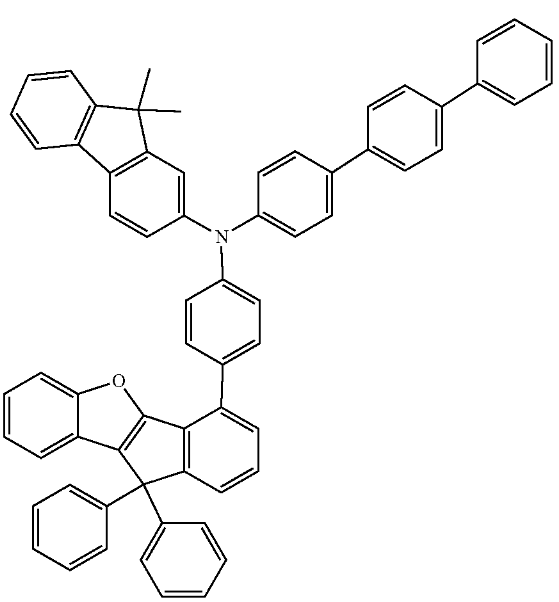
342
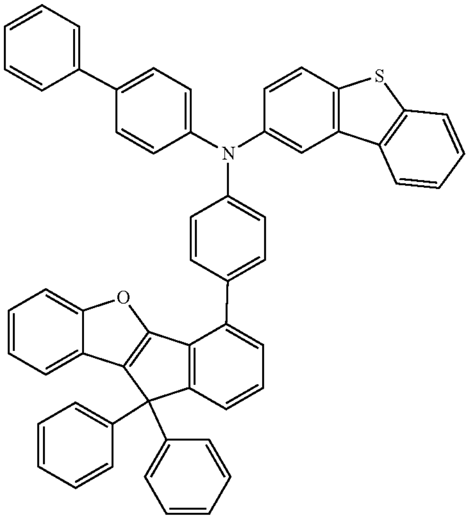
-continued
343
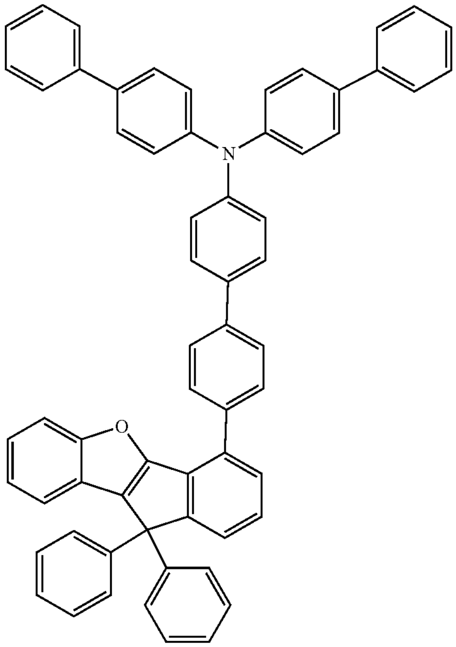
344
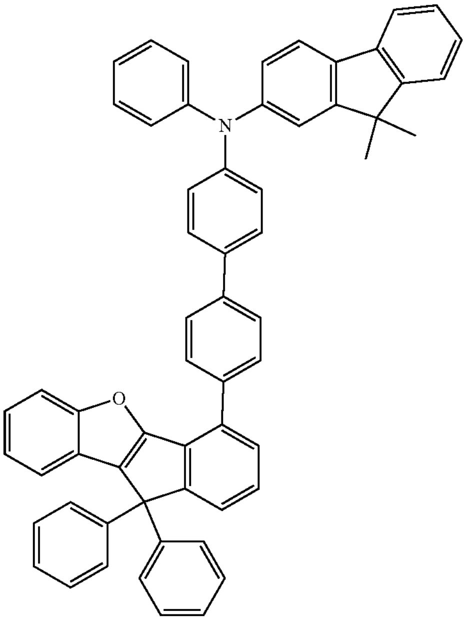

-continued
345
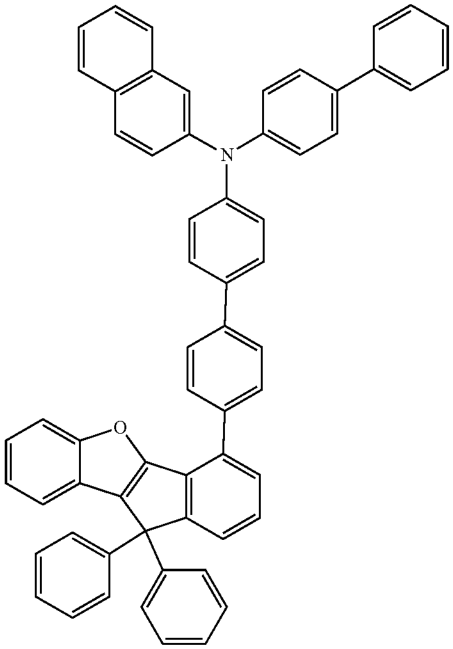
346
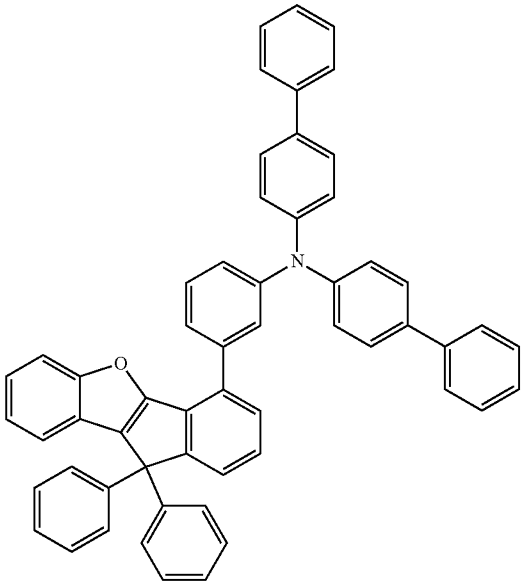
-continued
347
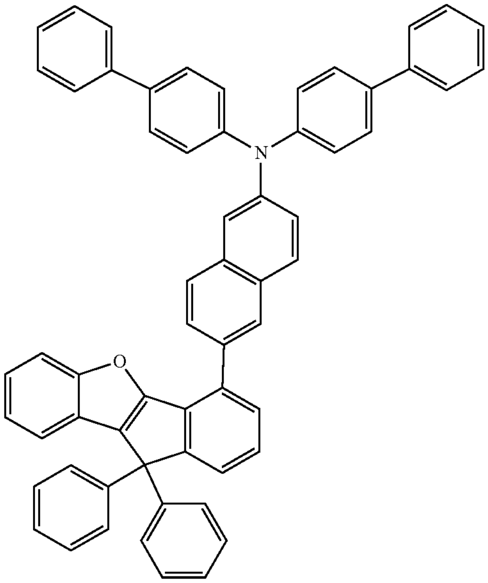
348
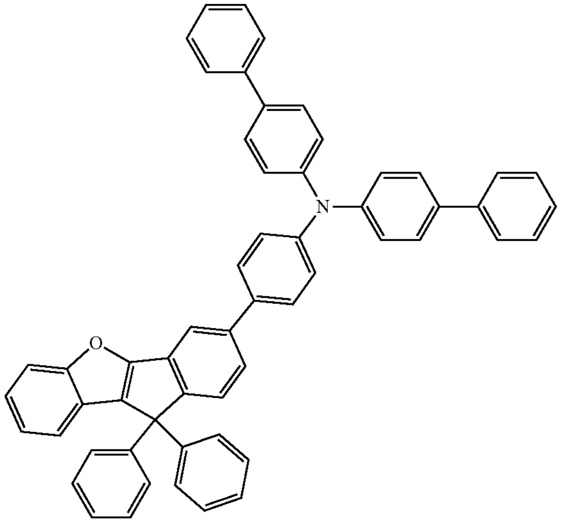
349
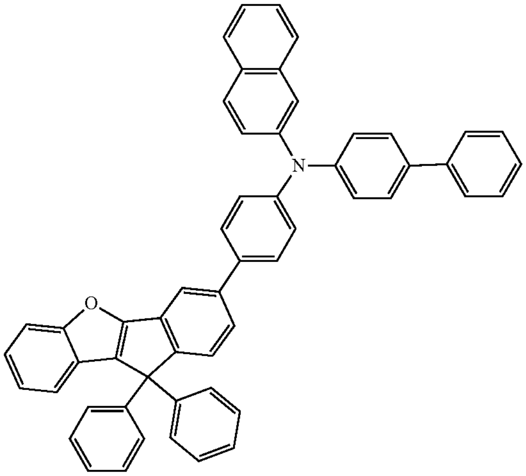

-continued
350
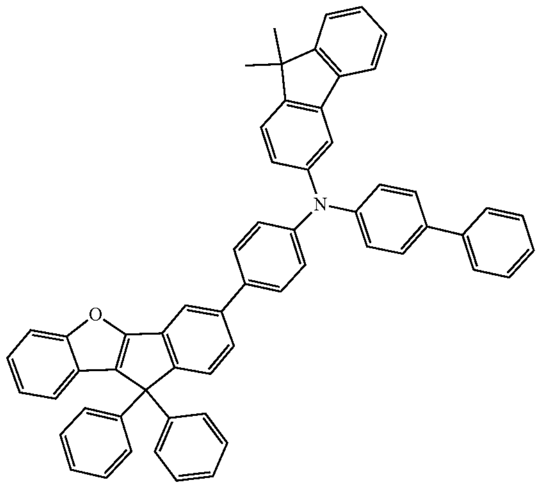
351
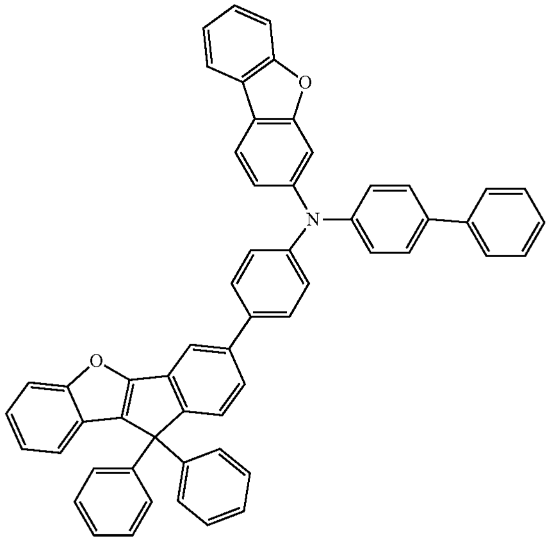
352
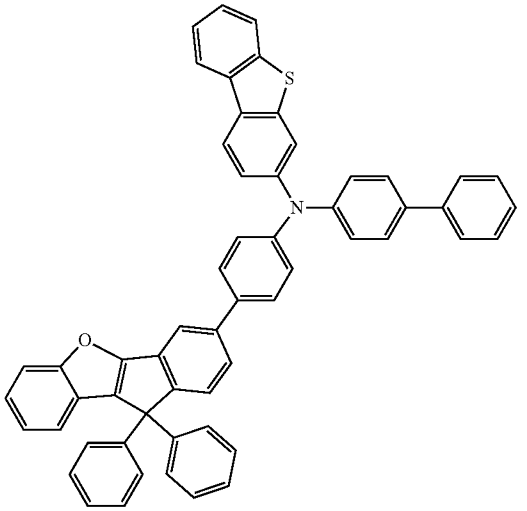
-continued
353
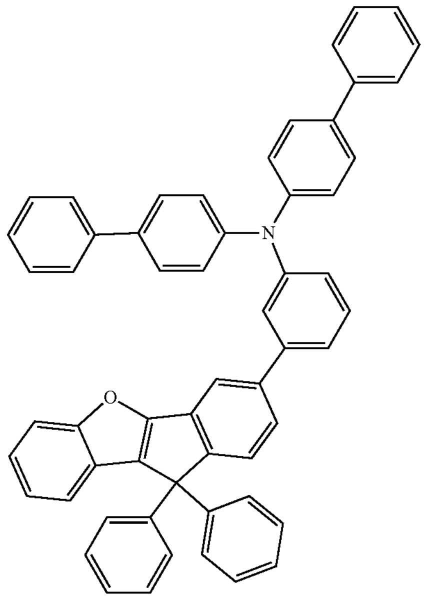
354
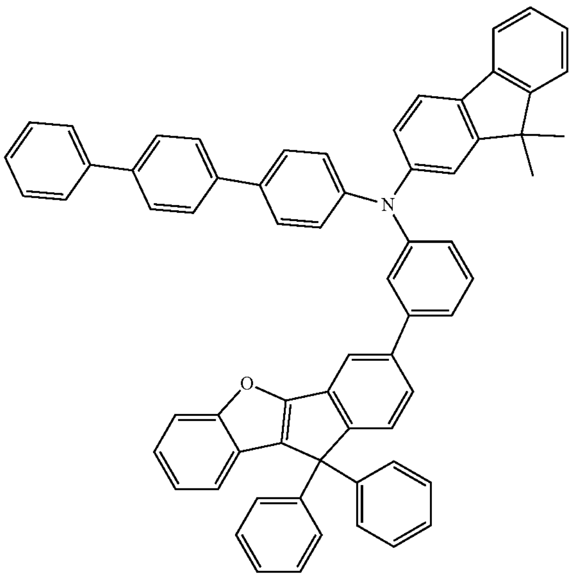

-continued
355
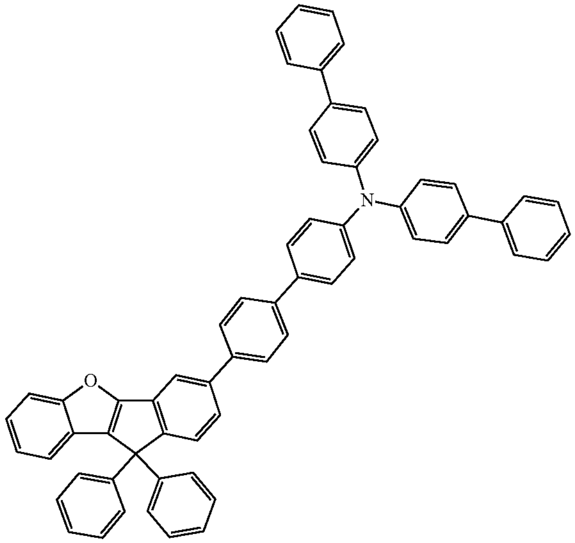
356
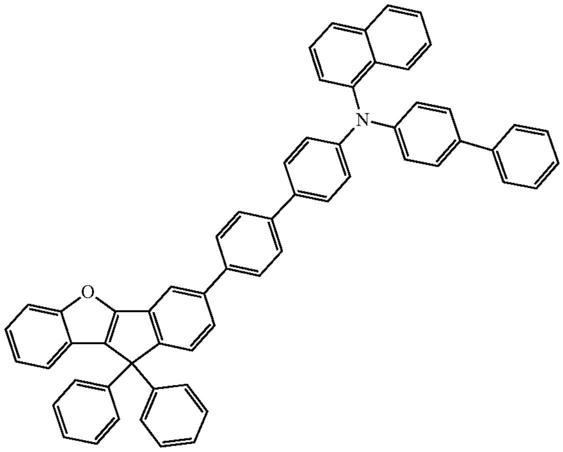
357
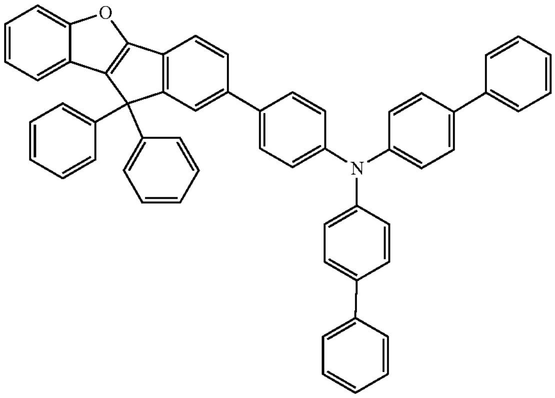
-continued
358
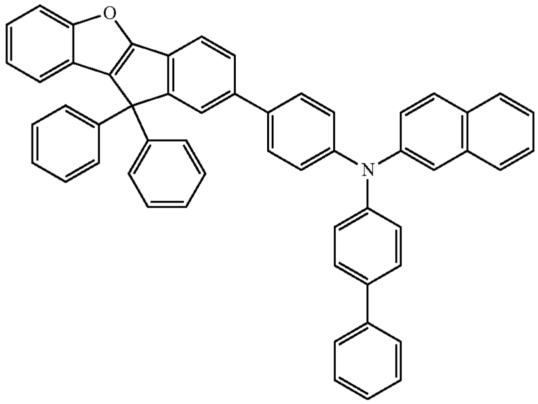
359
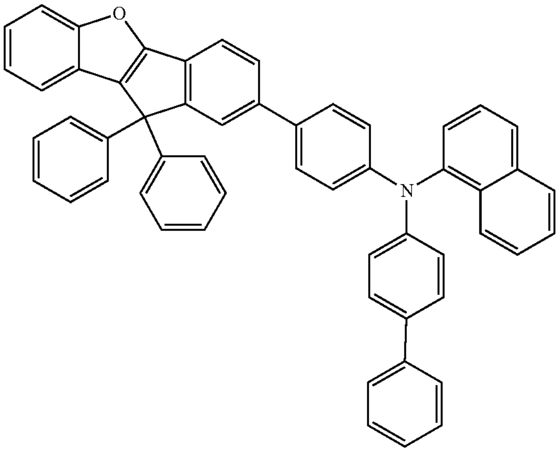
360
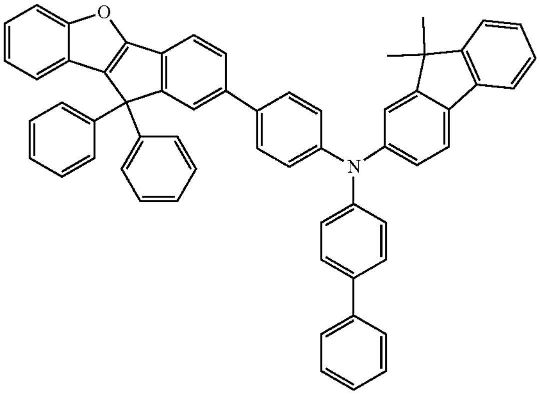

-continued
361
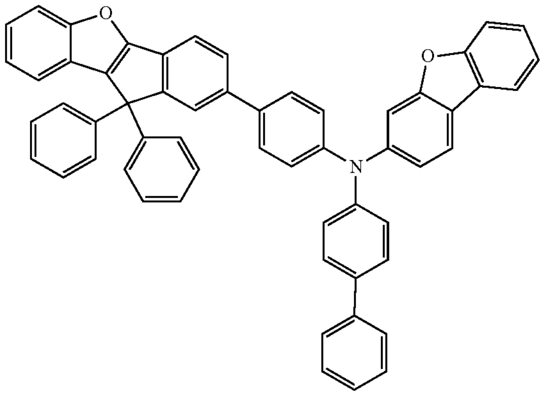
362
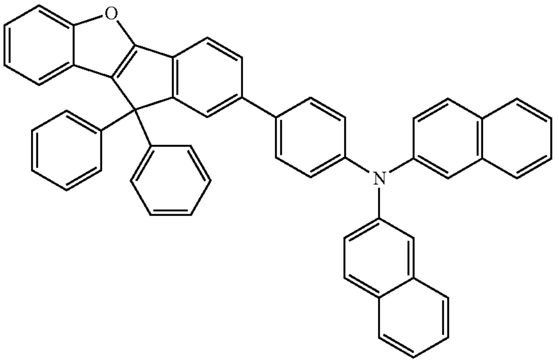
363
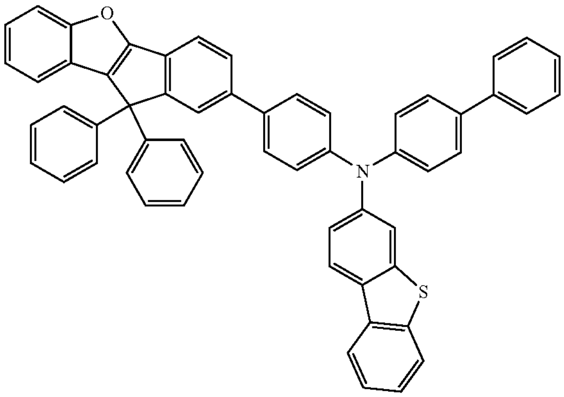
364
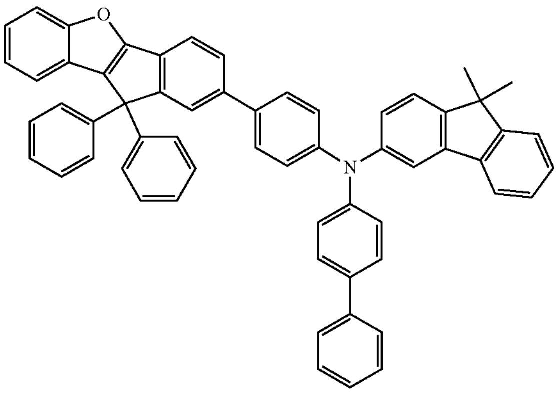
-continued
365
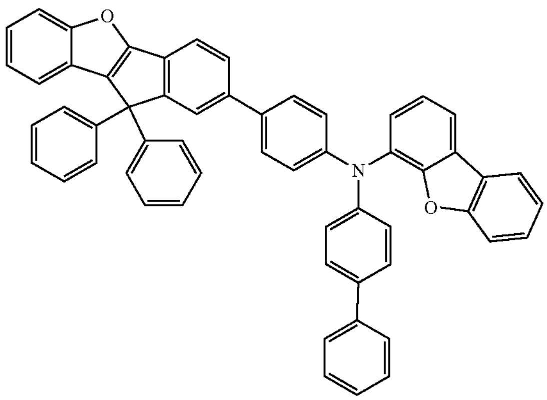
366
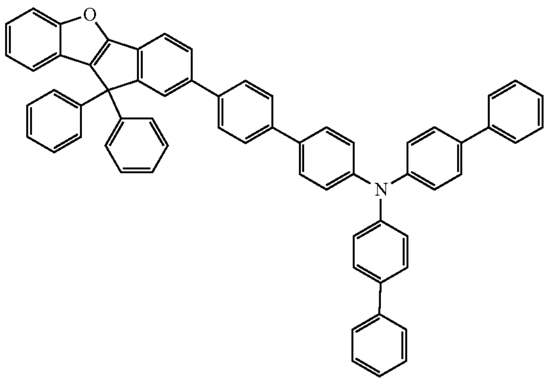
367
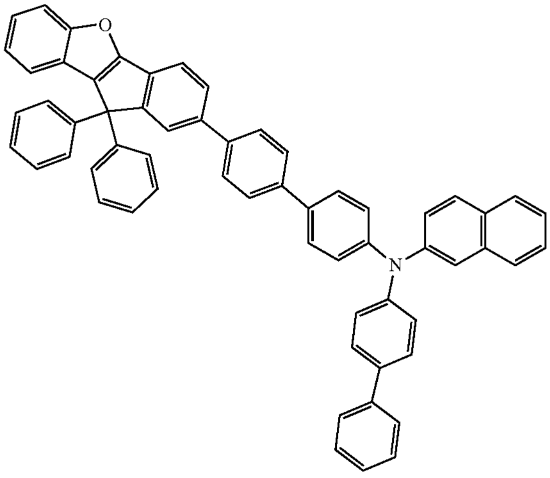

-continued
368
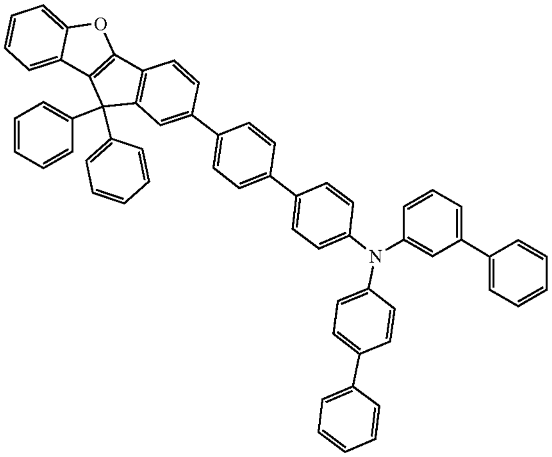
369
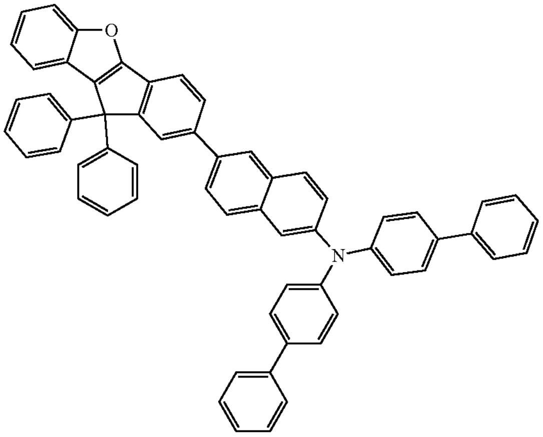
370
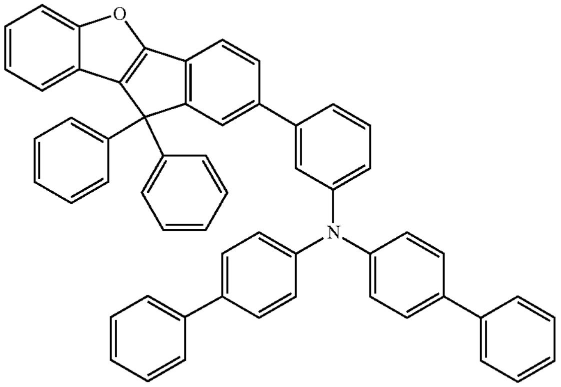
-continued
371
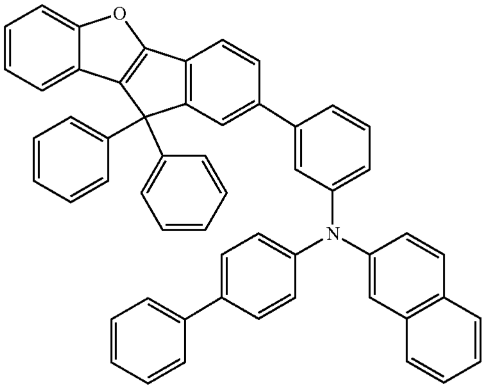
372
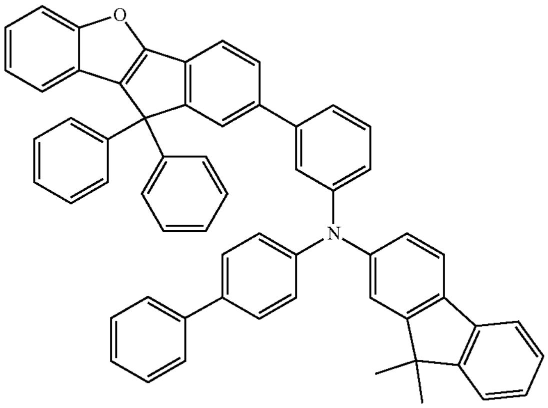
373
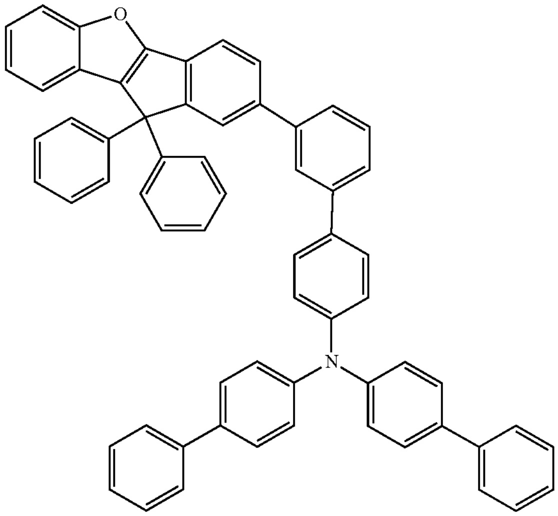

-continued
374
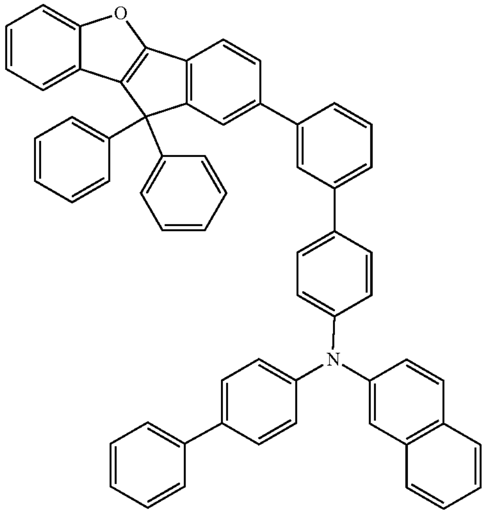
375
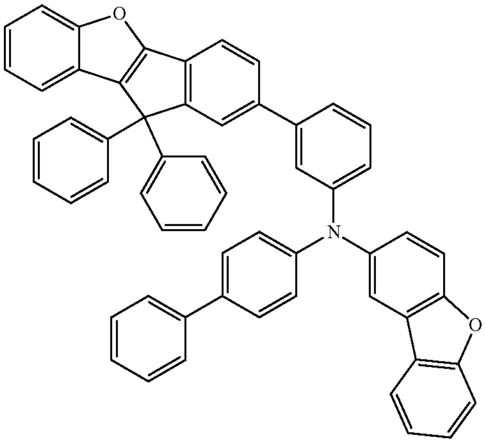
376
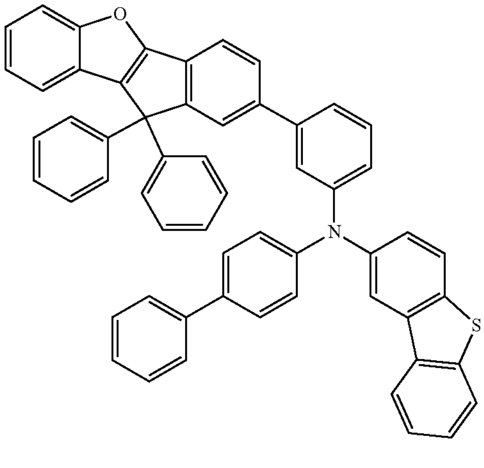
-continued
377
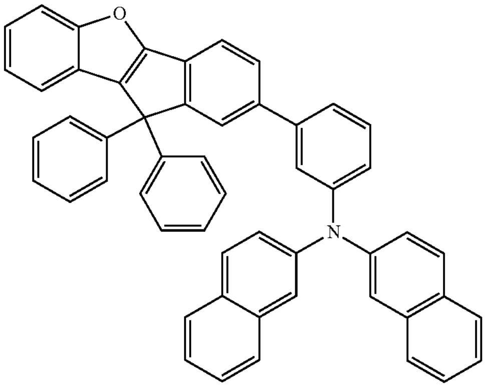
378
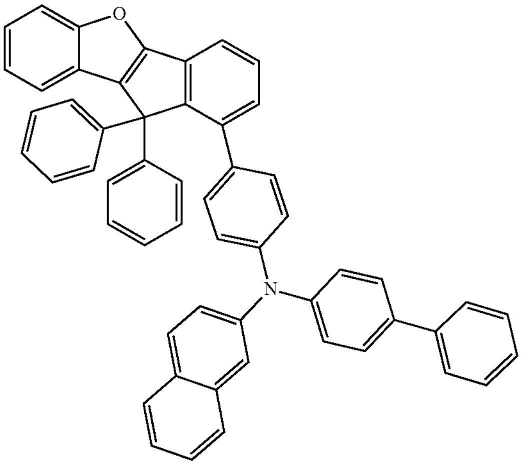
379
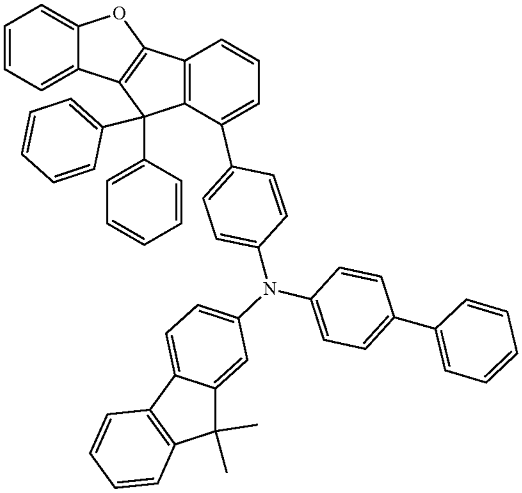

-continued

380

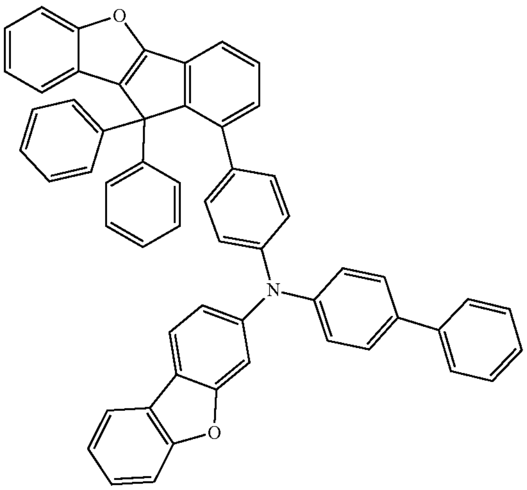

381

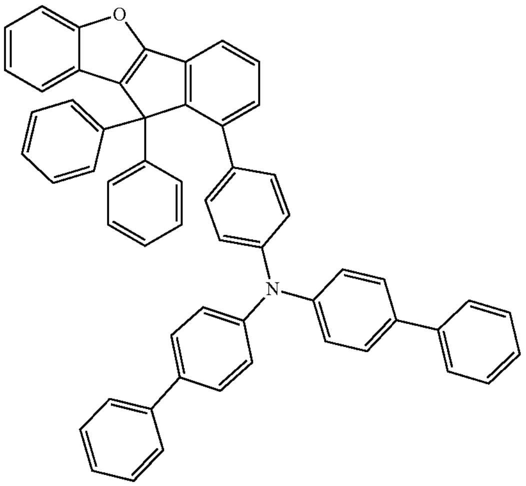

382

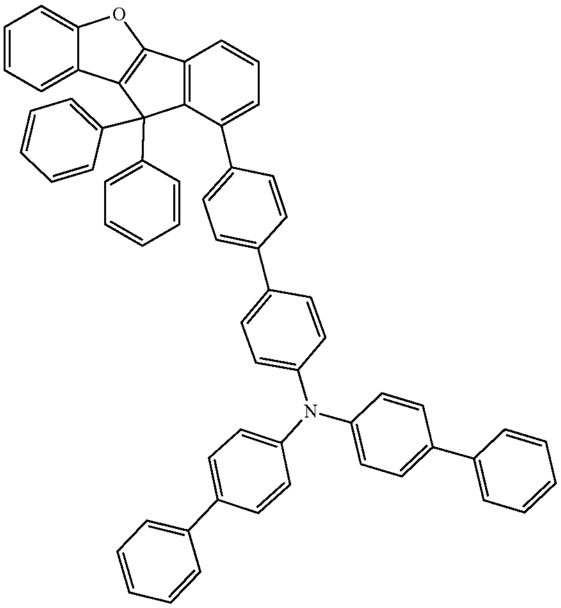

383

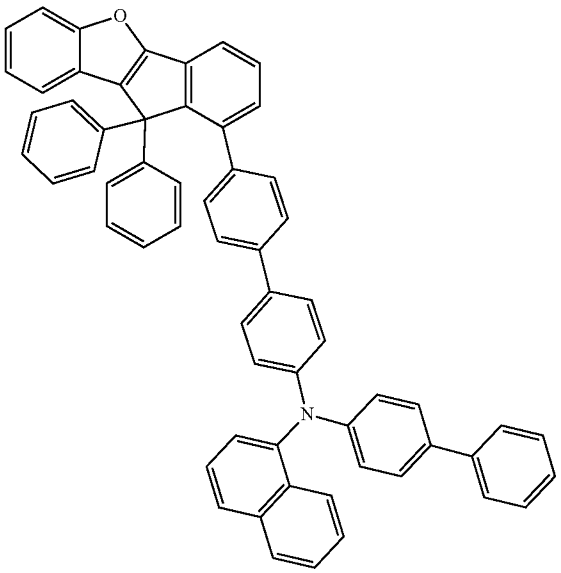

384

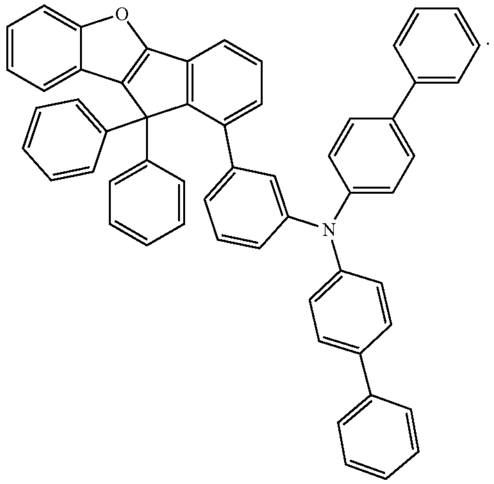

4. An organic light emitting device comprising:

a first electrode;

a second electrode provided opposite to the first electrode; and one or more organic material layers provided between the first electrode and the second electrode, wherein one or more layers of the organic material layers comprise the heterocyclic compound of claim 1.

5. The organic light emitting device of claim 4, wherein the organic material layer comprising the heterocyclic compound of Chemical Formula 1-B further comprises a heterocyclic compound represented by the following Chemical Formula 2:

[Chemical Formula 2]

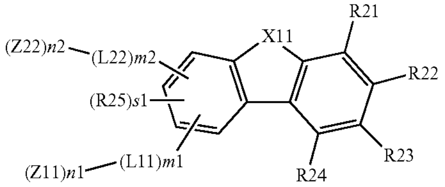

in Chemical Formula 2,

X11 is O; or S;

R21 to R25 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring;

L11 and L22 are the same as or different from each other, and each independently a direct bond; a substituted or unsubstituted C6 to C60 arylene group; or a substituted or unsubstituted C2 to C60 heteroarylene group;

Z11 and Z22 are the same as or different from each other, and each independently selected from the group consisting of a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group;

R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group;

m1 and m2 are an integer of 0 to 4;

s1 is an integer of 0 to 2; and n1 and n2 are an integer of 1 to 6.

6. The organic light emitting device of claim 5, wherein Chemical Formula 2 is any one of the following compounds:

2-1

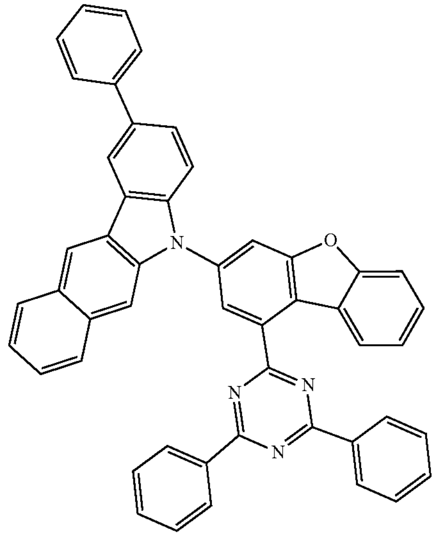

2-2

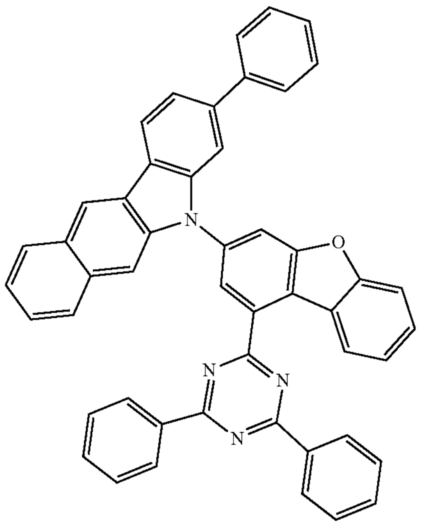

2-3

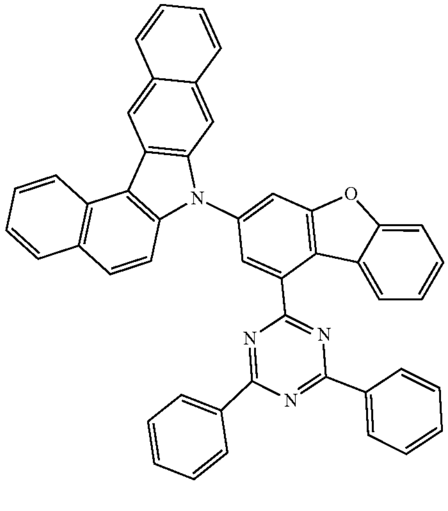

-continued
2-4
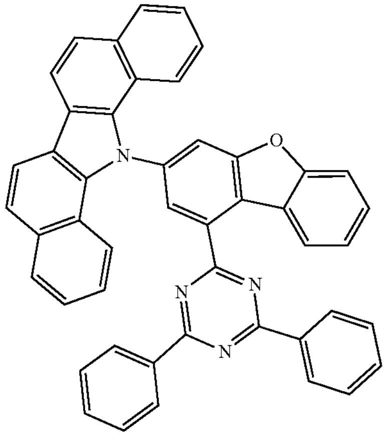
2-5
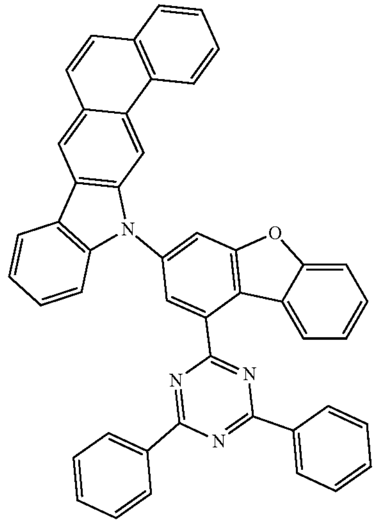
2-6
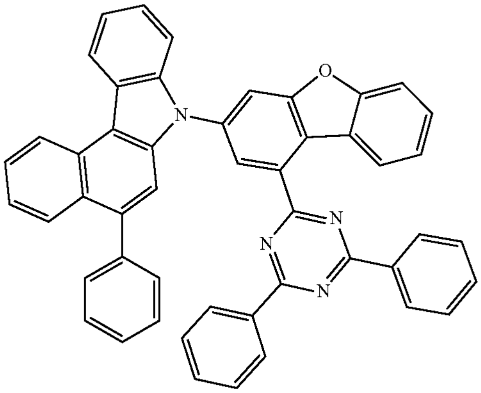
-continued
2-7
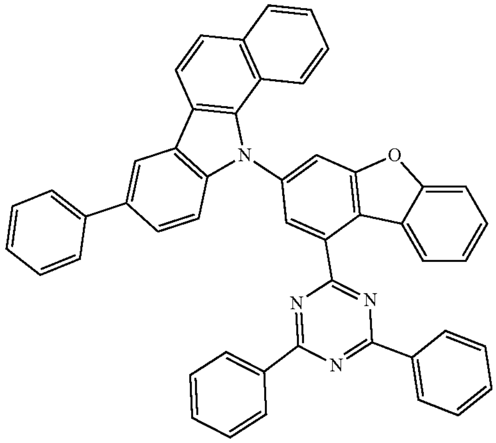
2-8
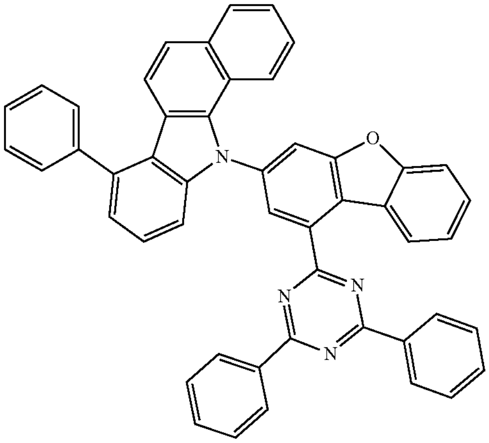
2-9
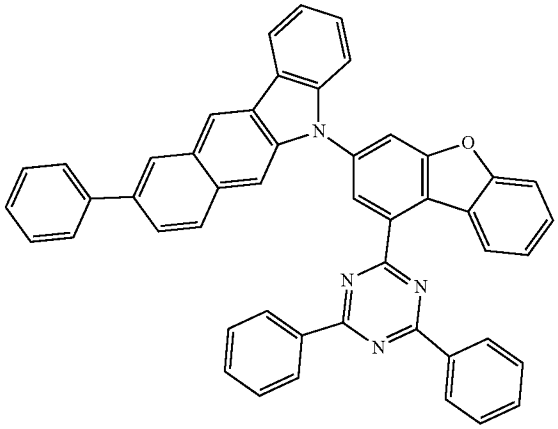

-continued
2-10
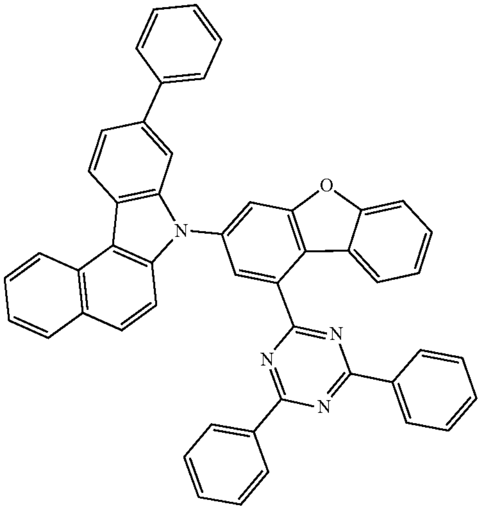
2-11
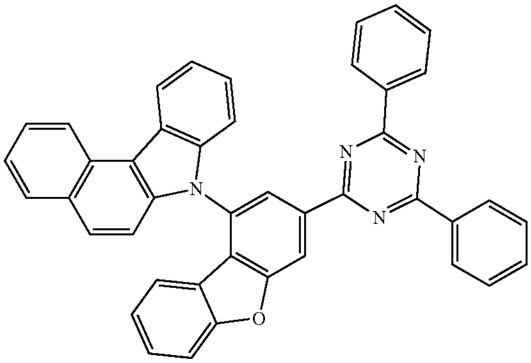
2-12
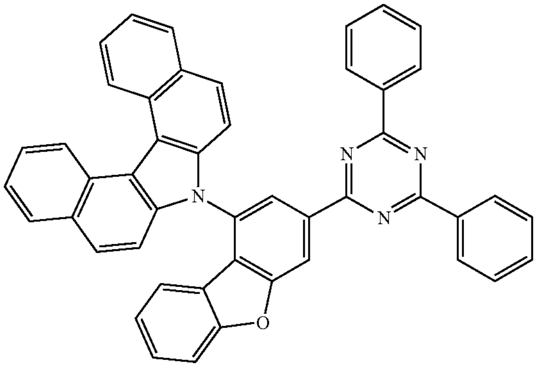
2-13
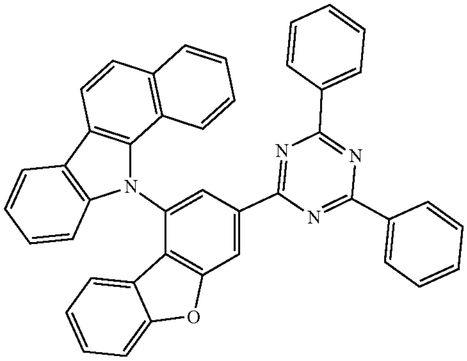
-continued
2-14
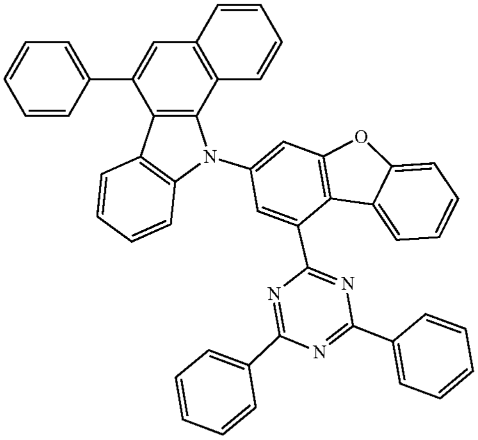
2-15
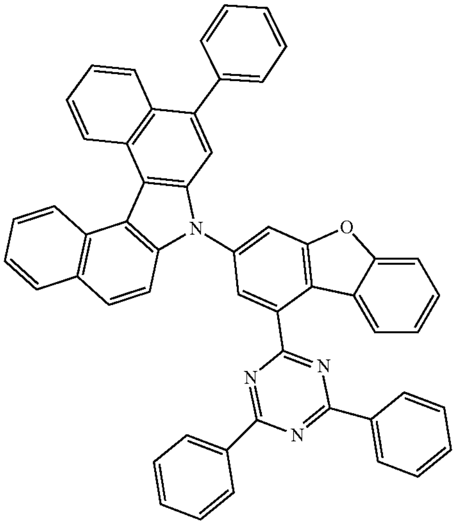
2-16
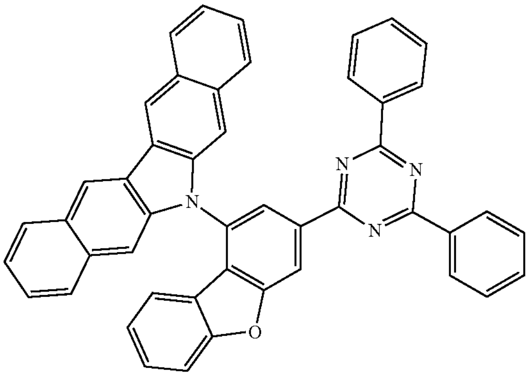

-continued
2-17
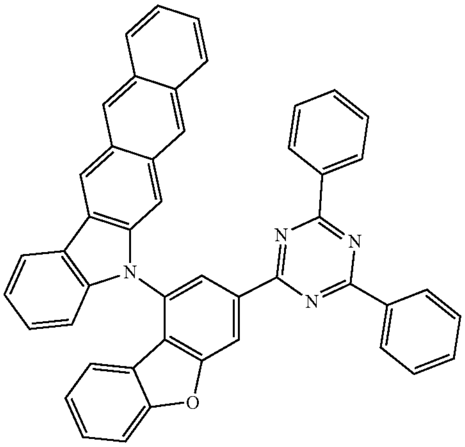
2-18
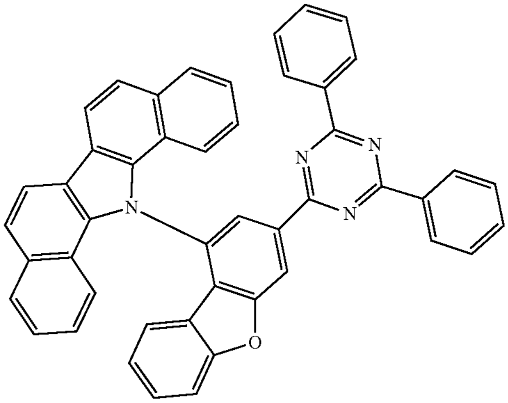
2-19
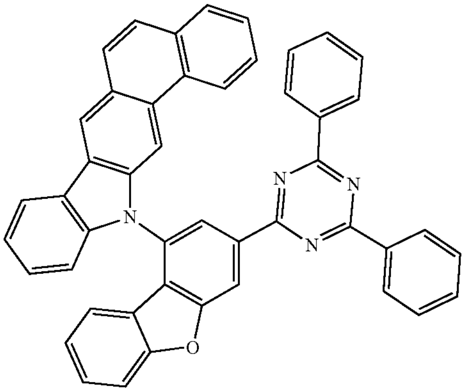
2-20
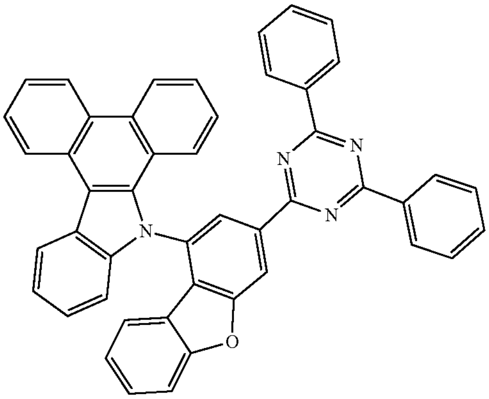
-continued
2-21
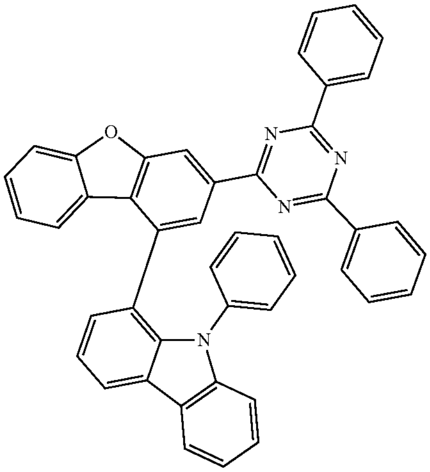
2-22
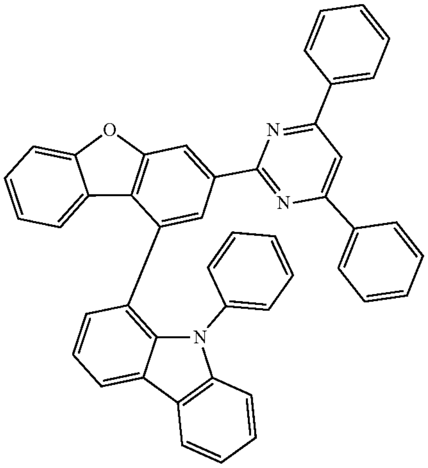
2-23
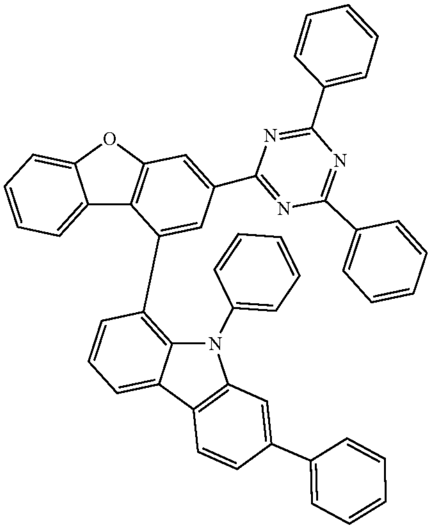

-continued
2-24
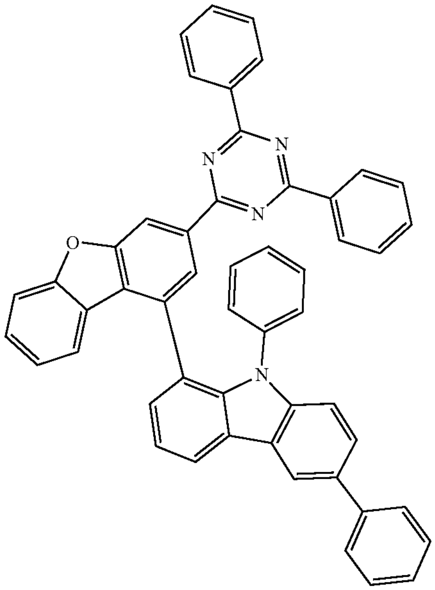
2-25
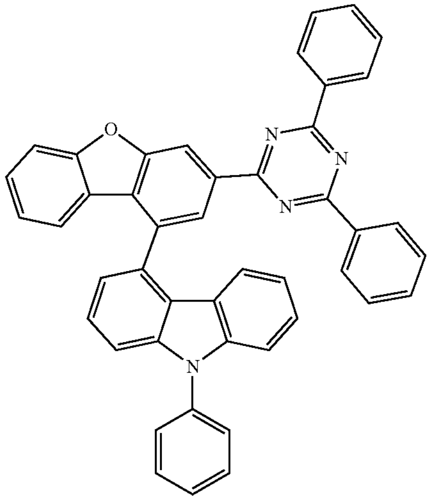
2-26
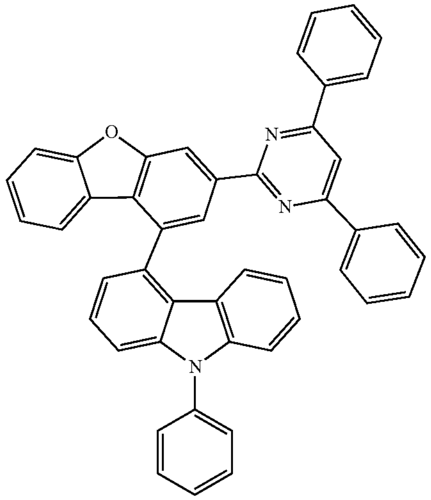
-continued
2-27
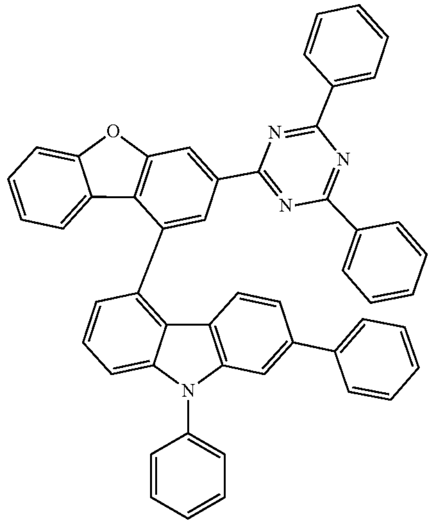
2-28
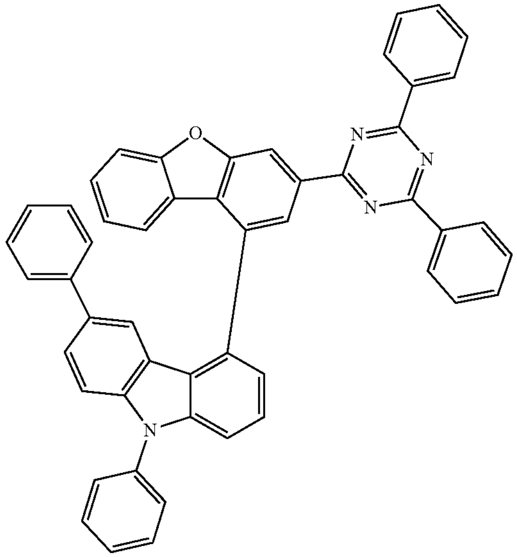
2-29
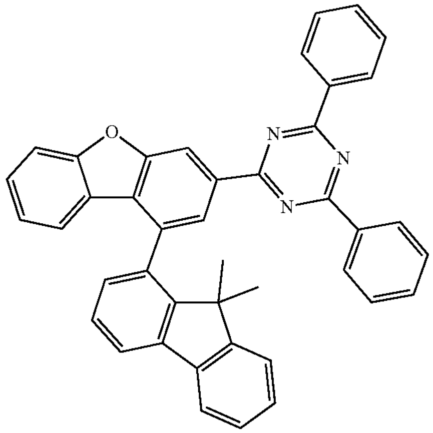

-continued
2-30
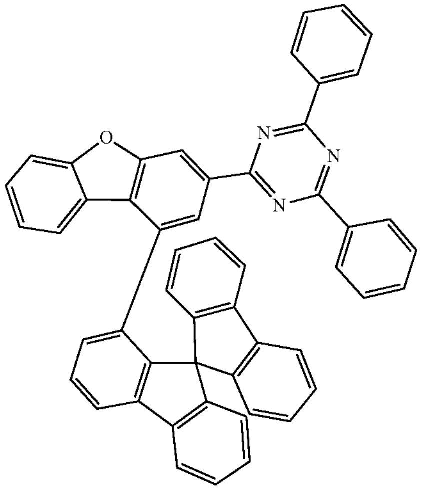
2-31
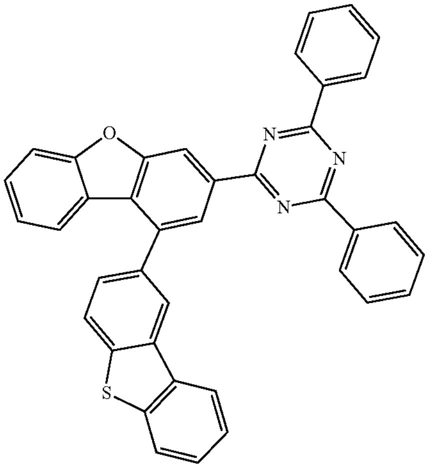
2-32
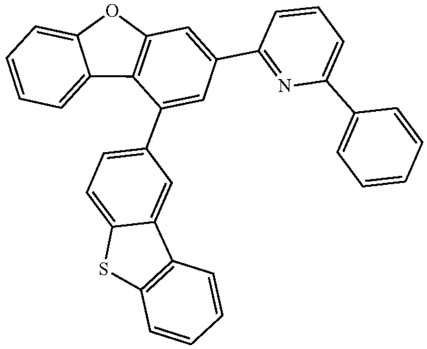
-continued
2-33
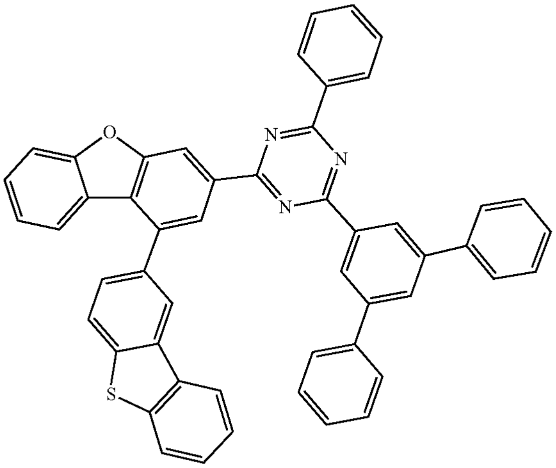
2-34
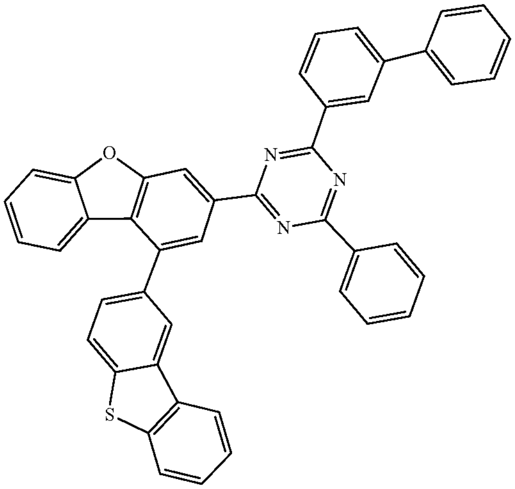
2-35
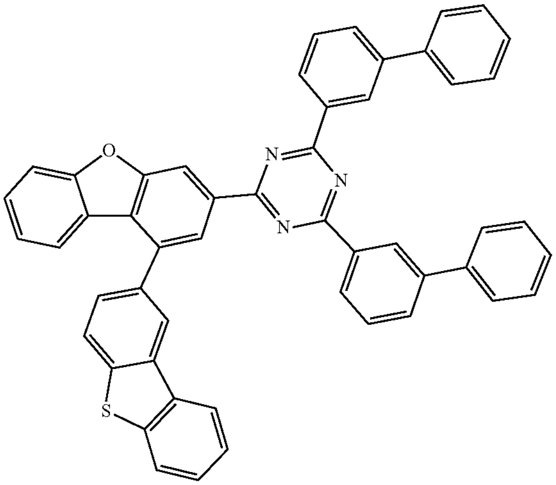

-continued
2-36
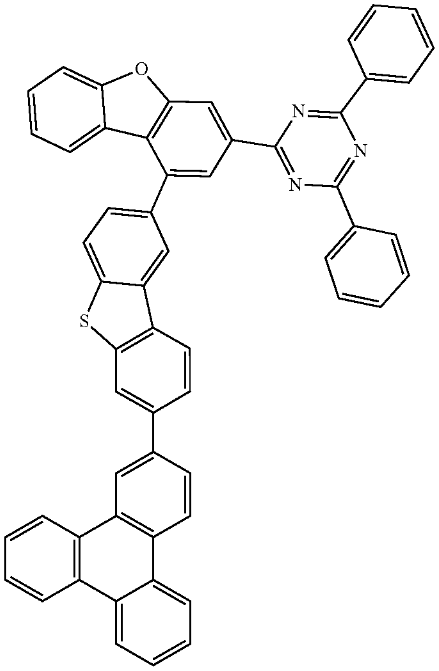
2-37
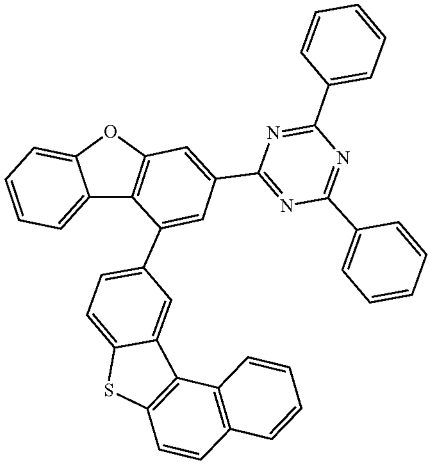
2-38
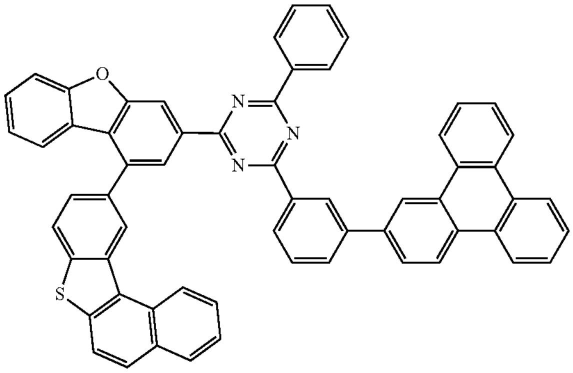
-continued
2-39
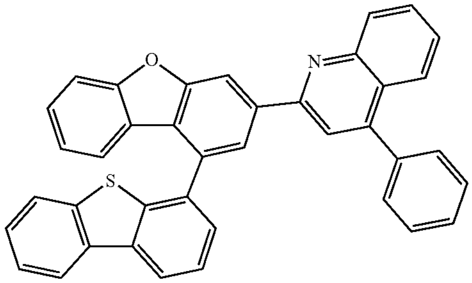
2-40
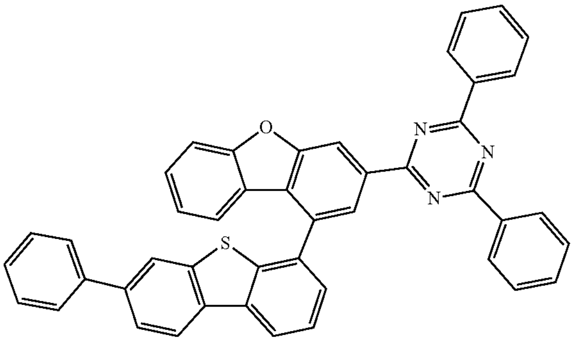
2-41
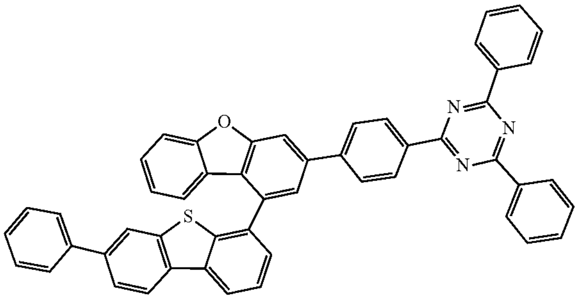
2-42
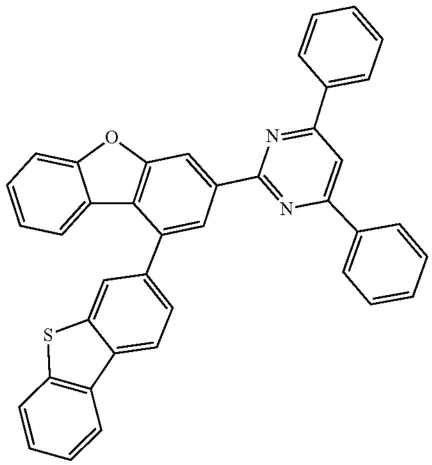

-continued
2-43
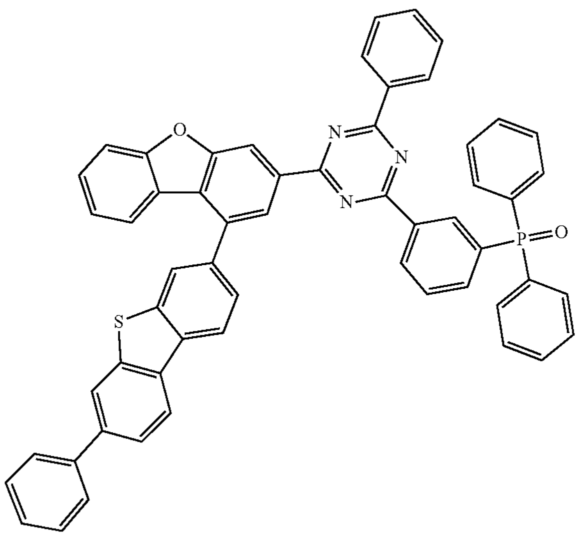
2-44
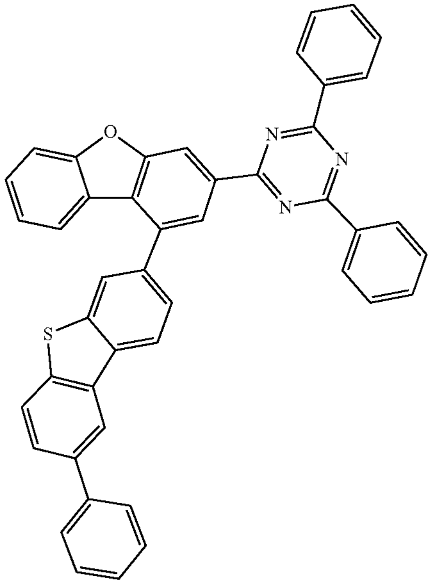
-continued
2-45
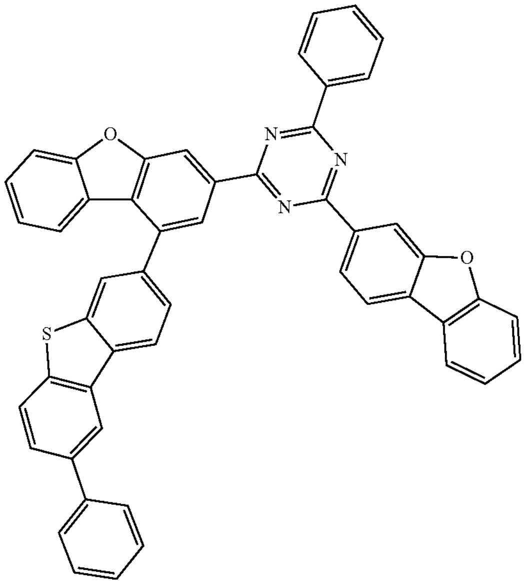
2-46
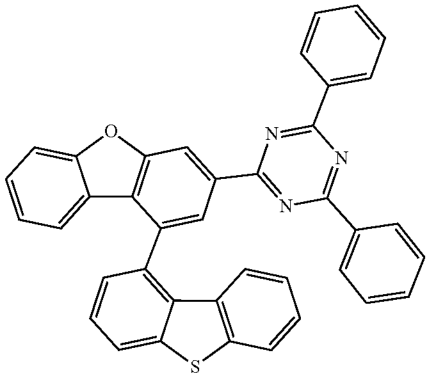
2-47
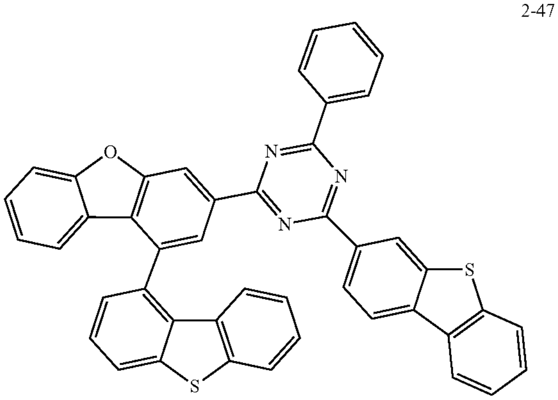

2-48
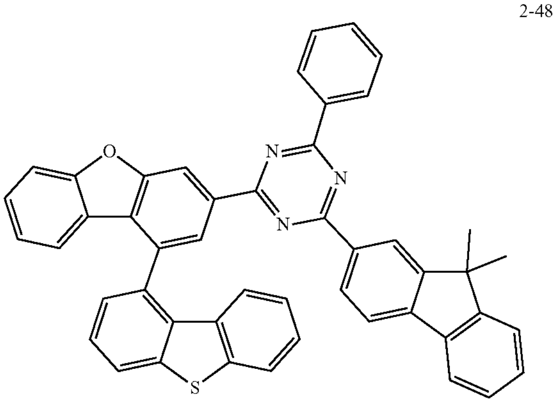
2-49
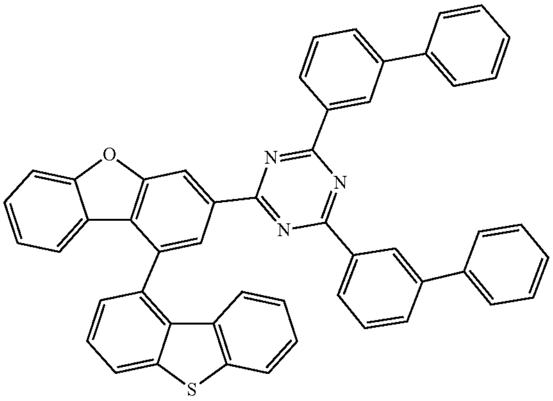
2-50
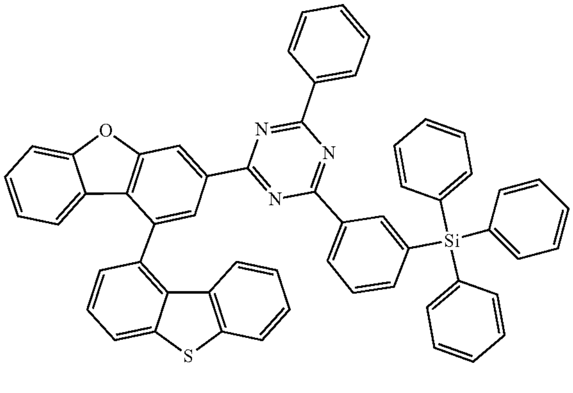
2-51
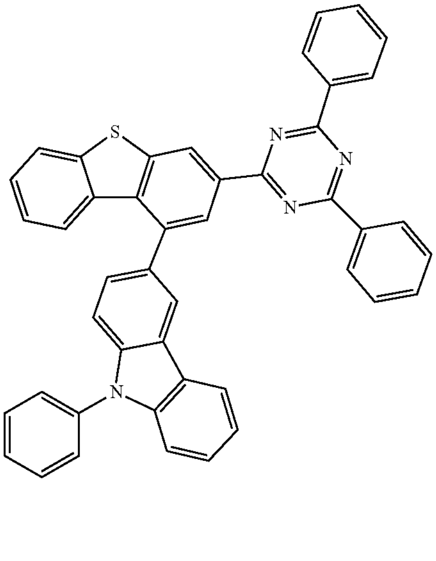
2-52
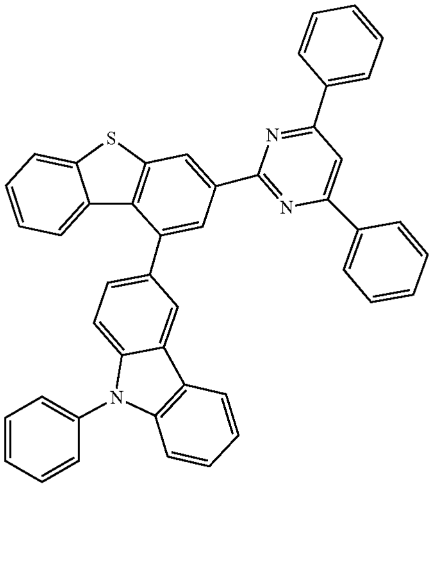
2-53
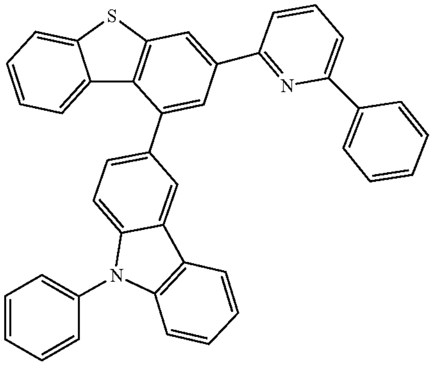

-continued
2-54
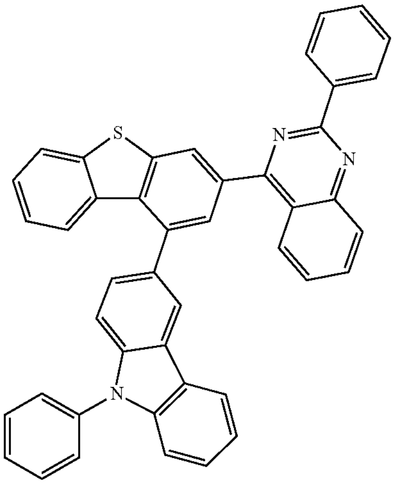
2-55
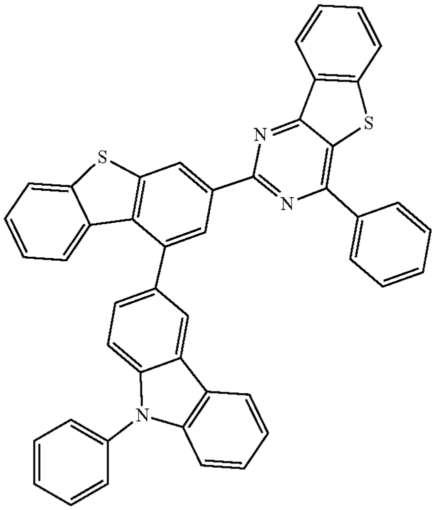
2-56
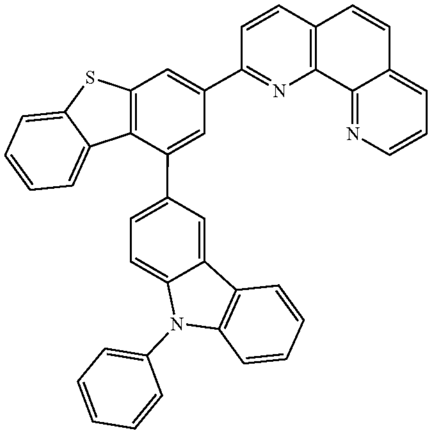
-continued
2-57
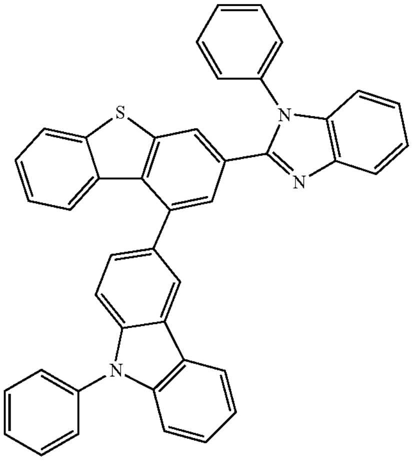
2-58
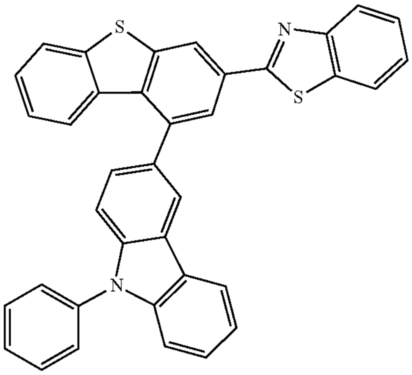
2-59
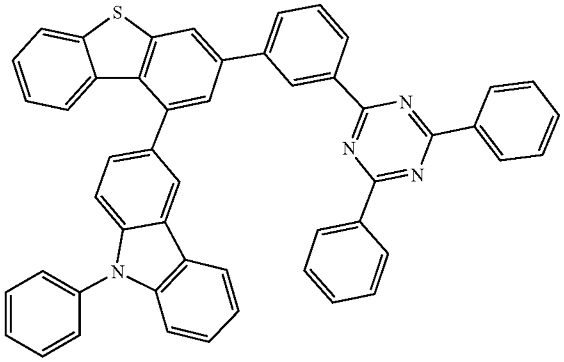

2-60
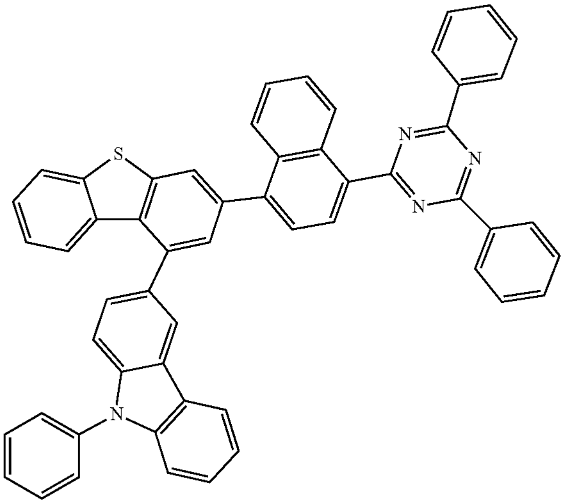
2-61
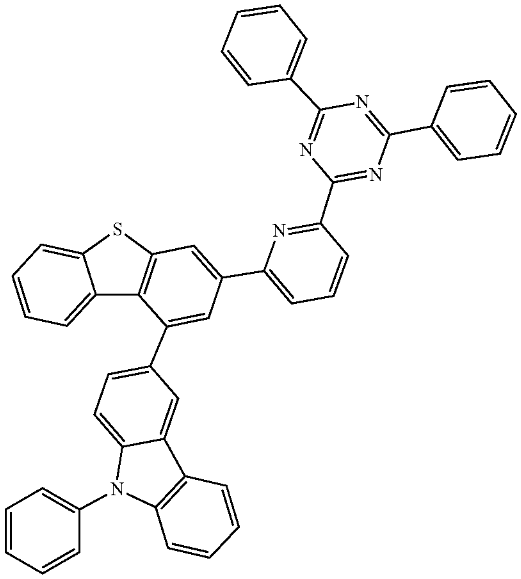
2-62
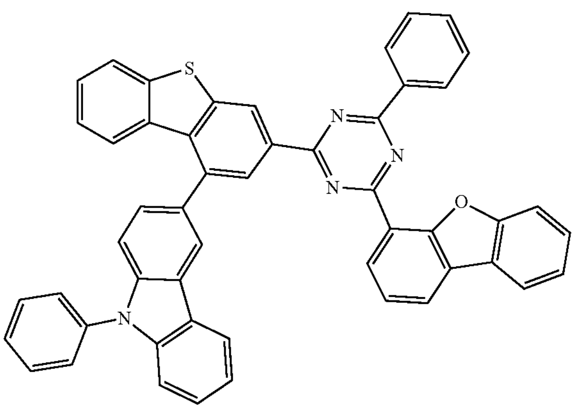
2-63
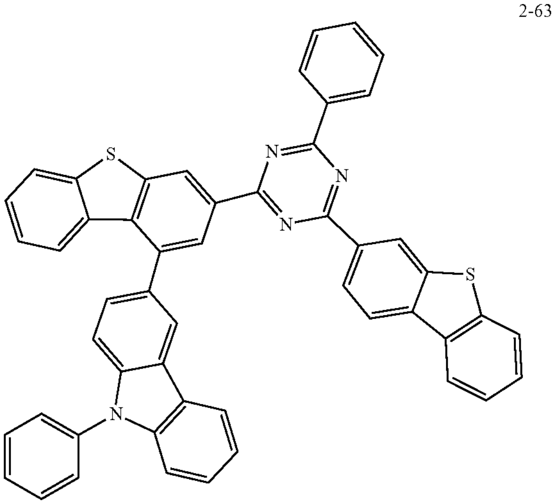
2-64
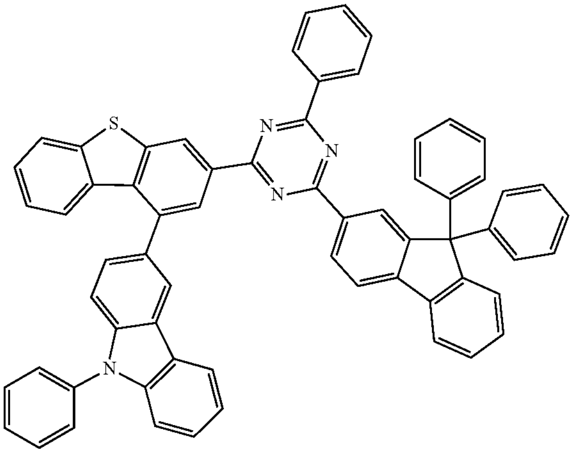
2-65
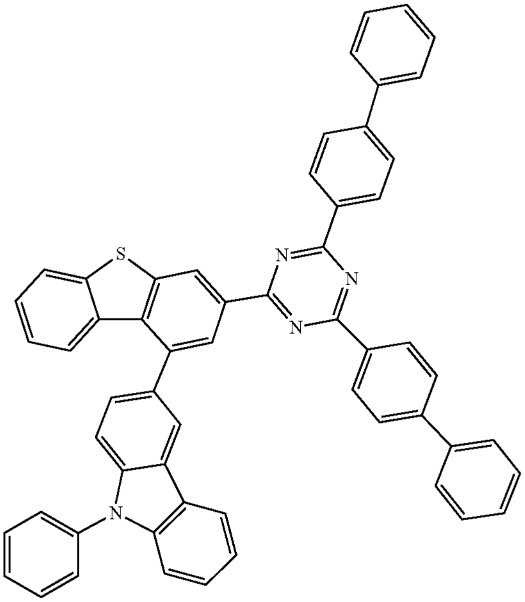

-continued
2-66
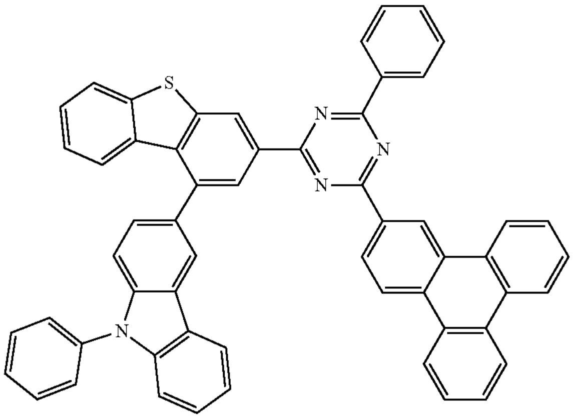
2-67
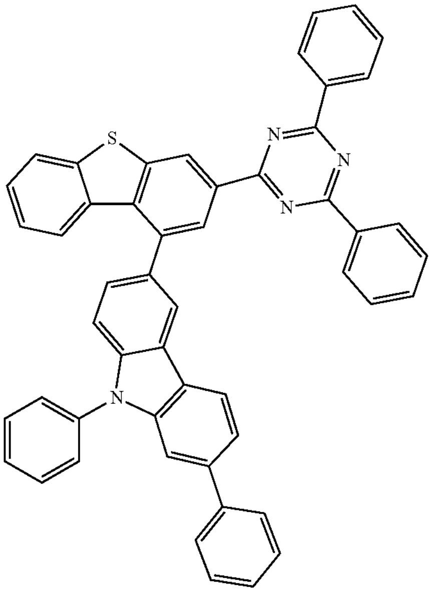
2-68
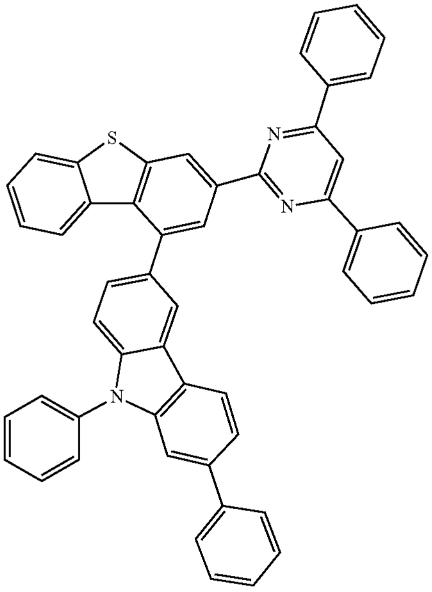
-continued
2-69
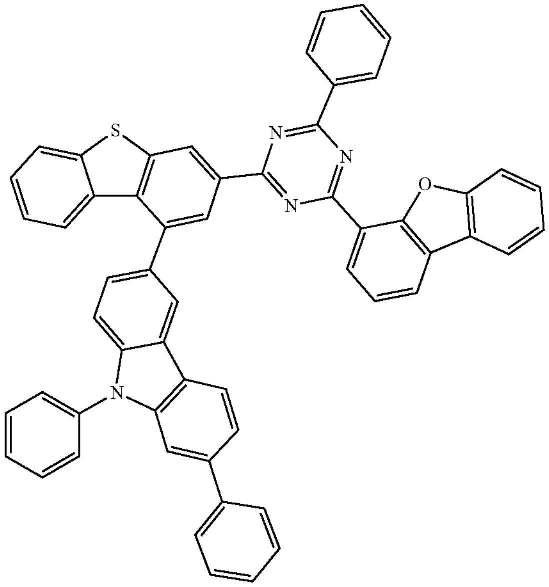
2-70
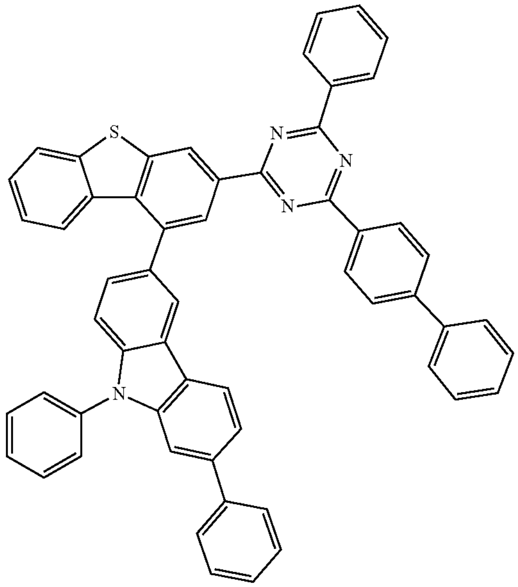
2-71
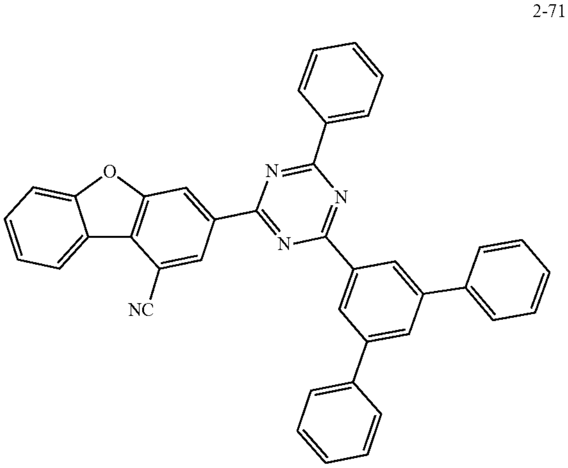

-continued
2-72
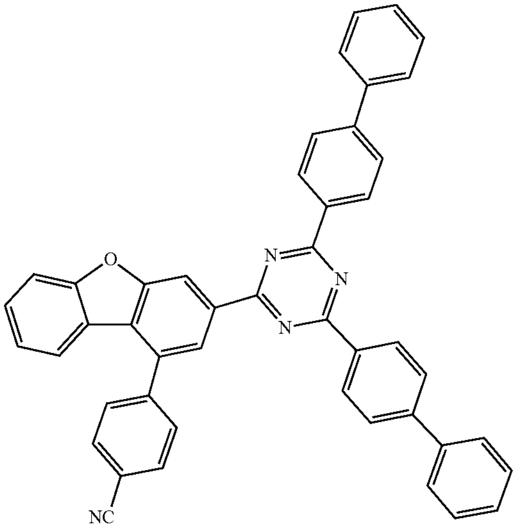
2-73
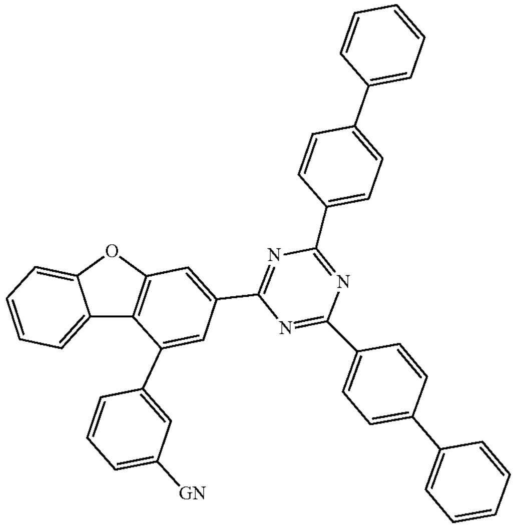
2-74
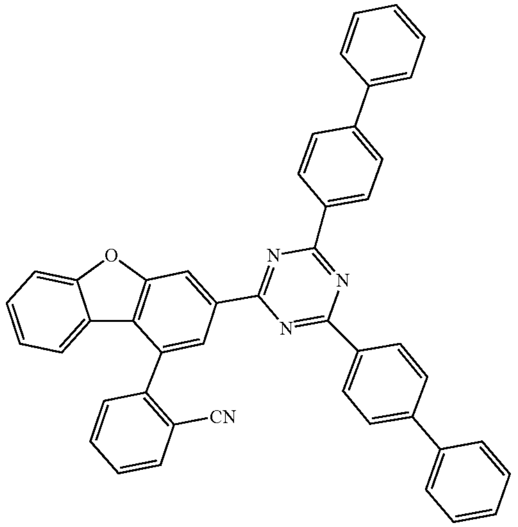
-continued
2-75
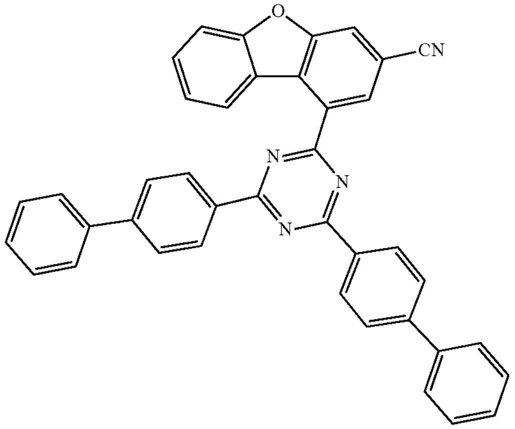
2-76
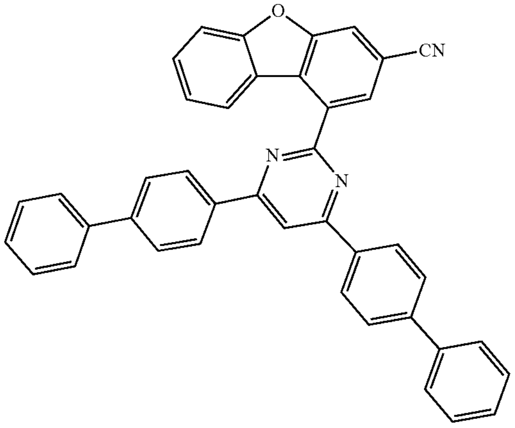
2-77
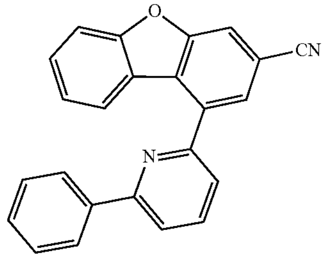
2-78
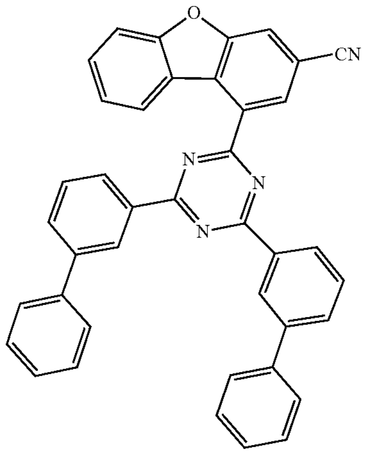

-continued
2-79
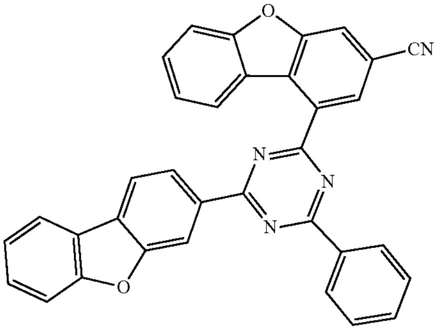
2-80
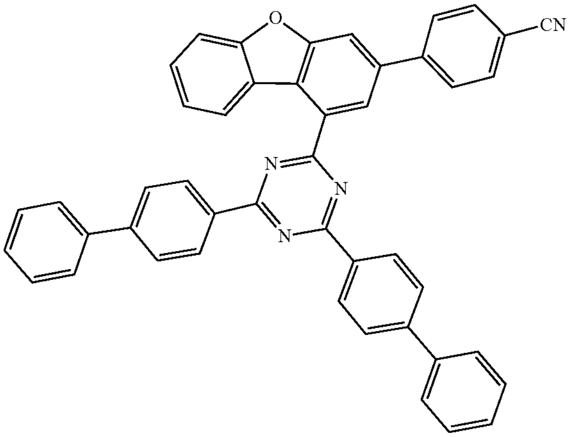
2-81
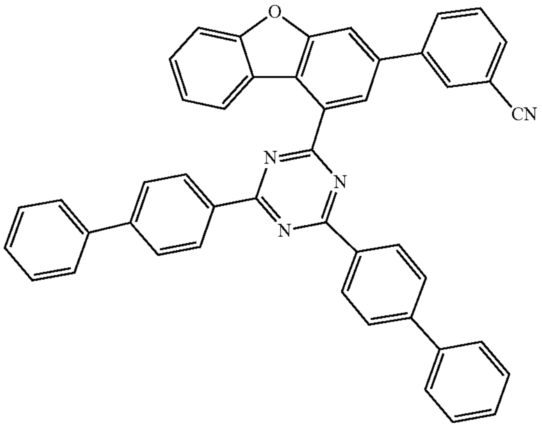
-continued
2-82
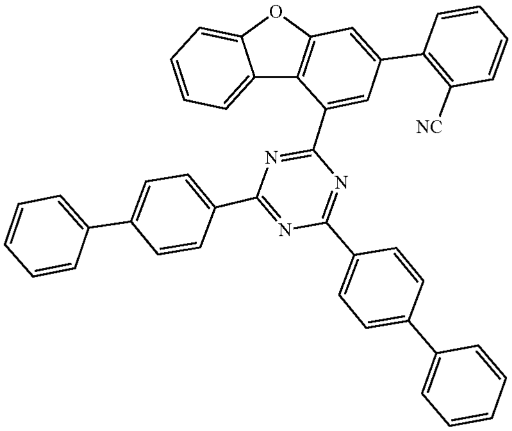
2-83
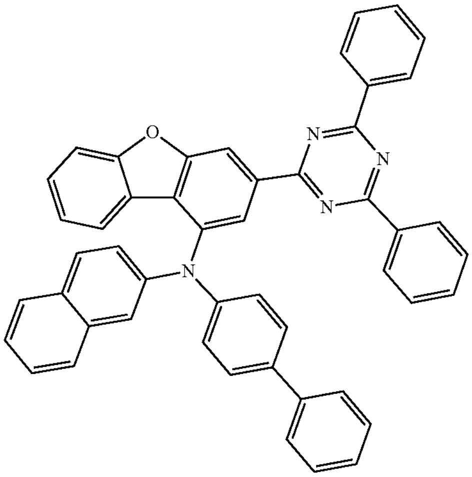
2-84
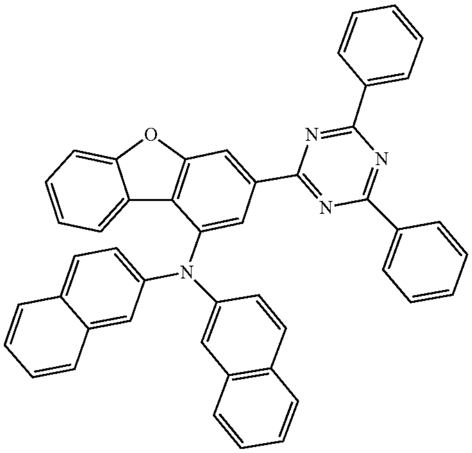

-continued
2-85
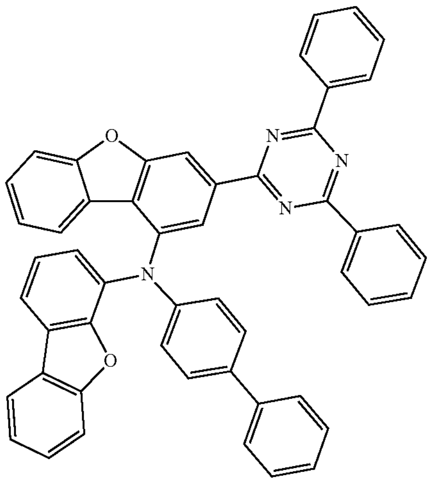
2-86
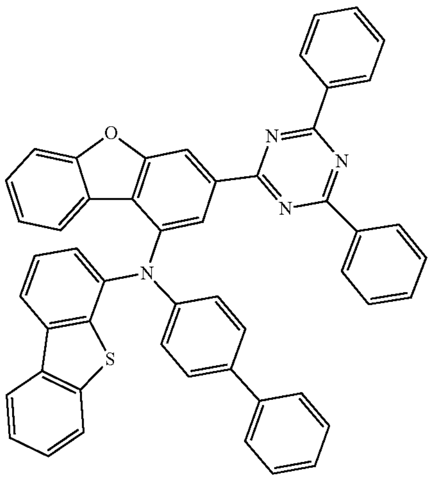
2-87
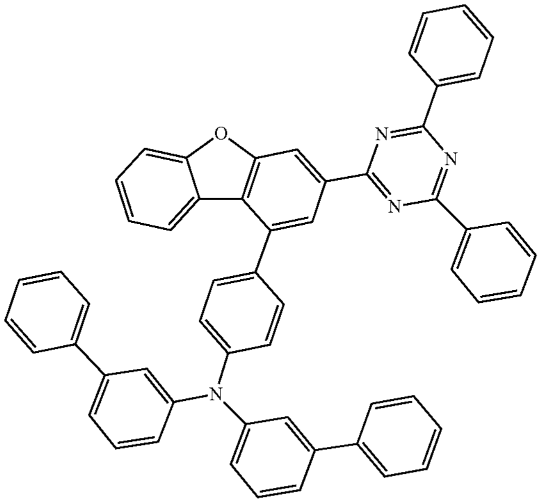
-continued
2-88
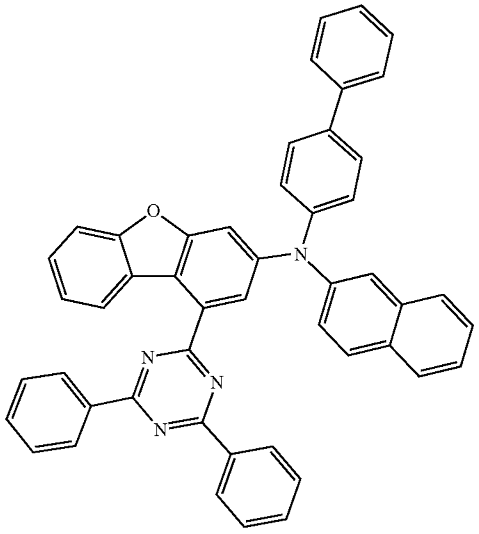
2-89
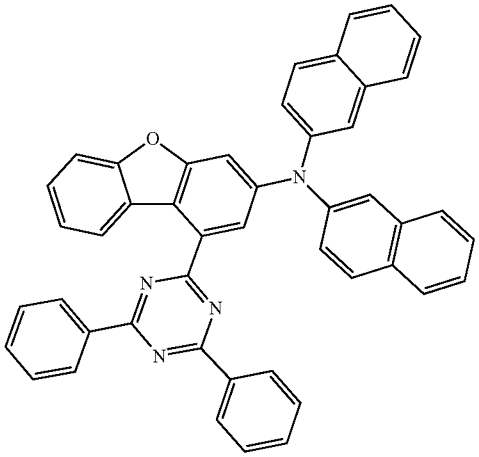
2-90
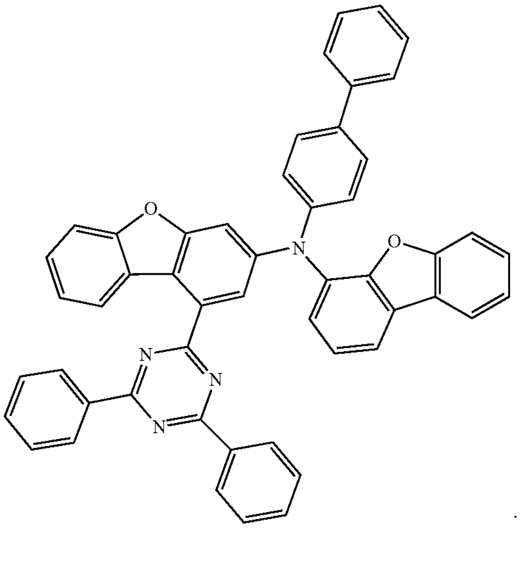
.
7. The organic light emitting device of claim 4, wherein the organic material layer comprises a light emitting layer, and the light emitting layer comprises the heterocyclic compound.

8. The organic light emitting device of claim 4, wherein the organic material layer comprises a light emitting layer, the light emitting layer comprises a host material, and the host material comprises the heterocyclic compound.

9. The organic light emitting device of claim 4, further comprising one, two or more layers selected from the group consisting of a light emitting layer, a hole injection layer, a hole transfer layer, an electron injection layer, an electron transfer layer, an electron blocking layer and a hole blocking layer.

10. A composition for an organic material layer of an organic light emitting device, the composition comprising:

the heterocyclic compound of claim 1; and a heterocyclic compound represented by the following Chemical Formula 2:

[Chemical Formla 2]

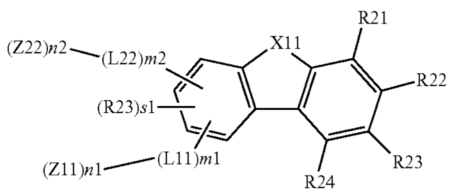

wherein, in Chemical Formula 2,

X11 is O; or S;

R21 to R25 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring;

L11 and L22 are the same as or different from each other, and each independently a direct bond; a substituted or unsubstituted C6 to C60 arylene group; or a substituted or unsubstituted C2 to C60 heteroarylene group;

Z11 and Z22 are the same as or different from each other, and each independently selected from the group consisting of a cyano group; a substituted or unsubstituted C1 to C60 alkyl group; a substituted or unsubstituted C6 to C60 aryl group; a substituted or unsubstituted C2 to C60 heteroaryl group; and a substituted or unsubstituted amine group;

R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group;

m1 and m2 are an integer of 0 to 4;

s1 is an integer of 0 to 2; and n1 and n2 are an integer of 1 to 6.

11. The composition for an organic material layer of an organic light emitting device of claim 10, wherein the heterocyclic compound represented by Chemical Formula 1-B and the heterocyclic compound represented by Chemical Formula 2 have a weight ratio of 1:10 to 10:1 in the composition.

12. A method for manufacturing an organic light emitting device, the method comprising:

preparing a substrate;

forming a first electrode on the substrate;

forming one or more organic material layers on the first electrode; and forming a second electrode on the organic material layer, wherein the forming of organic material layers comprises forming one or more organic material layers using the composition for an organic material layer of claim 10.

13. The method for manufacturing an organic light emitting device of claim 12, wherein the forming of organic material layers is forming using a thermal vacuum deposition method after pre-mixing the heterocyclic compound of Chemical Formula 1-B and the heterocyclic compound of Chemical Formula 2.

* * * * *